US011332524B2

(12) United States Patent
Hill et al.

(10) Patent No.: US 11,332,524 B2
(45) Date of Patent: May 17, 2022

(54) ANTI-IL-27 ANTIBODIES AND USES THEREOF

(71) Applicants: Surface Oncology, Inc., Cambridge, MA (US); Adimab LLC, Lebanon, NH (US)

(72) Inventors: Jonathan Hill, Salem, MA (US); Scott Chappel, Milton, MA (US); Michael Gladstone, Cambridge, MA (US); Bianka Prinz, Lebanon, NH (US); Andrew Lake, Westwood, MA (US); Christine Miller, Amesbury, MA (US); Kerry White, Danvers, MA (US); Jing Hua, Wellesley, MA (US); Pamela M. Holland, Belmont, MA (US); Matthew Rausch, Cambridge, MA (US); Devapregasan Moodley, Cambridge, MA (US)

(73) Assignees: Surface Oncology, Inc., Cambridge, MA (US); Adimab LLC, Lebanon, NH (US)

( * ) Notice: Subject to any disclaimer, the term of this patent is extended or adjusted under 35 U.S.C. 154(b) by 0 days.

(21) Appl. No.: 16/362,457

(22) Filed: Mar. 22, 2019

(65) Prior Publication Data

US 2019/0382474 A1 Dec. 19, 2019

Related U.S. Application Data

(60) Provisional application No. 62/646,496, filed on Mar. 22, 2018.

(51) Int. Cl.

| | |
|---|---|
| ***C07K 16/24*** | (2006.01) |
| ***A61K 39/395*** | (2006.01) |
| ***A61K 45/06*** | (2006.01) |
| ***A61P 35/00*** | (2006.01) |
| ***G01N 33/68*** | (2006.01) |
| *A61K 39/00* | (2006.01) |

(52) U.S. Cl.

CPC ........ *C07K 16/244* (2013.01); *A61K 39/3955* (2013.01); *A61K 45/06* (2013.01); *A61P 35/00* (2018.01); *G01N 33/6869* (2013.01); *A61K 2039/505* (2013.01); *C07K 2317/56* (2013.01); *C07K 2317/76* (2013.01); *C07K 2317/92* (2013.01); *G01N 2333/54* (2013.01)

(58) Field of Classification Search

None

See application file for complete search history.

(56) References Cited

U.S. PATENT DOCUMENTS

| | | | |
|---|---|---|---|
| 3,710,795 | A | 1/1973 | Higuchi et al. |
| 3,773,919 | A | 11/1973 | Boswell et al. |
| 4,676,980 | A | 6/1987 | Segal et al. |
| 4,863,457 | A | 9/1989 | Lee |
| 5,223,409 | A | 6/1993 | Ladner et al. |
| 5,403,484 | A | 4/1995 | Ladner et al. |
| 5,427,908 | A | 6/1995 | Dower et al. |
| 5,501,856 | A | 3/1996 | Ohtori et al. |
| 5,516,637 | A | 5/1996 | Huang et al. |
| 5,571,698 | A | 11/1996 | Ladner et al. |
| 5,580,717 | A | 12/1996 | Dower et al. |
| 5,624,821 | A | 4/1997 | Winter et al. |
| 5,648,260 | A | 7/1997 | Winter et al. |
| 5,658,727 | A | 8/1997 | Barbas et al. |
| 5,698,426 | A | 12/1997 | Huse |
| 5,733,743 | A | 3/1998 | Johnson et al. |
| 5,750,753 | A | 5/1998 | Kimae et al. |
| 5,780,225 | A | 7/1998 | Wigler et al. |
| 5,821,047 | A | 10/1998 | Garrard et al. |
| 5,969,108 | A | 10/1999 | McCafferty et al. |
| 6,001,329 | A | 12/1999 | Buchsbaum et al. |
| 6,005,079 | A | 12/1999 | Casterman et al. |
| 6,194,551 | B1 | 2/2001 | Idusogie et al. |
| 6,300,064 | B1 | 10/2001 | Knappik et al. |
| 6,933,368 | B2 | 8/2005 | Co et al. |
| 6,995,259 | B1 | 2/2006 | Vargeese et al. |
| 7,595,048 | B2 | 9/2009 | Honjo et al. |
| 7,943,743 | B2 | 5/2011 | Korman et al. |
| 8,008,449 | B2 | 8/2011 | Korman et al. |
| 8,354,509 | B2 | 1/2013 | Carven et al. |
| 8,691,953 | B2 | 4/2014 | Timans et al. |
| 8,728,474 | B2 | 5/2014 | Honjo et al. |
| 8,779,105 | B2 | 7/2014 | Korman et al. |

(Continued)

FOREIGN PATENT DOCUMENTS

| | | | |
|---|---|---|---|
| EP | 0036676 | B1 | 7/1984 |
| EP | 0133988 | A2 | 3/1985 |

(Continued)

OTHER PUBLICATIONS

International Search Report and Written Opinion in corresponding PCT Application No. PCT/US19/53036 dated Feb. 14, 2020, 18 pages.

(Continued)

*Primary Examiner* — Joanne Hama

*Assistant Examiner* — Fozia M Hamud

(74) *Attorney, Agent, or Firm* — Sterne Kessler Goldstein & Fox, P.L.L.C.; Brian Dudley

(57) ABSTRACT

The present disclosure relates to anti-IL-27 antibodies, and antigen-binding portions thereof. The disclosure also relates to methods for treating or ameliorating one or more symptoms of a disease, such as cancer, by administering the antibodies or antigen-binding portion thereof. The disclosure also relates to methods for detecting IL-27 in, for example, a subject or a sample.

19 Claims, 38 Drawing Sheets

Specification includes a Sequence Listing.

(56) References Cited

U.S. PATENT DOCUMENTS

| | | | |
|---|---|---|---|
| 8,900,587 | B2 | 12/2014 | Carven et al. |
| 8,952,136 | B2 | 2/2015 | Carven et al. |
| 9,067,999 | B1 | 6/2015 | Honjo et al. |
| 9,073,994 | B2 | 7/2015 | Honjo et al. |
| 2003/0054407 | A1 | 3/2003 | Peizhi |
| 2008/0124345 | A1 | 5/2008 | Rothe et al. |
| 2008/0241223 | A1 | 10/2008 | Nivaggioli et al. |
| 2009/0074793 | A1 | 3/2009 | Martin et al. |
| 2013/0189262 | A1 | 7/2013 | Wong et al. |
| 2015/0366987 | A1 | 12/2015 | Bodyak et al. |
| 2016/0051672 | A1 | 2/2016 | Stewart et al. |
| 2017/0058026 | A1 | 3/2017 | Kuchroo et al. |

FOREIGN PATENT DOCUMENTS

| | | | |
|---|---|---|---|
| EP | 0058481 | B1 | 10/1986 |
| EP | 0088046 | B1 | 12/1987 |
| EP | 0143949 | B1 | 10/1988 |
| EP | 0488401 | A1 | 6/1992 |
| EP | 0430539 | B1 | 10/1994 |
| EP | 1537878 | B1 | 9/2010 |
| EP | 2161336 | B1 | 7/2013 |
| EP | 2170959 | B1 | 10/2013 |
| WO | WO-9002809 | A1 | 3/1990 |
| WO | WO-9110737 | A1 | 7/1991 |
| WO | WO-9201047 | A1 | 1/1992 |
| WO | WO-9218619 | A1 | 10/1992 |
| WO | WO-9311236 | A1 | 6/1993 |
| WO | WO-9315722 | A1 | 8/1993 |
| WO | WO-9404678 | A1 | 3/1994 |
| WO | WO-9420069 | A1 | 9/1994 |
| WO | WO-9425591 | A1 | 11/1994 |
| WO | WO-9429351 | A2 | 12/1994 |
| WO | WO-9515982 | A2 | 6/1995 |
| WO | WO-9520401 | A1 | 8/1995 |
| WO | WO-9627011 | A1 | 9/1996 |
| WO | WO-9951642 | A1 | 10/1999 |
| WO | WO-2007024715 | A2 | 3/2007 |
| WO | WO-2008024188 | A2 | 2/2008 |
| WO | 2008135239 | A1 | 11/2008 |
| WO | WO-2009036379 | A2 | 3/2009 |
| WO | WO-2010027827 | A2 | 3/2010 |
| WO | WO-2010077634 | A1 | 7/2010 |
| WO | WO-2010105256 | A1 | 9/2010 |
| WO | WO-2011066342 | A2 | 6/2011 |
| WO | 2011133931 | A1 | 10/2011 |
| WO | 2011140151 | A1 | 11/2011 |
| WO | WO-2012009568 | A2 | 1/2012 |
| WO | WO-2013079174 | A1 | 6/2013 |
| WO | WO-2013173223 | A1 | 11/2013 |
| WO | WO-2015103072 | A1 | 7/2015 |
| WO | WO-2016106159 | A1 | 6/2016 |
| WO | WO-2019024979 | A1 | 2/2019 |
| WO | WO-2019183499 | A1 | 9/2019 |

OTHER PUBLICATIONS

Hunter et al., "Interleukin-27: Balancing Protective and Pathological Immunity," Immunity, 37:960-969 (2012).
Bender et al., "Interleukin-27 Displays Interferon-γ-Like Functions in Human Hepatoma Cells and Hepatocytes," Hepatology, 50:585-591 (2009).
Bosmann et al., "Modulation of inflammation by interleukin-27," Journal of Leukocyte Biology, 94:1159-1165 (2013).
Devergne et al., "A Novel Interleukin-12 p40-Related Protein Induced by Latent Epstein-Barr Virus Infection in B Lymphocytes," Journal of Virology, 70(2):1143-1153 (1996).
Devergne et al., "Expression of Epstein-Barr Virus-Induced Gene 3, an Interleukin-12 p40-Related Molecule, throughout Human Pregnancy," American Journal of Pathology, 159(5):1763-1776 (2001).
Diakowska et al., "Concentration of Serum Interleukin-27 Increase in Patients with Lymph Node Metastatic Gastroesophageal Cancer," Adv Clin Exp Med, 22(5):683-691 (2013).
Dietrich et al., "A Soluble Form of IL-27Rα is a Natural IL-27 Antagonist," The Journal of Immunology, 192:5382-5389 (2014).
Gonin et al., "Expression of IL-27 by Tumor Cells in InvasCutaneous and Metastatic Melanomas," PLOS ONE, 8(10):e75694 (2013).
Larousserie et al., "Analysis of Interleukin-27 (EBI3/p28) Expression in Epstein-Barr Virus- and Human T-Cell Leukemia Virus Type 1-Associated Lymphomas," American Journal of Pathology, 166(4):1217-1228 (2005).
Nishino et al., "Identification of Epstein-Barr Virus-Induced Gene 3 as a Novel Serum and Tissue Biomarker and a Therapeutic Target for Lung Cancer," Clin Cancer Res, 17(19):6272-6286 (2011).
Petretto et al., "Proteomic analysis uncovers common effects of IFN-γy and IL-27 on the HLA class I antigen presentation machinery in human cancer cells," Oncotarget, 7(45):72518-72536 (2016).
Pflanz et al., "WSX-1 and Glycoprotein 130 Constitute a Signal-Transducing Receptor for IL-27," The Journal of Immunology, 172:2225-2231 (2004).
Pu et al., "Association between polymorphisms in IL27 gene and renal cell carcinoma," Biomarkers, 20(3):202-205 (2015).
Rousseau et al., "IL-27 structural analysis demonstrates similarities with ciliary neurotrophic factor (CNTF) and leads to the identification of antagonistic variants," PNAS, 107(45): 19420-19425 (2010).
Song et al., "Downregulation of Epstein-Barr virus-induced gene 3 is associated with poor prognosis of hepatocellular carcinoma after curative resection," Oncology Letters, 15:7751-7759 (2018).
Tang et al., "Associations of IL-27 Polymorphisms and Serum IL-27p28 Levels With Osteosarcoma Risk," Medicine, 93(10):e56 (2014).
Yang e.t al., "Cell Origins and Diagnostic Accuracy of Interleukin 27 in Pleural Effusions," PLOS ONE, 7(7):e40450 (2012).
Zhang et al., "Association of 3 Common Polymorphisms of IL-27 Gene with Susceptibility to Cancer in Chinese: Evidence From an Updated Meta-Analysis of 27 Studies," Med Sci Monit, 21:2505-2513 (2015).
Yoshida et al., "The Immunobiology of Interleukin-27," Annu. Rev. Immunol, 33:417-443 (2015).
Zhou et al., "Polymorphisms and plasma levels of IL-27: impact on genetic susceptibility and clinical outcome of bladder cancer," BMC Cancer, 15:433 (2015).
International Search Report and Written Opinion in corresponding PCT Application No. PCT/US19/23625 dated Aug. 27, 2019, 23 pages.
Vander Heiden et al., Dysregulation of B Cell Repertoire Formation in Myasthenia Gravis Patients Revealed Through Deep Sequencing, Journal of Immunology, vol. 198, No. 4, Jan. 13, 2017, pp. 1460-1473.
Altschul, S.F., et al., "Basic Local Alignment Search Tool," Journal of Molecular Biology 215(3):403-410, Elsevier, United Kingdom (Oct. 1990).
Altschul, S. F., et al., "Gapped BLAST and PSI-BLAST: A New Generation of Protein Database Search Programs," Nucleic Acids Research 25(17):3389-3402, Oxford University Press, United Kingdom (Sep. 1997).
Ames, R. S., et al., "Conversion of Murine Fabs Isolated From a Combinatorial Phage Display Library to Full Length Immunoglobulins," Journal of Immunological Methods 184(2): 177-186, Elsevier, Netherlands (Aug. 1995).
Baldridge, J. R., and Crane, R. T., "Monophosphoryl lipid A (MPL) formulations for the next generation of vaccines," Methods 19(1):103-107, Elsevier, Netherlands (Sep. 1999).
Batzer, M. A., et al., "Enhanced evolutionary PCR using oligonucleotides with inosine at the 3'-terminus," Nucleic Acids Res 19(18):5081, Oxford University Press, United Kingdom (Sep. 1991).
Berge, S.M., et al., "Pharmaceutical Salts," Journal of Pharmaceutical Sciences 66(1):1-19, Wiley, United States (Jan. 1977).
Bieg, S., et al., "GAD65 and insulin B chain peptide (9-23) are not primary autoantigens in the type 1 diabetes syndrome of the BB rat," Autoimmunity 31(1):15-24, Informa Healthcare, United Kingdom (Jan. 1999).
Blank, C., et al., "Interaction of PD-L1 on tumor cells with PD-1 on tumor-specific T cells as a mechanism of immune evasion: implications for tumor immunotherapy," Cancer Immunol Immunother

(56) References Cited

OTHER PUBLICATIONS

54(4):307-314, Springer Science+Business Media, Germany (published online Dec. 2004, published in print Apr. 2005).
Blank, C., and Mackensen, A., "Contribution of the PD-L1/PD-1 pathway to T-cell exhaustion: an update on implications for chronic infections and tumor evasion," Cancer Immunol Immunother 56(5):739-745, Springer Science+Business Media, Germany (published online Dec. 2006, published in print May 2007).
Boder, E. T., and Wittrup, K. D., "Yeast surface display for directed evolution of protein expression, affinity, and stability," Methods Enzymol 328:430-444, Elsevier, Netherlands (2000).
Brennan, M., et al., "Preparation of bispecific antibodies by chemical recombination of monoclonal immunoglobulin G1 fragments," Science 229(4708):81-83, American Association for the Advancement of Science, United States (Jul. 1985).
Brinkmann, U., et al., "Phage Display of Disulfide-stabilized Fv Fragments," Journal of Immunological Methods 182(1):41-50, Elsevier, Netherlands (May 1995).
Brown, J. A., et al., "Blockade of programmed death-1 ligands on dendritic cells enhances T cell activation and cytokine production," J Immunol 170(3): 1257-1266, American Association of Immunologists, United States (Feb. 2003).
Burton, D. R. and Barbas, C. F. 3rd., "Human Antibodies From Combinatorial Libraries," Advances in Immunology 57:191-280, Academic Press, United States (Aug. 1993).
Canfield, S. M., and Morrison, S. L., "The binding affinity of human IgG for its high affinity Fc receptor is determined by multiple amino acids in the CH2 domain and is modulated by the hinge region," J Exp Med 173(6):1483-1491, Rockefeller University Press, United States (Jun. 1991).
Caron, P. C., et al., "Engineered humanized dimeric forms of IgG are more effective antibodies," J Exp Med 176(4):1191-1195, Rockefeller University Press, United States (Oct. 1992).
Cassol, S., et al., "Stability of dried blood spot specimens for detection of human immunodeficiency virus DNA by polymerase chain reaction," J Clin Microbiol 30(12):3039-3042, American Society for Microbiology, United States (Dec. 1992).
Chasteen, L., et al., "Eliminating helper phage from phage display," Nucleic Acids Res 34(21):e145, Oxford University Press, United Kingdom (Nov. 2006).
Chen, D. S., and Mellman, I., "Oncology meets immunology: the cancer-immunity cycle," Immunity 39(1):1-10, Cell Press, United States (Jul. 2013).
Cheung, R. C., et al., "Epitope-specific antibody response to the surface antigen of duck hepatitis B virus in infected ducks," Virology 176(2):546-552, BioMed Central Ltd, United States (Jun. 1990).
Co, M. S., et al., "Genetically engineered deglycosylation of the variable domain increases the affinity of ananti-CD33 monoclonal antibody," Mol Immunol 30(15):1361-1367, Pergamon Press, United Kingdom (Oct. 1993).
Cornelis, P., "Expressing genes in different *Escherichia coli* compartments," Curr Opin Biotechnol 11(5):450-454, Elsevier, Netherlands (Oct. 2000).
Deans, R. J., et al., "Expression of an immunoglobulin heavy chain gene transfected into lymphocytes," Proc Natl Acad Sci USA 81(5):1292-1296, National Academy of Science, United States (Mar. 1984).
Di Niro, R., et al., "Characterizing monoclonal antibody epitopes by filtered gene fragment phage display," Biochem J 388(Pt 3):889-894, Portland Press, United States (Jun. 2005).
Dong, H., et al., "Tumor-associated B7-H1 promotes T-cell apoptosis: a potential mechanism of immune evasion," Nat Med 8(8):793-800, Nature Publishing Group, United Kingdom (published online Jun. 2002, published in print Aug. 2002).
Dong, H., and Chen, L., "B7-H1 pathway and its role in the evasion of tumor immunity," J Mol Med (Berl) 81(5):281-287, Springer Science+Business Media, Germany (published online Apr. 2003, published in print May 2003).
Duncan, A. R., and Winter, G., "The binding site for Clq on IgG," Nature 332(6166):738-740, Nature Publishing Group, United Kingdom (Apr. 1988).
Engberg, J., et al., "Phage-display libraries of murine and human antibody Fab fragments," Methods Mol Biol 51:355-376, Humana Press, United States (1995).
Eppstein, D. A., et al., "Biological activity of liposome-encapsulated murine interferon gamma is mediated by a cell membrane receptor," Proc Natl Acad Sci USA 82(11):3688-3692, National Academy of Science, United States (Jun. 1985).
Estep, P., et al., "High throughput solution-based measurement of antibody-antigen affinity and epitope binning," mAbs 5(2):270-278, Landes Bioscience, United States (Mar-Apr. 2013).
Etz, H., et al., "Bacterial phage receptors, versatile tools for display of polypeptides on the cell surface," J Bacteriol 183(23):6924-6935, American Society for Microbiology, United States (Dec. 2001).
Fabbi, M., et al., "Dual Roles of IL-27 in Cancer Biology and Immunotherapy," Mediators of Inflammation 2017:3958069, Hindawi Publishing Corporation, United States (Feb. 2017).
Fergusson, J. R., et al., "CD161 defines a transcriptional and functional phenotype across distinct human T cell lineages," Cell Rep 9(3): 1075-1088, Cell Press, United States (published online Oct. 2014, published in print Nov. 2014).
Freeman, G. J., et al., "Protect the killer: CTLs need defenses against the tumor," Nat Med 8(8):787-789, Nature Publishing Group, United Kingdom (Aug. 2002).
Fursov, N., et al., "Development and utilization of activated STAT3 detection assays for screening a library of secreted proteins," Assay Drug Dev Technol 9(4):420-429, Mary Ann Liebert Inc., United States (published online Feb. 2011, published in print Aug. 2011).
Gao, Q., et al., "Overexpression of PD-L1 significantly associates with tumor aggressiveness and postoperative recurrence in human hepatocellular carcinoma," Clin Cancer Res 15(3):971-979, American Association for Cancer Research, United States (Feb. 2009).
Genbank, "hPD-1 [*Homo sapiens*]," Accession No. AAC51773.1, accessed at https://www.ncbi.nlm.nih.gov/protein/AAC51773, accessed on Aug. 23, 2021, 2 pages.
Genbank, "interleukin-6 receptor subunit beta isoform 1 precursor [*Homo sapiens*]," _ccession No. NP_002175.2, accessed at https://www.ncbi.nlm.nih.gov/protein/NP_002175.2 on Aug. 24, 2021, 5 pages.
Genbank, "interleukin-27 receptor subunit alpha precursor [*Homo sapiens*]," Accession No. NP_004834.1, accessed at https://www.ncbi.nlm.nih.gov/protein/NP_004834.1 on Aug. 24, 2021, 4 pages.
Genbank, "interleukin-27 subunit beta precursor [*Homo sapiens*]," Accession No. NP_005746.2, accessed at https://www.ncbi.nlm.nih.gov/protein/NP_005746.2 on Aug. 24, 2021, 3 pages.
Genbank, "interleukin-27 subunit alpha precursor [*Homo sapiens*]," Accession No. NP_663634.2, accessed at https://www.ncbi.nlm.nih.gov/protein/NP_663634.2 on Aug. 24, 2021, 3 pages.
Genbank, "stimulator of interferon genes protein isoform 2 [*Homo sapiens*]," Accession No. NP_001288667.1, accessed at https://www.ncbi.nlm.nih.gov/protein/NP_001288667.1/ on Aug. 24, 2021, 3 pages.
Genbank, "Programmed cell death 1 ligand 1," Accession No. Q9NZQ7, accessed at https://www.ncbi.nlm.nih.gov/protein/Q9NZQ7 on Sep. 16, 2020, 8 pages.
Ghebeh, H., et al., "The B7-H1 (PD-L1) T lymphocyte-inhibitory molecule is expressed in breast cancer patients with infiltrating ductal carcinoma: correlation with important high-risk prognostic factors," Neoplasia 8(3): 190-198, Neoplasia Press, United States (Mar. 2006).
Grabherr, R., and Ernst, W., "The baculovirus expression system as a tool for generating diversity by viral surface display," Combinatorial Chemistry & High Throughput Screening 4(2):185-192, Bentham Science Publishers B.V., United Arab Emirates (Apr. 2001).
Gruber, M., et al., "Efficient tumor cell lysis mediated by a bispecific single chain antibody expressed in *Escherichia coli*," J Immunol 152(11):5368-5374, American Association of Immunologists, United States (Jun. 1994).
Gupta, R. K., and Siber, G. R., "Adjuvants for human vaccines—current status, problems and future prospects," Vaccine 13(14): 1263-1276, Elsevier, Netherlands (Oct. 1995).

(56) References Cited

OTHER PUBLICATIONS

Hamanishi, J., et al., "Programmed cell death 1 ligand 1 and tumor-infiltrating CD8+ T lymphocytes are prognostic factors of human ovarian cancer," Proc Natl Acad Sci USA 104(9):3360-3365, National Academy of Science, United States (Feb. 2007).
Hanahan, D., and Weinberg, R. A., "Hallmarks of cancer: the next generation," Cell 144(5):646-674, Cell Press, United States (Mar. 2011).
Hanauske, A-R., et al., "Phase lb dose escalation study of erlotinib in combination with infusional 5-Fluorouracil, leucovorin, and oxaliplatin in patients with advanced solid tumors," Clin Cancer Res 13(2 Pt 1):523-531, American Association for Cancer Research, United States (Jan. 2007).
Hanes, J., et al., "Picomolar affinity antibodies from a fully synthetic naive library selected and evolved by ribosome display," Nat Biotechnol 18(12): 1287-1292, Nature Publishing Group, United Kingdom (Dec. 2000).
Harding, F. A., and Lonberg, N., "Class switching in human immunoglobulin transgenic mice," Annals of the New York Academy of Sciences 764:536-546, Wiley-Blackwell on behalf of the New York Academy of Sciences, United States (Sep. 1995).
Hetherington, S., et al., "Phase I dose escalation study to evaluate the safety and pharmacokinetic profile of tefibazumab in subjects with end-stage renal disease requiring hemodialysis," Antimicrobial Agents and Chemotherapy 50(10):3499-3500, American Society for Microbiology, United States (Oct. 2006).
Hino, R., et al., "Tumor cell expression of programmed cell death-1 ligand 1 is a prognostic factor for malignant melanoma," Cancer 116(7): 1757-1766, John Wiley and Sons Inc., United States (Apr. 2010).
Hisada, M., et al., "Potent antitumor activity of interleukin-27," Cancer Res 64(3):1152-1156, American Association for Cancer Research Inc., United States (Feb. 2004).
Holliger, P., et al., ""Diabodies": small bivalent and bispecific antibody fragments," Proc Natl Acad Sci USA 90(14):6444-6448, National Academy of Science, United States (Jul. 1993).
Hoogenboom, H. R., "Designing and optimizing library selection strategies for generating high-affinity antibodies," Trends Biotechnol 15(2):62-70, Cell Press, United States (Feb. 1997).
Hou, J., and Zhan, H., "Expression of active thrombopoietin and identification of its key residues responsible for receptor binding," Cytokine 10(5):319-330, Elsevier, Netherlands (May 1998).
Houdebine, L. M., "Antibody manufacture in transgenic animals and comparisons with other systems," Curr Opin Biotechnol 13(6):625-629, Elsevier, Netherlands (Dec. 2002).
Hudson, P. J., and Kortt, A. A., "High avidity scFv multimers; diabodies and triabodies," J Immunol Methods 231(1-2): 177-189, Elsevier, Netherlands (Dec. 1999).
Inman, B. A., et al., "PD-L1 (B7-H1) expression by urothelial carcinoma of the bladder and BCG-induced granulomata: associations with localized stage progression," Cancer 109(8): 1499-1505, John Wiley and Sons Inc., United States (Apr. 2007).
Irizarry, R. A., et al., "Exploration, normalization, and summaries of high density oligonucleotide array probe level data," Biostatistics 4(2):249-264, Oxford University Press, United Kingdom (Apr. 2003).
Ishida, Y., et al., "Induced expression of PD-1, a novel member of the immunoglobulin gene superfamily, upon programmed cell death," The EMBO Journal 11(11):3887-3895, European Molecular Biology Organization Press, Germany (Nov. 1992).
Isner, J. M., and Asahara, T., "Angiogenesis and vasculogenesis as therapeutic strategies for postnatal neovascularization," J Clin Invest 103(9): 1231-1236, American Society for Clinical Investigation, United States (May 1999).
Iwai, Y., et al., "Involvement of PD-L1 on tumor cells in the escape from host immune system and tumor immunotherapy by PD-L1 blockade," Proc Natl Acad Sci USA 99(19):12293-12297, National Academy of Sciences, United States (Sep. 2002).
Jankowski, M., et al., "Interleukin-27: biological properties and clinical application," Arch Immunol Ther Exp (Warsz) 58(6):417-425, Springer Nature, Switzerland (published online Sep. 2010, published in print Dec. 2010).
Johnson, D. A., et al., "3-O-Desacyl monophosphoryl lipid A derivatives: synthesis and immuno stimulant activities," J Med Chem 42(22):4640-4649, American Chemical Society, United States (Nov. 1999).
Kaszubska, W., et al., "Expression, purification, and characterization of human recombinant thrombopoietin in Chinese hamster ovary cells," Protein Expr Purif 18(2):213-220, Elsevier, Netherlands (Mar. 2000).
Kettleborough, C. A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (Apr. 1994).
Kieke, M. C., et al., "Isolation of anti-T cell receptor scFv mutants by yeast surface display," Protein Eng 10(11):1303-1310, Oxford University Press, United Kingdom (Nov. 1997).
Kim, S., et al., "Regulation of angiogenesis in vivo by ligation of integrin alpha5beta1 with the central cell-binding domain of fibronectin," Am J Pathol 156(4): 1345-1362, Elsevier, Netherlands (Apr. 2000).
Kim, S., et al., "Regulation of integrin alpha vbeta 3-mediated endothelial cell migration and angiogenesis by integrin alpha5beta1 and protein kinase A," J Biol Chem 275(43):33920-33928, Elsevier, Netherlands (Oct. 2000).
Kinstler, O., et al., "Mono-N-temunal poly (ethylene glycol)-protein conjugates," Adv Drug Deliv Rev 54(4):477-485, Elsevier, Netherlands (Jun. 2002).
Kirkland, T. N., et al., "Analysis of the fine specificity and cross-reactivity of monoclonal anti-lipid A antibodies," J Immunol 137(11):3614-3619, American Association of Immunologists, United States (Dec. 1986).
Kitano, A., et al., "Tumour-infiltrating lymphocytes are correlated with higher expression levels of PD-1 and PD-L1 in early breast cancer," ESMO Open 2(2):e000150, Elsevier, Netherlands (May 2017).
Kleffel, S., et al., "Melanoma Cell-Intrinsic PD-1 Receptor Functions Promote Tumor Growth," Cell 162(6): 1242-1256, Cell Press, United States (Sep. 2015).
Klemm, P., and Schembri, M. A., "Fimbrial surface display systems in bacteria: from vaccines to random libraries," Microbiology (Reading) 146 (Pt 12):3025-3032, Microbiology Society, United States (Dec. 2000).
Konishi, J., et al., "B7-H1 expression on non-small cell lung cancer cells and its relationship with tumor-infiltrating lymphocytes and their PD-1 expression," Clin Cancer Res 10(15):5094-5100, American Association for Cancer Research, United States (Aug. 2004).
Kostelny, S. A., et al., "Formation of a bispecific antibody by the use of leucine zippers," J Immunol 148(5):1547-1553, American Association of Immunologists, United States (Mar. 1992).
Langer, R., "Biocompatibility of polymeric delivery systems for macromolecules," Journal of Biomedical Materials Research 15(2):267-277, Heterocorporation, United States (Mar. 1981).
Langer, R., "Controlled release of macromolecules," Chem. Tech 12(2):98-105, American Chemical Society, United States (Feb. 1982).
Lee, L. S., et al., "Prolonged circulating lives of single-chain Fv proteins conjugated with polyethylene glycol: a comparison of conjugation chemistries and compounds," Bioconjug Chem 10(6):973-981, American Chemical Society, United States (Nov.-Dec. 1999).
Liu, L., et al., "IL-27-mediated activation of natural killer cells and inflammation produced antitumour effects for human oesophageal carcinoma cells," Scandinavian Journal of Immunology 68(1):22-29, Wiley-Blackwell Publishing Ltd., United Kingdom (published online May 2008, published in print Jul. 2008).
Lodmell, D. L., et al., "DNA vaccination of mice against rabies virus: effects of the route of vaccination and the adjuvant monophosphoryl lipid A (MPL)," Vaccine 18(11-12):1059-1066, Elsevier, Netherlands (Jan. 2000).

(56) References Cited

OTHER PUBLICATIONS

Lonberg, N., et al., "Antigen-specific human antibodies from mice comprising four distinct genetic modifications," Nature 368(6474):856-859, Nature Publishing Group, United Kingdom (Apr. 1994).
Lonberg, N., "Transgenic approaches to human monoclonal antibodies," in Handbook of Experimental Pharmacology, The Pharmacology of Monoclonal Antibodies, vol. 113, pp. 49-101, Rosenberg, M., et al., eds., Springer-Verlag Berlin Heidelberg, Germany (1994).
Lonberg, N., and Huszar, D., "Human antibodies from transgenic mice," International Reviews of Immunology 13(1):65-93, Informa Healthcare, United Kingdom (Jan. 1995).
Lonberg, N., "Human antibodies from transgenic animals," Nat Biotechnol 23(9):1117-1125, Nature Publishing Group, United Kingdom (Sep. 2005).
Lusky, M., and Botchan, M., "Inhibition of SV40 replication in simian cells by specific pBR322 DNA sequences," Nature 293(5827):79-81, Nature Publishing Group, United Kingdom (Sep. 1981).
Merz, D. C., et al., "Generating a phage display antibody library against an identified neuron," J Neurosci Methods 62(1-2):213-219, Elsevier, Netherlands (Nov. 1995).
Milstein, C., and Cuello, A. C., "Hybrid hybridomas and their use in immunohistochemistry," Nature 305(5934):537-540, Nature Publishing Group, United Kingdom (Oct. 1983).
Moldenhauer, G., et al., "Identity of HML-1 antigen on intestinal intraepithelial T cells and of B-ly7 antigen on hairy cell leukaemia," Scandinavian Journal of Immunology 32(2):77-82, Blackwell Scientific Publications, United Kingdom (Aug. 1990).
Morel, G. A., et al., "Monoclonal antibodies to bovine serum albumin: affinity and specificity determinations," Molecular Immunology 25(1):7-15, Pergamon Press, United Kingdom (Jan. 1988).
Motz, G. T., and Coukos, G., "Deciphering and reversing tumor immune suppression," Immunity 39(1):61-73, Cell Press, United States (Jul. 2013).
Mueller, J. P., et al., "Humanized porcine VCAM-specific monoclonal antibodies with chimeric IgG2/G4 constant regions block human leukocyte binding to porcine endothelial cells," Mol Immunol 34(6):441-452, Elsevier, Netherlands (Apr. 1997).
Mulligan, R. C., and Berg, P., "Selection for animal cells that express the *Escherichia coli* gene coding for xanthine-guanine phosphoribosyltransferase," Proc Natl Acad Sci USA 78(4):2072-2076, National Academy of Sciences, United States (Apr. 1981).
Muyldermans, S., et al., "Recognition of antigens by single-domain antibody fragments: the superfluous luxury of paired domains," Trends Biochem Sci 26(4):230-235, Cell Press, United States (Apr. 2001).
Myers, E. W., and Miller, W., "Optimal alignments in linear space," Comput Appl Biosci 4(1):11-17, IRL Press Ltd., United Kingdom (Mar. 1988).
Nakanishi, J., et al., "Overexpression of B7-H1 (PD-L1) significantly associates with tumor grade and postoperative prognosis in human urothelial cancers," Cancer Immunol Immunother 56(8):1173-1182, Springer Science+Business Media, Germany (published online Dec. 2006, published in print Aug. 2007).
Needleman, S.B., and Wunsch, C. D., "A general method applicable to the search for similarities in the amino acid sequence of two proteins," Journal of Molecular Biology 48(3):443-453, American Society for Biochemistry and Molecular Biology Inc., United States (Mar. 1970).
Nuttall, S. D., et al., "Immunoglobulin VH domains and beyond: design and selection of single-domain binding and targeting reagents," Current Pharmaceutical Biotechnology 1(3):253-263, Bentham Science Publishers B.V., United Arab Emirates (Nov. 2000).
Ohigashi, Y., et al., "Clinical significance of programmed death-1 ligand-1 and programmed death-1 ligand-2 expression in human esophageal cancer," Clin Cancer Res 11(8):2947-2953, American Association for Cancer Research, United States (Apr. 2005).
Ohtsuka, E., et al., "An alternative approach to deoxyoligonucleotides as hybridization probes by insertion of deoxyinosine at ambiguous codon positions," J Biol Chem 260(5):2605-2608, Elsevier, Netherlands (Mar. 1985).
Paolino, M., and Penninger, J. M., "The Role of TAM Family Receptors in Immune Cell Function: Implications for Cancer Therapy," Cancers 8(10):97, MDPI, Switzerland (Oct. 2016).
Pavisic, R., et al., "Recombinant human granulocyte colony stimulating factor pre-screening and screening of stabilizing carbohydrates and polyols," Int J Pharm 387(1-2): 110-119, Elsevier, Netherlands (published online Dec. 2009, published in print Mar. 2010).
Pearson, W.R., and Lipman, D.J., "Improved tools for biological sequence comparison," Proceedings of the National Academy of Sciences 85(8):2444-2448, National Academy of Sciences, United States (Apr. 1988).
Pereboev, A., et al., "Phage display of adenovirus type 5 fiber knob as a tool for specific ligand selection and validation," J Virol 75(15):7107-7113, American Society for Microbiology, United States (Aug. 2001).
Persic, L., et al., "An Integrated Vector System for the Eukaryotic Expression of Antibodies or Their Fragments After Selection From Phage Display Libraries," Gene 187( 1):9-18, Elsevier/North-Holland, Netherlands (Mar. 1997).
Poljak, R. J., "Production and structure of diabodies," Structure 2(12):1121-1123, Cell Press, United States (Dec. 1994).
Pollock, D. P., et al., "Transgenic milk as a method for the production of recombinant antibodies," J Immunol Methods 231(1-2):147-157, Elsevier, Netherlands (Dec. 1999).
Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).
Roberts, M. J., et al., "Chemistry for peptide and protein PEGylation," Adv Drug Deliv Rev 54(4):459-476, Elsevier, Netherlands (Jun. 2002).
Rogers, B. E., et al., "Localization of iodine-125-mIP-Des-Met14-bombesin (7-13)NH2 in ovarian carcinoma induced to express the gastrin releasing peptide receptor by adenoviral vector-mediated gene transfer," The Journal of Nuclear Medicine 38(8):1221-1229, Society of Nuclear Medicine and Molecular Imaging, United States (Aug. 1997).
Rondon, I. J., and Marasco, W. A., "Intracellular antibodies (intrabodies) for gene therapy of infectious diseases," Annual Review of Microbiology 51:257-283, Annual Reviews Inc., United States (1997).
Rossolini, G. M., et al., "Use of deoxyinosine-containing primers vs degenerate primers for polymerase chain reaction based on ambiguous sequence information," Mol Cell Probes 8(2):91-98, Elsevier, Netherlands (Apr. 1994).
Sarver, N., et al., "Transformation and replication in mouse cells of a bovine papillomavirus—pML2 plasmid vector that can be rescued in bacteria," Proc Natl Acad Sci USA 79(23):7147-7151, National Academy of Sciences, United States (Dec. 1982).
Sauer, K. A., et al., "Immunosurveillance of lung melanoma metastasis in EBI-3-deficient mice mediated by CD8+ T cells," J Immunol 181(9):6148-6157, American Association of Immunologists, United States (Nov. 2008).
Schaffitzel, C., et al., "Ribosome display: an in vitro method for selection and evolution of antibodies from libraries," J Immunol Methods 231(1-2):119-135, Elsever, Netherlands (Dec. 1999).
Schoonbroodt, S., et al., "Oligonucleotide-assisted cleavage and ligation: a novel directional DNA cloning technology to capture cDNAs. Application in the construction of a human immune antibody phage-display library," Nucleic Acids Res 33(9):e81, Oxford University Press, United Kingdom (May 2005).
Shalaby, M. R., et al., "Development of humanized bispecific antibodies reactive with cytotoxic lymphocytes and tumor cells overexpressing the HER2 protooncogene," J Exp Med 175(1):217-225, Rockefeller University Press, United States (Jan. 1992).
Shi, L., et al., "De novo selection of high-affinity antibodies from synthetic fab libraries displayed on phage as pIX fusion proteins," J Mol Biol 397(2):385-396, Elsevier, Netherlands (published online Jan. 2010, published in print Mar. 2010).
Shimauchi, T., et al., "Augmented expression of programmed death-1 in both neoplastic and non-neoplastic CD4+ T-cells in adult T-cell leukemia/lymphoma," Int J Cancer 121(12):2585-2590, John

(56) References Cited

OTHER PUBLICATIONS

Wiley & Sons on behalf of the Union for International Cancer Control, United States (Dec. 2007).
Shimizu, M., et al., "Antiangiogenic and antitumor activities of IL-27," J Immunol 176(12):7317-7324, American Association of Immunologists, United States (Jun. 2006).
Shiraishi, M., et al., "Short-step chemical synthesis of DNA by use of MMTrS group for protection of 5'-hydroxyl group," Nucleic Acids Symposium Series (Oxf) 51:129-130, Oxford University Press, United Kingdom (Nov. 2007).
Shopes, B., "A genetically engineered human IgG mutant with enhanced cytolytic activity," J Immunol 148(9):2918-2922, American Association of Immunologists, United States (May 1992).
Sidman, K. R., et al., "Controlled release of macromolecules and pharmaceuticals from synthetic polypeptides based on glutamic acid," Biopolymers 22(1):547-556, John Wiley and Sons Inc., United States (Jan. 1983).
Siegel, R. W., et al., "High efficiency recovery and epitope-specific sorting of an scFv yeast display library," J Immunol Methods 286(1-2):141-153, Elsevier, Netherlands (Mar. 2004).
Smith, T.F., and Waterman, M.S., "Comparison of biosequences," Advances in Applied Mathematics 2(4):482-498, Academic Press Inc., United States (1981).
Songsivilai, S. and Lachmann, P.J., "Bispecific Antibody: A Tool for Diagnosis and Treatment of Disease," Clinical and Experimental Immunology 79(3):315-321, Blackwell Scientific Publications, United Kingdom (Mar. 1990).
Southern, P. J., and Berg, P., "Transformation of mammalian cells to antibiotic resistance with a bacterial gene under control of the SV40 early region promoter," Journal of Applied Genetics 1(4):327-341, Springer, Germany (Jan. 1982).
Stahli, C., et al., "Distinction of epitopes by monoclonal antibodies," Methods in Enzymology 92:242-253, Academic Press, United States (1983).
Suresh, M. R., et al., "Bispecific monoclonal antibodies from hybrid hybridomas," Methods in Enzymology 121:210-228, Academic Press, United States (1986).
Takahashi, T., et al., "Ischemia- and cytokine-induced mobilization of bone marrow-derived endothelial progenitor cells for neovascularization," Nat Med 5(4):434-438, Nature Publishing Group, United Kingdom (Apr. 1999).
Thompson, R. H., and Kwon, E. D., "Significance of B7-H1 overexpression in kidney cancer," Clin Genitourin Cancer 5(3):206-211, Elsevier, Netherlands (Dec. 2006).
Tochizawa, S., et al., "A novel modification of a flow cytometric assay of phosphorylated STAT1 in whole blood lymphocytes for rapid detection of interferon-alpha signal in vivo," J Immunol Methods 313(1-2):29-37, Elsevier, Netherlands (published online May 2006, published in print Jun. 2006).
Todorovska, A., et al., "Design and application of diabodies, triabodies and tetrabodies for cancer targeting," J Immunol Methods 248(1-2):47-66, Elsevier, Netherlands (Feb. 2001).
Tutt, A., et al., "Trispecific F(ab')3 derivatives that use cooperative signaling via the TCR/CD3 complex and CD2 to activate and redirect resting cytotoxic T cells," J Immunol 147(1):60-69, American Association of Immunologists, United States (Jul. 1991).
UniProtKB, T-cell immunoreceptor with Ig and ITIM domains, Accession No. Q495A1, accessed at https://www.uniprot.org/uniprot/Q495A1, accessed on Aug. 23, 2021, 12 pages.
Van Gurp, E., et al., "Phase 1 dose-escalation study of CP-690 550 in stable renal allograft recipients: preliminary findings of safety, tolerability, effects on lymphocyte subsets and pharmacokinetics," American Journal of Transplantation 8(8):1711-1718, Wiley-Blackwell on behalf of the American Society of Transplant Surgeons and the American Society of Transplantation, United States (published online Jun. 2008, published in print Aug. 2008).
Van Kuik-Romeijn, P., et al., "Expression of a functional mouse-human chimeric anti-CD19 antibody in the milk of transgenic mice," Transgenic Research 9(2):155-159, Springer, Switzerland (Apr. 2000).
Varner, J. A., et al., "Inhibition of angiogenesis and tumor growth by murine 7E3, the parent antibody of c7E3 Fab (abciximab; ReoPro)," Angiogenesis 3(1):53-60, Springer, Netherlands (1999).
Wigler, M., et al., "Transformation of mammalian cells with genes from procaryotes and eucaryotes," Cell 16(4):777-785, Cell Press, United States (Apr. 1979).
Wright, A., et al., "Antibody variable region glycosylation: position effects on antigen binding and carbohydrate structure," EMBO J 10(10):2717-2723, European Molecular Biology Organization Press, Germany (Oct. 1991).
Wu, C., et al., "Simultaneous targeting of multiple disease mediators by a dual-variable-domain immunoglobulin," Nat Biotechnol 25(11):1290-1297, Nature Publishing Group, United Kingdom (published online Oct. 2007, published in print Nov. 2007).
Xu, Y., et al., "Addressing polyspecificity of antibodies selected from an in vitro yeast presentation system: a FACS-based, high-throughput selection and analytical tool," Protein Eng Des Sel 26(10):663-670, Oxford University Press, United Kingdom (published online Sep. 2013, published in print Oct. 2013).
Yang, W., et al., "PD-L1: PD-1 interaction contributes to the functional suppression of T-cell responses to human uveal melanoma cells in vitro," Investigative Ophthalmology & Visual Science 49(6):2518-2525, Association for Research in Vision and Ophthalmology, United States (published online Feb. 2008, published in print Jun. 2008).
Yeung, Y. A., and Wittrup, K. D., "Quantitative screening of yeast surface-displayed polypeptide libraries by magnetic bead capture," Biotechnology Progress 18(2):212-220, Wiley-Blackwell, United States (Mar-Apr. 2002).
Zapata, G., et al., "Engineering linear F(ab')2 fragments for efficient production in *Escherichia coli* and enhanced antiproliferative activity," Protein Engineering 8(10):1057-1062, Oxford University Press, United Kingdom (Oct. 1995).
Zhan, M-M., et al., "From monoclonal antibodies to small molecules: the development of inhibitors targeting the PD-1/PD-L1 pathway," DrugDiscov Today 21(6):1027-1036, Elsevier, Netherlands (published online Apr. 2016, published in print Jun. 2016).
Michael, S. I., et al., "Addition of a short peptide ligand to the adenovirus fiber protein," Gene Therapy 2(9):660-668, Nature Publishing Group, United Kingdom (1995).
Chaouat, G., et al., "Early Regulators in abortion and implications for a preeclampsia model," Journal of Reproductive Immunology 82(2):131-140, Elsevier Science Ireland, Ireland (Oct. 2009).
Xu, F., et al., "IL-27 is Elevated in Acute Lung Injury and Mediates Inflammation," Journal of Clinical Immunology: 1257-1268, Kluwer Academic Publishers, United States (Jul. 2013).
Yoshimoto, T., et al., "Potential Clinical application of interleukin-27 an antitumor agent," Cancer Science 106(9):1103-1110, Wiley Online Library, United States (Sep. 2015).

| Antibody | Forte Bio Affinity (IgG KD Human IL-27 Monovalent Pseudo-avidity) | MSD Affinity |
|---|---|---|
| SRF405 | 2.32E-10 | 1.00E-10 |
| SRF411 | 1.60E-09 | 4.30E-10 |
| SRF410 | 1.90E-09 | 3.90E-10 |
| SRF557 | 2.82E-10 | NA |
| SRF536 | 4.61E-10 | 4.80E-11 |
| SRF416 | 1.95E-10 | 1.30E-10 |
| SRF543 | 2.12E-10 | 2.60E-11 |
| SRF414 | 2.63E-10 | 5.20E-10 |
| SRF382 | 5.94E-10 | 1.30E-12 |
| SRF529 | 3.93E-10 | 5.90E-12 |
| SRF381 | 3.02E-10 | 2.80E-12 |
| SRF384 | 2.50E-09 | 7.50E-12 |
| SRF386 | 4.05E-10 | 2.40E-12 |
| SRF388 | 1.75E-09 | 3.40E-12 |
| Ab7 | NA | NA |

FIG. 1

| | (i) | | (ii) | (iii) | (iv) | (v) | (vi) |
|---|---|---|---|---|---|---|---|
| Antibody | Affinity hIL-27 (M) | Affinity mIL-27 (M) | WSX-1 competitive | Inhibition of pSTAT1 U937 | Inhibition of CD161 | Inhibition of PD-L1 in CD4 T cells | Enhances PD-1-mediated cytokine secretion |
| Ab7 | 1.00E-09 | N.B. | Yes | Yes | Yes | Yes | Not tested |
| 8B11 | N/A | N.B. | Binds WSX-1 | Yes | Yes | Yes | Not tested |
| SRF557 | 2.20E-09 | N.B. | No | No | No | No | Not tested |
| SRF536 | 4.80E-11 | 8.05E-08 | Yes | Yes | Yes | Yes | No |
| SRF416 | 1.30E-10 | N.B. | Yes | Yes | Yes | Yes | Not tested |
| SRF543 | 2.60E-11 | 6.21E-08 | Yes | Yes | Yes | Yes | Not tested |
| SRF414 | 5.20E-10 | P.F. | Yes | Yes | No | Yes | Not tested |
| SRF529 | 5.90E-12 | 1.33E-09 | Yes | Yes | Yes | Yes | Not tested |
| SRF381 | 2.80E-12 | 4.56E-10 | Yes | Yes | Yes | Yes | Yes |
| SRF388 | 1.30E-12 | 5.94E-10 | Yes | Yes | Yes | Yes | Yes |
| SRF382 | 7.50E-12 | 2.50E-09 | Yes | Yes | Yes | Yes | Not tested |
| SRF384 | 2.40E-12 | 4.05E-10 | Yes | Yes | Yes | Yes | Not tested |
| SRF386 | 3.40E-12 | 1.75E-09 | Yes | Yes | Yes | Yes | Not tested |
| SRF410 | 3.90E-10 | 5.81E-09 | No | Yes | No | No | Not tested |
| SRF411 | 4.30E-10 | 5.46E-10 | No | Yes | No | No | Not tested |
| SRF405 | 1.00E-10 | 5.02E-09 | No | Yes | No | No | Not tested |
| SRF573 | 7.40E-10 | N.B. | No | Yes | Yes | No | Not tested |
| SRF605 | P.F. | P.F. | No | No | No | No | Not tested |
| SRF535 | 1.15E-08 | N.B. | Yes | Yes | No | Yes | Not tested |
| SRF538 | 8.93E-09 | 1.82E-07 | Yes | Yes | No | No | Not tested |
| SRF541 | 9.44E-08 | N.B. | No | No | No | No | Not tested |
| SRF583 | 1.98E-09 | N.B. | No | No | Yes | No | Not tested |

FIG. 9

| Property | | |
|---|---|---|
| | | N.B. = non-binder |
| (i) | binds to human IL-27 with an equilibrium dissociation constant (KD) of 15 nM or less; | P.F. = poor fit |
| (ii) | blocks binding of IL-27 to IL-27 receptor; | |
| (iii) | inhibits or reduces STAT1 and/or STAT3 phosphorylation in a cell; | |
| (iv) | inhibits or reduces IL-27-mediated inhibition of CD161 expression in a cell; | |
| (v) | inhibits or reduces IL-27-mediated PD-L1 and/or TIM-3 expression in a cell; and | |
| (vi) | induces or enhances PD-1-mediated secretion of one or more cytokines from a cell. | |

FIG. 9 continued

| Name | VH FR1 | SEQ ID | VH CDR1 | SEQ ID | VH FR2 | SEQ ID | VH CDR2 | SEQ ID |
|---|---|---|---|---|---|---|---|---|
| SRF405 | QVQLVQSGAEVKKPGSSVKVSCKASG | 477 | GTF**VG**YAIS | 483 | WVRQAPGQGLEWMG | 499 | GIIPIFG**I**ANYAQKFQG | 504 |
| SRF410 | QVQLVQSGAEVKKPGSSVKVSCKASG | 477 | GTFS**A**YAIS | 484 | WVRQAPGQGLEWMG | 499 | GIIPIFGTANYAQKFQG | 505 |
| SRF411 | QVQLVQSGAEVKKPGSSVKVSCKASG | 477 | GTF**E**SY**T**IS | 485 | WVRQAPGQGLEWMG | 499 | GI**A**PIFGTA**H**YAQKFQG | 506 |
| SRF557 | QVQLVQSGAEVKKPGSSVKVSCKASG | 477 | GTFSSYAIS | 486 | WVRQAPGQGLEWMG | 499 | GIIPIFGTANYAQKFQG | 507 |
| SRF536 | QVQLQQWGAGLLKPSETLSLTCAVYG | 478 | GSFS**E**YYW**A** | 487 | WIRQPPGKGLEWIG | 500 | EI**DEV**GSTNYNPSLKS | 508 |
| SRF414 | QVQLQQWGAGLLKPSETLSLTCAVYG | 478 | GSFS**R**YYWS | 488 | WIRQPPGKGLEWIG | 500 | **S**I**DY**SGST**E**YNPSLKS | 509 |
| SRF416 | QVQLQQWGAGLLKPSETLSLTCAVYG | 478 | GSFSGYYWS | 489 | WIRQPPGKGLEWIG | 500 | EI**DVD**GSTNYNPSLKS | 510 |
| SRF529 | EVQLVESGGGLVKPGGSLRLSCAASG | 479 | FTFSSYSMN | 490 | WVRQAPGKGLEWVS | 501 | SISSSSSYIYYADSVKG | 511 |
| SRF381 | EVQLVESGGGLVKPGGSLRLSCAASG | 479 | FTF**R**SY**G**MN | 491 | WVRQAPGKGLEWVS | 501 | SISSSSSYIYYADSVKG | 511 |
| SRF382 | EVQLVESGGGLVKPGGSLRLSCAASG | 479 | FTFS**RTG**MN | 492 | WVRQAPGKGLEWVS | 501 | SISSSSSYIYYADSVKG | 511 |
| SRF384 | EVQLVESGGGLVKPGGSLRLSCAASG | 479 | FTFS**R**Y**G**MN | 493 | WVRQAPGKGLEWVS | 501 | SISSSS**A**YI**L**YADSVKG | 512 |
| SRF386 | EVQLVESGGGLVKPGGSLRLSCAASG | 479 | FTF**A**SY**G**MN | 494 | WVRQAPGKGLEWVS | 501 | SISSSSSYIYYADSVKG | 511 |
| SRF388 | EVQLVESGGGLVKPGGSLRLSCAASG | 479 | FTF**R**SY**G**MN | 495 | WVRQAPGKGLEWVS | 501 | **G**ISSS**G**SYIYYADSVKG | 513 |
| SRF535 | EVQLVESGGGLVQPGGSLRLSCAASG | 480 | FTFSSY**G**MS | 496 | WVRQAPGKGLEWVA | 502 | NIKQDGSEKYYVDSVKG | 514 |
| SRF538 | QVQLVESGGGVVQPGRSLRLSCAASG | 481 | FTFSSYGMH | 497 | WVRQAPGKGLEWVA | 502 | VIWYDGSNKYYADSVKG | 515 |
| SRF543 | QVQLQQWGAGLLKPSETLSLTCAVYG | 482 | GSFS**DYE**WS | 498 | WIRQPPGKGLEWIG | 503 | EI**DW**SG**I**TNYNPSLKS | 516 |

FIG. 10A

| Name | VH FR3 | SEQ ID | VHCDR3 | SEQ ID | VH FR4 | SEQ ID |
|---|---|---|---|---|---|---|
| SRF405 | RVTITADESTSTAYMELSSLRSEDTAVYYC | 517 | ARSYYSSRWHYYYYMDV | 522 | WGKGTTVTVSS | 531 |
| SRF410 | RVTITADESTSTAYMELSSLRSEDTAVYYC | 517 | ARSYYSSRWHYYYYMDV | 522 | WGKGTTVTVSS | 531 |
| SRF411 | RVTITADESTSTAYMELSSLRSEDTAVYYC | 517 | ARSYYSSRWHYYYYMDV | 522 | WGKGTTVTVSS | 531 |
| SRF557 | RVTITADESTSTATMELSSLRSEDTAVYYC | 517 | ARLGGRGYADEGWYFDL | 523 | WGRGTLVTVSS | 532 |
| SRF536 | RVTISVDTSKNQFSLKLSSVTAADTAVYYC | 518 | ARLPMYYYDSSDLPMDV | 524 | WGQGTTVTVSS | 533 |
| SRF414 | RVTISVDTSKNQFSLKLSSVTAADTAVYYC | 518 | ARDGVYYDSSDLGFDI | 525 | WGQGTMVTVSS | 534 |
| SRF416 | RVTISVDTSKNQFSLKLSSVTAADTAVYYC | 518 | ARDGYYYDTSPYDV | 526 | WGQGTMVTVSS | 534 |
| SRF529 | RFTISRDNAKNSLYLQMNSLRAEDTAVYYC | 519 | ARDGGRTSYTATAHNWFDP | 527 | WGQGTLVTVSS | 535 |
| SRF381 | RFTISRDNAKNSLYLQMNSLRAEDTAVYYC | 519 | ARDGGRTSYTATAHNWFDP | 527 | WGQGTLVTVSS | 535 |
| SRF382 | RFTISRDNAKNSLYLQMNSLRAEDTAVYYC | 519 | ARDGGRTSYTATAHNWFDP | 527 | WGQGTLVTVSS | 535 |
| SRF384 | RFTISRDNAKNSLYLQMNSLRAEDTAVYYC | 519 | ARDGGRTSYTATAHNWFDP | 527 | WGQGTLVTVSS | 535 |
| SRF386 | RFTISRDNAKNSLYLQMNSLRAEDTAVYYC | 519 | ARDGGRTSYTATAHNWFDP | 527 | WGQGTLVTVSS | 535 |
| SRF388 | RFTISRDNAKNSLYLQMNSLRAEDTAVYYC | 519 | ARDGGRTSYTATAHNWFDP | 527 | WGQGTLVTVSS | 535 |
| SRF535 | RFTISRDNAKNSLYLQMNSLRAEDTAVYYC | 519 | ARDAPWDIYDYYMDV | 528 | WGKGTTVTVSS | 536 |
| SRF538 | RFTISRDNSKNTLYLQMNSLRAEDTAVYYC | 520 | ARGAPEYVDV | 529 | WGQGTMVTVSS | 537 |
| SRF543 | RVTISVDTSKNQFSLKLSSVTAADTAVYYC | 521 | ARLPMYYYDSSVSTGSVDV | 530 | WGQGTMVTVSS | 537 |

FIG. 10A (Continued)

| Name | VL FR1 | SEQ ID | VL CDR1 | SEQ ID | VL FR2 | SEQ ID | V CDR2 | SEQ ID |
|---|---|---|---|---|---|---|---|---|
| SRF405 | DIQMTQSPSSVSASVGDRVTITC | 538 | RASQGISSWLA | 545 | WYQQKPGKAPKLLIY | 552 | AAS**N**LQS | 559 |
| SRF410 | DIQMTQSPSSVSASVGDRVTITC | 538 | RASQGISSWLA | 545 | WYQQKPGKAPKLLIY | 552 | AAS**N**LQS | 559 |
| SRF411 | DIQMTQSPSSVSASVGDRVTITC | 538 | RASQGISSWLA | 545 | WYQQKPGKAPKLLIY | 552 | AAS**N**LQS | 559 |
| SRF557 | EIVLTQSPGTLSLSPGERATLSC | 539 | RASQSVSSSYLA | 546 | WYQQKPGQAPRLLIY | 553 | GASSRAT | 560 |
| SRF536 | DIQMTQSPSSLSASVGDRVTITC | 540 | QASQDISNYLN | 547 | WYQQKPGKAPKLLIY | 554 | DASNL**A**T | 561 |
| SRF414 | DIQMTQSPSSLSASVGDRVTITC | 540 | QASQDISNYLN | 547 | WYQQKPGKAPKLLIY | 554 | DASNLET | 562 |
| SRF416 | EIVLTQSPATLSLSPGERATLSC | 541 | RASQSVSSYLA | 548 | WYQQKPGQAPRLLIY | 555 | DASNRAT | 563 |
| SRF529 | DIVMTQSPDSLAVSLGERATINC | 542 | KSSQSVL**F**SSNNKNYLA | 549 | WYQQKPGQPPKLLIY | 556 | WASTRES | 564 |
| SRF381 | DIVMTQSPDSLAVSLGERATINC | 542 | KSSQSVL**F**SSNNKNYLA | 549 | WYQQKPGQPPKLLIY | 556 | WASTRES | 564 |
| SRF382 | DIVMTQSPDSLAVSLGERATINC | 542 | KSSQSVL**F**SSNNKNYLA | 549 | WYQQKPGQPPKLLIY | 556 | WASTRES | 564 |
| SRF384 | DIVMTQSPDSLAVSLGERATINC | 542 | KSSQSVL**F**SSNNKNYLA | 549 | WYQQKPGQPPKLLIY | 556 | WASTRES | 564 |
| SRF386 | DIVMTQSPDSLAVSLGERATINC | 542 | KSSQSVL**F**SSNNKNYLA | 549 | WYQQKPGQPPKLLIY | 556 | WASTRES | 564 |
| SRF388 | DIVMTQSPDSLAVSLGERATINC | 542 | KSSQSVL**F**SSNNKNYLA | 549 | WYQQKPGQPPKLLIY | 556 | WASTRES | 564 |
| SRF535 | DIQMTQSPSSLSASVGDRVTITC | 543 | RASQSISSYLN | 550 | WYQQKPGKAPKLLIY | 557 | AASSLQS | 565 |
| SRF538 | EIVLTQSPATLSLSPGERATLSC | 544 | RASQSVSSYLA | 551 | WYQQKPGQAPRLLIY | 558 | D**S**SNRAT | 566 |
| SRF543 | EIVLTQSPATLSLSPGERATLSC | 544 | RASQSVSSYLA | 551 | WYQQKPGQAPRLLIY | 558 | D**S**SNRAT | 566 |

FIG. 10A (Continued)

| Name | VL FR3 | SEQ ID | VL CDR3 | SEQ ID | VH FR4 | SEQ ID |
|---|---|---|---|---|---|---|
| SRF405 | GVPSRFSGSGSGTDFTLTISSLQPEDFATYYC | 567 | QQADDLPLT | 574 | FGGGTKVEIK | 583 |
| SRF410 | GVPSRFSGSGSGTDFTLTISSLQPEDFATYYC | 567 | QQADDLPLT | 574 | FGGGTKVEIK | 583 |
| SRF411 | GVPSRFSGSGSGTDFTLTISSLQPEDFATYYC | 567 | QQADDLPLT | 574 | FGGGTKVEIK | 583 |
| SRF557 | GIPDRFSGSGSGTDFTLTISRLEPEDFAVYYC | 568 | QQYYGSPIT | 575 | FGGGTKVEIK | 583 |
| SRF536 | GVPSRFSGSGSGTDFTFTISSLQPEDIATYYC | 569 | QQYDTLPLT | 576 | FGGGTKVEIK | 583 |
| SRF414 | GVPSRFSGSGSGTDFTFTISSLQPEDIATYYC | 569 | QQYDDTLPLT | 577 | FGGGTKVEIK | 583 |
| SRF416 | GIPARFSGSGSGTDFTLTISSLEPEDFAVYYC | 570 | QQRDSFPLT | 578 | FGGGTKVEIK | 583 |
| SRF529 | GVPDRFSGSGSGTDFTLTISSLQAEDVAVYYC | 571 | QQHASAPPT | 579 | FGGGTKVEIK | 583 |
| SRF381 | GVPDRFSGSGSGTDFTLTISSLQAEDVAVYYC | 571 | QQHASAPPT | 579 | FGGGTKVEIK | 583 |
| SRF382 | GVPDRFSGSGSGTDFTLTISSLQAEDVAVYYC | 571 | QQHASAPPT | 579 | FGGGTKVEIK | 583 |
| SRF384 | GVPDRFSGSGSGTDFTLTISSLQAEDVAVYYC | 571 | QQHASAPPT | 579 | FGGGTKVEIK | 583 |
| SRF386 | GVPDRFSGSGSGTDFTLTISSLQAEDVAVYYC | 571 | QQHASAPPT | 579 | FGGGTKVEIK | 583 |
| SRF388 | GVPDRFSGSGSGTDFTLTISSLQAEDVAVYYC | 571 | QQHASAPPT | 579 | FGGGTKVEIK | 583 |
| SRF535 | GVPSRFSGSGSGTDFTLTISSLQPEDFATYYC | 572 | QQSYVPPWT | 580 | FGGGTKVEIK | 583 |
| SRF538 | GIPARFSGSGSGTDFTLTISSLEPEDFAVYYC | 573 | QQYSLYPT | 581 | FGGGTKVEIK | 583 |
| SRF543 | GIPARFSGSGSGTDFTLTISSLEPEDFAVYYC | 573 | QQDSDHPIT | 582 | FGGGTKVEIK | 583 |

FIG. 10A (Continued)

| IMGT annotation: Name | VH FR1 | SEQ ID | VH CDR1 | SEQ ID | VH FR2 | SEQ ID | VH CDR2 | SEQ ID |
|---|---|---|---|---|---|---|---|---|
| SRF405 | QVQLVQSGAEVKKPGSSVKVSCKAS | 584 | GGTF**VG**YA | 590 | ISWVRQAPGQGLEWMGG | 605 | IIPIFG**I**A | 614 |
| SRF410 | QVQLVQSGAEVKKPGSSVKVSCKAS | 584 | GGTFS**A**YA | 591 | ISWVRQAPGQGLEWMGG | 605 | IIPIFGTA | 615 |
| SRF411 | QVQLVQSGAEVKKPGSSVKVSCKAS | 584 | GGTF**E**SY**T** | 592 | ISWVRQAPGQGLEWMGG | 605 | I**A**PIFGTA | 616 |
| SRF557 | QVQLVQSGAEVKKPGSSVKVSCKAS | 584 | GGTFSSYA | 593 | ISWVRQAPGQGLEWMGG | 605 | IIPIFGTA | 615 |
| SRF536 | QVQLQQWGAGLLKPSETLSLTCAVY | 585 | GGSFS**E**YY | 594 | **W**AWIRQPPGKGLEWIGE | 606 | I**DEV**GST | 617 |
| SRF414 | QVQLQQWGAGLLKPSETLSLTCAVY | 585 | GGSFS**R**YY | 595 | WSWIRQPPGKGLEWIG**S** | 607 | I**DY**SGST | 618 |
| SRF416 | QVQLQQWGAGLLKPSETLSLTCAVY | 585 | GGSFSGYY | 596 | WSWIRQPPGKGLEWIGE | 608 | I**DVD**GST | 619 |
| SRF529 | EVQLVESGGGLVKPGGSLRLSCAAS | 586 | GFTFSSYS | 597 | MNWVRQAPGKGLEWVSS | 609 | ISSSSSYI | 620 |
| SRF381 | EVQLVESGGGLVKPGGSLRLSCAAS | 586 | GFTF**R**SY**G** | 598 | MNWVRQAPGKGLEWVSS | 609 | ISSSSSYI | 620 |
| SRF382 | EVQLVESGGGLVKPGGSLRLSCAAS | 586 | GFTFS**RTG** | 599 | MNWVRQAPGKGLEWVSS | 609 | ISSSSSYI | 620 |
| SRF384 | EVQLVESGGGLVKPGGSLRLSCAAS | 586 | GFTFS**R**Y**G** | 600 | MNWVRQAPGKGLEWVSS | 609 | ISSSS**A**YI | 621 |
| SRF386 | EVQLVESGGGLVKPGGSLRLSCAAS | 586 | GFTF**A**SY**G** | 601 | MNWVRQAPGKGLEWVSS | 609 | ISSSSSYI | 620 |
| SRF388 | EVQLVESGGGLVKPGGSLRLSCAAS | 586 | GFTF**R**SY**G** | 602 | MNWVRQAPGKGLEWVS**G** | 610 | ISSS**G**SYI | 622 |
| SRF535 | EVQLVESGGGLVQPGGSLRLSCAAS | 587 | GFTFSSY**G** | 603 | MSWVRQAPGKGLEWVAN | 611 | IKQDGSEK | 623 |
| SRF538 | QVQLVESGGGVVQPGRSLRLSCAAS | 588 | GFTFSSY**G** | 603 | MHWVRQAPGKGLEWVAV | 612 | IWYDGSNK | 624 |
| SRF543 | QVQLQQWGAGLLKPSETLSLTCAVY | 589 | GGSFS**DYE** | 604 | WSWIRQPPGKGLEWIGE | 613 | I**DW**SG**I**T | 625 |

FIG. 10B

| IMGT annotation: Name | VH FR3 | SEQ ID | VHCDR3 | SEQ ID | VH FR2 | SEQ ID |
|---|---|---|---|---|---|---|
| SRF405 | NYAQKFQGRVTITADESTSTAYMELSSLRSEDTAVYYC | 626 | ARSYYSSRWHYYYYMDV | 637 | WGKGTTVTVSS | 646 |
| SRF410 | NYAQKFQGRVTITADESTSTAYMELSSLRSEDTAVYYC | 626 | ARSYYSSRWHYYYYMDV | 637 | WGKGTTVTVSS | 646 |
| SRF411 | **H**YAQKFQGRVTITADESTSTAYMELSSLRSEDTAVYYC | 627 | ARSYYSSRWHYYYYMDV | 637 | WGKGTTVTVSS | 646 |
| SRF557 | NYAQKFQGRVTITADESTSTAYMELSSLRSEDTAVYYC | 628 | ARLGGRGYADEGWYFDL | 638 | WGRGTLVTVSS | 647 |
| SRF536 | NYNPSLKSRVTISVDTSKNQFSLKLSSVTAADTAVYYC | 629 | ARLPMYYYDSSDLPMDV | 639 | WGQGTTVTVSS | 648 |
| SRF414 | **E**YNPSLKSRVTISVDTSKNQFSLKLSSVTAADTAVYYC | 630 | ARDGVYYDSSDLGFDL | 640 | WGQGTMVTVSS | 649 |
| SRF416 | NYNPSLKSRVTISVDTSKNQFSLKLSSVTAADTAVYYC | 629 | ARDGYYYDTSPYDV | 641 | WGQGTMVTVSS | 649 |
| SRF529 | YYADSVKGRFTISRDNAKNSLYLQMNSLRAEDTAVYYC | 631 | ARDGGRTSYTATAHNWFDP | 642 | WGQGTLVTVSS | 650 |
| SRF381 | YYADSVKGRFTISRDNAKNSLYLQMNSLRAEDTAVYYC | 631 | ARDGGRTSYTATAHNWFDP | 642 | WGQGTLVTVSS | 650 |
| SRF382 | YYADSVKGRFTISRDNAKNSLYLQMNSLRAEDTAVYYC | 631 | ARDGGRTSYTATAHNWFDP | 642 | WGQGTLVTVSS | 650 |
| SRF384 | **L**YADSVKGRFTISRDNAKNSLYLQMNSLRAEDTAVYYC | 632 | ARDGGRTSYTATAHNWFDP | 642 | WGQGTLVTVSS | 650 |
| SRF386 | YYADSVKGRFTISRDNAKNSLYLQMNSLRAEDTAVYYC | 633 | ARDGGRTSYTATAHNWFDP | 642 | WGQGTLVTVSS | 650 |
| SRF388 | YYADSVKGRFTISRDNAKNSLYLQMNSLRAEDTAVYYC | 633 | ARDGGRTSYTATAHNWFDP | 642 | WGQGTLVTVSS | 650 |
| SRF535 | YYVDSVKGRFTISRDNAKNSLYLQMNSLRAEDTAVYYC | 634 | ARDAPWDIYDYYMDV | 643 | WGKGTTVTVSS | 651 |
| SRF538 | YYADSVKGRFTISRDNSKNTLYLQMNSLRAEDTAVYYC | 635 | ARGAPEYVDV | 644 | WGQGTMVTVSS | 652 |
| SRF543 | NYNPSLKSRVTISVDTSKNQFSLKLSSVTAADTAVYYC | 636 | ARLPMYYYDSSVSTGSVDV | 645 | WGQGTMVTVSS | 652 |

FIG. 10B (Continued)

| IMGT annotation: Name | VL FR1 | SEQ ID | VL CDR1 | SEQ ID | VL FR2 | SEQ ID | VL CDR2 | SEQ ID |
|---|---|---|---|---|---|---|---|---|
| SRF405 | DIQMTQSPSSVSASVGDRVTITCRAS | 653 | QGISSW | 660 | LAWYQQKPGKAPKLLIY | 667 | AAS | 674 |
| SRF410 | DIQMTQSPSSVSASVGDRVTITCRAS | 653 | QGISSW | 660 | LAWYQQKPGKAPKLLIY | 667 | AAS | 674 |
| SRF411 | DIQMTQSPSSVSASVGDRVTITCRAS | 653 | QGISSW | 660 | LAWYQQKPGKAPKLLIY | 667 | AAS | 674 |
| SRF557 | EIVLTQSPGTLSLSPGERATLSCRAS | 654 | QSVSSSY | 661 | LAWYQQKPGQAPRLLIY | 668 | GAS | 675 |
| SRF536 | DIQMTQSPSSLSASVGDRVTITCQAS | 655 | QDISNY | 662 | LNWYQQKPGKAPKLLIY | 669 | DAS | 676 |
| SRF414 | DIQMTQSPSSLSASVGDRVTITCQAS | 655 | QDISNY | 662 | LNWYQQKPGKAPKLLIY | 669 | DAS | 676 |
| SRF416 | EIVLTQSPATLSLSPGERATLSCRA | 656 | SQSVSSY | 663 | LAWYQQKPGQAPRLLIY | 670 | DAS | 676 |
| SRF529 | DIVMTQSPDSLAVSLGERATINCKSS | 657 | QSVL**F**SSNNKNY | 664 | LAWYQQKPGQPPKLLIY | 671 | WAS | 677 |
| SRF381 | DIVMTQSPDSLAVSLGERATINCKSS | 657 | QSVL**F**SSNNKNY | 664 | LAWYQQKPGQPPKLLIY | 671 | WAS | 677 |
| SRF382 | DIVMTQSPDSLAVSLGERATINCKSS | 657 | QSVL**F**SSNNKNY | 664 | LAWYQQKPGQPPKLLIY | 671 | WAS | 677 |
| SRF384 | DIVMTQSPDSLAVSLGERATINCKSS | 657 | QSVL**F**SSNNKNY | 664 | LAWYQQKPGQPPKLLIY | 671 | WAS | 677 |
| SRF386 | DIVMTQSPDSLAVSLGERATINCKSS | 657 | QSVL**F**SSNNKNY | 664 | LAWYQQKPGQPPKLLIY | 671 | WAS | 677 |
| SRF388 | DIVMTQSPDSLAVSLGERATINCKSS | 657 | QSVL**F**SSNNKNY | 664 | LAWYQQKPGQPPKLLIY | 671 | WAS | 677 |
| SRF535 | DIQMTQSPSSLSASVGDRVTITCRAS | 658 | QSISSY | 665 | LNWYQQKPGKAPKLLIY | 672 | AAS | 678 |
| SRF538 | EIVLTQSPATLSLSPGERATLSCRAS | 659 | QSVSSY | 666 | LAWYQQKPGQAPRLLIY | 673 | D**S**S | 679 |
| SRF543 | EIVLTQSPATLSLSPGERATLSCRAS | 659 | QSVSSY | 666 | LAWYQQKPGQAPRLLIY | 673 | D**S**S | 679 |

FIG. 10B (Continued)

| IMGT annotation: Name | VL FR3 | SEQ ID | VL CDR3 | SEQ ID | VH FR4 | SEQ ID |
|---|---|---|---|---|---|---|
| SRF405 | **N**LQSGVPSRFSGSGSGTDFTLTISSLQPEDFATYYC | 680 | QQADDLPLT | 688 | FGGGTKVEIK | 697 |
| SRF410 | **N**LQSGVPSRFSGSGSGTDFTLTISSLQPEDFATYYC | 680 | QQADDLPLT | 688 | FGGGTKVEIK | 697 |
| SRF411 | **N**LQSGVPSRFSGSGSGTDFTLTISSLQPEDFATYYC | 680 | QQADDLPLT | 688 | FGGGTKVEIK | 697 |
| SRF557 | SRATGIPTDRFSGSGSGTDFTLTISRLEPEDFAVYYC | 681 | QQYYGSPIT | 689 | FGGGTKVEIK | 697 |
| SRF536 | NL**A**TGVPSRFSGSGSGTDFTFTISSLQPEDIATYYC | 682 | QQYDLPLT | 690 | FGGGTKVEIK | 697 |
| SRF414 | NLETGVPSRFSGSGSGTDFTFTISSLQPEDIATYYC | 683 | QQYDDTLPIT | 691 | FGGGTKVEIK | 697 |
| SRF416 | NRATGIPARFSGSGSGTDFTLTISSLEPEDFAVYYC | 684 | QQRDSFPLT | 692 | FGGGTKVEIK | 697 |
| SRF529 | TRESGVPDRFSGSGSGTDFTLTISSLQAEDVAVYYC | 685 | QQHASAPPT | 693 | FGGGTKVEIK | 697 |
| SRF381 | TRESGVPDRFSGSGSGTDFTLTISSLQAEDVAVYYC | 685 | QQHASAPPT | 693 | FGGGTKVEIK | 697 |
| SRF382 | TRESGVPDRFSGSGSGTDFTLTISSLQAEDVAVYYC | 685 | QQHASAPPT | 693 | FGGGTKVEIK | 697 |
| SRF384 | TRESGVPDRFSGSGSGTDFTLTISSLQAEDVAVYYC | 685 | QQHASAPPT | 693 | FGGGTKVEIK | 697 |
| SRF386 | TRESGVPDRFSGSGSGTDFTLTISSLQAEDVAVYYC | 685 | QQHASAPPT | 693 | FGGGTKVEIK | 697 |
| SRF388 | TRESGVPDRFSGSGSGTDFTLTISSLQAEDVAVYYC | 685 | QQHASAPPT | 693 | FGGGTKVEIK | 697 |
| SRF535 | SLQSGVPSRFSGSGSGTDFTLTISSLQPEDFATYYC | 686 | QQSYVPPWT | 694 | FGGGTKVEIK | 697 |
| SRF538 | NRATGIPARFSGSGSGTDFTLTISSLEPEDFAVYYC | 687 | QQYSLYPT | 695 | FGGGTKVEIK | 697 |
| SRF543 | NRATGIPARFSGSGSGTDFTLTISSLEPEDFAVYYC | 687 | QQDSDHPIT | 696 | FGGGTKVEIK | 697 |

FIG. 10B (Continued)

ANTI-IL-27 ANTIBODIES AND USES THEREOF

CROSS REFERENCE TO RELATED APPLICATIONS

This application claims the benefit of U.S. Provisional Application No. 62/646,496, filed Mar. 22, 2018, the entire contents of which are incorporated herein by reference.

FIELD

The present disclosure relates generally to compositions and methods for modulating IL-27 signaling. More particularly, the present disclosure relates to immunogenic compositions (e.g., antibodies, antibody fragments, and the like) that bind to IL-27 and modulate IL-27 signaling.

SEQUENCE LISTING

This application includes a Sequence Listing in electronic format. The Sequence Listing is entitled "Surface501001US_SeqList_ST25", was created on Sep. 5, 2019, and is 503,976 bytes in size. The information in the electronic format of the Sequence Listing is part of the present application and is incorporated herein by reference in its entirety.

BACKGROUND

In recent years, an increasing body of evidence suggests that the immune system operates as a significant barrier to tumor formation and progression. The principle that naturally-occurring T cells with anti-tumor potential or activity exist in a patient with cancer has rationalized the development of immunotherapeutic approaches in oncology. Immune cells, such as T cells, macrophages, and natural killer cells, can exhibit anti-tumor activity and effectively control the occurrence and growth of malignant tumors. Tumor-specific or -associated antigens can induce immune cells to recognize and eliminate malignancies (Chen & Mellman, (2013) *Immunity* 39(1):1-10). In spite of the existence of tumor-specific immune responses, malignant tumors often evade or avoid immune attack through a variety of immunomodulatory mechanisms resulting in the failure to control tumor occurrence and progression (Motz & Coukos, (2013) *Immunity* 39(1):61-730). Indeed, an emerging hallmark of cancer is the exploitation of these immunomodulatory mechanisms and the disablement of anti-tumor immune responses, resulting in tumor evasion and escape from immunological killing (Hanahan and Weinberg (2011) *Cell* 144(5):646-674).

IL-27 is a heterodimeric cytokine, composed of two subunits (EBI3 and IL-27p28). IL-27 is structurally related to both the IL-12 and IL-6 cytokine families. IL-27 binds to and mediates signaling through a heterodimer receptor consisting of IL-27Rα (WSX1) and gp130 chains, which mediate signaling predominantly through STAT1 and STAT3. Initial reports characterized IL-27 as an immune-enhancing cytokine that supports CD4+ T cell proliferation, T helper (Th)1 cell differentiation, and IFN-γ production, often acting in concert with IL-12. Subsequent studies have shown that IL-27 displays complex immunomodulatory functions, resulting in either proinflammatory or anti-inflammatory effects depending on the biological context and experimental models being used. IL-27 may drive the expression of different immune-regulatory molecules in human cancer cells, which may support local derangement of the immune response in vivo (Fabbi et al., (2017) Mediators Inflamm 3958069. Published online 2017 Feb. 1. doi:10.1155/2017/3958069, and references contained therein).

Despite the significant advances being made in cancer treatment and management, there is still an ongoing need for new and effective therapies for treating and managing cancer.

SUMMARY OF THE DISCLOSURE

Disclosed herein are antibodies, or antigen binding portions thereof, that specifically bind to and antagonize human IL-27 (Interleukin 27) with high affinity and specificity. Nucleic acid molecules encoding the antibody molecules, expression vectors, host cells and methods for making the antibody molecules are also provided. Pharmaceutical compositions comprising the antibody molecules are also provided. The anti-IL-27 antibodies, or antigen binding portions thereof, disclosed herein can be used (alone or in combination with other therapeutic agents or procedures) to treat, prevent and/or diagnose disorders, including immune disorders and cancer. Thus, compositions and methods for treating and/or diagnosing various disorders, including cancer and immune disorders, using the anti-IL-27 antibody molecules are disclosed herein.

In some embodiments, the disclosure provides an isolated monoclonal antibody that specifically binds to and antagonizes human IL-27, or an antigen binding portion thereof, wherein the antibody or antigen binding portion thereof exhibits at least one or more of the following properties: (i) binds to human IL-27 with an equilibrium dissociation constant ($K_D$) of 15 nM or less; (ii) blocks binding of IL-27 to IL-27 receptor; (iii) inhibits or reduces STAT1 and/or STAT3 phosphorylation in a cell; (iv) inhibits or reduces inhibition of CD161 expression in a cell; (v) inhibits or reduces PD-L1 and/or TIM-3 expression in a cell; (vi) induces or enhances PD-1 mediated secretion of one or more cytokines from a cell; and (vii) a combination of (i)-(vi).

In some embodiments, the isolated monoclonal antibody, or antigen binding portion thereof, binds to human IL-27 with an equilibrium dissociation constant ($K_D$) of 15 nM or less.

In some embodiments, the isolated monoclonal antibody, or antigen binding portion thereof, binds to recombinant human IL-27 or to murine IL-27.

In one aspect, the instant disclosure provides an isolated monoclonal antibody that specifically binds to and antagonizes human IL-27, or antigen binding portion thereof, where the antibody or antigen binding portion thereof has heavy and light chain CDRs that are: (i) heavy chain CDR1 is N-GFTFXXXX-C (SEQ ID NO: 408), heavy chain CDR2 is N-ISSSXXYI-C (SEQ ID NO: 409), and heavy chain CDR3 sequence is SEQ ID NO: 163; light chain CDR1, CDR2 and CDR3 sequences are SEQ ID NOs: 169, 170 and 171, respectively; or (ii) heavy chain CDR1 is N-FTFXXXXMN-C (SEQ ID NO: 410), heavy chain CDR2 is N-XISSSXXYIXYADSVKG-C (SEQ ID NO: 411), and heavy chain CDR3 sequence is SEQ ID NO: 166; light chain CDR1, CDR2 and CDR3 sequences are SEQ ID NOs: 172, 173 and 174, respectively.

In one embodiment, the heavy chain CDR1 is N-GFTF[S/A/R][S/R][T/Y][G/S]-C (SEQ ID NO: 412) and the heavy chain CDR2 is N-ISSS[S/G][S/A]YI-C (SEQ ID NO: 413); or the heavy chain CDR1 is N-FTF[S/A/R][S/R][T/

Y][G/S]MN-C (SEQ ID NO: 414) and the heavy chain CDR2 is N-[G/S]ISSS[S/G][S/A]YI[L/Y]YADSVKG-C (SEQ ID NO: 415).

In another embodiment, the respective heavy chain and light chain CDRs are: (i) the heavy chain CDR1, CDR2 and CDR3 sequences are SEQ ID NOs: 161, 162 and 163, respectively, and the light chain CDR1, CDR2 and CDR3 sequences are SEQ ID NOs: 169, 170 and 171, respectively; (ii) the heavy chain CDR1, CDR2 and CDR3 sequences are SEQ ID NOs: 164, 165 and 166, respectively, and the light chain CDR1, CDR2 and CDR3 sequences are SEQ ID NOs: 172, 173 and 174, respectively; (iii) the heavy chain CDR1, CDR2 and CDR3 sequences are SEQ ID NOs: 73, 74 and 75, respectively, and the light chain CDR1, CDR2 and CDR3 sequences are SEQ ID NOs: 81, 82 and 83, respectively; (iv) the heavy chain CDR1, CDR2 and CDR3 sequences are SEQ ID NOs: 76, 77 and 78, respectively, and the light chain CDR1, CDR2 and CDR3 sequences are SEQ ID NOs: 84, 85 and 86, respectively; (v) the heavy chain CDR1, CDR2 and CDR3 sequences are SEQ ID NOs: 95, 96 and 97, respectively, and the light chain CDR1, CDR2 and CDR3 sequences are SEQ ID NOs: 103, 104 and 105, respectively; (vi) the heavy chain CDR1, CDR2 and CDR3 sequences are SEQ ID NOs: 98, 99 and 100, respectively, and the light chain CDR1, CDR2 and CDR3 sequences are SEQ ID NOs: 106, 107 and 108, respectively; (vii) the heavy chain CDR1, CDR2 and CDR3 sequences are SEQ ID NOs: 117, 118 and 119, respectively, and the light chain CDR1, CDR2 and CDR3 sequences are SEQ ID NOs: 125, 126 and 127, respectively; (viii) the heavy chain CDR1, CDR2 and CDR3 sequences are SEQ ID NOs: 120, 121 and 122, respectively, and the light chain CDR1, CDR2 and CDR3 sequences are SEQ ID NOs: 128, 129 and 130, respectively; (ix) the heavy chain CDR1, CDR2 and CDR3 sequences are SEQ ID NOs: 139, 140 and 141, respectively, and the light chain CDR1, CDR2 and CDR3 sequences are SEQ ID NOs: 147, 148 and 149, respectively; (x) the heavy chain CDR1, CDR2 and CDR3 sequences are SEQ ID NOs: 142, 143 and 144, respectively, and the light chain CDR1, CDR2 and CDR3 sequences are SEQ ID NOs: 150, 151 and 152, respectively; (xi) the heavy chain CDR1, CDR2 and CDR3 sequences are SEQ ID NOs: 51, 52 and 53, respectively, and the light chain CDR1, CDR2 and CDR3 sequences are SEQ ID NOs: 59, 60 and 61, respectively; or (xii) the heavy chain CDR1, CDR2 and CDR3 sequences are SEQ ID NOs: 54, 55 and 56, respectively, and the light chain CDR1, CDR2 and CDR3 sequences are SEQ ID NOs: 62, 63 and 64, respectively.

Another aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1 is N-GGSFSXYX-C (SEQ ID NO: 416), heavy chain CDR2 is N-IDXSGXT-C (SEQ ID NO: 417), and heavy chain CDR3 is N-ARXXXYY$[X]_{n=0-1}$ DSS$[X]_{n=4-6}$DX-C (SEQ ID NO: 418); and light chain CDR1 is N-QXXSXY-C (SEQ ID NO: 419), light chain CDR2 is N-DXS-C (SEQ ID NO: 420), and light chain CDR3 is N-QQXXDXPIT-C (SEQ ID NO: 421), respectively; or (ii) heavy chain CDR1 is N-GSFSXYXWS-C (SEQ ID NO: 422), heavy chain CDR2 is N-SIDXSGXTXYNPSLKS-C (SEQ ID NO: 423), and heavy chain CDR3 sequence is N-ARXXXYY$[X]_{n=0-1}$DSS $[X]_{n=4-6}$DX-C (SEQ ID NO: 418); and light chain CDR1 is N-XASQXXSXYLX-C (SEQ ID NO: 424), light chain CDR2 is N-DXSNXXT-C (SEQ ID NO: 425), and light chain CDR3 is N-QQXXDXPIT-C (SEQ ID NO: 421), respectively.

In certain embodiments, (i) the heavy chain CDR1 is N-GGSFS[R/D]Y[E/Y]-C (SEQ ID NO: 426), the heavy chain CDR2 is N-ID[W/Y]SG[I/S]T-C (SEQ ID NO: 427), the heavy chain CDR3 is N-AR[D/L][P/G][M/V]YY[-/Y] DSS[VSTGSV/DLGF]D[V/I]-C (SEQ ID NO: 428); and the light chain CDR1 is N-Q[S/D][V/I]S[S/N]Y-C (SEQ ID NO: 429), the light chain CDR2 is N-D[S/A]S-C (SEQ ID NO: 430), and the light chain CDR3 is N-QQ[D/Y][S/D]D[H/L] PIT-C (SEQ ID NO: 431), respectively; or (ii) the heavy chain CDR1 is N-GSFS[R/D]Y[E/Y]WS-C (SEQ ID NO: 432), the heavy chain CDR2 is N-SID[W/Y]SG[I/S]T[N/E] YNPSLKS-C (SEQ ID NO: 433), the heavy chain CDR3 is N-AR[D/L][P/G][M/V]YY[-/Y]DSS[VSTGSV/DLGF]D [V/I]-C (SEQ ID NO: 428); and the light chain CDR1 is N-[Q/R]ASQ[S/D][V/I]S[S/N]YL[N/A]-C (SEQ ID NO: 434), the light chain CDR2 is N-D[S/A]SN[R/L][A/E]T-C (SEQ ID NO: 435), and the light chain CDR3 is N-QQ[D/ Y][S/D]D[H/L]PIT-C (SEQ ID NO: 431), respectively.

In some embodiments, (i) the heavy chain CDR1, CDR2 and CDR3 sequences are SEQ ID NOs: 229, 230 and 231, respectively, and the light chain CDR1, CDR2 and CDR3 sequences are SEQ ID NOs: 237, 238 and 239, respectively; or (ii) the heavy chain CDR1, CDR2 and CDR3 sequences are SEQ ID NOs: 232, 233 and 234, respectively, and the light chain CDR1, CDR2 and CDR3 sequences are SEQ ID NOs: 240, 241 and 242, respectively.

In certain embodiments, (i) the heavy chain CDR1, CDR2 and CDR3 sequences are SEQ ID NOs: 251, 252 and 253, respectively, and the light chain CDR1, CDR2 and CDR3 sequences are SEQ ID NOs: 259, 260 and 261, respectively; or (ii) the heavy chain CDR1, CDR2 and CDR3 sequences are SEQ ID NOs: 254, 255 and 256, respectively, and the light chain CDR1, CDR2 and CDR3 sequences are SEQ ID NOs: 262, 263 and 264, respectively.

Another aspect of the instant disclosure provides an isolated monoclonal antibody that specifically binds to and antagonizes human IL-27, or antigen binding portion thereof, where the antibody or antigen binding portion thereof includes heavy and light chain CDRs that are heavy chain CDR1, CDR2 and CDR3 sequences SEQ ID NOs: 23, 24 and 25, respectively, and light chain CDR1, CDR2 and CDR3 sequences SEQ ID NOs: 26, 27 and 28, respectively.

An additional aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1, CDR2 and CDR3 sequences SEQ ID NOs: 339, 340 and 341, respectively, and light chain CDR1, CDR2 and CDR3 sequences SEQ ID NOs: 347, 348 and 349, respectively; or (ii) heavy chain CDR1, CDR2 and CDR3 sequences SEQ ID NOs: 342, 343 and 344, respectively, and light chain CDR1, CDR2 and CDR3 sequences SEQ ID NOs: 350, 351 and 352, respectively.

Another aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1, CDR2 and CDR3 sequences SEQ ID NOs: 185, 186 and 187, respectively, and light chain CDR1, CDR2 and CDR3 sequences SEQ ID NOs: 193, 194 and 195, respectively; or (ii) heavy chain CDR1, CDR2 and CDR3 sequences SEQ ID NOs: 188, 189 and 190, respectively, and light chain CDR1, CDR2 and CDR3 sequences SEQ ID NOs: 196, 197 and 198, respectively.

One aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1, CDR2 and CDR3 sequences SEQ ID NOs: 207, 208 and 209, respectively, and light chain CDR1, CDR2 and CDR3 sequences SEQ ID NOs: 215, 216 and 217, respectively; or (ii) heavy chain CDR1, CDR2 and CDR3 sequences SEQ ID NOs: 210, 211 and 212, respectively, and light chain CDR1, CDR2 and CDR3 sequences SEQ ID NOs: 218, 219 and 220, respectively.

An additional aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1, CDR2 and CDR3 sequences SEQ ID NOs: 273, 274 and 275, respectively, and light chain CDR1, CDR2 and CDR3 sequences SEQ ID NOs: 281, 282 and 283, respectively; or (ii) heavy chain CDR1, CDR2 and CDR3 sequences SEQ ID NOs: 276, 277 and 278, respectively, and light chain CDR1, CDR2 and CDR3 sequences SEQ ID NOs: 284, 285 and 286, respectively.

One aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1 is N-GFTFSSYG-C (SEQ ID NO: 361), heavy chain CDR2 is N-IXXDGSXK-C (SEQ ID NO: 436), and heavy chain CDR3 is N-ARXAP$[X]_{n=3-8}$DV-C (SEQ ID NO: 437); and light chain CDR1 is N-QSXSSY-C (SEQ ID NO: 438), light chain CDR2 is N-XXS-C (SEQ ID NO: 439), and light chain CDR3 is N-QQXXXXP$[X]_{n=0-1}$T-C (SEQ ID NO: 440), respectively; or (ii) heavy chain CDR1 is N-FTFSSYGMX-C (SEQ ID NO: 441), heavy chain CDR2 is N-XIXXDGSXKYYXDSVKG-C (SEQ ID NO: 442), and heavy chain CDR3 is N-ARXAP$[X]_{n=3-8}$DV-C (SEQ ID NO: 437); and light chain CDR1 is N-RASQSXSSYLX-C (SEQ ID NO: 443) light chain CDR2 is N-$[X]_{n=1-2}$SS$[X]_{n=3-4}$-C (SEQ ID NO: 444), and light chain CDR3 is N-QQXXXXP$[X]_{n=0-1}$T-C (SEQ ID NO: 440), respectively.

In certain embodiments, (i) the heavy chain CDR1 is N-GFTFSSYG-C (SEQ ID NO: 361), heavy chain CDR2 is N-I[K/W][Q/Y]DGS[E/N]K-C (SEQ ID NO: 445), and heavy chain CDR3 is N-AR[D/G]AP[WDIYDYYM/EYV]DV-C (SEQ ID NO: 446); and light chain CDR1 is N-QS[I/V]SSY-C (SEQ ID NO: 447), light chain CDR2 is N-[A/D][A/S]S-C (SEQ ID NO: 448), and light chain CDR3 is N-QQ[S/Y][Y/S][V/L][P/Y]P[W/-]T-C (SEQ ID NO: 449), respectively; or (ii) the heavy chain CDR1 is N-FTFSSYGM[S/H]-C (SEQ ID NO: 450); heavy chain CDR2 is N-[N/V]I[K/W][Q/Y]DGS[E/N]KYY[V/A]DSVKG-C (SEQ ID NO: 451), and heavy chain CDR3 is N-AR[D/G]AP[WDIYDYYM/EYV]DV-C (SEQ ID NO: 446); and light chain CDR1 is N-RASQS[I/V]SSYL[N/A]-C (SEQ ID NO: 452), light chain CDR2 is N-[AA/D]SS[LQS/NRAT]-C (SEQ ID NO: 453), and light chain CDR3 is N-QQ[S/Y][Y/S][V/L][P/Y]P[W/-]T-C (SEQ ID NO: 449), respectively.

In some embodiments, (i) the heavy chain CDR1, CDR2 and CDR3 sequences are SEQ ID NOs: 361, 362 and 363, respectively, and the light chain CDR1, CDR2 and CDR3 sequences are SEQ ID NOs: 369, 370 and 371, respectively; or (ii) the heavy chain CDR1, CDR2 and CDR3 sequences are SEQ ID NOs: 364, 365 and 366, respectively, and the light chain CDR1, CDR2 and CDR3 sequences are SEQ ID NOs: 372, 373 and 374, respectively.

In one embodiment, (i) the heavy chain CDR1, CDR2 and CDR3 sequences are SEQ ID NOs: 383, 384 and 385, respectively, and the light chain CDR1, CDR2 and CDR3 sequences are SEQ ID NOs: 391, 392 and 393, respectively; or (ii) the heavy chain CDR1, CDR2 and CDR3 sequences are SEQ ID NOs: 386, 387 and 388, respectively, and the light chain CDR1, CDR2 and CDR3 sequences are SEQ ID NOs: 394, 395 and 396, respectively.

Another aspect of the instant disclosure provides an isolated monoclonal antibody that specifically binds to and antagonizes human IL-27, or antigen binding portion thereof, where the antibody or antigen binding portion thereof includes heavy and light chain CDRs that are: (i) heavy chain CDR1 is N-GFTFXXXX-C (SEQ ID NO: 408), heavy chain CDR2 is N-IXXXXXXX-C (SEQ ID NO: 456), and heavy chain CDR3 is N-AR$[X]_{n=6-15}$DX-C (SEQ ID NO: 458); and light chain CDR1 is N-QS$[X]_{n=1-3}$SS$[X]_{n=0-4}$Y-C (SEQ ID NO: 460), light chain CDR2 is N-XXS-C (SEQ ID NO: 462), and light chain CDR3 is N-QQXXXXP$[X]_{n=0-1}$T-C (SEQ ID NO: 464), respectively; or (ii) heavy chain CDR1 is N-FTFXXXXMX-C (SEQ ID NO: 466), heavy chain CDR2 is N-XIXXXXXXXXYXDSVKG-C (SEQ ID NO: 468), and heavy chain CDR3 is N-AR$[X]_{n=6-15}$DX-C (SEQ ID NO: 470); and light chain CDR1 is N-RASQSXSSYLX-C (SEQ ID NO: 472), light chain CDR2 is N-$[X]_{n=1-2}$S$[X]_{n=4-5}$-C (SEQ ID NO: 474), and light chain CDR3 is N-QQXXXXP$[X]_{n=0-1}$T-C (SEQ ID NO: 476), respectively.

In certain embodiments, (i) the heavy chain CDR1 is N-GFTF[S/A/R][S/R][T/Y][G/S]-C (SEQ ID NO: 454), heavy chain CDR2 is N-I[S/K/W][S/Q/Y][S/D][S/G][S/A][Y/E/N][I/K]-C (SEQ ID NO: 455), and heavy chain CDR3 is N-AR[DGGRTSYTATAHNWF/DAPWDIYDYYM/GAPEYV]D[P/V]-C (SEQ ID NO: 457); and light chain CDR1 is N-QS[VLF/I/V]SS[NNKN/-]Y-C (SEQ ID NO: 459), light chain CDR2 is N-[W/A/D][A/S]S-C (SEQ ID NO: 461), and light chain CDR3 is N-QQ[H/S/Y][A/Y/S][S/V/L][A/P/Y]P[P/W/-]T-C (SEQ ID NO: 463), respectively; or (ii) the heavy chain CDR1 is N-FTF[S/A/R][S/R][T/Y][G/S]M[N/S/H]-C (SEQ ID NO: 465), heavy chain CDR2 is N-[G/S/N/V]I[S/K/W][ S/Q/Y][ S/D][ S/G][ S/A][Y/E/N][I/K][L/Y]Y[V/A]DSVKG-C (SEQ ID NO: 467), and heavy chain CDR3 is N-AR[D/G][GGRTSYTATAHNWF/APWDIYDYYM/APEYV]D[P/V]-C (SEQ ID NO: 469); and light chain CDR1 is N-RASQS[IN]SSYL[N/A]-C (SEQ ID NO: 471), light chain CDR2 is N-[WA/AA/D]S[TRES/SLQS/SNRAT]-C (SEQ ID NO: 473), and light chain CDR3 is N-QQ[H/S/Y][A/Y/S][SN/L][A/P/Y]P[P/W/-]T-C (SEQ ID NO: 475), respectively.

In some embodiments, the isolated monoclonal antibody, or antigen binding portion thereof, inhibits or reduces STAT1 and/or STAT3 phosphorylation in a cell. In some embodiments, the cell is an immune cell. In some embodiments, the cell is a cancer cell.

In some embodiments, the isolated monoclonal antibody, or antigen binding portion thereof, inhibits or reduces inhibition of CD161 expression in a cell (e.g. ameliorates or relieves the inhibition of CD161 expression in a cell). In some embodiments, the cell is an immune cell.

In some embodiments, the isolated monoclonal antibody, or antigen binding portion thereof, inhibits or reduces IL-27-mediated PD-L1 and/or TIM-3 expression in a cell. In some embodiments, PD-L1 expression is inhibited or reduced. In some embodiments, TIM-3 expression is inhibited or reduced. In some embodiments, both PD-L1 expression and TIM-3 expression is reduced. In some embodiments, the cell is an immune cell.

In some embodiments, the isolated monoclonal antibody, or antigen binding portion thereof, induces or enhances the PD-1-mediated secretion of one or more cytokines from a cell. In some embodiments, the one or more cytokines is TNFα. In some embodiments, the one or more cytokine is IL-6. In some embodiments, the one or more cytokines is TNFα and IL-6. In some embodiments, the cell is an immune cell.

In some embodiments, the isolated monoclonal antibody, or antigen binding portion thereof, is selected from the group consisting of an IgG1, an IgG2, an IgG3, an IgG4, an IgM, an IgA1 an IgA2, an IgD, and an IgE antibody. In some embodiments, the antibody is an IgG1 antibody or an IgG4 antibody. In some embodiments, the antibody comprises a wild type IgG1 heavy chain constant region. In some embodiments, the antibody comprises a wild type IgG4 heavy chain constant region. In some embodiments, the antibody comprises an Fc domain comprising at least one mutation. In some embodiments, the antibody comprises a mutant IgG1 heavy chain constant region. In some embodiments, the antibody comprises a mutant IgG4 heavy chain constant region. In some embodiments, the mutant IgG4 heavy chain constant region comprises any one of the substitutions S228P, L235E, L235A, or a combination thereof, according to EU numbering.

In some embodiments, the disclosure provides an isolated monoclonal antibody, or antigen binding portion thereof, that binds to substantially the same epitope on IL-27 as the antibody, or antigen binding portion thereof, according to any one of the aforementioned embodiments.

In some embodiments, the disclosure provides an isolated monoclonal antibody, or antigen binding portion thereof, that binds to at least one of the amino acid residues comprising IL-27 bound by the antibody, or antigen binding portion thereof, according to any one of the aforementioned embodiments.

In some embodiments, the disclosure provides an isolated monoclonal antibody, or antigen binding portion thereof, wherein a mutation of the epitope on IL-27 bound by the antibody or antigen binding portion thereof inhibits, reduces, or blocks binding to both the antibody or antigen binding portion thereof and to the antibody or antigen binding portion thereof according to any one of the aforementioned embodiments.

In some embodiments, the disclosure provides an isolated monoclonal antibody, or antigen binding portion thereof, that binds to an epitope on IL-27, wherein the epitope is the same or is similar to the epitope bound by an antibody molecule described in Table 12.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs selected from the group consisting of:

(i) heavy chain CDR1, CDR2 and CDR3 sequences set forth in SEQ ID NOs: 51, 52 and 53, respectively, and light chain CDR1, CDR2 and CDR3 sequences set forth in SEQ ID NOs: 59, 60 and 61, respectively;

(ii) heavy chain CDR1, CDR2 and CDR3 sequences set forth in SEQ ID NOs: 73, 74 and 75, respectively, and light chain CDR1, CDR2 and CDR3 sequences set forth in SEQ ID NOs: 81, 82 and 83, respectively;

(iii) heavy chain CDR1, CDR2 and CDR3 sequences set forth in SEQ ID NOs: 95, 96 and 97, respectively, and light chain CDR1, CDR2 and CDR3 sequences set forth in SEQ ID NOs: 103, 104 and 105, respectively;

(iv) heavy chain CDR1, CDR2 and CDR3 sequences set forth in SEQ ID NOs: 117, 118 and 119, respectively, and light chain CDR1, CDR2 and CDR3 sequences set forth in SEQ ID NOs: 125, 126 and 127, respectively;

(v) heavy chain CDR1, CDR2 and CDR3 sequences set forth in SEQ ID NOs: 139, 140 and 141, respectively, and light chain CDR1, CDR2 and CDR3 sequences set forth in SEQ ID NOs: 147, 148 and 149, respectively;

(vi) heavy chain CDR1, CDR2 and CDR3 sequences set forth in SEQ ID NOs: 161, 162 and 163, respectively, and light chain CDR1, CDR2 and CDR3 sequences set forth in SEQ ID NOs: 169, 170 and 171, respectively;

(vii) heavy chain CDR1, CDR2 and CDR3 sequences set forth in SEQ ID NOs: 185, 186 and 187, respectively, and light chain CDR1, CDR2 and CDR3 sequences set forth in SEQ ID NOs: 193, 194 and 195, respectively;

(viii) heavy chain CDR1, CDR2 and CDR3 sequences set forth in SEQ ID NOs: 207, 208 and 209, respectively, and light chain CDR1, CDR2 and CDR3 sequences set forth in SEQ ID NOs: 215, 216 and 217, respectively;

(ix) heavy chain CDR1, CDR2 and CDR3 sequences set forth in SEQ ID NOs: 229, 230 and 231, respectively, and light chain CDR1, CDR2 and CDR3 sequences set forth in SEQ ID NOs: 237, 238 and 239, respectively;

(x) heavy chain CDR1, CDR2 and CDR3 sequences set forth in SEQ ID NOs: 251, 252 and 253, respectively, and light chain CDR1, CDR2 and CDR3 sequences set forth in SEQ ID NOs: 259, 260 and 261, respectively;

(xi) heavy chain CDR1, CDR2 and CDR3 sequences set forth in SEQ ID NOs: 273, 274 and 275, respectively, and light chain CDR1, CDR2 and CDR3 sequences set forth in SEQ ID NOs: 281, 282 and 283, respectively;

(xii) heavy chain CDR1, CDR2 and CDR3 sequences set forth in SEQ ID NOs: 295, 296 and 297, respectively, and light chain CDR1, CDR2 and CDR3 sequences set forth in SEQ ID NOs: 303, 304 and 305, respectively;

(xiii) heavy chain CDR1, CDR2 and CDR3 sequences set forth in SEQ ID NOs: 317, 318 and 319, respectively, and light chain CDR1, CDR2 and CDR3 sequences set forth in SEQ ID NOs: 325, 326 and 327, respectively;

(xiv) heavy chain CDR1, CDR2 and CDR3 sequences set forth in SEQ ID NOs: 339, 340 and 341, respectively, and light chain CDR1, CDR2 and CDR3 sequences set forth in SEQ ID NOs: 347, 348 and 349, respectively;

(xv) heavy chain CDR1, CDR2 and CDR3 sequences set forth in SEQ ID NOs: 361, 362 and 363, respectively, and light chain CDR1, CDR2 and CDR3 sequences set forth in SEQ ID NOs: 369, 370 and 371, respectively; and (xvi) heavy chain CDR1, CDR2 and CDR3 sequences set forth in SEQ ID NOs: 383, 384 and 385, respectively, and light chain CDR1, CDR2 and CDR3 sequences set forth in SEQ ID NOs: 391, 392 and 393, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 161, 162 and 163, respectively, and the light chain CDR1, CDR2 and CDR3 sequences are set forth in SEQ ID NOs: 169, 170 and 171, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs selected from the group consisting of:

(i) heavy chain CDR1, CDR2 and CDR3 sequences set forth in SEQ ID NOs: 54, 55 and 56, respectively, and light chain CDR1, CDR2 and CDR3 sequences set forth in SEQ ID NOs: 62, 63 and 64, respectively;

(ii) heavy chain CDR1, CDR2 and CDR3 sequences set forth in SEQ ID NOs: 76, 77 and 78, respectively, and light chain CDR1, CDR2 and CDR3 sequences set forth in SEQ ID NOs: 84, 85 and 86, respectively;

(iii) heavy chain CDR1, CDR2 and CDR3 sequences set forth in SEQ ID NOs: 98, 99 and 100, respectively, and light chain CDR1, CDR2 and CDR3 sequences set forth in SEQ ID NOs: 106, 107 and 108, respectively;

(iv) heavy chain CDR1, CDR2 and CDR3 sequences set forth in SEQ ID NOs: 120, 121 and 122, respectively, and light chain CDR1, CDR2 and CDR3 sequences set forth in SEQ ID NOs: 128, 129 and 130, respectively;

(v) heavy chain CDR1, CDR2 and CDR3 sequences set forth in SEQ ID NOs: 142, 143 and 144, respectively, and light chain CDR1, CDR2 and CDR3 sequences set forth in SEQ ID NOs: 150, 151 and 152, respectively;

(vi) heavy chain CDR1, CDR2 and CDR3 sequences set forth in SEQ ID NOs: 164, 165 and 166, respectively, and light chain CDR1, CDR2 and CDR3 sequences set forth in SEQ ID NOs: 172, 173 and 174, respectively;

(vii) heavy chain CDR1, CDR2 and CDR3 sequences set forth in SEQ ID NOs: 188, 189 and 190, respectively, and light chain CDR1, CDR2 and CDR3 sequences set forth in SEQ ID NOs: 196, 197 and 198, respectively;

(viii) heavy chain CDR1, CDR2 and CDR3 sequences set forth in SEQ ID NOs: 210, 211 and 212, respectively, and light chain CDR1, CDR2 and CDR3 sequences set forth in SEQ ID NOs: 218, 219 and 220, respectively;

(ix) heavy chain CDR1, CDR2 and CDR3 sequences set forth in SEQ ID NOs: 232, 233 and 234, respectively, and light chain CDR1, CDR2 and CDR3 sequences set forth in SEQ ID NOs: 240, 241 and 242, respectively;

(x) heavy chain CDR1, CDR2 and CDR3 sequences set forth in SEQ ID NOs: 254, 255 and 256, respectively, and light chain CDR1, CDR2 and CDR3 sequences set forth in SEQ ID NOs: 262, 263 and 264, respectively;

(xi) heavy chain CDR1, CDR2 and CDR3 sequences set forth in SEQ ID NOs: 276, 277 and 278, respectively, and light chain CDR1, CDR2 and CDR3 sequences set forth in SEQ ID NOs: 284, 285 and 286, respectively;

(xii) heavy chain CDR1, CDR2 and CDR3 sequences set forth in SEQ ID NOs: 298, 299 and 300, respectively, and light chain CDR1, CDR2 and CDR3 sequences set forth in SEQ ID NOs: 306, 307 and 308, respectively;

(xiii) heavy chain CDR1, CDR2 and CDR3 sequences set forth in SEQ ID NOs: 320, 321 and 322, respectively, and light chain CDR1, CDR2 and CDR3 sequences set forth in SEQ ID NOs: 328, 329 and 330, respectively;

(xiv) heavy chain CDR1, CDR2 and CDR3 sequences set forth in SEQ ID NOs: 342, 343 and 344, respectively, and light chain CDR1, CDR2 and CDR3 sequences set forth in SEQ ID NOs: 350, 351 and 352, respectively;

(xv) heavy chain CDR1, CDR2 and CDR3 sequences set forth in SEQ ID NOs: 364, 365 and 366, respectively, and light chain CDR1, CDR2 and CDR3 sequences set forth in SEQ ID NOs: 372, 373 and 374, respectively; and (xvi) heavy chain CDR1, CDR2 and CDR3 sequences set forth in SEQ ID NOs: 386, 387 and 388, respectively, and light chain CDR1, CDR2 and CDR3 sequences set forth in SEQ ID NOs: 394, 395 and 396, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 164, 165 and 166, respectively, and the light chain CDR1, CDR2 and CDR3 sequences are set forth in SEQ ID NOs: 172, 173 and 174, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs, wherein the amino acid sequences of heavy chain CDR1, CDR2 and CDR3 are SYSMS (SEQ ID NO: 23), YISYDGGSAYYPDTVKG (SEQ ID NO: 24) and HGDYDDDDAMDY (SEQ ID NO: 25), respectively, and wherein the amino acid sequences of light chain CDR1, CDR2 and CDR3 are RASENIYSYLA (SEQ ID NO: 26), NAETLTE (SEQ ID NO: 27) and QHHYGTPLT (SEQ ID NO: 28), respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions, wherein the heavy chain variable region comprises an amino acid sequence selected from the group consisting of SEQ ID NOs: 57, 79, 101, 123, 145, 167, 191, 213, 235, 257, 279, 301, 323, 345, 367 and 389; and wherein the light chain variable region comprises an amino acid sequence selected from the group consisting of SEQ ID NOs: 65, 87, 109, 131, 153, 175, 199, 221, 243, 265, 287, 309, 331, 353, 375 and 397.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences selected from the group consisting of:

(i) SEQ ID NO: 57 and 65, respectively;
(ii) SEQ ID NO: 79 and 87, respectively;
(iii) SEQ ID NO: 101 and 109, respectively;
(iv) SEQ ID NO: 123 and 131, respectively;
(v) SEQ ID NO: 145 and 153, respectively;
(vi) SEQ ID NO: 167 and 175, respectively;
(vii) SEQ ID NO: 191 and 199, respectively;
(viii) SEQ ID NO: 213 and 221, respectively;
(ix) SEQ ID NO: 235 and 243, respectively;
(x) SEQ ID NO: 257 and 265, respectively;
(xi) SEQ ID NO: 279 and 287, respectively;
(xii) SEQ ID NO: 301 and 309, respectively;
(xiii) SEQ ID NO: 323 and 331, respectively;
(xiv) SEQ ID NO: 345 and 353, respectively;
(xv) SEQ ID NO: 367 and 375, respectively; and
(xvi) SEQ ID NO: 389 and 397, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions, wherein the heavy chain variable region comprises an amino acid sequence which is at least 90% identical to the amino acid sequence selected from the group consisting of SEQ ID NOs: 57, 79, 101, 123, 145, 167, 191, 213, 235, 257, 279, 301, 323, 345, 367 and 389; and wherein the light chain variable region comprises an amino acid sequence which is at least 90% identical to the amino acid sequence selected from the group consisting of SEQ ID NOs: 65, 87, 109, 131, 153, 175, 199, 221, 243, 265, 287, 309, 331, 353, 375 and 397.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences at least 90% identical to the amino acid sequences selected from the group consisting of:

(i) SEQ ID NO: 57 and 65, respectively;
(ii) SEQ ID NO: 79 and 87, respectively;
(iii) SEQ ID NO: 101 and 109, respectively;
(iv) SEQ ID NO: 123 and 131, respectively;
(v) SEQ ID NO: 145 and 153, respectively;
(vi) SEQ ID NO: 167 and 175, respectively;
(vii) SEQ ID NO: 191 and 199, respectively;
(viii) SEQ ID NO: 213 and 221, respectively;
(ix) SEQ ID NO: 235 and 243, respectively;
(x) SEQ ID NO: 257 and 265, respectively;
(xi) SEQ ID NO: 279 and 287, respectively;
(xii) SEQ ID NO: 301 and 309, respectively;
(xiii) SEQ ID NO: 323 and 331, respectively;
(xiv) SEQ ID NO: 345 and 353, respectively;
(xv) SEQ ID NO: 367 and 375, respectively; and
(xvi) SEQ ID NO: 389 and 397, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences set forth in SEQ ID NO: 167 and 175, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences at least 90% identical to the amino acid sequences set forth in SEQ ID NO: 167 and 175, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain, wherein the heavy chain comprises an amino acid sequence selected from the group consisting of SEQ ID NOs: 67, 89, 111, 133, 155, 177, 201, 223, 245, 267, 289, 311, 333, 355, 377 and 399; and wherein the light chain comprises an amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy and a light chain, wherein the heavy chain comprises an amino acid sequence which is at least 90% identical to the amino acid sequence selected from the group consisting of SEQ ID NOs: 67, 89, 111, 133, 155, 177, 201, 223, 245, 267, 289, 311, 333, 355, 377 and 399; and wherein the light chain comprises an amino acid sequence which is at least 90% identical to the amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain, wherein the heavy chain comprises an amino acid sequence selected from the group consisting of SEQ ID NOs: 71, 93, 115, 137, 159, 181, 205, 227, 249, 271, 293, 315, 337, 359, 381 and 403; and wherein the light chain comprises an amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy and a light chain, wherein the heavy chain comprises an amino acid sequence which is at least 90% identical to the amino acid sequence selected from the group consisting of SEQ ID NOs: 71, 93, 115, 137, 159, 181, 205, 227, 249, 271, 293, 315, 337, 359, 381 and 403; and wherein the light chain comprises an amino acid sequence which is at least 90% identical to the amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences selected from the group consisting of:

(i) SEQ ID NO: 67 and 69, respectively;
(ii) SEQ ID NO: 89 and 91, respectively;
(iii) SEQ ID NO: 111 and 113, respectively;
(iv) SEQ ID NO: 133 and 135, respectively;
(v) SEQ ID NO: 155 and 157, respectively;
(vi) SEQ ID NO: 177 and 179, respectively;
(vii) SEQ ID NO: 201 and 203, respectively;
(viii) SEQ ID NO: 223 and 225, respectively;
(ix) SEQ ID NO: 245 and 247, respectively;
(x) SEQ ID NO: 267 and 269, respectively;
(xi) SEQ ID NO: 289 and 291, respectively;
(xii) SEQ ID NO: 311 and 313, respectively;
(xiii) SEQ ID NO: 333 and 335, respectively;
(xiv) SEQ ID NO: 355 and 357, respectively;
(xv) SEQ ID NO: 377 and 379, respectively; and
(xvi) SEQ ID NO: 399 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences at least 90% identical to the amino acid sequences selected from the group consisting of:

(i) SEQ ID NO: 67 and 69, respectively;
(ii) SEQ ID NO: 89 and 91, respectively;
(iii) SEQ ID NO: 111 and 113, respectively;
(iv) SEQ ID NO: 133 and 135, respectively;
(v) SEQ ID NO: 155 and 157, respectively;
(vi) SEQ ID NO: 177 and 179, respectively;
(vii) SEQ ID NO: 201 and 203, respectively;
(viii) SEQ ID NO: 223 and 225, respectively;
(ix) SEQ ID NO: 245 and 247, respectively;

(x) SEQ ID NO: 267 and 269, respectively;
(xi) SEQ ID NO: 289 and 291, respectively;
(xii) SEQ ID NO: 311 and 313, respectively;
(xiii) SEQ ID NO: 333 and 335, respectively;
(xiv) SEQ ID NO: 355 and 357, respectively;
(xv) SEQ ID NO: 377 and 379, respectively; and
(xvi) SEQ ID NO: 399 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy and a light chain comprising amino acid sequences selected from the group consisting of:

(i) SEQ ID NO: 71 and 69, respectively;
(ii) SEQ ID NO: 93 and 91, respectively;
(iii) SEQ ID NO: 115 and 113, respectively;
(iv) SEQ ID NO: 137 and 135, respectively;
(v) SEQ ID NO: 159 and 157, respectively;
(vi) SEQ ID NO: 181 and 179, respectively;
(vii) SEQ ID NO: 205 and 203, respectively;
(viii) SEQ ID NO: 227 and 225, respectively;
(ix) SEQ ID NO: 249 and 247, respectively;
(x) SEQ ID NO: 271 and 269, respectively;
(xi) SEQ ID NO: 293 and 291, respectively;
(xii) SEQ ID NO: 315 and 313, respectively;
(xiii) SEQ ID NO: 337 and 335, respectively;
(xiv) SEQ ID NO: 359 and 357, respectively;
(xv) SEQ ID NO: 381 and 379, respectively; and
(xvi) SEQ ID NO: 403 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy and a light chain comprising amino acid sequences at least 90% identical to the amino acid sequences selected from the group consisting of:

(i) SEQ ID NO: 71 and 69, respectively;
(ii) SEQ ID NO: 93 and 91, respectively;
(iii) SEQ ID NO: 115 and 113, respectively;
(iv) SEQ ID NO: 137 and 135, respectively;
(v) SEQ ID NO: 159 and 157, respectively;
(vi) SEQ ID NO: 181 and 179, respectively;
(vii) SEQ ID NO: 205 and 203, respectively;
(viii) SEQ ID NO: 227 and 225, respectively;
(ix) SEQ ID NO: 249 and 247, respectively;
(x) SEQ ID NO: 271 and 269, respectively;
(xi) SEQ ID NO: 293 and 291, respectively;
(xii) SEQ ID NO: 315 and 313, respectively;
(xiii) SEQ ID NO: 337 and 335, respectively;
(xiv) SEQ ID NO: 359 and 357, respectively;
(xv) SEQ ID NO: 381 and 379, respectively; and
(xvi) SEQ ID NO: 403 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences set forth in SEQ ID NO: 177 and 179, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences at least 90% identical to the amino acid sequences set forth in SEQ ID NO: 177 and 179, respectively.

In some embodiments, the disclosure provides an isolated monoclonal antibody that specifically binds to and antagonizes human IL-27, or antigen binding portion thereof, wherein the antibody or antigen binding portion thereof comprises a heavy and a light chain comprising amino acid sequences set forth in SEQ ID NO: 181 and 179, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences at least 90% identical to the amino acid sequences set forth in SEQ ID NO: 181 and 179, respectively.

In some embodiments, the disclosure provides a method to inhibit or reduce STAT1 and/or STAT3 phosphorylation in a cell, the method comprising contacting the cell with an isolated monoclonal antibody, or antigen binding fragment, provided by the disclosure, wherein the antibody, or antigen binding portion thereof, inhibits or reduces STAT1 and/or STAT3 phosphorylation in a cell.

In some embodiments, the disclosure provides a method to inhibit or reduce IL-27 mediated inhibition of CD161 expression in a cell, the method comprising contacting the cell with an isolated monoclonal antibody, or antigen binding fragment, provided by the disclosure, wherein the antibody, or antigen binding portion thereof, inhibits or reduces inhibition of CD161 expression in a cell.

In some embodiments, the disclosure provides a method to inhibit or reduce IL-27 mediated expression of PD-L1 and/or TIM-3 expression in a cell, the method comprising contacting the cell with an isolated monoclonal antibody, or antigen binding fragment, provided by the disclosure, wherein the antibody, or antigen binding portion thereof, inhibits or PD-L1 and/or TIM-3 expression in a cell.

In some embodiments, the disclosure provides a method to induce or enhance secretion of one or more cytokines from a cell, the method comprising contacting the cell with the isolated monoclonal antibody, or antigen binding fragment, provided by the disclosure, wherein the antibody, or antigen binding portion thereof, induces or enhances PD-1 mediated secretion of one or more cytokines from a cell.

In some embodiments, the disclosure provides a method of stimulating an immune response in a subject, the method comprising administering to the subject an effective amount of an isolated monoclonal antibody, or antigen binding portion thereof, that specifically binds to and antagonizes IL-27, provided by the disclosure, or a pharmaceutical composition comprising the antibody or antigen binding portion thereof, and a pharmaceutically acceptable carrier.

In some embodiments, the disclosure provides a method of treating a cancer in a subject, the method comprising administering to the subject an effective amount an isolated monoclonal antibody, or antigen binding portion thereof, that specifically binds to and antagonizes IL-27, provided by the disclosure, or a pharmaceutical composition comprising the antibody or antigen binding portion thereof, and a pharmaceutically acceptable carrier.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, inhibits or reduces STAT1 and/or STAT3 phosphorylation in a cell, thereby stimulating the immune response, or treating the cancer.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, inhibits or reduces IL-27 mediated inhibition of CD161 expression in a cell, thereby stimulating the immune response, or treating the cancer.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, inhibits or reduces IL-27 mediated expression of PD-L1 and/or TIM-3 expression in a cell, thereby stimulating the immune response, or treating the cancer.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, induces or enhances PD-1-mediated secretion of one or more cytokines from a cell, thereby stimulating the immune response, or treating the cancer.

In some embodiments, the cancer is chosen from lung cancer (e.g., non-small cell lung cancer), sarcoma, testicular cancer, ovarian cancer, pancreas cancer, breast cancer (e.g., triple-negative breast cancer), melanoma (including, e.g., uveal melanoma, etc.), head and neck cancer (e.g., squamous head and neck cancer), colorectal cancer, bladder cancer, endometrial cancer, prostate cancer, thyroid cancer, hepatocellular carcinoma, gastric cancer, brain cancer, lymphoma (e.g., DL-BCL), leukemia (e.g., AML) or renal cancer (e.g., renal cell carcinoma, e.g., renal clear cell carcinoma).

In some embodiments, the disclosure provides a method of treating cancer in a subject, the method comprising administering to the subject an effective amount of an isolated monoclonal antibody, or antigen binding portion thereof, that specifically binds to and antagonizes IL-27, provided by the disclosure, in combination with one or more additional therapeutic agents or procedure, wherein the second therapeutic agent or procedure is selected from the group consisting of: a chemotherapy, a targeted anti-cancer therapy (including, e.g., Tyrosine Kinase Inhibitors (TKIs), an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

In some embodiments, the one or more additional therapeutic agents is a PD-1 antagonist, a PD-L1 inhibitor, a TIM-3 inhibitor, a LAG-3 inhibitor, a TIGIT inhibitor, a CD112R inhibitor, a TAM inhibitor, a STING agonist, a 4-1BB agonist, or a combination thereof.

In some embodiments, the one or more additional therapeutic agents is a PD-1 antagonist. In some embodiments, the PD-1 antagonist is selected from the group consisting of: PDR001, nivolumab, pembrolizumab, pidilizumab, MEDI0680, REGN2810, TSR-042, PF-06801591, and AMP-224.

In certain embodiments, the one or more additional therapeutic agents is a PD-L1 inhibitor. In some embodiments, the PD-L1 inhibitor is selected from the group consisting of: FAZ053, Atezolizumab, Avelumab, Durvalumab, and BMS-936559. In some embodiments, the disclosure provides a method of enhancing one or more activities of an anti-PD-1 antibody (e.g., enhances PD-1-mediated cytokine secretion; enhances anti-PD-1 mediated TNFα secretion; enhances anti-PD-1 mediated IL-6 secretion from a cell exposed to anti-PD-1 antibodies), the method comprising exposing a cell to an antibody, or antigen binding portion thereof, provided by the disclosure, concurrently with or sequentially to an anti-PD-1 antibody, thereby to enhance one or more activities of the anti-PD1 antibody.

In certain embodiments, the instant disclosure provides a pharmaceutical composition that includes an anti-PD-1 antibody and/or an anti-PD-L1 antibody, and an antibody or antigen binding portion thereof as disclosed herein (e.g., an anti-IL-27 antibody), and a pharmaceutically acceptable carrier.

In a related embodiment, the instant disclosure provides a kit that includes an anti-PD-1 antibody and/or an anti-PD-L1 antibody, and an antibody or antigen binding portion thereof as disclosed herein (e.g., an anti-IL-27 antibody), for concurrent or sequential administration, and instructions for its use.

In some embodiments, the one or more additional therapeutic agents is a TIM-3 inhibitor, optionally wherein the TIM-3 inhibitor is MGB453 or TSR-022.

In some embodiments, the one or more additional therapeutic agents is a LAG-3 inhibitor, optionally wherein the LAG-3 inhibitor is selected from the group consisting of LAG525, BMS-986016, and TSR-033.

In some embodiments, the one or more additional therapeutic agents is a TIGIT inhibitor. In some embodiments, the one or more additional therapeutic agents is a CD112R inhibitor. In some embodiments, the one or more additional therapeutic agents is a TAM (Axl, Mer, Tyro) inhibitor. In some embodiments, the one or more additional therapeutic agents is a STING agonist. In some embodiments, the one or more additional therapeutic agents is a 4-1BB agonist.

In some embodiments, the disclosure provides a method of detecting IL-27 in a sample from a subject, the method comprising (a) contacting a sample from the subject with a detection antibody under conditions to permit the detection antibody to form a detection antibody-IL-27 complex, if IL-27 is present in the sample, wherein the detection antibody is an antibody, or antigen binding fragment thereof, provided by the disclosure; and (b) detecting the presence of the complex, if any, produced in step (a).

In some embodiments, the disclosure provides a method of detecting an IL-27-associated cancer in a subject, the method comprising the steps of: (a) contacting a sample from a subject suspected of having an IL-27-associated cancer with a detection antibody under conditions to permit the detection antibody to form a detection antibody-IL-27 complex, if IL-27 is present in the sample, wherein the detection antibody is an antibody, or antigen binding portion thereof, provided by the disclosure; and (b) detecting the presence of the complex, if any, produced in step (a). In some embodiments, the detection antibody is coupled to a detectable label. In some embodiments, the method further comprises contacting the sample with a capture antibody to produce a complex comprising IL-27 and the capture antibody, if IL-27 is present in the sample, wherein the capture antibody is an antibody, or antigen binding portion thereof, provided by the disclosure.

In some embodiments, the detection antibody or the capture antibody comprises heavy and light chain CDRs, wherein the amino acid sequences of heavy chain CDR1, CDR2 and CDR3 are SYSMS (SEQ ID NO: 23), YISYDGGSAYYPDTVKG (SEQ ID NO: 24) and HGDYDDDDAMDY (SEQ ID NO: 25), respectively, and wherein the amino acid sequences of light chain CDR1, CDR2 and CDR3 are RASENIYSYLA (SEQ ID NO: 26), NAETLTE (SEQ ID NO: 27) and QHHYGTPLT (SEQ ID NO: 28), respectively.

In some embodiments, the detection antibody or the capture antibody comprises heavy and light chain variable regions comprising amino acid sequences set forth in SEQ ID NO: 1 and SEQ ID NO: 3, respectively.

In some embodiments, the capture antibody is immobilized on a solid support. In some embodiments, the sample is contacted with the capture antibody before the detection antibody. In some embodiments, the sample is a body fluid sample. In some embodiments, the fluid sample is blood, serum, plasma, cell lysates or tissue lysates.

In some embodiments, the cancer is selected from renal cell carcinoma (RCC), hepatocellular carcinoma (HCC), lung cancer, gastroesophageal cancer, ovarian cancer, endometrial cancer, melanoma, leukemia and lymphoma. In some embodiments, the cancer is renal cell carcinoma (RCC). In other embodiments, the cancer is hepatocellular carcinoma (HCC). In some embodiments, the cancer is selected from leukemia and lymphoma. In some embodiments, the cancer is acute myeloid leukemia (AML).

Definitions

Terms used in the claims and specification are defined as set forth below unless otherwise specified.

It must be noted that, as used in the specification and the appended claims, the singular forms "a," "an" and "the" include plural references unless the context clearly dictates otherwise.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "agonist" refers to any molecule that partially or fully promotes, induces, increases, and/or activates a biological activity of a native polypeptide disclosed herein. Suitable agonist molecules specifically include agonist antibodies or antibody fragments, fragments or amino acid sequence variants of native polypeptides, peptides or proteins. In some embodiments, activation in the presence of the agonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an agonist to bind the polypeptide of interest (e.g., a receptor or ligand) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

As used herein, the term "alanine scanning" refers to a technique used to determine the contribution of a specific wild-type residue to the stability or function(s) (e.g., binding affinity) of given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "amount" or "level" is used in the broadest sense and refers to a quantity, concentration or abundance of a substance (e.g., a metabolite, a small molecule, a protein, an mRNA, a marker). When referring to a metabolite or small molecule (e.g. a drug), the terms "amount", "level" and "concentration" are generally used interchangeably and generally refer to a detectable amount in a biological sample. "Elevated levels" or "increased levels" refers to an increase in the quantity, concentration or abundance of a substance within a sample relative to a control sample, such as from an individual or individuals who are not suffering from the disease or disorder (e.g., cancer) or an internal control. In some embodiments, the elevated level of a substance (e.g., a drug) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., HPLC). "Reduced levels" refers to a decrease in the quantity, concentration or abundance of a substance (e.g., a drug) in an individual relative to a control, such as from an individual or individuals who are not suffering from the disease or disorder (e.g., cancer) or an internal control. In some embodiments, a reduced level is little or no detectable quantity, concentration or abundance. In some embodiments, the reduced level of a substance (e.g., a drug) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g, HPLC).

When referring to a protein, mRNA or a marker, such as those described herein, the terms "level of expression" or "expression level" in general are used interchangeably and generally refer to a detectable amount of a protein, mRNA, or marker in a biological sample. In some aspects, a detectable amount or detectable level of a protein, mRNA or a marker is associated with a likelihood of a response to an agent, such as those described herein. "Expression" generally refers to the process by which information contained within a gene is converted into the structures (e.g., a protein marker, such as PD-L1) present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., posttranslational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). "Elevated expression," "elevated expression levels," or "elevated levels" refers to an increased expression or increased levels of a substance within a sample relative to a control sample, such as an individual or individuals who are not suffering from the disease or disorder (e.g., cancer) or an internal control. In some embodiments, the elevated expression of a substance (e.g., a protein marker, such as PD-L1) in a sample refers to an increase in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g., FACS). "Reduced expression," "reduced expression levels," or "reduced levels" refers to a decrease expression or decreased levels of a substance (e.g., a protein marker) in an individual relative to a control, such as an individual or individuals who are not suffering from the disease or disorder (e.g., cancer) or an internal control. In some embodiments, reduced expression is little or no expression. In some embodiments, the reduced expression of a substance (e.g., a protein marker) in a sample refers to a decrease in the amount of the substance of about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% relative to the amount of the substance in a control sample, as determined by techniques known in the art (e.g, FACS).

As used herein, the term "angiogenesis" or "neovascularization" refers to the process by which new blood vessels develop from pre-existing vessels (Varner et al., (1999) *Angiogen.* 3:53-60; Mousa et al., (2000) *Angiogen. Stim. Inhib.* 35:42-44; Kim et al., (2000) *Amer. J. Path.* 156:1345-1362; Kim et al., (2000) *J. Biol. Chem.* 275:33920-33928; Kumar et al. (2000) *Angiogenesis: From Molecular to Integrative Pharm.* 169-180), Endothelial cells from pre-existing blood vessels or from circulating endothelial stem cells (Takahashi et al., (1995) *Nat. Med* 5:434-438; Ismer et al., (1999) J. Clin. Invest. 103:1231-1236) become activated to migrate, proliferate, and differentiate into structures with lumens, forming new blood vessels, in response to growth factor or hormonal cues, or hypoxic or ischemic conditions, During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

As used herein, the term "antagonist" refers to any molecule that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides or proteins. In some embodiments, inhibition in the presence of the antagonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), Forte Bio© systems, radioimmunoassay (RIA), Meso Scale Discovery assay (e.g., Meso Scale Discovery Electrochemiluminescence (MSD-ECL), and bead-based Luminex® assay. These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the phrase "antibody that antagonizes human IL-27, or an antigen binding portion thereof" refers to an antibody that antagonizes at least one art-recognized activity of human IL-27 (e.g., IL-27 biological activity and/or downstream pathway(s) mediated by IL-27 signaling or other IL-27-mediated function), for example, relating to a decrease (or reduction) in human IL-27 activity that is at least 5%, 10%, 20%, 30%, 40%, 50%, 60%, 70%, 80%, 90%, or more. Additional examples of IL-27 biological activities and/or downstream pathway(s) mediated by IL-27 signaling or other IL-27-mediated function are described in additional detail below and elsewhere herein.

As used herein, the term "anti-IL-27 antagonist antibody" (interchangeably termed "anti-IL-27 antibody") refers to an antibody that specifically binds to IL-27 and inhibits IL-27 biological activity and/or downstream pathway(s) mediated by IL-27 signaling or other IL-27-mediated function. An anti-IL-27 antagonist antibody encompasses antibodies that block, antagonize, suppress, inhibit or reduce an IL-27 biological activity (e.g., ligand binding, enzymatic activity), including downstream pathways mediated by IL-27 signaling or function, such as receptor binding and/or elicitation of a cellular response to IL-27 or its metabolites. In some embodiments, an anti-IL-27 antagonist antibody provided by the disclosure binds to human IL-27 and prevents, blocks, or inhibits binding of human IL-27 to its cognate or normal receptor (e.g., IL-27 receptor), or one or more receptor subunits (e.g., gp130 and/or IL-27Rα (also known as WSX1/TCCR)). In some embodiments, the anti-IL-27 antagonist antibody prevents, blocks, or inhibits the binding of human IL-27 to the gp130. In some embodiments, the anti-IL-27 antagonist antibody prevents, blocks, or inhibits the binding of human IL-27 to the IL-27Rα. In some embodiments, the anti-IL-27 antagonist antibody prevents, blocks, or inhibits the dimerization of IL-27 monomers. In some embodiments, the anti-IL-27 antibody specifically binds to the EBI3 monomer. In some embodiments, the anti-IL-27 antibody specifically binds to the IL-27p28 monomer. In some embodiments, the anti-IL-27 antibody specifically binds to both IL-27 monomers. In some embodiments, the anti-IL-27 antibody specifically binds to a non-contiguous epitope comprising both EBI3 and P28. In some embodiments, the anti-IL-27 antibody inhibits or reduces STAT1 and/or STAT3 phosphorylation in a cell. In some embodiments, the anti-IL-27 antibody inhibits or reduces inhibition of CD161 expression in a cell (e.g., ameliorates or relieves IL-27 mediated inhibition of CD161 expression in a cell). In some embodiments, the anti-IL-27 antibody inhibits or reduces PD-L1 and/or TIM-3 expression in a cell. In some embodiments, the anti-IL-27 induces or enhances PD-1-mediated secretion of one or more cytokines from a cell. In some embodiments, an anti-IL-27 antagonist antibody binds to human IL-27 and stimulates or enhances an anti-tumor response. In some embodiments, the anti-IL-27 antagonist antibody binds to human IL-27 with an affinity of 15 nM or less. In some embodiments, the anti-IL-27 antagonist antibody binds to human IL-27 and comprises a wild type or mutant IgG1 heavy chain constant region or a wild type or mutant IgG4 heavy chain constant region. Examples of anti-IL-27 antagonist antibodies are provided herein.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody. As used herein, the term "antibody fragment," "antigen-binding fragment," or similar terms refer to a fragment of an antibody that retains the ability to bind to a target antigen (e.g., IL-27) and inhibit the activity of the target antigen. Such fragments include, e.g., a single chain antibody, a single chain Fv fragment (scFv), an Fd fragment, an Fab fragment, an Fab' fragment, or an F(ab')2 fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al., (2001) *J. Immunol. Methods* 248(1):47-66; Hudson and Kortt, (1999) *J. Immunol. Methods* 231(1):177-189; Poljak, (1994) *Structure* 2(12): 1121-1123; Rondon and Marasco, (1997) *Annu. Rev. Microbiol.* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al., (2001) *Trends Biochem. Sci.* 26:230-235; Nuttall et al., (2000) *Curr. Pharm. Biotech.* 1:253-263; Reichmann et al., (1999) *J. Immunol. Meth.* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

In some embodiments, an antigen-binding fragment includes the variable region of a heavy chain polypeptide and the variable region of a light chain polypeptide. In some embodiments, an antigen-binding fragment described herein comprises the CDRs of the light chain and heavy chain polypeptide of an antibody.

The term "antigen presenting cell" or "APC" is a cell that displays foreign antigen complexed with MHC on its surface. T cells recognize this complex using T cell receptor (TCR). Examples of APCs include, but are not limited to, B cells, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "apoptosis" refers to the process of programmed cell death that occurs in multicellular organisms (e.g. humans). The highly-regulated biochemical and molecular events that result in apoptosis can lead to observable and characteristic morphological changes to a cell, including membrane blebbing, cell volume shrinkage, chromosomal DNA condensation and fragmentation, and mRNA decay. A common method to identify cells, including T cells, undergoing apoptosis is to expose cells to a fluorophore-conjugated protein (Annexin V). Annexin V is commonly used to detect apoptotic cells by its ability to bind to phosphatidylserine on the outer leaflet of the plasma membrane, which is an early indicator that the cell is undergoing the process of apoptosis.

As used herein, the term "B cell" (alternatively "B lymphocyte") refers to a type of white blood cell of the lymphocyte subtype. B cells function in the humoral immunity component of the adaptive immune system by secreting antibodies. B cells also present antigen and secrete cytokines. B cells, unlike the other two classes of lymphocytes, T cells and natural killer cells, express B cell receptors (BCRs) on their cell membrane. BCRs allow the B cell to bind to a specific antigen, against which it will initiate an antibody response.

As used herein, the term "binds to immobilized IL-27," refers to the ability of an antibody of the disclosure to bind to IL-27, for example, expressed on the surface of a cell or which is attached to a solid support.

As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) J. Immunol. 148:1547-1553.

Traditionally, the recombinant production of bispecific antibodies is based on the co-expression of two immunoglobulin heavy-chain/light-chain pairs, where the two heavy chain/light-chain pairs have different specificities (Milstein and Cuello, (1983) Nature 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al., (1986) *Methods Enzymol.* 121:210; PCT Publication No. WO 96/27011; Brennan et al., (1985) *Science* 229:81; Shalaby et al., *J. Exp. Med.* (1992) 175:217-225; Kostelny et al., (1992) *J. Immunol.* 148(5): 1547-1553; Hollinger et al., (1993) *Proc. Natl. Acad. Sci. USA* 90:6444-6448; Gruber et al., (1994) *J. Immunol.* 152: 5368; and Tutt et al., (1991) *J. Immunol.* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368. Alternatively, the antibodies can be "linear antibodies" as described in, e.g., Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

Antibodies with more than two valencies (e.g., trispecific antibodies) are contemplated and described in, e.g., Tutt et al. (1991) J Immunol 147:60.

The disclosure also embraces variant forms of multi-specific antibodies such as the dual variable domain immunoglobulin (DVD-Ig) molecules described in Wu et al. (2007) Nat Biotechnol 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715. In some embodiments, the bispecific antibody is a Fabs-in-Tandem immunoglobulin, in which the light chain variable region with a second specificity is fused to the heavy chain variable region of a whole antibody. Such antibodies are described in, e.g., International Patent Application Publication No. WO 2015/103072.

As used herein, "cancer antigen" or "tumor antigen" refers to (i) tumor-specific antigens, (ii) tumor-associated antigens, (iii) cells that express tumor-specific antigens, (iv)

cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, the term "cancer-specific immune response" refers to the immune response induced by the presence of tumors, cancer cells, or cancer antigens. In certain embodiments, the response includes the proliferation of cancer antigen specific lymphocytes. In certain embodiments, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain embodiments, the cancer-specific immune response is a T cell response.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-IL-27 antibodies described herein can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein, the term "CD112R" refers to a member of poliovirus receptor-like proteins and is a co-inhibitory receptor for human T cells. CD112R is preferentially expressed on T cells and inhibits T cell receptor-mediated signals. CD112, widely expressed on antigen-presenting cells and tumor cells, is the ligand for CD112R. CD112R competes with CD226 to bind to CD112. Disrupting the CD112R-CD112 interaction enhances human T cell response. CD112R as a novel checkpoint for human T cells via interaction with CD112. As used herein the term "CD112R inhibitor" refers to an agent that disrupts, blocks or inhibits the biological function or activity of CD112R.

As used herein, the term "CD137" (alternatively "4-1BB") refers to a member of the tumor necrosis factor (TNF) receptor superfamily. 4-1BB is a co-stimulatory immune checkpoint molecule, primarily for activated T cells. Crosslinking of CD137 enhances T cell proliferation, IL-2 secretion, survival and cytolytic activity. As used herein, the term "4-1BB agonist" refers to an agent that stimulates, induces or increases one or more function of 4-1BB. An exemplary 4-1BB agonist is Utomilumab (PF-05082566), a fully human IgG2 monoclonal antibody that targets this 4-1BB to stimulate T cells.

As used herein, the term "CD161" (alternatively known as Killer cell lectin-like receptor subfamily B, member 1 (KLRB1); NK1.1, or NKR-P1A) refers to a member of the C-type lectin superfamily. CD161 is a marker of T cells and CD161 expression has been associated with T cell infiltration into the tumor microenvironment for a number of different cancer types. CD161 is further described in Fergusson et al., (2014) Cell Reports 9(3):1075-1088, which is incorporated herein by reference it its entirety.

As used herein, the term "IL-27" or "interleukin 27" refers to the IL-27 cytokine. IL-27 is related to the IL-6/IL-12 cytokine families, and is a heterodimeric cytokine that comprises a first subunit known as Epstein-Barr Virus Induced Gene 3 (EBI3; also known as IL-27 subunit β and IL-27B) and a second subunit known as IL-27p28 (also known as IL30, IL-27 subunit α and IL-27A). IL-27 is predominantly synthesized by activated antigen-presenting cells including monocytes, endothelial cells and dendritic cells (Jankowski et al. (2010) Arch Immunol. Ther. Exp. 58:417-425, Diakowski et al. (2013) Adv. Clin. Exp. Med. (2013) 22(5): 683-691). Although IL-27 can have proinflammatory effects, many studies suggest an important role of IL-27 as an immunosuppressive agent (Shimizu et al. (2006) J. Immunol. 176:7317-7324, Hisada et al. (2004) Cancer Res. 64:1152-1156, Diakowski (2013) supra). Although it was initially described as a factor promoting the initiation of Th1 responses, IL-27 was later found to play a major T-cell suppressive function by limiting Th1 responses, inhibiting Th2 and Th17 cell differentiation, and regulating the development of Tr1 and other T regulatory cell populations (Dietrich et al. (2014) J. Immunol. 192:5382-5389). In addition to its role as an immunoregulator, IL-27 also regulates angiogenesis, hematopoiesis, and osteocalstogenesis (Id.).

IL-27 signals through a heterodimeric type I cytokine receptor (the IL-27 receptor or IL-27R) that comprises a first subunit known as WSX1 (also known as IL-27 receptor subunit a, IL-27RA, T-Cell Cytokine Receptor Type 1 (TCCR), and Cytokine Receptor-Like 1 (CRL1)) and a second subunit known as gp130 (also known as Interleukin-6 Signal Transducer (IL6ST), Interleukin-6 Receptor Subunit β (IL-6RB), and Oncostatin M Receptor). gp130 is also a receptor subunit for the IL-6 family cytokines (Liu et al. (2008) Scan. J. Immunol. 68:22-299, Diakowski (2013) supra). IL-27 signaling through IL-27R activates multiple signaling cascades, including the JAK-STAT and p38 MAPK pathways.

EBI3 is also believed to have biological functions independent of p28 or the IL-27 heterodimer. For example, EBI3 also interacts with p35 to form the heterodimeric cytokine IL-35 (Yoshida et al. (2015) Annu. Rev Immunol. 33:417-43) and has been shown to be selectively overexpressed in certain cell types without a corresponding increase in p28 or IL-27 (Larousserie et al. (2005) Am. J. Pathol. 166(4):1217-28).

An amino acid sequence of an exemplary human EBI3 protein is provided in SEQ ID NO: 698 (NCBI Reference Sequence: NP_005746.2;

```
N-MTPQLLLALVLWASCPPCSGRKGPPAALTLPRVQCRASRYPIAVDCSW
TLPPAPNSTSPVSFIATYRLGMAARGHSWPCLQQTPTSTSCTITDVQLFS
MAPYVLNVTAVHPWGSSSSFVPFITEHIIKPDPPEGVRLSPLAERQLQVQ
WEPPGSWPFPEIFSLKYWIRYKRQGAARFHRVGPIEATSFILRAVRPRAR
YYVQVAAQDLTDYGELSDWSLPATATMSLGK-C).
```

An amino acid sequence of an exemplary human p28 protein is provided in SEQ ID NO: 699 (NCBI Reference Sequence: NP_663634.2;

N-MGQTAGDLGWRLSLLLLPLLLVQAGVWGFPRPPGRPQLSLQELRREFT
VSLHLARKLLSEVRGQAHRFAESHLPGVNLYLLPLGEQLPDVSLTFQAWR
RLSDPERLCFISTTLQPFHALLGGLGTQGRWTNMERMQLWAMRLDLRDLQ
RHLRFQVLAAGFNLPEEEEEEEEEEEEERKGLLPGALGSALQGPAQVSWP
QLLSTYRLLHSLELVLSRAVRELLLLSKAGHSVWPLGFPTLSPQP-C).

An amino acid sequence of an exemplary human WSX1 protein is provided in SEQ ID NO: 700 (NCBI Reference Sequence: NP_004834.1;

N-MRGGRGAPFWLWPLPKLALLPLLWVLFQRTRPQGSAGPLQCYGVGPLG
DLNCSWEPLGDLGAPSELHLQSQKYRSNKTQTVAVAAGRSWVAIPREQLT
MSDKLLVWGTKAGQPLWPPVFVNLETQMKPNAPRLGPDVDFSEDDPLEAT
VHWAPPTWPSHKVLICQFHYRRCQEAAWTLLEPELKTIPLTPVEIQDLEL
ATGYKVYGRCRMEKEEDLWGEWSPILSFQTPPSAPKDVWVSGNLCGTPGG
EEPLLLWKAPGPCVQVSYKVWFWVGGRELSPEGITCCCSLIPSGAEWARV
SAVNATSWEPLTNLSLVCLDSASAPRSVAVSSIAGSTELLVTWQPGPGEP
LEHVVDWARDGDPLEKLNWVRLPPGNLSALLPGNFTVGVPYRITVTAVSA
SGLASASSVWGFREELAPLVGPTLWRLQDAPPGTPAIAWGEVPRHQLRGH
LTHYTLCAQSGTSPSVCMNVSGNTQSVTLPDLPWGPCELWVTASTIAGQG
PPGPILRLHLPDNTLRWKVLPGILFLWGLFLLGCGLSLATSGRCYHLRHK
VLPRWVWEKVPDPANSSSGQPHMEQVPEAQPLGDLPILEVEEMEPPPVME
SSQPAQATAPLDSGYEKHFLPTPEELGLLGPPRPQVLA-C).

An amino acid sequence of an exemplary human gp130 protein is provided in SEQ ID NO: 701 (NCBI Reference Sequence: NP_002175.2;

N-MLTLQTWLVQALFIFLTTESTGELLDPCGYISPESPVVQLHSNFTAVC
VLKEKCMDYFHVNANYIVWKTNHFTIPKEQYTIINRTASSVTFTDIASLN
IQLTCNILTFGQLEQNVYGITIISGLPPEKPKNLSCIVNEGKKMRCEWDG
GRETHLETNFTLKSEWATHKFADCKAKRDTPTSCTVDYSTVYFVNIEVWV
EAENALGKVTSDHINFDPVYKVKPNPPHNLSVINSEELSSILKLTWTNPS
IKSVIILKYNIQYRTKDASTWSQIPPEDTASTRSSFTVQDLKPFTEYVFR
IRCMKEDGKGYWSDWSEEASGITYEDRPSKAPSFWYKIDPSHTQGYRTVQ
LVWKTLPPFEANGKILDYEVTLTRWKSHLQNYTVNATKLTVNLTNDRYLA
TLTVRNLVGKSDAAVLTIPACDFQATHPVMDLKAFPKDNMLWVEWTTPRE
SVKKYILEWCVLSDKAPCITDWQQEDGTVHRTYLRGNLAESKCYLITVTP
VYADGPGSPESIKAYLKQAPPSKGPTVRTKKVGKNEAVLEWDQLPVDVQN
GFIRNYTIFYRTIIGNETAVNVDSSHTEYTLSSLTSDTLYMVRMAAYTDE
GGKDGPEFTETTPKFAQGEIEAIVVPVCLAELLTTLLGVLECFNKRDLIK
KHIWPNVPDPSKSHIAQWSPHTPPRHNFNSKDQMYSDGNFTDVSVVEIEA
NDKKPFPEDLKSLDLFKKEKINTEGHSSGIGGSSCMSSSRPSISSSDENE
SSQNTSSTVQYSTVVHSGYRHQVPSVQVFSRSESTQPLLDSEERPEDLQL
VDHVDGGDGILPRQQYFKQNCSQHESSPDISHFERSKQVSSVNEEDFVRL

-continued

KQQISDHISQSCGSGQMKMFQEVSAADAFGPGTEGQVERFETVGMEAATD
EGMPKSYLPQTVRQGGYMPQ-C).

As used herein the term "compete", when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody) to a common antigen (e.g., IL-27 or a fragment thereof).

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in Table 12. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in Table 12. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in Table 12. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from a sequence set forth in Table 12.

In certain embodiments, the antibodies of the disclosure are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like. In certain embodiments, the nucleotide sequence of the invention comprises, consists of, or consists essentially of, a nucleotide sequence selected from a sequence set forth in Table 12. In certain embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence selected from a sequence set forth in Table 12. In certain embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence selected from a sequence set forth in Table 12. In certain embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence selected from a sequence set forth in Table 12.

It will also be understood by one of ordinary skill in the art that the antibodies suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The antibodies suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term antigen "cross-presentation" refers to presentation of exogenous protein antigens to T cells via MHC class I and class II molecules on APCs.

As used herein, the term "cross-reacts" refers to the ability of an antibody of the disclosure to bind to IL-27 from a different species. For example, an antibody of the present disclosure which binds human IL-27 may also bind another species of IL-27. As used herein, cross-reactivity is measured by detecting a specific reactivity with purified antigen in binding assays (e.g., SPR, ELISA) or binding to, or otherwise functionally interacting with, cells physiologically expressing IL-27. Methods for determining cross-reactivity include standard binding assays as described herein, for example, by Biacore™ surface plasmon resonance (SPR) analysis using a Biacore 2000 SPR instrument (Biacore AB, Uppsala, Sweden), or flow cytometric techniques.

As used herein, the term "cytotoxic T lymphocyte (CTL) response" refers to an immune response induced by cytotoxic T cells. CTL responses are mediated primarily by $CD8^+$ T cells.

As used herein, the term "dendritic cell" or "DC" refers to type of antigen-presenting cells that are bone marrow (BM)-derived leukocytes and are the most potent type of antigen-presenting cells. DCs are capture and process antigens, converting proteins to peptides that are presented on major histocompatibility complex (MEW) molecules recognized by T cells. DCs are heterogeneous, e.g. myeloid and plasmacytoid DCs; although all DCs are capable of antigen uptake, processing and presentation to naive T cells, the DC subtypes have distinct markers and differ in location, migratory pathways, detailed immunological function and dependence on infections or inflammatory stimuli for their generation. During the development of an adaptive immune response, the phenotype and function of DCs play a role in initiating tolerance, memory, and polarized T-helper 1 (Th1), Th2 and Th17 differentiation.

As used herein, the term "dendritic cell activation" refers to the transition from immature to mature dendritic cell; and the activated dendritic cells encompass mature dendritic cells and dendritic cells in the process of the transition, wherein the expression of CD80 and CD86 that induce costimulatory signals are elevated by the activating stimuli. Mature human dendritic cells are cells that are positive for the expression of CD40, CD80, CD86, and HLA-class II (e.g., HLA-DR). An immature dendritic cell can be distinguished from a mature dendritic cell, for example, based on markers selected from the group consisting of CD80 and CD86. An immature dendritic cell is weakly positive and preferably negative for these markers, while a mature dendritic cell is positive. Discrimination of mature dendritic cells is routinely performed by those skilled in the art, and the respective markers described above and methods for measuring their expression are also well known to those skilled in the art.

As used herein, the term "$EC_{50}$" refers to the concentration of an antibody or an antigen-binding portion thereof, which induces a response, either in an in vitro or an in vivo assay, which is 50% of the maximal response, i.e., halfway between the maximal response and the baseline.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a site on an antigen to which an immunoglobulin or antibody specifically binds. The term "epitope mapping" refers to a process or method of identifying the binding site, or epitope, of an antibody, or antigen binding fragment thereof, on its target protein antigen. Epitope mapping methods and techniques are provided herein. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from IL-27 are tested for reactivity with the given anti-IL-27 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Also encompassed by the present disclosure are antibodies that bind to an epitope on IL-27 which comprises all or a portion of an epitope recognized by the particular antibodies described herein (e.g., the same or an overlapping region or a region between or spanning the region).

Also encompassed by the present disclosure are antibodies that bind the same epitope and/or antibodies that compete for binding to human IL-27 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as IL-27. Numerous types of competitive binding assays are known, for example: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen: antibody complexes which provides atomic resolution of the epitope and mass spectrometry combined with hydrogen/deuterium (H/D) exchange which studies the conformation and dynamics of antigen:antibody interactions. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "Fc-mediated effector functions" or "Fc effector functions" refer to the biological activities of an antibody other than the antibody's primary function and purpose. For example, the effector functions of a therapeutic agnostic antibody are the biological activities other than the activation of the target protein or pathway. Examples of antibody effect functions include C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. Many effector functions begin with Fc binding to an Fcγ receptor. In some embodiments, the tumor antigen-targeting antibody has effector function, e.g., ADCC activity. In some embodiments, a tumor antigen-targeting antibody described herein comprises a variant constant region having increased effector function (e.g. increased ability to mediate ADCC) relative to the unmodified form of the constant region.

As used herein, the term "Fc receptor" refers to a polypeptide found on the surface of immune effector cells, which is bound by the Fc region of an antibody. In some embodiments, the Fc receptor is an Fcγ receptor. There are three subclasses of Fcγ receptors, FcγRI (CD64), FcγRII (CD32) and FγcRIII (CD16). All four IgG isotypes (IgG1, IgG2, IgG3 and IgG4) bind and activate Fc receptors FcγRI, FcγRIIA and FcγRIIIA FcγRIIB is an inhibitory receptor, and therefore antibody binding to this receptor does not activate complement and cellular responses. FcγRI is a high affinity receptor that binds to IgG in monomeric form, whereas FcγRIIA and FcγRIIA are low affinity receptors that bind IgG only in multimeric form and have slightly lower affinity. The binding of an antibody to an Fc receptor and/or C1q is governed by specific residues or domains within the Fc regions. Binding also depends on residues located within the hinge region and within the CH2 portion of the antibody. In some embodiments, the agonistic and/or therapeutic activity of the antibodies described herein is dependent on binding of the Fc region to the Fc receptor (e.g., FcγR). In some embodiments, the agonistic and/or therapeutic activity of the antibodies described herein is enhanced by binding of the Fc region to the Fc receptor (e.g., FcγR).

A list of certain Fc receptor sequences employed in the instant disclosure is set forth as Table 13 below.

As used herein, the term "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e. humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The terms "inducing an immune response" and "enhancing an immune response" are used interchangeably and refer the stimulation of an immune response (i.e., either passive or adaptive) to a particular antigen. The terms "induce" as used with respect to inducing CDC or ADCC refer to the stimulation of particular direct cell killing mechanisms.

As used herein, the term "immunogenic cell death" (alternatively known as "immunogenic apoptosis" refers to a cell death modality associated with the activation of one or more signaling pathways that induces the pre-mortem expression and emission of damaged-associated molecular pattern (DAMPs) molecules (e.g., adenosine triphosphate, ATP) from the tumor cell, resulting in the increase of immunogenicity of the tumor cell and the death of the tumor cell in an immunogenic manner (e.g., by phagocytosis). As used herein, the term "immunogenic cell death-inducing agent" refers to a chemical, biological, or pharmacological agent that induces an immunogenic cell death process, pathway, or modality.

As used herein, the terms "inhibits", "reduces" or "blocks" (e.g., referring to inhibition or reduction of human IL-27-mediated phosphorylation of STAT1 and/or STAT3 in a cell) are used interchangeably and encompass both partial and complete inhibition/blocking. The inhibition/blocking of IL-27 reduces or alters the normal level or type of activity that occurs without inhibition or blocking. Inhibition and blocking are also intended to include any measurable decrease in the binding affinity of IL-27 when in contact with an anti-IL-27 antibody as compared to IL-27 not in contact with an anti-IL-27 antibody, e.g., inhibits binding of IL-27 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%.

As used herein, the terms "inhibits angiogenesis," "diminishes angiogenesis," and "reduces angiogenesis" refer to reducing the level of angiogenesis in a tissue to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control tissue, and most preferably is at the same level which is observed in a control tissue.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-IL-27 antibody).

The term "in vivo" refers to processes that occur in a living organism.

As used herein, the term "isolated antibody" is intended to refer to an antibody which is substantially free of other antibodies having different antigenic specificities (e.g., an isolated antibody that specifically binds to human IL-27 is substantially free of antibodies that specifically bind antigens other than IL-27). An isolated antibody that specifically binds to an epitope may, however, have cross-reactivity to other IL-27 proteins from different species. However, the antibody continues to display specific binding to human IL-27 in a specific binding assay as described herein. In addition, an isolated antibody is typically substantially free of other cellular material and/or chemicals. In some embodiments, a combination of "isolated" antibodies having different IL-27 specificities is combined in a well-defined composition.

As used herein, the term "isolated nucleic acid molecule" refers to nucleic acids encoding antibodies or antibody portions (e.g., $V_H$, $V_L$, CDR3) that bind to IL-27, is intended to refer to a nucleic acid molecule in which the nucleotide sequences encoding the antibody or antibody portion are free of other nucleotide sequences encoding antibodies or antibody portions that bind antigens other than IL-27, which other sequences may naturally flank the nucleic acid in human genomic DNA. For example, a sequence selected from a sequence set forth in Table 12 corresponds to the nucleotide sequences comprising the heavy chain ($V_H$) and light chain ($V_L$) variable regions of anti-IL-27 antibody monoclonal antibodies described herein.

As used herein, "isotype" refers to the antibody class (e.g., IgM or IgG1) that is encoded by heavy chain constant region genes. In some embodiments, a human monoclonal antibody of the disclosure is of the IgG1 isotype. In some embodiments, a human monoclonal antibody of the disclosure is of the IgG2 isotype. In some embodiments, a human monoclonal antibody of the disclosure is of the IgG3 isotype. In some embodiments, a human monoclonal antibody of the disclosure is of the IgG4 isotype. As is apparent to a skilled artisan, identification of antibody isotypes (e.g., IgG1, IgG2, IgG3, IgG4, IgM, IgA1 IgA2, IgD, and IgE) is routine in the art and commonly involves a combination of sequence alignments with known antibodies, published Fc variant sequences and conserved sequences.

As used herein, the term "isotype switching" refers to the phenomenon by which the class, or isotype, of an antibody changes from one Ig class to one of the other Ig classes.

As used herein the term "KD" or "$K_D$" refers to the equilibrium dissociation constant of a binding reaction between an antibody and an antigen. The value of $K_D$ is a numeric representation of the ratio of the antibody off-rate constant (kd) to the antibody on-rate constant (ka). The value of $K_D$ is inversely related to the binding affinity of an antibody to an antigen. The smaller the $K_D$ value the greater the affinity of the antibody for its antigen. Affinity is the strength of binding of a single molecule to its ligand and is typically measured and reported by the equilibrium dissociation constant ($K_D$), which is used to evaluate and rank order strengths of bimolecular interactions.

As used herein, the term "kd" or "$k_d$" (alternatively "koff" or "$k_{off}$") is intended to refer to the off-rate constant for the dissociation of an antibody from an antibody/antigen complex. The value of kd is a numeric representation of the fraction of complexes that decay or dissociate per second, and is expressed in units $sec^{-1}$.

As used herein, the term "ka" or "$k_a$" (alternatively "kon" or "$k_{on}$" is intended to refer to the on-rate constant for the association of an antibody with an antigen. The value of ka is a numeric representation of the number of antibody/antigen complexes formed per second in a 1 molar (1M) solution of antibody and antigen, and is expressed in units $M^{-1}sec^{-1}$.

As used herein, the term "leukocyte" refers to a type of white blood cell involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes).

As used herein, the term "lymphocytes" refers to a type of leukocyte or white blood cell that is involved in the immune defenses of the body. There are two main types of lymphocytes: B-cells and T-cells.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "monocyte" refers to a type of leukocyte and can differentiate into macrophages and dendritic cells to effect an immune response.

As used herein, the term "natural killer (NK) cell" refers to a type of cytotoxic lymphocyte. These are large, usually granular, non-T, non-B lymphocytes, which kill certain tumor cells and play an important in innate immunity to viruses and other intracellular pathogens, as well as in antibody-dependent cell-mediated cytotoxicity (ADCC).

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

As used herein, the term "PD-1 antagonist" refers to any chemical compound or biological molecule that inhibits the PD-1 signaling pathway or that otherwise inhibits PD-1 function in a cell (e.g. an immune cell). In some embodiments, a PD-1 antagonist blocks binding of PD-L1 to PD-1 and/or PD-L2 to PD-1. In some embodiments, the PD-1 antagonist specifically binds PD-1. In some embodiments, the PD-1 antagonist specifically binds PD-L1.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "Programmed Cell Death Protein 1" or "PD-1" refers to the Programmed Cell Death Protein 1 polypeptide, an immune-inhibitory receptor belonging to the CD28 family and is encoded by the PDCD1 gene in humans. Alternative names or synonyms for PD-1 include: PDCD1, PD1, CD279 and SLEB2. PD-1 is expressed predominantly on previously activated T cells, B cells, and myeloid cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773.

As used herein, the term "Programmed Death Ligand-1" or "PD-L1" is one of two cell surface glycoprotein ligands for PD-1 (the other being PD-L2) that downregulates T cell activation and cytokine secretion upon binding to PD-1. Alternative names and synonyms for PD-L1 include: PDCD1L1, PDL1, B7H1, B7-4, CD274 and B7-H. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

PD-1 is known as an immune-inhibitory protein that negatively regulates TCR signals (Ishida, Y. et al. (1992) EMBO J. 11:3887-3895; Blank, C. et al. (Epub 2006 Dec. 29) Immunol. Immunother. 56(5):739-745). The interaction between PD-1 and PD-L1 can act as an immune checkpoint, which can lead to a decrease in T-cell receptor mediated proliferation (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

For several cancers, tumor survival and proliferation is sustained by tumor-mediated immune checkpoint modulation. This modulation can result in the disruption of anticancer immune system functions. For example, recent studies have indicated that the expression of immune checkpoint receptors ligands, such as PD-L1 or PD-L2, by tumor cells can downregulate immune system activity in the tumor microenvironment and promote cancer immune evasion. particularly by suppressing T cells. PD-L1 is abundantly expressed by a variety of human cancers (Dong et al., (2002) Nat Med 8:787-789). The receptor for PD-L1, PD-1, is expressed on lymphocytes (e.g., activated T cells) and is normally involved in down-regulating the immune system and promoting self-tolerance, particularly by suppressing T cells. However, when PD-1 receptors expressed on T cells bind to cognate PD-L1 ligands on tumor cells, the resulting T cell suppression contributes to an impaired immune response against the tumor (e.g., a decrease in tumor infiltrating lymphocytes or the establishment of immune evasion by cancer cells).

In large sample sets of e.g. ovarian, renal, colorectal, pancreatic, liver cancers and melanoma, it was shown that PD-L1 expression correlated with poor prognosis and reduced overall survival irrespective of subsequent treatment (see e.g., Dong et al., (2002) Nat Med 8(8):793-800; Yang et al., (2008) Invest Ophthalmol Vis Sci 49(6):2518-2525; Ghebeh et al., (2006) Neoplasia 8:190-198; Hamanishi et al., (2007) Proc Nat Acad Sci USA 104:3360-3365; Thompson et al., (2006) Clin Genitourin Cancer 5:206-211; Nomi et al., (2005) Clin Cancer Res 11:2947-2953; Inman et al., (2007) Cancer 109:1499-1505; Shimauchi et al., (2007) Int J Cancer 121:2585-2590; Gao et al., (2009) Clin Cancer Res 15:971-979; Nakanishi et al., (2007) Cancer Immunol Immunother 56:1173-1182; Hino et al., (2010) Cancer 116(7):1757-1766). Similarly, PD-1 expression on tumor lymphocytes was found to mark dysfunctional T cells in breast cancer (Kitano et al., (2017) ESMO Open 2(2): e000150) and melanoma (Kleffel et al., (2015) Cell 162(6): 1242-1256). PD-1 antagonists, such as those that affect the function of the PD-1/PD-L1/PD-L2 signaling axis and/or disrupt the interaction between PD-1 and PD-L1 and/or PD-L2, for example, have been developed and represent a novel class of anti-tumor inhibitors that function via modulation of immune cell-tumor cell interaction.

As used herein, the term "rearranged" refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the term "reference antibody" (used interchangeably with "reference mAb") or "reference antigen-binding protein" refers to an antibody, or an antigen-binding fragment thereof, that binds to a specific epitope on IL-27 and is used to establish a relationship between itself and one or more distinct antibodies, wherein the relationship is the binding of the reference antibody and the one or more distinct antibodies to the same epitope on IL-27. As used herein, the term connotes an anti-IL-27 antibody that is useful in a test or assay, such as those described herein, (e.g., a competitive binding assay), as a competitor, wherein the assay is useful for the discovery, identification or development, of one or more distinct antibodies that bind to the same epitope.

As used herein, the terms “specific binding,” “selective binding,” “selectively binds,” and “specifically binds,” refer to antibody binding to an epitope on a predetermined antigen. Typically, the antibody binds with an equilibrium dissociation constant ($K_D$) of approximately less than $10^{-6}$ M, such as approximately less than $10^{-7}$, $10^{-8}$M, $10^{-9}$M or $10^{-10}$ M or even lower when determined by surface plasmon resonance (SPR) technology in a BIACORE 2000 instrument using recombinant human IL-27 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. In certain embodiments, an antibody that specifically binds to IL-27 binds with an equilibrium dissociation constant ($K_D$) of approximately less than 100 nM ($10^{-7}$ M), optionally approximately less than 50 nM ($5\times10^{-8}$M), optionally approximately less than 15 nM ($1.5\times10^{-8}$ M), optionally approximately less than 10 nM ($10^{-8}$ M), optionally approximately less than 5 nM ($5\times10^{-9}$M), optionally approximately less than 1 nM ($10^{-9}$M), optionally approximately less than 0.1 nM ($10^{-10}$ M), optionally approximately less than 0.01 nM ($10^{-11}$ M), or even lower, when determined by surface plasmon resonance (SPR) technology in a BIACORE 2000 instrument using recombinant human IL-27 as the analyte and the antibody as the ligand, where binding to the predetermined antigen occurs with an affinity that is at least two-fold greater than the antibody's affinity for binding to a non-specific antigen (e.g., BSA, casein) other than the predetermined antigen or a closely-related antigen The phrases “an antibody recognizing an antigen” and “an antibody specific for an antigen” are used interchangeably herein with the term “an antibody which binds specifically to an antigen.”

As used herein, the term “STAT1 phosphorylation” refers to the phosphorylation of the Signal Transducer and Activator of Transcription 1 (STAT1) polypeptide, a transcription factor encoded by the STAT1 gene in humans. STAT molecules are phosphorylated by receptor associated kinases, that cause activation and dimerization by forming homo- or heterodimers which translocate to the nucleus to work as transcription factors. STAT1 can be activated (i.e., phosphorylated) in response to signaling via several ligands, including IL-27. IL-27 signaling through the IL-27R results in phosphorylation of STAT1 (pSTAT1). STAT1 has a key role in gene expression involved in survival of the cell, viability or pathogen response. Methods to determine STAT1 phosphorylation as a result of IL-27 signaling include, but are not limited to, flow cytometric analysis of cells labeled with antibodies that specifically recognize phosphorylated STAT1 (see e.g., Tochizawa et al., (2006) J Immunol Methods 313(1-2):29-37).

As used herein, the term “STAT3 phosphorylation” refers to the phosphorylation of the Signal Transducer and Activator of Transcription 3 (STAT3) polypeptide, a transcription factor encoded by the STAT3 gene in humans. STAT3 mediates the expression of a variety of genes in response to cell stimuli, and thus plays a key role in many cellular processes such as cell growth and apoptosis. Methods to determine STAT3 phosphorylation as a result of IL-27 signaling include, but are not limited to, analysis of cells or cell extracts labeled with antibodies that specifically recognize phosphorylated STAT3 (see e.g., Fursov et al., (2011) Assay Drug Dev Technol 9(4):420-429).

As used herein, the term “switch sequence” refers to those DNA sequences responsible for switch recombination. A “switch donor” sequence, typically a μ switch region, will be 5' (i.e., upstream) of the construct region to be deleted during the switch recombination. The “switch acceptor” region will be between the construct region to be deleted and the replacement constant region (e.g., γ, ε, etc.). As there is no specific site where recombination always occurs, the final gene sequence will typically not be predictable from the construct.

As used herein, the term “subject” includes any human or non-human animal. For example, the methods and compositions of the present invention can be used to treat a subject with an immune disorder. The term “non-human animal” includes all vertebrates, e.g., mammals and non-mammals, such as non-human primates, sheep, dog, cow, chickens, amphibians, reptiles, etc.

For nucleic acids, the term “substantial homology” indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a “query sequence” to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See ncbi.nlm-.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, the term "STING" (alternatively TMEM173) refers to the Stimulator of Interferon Genes, a protein that functions both as a direct cytosolic DNA sensor and as an adaptor protein. In humans, STING is encoded by the TMEM173 gene. STING plays an important role in innate immunity. STING induces type I interferon production when cells are infected with intracellular pathogens, such as viruses, mycobacteria and intracellular parasites. Type I interferon, mediated by STING, protects infected cells and nearby cells from local infection by binding to the same cell that secretes it and nearby cells. An exemplary amino acid sequence for STING is provided by the NCBI Genbank database under the accession number NP_001288667.

The term "T cell" refers to a type of white blood cell that can be distinguished from other white blood cells by the presence of a T cell receptor on the cell surface. There are several subsets of T cells, including, but not limited to, T helper cells (a.k.a. $T_H$ cells or $CD4^+$ T cells) and subtypes, including $T_H1$, $T_H2$, $T_H3$, $T_H17$, $T_H9$, and $T_{FH}$ cells, cytotoxic T cells (a.k.a $T_C$ cells, $CD8^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including $CD4^+$ $FOXP3^+$ $T_{reg}$ cells, $CD4^+$ $FOXP3^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

As used herein, the term "T cell-mediated response" refers to any response mediated by T cells, including, but not limited to, effector T cells (e.g., $CD8^+$ cells) and helper T cells (e.g., $CD4^+$ cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., an anti-IL-27 antibody or an antigen-binding fragment thereof) that will elicit the desired biological or medical response (e.g., an improvement in one or more symptoms of a cancer).

As used herein, the term "TAM receptor" refers to the TAM receptor protein tyrosine kinases (TYRO3, AXL and MER). TAM receptors are involved in the regulation of immune system homeostasis. In a cancer setting, TAM receptors have a dual regulatory role, controlling the initiation and progression of tumor development and, at the same time, the associated anti-tumor responses of diverse immune cells. Further description of TAM receptors is found in Paolino and Penninger (2016) Cancers 8(97): doi:10.3390/cancers8100097). As used herein, the term "TAM receptor inhibitor" or "TAM inhibitor" refers to an agent that inhibits, blocks or reduces the function or activity of a TAM receptor.

As used herein, the term "TIGIT" or "T-cell immunoreceptor with Ig and ITIM domains" refers to any native TIGIT from any vertebrate source, including mammals such as primates (e.g., humans) and rodents (e.g., mice and rats), unless otherwise indicated. TIGIT is also known in the art as DKFZp667A205, FLJ39873, V-set and immunoglobulin domain-containing protein 9, V-set and transmembrane domain-containing protein 3, VSIG9, VSTM3, and WUCAM. The term also encompasses naturally occurring variants of TIGIT, e.g., splice variants or allelic variants. The amino acid sequence of an exemplary human TIGIT may be found under UniProt Accession Number Q495A1.

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

As used herein, the term "unrearranged" or "germline configuration" refers to the configuration wherein the V segment is not recombined so as to be immediately adjacent to a D or J segment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

BRIEF DESCRIPTION OF THE DRAWINGS

FIG. 1 is a table that provides affinity data for anti-IL-27 antibodies, as indicated. Affinity measurements were performed using ForteBio and Meso Scale Discovery methods.

FIG. 3A is a graph depicting the inhibition of IL-27-mediated phosphorylation of STAT1 in human whole blood by anti-IL-27 antibodies, as indicated, as measured by flow cytometry. FIG. 3B is a graph depicting the inhibition of IL-27-mediated phosphorylation of STAT1 in human PBMCs by anti-IL-27 antibodies, as indicated, as measured by flow cytometry. FIG. 3C is a graph depicting the inhibition of IL-27-mediated phosphorylation of STAT1 in U937 cells by anti-IL-27 antibodies, as indicated, as measured by flow cytometry. FIG. 3D is a graph depicting the inhibition of IL-27-mediated phosphorylation of STAT1 in HUT-78 cells by anti-IL-27 antibodies, as indicated, as measured by flow cytometry. FIG. 3E is graph showing that SRF388 inhibits IL-27-mediated pSTAT1 in human whole blood T cells.

mediated antibody blockade and with anti-PD-1+anti-CTLA-4 combination therapy.

Figure 8A:
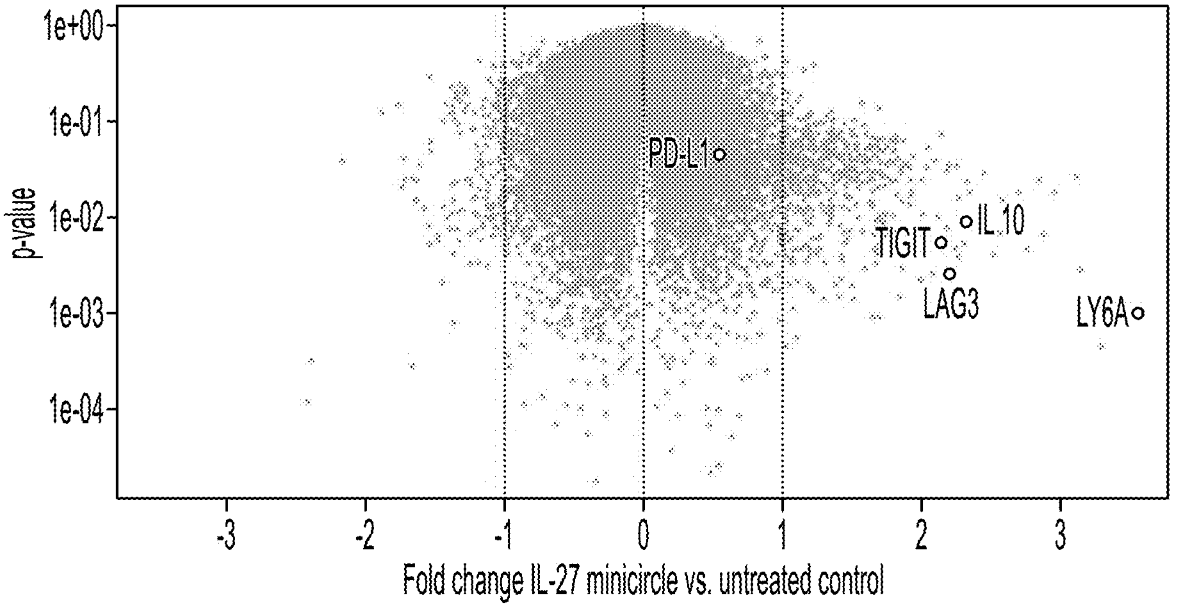
Figure 8B:
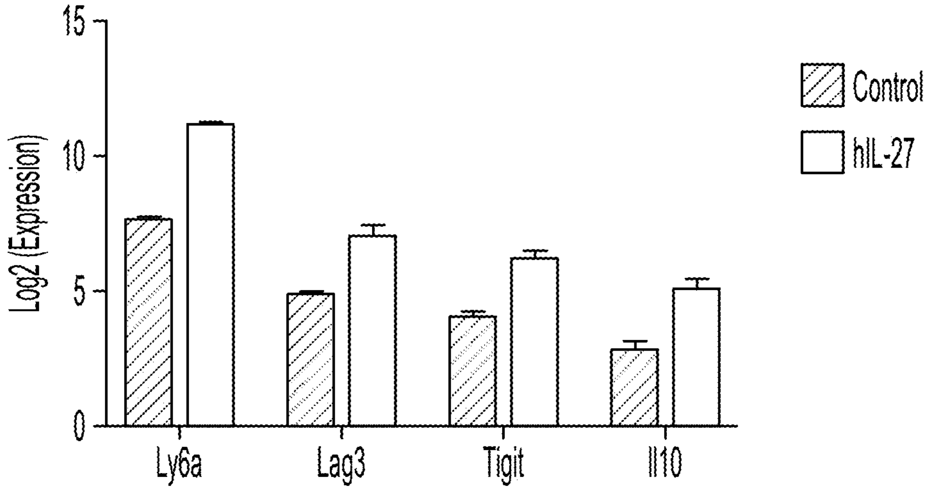
Figure 8C:
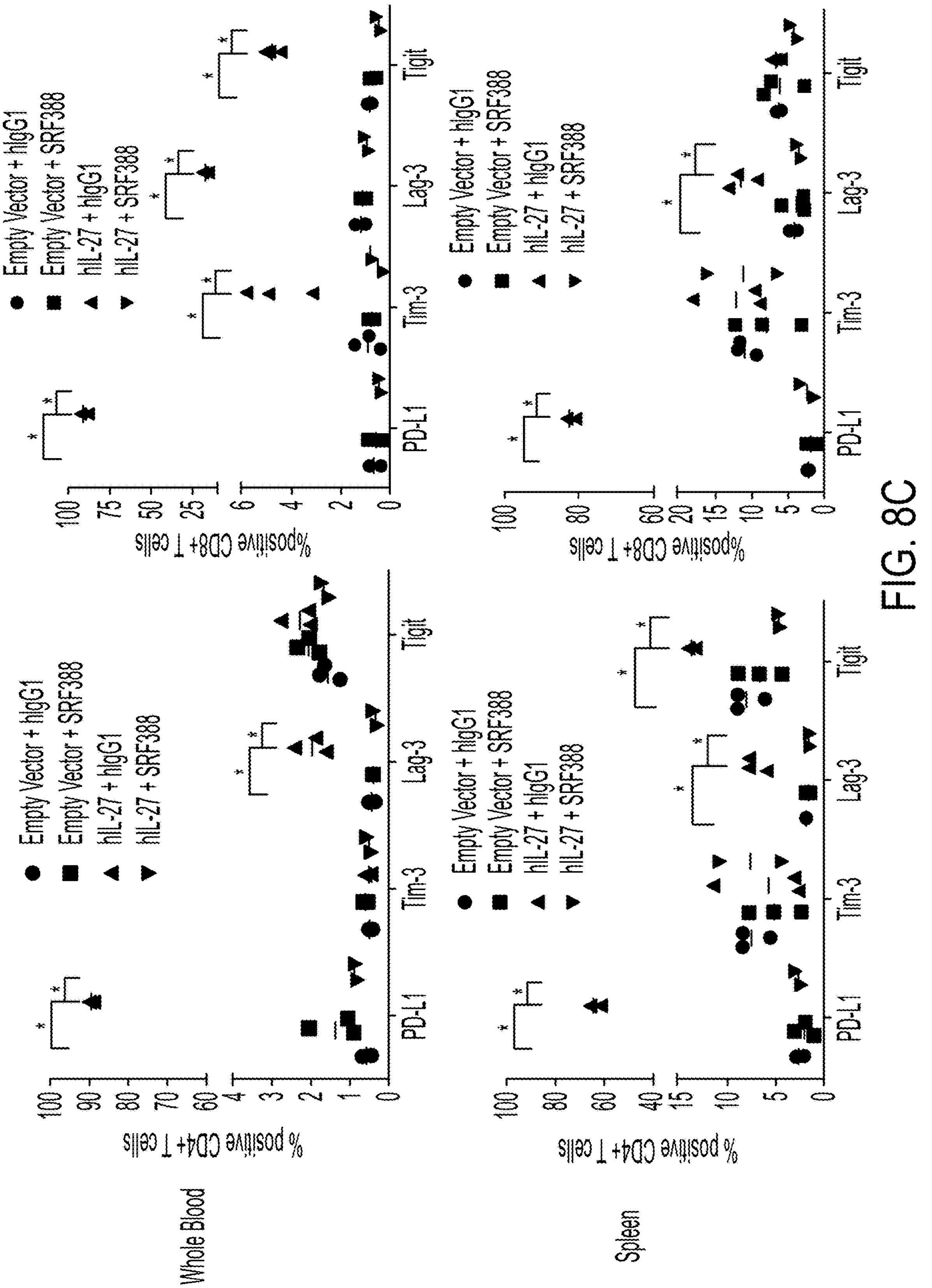
Figure 8D:
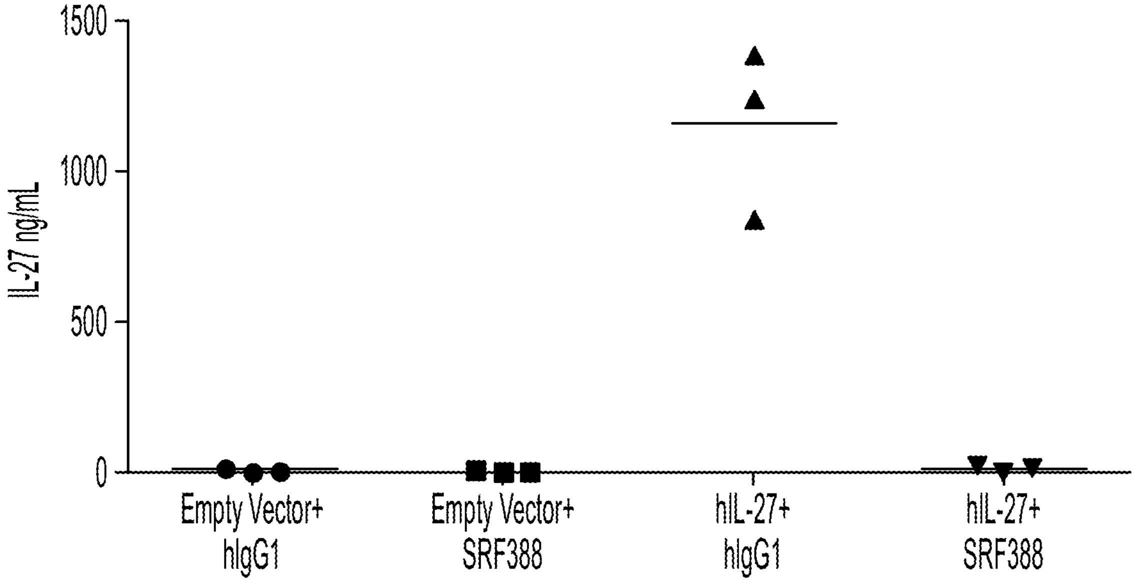

FIG. 8A provides a scatterplot depicting microarray data of genes with an expression change >1.0 $log_2$ fold change (black dots) in splenocytes isolated from mice overexpressing IL-27 following treatment with IL-27 minicircles. FIG. 8B provides a graph depicting the expression level of select immunomodulatory genes, as indicated, in splenocytes as in FIG. 8A. FIG. 8C shows ectopic expression of human IL-27 induces inhibitory receptor expression on murine T cells in vivo and that SRF388 reduces inhibitory receptor expression on T cells in vivo after IL-27 minicircle treatment. Six-week-old female Balb/c mice were injected with empty vector (control) or hIL-27 minicircle. (top left and right panels) PBMCs and (bottom left and right panels) total splenocytes were collected 5 days after transfection and cells were stained and analyzed by flow cytometry. Expression of the indicated markers were analyzed on CD4+ T cells (top left and bottom left panels) and CD8+ T cells (top right and bottom right panels). Analysis was performed using FlowJo software. FIG. 8D shows that SRF388 inhibits detection of minicircle-derived human IL-27 in murine plasma.

FIG. 9 presents a tabulated summary of select monoclonal antibody properties.

FIG. 10A presents a chart of antibody sequences, with sequence partitioning reflecting NT numbering. FIG. 10B presents a chart of antibody sequences (corresponding to the sequence chart of FIG. 10A), with sequence partitioning reflecting ImMunoGeneTics (IMGT) numbering. In both FIG. 10A and FIG. 10B, highlighted amino acids in CDR sequences show mutations from germline-encoded sequence. As will be apparent to the skilled artisan, antibody numbering, including determination of CDR sequences, framework sequences, etc., can be performed in a number of art-recognized manners, including via the NT and IMGT numbering systems presented in FIG. 10A and FIG. 10B and employed elsewhere herein.

DETAILED DESCRIPTION

The present disclosure provides, at least in part, antibody molecules that bind to human IL-27 with high affinity and specificity. In one embodiment, disclosed herein are human antibodies that bind to IL-27. The terms “IL-27” and “IL27” as used herein refer interchangeably to the heterodimeric cytokine, IL-27 that is composed of two distinct subunits, encoded by two different genes: Epstein-Barr virus-induced gene 3 (EBI3) and IL-27p28. IL-27 has both pro- and anti-inflammatory properties with diverse effects on—hematopoietic and non-hematopoietic cells.

Accordingly, in one aspect, the disclosure provides a monoclonal antibody that specifically binds to and antagonizes human IL-27, or an antigen binding portion thereof, wherein the antibody or antigen binding portion thereof exhibits at least one or more of the following properties:

(i) binds to human IL-27 with an equilibrium dissociation constant ($K_D$) of 15 nM or less;

(ii) blocks binding of IL-27 to IL-27 receptor;

(iii) inhibits or reduces STAT1 and/or STAT3 phosphorylation in a cell;

(iv) inhibits or reduces IL-27 mediated inhibition of CD161 expression in a cell;

(v) inhibits or reduces IL-27 mediated PD-L1 and/or TIM-3 expression in a cell;

(vi) induces or enhances PD-1 mediated secretion of one or more cytokines from a cell; and (vii) a combination of (i)-(vi).

In other aspects, the disclosure provides a monoclonal antibody or antigen binding portion thereof that specifically binds human IL-27 and inhibits or reduces an IL-27 biological activity or IL-27 signaling.

Additional aspects of the invention include nucleic acid molecules encoding the antibody molecules, expression vectors, host cells and methods for making the antibody molecules. Immunoconjugates, multi- or bispecific molecules and pharmaceutical compositions comprising the antibody molecules are also provided. The anti-IL-27 antibody molecules disclosed herein can be used to treat, prevent and/or diagnose cancerous or malignant disorders, e.g., solid and liquid tumors (e.g., leukemia, e.g., lymphoma, e.g., AML), lung cancer (e.g., non-small cell lung cancer), pancreatic cancer, breast cancer (e.g., triple-negative breast cancer), melanoma, testicular cancer, sarcoma, head and neck cancer (e.g., squamous head and neck cancer), liver cancer (e.g., hepatocellular carcinoma (HCC)), colorectal cancer, ovarian cancer, brain cancer (e.g., glioblastoma multiforme), or renal cancer (e.g., renal cell carcinoma, e.g. renal clear cell carcinoma).

Anti-IL-27 Antibodies and Antigen-Binding Fragments Thereof

The present disclosure provides antibodies, and antigen binding portions thereof, that specifically bind to and antagonize IL-27, in particular human IL-27. Provided herein are isolated monoclonal antibodies or antigen binding portion thereof that specifically bind to human IL-27, comprising heavy and light chain CDRs and variable sequences as set forth in Table 12.

In some embodiments, the disclosure provides an isolated monoclonal antibody that specifically binds to and antagonizes human IL-27, or an antigen binding portion thereof, wherein the antibody or antigen binding portion thereof exhibits at least one or more of the following properties: (i) binds to human IL-27 with an equilibrium dissociation constant ($K_D$) of 15 nM or less; (ii) blocks binding of IL-27 to IL-27 receptor; (iii) inhibits or reduces STAT1 and/or STAT3 phosphorylation in a cell; (iv) inhibits or reduces inhibition of CD161 expression in a cell; (v) inhibits or reduces PD-L1 and/or TIM-3 expression in a cell; (vi) induces or enhances PD-1 mediated secretion of one or more cytokines from a cell; and (vii) a combination of (i)-(vi).

In some embodiments, the isolated monoclonal antibody, or antigen binding portion thereof, binds to human IL-27 with an equilibrium dissociation constant ($K_D$) of 15 nM or less.

In some embodiments, the isolated monoclonal antibody, or antigen binding portion thereof, binds to recombinant human IL-27 or to murine IL-27.

In some embodiments, the isolated monoclonal antibody, or antigen binding portion thereof, inhibits or reduces STAT1 and/or STAT3 phosphorylation in a cell. In some embodiments, the cell is an immune cell. In some embodiments, the cell is a cancer cell.

In some embodiments, the isolated monoclonal antibody, or antigen binding portion thereof, inhibits or reduces inhibition of CD161 expression in a cell (e.g. ameliorates or relieves the inhibition of CD161 expression in a cell). In some embodiments, the cell is an immune cell.

In some embodiments, the isolated monoclonal antibody, or antigen binding portion thereof, inhibits or reduces PD-L1 and/or TIM-3 expression in a cell. In some embodiments, PD-L1 expression is inhibited or reduced. In some embodiments, TIM-3 expression is inhibited or reduced. In some embodiments, both PD-L1 expression and TIM-3 expression is reduced. In some embodiments, the cell is an immune cell.

In some embodiments, the isolated monoclonal antibody, or antigen binding portion thereof, induces or enhances the PD-1-mediated secretion of one or more cytokines from a cell. In some embodiments, the one or more cytokines is TNFα. In some embodiments, the one or more cytokine is IL-6. In some embodiments, the one or more cytokine is TNFα and IL-6. In some embodiments, the cell is an immune cell.

In some embodiments, the isolated monoclonal antibody, or antigen binding portion thereof, is selected from the group consisting of an IgG1, an IgG2, an IgG3, an IgG4, an IgM, an IgA1 an IgA2, an IgD, and an IgE antibody. In some embodiments, the antibody is an IgG1 antibody or an IgG4 antibody. In some embodiments, the antibody comprises a wild type IgG1 heavy chain constant region. In some embodiments, the antibody comprises a wild type IgG4 heavy chain constant region. In some embodiments, the antibody comprises an Fc domain comprising at least one mutation. In some embodiments, the antibody comprises a mutant IgG1 heavy chain constant region. In some embodiments, the antibody comprises a mutant IgG4 heavy chain constant region. In some embodiments, the mutant IgG4 heavy chain constant region comprises any one of the substitutions S228P, L235E, L235A, or a combination thereof, according to EU numbering.

In some embodiments, the disclosure provides an isolated monoclonal antibody, or antigen binding portion thereof, that binds to substantially the same epitope on IL-27 as the antibody, or antigen binding portion thereof, according to any one of the aforementioned embodiments.

In some embodiments, the disclosure provides an isolated monoclonal antibody, or antigen binding portion thereof, that binds to at least one of the amino acid residues comprising IL-27 bound by the antibody, or antigen binding portion thereof, according to any one of the aforementioned embodiments.

In some embodiments, the disclosure provides an isolated monoclonal antibody, or antigen binding portion thereof, wherein a mutation of the epitope on IL-27 bound by the antibody or antigen binding portion thereof inhibits, reduces, or blocks binding to both the antibody or antigen binding portion thereof and to the antibody or antigen binding portion thereof according to any one of the aforementioned embodiments.

In some embodiments, the disclosure provides an isolated monoclonal antibody, or antigen binding portion thereof, that binds to an epitope on IL-27, wherein the epitope is the same or is similar to the epitope bound by an antibody molecule described in Table 12.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs selected from the group consisting of:

(i) heavy chain CDR1, CDR2 and CDR3 sequences set forth in SEQ ID NOs: 51, 52 and 53, respectively, and light chain CDR1, CDR2 and CDR3 sequences set forth in SEQ ID NOs: 59, 60 and 61, respectively;

(ii) heavy chain CDR1, CDR2 and CDR3 sequences set forth in SEQ ID NOs: 73, 74 and 75, respectively, and light chain CDR1, CDR2 and CDR3 sequences set forth in SEQ ID NOs: 81, 82 and 83, respectively;

(iii) heavy chain CDR1, CDR2 and CDR3 sequences set forth in SEQ ID NOs: 95, 96 and 97, respectively, and light chain CDR1, CDR2 and CDR3 sequences set forth in SEQ ID NOs: 103, 104 and 105, respectively;

(iv) heavy chain CDR1, CDR2 and CDR3 sequences set forth in SEQ ID NOs: 117, 118 and 119, respectively, and light chain CDR1, CDR2 and CDR3 sequences set forth in SEQ ID NOs: 125, 126 and 127, respectively;

(v) heavy chain CDR1, CDR2 and CDR3 sequences set forth in SEQ ID NOs: 139, 140 and 141, respectively, and light chain CDR1, CDR2 and CDR3 sequences set forth in SEQ ID NOs: 147, 148 and 149, respectively;

(vi) heavy chain CDR1, CDR2 and CDR3 sequences set forth in SEQ ID NOs: 161, 162 and 163, respectively, and light chain CDR1, CDR2 and CDR3 sequences set forth in SEQ ID NOs: 169, 170 and 171, respectively;

(vii) heavy chain CDR1, CDR2 and CDR3 sequences set forth in SEQ ID NOs: 185, 186 and 187, respectively, and light chain CDR1, CDR2 and CDR3 sequences set forth in SEQ ID NOs: 193, 194 and 195, respectively;

(viii) heavy chain CDR1, CDR2 and CDR3 sequences set forth in SEQ ID NOs: 207, 208 and 209, respectively, and light chain CDR1, CDR2 and CDR3 sequences set forth in SEQ ID NOs: 215, 216 and 217, respectively;

(ix) heavy chain CDR1, CDR2 and CDR3 sequences set forth in SEQ ID NOs: 229, 230 and 231, respectively, and light chain CDR1, CDR2 and CDR3 sequences set forth in SEQ ID NOs: 237, 238 and 239, respectively;

(x) heavy chain CDR1, CDR2 and CDR3 sequences set forth in SEQ ID NOs: 251, 252 and 253, respectively, and light chain CDR1, CDR2 and CDR3 sequences set forth in SEQ ID NOs: 259, 260 and 261, respectively;

(xi) heavy chain CDR1, CDR2 and CDR3 sequences set forth in SEQ ID NOs: 273, 274 and 275, respectively, and light chain CDR1, CDR2 and CDR3 sequences set forth in SEQ ID NOs: 281, 282 and 283, respectively;

(xii) heavy chain CDR1, CDR2 and CDR3 sequences set forth in SEQ ID NOs: 295, 296 and 297, respectively, and light chain CDR1, CDR2 and CDR3 sequences set forth in SEQ ID NOs: 303, 304 and 305, respectively;

(xiii) heavy chain CDR1, CDR2 and CDR3 sequences set forth in SEQ ID NOs: 317, 318 and 319, respectively, and light chain CDR1, CDR2 and CDR3 sequences set forth in SEQ ID NOs: 325, 326 and 327, respectively;

(xiv) heavy chain CDR1, CDR2 and CDR3 sequences set forth in SEQ ID NOs: 339, 340 and 341, respectively, and light chain CDR1, CDR2 and CDR3 sequences set forth in SEQ ID NOs: 347, 348 and 349, respectively;

(xv) heavy chain CDR1, CDR2 and CDR3 sequences set forth in SEQ ID NOs: 361, 362 and 363, respectively, and light chain CDR1, CDR2 and CDR3 sequences set forth in SEQ ID NOs: 369, 370 and 371, respectively; and (xvi) heavy chain CDR1, CDR2 and CDR3 sequences set forth in SEQ ID NOs: 383, 384 and 385, respectively, and light chain CDR1, CDR2 and CDR3 sequences set forth in SEQ ID NOs: 391, 392 and 393, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 161, 162 and 163, respectively, and the light chain CDR1, CDR2 and CDR3 sequences are set forth in SEQ ID NOs: 169, 170 and 171, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs selected from the group consisting of:

(i) heavy chain CDR1, CDR2 and CDR3 sequences set forth in SEQ ID NOs: 54, 55 and 56, respectively, and light chain CDR1, CDR2 and CDR3 sequences set forth in SEQ ID NOs: 62, 63 and 64, respectively;

(ii) heavy chain CDR1, CDR2 and CDR3 sequences set forth in SEQ ID NOs: 76, 77 and 78, respectively, and light chain CDR1, CDR2 and CDR3 sequences set forth in SEQ ID NOs: 84, 85 and 86, respectively;

(iii) heavy chain CDR1, CDR2 and CDR3 sequences set forth in SEQ ID NOs: 98, 99 and 100, respectively, and light chain CDR1, CDR2 and CDR3 sequences set forth in SEQ ID NOs: 106, 107 and 108, respectively;

(iv) heavy chain CDR1, CDR2 and CDR3 sequences set forth in SEQ ID NOs: 120, 121 and 122, respectively, and light chain CDR1, CDR2 and CDR3 sequences set forth in SEQ ID NOs: 128, 129 and 130, respectively;

(v) heavy chain CDR1, CDR2 and CDR3 sequences set forth in SEQ ID NOs: 142, 143 and 144, respectively, and light chain CDR1, CDR2 and CDR3 sequences set forth in SEQ ID NOs: 150, 151 and 152, respectively;

(vi) heavy chain CDR1, CDR2 and CDR3 sequences set forth in SEQ ID NOs: 164, 165 and 166, respectively, and light chain CDR1, CDR2 and CDR3 sequences set forth in SEQ ID NOs: 172, 173 and 174, respectively;

(vii) heavy chain CDR1, CDR2 and CDR3 sequences set forth in SEQ ID NOs: 188, 189 and 190, respectively, and light chain CDR1, CDR2 and CDR3 sequences set forth in SEQ ID NOs: 196, 197 and 198, respectively;

(viii) heavy chain CDR1, CDR2 and CDR3 sequences set forth in SEQ ID NOs: 210, 211 and 212, respectively, and light chain CDR1, CDR2 and CDR3 sequences set forth in SEQ ID NOs: 218, 219 and 220, respectively;

(ix) heavy chain CDR1, CDR2 and CDR3 sequences set forth in SEQ ID NOs: 232, 233 and 234, respectively, and light chain CDR1, CDR2 and CDR3 sequences set forth in SEQ ID NOs: 240, 241 and 242, respectively;

(x) heavy chain CDR1, CDR2 and CDR3 sequences set forth in SEQ ID NOs: 254, 255 and 256, respectively, and light chain CDR1, CDR2 and CDR3 sequences set forth in SEQ ID NOs: 262, 263 and 264, respectively;

(xi) heavy chain CDR1, CDR2 and CDR3 sequences set forth in SEQ ID NOs: 276, 277 and 278, respectively, and light chain CDR1, CDR2 and CDR3 sequences set forth in SEQ ID NOs: 284, 285 and 286, respectively;

(xii) heavy chain CDR1, CDR2 and CDR3 sequences set forth in SEQ ID NOs: 298, 299 and 300, respectively, and light chain CDR1, CDR2 and CDR3 sequences set forth in SEQ ID NOs: 306, 307 and 308, respectively;

(xiii) heavy chain CDR1, CDR2 and CDR3 sequences set forth in SEQ ID NOs: 320, 321 and 322, respectively, and light chain CDR1, CDR2 and CDR3 sequences set forth in SEQ ID NOs: 328, 329 and 330, respectively;

(xiv) heavy chain CDR1, CDR2 and CDR3 sequences set forth in SEQ ID NOs: 342, 343 and 344, respectively, and light chain CDR1, CDR2 and CDR3 sequences set forth in SEQ ID NOs: 350, 351 and 352, respectively;

(xv) heavy chain CDR1, CDR2 and CDR3 sequences set forth in SEQ ID NOs: 364, 365 and 366, respectively, and light chain CDR1, CDR2 and CDR3 sequences set forth in SEQ ID NOs: 372, 373 and 374, respectively; and (xvi) heavy chain CDR1, CDR2 and CDR3 sequences set forth in SEQ ID NOs: 386, 387 and 388, respectively, and light chain CDR1, CDR2 and CDR3 sequences set forth in SEQ ID NOs: 394, 395 and 396, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 164, 165 and 166, respectively, and the light chain CDR1, CDR2 and CDR3 sequences are set forth in SEQ ID NOs: 172, 173 and 174, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain CDRs, wherein the amino acid sequences of heavy chain CDR1, CDR2 and CDR3 are SYSMS (SEQ ID NO: 23), YISYDGGSAYYPDTVKG (SEQ ID NO: 24) and HGDYDDDDAMDY (SEQ ID NO: 25), respectively, and wherein the amino acid sequences of light chain CDR1, CDR2 and CDR3 are RASENIYSYLA (SEQ ID NO: 26), NAETLTE (SEQ ID NO: 27) and QHHYGTPLT (SEQ ID NO: 28), respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions, wherein the heavy chain variable region comprises an amino acid sequence selected from the group consisting of SEQ ID NOs: 57, 79, 101, 123, 145, 167, 191, 213, 235, 257, 279, 301, 323, 345, 367 and 389; and wherein the light chain variable region comprises an amino acid sequence selected from the group consisting of SEQ ID NOs: 65, 87, 109, 131, 153, 175, 199, 221, 243, 265, 287, 309, 331, 353, 375 and 397.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences selected from the group consisting of:

(i) SEQ ID NO: 57 and 65, respectively;
(ii) SEQ ID NO: 79 and 87, respectively;
(iii) SEQ ID NO: 101 and 109, respectively;
(iv) SEQ ID NO: 123 and 131, respectively;
(v) SEQ ID NO: 145 and 153, respectively;
(vi) SEQ ID NO: 167 and 175, respectively;
(vii) SEQ ID NO: 191 and 199, respectively;
(viii) SEQ ID NO: 213 and 221, respectively;
(ix) SEQ ID NO: 235 and 243, respectively;
(x) SEQ ID NO: 257 and 265, respectively;
(xi) SEQ ID NO: 279 and 287, respectively;
(xii) SEQ ID NO: 301 and 309, respectively;
(xiii) SEQ ID NO: 323 and 331, respectively;
(xiv) SEQ ID NO: 345 and 353, respectively;
(xv) SEQ ID NO: 367 and 375, respectively; and
(xvi) SEQ ID NO: 389 and 397, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions, wherein the heavy chain variable region comprises an amino acid sequence which is at least 90% identical to the amino acid sequence selected from the group consisting of SEQ ID NOs: 57, 79, 101, 123, 145, 167, 191, 213, 235, 257, 279, 301, 323, 345, 367 and 389; and wherein the light chain variable region comprises an amino acid sequence which is at least 90% identical to the amino acid sequence selected from the group consisting of SEQ ID NOs: 65, 87, 109, 131, 153, 175, 199, 221, 243, 265, 287, 309, 331, 353, 375 and 397.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences at least 90% identical to the amino acid sequences selected from the group consisting of:

(i) SEQ ID NO: 57 and 65, respectively;
(ii) SEQ ID NO: 79 and 87, respectively;
(iii) SEQ ID NO: 101 and 109, respectively;
(iv) SEQ ID NO: 123 and 131, respectively;
(v) SEQ ID NO: 145 and 153, respectively;
(vi) SEQ ID NO: 167 and 175, respectively;
(vii) SEQ ID NO: 191 and 199, respectively;
(viii) SEQ ID NO: 213 and 221, respectively;
(ix) SEQ ID NO: 235 and 243, respectively;
(x) SEQ ID NO: 257 and 265, respectively;
(xi) SEQ ID NO: 279 and 287, respectively;
(xii) SEQ ID NO: 301 and 309, respectively;
(xiii) SEQ ID NO: 323 and 331, respectively;
(xiv) SEQ ID NO: 345 and 353, respectively;
(xv) SEQ ID NO: 367 and 375, respectively; and
(xvi) SEQ ID NO: 389 and 397, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences set forth in SEQ ID NO: 167 and 175, respectively.

In some embodiments, the disclosure provides an isolated monoclonal antibody that specifically binds to and antagonizes human IL-27, or antigen binding portion thereof, wherein the antibody or antigen binding portion thereof comprises heavy and light chain variable regions comprising amino acid sequences at least 90% identical to the amino acid sequences set forth in SEQ ID NO: 167 and 175, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain, wherein the heavy chain comprises an amino acid sequence selected from the group consisting of SEQ ID NOs: 67, 89, 111, 133, 155, 177, 201, 223, 245, 267, 289, 311, 333, 355, 377 and 399; and wherein the light chain comprises an amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy and a light chain, wherein the heavy chain comprises an amino acid sequence which is at least 90% identical to the amino acid sequence selected from the group consisting of SEQ ID NOs: 67, 89, 111, 133, 155, 177, 201, 223, 245, 267, 289, 311, 333, 355, 377 and 399; and wherein the light chain comprises an amino acid sequence which is at least 90% identical to the amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain, wherein the heavy chain comprises an amino acid sequence selected from the group consisting of SEQ ID NOs: 71, 93, 115, 137, 159, 181, 205, 227, 249, 271, 293, 315, 337, 359, 381 and 403; and wherein the light chain comprises an amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy and a light chain, wherein the heavy chain comprises an amino acid sequence which is at least 90% identical to the amino acid sequence selected from the group consisting of SEQ ID NOs: 71, 93, 115, 137, 159, 181, 205, 227, 249, 271, 293, 315, 337, 359, 381 and 403; and wherein the light chain comprises an amino acid sequence which is at least 90% identical to the amino acid sequence selected from the group consisting of SEQ ID NOs: 69, 91, 113, 135, 157, 179, 203, 225, 247, 269, 291, 313, 335, 357, 379 and 401.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences selected from the group consisting of:

(i) SEQ ID NO: 67 and 69, respectively;
(ii) SEQ ID NO: 89 and 91, respectively;
(iii) SEQ ID NO: 111 and 113, respectively;
(iv) SEQ ID NO: 133 and 135, respectively;
(v) SEQ ID NO: 155 and 157, respectively;
(vi) SEQ ID NO: 177 and 179, respectively;
(vii) SEQ ID NO: 201 and 203, respectively;
(viii) SEQ ID NO: 223 and 225, respectively;
(ix) SEQ ID NO: 245 and 247, respectively;
(x) SEQ ID NO: 267 and 269, respectively;
(xi) SEQ ID NO: 289 and 291, respectively;
(xii) SEQ ID NO: 311 and 313, respectively;
(xiii) SEQ ID NO: 333 and 335, respectively;
(xiv) SEQ ID NO: 355 and 357, respectively;
(xv) SEQ ID NO: 377 and 379, respectively; and
(xvi) SEQ ID NO: 399 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences at least 90% identical to the amino acid sequences selected from the group consisting of:

(i) SEQ ID NO: 67 and 69, respectively;
(ii) SEQ ID NO: 89 and 91, respectively;
(iii) SEQ ID NO: 111 and 113, respectively;
(iv) SEQ ID NO: 133 and 135, respectively;
(v) SEQ ID NO: 155 and 157, respectively;
(vi) SEQ ID NO: 177 and 179, respectively;
(vii) SEQ ID NO: 201 and 203, respectively;
(viii) SEQ ID NO: 223 and 225, respectively;
(ix) SEQ ID NO: 245 and 247, respectively;

(x) SEQ ID NO: 267 and 269, respectively;
(xi) SEQ ID NO: 289 and 291, respectively;
(xii) SEQ ID NO: 311 and 313, respectively;
(xiii) SEQ ID NO: 333 and 335, respectively;
(xiv) SEQ ID NO: 355 and 357, respectively;
(xv) SEQ ID NO: 377 and 379, respectively; and
(xvi) SEQ ID NO: 399 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy and a light chain comprising amino acid sequences selected from the group consisting of:
(i) SEQ ID NO: 71 and 69, respectively;
(ii) SEQ ID NO: 93 and 91, respectively;
(iii) SEQ ID NO: 115 and 113, respectively;
(iv) SEQ ID NO: 137 and 135, respectively;
(v) SEQ ID NO: 159 and 157, respectively;
(vi) SEQ ID NO: 181 and 179, respectively;
(vii) SEQ ID NO: 205 and 203, respectively;
(viii) SEQ ID NO: 227 and 225, respectively;
(ix) SEQ ID NO: 249 and 247, respectively;
(x) SEQ ID NO: 271 and 269, respectively;
(xi) SEQ ID NO: 293 and 291, respectively;
(xii) SEQ ID NO: 315 and 313, respectively;
(xiii) SEQ ID NO: 337 and 335, respectively;
(xiv) SEQ ID NO: 359 and 357, respectively;
(xv) SEQ ID NO: 381 and 379, respectively; and
(xvi) SEQ ID NO: 403 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy and a light chain comprising amino acid sequences at least 90% identical to the amino acid sequences selected from the group consisting of:
(i) SEQ ID NO: 71 and 69, respectively;
(ii) SEQ ID NO: 93 and 91, respectively;
(iii) SEQ ID NO: 115 and 113, respectively;
(iv) SEQ ID NO: 137 and 135, respectively;
(v) SEQ ID NO: 159 and 157, respectively;
(vi) SEQ ID NO: 181 and 179, respectively;
(vii) SEQ ID NO: 205 and 203, respectively;
(viii) SEQ ID NO: 227 and 225, respectively;
(ix) SEQ ID NO: 249 and 247, respectively;
(x) SEQ ID NO: 271 and 269, respectively;
(xi) SEQ ID NO: 293 and 291, respectively;
(xii) SEQ ID NO: 315 and 313, respectively;
(xiii) SEQ ID NO: 337 and 335, respectively;
(xiv) SEQ ID NO: 359 and 357, respectively;
(xv) SEQ ID NO: 381 and 379, respectively; and
(xvi) SEQ ID NO: 403 and 401, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences set forth in SEQ ID NO: 177 and 179, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences at least 90% identical to the amino acid sequences set forth in SEQ ID NO: 177 and 179, respectively.

In some embodiments, the disclosure provides an isolated monoclonal antibody that specifically binds to and antagonizes human IL-27, or antigen binding portion thereof, wherein the antibody or antigen binding portion thereof comprises a heavy and a light chain comprising amino acid sequences set forth in SEQ ID NO: 181 and 179, respectively.

In some embodiments, the disclosure provides an isolated monoclonal antibody that specifically binds to and antagonizes human IL-27, or antigen binding portion thereof, wherein the antibody or antigen binding portion thereof comprises a heavy chain and a light chain comprising amino acid sequences at least 90% identical to the amino acid sequences set forth in SEQ ID NO: 181 and 179, respectively.

Methods for Producing the Anti-IL-27 Antibodies and Antigen-binding Fragments Thereof The disclosure also features methods for producing any of the anti-IL-27 antibodies or antigen-binding fragments thereof described herein. In some embodiments, methods for preparing an antibody described herein can include immunizing a subject (e.g., a non-human mammal) with an appropriate immunogen. Suitable immunogens for generating any of the antibodies described herein are set forth herein. For example, to generate an antibody that binds to IL-27, a skilled artisan can immunize a suitable subject (e.g., a non-human mammal such as a rat, a mouse, a gerbil, a hamster, a dog, a cat, a pig, a goat, a horse, or a non-human primate) with IL-27. In some embodiments, a full-length human IL-27 EBI3 monomer polypeptide comprising the amino acid sequence set forth in SEQ ID NO: 97 is used as the immunogen. In some embodiments, a full-length human IL-27p28 monomer polypeptide comprising the amino acid sequence set forth in SEQ ID NO: 98 is used as the immunogen.

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) *Autoimmunity* 31(1):15-24. See also, e.g., Lodmell et al. (2000) *Vaccine* 18:1059-1066; Johnson et al. (1999) *J Med Chem* 42:4640-4649; Baldridge et al. (1999) *Methods* 19:103-107; and Gupta et al. (1995) *Vaccine* 13(14): 1263-1276.

In some embodiments, the methods include preparing a hybridoma cell line that secretes a monoclonal antibody that binds to the immunogen. For example, a suitable mammal such as a laboratory mouse is immunized with a IL-27 polypeptide as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies, e.g., an antibody that binds to human IL-27 and In some embodiments, a skilled artisan can identify an anti-IL-27 antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with IL-27 polypeptide as described above. mRNA can be isolated from the cells and converted to cDNA using standard molecular biology techniques. See, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human IL-27) using any immunological or biochemical based method known in the art. For example, specific binding of an antibody to IL-27, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

It is understood that the above methods can also be used to determine if, e.g., an anti-IL-27 antibody does not bind to full-length, human IL-27 and/or IL-27 proteins.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some embodiments, the anti-IL-27 antibodies described herein comprise an altered heavy chain constant region that has reduced (or no) effector function relative to its corresponding unaltered constant region. Effector functions involving the constant region of the anti-IL-27 antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

In one embodiment, the anti-IL-27 antibodies described herein comprise an IgG4 heavy chain constant region. In one embodiment, the IgG4 heavy chain constant region is a wild type IgG4 heavy chain constant region. In another embodiment, the IgG4 constant region comprises a mutation, e.g., one or both of S228P and L235E or L235A, e.g., according to EU numbering (Kabat, E. A., et al., supra). Representative sequences for use in antibodies of the disclosure of wild-type and mutant IgG4 constant regions are set forth in Table 12. In one embodiment, the anti-IL-27 antibodies described herein comprise an IgG1 constant region. In one embodiment, the IgG1 heavy chain constant region is a wild type IgG1 heavy chain constant region. In another embodiment, the IgG1 heavy chain constant region comprises a mutation. Representative sequences for use in antibodies of the disclosure of wild-type and mutant IgG4 constant regions are set forth in Table 12.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the anti-IL-27 antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An anti-IL-27 antibody described herein comprising an altered constant region displaying reduced ADCC and/or CDC may exhibit reduced or no ADCC and/or CDC activity.

In some embodiments, an anti-IL-27 antibody described herein exhibits reduced or no effector function. In some embodiments, an anti-IL-27 antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In some embodiments, an anti-IL-27 antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

Recombinant Antibody Expression and Purification

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2): 155-159; and Pollock et al. (1999) *J Immunol Methods* 231(1-2): 147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3rd edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

Modification of the Antibodies or Antigen-Binding Fragments Thereof

The antibodies or antigen-binding fragments thereof can be modified following their expression and purification. The modifications can be covalent or non-covalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (FLAG (DYKDDDDK (SEQ ID NO: 405)), polyhistidine (6-His; HHHHHH (SEQ ID NO: 406), hemagglutinin (HA; YPYDVPDYA (SEQ ID NO: 407)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NETS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Pharmaceutical Compositions and Formulations

In certain embodiments, the invention provides for a pharmaceutical composition comprising an anti-IL-27 antibody with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and/or rate of in vivo clearance of the anti-IL-27 antibody.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an anti-IL-27 antibody can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an anti-IL-27 antibody can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an anti-IL-27 antibody, in a pharmaceutically acceptable vehicle. In certain embodiments, a vehicle for parenteral injection is sterile distilled water in which an anti-IL-27 antibody is formulated as a sterile, isotonic solution, and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an anti-IL-27 antibody can be formulated as a dry powder for inhalation. In certain embodiments, an inhalation solution comprising an anti-IL-27 antibody can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an anti-IL-27 antibody that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an anti-IL-27 antibody. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an anti-IL-27 antibody in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an anti-IL-27 antibody in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an anti-IL-27 antibody to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an anti-IL-27 antibody is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of an anti-IL-27 antibody in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intraocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an anti-IL-27 antibody in an ex vivo manner. In such instances, cells, tissues and/or organs that have been removed from the patient are exposed to a pharmaceutical composition comprising an anti-IL-27 antibody after which the cells, tissues and/or organs are subsequently implanted back into the patient.

In certain embodiments, an anti-IL-27 antibody can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Applications

The compositions described herein can be used in a number of diagnostic and therapeutic applications. For example, detectably-labeled antigen-binding molecules can be used in assays to detect the presence or amount of the target antigens in a sample (e.g., a biological sample). The compositions can be used in in vitro assays for studying inhibition of target antigen function. In some embodiments, e.g., in which the compositions bind to and inhibit a complement protein, the compositions can be used as positive controls in assays designed to identify additional novel compounds that inhibit complement activity or otherwise are useful for treating a complement-associated disorder. For example, a IL-27-inhibiting composition can be used as a positive control in an assay to identify additional compounds (e.g., small molecules, aptamers, or antibodies) that reduce or abrogate IL-27 production. The compositions can also be used in therapeutic methods as elaborated on below.

In some embodiments, the disclosure provides a method of detecting IL-27 in a biological sample or in a subject, comprising (i) contacting the sample or the subject (and optionally, a reference sample or subject) with any antibody described herein under conditions that allow interaction of the antibody molecule and IL-27 to occur, and (ii) detecting formation of a complex between the antibody molecule and the sample or the subject (and optionally, the reference sample or subject).

Kits

A kit can include an anti-IL-27 antibody as disclosed herein, and instructions for use. The kits may comprise, in a suitable container, an anti-IL-27 antibody, one or more controls, and various buffers, reagents, enzymes and other standard ingredients well known in the art. In some aspects, the disclosure provides a kit comprising an anti-IL-27 antibody or antigen-binding portion as disclosed herein, and instructions for use in stimulating an immune response in a subject, or treating cancer in a subject, optionally with instructions for use in combination with one or more additional therapeutic agents or procedure as disclosed herein.

The container can include at least one vial, well, test tube, flask, bottle, syringe, or other container means, into which an anti-IL-27 antibody may be placed, and in some instances, suitably aliquoted. Where an additional component is provided, the kit can contain additional containers into which this component may be placed. The kits can also include a means for containing an anti-IL-27 antibody and any other reagent containers in close confinement for commercial sale. Such containers may include injection or blow-molded plastic containers into which the desired vials are retained. Containers and/or kits can include labeling with instructions for use and/or warnings.

Methods of Use

The compositions of the present invention have numerous in vitro and in vivo utilities involving the detection and/or quantification of IL-27 and/or the antagonism of IL-27 function.

In some embodiments, the disclosure provides a method to inhibit or reduce STAT1 and/or STAT3 phosphorylation in a cell, the method comprising contacting the cell with an isolated monoclonal antibody, or antigen binding fragment, provided by the disclosure, wherein the antibody, or antigen binding portion thereof, inhibits or reduces STAT1 and/or STAT3 phosphorylation in a cell.

In some embodiments, the disclosure provides a method to inhibit or reduce inhibition of CD161 expression in a cell, the method comprising contacting the cell with an isolated monoclonal antibody, or antigen binding fragment, provided by the disclosure, wherein the antibody, or antigen binding portion thereof, inhibits or reduces inhibition of CD161 expression in a cell.

In some embodiments, the disclosure provides a method to inhibit or reduce PD-L1 and/or TIM-3 expression in a cell, the method comprising contacting the cell with an isolated monoclonal antibody, or antigen binding fragment, provided by the disclosure, wherein the antibody, or antigen binding portion thereof, inhibits or PD-L1 and/or TIM-3 expression in a cell.

In some embodiments, the disclosure provides a method to induce or enhance secretion of one or more cytokines from a cell, the method comprising contacting the cell with the isolated monoclonal antibody, or antigen binding fragment, provided by the disclosure, wherein the antibody, or antigen binding portion thereof, induces or enhances PD-1 mediated secretion of one or more cytokines from a cell.

In some embodiments, the disclosure provides a method of stimulating an immune response in a subject, the method comprising administering to the subject an effective amount of an isolated monoclonal antibody, or antigen binding portion thereof, that specifically binds to and antagonizes IL-27, provided by the disclosure, or a pharmaceutical composition comprising the antibody or antigen binding portion thereof, and a pharmaceutically acceptable carrier.

In some embodiments, the disclosure provides a method of treating a cancer in a subject, the method comprising administering to the subject an effective amount an isolated monoclonal antibody, or antigen binding portion thereof, that specifically binds to and antagonizes IL-27, provided by the disclosure, or a pharmaceutical composition comprising the antibody or antigen binding portion thereof, and a pharmaceutically acceptable carrier.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, inhibits or reduces STAT1 and/or STAT3 phosphorylation in a cell, thereby stimulating the immune response, or treating the cancer.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, inhibits or reduces inhibition of CD161 expression in a cell, thereby stimulating the immune response, or treating the cancer.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, inhibits or reduces PD-L1 and/or TIM-3 expression in a cell, thereby stimulating the immune response, or treating the cancer.

In some embodiments, the disclosure provides a method of stimulating an immune response, or treating a cancer in a subject, the method comprising administering to the subject an effective amount of an isolated monoclonal antibody, or antigen binding fragment, provided by the disclosure, or a pharmaceutical composition comprising the antibody or antigen binding portion thereof, and a pharmaceutically acceptable carrier, wherein the antibody, or antigen binding portion thereof, or the pharmaceutical composition, induces or enhances PD-1-mediated secretion of one or more cytokines from a cell, thereby stimulating the immune response, or treating the cancer.

In some embodiments, the cancer is chosen from lung cancer (e.g., non-small cell lung cancer), sarcoma, testicular cancer, ovarian cancer, pancreas cancer, breast cancer (e.g., triple-negative breast cancer), melanoma, head and neck cancer (e.g., squamous head and neck cancer), colorectal cancer, bladder cancer, endometrial cancer, prostate cancer, thyroid cancer, hepatocellular carcinoma, gastric cancer, brain cancer, lymphoma (e.g., DL-BCL), leukemia (e.g., AML) or renal cancer (e.g., renal cell carcinoma, e.g., renal clear cell carcinoma).

The above-described compositions are useful in, inter alia, methods for treating or preventing a variety of cancers in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an anti-IL-27 antibody or antigen-binding fragment thereof is therapeutically delivered to a subject by way of local administration.

A suitable dose of an antibody or fragment thereof described herein, which dose is capable of treating or preventing cancer in a subject, can depend on a variety of factors including, e.g., the age, sex, and weight of a subject to be treated and the particular inhibitor compound used. For example, a different dose of a whole anti-IL-27 antibody may be required to treat a subject with cancer as compared to the dose of a IL-27-binding Fab' antibody fragment required to treat the same subject. Other factors affecting the dose administered to the subject include, e.g., the type or severity of the cancer. For example, a subject having metastatic melanoma may require administration of a different dosage of an anti-IL-27 antibody than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse). Suitable dosages are described herein.

A pharmaceutical composition can include a therapeutically effective amount of an anti-IL-27 antibody or antigen-binding fragment thereof described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., reduction in tumor growth. For example, a therapeutically effective amount of an anti-IL-27 antibody can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the antibodies or fragments thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

In some embodiments, the composition contains any of the antibodies or antigen-binding fragments thereof described herein and one or more (e.g., two, three, four, five, six, seven, eight, nine, 10, or 11 or more) additional therapeutic agents such that the composition as a whole is therapeutically effective. For example, a composition can contain an anti-IL-27 antibody described herein and an alkylating agent, wherein the antibody and agent are each at a concentration that when combined are therapeutically effective for treating or preventing a cancer (e.g., melanoma) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or antigen-binding fragment thereof that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. For an anti-IL-27 antibody described herein, the therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the compositions described herein (e.g., anti-IL-27 compositions) can be used to treat a variety of cancers such as but not limited to: Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma (HCC), hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system.

Combination Therapy

In some embodiments, an anti-IL-27 antibody, or antigen binding portion thereof, provided by the disclosure, can be combined with one or more additional therapeutics or treatments, e.g., another therapeutic or treatment for a cancer. For example, the anti-IL-27 antibody, or antigen binding portion thereof, can be administered to a subject (e.g., a human patient) in combination with one or more additional therapeutics, wherein the combination provides a therapeutic benefit to a subject who has, or is at risk of developing, cancer.

In some embodiments, an anti-IL-27 antibody, or antigen binding portion thereof, and the one or more additional therapeutics are administered at the same time (e.g., simultaneously). In other embodiments, the anti-IL-27 antibody, or antigen binding portion thereof, is administered first in time and the one or more additional therapeutics are administered second in time (e.g., sequentially). In some embodiments, the one or more additional therapeutics are administered first in time and the anti-IL-27 antibody is administered second in time.

An anti-IL-27 antibody or an antigen-binding fragment thereof described herein can replace or augment a previously or currently administered therapy. For example, upon treating with an anti-IL-27 antibody or antigen-binding fragment thereof, administration of the one or more additional therapeutics can cease or diminish, e.g., be administered at lower levels. In some embodiments, administration of the previous therapy can be maintained. In some embodiments, a previous therapy will be maintained until the level of the anti-IL-27 antibody reaches a level sufficient to provide a therapeutic effect.

In some embodiments, the disclosure provides a method of treating cancer in a subject, the method comprising administering to the subject an effective amount of an isolated monoclonal antibody, or antigen binding portion thereof, that specifically binds to and antagonizes IL-27, provided by the disclosure, in combination with one or more additional therapeutic agents or procedure, wherein the second therapeutic agent or procedure is selected from the group consisting of: a chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule, a vaccine, or a cellular immunotherapy, or a combination thereof.

In some embodiments, the one or more additional therapeutic agents is a PD-1 antagonist, a TIM-3 inhibitor, a LAG-3 inhibitor, a TIGIT inhibitor, a CD112R inhibitor, a TAM inhibitor, a STING agonist, a 4-1BB agonist, or a combination thereof.

In some embodiments, the one or more additional therapeutic agents is a PD-1 antagonist. In some embodiments, the PD-1 antagonist is selected from the group consisting of: PDR001, nivolumab, pembrolizumab, pidilizumab, MEDI0680, REGN2810, TSR-042, PF-06801591, and AMP-224. In certain embodiments, the one or more additional therapeutic agents is a PD-L1 inhibitor. In some embodiments, the PD-L1 inhibitor is selected from the group consisting of: FAZ053, Atezolizumab, Avelumab, Durvalumab, and BMS-936559. In some embodiments, the disclosure provides a method of enhancing one or more activities of an anti-PD-1 antibody (e.g., enhances PD-1-mediated cytokine secretion; enhances anti-PD-1 mediated TNFα secretion; enhances anti-PD-1 mediated IL-6 secretion from a cell exposed to anti-PD-1 antibodies), the method comprising exposing a cell to an antibody, or antigen binding portion thereof, provided by the disclosure, concurrently with or sequentially to an anti-PD-1 antibody, thereby to enhance one or more activities of the anti-PD1 antibody.

In some embodiments, the one or more additional therapeutic agents is sunitinib (Sutent®), Cabozantinib (Cabometyx®), Axitinib (Inlyta®), Lenvatinib (Lenvima®), Everolimus (Afinitor®), Bevacizumab (Avastin®), epacadostat, NKTR-214 (CD-122-biased agonist), tivozanib (Fotivda®), abexinostat, Ipilimumab (Yervoy®), tremelimumab, Pazopanib (Votrient®), Sorafenib (Nexavar®), Temsirolimus (Torisel®), Ramucirumab (Cyramza®), niraparib, savolitinib, vorolanib (X-82), Regorafenib (Stivargo®), Donafenib (multikinase inhibitor), Camrelizumab (SHR-1210), pexastimogene devacirepvec (JX-594), Ramucirumab (Cyramza®), apatinib (YN968D1), encapsulated doxorubicin (Thermodox®), Tivantinib (ARQ197), ADI-PEG 20, binimetinib, apatinib mesylate, nintedanib, lirilumab, Nivolumab (Opdivo®), Pembrolizumab (Keytruda®), Atezolizumab (Tecentriq®), Avelumab (Bavencio®), Durvalumab (Imfimzi®), cemiplimab-rwlc (Libtayo®), tislelizumab, and/or spartalizumab.

In some embodiments, the one or more additional therapeutic agents is a TIM-3 inhibitor, optionally wherein the TIM-3 inhibitor is MGB453 or TSR-022.

In some embodiments, the one or more additional therapeutic agents is a LAG-3 inhibitor, optionally wherein the LAG-3 inhibitor is selected from the group consisting of LAG525, BMS-986016, and TSR-033.

In some embodiments, the one or more additional therapeutic agents is a TIGIT inhibitor. In some embodiments, the one or more additional therapeutic agents is a CD112R inhibitor. In some embodiments, the one or more additional therapeutic agents is a TAM (Axl, Mer, Tyro) inhibitor. In some embodiments, the one or more additional therapeutic agents is a STING agonist. In some embodiments, the one or more additional therapeutic agents is a 4-1BB agonist.

Combination with Chemotherapeutic Agents

Chemotherapeutic agents suitable for combination and/or co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and anti-mitotic agents (e.g. vincristine and vinblastine) and temozolomide.

Combination with PD-1/PD-L1 Antagonists

In some embodiments, the anti-IL-27 antibodies, or antigen binding portions thereof, provided by the disclosure are combined (e.g., administered in combination) with one or more PD-1 antagonist that specifically binds to human PD-1 or PD-L1 and inhibits PD-1/PD-L1 biological activity and/or downstream pathway(s) and/or cellular processed mediated by human PD-1/PD-L1 signaling or other human PD-1/PD-L1-mediated functions.

Accordingly, provided herein are PD-1 antagonists that directly or allosterically block, antagonize, suppress, inhibit or reduce PD-1/PD-L1 biological activity, including downstream pathways and/or cellular processes mediated by PD-1/PD-L1 signaling, such as receptor binding and/or elicitation of a cellular response to PD-1/PD-L1. Also provided herein are PD-1 antagonists that reduce the quantity or amount of human PD-1 or PD-L1 produced by a cell or subject.

In some embodiments, the disclosure provides a PD-1 antagonist that binds human PD-1 and prevents, inhibits or reduces PD-L1 binding to PD-1. In some aspects, the PD-1 antagonist binds to the mRNA encoding PD-1 or PD-L1 and prevents translation. In some embodiments, the PD-1 antagonist binds to the mRNA encoding PD-1 or PD-L1 and causes degradation and/or turnover.

In some embodiments, the PD-1 antagonist inhibits PD-1 signaling or function. In some embodiments, the PD-1 antagonist blocks binding of PD-1 to PD-L1, PD-L2, or to both PD-L1 and PD-L2. In some embodiments, the PD-1 antagonist blocks binding of PD-1 to PD-L1. In some embodiments, the PD-1 antagonist blocks binding of PD-1 to PD-L2. In some embodiments, the PD-1 antagonist blocks the binding of PD-1 to PD-L1 and PD-L2. In some embodiments, the PD-1 antagonist specifically binds PD-1. In some embodiments, the PD-1 antagonist specifically binds PD-L1. In some embodiments, the PD-1 antagonist specifically binds PD-L2.

In some embodiments, the PD-1 antagonist inhibits the binding of PD-1 to its cognate ligand. In some embodiments, the PD-1 antagonist inhibits the binding of PD-1 to PD-L1, PD-1 to PD-L2, or PD-1 to both PD-L1 and PD-L2. In some embodiments, the PD-1 antagonist does not inhibit the binding of PD-1 to its cognate ligand.

In some embodiments, the PD-1 antagonist is an isolated monoclonal antibody (mAb), or antigen binding fragment thereof, which specifically binds to PD-1 or PD-L1. In some embodiments, the PD-1 antagonist is an antibody or antigen binding fragment thereof that specifically binds to human PD-1. In some embodiments, the PD-1 antagonist is an antibody or antigen binding fragment thereof that specifically binds to human PD-L1. In some embodiments, the PD-1 antagonist is an antibody or antigen binding fragment that binds to human PD-L1 and inhibits the binding of PD-L1 to PD-1. In some embodiments, the PD-1 antagonist is an antibody or antigen binding fragment that binds to human PD-1 and inhibits the binding of PD-L1 to PD-1.

Several immune checkpoint antagonists that inhibit or disrupt the interaction between PD-1 and either one or both of its ligands PD-L1 and PD-L2 are in clinical development or are currently available to clinicians for treating cancer.

Examples of anti-human PD-1 monoclonal antibodies, or antigen binding fragments thereof, that may comprise the PD-1 antagonist in any of the compositions, methods, and uses provided by the disclosure include, but are not limited to: KEYTRUDA® (pembrolizumab, MK-3475, h409A11; see U.S. Pat. Nos. 8,952,136, 8,354,509, 8,900,587, and EP2170959, all of which are included herein by reference in their entirety; Merck), OPDIVO® (nivolumab, BMS-936558, MDX-1106, ONO-4538; see U.S. Pat. Nos. 7,595,048, 8,728,474, 9,073,994, 9,067,999, EP1537878, U.S. Pat. Nos. 8,008,449, 8,779,105, and EP2161336, all of which are included herein by reference in their entirety; Bristol Myers Squibb), MEDI0680 (AMP-514), BGB-A317 and BGB-108 (BeiGene), 244C8 and 388D4 (see WO2016106159, which is incorporated herein by reference in its entirety; Enumeral Biomedical), PDR001 (Novartis), and REGN2810 (Regeneron). Accordingly, in some embodiments the PD-1 antagonist is pembrolizumab. In some embodiments, the PD-1 antagonist is nivolumab.

Examples of anti-human PD-L1 monoclonal antibodies, or antigen binding fragments thereof, that may comprise the PD-1 antagonist in any of the compositions, methods, and uses provided by the disclosure include, but are not limited to: BAVENCIO® (avelumab, MSB0010718C, see WO2013/79174, which is incorporated herein by reference in its entirety; Merck/Pfizer), IMFINZI® (durvalumab, MEDI4736), TECENTRIQ® (atezolizumab, MPDL3280A, RG7446; see WO2010/077634, which is incorporated herein by reference in its entirety; Roche), MDX-1105 (BMS-936559, 12A4; see U.S. Pat. No. 7,943,743 and WO2013/173223, both of which are incorporated herein by reference in their entirety; Medarex/BMS), and FAZ053 (Novartis). Accordingly, in some embodiments the PD-1 antagonist is avelumab. In some embodiments, the PD-1 antagonist is durvalumab. In some embodiments, the PD-1 antagonist is atezolizumab.

In some embodiments, the PD-1 antagonist is an immunoadhesin that specifically bind to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342, both of which are incorporated herein by reference in their entirety. In some embodiments, the PD-1 antagonist is AMP-224 (also known as B7-DCIg), which is a PD-L2-FC fusion protein that specifically binds to human PD-1.

It will be understood by one of ordinary skill that any PD-1 antagonist which binds to PD-1 or PD-L1 and disrupts the PD-1/PD-L1 signaling pathway, is suitable for compositions, methods, and uses disclosed herein.

In some embodiments, the PD-1/PD-L1 antagonist is a small molecule, a nucleic acid, a peptide, a peptide mimetic, a protein, a carbohydrate, a carbohydrate derivative, or a glycopolymer. Exemplary small molecule PD-1 inhibitors are described in Zhan et al., (2016) Drug Discov Today 21(6):1027-1036.

Combinations with TIM-3 Inhibitors

In some embodiments, an anti-IL-27 antibody, or antigen binding portion thereof, provided by the disclosure is combined (e.g., administered in combination) with a TIM-3 inhibitor. The TIM-3 inhibitor may be an antibody, an antigen binding fragment thereof, an immunoadhesin, a fusion protein, or an oligopeptide. In some embodiments, the TIM-3 inhibitor is chosen from MGB453 (Novartis), TSR-022 (Tesaro), or LY3321367 (Eli Lilly). In some embodiments, the anti-IL-27 antibody, or antigen binding portion thereof, is administered in combination with MGB453. In some embodiments, the anti-IL-27 antibody, or antigen binding portion thereof, is administered in combination with TSR-022.

Combinations with LAG-3 Inhibitors

In some embodiments, an anti-IL-27 antibody, or antigen binding portion thereof, provided by the disclosure is combined (e.g., administered in combination) with a LAG-3 inhibitor. The LAG-3 inhibitor may be an antibody, an antigen binding fragment thereof, an immunoadhesin, a fusion protein, or oligopeptide. In some embodiments, the LAG-3 inhibitor is chosen from LAG525 (Novartis), BMS-986016 (Bristol-Myers Squibb), TSR-033 (Tesaro), MK-4280 (Merck & Co), or REGN3767 (Regeneron).

Other Combinations

In some embodiments, an anti-IL-27 antibody, or antigen binding portion thereof, provided by the disclosure is combined (e.g., administered in combination) with a TIGIT inhibitor, a kinase inhibitor (e.g., a tyrosine kinase inhibitor (TKI)), a CD112R inhibitor, a TAM receptor inhibitor, a STING agonist and/or a 4-1BB agonist, or a combination thereof.

Methods of Detection

In some embodiments, an anti-IL-27 antibody or an antigen-binding fragment thereof described herein can be employed in methods of detection and/or quantification of human IL-27 in a biological sample. Accordingly, an anti-IL-27 antibody, or an antigen-binding fragment thereof, as described herein is useful to diagnose, prognose and/or determine progression of disease (e.g., cancer) in a patient.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, the disclosure provides a method of detecting IL-27 in a sample from a subject, the method comprising the (a) contacting a sample from the subject with a detection antibody under conditions to permit the detection antibody to form a detection antibody-IL-27 complex, if IL-27 is present in the sample, wherein the detection antibody is an antibody, or antigen binding fragment thereof, provided by the disclosure; and (b) detecting the presence of the complex, if any, produced in step (a).

In some embodiments, the disclosure provides a method of detecting an IL-27-associated cancer in a subject, the method comprising the steps of: (a) contacting a sample from a subject suspected of having an IL-27-associated cancer with a detection antibody under conditions to permit the detection antibody to form a detection antibody-IL-27 complex, if IL-27 is present in the sample, wherein the detection antibody is an antibody, or antigen binding portion thereof, provided by the disclosure; and (b) detecting the presence of the complex, if any, produced in step (a). In some embodiments, the detection antibody is coupled to a detectable label. In some embodiments, the method further comprises contacting the sample with a capture antibody to produce a complex comprising IL-27 and the capture antibody, if IL-27 is present in the sample, wherein the capture antibody is an antibody, or antigen binding portion thereof, provided by the disclosure.

In some embodiments, the capture antibody is immobilized on a solid support. In some embodiments, the sample is contacted with the capture antibody before the detection antibody. In some embodiments, the sample is a body fluid sample. In some embodiments, the fluid sample is blood, serum, plasma, cell lysates or tissue lysates.

In some embodiments, the cancer is selected from renal cell carcinoma (RCC), hepatocellular carcinoma, lung cancer, gastroesophageal cancer, ovarian cancer, endometrial cancer, melanoma, leukemia and lymphoma. In some embodiments, the cancer is renal cell carcinoma (RCC). In other embodiments, the cancer is hepatocellular carcinoma (HCC). In some embodiments, the cancer is selected from leukemia and lymphoma. In some embodiments, the cancer is acute myeloid leukemia (AML).

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: Generation and Characterization of Anti-IL-27 Antibodies that Specifically Bind the IL-27 EBI3 Monomer This Example describes the production of anti-IL-27 antibodies that specifically bind to the EBI3 subunit of human IL-27. Briefly, BALB/c mice were immunized with a human EBI3 immunization vector (Aldevron) and used in the generation and isolation of hybridomas expressing anti-EBI3 monoclonal antibodies. Isolated hybridomas included hybridomas expressing anti-IL-27 antibody molecules referred to herein as Ab1, Ab2, Ab3, Ab4, Ab5, Ab6, Ab7, and Ab8. Hybridoma supernatants were analyzed by flow cytometry on mammalian cells expressing a surface-targeted human EBI3. All the hybridoma clone supernatants tested bound to EBI3 expressing cells (data not shown).

An exemplary isolated anti-EBI3 antibody Ab7 (hereafter referred to as "Ab7", comprising an immunoglobulin heavy chain variable region hereafter referred to as "Ab7-$V_{H0}$" and an immunoglobulin light chain variable region hereafter referred to as "Ab7-$V_{L0}$") was sequenced and further characterized below (amino terminal signal peptide sequences are not shown).

The heavy chain variable region of the isolated Ab7 antibody (Ab7-$V_{H0}$) has the following sequence (FR1-CDR1-FR2-CDR2-FR3-CDR3-FR4-Constant region):

(SEQ ID NO: 1)

EVKLVESGGGLVQPGGSLKLFCAASGFTFTSYSMSWVRQTPEKRLEWVAY

ISYDGGSAYYPDTVKGRFSISRDNAKKTLYLQMSSLKSEDTAMYYCARHG

DYDDDDAMDYWGQGTSVTVSS.

A nucleic acid sequence encoding the heavy chain variable region Ab7-$V_{H0}$ has the following sequence (FR1-CDR1-FR2-CDR2-FR3-CDR3-FR4):

(SEQ ID NO: 2)

GAGGTGAAGCTGGTGGAGTCTGGGGGAGGCTTGGTACAGCCTGGGGGGTC

CCTGAAACTCTTCTGTGCAGCCTCTGGATTCACCTTTACCAGCTATTCCA

TGAGCTGGGTCCGCCAGACTCCAGAGAAGAGGCTGGAGTGGGTCGCATAC

ATTAGTTATGATGGTGGTAGCGCCTACTACCCTGACACTGTGAAGGGCCG

GTTCTCCATCTCCAGAGACAATGCCAAGAAAACCCTGTATCTGCAAATGA

GCAGCCTGAAGTCTGAGGACACGGCCATGTATTACTGTGCAAGACATGGA

GACTATGACGACGACGACGCGATGGACTACTGGGGCCAAGGAACCTCAGT

CACCGTCTCCTCA.

The light chain variable region of the isolated Ab7 antibody (Ab7-V$_{L0}$) has the following sequence (FR1-CDR1-FR2-CDR2-FR3-CDR3-FR4-Constant region):

(SEQ ID NO: 3)
DIQMTQSPASLSASVGETVTITCRASENIYSYLAWYQQKQGKSPQLLVYN

AETLTEGVPSRFSGSGSGTQFSLKINSLQPEDFGNYYCQHHYGTPLTFGA

GTKLDLK.

The heavy chain of the isolated Ab7 antibody (Ab7-V$_{H0}$-mIgG2a) has the following sequence (FR1-CDR1-FR2-CDR2-FR3-CDR3-FR4-Constant region):

(SEQ ID NO: 183)
EVKLVESGGGLVQPGGSLKLFCAASGFTFTSYSMSWVRQTPEKRLEWVAY

ISYDGGSAYYPDTVKGRFSISRDNAKKTLYLQMSSLKSEDTAMYYCARHG

DYDDDDAMDYWGQGTSVTVSSAKTTAPSVYPLAPVCGDTTGSSVTLGCLV

KGYFPEPVTLTWNSGSLSSGVHTFPAVLQSDLYTLSSSVTVTSSTWPSQS

ITCNVAHPASSTKVDKKIEPRGPTIKPCPPCKCPAPNLLGGPSVFIFPPK

IKDVLMISLSPIVTCVVVDVSEDDPDVQISWFVNNVEVHTAQTQTHREDY

NSTLRVVSALPIQHQDWMSGKEFKCKVNNKDLPAPIERTISKPKGSVRAP

QVYVLPPPEEEMTKKQVTLTCMVTDFMPEDIYVEWTNNGKTELNYKNTEP

VLDSDGSYFMYSKLRVEKKNWVERNSYSCSVVHEGLHNHHTTKSFSRTPG

K.

A nucleic acid sequence encoding the light chain variable region Ab7-V$_{L0}$ has the following sequence (FR1-CDR1-FR2-CDR2-FR3-CDR3-FR4):

(SEQ ID NO: 4)
GACATCCAGATGACCCAGTCTCCAGCCTCCCTGTCTGCATCTGTAGGAGA

AACTGTCACCATCACTTGCCGGGCAAGTGAGAACATTTACAGCTATTTAG

CATGGTATCAGCAGAAACAGGGGAAATCTCCTCAGCTCCTGGTCTATAAT

GCAGAAACCTTGACAGAAGGGGTCCCATCAAGGTTCAGCGGCAGTGGATC

TGGGACACAATTCTCTCTCAAGATCAACAGTCTGCAACCTGAAGATTTTG

GGAATTACTACTGTCAACATCATTACGGTACCCCGCTCACATTCGGCGCT

GGGACCAAGCTGGATCTGAAA.

The light chain of the isolated Ab7 antibody (Ab7-V$_{L0}$-mKappa) has the following sequence (FR1-CDR1-FR2-CDR2-FR3-CDR3-FR4-Constant region):

(SEQ ID NO: 184)
DIQMTQSPASLSASVGETVTITCRASENIYSYLAWYQQKQGKSPQLLVYN

AETLTEGVPSRFSGSGSGTQFSLKINSLQPEDFGNYYCQHHYGTPLTFGA

GTKLDLKADAAPTVSIFPPSSEQLTSGGASVVCFLNNFYPKDINVKWKID

GSERQNGVLNSWTDQDSKDSTYSMSSTLTLTKDEYERHNSYTCEATHKTS

TSPIVKSFNRNEC.

Humanized Ab7 antibodies were designed using methods known in the art. Briefly, the V region gene sequences encoding the mouse monoclonal Ab7 antibody were used to construct a series of fully humanized antibodies. Variable region genes were cloned into vectors encoding a human IgG1 heavy chain constant domain and a human kappa light chain constant domain. Chimeric and humanized antibodies were transiently expressed in mammalian cells. Humanization of the isolated Ab7 heavy chain variable region resulted in 5 humanized heavy chain variable region variants (hereafter referred to as "Ab7-V$_{H1}$," "Ab7-V$_{H2}$," "Ab7-V$_{H3}$," "Ab7-V$_{H4}$," and "Ab7-V$_{H5}$"). Humanization of the isolated Ab7 light chain variable region resulted in 4 humanized light chain variable region variants (hereafter referred to as "Ab7-V$_{L1}$," "Ab7-V$_{L2}$," "Ab7-V$_{L3}$," and "Ab7-V$_{L4}$").

The protein sequences defining the humanized Ab7 variant variable regions, and nucleotide sequences encoding the humanized Ab7 variant variable regions, are summarized below (amino terminal signal peptide sequences are not shown).

The heavy chain variable region Ab7-V$_{H1}$ has the following sequence (FR1-CDR1-FR2-CDR2-FR3-CDR3-FR4):

(SEQ ID NO: 5)
EVKLVESGGGLVQPGGSLRLSCAASGFTFTSYSMSWVRQAPGKGLEWVAY

ISYDGGSAYYPDTVKGRFTISRDNSKKTLYLQMSSLKSEDTAMYYCARHG

DYDDDDAMDYWGQGTSVTVSS.

A nucleic acid sequence encoding the heavy chain variable region Ab7-V$_{H1}$ has the following sequence (FR1-CDR1-FR2-CDR2-FR3-CDR3-FR4):

(SEQ ID NO: 6)
GAGGTGAAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTACCCTGACACTGTGAAGGGCCG

GTTCACCATCTCCAGAGACAATTCCAAGAAAACCCTGTATCTGCAAATGA

GCAGCCTGAAGTCTGAGGACACGGCCATGTATTACTGTGCAAGACATGGA

GACTATGACGACGACGACGCGATGGACTACTGGGGCCAAGGAACCTCAGT

CACCGTCTCCTCA.

The heavy chain variable region Ab7-V$_{H2}$ has the following sequence (FR1-CDR1-FR2-CDR2-FR3-CDR3-FR4):

(SEQ ID NO: 7)

EVQLVESGGGLVQPGGSLRLSCAASGFTFTSYSMSWVRQAPGKGLEWVAY

ISYDGGSAYYPDTVKGRFTISRDNSKNTLYLQMSSLKSEDTAMYYCARHG

DYDDDDAMDYWGQGTLVTVSS.

A nucleic acid sequence encoding the heavy chain variable region Ab7-$V_{H2}$ has the following sequence (FR1-CDR1-FR2-CDR2-FR3-CDR3-FR4):

(SEQ ID NO: 8)

GAGGTGCAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTACCCTGACACTGTGAAGGGCCG

GTTCACCATCTCCAGAGACAATTCCAAGAACACCCTGTATCTGCAAATGA

GCAGCCTGAAGTCTGAGGACACGGCCATGTATTACTGTGCAAGACATGGA

GACTATGACGACGACGACGCGATGGACTACTGGGGCCAAGGAACCCTGGT

CACCGTCTCCTCA.

The heavy chain variable region Ab7-$V_{H3}$ has the following sequence (FR1-CDR1-FR2-CDR2-FR3-CDR3-FR4):

(SEQ ID NO: 9)

EVKLVESGGGLVQPGGSLRLSCAASGFTFTSYSMSWVRQAPGKGLEWVAY

ISYDGGSAYYPDTVKGRFTISRDNSKKTLYLQMNSLRAEDTAVYYCARHG

DYDDDDAMDYWGQGTLVTVSS.

A nucleic acid sequence encoding the heavy chain variable region Ab7-$V_{H3}$ has the following sequence (FR1-CDR1-FR2-CDR2-FR3-CDR3-FR4):

(SEQ ID NO: 10)

GAGGTGAAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTATCCTGACACTGTGAAGGGCCG

GTTCACCATCTCCAGAGACAATTCCAAGAAAACCCTGTATCTGCAAATGA

ACAGCCTGAGAGCCGAGGACACGGCCGTATATTACTGTGCAAGACATGGA

GACTATGACGACGACGACGCGATGGACTACTGGGGCCAAGGAACCCTGGT

CACCGTCTCCTCA.

The heavy chain variable region Ab7-$V_{H4}$ has the following sequence (FR1-CDR1-FR2-CDR2-FR3-CDR3-FR4):

(SEQ ID NO: 11)

EVQLVESGGGLVQPGGSLRLSCAASGFTFTSYSMSWVRQAPGKGLEWVAY

ISYDGGSAYYPDTVKGRFTISRDNSKNTLYLQMNSLRAEDTAVYYCARHG

DYDDDDAMDYWGQGTLVTVSS.

A nucleic acid sequence encoding the heavy chain variable region Ab7-$V_{H4}$ has the following sequence (FR1-CDR1-FR2-CDR2-FR3-CDR3-FR4):

(SEQ ID NO: 12)

GAGGTGCAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTATCCTGACACTGTGAAGGGCCG

GTTCACCATCTCCAGAGACAATTCCAAGAACACCCTGTATCTGCAAATGA

ACAGCCTGAGAGCCGAGGACACGGCCGTATATTACTGTGCAAGACATGGA

GACTATGACGACGACGACGCGATGGACTACTGGGGCCAAGGAACCCTGGT

CACCGTCTCCTCA.

The heavy chain variable region Ab7-$V_{H5}$ has the following sequence (FR1-CDR1-FR2-CDR2-FR3-CDR3-FR4):

(SEQ ID NO: 13)

EVQLVESGGGLVQPGGSLRLSCAASGFTFTSYSMSWVRQAPGKGLEWVSY

ISYDGGSAYYPDTVKGRFTISRDNSKNTLYLQMNSLRAEDTAVYYCARHG

DYDDDDAMDYWGQGTLVTVSS.

A nucleic acid sequence encoding the heavy chain variable region Ab7-$V_{H5}$ has the following sequence (FR1-CDR1-FR2-CDR2-FR3-CDR3-FR4):

(SEQ ID NO: 14)

GAGGTGCAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTGTCTTAC

ATTAGTTATGATGGTGGTAGCGCCTACTATCCTGACACTGTGAAGGGCCG

GTTCACCATCTCCAGAGACAATTCCAAGAACACCCTGTATCTGCAAATGA

ACAGCCTGAGAGCCGAGGACACGGCCGTATATTACTGTGCAAGACATGGA

GACTATGACGACGACGACGCGATGGACTACTGGGGCCAAGGAACCCTGGT

CACCGTCTCCTCA.

The light chain variable region Ab7-$V_{L1}$ has the following sequence (FR1-CDR1-FR2-CDR2-FR3-CDR3-FR4):

(SEQ ID NO: 15)

DIQMTQSPSSLSASVGDRVTITCRASENIYSYLAWYQQKQGKAPKLLVYN

AETLTEGVPSRFSGSGSGTDFTLTISSLQPEDFANYYCQHHYGTPLTFGQ

GTKLDIK.

A nucleic acid sequence encoding the light chain variable region Ab7-$V_{L1}$ has the following sequence (FR1-CDR1-FR2-CDR2-FR3-CDR3-FR4):

(SEQ ID NO: 16)

GACATCCAGATGACCCAGTCTCCATCCTCCCTGTCTGCATCTGTAGGAGA

CAGAGTCACCATCACTTGCCGGGCAAGTGAGAACATTTACAGCTATTTAG

CATGGTATCAGCAGAAACAGGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

-continued

CAAATTACTACTGTCAACATCATTACGGTACCCCGCTCACATTCGGCCAA

GGGACCAAGCTGGATATCAAA.

The light chain variable region Ab7-$V_{L2}$ has the following sequence (FR1-CDR1-FR2-CDR2-FR3-CDR3-FR4):

(SEQ ID NO: 17)

DIQMTQSPSSLSASVGDRVTITCRASENIYSYLAWYQQKPGKAPKLLVYN

AETLTEGVPSRFSGSGSGTDFTLTISSLQPEDFANYYCQHHYGTPLTFGQ

GTKLEIK.

A nucleic acid sequence encoding the light chain variable region Ab7-$V_{L2}$ has the following sequence (FR1-CDR1-FR2-CDR2-FR3-CDR3-FR4):

(SEQ ID NO: 18)

GACATCCAGATGACCCAGTCTCCATCCTCCCTGTCTGCATCTGTAGGAGA

CAGAGTCACCATCACTTGCCGGGCAAGTGAGAACATTTACAGCTATTTAG

CATGGTATCAGCAGAAACCAGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAAATTACTACTGTCAACATCATTACGGTACCCCGCTCACATTCGGCCAA

GGGACCAAGCTGGAAATCAAA.

The light chain variable region Ab7-$V_{L3}$ has the following sequence (FR1-CDR1-FR2-CDR2-FR3-CDR3-FR4):

(SEQ ID NO: 19)

DIQMTQSPSSLSASVGDRVTITCRASENIYSYLAWYQQKPGKAPKLLVYN

AETLTEGVPSRFSGSGSGTDFTLTISSLQPEDFATYYCQHHYGTPLTFGQ

GTKLEIK.

A nucleic acid sequence encoding the light chain variable region Ab7-$V_{L3}$ has the following sequence (FR1-CDR1-FR2-CDR2-FR3-CDR3-FR4):

(SEQ ID NO: 20)

GACATCCAGATGACCCAGTCTCCATCCTCCCTGTCTGCATCTGTAGGAGA

CAGAGTCACCATCACTTGCCGGGCAAGTGAGAACATTTACAGCTATTTAG

CATGGTATCAGCAGAAACCAGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAACTTACTACTGTCAACATCATTACGGTACCCCGCTCACATTCGGCCAA

GGGACCAAGCTGGAAATCAAA.

The light chain variable region Ab7-$V_{L4}$ has the following sequence (FR1-CDR1-FR2-CDR2-FR3-CDR3-FR4):

(SEQ ID NO: 21)

DIQMTQSPSSLSASVGDRVTITCRASENIYSYLNWYQQKPGKAPKLLVYN

AETLTEGVPSRFSGSGSGTDFTLTISSLQPEDFATYYCQHHYGTPLTFGQ

GTKLEIK.

A nucleic acid sequence encoding the light chain variable region Ab7-$V_{L4}$ has the following sequence (FR1-CDR1-FR2-CDR2-FR3-CDR3-FR4):

(SEQ ID NO: 22)

GACATCCAGATGACCCAGTCTCCATCCTCCCTGTCTGCATCTGTAGGAGA

CAGAGTCACCATCACTTGCCGGGCAAGTGAGAACATTTACAGCTATTTAA

ATTGGTATCAGCAGAAACCAGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAACTTACTACTGTCAACATCATTACGGTACCCCGCTCACATTCGGCCAA

GGGACCAAGCTGGAAATCAAA.

The heavy chain and light chain CDR amino acid sequences of the isolated parental Ab7 antibody (Kabat definition) are shown in Table 1.

TABLE 1

| Heavy Chain Variable Region | HCDR1 | HCDR2 | HCDR3 |
|---|---|---|---|
| Ab7-$V_{H0}$ (SEQ ID NO: 16) | SYSMS (SEQ ID NO: 23) | YISYDGGSAYYPDTVKG (SEQ ID NO: 24) | HGDYDDDDAMDY (SEQ ID NO: 25) |

| Light Chain Variable Region | LCDR1 | LCDR2 | LCDR3 |
|---|---|---|---|
| Ab7-$V_{L0}$ (SEQ ID NO: 29) | RASENIYSYLA (SEQ ID NO: 26) | NAETLTE (SEQ ID NO: 27) | QHHYGTPLT (SEQ ID NO: 28) |

To create the complete chimeric and humanized heavy or light chain antibody sequences, each heavy chain variable region described above was combined with a human IgG1 constant region, and each light chain variable region described above was combined a human kappa constant region.

The protein sequences defining the complete heavy chain and light chain of the chimeric and humanized Ab7 variants are summarized below (amino terminal signal peptide sequences are not shown).

The heavy chain Ab7-$V_{H0}$-IgG1 has the following sequence (FR1-CDR1-FR2-CDR2-FR3-CDR3-FR4-Constant region):

(SEQ ID NO: 29)

EVKLVESGGGLVQPGGSLKLFCAASGFTFTSYSMSWVRQTPEKRLEWVAY
ISYDGGSAYYPDTVKGRFSISRDNAKKTLYLQMSSLKSEDTAMYYCARHG
DYDDDDAMDYWGQGTSVTVSS*ASTKGPSVFPLAPSSKSTSGGTAALGCLV*
*KDYFPEPVTVSWNSGALTSGVHTFPAVLQSSGLYSLSSVVTVPSSSLGTQ*
*TYICNVNHKPSNTKVDKKVEPKSCDKTHTCPPCPAPELLGGPSVFLFPPK*
*PKDTLMISRTPEVTCVVVDVSHEDPEVKFNWYVDGVEVHNAKTKPREEQY*
*NSTYRVVSVLTVLHQDWLNGKEYKCKVSNKALPAPIEKTISKAKGQPREP*
*QVYTLPPSRDELTKNQVSLTCLVKGFYPSDIAVEWESNGQPENNYKTTPP*
*VLDSDGSFFLYSKLTVDKSRWQQGNVFSCSVMHEALHNHYTQKSLSLSPG*
*K.*

A nucleic acid sequence encoding the heavy chain Ab7-$V_{H0}$-IgG1 has the following sequence (FR1-CDR1-FR2-CDR2-FR3-CDR3-FR4-Constant region):

(SEQ ID NO: 30)

GAGGTGAAGCTGGTGGAGTCTGGGGGAGGCTTGGTACAGCCTGGGGGGTC
CCTGAAACTCTTCTGTGCAGCCTCTGGATTCACCTTTACCAGCTATTCCA
TGAGCTGGGTCCGCCAGACTCCAGAGAAGAGGCTGGAGTGGGTCGCATAC
ATTAGTTATGATGGTGGTAGCGCCTACTACCCTGACACTGTGAAGGGCCG
GTTCTCCATCTCCAGAGACAATGCCAAGAAAACCCTGTATCTGCAAATGA
GCAGCCTGAAGTCTGAGGACACGGCCATGTATTACTGTGCAAGACATGGA
GACTATGACGACGACGACGCGATGGACTACTGGGGCCAAGGAACCTCAGT
CACCGTCTCCTCA*GCCTCCACCAAAGGCCCCAGCGTCTTCCCCCTCGCGC*
*CGTCCTCCAAGTCCACCTCGGGTGGCACCGCCGCCCTGGGCTGCCTGGTC*
*AAGGACTACTTCCCGGAGCCTGTGACCGTGTCCTGGAACTCGGGCGCGCT*
*CACGAGCGGCGTACACACCTTCCCGGCGGTGCTCCAGTCCTCCGGGCTGT*
*ACTCGCTCTCGTCGGTCGTCACGGTGCCGTCCTCCTCCCTGGGCACCCAG*
*ACCTACATCTGCAACGTGAACCACAAGCCGTCCAACACCAAGGTGGATAA*
*GAAGGTCGAGCCCAAGTCGTGCGACAAGACGCACACGTGCCCGCCGTGCC*
*CGGCCCCGGAGCTGCTGGGCGGCCCCTCGGTCTTCCTGTTCCCCCCGAAG*
*CCCAAGGATACGCTGATGATCTCCCGCACCCCGGAGGTCACCTGCGTGGT*
*GGTGGACGTCTCCCACGAGGACCCGGAGGTGAAATTCAACTGGTACGTCG*
*ACGGAGTGGAGGTCCACAACGCCAAGACCAAGCCCCGGGAGGAGCAGTAC*

-continued

*AACTCCACGTACCGCGTCGTCTCCGTCCTGACCGTCCTCCACCAGGACTG*
*GCTGAACGGCAAGGAGTACAAGTGTAAGGTCTCCAACAAGGCGCTGCCCG*
*CCCCCATCGAGAAGACCATCTCCAAGGCAAAGGGTCAGCCGCGGGAGCCG*
*CAGGTCTATACCCTCCCCCCGTCCCGCGACGAGCTGACGAAAAACCAGGT*
*CTCCCTGACCTGCCTGGTGAAGGGTTTCTACCCCTCCGACATCGCGGTCG*
*AGTGGGAGTCGAACGGCCAGCCGGAGAACAACTACAAGACCACCCCCCCC*
*GTGCTCGACAGTGACGGCTCGTTCTTCCTGTACTCGAAGCTGACCGTCGA*
*CAAGTCGCGCTGGCAGCAGGGCAACGTCTTCTCGTGCTCCGTTATGCACG*
*AGGCCCTGCACAACCACTACACGCAGAAGAGTCTTTCGCTGTCCCCGGGG*
*AAGTGA.*

The heavy chain Ab7-$V_{H1}$-IgG1 has the following sequence (FR1-CDR1-FR2-CDR2-FR3-CDR3-FR4-Constant region):

(SEQ ID NO: 31)

EVKLVESGGGLVQPGGSLRLSCAASGFTFTSYSMSWVRQAPGKGLEWVAY
ISYDGGSAYYPDTVKGRFTISRDNSKKTLYLQMSSLKSEDTAMYYCARHG
DYDDDDAMDYWGQGTSVTVSS*ASTKGPSVFPLAPSSKSTSGGTAALGCLV*
*KDYFPEPVTVSWNSGALTSGVHTFPAVLQSSGLYSLSSVVTVPSSSLGTQ*
*TYICNVNHKPSNTKVDKKVEPKSCDKTHTCPPCPAPELLGGPSVFLFPPK*
*PKDTLMISRTPEVTCVVVDVSHEDPEVKFNWYVDGVEVHNAKTKPREEQY*
*NSTYRVVSVLTVLHQDWLNGKEYKCKVSNKALPAPIEKTISKAKGQPREP*
*QVYTLPPSRDELTKNQVSLTCLVKGFYPSDIAVEWESNGQPENNYKTTPP*
*VLDSDGSFFLYSKLTVDKSRWQQGNVFSCSVMHEALHNHYTQKSLSLSPG*
*K.*

A nucleic acid sequence encoding the heavy chain Ab7-$V_{H1}$-IgG1 has the following sequence (FR1-CDR1-FR2-CDR2-FR3-CDR3-FR4-Constant region):

(SEQ ID NO: 32)

GAGGTGAAGCTGGTGGAGTCTGGGGGAGGCTTGGTACAGCCTGGGGGGTC
CCTGAGACTCTCCTGTGCAGCCTCTGGATTCACCTTTACCAGCTATTCCA
TGAGCTGGGTCCGCCAGGCTCCAGGGAAGGGGCTGGAGTGGGTCGCATAC
ATTAGTTATGATGGTGGTAGCGCCTACTACCCTGACACTGTGAAGGGCCG
GTTCACCATCTCCAGAGACAATTCCAAGAAAACCCTGTATCTGCAAATGA
GCAGCCTGAAGTCTGAGGACACGGCCATGTATTACTGTGCAAGACATGGA
GACTATGACGACGACGACGCGATGGACTACTGGGGCCAAGGAACCTCAGT
CACCGTCTCCTCA*GCCTCCACCAAAGGCCCCAGCGTCTTCCCCCTCGCGC*
*CGTCCTCCAAGTCCACCTCGGGTGGCACCGCCGCCCTGGGCTGCCTGGTC*
*AAGGACTACTTCCCGGAGCCTGTGACCGTGTCCTGGAACTCGGGCGCGCT*
*CACGAGCGGCGTACACACCTTCCCGGCGGTGCTCCAGTCCTCCGGGCTGT*
*ACTCGCTCTCGTCGGTCGTCACGGTGCCGTCCTCCTCCCTGGGCACCCAG*
*ACCTACATCTGCAACGTGAACCACAAGCCGTCCAACACCAAGGTGGATAA*

-continued

*GAAGGTCGAGCCCAAGTCGTGCGACAAGACGCACACGTGCCCGCCGTGCC*

*CGGCCCCGGAGCTGCTGGGCGGCCCCTCGGTCTTCCTGTTCCCCCCGAAG*

*CCCAAGGATACGCTGATGATCTCCCGCACCCCGGAGGTCACCTGCGTGGT*

*GGTGGACGTCTCCCACGAGGACCCGGAGGTGAAATTCAACTGGTACGTCG*

*ACGGAGTGGAGGTCCACAACGCCAAGACCAAGCCCCGGGAGGAGCAGTAC*

*AACTCCACGTACCGCGTCGTCTCCGTCCTGACCGTCCTCCACCAGGACTG*

*GCTGAACGGCAAGGAGTACAAGTGTAAGGTCTCCAACAAGGCGCTGCCCG*

*CCCCCATCGAGAAGACCATCTCCAAGGCAAAGGGTCAGCCGCGGGAGCCG*

*CAGGTCTATACCCTCCCCCCGTCCCGCGACGAGCTGACGAAAAACCAGGT*

*CTCCCTGACCTGCCTGGTGAAGGGTTTCTACCCCTCCGACATCGCGGTCG*

*AGTGGGAGTCGAACGGCCAGCCGGAGAACAACTACAAGACCACCCCCCCC*

*GTGCTCGACAGTGACGGCTCGTTCTTCCTGTACTCGAAGCTGACCGTCGA*

*CAAGTCGCGCTGGCAGCAGGGCAACGTCTTCTCGTGCTCCGTTATGCACG*

*AGGCCCTGCACAACCACTACACGCAGAAGAGTCTTTCGCTGTCCCCGGGG*

*AAGTGA.*

The heavy chain Ab7-$V_{H2}$-IgG1 has the following sequence (FR1-CDR1-FR2-CDR2-FR3-CDR3-FR4-Constant region):

(SEQ ID NO: 33)

EVQLVESGGGLVQPGGSLRLSCAASGFTFTSYSMSWVRQAPGKGLEWVAY

ISYDGGSAYYPDTVKGRFTISRDNSKNTLYLQMSSLKSEDTAMYYCARHG

DYDDDDAMDYWGQGTLVTVSS*ASTKGPSVFPLAPSSKSTSGGTAALGCLV*

*KDYFPEPVTVSWNSGALTSGVHTFPAVLQSSGLYSLSSVVTVPSSSLGTQ*

*TYICNVNHKPSNTKVDKKVEPKSCDKTHTCPPCPAPELLGGPSVFLFPPK*

*PKDTLMISRTPEVTCVVVDVSHEDPEVKFNWYVDGVEVHNAKTKPREEQY*

*NSTYRVVSVLTVLHQDWLNGKEYKCKVSNKALPAPIEKTISKAKGQPREP*

*QVYTLPPSRDELTKNQVSLTCLVKGFYPSDIAVEWESNGQPENNYKTTPP*

*VLDSDGSFFLYSKLTVDKSRWQQGNVFSCSVMHEALHNHYTQKSLSLSPG*

*K.*

A nucleic acid sequence encoding the heavy chain Ab7-$V_{H2}$-IgG1 has the following sequence (FR1-CDR1-FR2-CDR2-FR3-CDR3-FR4-Constant region):

(SEQ ID NO: 34)

GAGGTGCAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTACCCTGACACTGTGAAGGGCCG

GTTCACCATCTCCAGAGACAATTCCAAGAACACCCTGTATCTGCAAATGA

GCAGCCTGAAGTCTGAGGACACGGCCATGTATTACTGTGCAAGACATGGA

GACTATGACGACGACGACGCGATGGACTACTGGGGCCAAGGAACCCTGGT

CACCGTCTCCTCA*GCCTCCACCAAAGGCCCCAGCGTCTTCCCCCTCGCGC*

*CGTCCTCCAAGTCCACCTCGGGTGGCACCGCCGCCCTGGGCTGCCTGGTC*

-continued

*AAGGACTACTTCCCGGAGCCTGTGACCGTGTCCTGGAACTCGGGCGCGCT*

*CACGAGCGGCGTACACACCTTCCCGGCGGTGCTCCAGTCCTCCGGGCTGT*

*ACTCGCTCTCGTCGGTCGTCACGGTGCCGTCCTCCTCCCTGGGCACCCAG*

*ACCTACATCTGCAACGTGAACCACAAGCCGTCCAACACCAAGGTGGATAA*

*GAAGGTCGAGCCCAAGTCGTGCGACAAGACGCACACGTGCCCGCCGTGCC*

*CGGCCCCGGAGCTGCTGGGCGGCCCCTCGGTCTTCCTGTTCCCCCCGAAG*

*CCCAAGGATACGCTGATGATCTCCCGCACCCCGGAGGTCACCTGCGTGGT*

*GGTGGACGTCTCCCACGAGGACCCGGAGGTGAAATTCAACTGGTACGTCG*

*ACGGAGTGGAGGTCCACAACGCCAAGACCAAGCCCCGGGAGGAGCAGTAC*

*AACTCCACGTACCGCGTCGTCTCCGTCCTGACCGTCCTCCACCAGGACTG*

*GCTGAACGGCAAGGAGTACAAGTGTAAGGTCTCCAACAAGGCGCTGCCCG*

*CCCCCATCGAGAAGACCATCTCCAAGGCAAAGGGTCAGCCGCGGGAGCCG*

*CAGGTCTATACCCTCCCCCCGTCCCGCGACGAGCTGACGAAAAACCAGGT*

*CTCCCTGACCTGCCTGGTGAAGGGTTTCTACCCCTCCGACATCGCGGTCG*

*AGTGGGAGTCGAACGGCCAGCCGGAGAACAACTACAAGACCACCCCCCCC*

*GTGCTCGACAGTGACGGCTCGTTCTTCCTGTACTCGAAGCTGACCGTCGA*

*CAAGTCGCGCTGGCAGCAGGGCAACGTCTTCTCGTGCTCCGTTATGCACG*

*AGGCCCTGCACAACCACTACACGCAGAAGAGTCTTTCGCTGTCCCCGGGG*

*AAGTGA.*

The heavy chain Ab7-$V_{H3}$-IgG1 has the following sequence (FR1-CDR1-FR2-CDR2-FR3-CDR3-FR4-Constant region):

(SEQ ID NO: 35)

EVKLVESGGGLVQPGGSLRLSCAASGFTFTSYSMSWVRQAPGKGLEWVAY

ISYDGGSAYYPDTVKGRFTISRDNSKKTLYLQMNSLRAEDTAVYYCARHG

DYDDDDAMDYWGQGTLVTVSS*ASTKGPSVFPLAPSSKSTSGGTAALGCLV*

*KDYFPEPVTVSWNSGALTSGVHTFPAVLQSSGLYSLSSVVTVPSSSLGTQ*

*TYICNVNHKPSNTKVDKKVEPKSCDKTHTCPPCPAPELLGGPSVFLFPPK*

*PKDTLMISRTPEVTCVVVDVSHEDPEVKFNWYVDGVEVHNAKTKPREEQY*

*NSTYRVVSVLTVLHQDWLNGKEYKCKVSNKALPAPIEKTISKAKGQPREP*

*QVYTLPPSRDELTKNQVSLTCLVKGFYPSDIAVEWESNGQPENNYKTTPP*

*VLDSDGSFFLYSKLTVDKSRWQQGNVFSCSVMHEALHNHYTQKSLSLSPG*

*K.*

A nucleic acid sequence encoding the heavy chain Ab7-$V_{H3}$-IgG1 has the following sequence (FR1-CDR1-FR2-CDR2-FR3-CDR3-FR4-Constant region):

(SEQ ID NO: 36)

GAGGTGAAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTATCCTGACACTGTGAAGGGCCG

-continued

GTTCACCATCTCCAGAGACAATTCCAAGAAAACCCTGTATCTGCAAATGA

ACAGCCTGAGAGCCGAGGACACGGCCGTATATTACTGTGCAAGACATGGA

GACTATGACGACGACGACGCGATGGACTACTGGGGCCAAGGAACCCTGGT

CACCGTCTCCTCA*GCCTCCACCAAAGGCCCCAGCGTCTTCCCCCTCGCGC*

*CGTCCTCCAAGTCCACCTCGGGTGGCACCGCCGCCCTGGGCTGCCTGGTC*

*AAGGACTACTTCCCGGAGCCTGTGACCGTGTCCTGGAACTCGGGCGCGCT*

*CACGAGCGGCGTACACACCTTCCCGGCGGTGCTCCAGTCCTCCGGGCTGT*

*ACTCGCTCTCGTCGGTCGTCACGGTGCCGTCCTCCTCCCTGGGCACCCAG*

*ACCTACATCTGCAACGTGAACCACAAGCCGTCCAACACCAAGGTGGATAA*

*GAAGGTCGAGCCCAAGTCGTGCGACAAGACGCACACGTGCCCGCCGTGCC*

*CGGCCCCGGAGCTGCTGGGCGGCCCCTCGGTCTTCCTGTTCCCCCCGAAG*

*CCCAAGGATACGCTGATGATCTCCCGCACCCCGGAGGTCACCTGCGTGGT*

*GGTGGACGTCTCCCACGAGGACCCGGAGGTGAAATTCAACTGGTACGTCG*

*ACGGAGTGGAGGTCCACAACGCCAAGACCAAGCCCCGGGAGGAGCAGTAC*

*AACTCCACGTACCGCGTCGTCTCCGTCCTGACCGTCCTCCACCAGGACTG*

*GCTGAACGGCAAGGAGTACAAGTGTAAGGTCTCCAACAAGGCGCTGCCCG*

*CCCCCATCGAGAAGACCATCTCCAAGGCAAAGGGTCAGCCGCGGGAGCCG*

*CAGGTCTATACCCTCCCCCCGTCCCGCGACGAGCTGACGAAAAACCAGGT*

*CTCCCTGACCTGCCTGGTGAAGGGTTTCTACCCCTCCGACATCGCGGTCG*

*AGTGGGAGTCGAACGGCCAGCCGGAGAACAACTACAAGACCACCCCCCCC*

*GTGCTCGACAGTGACGGCTCGTTCTTCCTGTACTCGAAGCTGACCGTCGA*

*CAAGTCGCGCTGGCAGCAGGGCAACGTCTTCTCGTGCTCCGTTATGCACG*

*AGGCCCTGCACAACCACTACACGCAGAAGAGTCTTTCGCTGTCCCCGGGG*

*AAGTGA*.

The heavy chain Ab7-$V_{H4}$-IgG1 has the following sequence (FR1-CDR1-FR2-CDR2-FR3-CDR3-FR4-Constant region):

(SEQ ID NO: 37)

EVQLVESGGGLVQPGGSLRLSCAASGFTFTSYSMSWVRQAPGKGLEWVAY

ISYDGGSAYYPDTVKGRFTISRDNSKNTLYLQMNSLRAEDTAVYYCARHG

DYDDDDAMDYWGQGTLVTVSS*ASTKGPSVFPLAPSSKSTSGGTAALGCLV*

*KDYFPEPVTVSWNSGALTSGVHTFPAVLQSSGLYSLSSVVTVPSSSLGTQ*

*TYICNVNHKPSNTKVDKKVEPKSCDKTHTCPPCPAPELLGGPSVFLFPPK*

*PKDTLMISRTPEVTCVVVDVSHEDPEVKFNWYVDGVEVHNAKTKPREEQY*

*NSTYRVVSVLTVLHQDWLNGKEYKCKVSNKALPAPIEKTISKAKGQPREP*

*QVYTLPPSRDELTKNQVSLTCLVKGFYPSDIAVEWESNGQPENNYKTTPP*

*VLDSDGSFFLYSKLTVDKSRWQQGNVFSCSVMHEALHNHYTQKSLSLSPG*

*K*.

A nucleic acid sequence encoding the heavy chain Ab7-$V_{H4}$-IgG1 has the following sequence (FR1-CDR1-FR2-CDR2-FR3-CDR3-FR4-Constant region):

(SEQ ID NO: 38)

GAGGTGCAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTCGCATAC

ATTAGTTATGATGGTGGTAGCGCCTACTATCCTGACACTGTGAAGGGCCG

GTTCACCATCTCCAGAGACAATTCCAAGAACACCCTGTATCTGCAAATGA

ACAGCCTGAGAGCCGAGGACACGGCCGTATATTACTGTGCAAGACATGGA

GACTATGACGACGACGACGCGATGGACTACTGGGGCCAAGGAACCCTGGT

CACCGTCTCCTCA*GCCTCCACCAAAGGCCCCAGCGTCTTCCCCCTCGCGC*

*CGTCCTCCAAGTCCACCTCGGGTGGCACCGCCGCCCTGGGCTGCCTGGTC*

*AAGGACTACTTCCCGGAGCCTGTGACCGTGTCCTGGAACTCGGGCGCGCT*

*CACGAGCGGCGTACACACCTTCCCGGCGGTGCTCCAGTCCTCCGGGCTGT*

*ACTCGCTCTCGTCGGTCGTCACGGTGCCGTCCTCCTCCCTGGGCACCCAG*

*ACCTACATCTGCAACGTGAACCACAAGCCGTCCAACACCAAGGTGGATAA*

*GAAGGTCGAGCCCAAGTCGTGCGACAAGACGCACACGTGCCCGCCGTGCC*

*CGGCCCCGGAGCTGCTGGGCGGCCCCTCGGTCTTCCTGTTCCCCCCGAAG*

*CCCAAGGATACGCTGATGATCTCCCGCACCCCGGAGGTCACCTGCGTGGT*

*GGTGGACGTCTCCCACGAGGACCCGGAGGTGAAATTCAACTGGTACGTCG*

*ACGGAGTGGAGGTCCACAACGCCAAGACCAAGCCCCGGGAGGAGCAGTAC*

*AACTCCACGTACCGCGTCGTCTCCGTCCTGACCGTCCTCCACCAGGACTG*

*GCTGAACGGCAAGGAGTACAAGTGTAAGGTCTCCAACAAGGCGCTGCCCG*

*CCCCCATCGAGAAGACCATCTCCAAGGCAAAGGGTCAGCCGCGGGAGCCG*

*CAGGTCTATACCCTCCCCCCGTCCCGCGACGAGCTGACGAAAAACCAGGT*

*CTCCCTGACCTGCCTGGTGAAGGGTTTCTACCCCTCCGACATCGCGGTCG*

*AGTGGGAGTCGAACGGCCAGCCGGAGAACAACTACAAGACCACCCCCCCC*

*GTGCTCGACAGTGACGGCTCGTTCTTCCTGTACTCGAAGCTGACCGTCGA*

*CAAGTCGCGCTGGCAGCAGGGCAACGTCTTCTCGTGCTCCGTTATGCACG*

*AGGCCCTGCACAACCACTACACGCAGAAGAGTCTTTCGCTGTCCCCGGGG*

*AAGTGA*.

The heavy chain Ab7-$V_{H5}$-IgG1 has the following sequence (FR1-CDR1-FR2-CDR2-FR3-CDR3-FR4-Constant region):

(SEQ ID NO: 39)

EVQLVESGGGLVQPGGSLRLSCAASGFTFTSYSMSWVRQAPGKGLEWVSY

ISYDGGSAYYPDTVKGRFTISRDNSKNTLYLQMNSLRAEDTAVYYCARHG

DYDDDDAMDYWGQGTLVTVSS*ASTKGPSVFPLAPSSKSTSGGTAALGCLV*

*KDYFPEPVTVSWNSGALTSGVHTFPAVLQSSGLYSLSSVVTVPSSSLGTQ*

*TYICNVNHKPSNTKVDKKVEPKSCDKTHTCPPCPAPELLGGPSVFLFPPK*

*PKDTLMISRTPEVTCVVVDVSHEDPEVKFNWYVDGVEVHNAKTKPREEQY*

*NSTYRVVSVLTVLHQDWLNGKEYKCKVSNKALPAPIEKTISKAKGQPREP*

-continued

*QVYTLPPSRDELTKNQVSLTCLVKGFYPSDIAVEWESNGQPENNYKTTPP*

*VLDSDGSFFLYSKLTVDKSRWQQGNVFSCSVMHEALHNHYTQKSLSLSPG*

*K.*

A nucleic acid sequence encoding the heavy chain Ab7-$V_{H5}$-IgG1 has the following sequence (FR1-CDR1-FR2-CDR2-FR3-CDR3-FR4-Constant region):

(SEQ ID NO: 40)

GAGGTGCAGCTGGTGGAGTCTGGGGGAGGCTTGGTACAGCCTGGGGGGTC

CCTGAGACTCTCCTGTGCAGCCTCTGGATTCACCTTTACCAGCTATTCCA

TGAGCTGGGTCCGCCAGGCTCCAGGGAAGGGGCTGGAGTGGGTGTCTTAC

ATTAGTTATGATGGTGGTAGCGCCTACTATCCTGACACTGTGAAGGGCCG

GTTCACCATCTCCAGAGACAATTCCAAGAACACCCTGTATCTGCAAATGA

ACAGCCTGAGAGCCGAGGACACGGCCGTATATTACTGTGCAAGACATGGA

GACTATGACGACGACGACGCGATGGACTACTGGGGCCAAGGAACCCTGGT

CACCGTCTCCTCA*GCCTCCACCAAAGGCCCCAGCGTCTTCCCCCTCGCGC*

*CGTCCTCCAAGTCCACCTCGGGTGGCACCGCCGCCCTGGGCTGCCTGGTC*

*AAGGACTACTTCCCGGAGCCTGTGACCGTGTCCTGGAACTCGGGCGCGCT*

*CACGAGCGGCGTACACACCTTCCCGGCGGTGCTCCAGTCCTCCGGGCTGT*

*ACTCGCTCTCGTCGGTCGTCACGGTGCCGTCCTCCTCCCTGGGCACCCAG*

*ACCTACATCTGCAACGTGAACCACAAGCCGTCCAACACCAAGGTGGATAA*

*GAAGGTCGAGCCCAAGTCGTGCGACAAGACGCACACGTGCCCGCCGTGCC*

*CGGCCCCGGAGCTGCTGGGCGGCCCCTCGGTCTTCCTGTTCCCCCCGAAG*

*CCCAAGGATACGCTGATGATCTCCCGCACCCCGGAGGTCACCTGCGTGGT*

*GGTGGACGTCTCCCACGAGGACCCGGAGGTGAAATTCAACTGGTACGTCG*

*ACGGAGTGGAGGTCCACAACGCCAAGACCAAGCCCCGGGAGGAGCAGTAC*

*AACTCCACGTACCGCGTCGTCTCCGTCCTGACCGTCCTCCACCAGGACTG*

*GCTGAACGGCAAGGAGTACAAGTGTAAGGTCTCCAACAAGGCGCTGCCCG*

*CCCCCATCGAGAAGACCATCTCCAAGGCAAAGGGTCAGCCGCGGGAGCCG*

*CAGGTCTATACCCTCCCCCCGTCCCGCGACGAGCTGACGAAAAACCAGGT*

*CTCCCTGACCTGCCTGGTGAAGGGTTTCTACCCCTCCGACATCGCGGTCG*

*AGTGGGAGTCGAACGGCCAGCCGGAGAACAACTACAAGACCACCCCCCCC*

*GTGCTCGACAGTGACGGCTCGTTCTTCCTGTACTCGAAGCTGACCGTCGA*

*CAAGTCGCGCTGGCAGCAGGGCAACGTCTTCTCGTGCTCCGTTATGCACG*

*AGGCCCTGCACAACCACTACACGCAGAAGAGTCTTTCGCTGTCCCCGGGG*

*AAGTGA.*

The light chain Ab7-$V_{L0}$-Kappa has the following sequence (FR1-CDR1-FR2-CDR2-FR3-CDR3-FR4-Constant region):

(SEQ ID NO: 41)

DIQMTQSPASLSASVGETVTITCRASENIYSYLAWYQQKQGKSPQLLVYN

AETLTEGVPSRFSGSGSGTQFSLKINSLQPEDFGNYYCQHHYGTPLTFGA

GTKLDLK*RTVAAPSVFIFPPSDEQLKSGTASVVCLLNNFYPREAKVQWKV*

-continued

*DNALQSGNSQESVTEQDSKDSTYSLSSTLTLSKADYEKHKVYACEVTHQG*

*LSSPVTKSFNRGEC.*

A nucleic acid sequence encoding the light chain Ab7-$V_{L0}$-Kappa has the following sequence (FR1-CDR1-FR2-CDR2-FR3-CDR3-FR4-Constant region):

(SEQ ID NO: 42)

GACATCCAGATGACCCAGTCTCCAGCCTCCCTGTCTGCATCTGTAGGAGA

AACTGTCACCATCACTTGCCGGGCAAGTGAGAACATTTACAGCTATTTAG

CATGGTATCAGCAGAAACAGGGGAAATCTCCTCAGCTCCTGGTCTATAAT

GCAGAAACCTTGACAGAAGGGGTCCCATCAAGGTTCAGCGGCAGTGGATC

TGGGACACAATTCTCTCTCAAGATCAACAGTCTGCAACCTGAAGATTTTG

GGAATTACTACTGTCAACATCATTACGGTACCCCGCTCACATTCGGCGCT

GGGACCAAGCTGGATCTGAAA*CGAACGGTGGCCGCGCCGAGCGTCTTCAT*

*CTTCCCGCCTTCCGACGAGCAGCTCAAGTCCGGGACCGCCTCCGTAGTAT*

*GCCTCCTCAATAACTTCTACCCCCGGGAGGCGAAGGTCCAGTGGAAGGTC*

*GACAACGCCCTCCAATCGGGCAACTCCCAGGAGTCGGTGACCGAGCAGGA*

*TTCCAAGGACTCGACCTACAGTCTAAGCTCCACCCTCACACTGTCGAAGG*

*CGGACTACGAGAAGCACAAGGTGTACGCCTGCGAGGTCACCCACCAGGGC*

*CTGAGCAGCCCGGTCACCAAGTCCTTCAACCGGGGCGAGTGCTGA.*

The light chain Ab7-$V_{L1}$-Kappa has the following sequence (FR1-CDR1-FR2-CDR2-FR3-CDR3-FR4-Constant region):

(SEQ ID NO: 43)

DIQMTQSPSSLSASVGDRVTITCRASENIYSYLAWYQQKQGKAPKLLVYN

AETLTEGVPSRFSGSGSGTDFTLTISSLQPEDFANYYCQHHYGTPLTFGQ

GTKLDIK*RTVAAPSVFIFPPSDEQLKSGTASVVCLLNNFYPREAKVQWKV*

*DNALQSGNSQESVTEQDSKDSTYSLSSTLTLSKADYEKHKVYACEVTHQG*

*LSSPVTKSFNRGEC.*

A nucleic acid sequence encoding the light chain Ab7-$V_{L1}$-Kappa has the following sequence (FR1-CDR1-FR2-CDR2-FR3-CDR3-FR4-Constant region):

(SEQ ID NO: 44)

GACATCCAGATGACCCAGTCTCCATCCTCCCTGTCTGCATCTGTAGGAGA

CAGAGTCACCATCACTTGCCGGGCAAGTGAGAACATTTACAGCTATTTAG

CATGGTATCAGCAGAAACAGGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAAATTACTACTGTCAACATCATTACGGTACCCCGCTCACATTCGGCCAA

GGGACCAAGCTGGATATCAAA*CGAACGGTGGCCGCGCCGAGCGTCTTCAT*

*CTTCCCGCCTTCCGACGAGCAGCTCAAGTCCGGGACCGCCTCCGTAGTAT*

*GCCTCCTCAATAACTTCTACCCCCGGGAGGCGAAGGTCCAGTGGAAGGTC*

*GACAACGCCCTCCAATCGGGCAACTCCCAGGAGTCGGTGACCGAGCAGGA*

-continued

*TTCCAAGGACTCGACCTACAGTCTAAGCTCCACCCTCACACTGTCGAAGG*

*CGGACTACGAGAAGCACAAGGTGTACGCCTGCGAGGTCACCCACCAGGGC*

*CTGAGCAGCCCGGTCACCAAGTCCTTCAACCGGGGCGAGTGCTGA*.

The light chain Ab7-$V_{L2}$-Kappa has the following sequence (FR1-CDR1-FR2-CDR2-FR3-CDR3-FR4-Constant region):

(SEQ ID NO: 45)

DIQMTQSPSSLSASVGDRVTITCRASENIYSYLAWYQQKPGKAPKLLVYN

AETLTEGVPSRFSGSGSGTDFTLTISSLQPEDFANYYCQHHYGTPLTFGQ

GTKLEIK*RTVAAPSVFIFPPSDEQLKSGTASVVCLLNNFYPREAKVQWKV*

*DNALQSGNSQESVTEQDSKDSTYSLSSTLTLSKADYEKHKVYACEVTHQG*

*LSSPVTKSFNRGEC*.

A nucleic acid sequence encoding the light chain Ab7-$V_{L2}$-Kappa has the following sequence (FR1-CDR1-FR2-CDR2-FR3-CDR3-FR4-Constant region):

(SEQ ID NO: 46)

GACATCCAGATGACCCAGTCTCCATCCTCCCTGTCTGCATCTGTAGGAGA

CAGAGTCACCATCACTTGCCGGGCAAGTGAGAACATTTACAGCTATTTAG

CATGGTATCAGCAGAAACCAGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAAATTACTACTGTCAACATCATTACGGTACCCCGCTCACATTCGGCCAA

GGGACCAAGCTGGAAATCAAA*CGAACGGTGGCCGCGCCGAGCGTCTTCAT*

*CTTCCCGCCTTCCGACGAGCAGCTCAAGTCCGGGACCGCCTCCGTAGTAT*

*GCCTCCTCAATAACTTCTACCCCCGGGAGGCGAAGGTCCAGTGGAAGGTC*

*GACAACGCCCTCCAATCGGGCAACTCCCAGGAGTCGGTGACCGAGCAGGA*

*TTCCAAGGACTCGACCTACAGTCTAAGCTCCACCCTCACACTGTCGAAGG*

*CGGACTACGAGAAGCACAAGGTGTACGCCTGCGAGGTCACCCACCAGGGC*

*CTGAGCAGCCCGGTCACCAAGTCCTTCAACCGGGGCGAGTGCTGA*.

The light chain Ab7-$V_{L3}$-Kappa has the following sequence (FR1-CDR1-FR2-CDR2-FR3-CDR3-FR4-Constant region):

(SEQ ID NO: 47)

DIQMTQSPSSLSASVGDRVTITCRASENIYSYLAWYQQKPGKAPKLLVYN

AETLTEGVPSRFSGSGSGTDFTLTISSLQPEDFATYYCQHHYGTPLTFGQ

GTKLEIK*RTVAAPSVFIFPPSDEQLKSGTASVVCLLNNFYPREAKVQWKV*

*DNALQSGNSQESVTEQDSKDSTYSLSSTLTLSKADYEKHKVYACEVTHQG*

*LSSPVTKSFNRGEC*.

A nucleic acid sequence encoding the light chain Ab7-$V_{L3}$-Kappa has the following sequence (FR1-CDR1-FR2-CDR2-FR3-CDR3-FR4-Constant region):

(SEQ ID NO: 48)

GACATCCAGATGACCCAGTCTCCATCCTCCCTGTCTGCATCTGTAGGAGA

CAGAGTCACCATCACTTGCCGGGCAAGTGAGAACATTTACAGCTATTTAG

CATGGTATCAGCAGAAACCAGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAACTTACTACTGTCAACATCATTACGGTACCCCGCTCACATTCGGCCAA

GGGACCAAGCTGGAAATCAAA*CGAACGGTGGCCGCGCCGAGCGTCTTCAT*

*CTTCCCGCCTTCCGACGAGCAGCTCAAGTCCGGGACCGCCTCCGTAGTAT*

*GCCTCCTCAATAACTTCTACCCCCGGGAGGCGAAGGTCCAGTGGAAGGTC*

*GACAACGCCCTCCAATCGGGCAACTCCCAGGAGTCGGTGACCGAGCAGGA*

*TTCCAAGGACTCGACCTACAGTCTAAGCTCCACCCTCACACTGTCGAAGG*

*CGGACTACGAGAAGCACAAGGTGTACGCCTGCGAGGTCACCCACCAGGGC*

*CTGAGCAGCCCGGTCACCAAGTCCTTCAACCGGGGCGAGTGCTGA*.

The light chain Ab7-$V_{L4}$-Kappa has the following sequence (FR1-CDR1-FR2-CDR2-FR3-CDR3-FR4-Constant region):

(SEQ ID NO: 49)

DIQMTQSPSSLSASVGDRVTITCRASENIYSYLNWYQQKPGKAPKLLVYN

AETLTEGVPSRFSGSGSGTDFTLTISSLQPEDFATYYCQHHYGTPLTFGQ

GTKLEIK*RTVAAPSVFIFPPSDEQLKSGTASVVCLLNNFYPREAKVQWKV*

*DNALQSGNSQESVTEQDSKDSTYSLSSTLTLSKADYEKHKVYACEVTHQG*

*LSSPVTKSFNRGEC*.

A nucleic acid sequence encoding the light chain Ab7-$V_{L4}$-Kappa has the following sequence (FR1-CDR1-FR2-CDR2-FR3-CDR3-FR4-Constant region):

(SEQ ID NO: 50)

GACATCCAGATGACCCAGTCTCCATCCTCCCTGTCTGCATCTGTAGGAGA

CAGAGTCACCATCACTTGCCGGGCAAGTGAGAACATTTACAGCTATTTAA

ATTGGTATCAGCAGAAACCAGGGAAAGCCCCTAAGCTCCTGGTCTATAAT

GCAGAAACCTTGACAGAAGGGGTCCCATCAAGGTTCAGCGGCAGTGGATC

TGGGACAGATTTCACTCTCACCATCAGCAGTCTGCAACCTGAAGATTTTG

CAACTTACTACTGTCAACATCATTACGGTACCCCGCTCACATTCGGCCAA

GGGACCAAGCTGGAAATCAAA*CGAACGGTGGCCGCGCCGAGCGTCTTCAT*

*CTTCCCGCCTTCCGACGAGCAGCTCAAGTCCGGGACCGCCTCCGTAGTAT*

*GCCTCCTCAATAACTTCTACCCCCGGGAGGCGAAGGTCCAGTGGAAGGTC*

*GACAACGCCCTCCAATCGGGCAACTCCCAGGAGTCGGTGACCGAGCAGGA*

*TTCCAAGGACTCGACCTACAGTCTAAGCTCCACCCTCACACTGTCGAAGG*

*CGGACTACGAGAAGCACAAGGTGTACGCCTGCGAGGTCACCCACCAGGGC*

*CTGAGCAGCCCGGTCACCAAGTCCTTCAACCGGGGCGAGTGCTGA*.

It is also contemplated that the variable region sequences can be fused to other antibody constant region sequences to produce full length immunoglobulin heavy and light chains. For example, the Ab7-$V_{H0}$, Ab7-$V_{H1}$, Ab7-$V_H$2, Ab7-$V_H$3, Ab7-$V_H$4, or Ab7-$V_H$5 heavy chain variable regions may be combined with a human IgG2, IgG3, IgG4, or an IgG4 comprising one or more amino acid substitutions in the constant region (e.g., IgG4mt, or IgG4mt2). Similarly, the Ab7-$V_L$0, Ab7-$V_L$1, Ab7-$V_L$2, Ab7-$V_L$3 or Ab7-$V_L$4 light chain variable regions may be combined with a human lambda constant region.

DNA fragments encoding the heavy and light chain variable regions of Ab7 and the humanized Ab7 variants described above were synthesized with flanking restriction enzyme sites for cloning into a pANT expression vector (Antitope) system for IgG1 heavy and kappa light chains. All constructs were confirmed by sequencing. Heavy and light chain combinations shown in Table 2 were transiently transfected into HEK293 EBNA adherent cells (LGC Standards, Teddington, UK) using a PEI transfection method and incubated for seven days post-transfection.

TABLE 2

| Antibody | Heavy Chain | Light Chain |
|---|---|---|
| Ab7.1 | Ab7-$V_{H0}$-IgG1 (SEQ ID NO: 29) | Ab7-$V_{L0}$-Kappa (SEQ ID NO: 41) |
| Ab7.2 | Ab7-$V_{H0}$-IgG1 (SEQ ID NO: 29) | Ab7-$V_{L1}$-Kappa (SEQ ID NO: 43) |
| Ab7.3 | Ab7-$V_{H1}$-IgG1 (SEQ ID NO: 31) | Ab7-$V_{L0}$-Kappa (SEQ ID NO: 41) |
| Ab7.4 | Ab7-$V_{H1}$-IgG1 (SEQ ID NO: 31) | Ab7-$V_{L1}$-Kappa (SEQ ID NO: 43) |
| Ab7.5 | Ab7-$V_{H1}$-IgG1 (SEQ ID NO: 31) | Ab7-$V_{L2}$-Kappa (SEQ ID NO: 45) |
| Ab7.6 | Ab7-$V_{H1}$-IgG1 (SEQ ID NO: 31) | Ab7-$V_{L3}$-Kappa (SEQ ID NO: 47) |
| Ab7.7 | Ab7-$V_{H1}$-IgG1 (SEQ ID NO: 31) | Ab7-$V_{L4}$-Kappa (SEQ ID NO: 49) |
| Ab7.8 | Ab7-$V_{H2}$-IgG1 (SEQ ID NO: 33) | Ab7-$V_{L1}$-Kappa (SEQ ID NO: 43) |
| Ab7.9 | Ab7-$V_{H2}$-IgG1 (SEQ ID NO: 33) | Ab7-$V_{L2}$-Kappa (SEQ ID NO: 45) |
| Ab7.10 | Ab7-$V_{H2}$-IgG1 (SEQ ID NO: 33) | Ab7-$V_{L3}$-Kappa (SEQ ID NO: 47) |
| Ab7.11 | Ab7-$V_{H2}$-IgG1 (SEQ ID NO: 33) | Ab7-$V_{L4}$-Kappa (SEQ ID NO: 49) |
| Ab7.12 | Ab7-$V_{H3}$-IgG1 (SEQ ID NO: 35) | Ab7-$V_{L1}$-Kappa (SEQ ID NO: 43) |
| Ab7.13 | Ab7-$V_{H3}$-IgG1 (SEQ ID NO: 35) | Ab7-$V_{L2}$-Kappa (SEQ ID NO: 45) |
| Ab7.14 | Ab7-$V_{H3}$-IgG1 (SEQ ID NO: 35) | Ab7-$V_{L3}$-Kappa (SEQ ID NO: 47) |
| Ab7.15 | Ab7-$V_{H3}$-IgG1 (SEQ ID NO: 35) | Ab7-$V_{L4}$-Kappa (SEQ ID NO: 49) |
| Ab7.16 | Ab7-$V_{H4}$-IgG1 (SEQ ID NO: 37) | Ab7-$V_{L1}$-Kappa (SEQ ID NO: 43) |
| Ab7.17 | Ab7-$V_{H4}$-IgG1 (SEQ ID NO: 37) | Ab7-$V_{L2}$-Kappa (SEQ ID NO: 45) |
| Ab7.18 | Ab7-$V_{H4}$-IgG1 (SEQ ID NO: 37) | Ab7-$V_{L3}$-Kappa (SEQ ID NO: 47) |
| Ab7.19 | Ab7-$V_{H4}$-IgG1 (SEQ ID NO: 37) | Ab7-$V_{L4}$-Kappa (SEQ ID NO: 49) |
| Ab7.20 | Ab7-$V_{H5}$-IgG1 (SEQ ID NO: 39) | Ab7-$V_{L1}$-Kappa (SEQ ID NO: 43) |
| Ab7.21 | Ab7-$V_{H5}$-IgG1 (SEQ ID NO: 39) | Ab7-$V_{L2}$-Kappa (SEQ ID NO: 45) |
| Ab7.22 | Ab7-$V_{H5}$-IgG1 (SEQ ID NO: 39) | Ab7-$V_{L3}$-Kappa (SEQ ID NO: 47) |
| Ab7.23 | Ab7-$V_{H5}$-IgG1 (SEQ ID NO: 39) | Ab7-$V_{L4}$-Kappa (SEQ ID NO: 49) |

Antibodies were purified from cell culture supernatants on Protein A-conjugated sepharose columns (GE Healthcare, Little Chalfont, UK), buffer exchanged into 1×DPBS pH 7.2 and quantified by $OD_{280\ nm}$ using an extinction coefficient ($Ec_{(0.1\%)}$) based on the predicted amino acid sequence. 1 μg of each antibody was analyzed by SDS-PAGE and bands corresponding to the profile of a typical antibody were observed (data not shown).

In Vitro Characterization of Anti-EBI3 Antibodies

The Ab7 antibody and Ab7 antibody variants produced as described in Table 2 were tested in a series of in vitro assays to ascertain their biological characteristics and activities.

In order to assess the binding of the humanized Ab7 antibody variants relative to the chimeric Ab7.1 antibody, a binding competition ELISA was established. Assay plates were coated with 1 μg/mL of human IL-27 (hIL-27) (R&D Systems, Abingdon, UK) diluted in 1×DPBS pH 7.2 and incubated overnight at 4° C. All antibodies were diluted in 2% BSA/DPBS to 25 μg/mL and serially diluted three-fold down the plate to generate an eight point binding curve. Antibody dilutions were pre-mixed with biotinylated Ab7.1 antibody at a constant final concentration of 0.08 μg/mL. The antibody mixtures were then transferred onto the coated assay plates and incubated for 1 hour at room temperature. The binding of biotinylated Ab7.1 antibody was detected with streptavidin-peroxidase conjugate (Sigma-Aldrich, Gillingham, UK) and TMB substrate (ThermoFisher, Loughborough, UK). The reaction was stopped with 1M HCl and absorbance read at 450 nm on a Dynex Technologies MRX TC II plate reader.

Absolute $IC_{50}$ values of the tested antibodies were determined using a four-parameter logistic curve. $IC_{50}$ normalized relative to the $IC_{50}$ of the chimeric antibody on each plate are summarized in Table 3. The results show that all humanized Ab7 variants generated, with the exception of variants containing the Ab7-$V_{L4}$ light chain, have similar binding profiles to the chimeric Ab7.1 antibody, with most variants competing within two-fold of the chimeric Ab7.1 antibody.

TABLE 3

| Antibody | Average Relative $IC_{50}$ to Ab7.1 | Standard Deviation | No. of Repeats |
|---|---|---|---|
| Ab7.1 | 1 | | |
| Ab7.2 | 0.76 | 0 | 2 |
| Ab7.3 | 0.76 | 0.27 | 2 |
| Ab7.4 | 0.97 | 0.46 | 2 |
| Ab7.4 | 0.73 | 0.25 | 2 |
| Ab7.5 | 1.39 | 0.13 | 2 |
| Ab7.6 | ND | — | 1 |
| Ab7.8 | 1.43 | 0.05 | 2 |
| Ab7.9 | 1.85 | 0.21 | 2 |
| Ab7.10 | 1.85 | 0.22 | 2 |
| Ab7.11 | ND | — | 1 |
| Ab7.12 | 1.33 | 0.21 | 2 |
| Ab7.13 | 1.37 | 0.08 | 2 |
| Ab7.14 | 1.48 | 0.07 | 2 |
| Ab7.15 | ND | — | 1 |
| Ab7.16 | 1.81 | 0.35 | 2 |
| Ab7.17 | 1.55 | 0.44 | 2 |
| Ab7.18 | 1.39 | 0.37 | 2 |
| Ab7.19 | ND | — | 1 |
| Ab7.20 | 1.6 | 0.06 | 2 |
| Ab7.21 | 2.16 | 0.33 | 2 |
| Ab7.22 | 2.50 | 0.95 | 2 |
| Ab7.23 | ND | — | 1 |

The antibodies were further characterized by surface plasmon resonance (SPR). Kinetic experiments were performed on a Biacore T200 (GE Healthcare, Uppsala, Sweden). All experiments were run at 25° C. with HBS-P+ running buffer (pH 7.4) (GE Healthcare, Little Chalfont, UK) using hIL-27 (R&D Systems, Abingdon, UK). Human IL-27 (hIL-27) antigen was captured on a CM5 chip to ~16 RU. Immobilization was carried out at a protein concentration of 1 μg/mL in 10 mM acetate buffer pH 5.0. A three point, three-fold dilution range from 3.3 nM to 30 nM of antibody diluted in HB S-P+ buffer without regeneration between each concentration was used. The association phase for the three injections of increasing concentrations of antibody was monitored for 75 seconds each time and a single dissociation phase was measured for 250 seconds following the last injection of antibody. Regeneration of the hIL-27 surface was conducted using a single injection of 2M $MgCl_2$ for 120 s. Multiple repeats (n=4) of the chimeric antibody were performed throughout the assay to check the stability of the surface and analyte over the kinetic cycles.

Both 1:1 binding and bivalent analyte models were used to analyze the data due to the bivalent nature of the antibody. The results from the 1:1 binding model analysis are summarized in Table 4 and results from the bivalent analyte model are summarized in Table 5.

TABLE 4

| Antibody | ka (1/Ms) | kd (1/s) | KD (M) | $Chi^2$ ($RU^2$) | Relative KD to Ab7.1 |
|---|---|---|---|---|---|
| Ab7.1 | $1.4 \times 10^6$ | $1.5 \times 10^{-3}$ | $1.0 \times 10^{-9}$ | 0.282 | 1.0 |
| Ab7.2 | $1.5 \times 10^6$ | $1.8 \times 10^{-3}$ | $1.2 \times 10^{-9}$ | 0.237 | 1.2 |
| Ab7.3 | $1.5 \times 10^6$ | $1.5 \times 10^{-3}$ | $9.6 \times 10^{-10}$ | 0.321 | 0.9 |
| Ab7.4 | $1.5 \times 10^6$ | $1.8 \times 10^{-3}$ | $1.2 \times 10^{-9}$ | 0.235 | 1.2 |
| Ab7.4 | $1.5 \times 10^6$ | $1.8 \times 10^{-3}$ | $1.3 \times 10^{-9}$ | 0.212 | 1.2 |
| Ab7.5 | $1.5 \times 10^6$ | $1.8 \times 10^{-3}$ | $1.2 \times 10^{-9}$ | 0.222 | 1.2 |
| Ab7.6 | — | — | — | — | — |
| Ab7.8 | $1.3 \times 10^6$ | $1.8 \times 10^{-3}$ | $1.5 \times 10^{-9}$ | 0.0932 | 1.4 |
| Ab7.9 | $1.3 \times 10^6$ | $1.9 \times 10^{-3}$ | $1.5 \times 10^{-9}$ | 0.0953 | 1.5 |
| Ab7.10 | $1.3 \times 10^6$ | $1.8 \times 10^{-3}$ | $1.4 \times 10^{-9}$ | 0.105 | 1.4 |
| Ab7.11 | — | — | — | — | — |
| Ab7.12 | $1.5 \times 10^6$ | $1.8 \times 10^{-3}$ | $1.2 \times 10^{-9}$ | 0.265 | 1.2 |
| Ab7.13 | $1.5 \times 10^6$ | $1.8 \times 10^{-3}$ | $1.2 \times 10^{-9}$ | 0.235 | 1.2 |
| Ab7.14 | $1.5 \times 10^6$ | $1.8 \times 10^{-3}$ | $1.2 \times 10^{-9}$ | 0.232 | 1.2 |
| Ab7.15 | — | — | — | — | — |
| Ab7.16 | $1.3 \times 10^6$ | $1.8 \times 10^{-3}$ | $1.5 \times 10^{-9}$ | 0.092 | 1.4 |
| Ab7.17 | $1.3 \times 10^6$ | $1.9 \times 10^{-3}$ | $1.5 \times 10^{-9}$ | 0.101 | 1.5 |
| Ab7.18 | $1.3 \times 10^6$ | $1.9 \times 10^{-3}$ | $1.5 \times 10^{-9}$ | 0.0969 | 1.4 |
| Ab7.19 | — | — | — | — | — |
| Ab7.20 | $1.3 \times 10^6$ | $1.8 \times 10^{-3}$ | $1.4 \times 10^{-9}$ | 0.109 | 1.4 |
| Ab7.21 | $1.2 \times 10^6$ | $1.9 \times 10^{-3}$ | $1.5 \times 10^{-9}$ | 0.0793 | 1.5 |
| Ab7.22 | $1.3 \times 10^6$ | $1.9 \times 10^{-3}$ | $1.5 \times 10^{-9}$ | 0.081 | 1.5 |
| Ab7.23 | — | — | — | — | — |

TABLE 5

| Analyte | ka1 (1/Ms) | ka2 (1/RUs) | kd1 (1/s) | kd2 (1/s) | $Chi^2$ ($RU^2$) |
|---|---|---|---|---|---|
| Ab7.1 | $6.7 \times 10^5$ | $2.1 \times 10^{-2}$ | $2.2 \times 10^{-3}$ | $4.6 \times 10^{-2}$ | 0.138 |
| Ab7.2 | $7.0 \times 10^5$ | $3.5 \times 10^{-2}$ | $2.7 \times 10^{-3}$ | $8.7 \times 10^{-2}$ | 0.108 |
| Ab7.3 | $7.5 \times 10^5$ | $2.9 \times 10^{-2}$ | $2.2 \times 10^{-3}$ | $6.3 \times 10^{-2}$ | 0.132 |
| Ab7.4 | $7.2 \times 10^5$ | $7.2 \times 10^{-2}$ | $2.6 \times 10^{-3}$ | $1.9 \times 10^{-1}$ | 0.106 |
| Ab7.4 | $7.1 \times 10^5$ | $1.7 \times 10^{-2}$ | $2.5 \times 10^{-3}$ | $4.9 \times 10^{-2}$ | 0.103 |
| Ab7.5 | $6.8 \times 10^5$ | $2.8 \times 10^{-2}$ | $2.7 \times 10^{-3}$ | $6.8 \times 10^{-2}$ | 0.104 |
| Ab7.6 | — | — | — | — | — |
| Ab7.8 | $5.8 \times 10^5$ | $6.4 \times 10^{-2}$ | $2.7 \times 10^{-3}$ | $1.5 \times 10^{-1}$ | 0.0514 |
| Ab7.9 | $5.9 \times 10^5$ | $4.3 \times 10^{-2}$ | $2.8 \times 10^{-3}$ | $1.1 \times 10^{-1}$ | 0.0526 |
| Ab7.10 | $6.0 \times 10^5$ | $8.4 \times 10^{-2}$ | $2.5 \times 10^{-3}$ | $2.0 \times 10^{-1}$ | 0.0573 |
| Ab7.11 | — | — | — | — | — |
| Ab7.12 | $7.5 \times 10^5$ | $1.1 \times 10^{-1}$ | $2.6 \times 10^{-3}$ | $2.9 \times 10^{-1}$ | 0.119 |
| Ab7.13 | $7.4 \times 10^5$ | $2.0 \times 10^{-2}$ | $2.6 \times 10^{-3}$ | $5.3 \times 10^{-2}$ | 0.109 |
| Ab7.14 | $7.0 \times 10^5$ | $3.9 \times 10^{-2}$ | $2.6 \times 10^{-3}$ | $9.9 \times 10^{-2}$ | 0.106 |
| Ab7.15 | — | — | — | — | — |
| Ab7.16 | $5.7 \times 10^5$ | $4.0 \times 10^{-2}$ | $2.7 \times 10^{-3}$ | $9.1 \times 10^{-2}$ | 0.0512 |
| Ab7.17 | $5.8 \times 10^5$ | $3.9 \times 10^{-2}$ | $2.9 \times 10^{-3}$ | $9.0 \times 10^{-2}$ | 0.0569 |
| Ab7.18 | $5.7 \times 10^5$ | $5.3 \times 10^{-2}$ | $2.8 \times 10^{-3}$ | $1.1 \times 10^{-1}$ | 0.054 |
| Ab7.19 | — | — | — | — | — |
| Ab7.20 | $6.2 \times 10^5$ | $3.6 \times 10^{-2}$ | $2.5 \times 10^{-3}$ | $8.6 \times 10^{-2}$ | 0.0604 |
| Ab7.21 | $5.5 \times 10^5$ | $4.3 \times 10^{-2}$ | $2.7 \times 10^{-3}$ | $9.7 \times 10^{-2}$ | 0.0459 |
| Ab7.22 | $5.8 \times 10^5$ | $4.9 \times 10^{-1}$ | $2.7 \times 10^{-3}$ | 1.11 | 0.0432 |
| Ab7.23 | — | — | — | — | — |

Single cycle kinetics using the 1:1 model (Table 4) demonstrated that Ab7-$V_{L4}$ humanized variants did not bind to hIL-27 and the remaining variants bound within two-fold of the chimeric antibody, consistent with results from the bivalent analyte model (Table 5) and the competition ELISA.

In summary, the binding affinity of the Ab7.1 chimeric antibody as determined by single cycle kinetics and using a 1:1 binding model was 1 nM. All of the humanized variants had a KD of 1.5 nM or lower, with the exception of the Ab7-$V_{L4}$ containing variants in which binding was abolished. These results demonstrate that the Ab7 antibody and the Ab7 antibody variants bind with high affinity to the EBI3 subunit of IL-27.

Example 2: Generation of Anti-IL-27 Antibodies in Yeast that Specifically Bind EBI3 and/or P28 Subunits of Human IL-27

Additional anti-IL-27 monoclonal antibodies representing multiple epitope bins were selected from eight naïve human synthetic yeast libraries using methods described below.

Materials and Methods

Eight naïve human synthetic yeast libraries each of ~$10^9$ diversity was propagated as previously described (see e.g., Xu et al., (2013) Protein Eng Des Sel 26(10):663-670; WO2009036379; WO2010105256; and WO2012009568, all of which are incorporated herein by reference in their entireties). For the first two rounds of selection, a magnetic bead sorting technique utilizing the Miltenyi MACS system was performed, as previously described (see e.g., Siegel et al. (2004) J Immunol Methods 286(1-2):141-153, which is incorporated herein by reference in its entirety).

Briefly, yeast cells (~$10^{10}$ cells/library) were incubated with 3 ml of 100 nM biotinylated antigen (recombinant human IL-27; R&D Systems) for 30 min at 30° C. in wash buffer (phosphate-buffered saline (PBS)/0.1.% bovine serum albumin (BSA)). After washing once with 40 ml ice-cold wash buffer, the cell pellet was resuspended in 20 mL wash buffer; and Streptavidin MicroBeads (500 µl) were added to the yeast and incubated for 15 min at 4° C. Next, the yeast cells were pelleted, resuspended in 20 mL wash buffer, and loaded onto a Miltenyi LS column. After the 20 mL was loaded, the column was washed 3 times with 3 ml wash buffer. The column was then removed from the magnetic field, and the yeast cells were eluted with 5 mL of growth media and then grown overnight. The following rounds of selection were performed using flow cytometry. Approximately $2\times10^7$ yeast cells were pelleted, washed three times with wash buffer, and incubated at 30° C. with either decreasing concentrations of biotinylated antigen (100 to 1 nM) under equilibrium conditions, 30 nM biotinylated antigens of different species in order to obtain species cross-reactivity, or with a poly-specificity depletion reagent (PSR) to remove non-specific antibodies from the selection. For the PSR depletion, the libraries were incubated with a 1:10 dilution of biotinylated PSR reagent.

Yeast cells were then washed twice with wash buffer and stained with LC-FITC (diluted 1:100) and either SA-633 (diluted 1:500) or EAPE (diluted 1:50) secondary reagents for 15 miii at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast cells were plated and individual colonies were picked for characterization.

Light Chain Diversification

Light chain diversification protocol was used during the primary discovery phase for further discovery and improvement of antibodies.

Light chain batch diversification protocol: Heavy chain plasmids from a naïve selection output were extracted from the yeast via smash and grab, propagated in and subsequently purified from *E. coli* and transformed into a light chain library with a diversity of $5\times10^6$. Selections were performed with one round of MACS and four rounds of FACS employing the same conditions as the naïve discovery.

Antibody Optimization

Optimization of antibodies was performed by introducing diversities into the heavy chain and light chain variable regions as described below.

CDRH1 and CDRH2 selection: The CDRH3 of a single antibody was recombined into a premade library with CDRH1 and CDRH2 variants of a diversity of $1\times10^8$ and selections were performed with one round of MACS and four rounds of FACS as described in the naïve discovery. In the different FACS rounds the libraries were looked at for PSR binding, species cross-reactivity, and affinity pressure by titration or parental Fab pre-complexing, and sorting was performed in order to obtain a population with the desired characteristics.

Antibody Production and Purification

Yeast clones were grown to saturation and then induced for 48 h at 30° C. with shaking, After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

ForteBio $K_D$ Measurements

ForteBio affinity measurements were performed on an Octet RED384 generally as previously described (see, e.g., Estep et al, High throughput solution-based measurement of antibody-antigen affinity and epitope binning. *Mabs* 5(2), 270-278 (2013), herein incorporated by reference in its entirety). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. All kinetics were analyzed using the 1:1 binding model. Recombinant Human IL-27 Protein (R&D Systems Cat: 2526-IL) was used as an antigen. Affinity measurements for anti-IL-27 antibodies is shown in FIG. 1.

ForteBio Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

MSD-SET Kinetic Assay

Equilibrium affinity measurements performed as previously described (Estep et al., 2013). Solution equilibrium titrations (SET) were performed in PBS+0.1% IgG-Free BSA (PBSF) with antigen held constant at 10-100 PM and incubated with 3-to 5-fold serial dilutions of antibody starting at 5-100 nM (experimental condition is sample dependent). Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150 s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Example 3: Binding of Anti-IL-27 Antibodies to Recombinant Human IL-27

The ability of anti-IL-27 antibodies described in Example 2 to bind to recombinant human IL-27 was assessed by ELISA. Briefly, Nunc MaxiSorp ELISA Plates (Affymetrix #44-2404-21) were coated with 100 μL/well recombinant human IL-27 (R&D Systems #2526-IL/CF) (0.5 μg/mL diluted in PBS), sealed and incubated overnight at 4° C. Plates were washed 3 times with 100 μL/well of wash buffer (PBS+0.01% Tween). Plates were then blocked with 200 μL/well of blocking buffer (PBS+0.1% BSA+0.01% Tween) for 1 hour at room temperature (RT) with shaking. Blocking buffer was decanted and 100 μL per well of diluted control and anti-IL-27 antibodies were added, as indicated. A 10-point serial dilution was created for each antibody by diluting antibodies 1:10 starting from a top concentration of 1 μg/mL. Plates were incubated for 1-2 hours at RT with shaking. Plates were washed 3 times with 100 μL/well of wash buffer. 100 μL/well of anti-human IgG secondary antibody (SouthernBiotech; Cat. #2014-05) was added (1:5000 diluted in blocking buffer). Plates were then incubated for 1 hour at RT with shaking. After the 1 hour incubation, plates were washed 3 times with 100 μL/well of wash buffer. To develop the plates 100 μL/well TMB Buffer (Life Technologies #00-2023) was added. The development of blue color in the wells of the standard curve was observed and as soon as the highest concentration of diluted control antibodies reached a deep blue (5-10 minutes), 50 μL/well STOP Solution (Thermo Fisher #SS04) was added (the color will change to yellow). The developed plates were read at 450 nm (minus 570 nm for wavelength correction) within 30 minutes of stopping the reaction.

Figure 2:
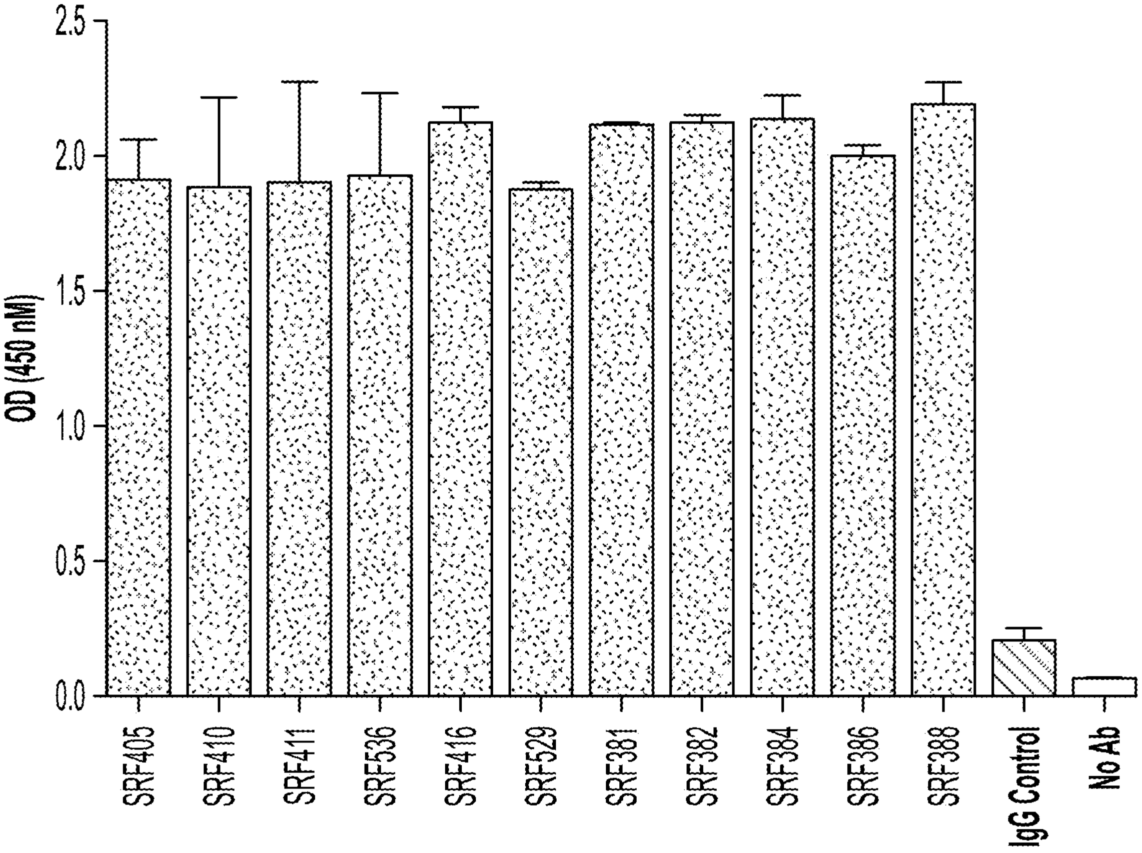
FIG. 2 is a graph depicting the binding of anti-IL-27 antibodies, as indicated, to plate-bound recombinant IL-27 as measured by ELISA.

As shown in FIG. 2, anti-IL-27 antibodies bind to recombinant human IL-27. An IgG isotype control antibody (IgG Control) was used as a comparator.

For example, biochemical affinity and specificity studies showed that the anti-IL-27 antibody SRF388 binds to the p28 subunit (but not the EBI3 subunit) of the heterodimeric cytokine IL-27. SRF388 bound to human, nonhuman primate, and rodent recombinant IL-27, and the extent of the binding differed between species. The binding specificity of SRF388 to IL-27 was confirmed by testing against a panel of 4500 cell surface and soluble molecules, and no off-target binding was observed. The binding specificity of IL-27 for its receptor IL-27RA (WSX-1) was also confirmed; no other cell surface receptor bound human IL-27. The ability of SRF388 to block the interaction between human IL-27 and IL-27RA (WSX-1) was confirmed by Surface Plasmon Resonance.

Binding of the antibodies disclosed herein was assessed in several model systems. Since human IL-27 is biologically active on mouse cells, systemic overexpression of human IL-27 in mice using DNA minicircle delivery was utilized to analyze IL-27-mediated effects in vivo by whole-genome microarray analysis, flow cytometry, and serum cytokine analysis. Many of the markers that were modulated by IL-27 in vivo were consistent with findings in human cell-based assays. SRF381 was also evaluated in a disseminated B16 tumor model. In that setting, treatment with SRF381 showed results consistent with phenotypes observed in mice deficient for various components of IL-27 ligand (IL-27 p28, EBI3) or receptor (IL-27RA).

Collectively, these studies demonstrate that SRF388 (and its sibling SRF381) can phenocopy IL 27 deficiency in mice, binds specifically and with high affinity to IL-27 and can inhibit its immunosuppressive effects, either alone or in combination with PD-L1 blocking agents.

Example 4: Anti-IL27 Antibodies Inhibit Phosphorylation of STAT1 In Vitro

IL-27 signaling through the IL-27 receptor (IL-27R) results in the phosphorylation of the Signal Transducer And Activator Of Transcription 1 (STAT1) polypeptide (pSTAT1). Anti-IL-27 antibodies described in Example 2 were tested for their ability to inhibit IL-27-mediated phosphorylation of STAT1 in human whole blood, human PBMCs, the U937 myeloid cells (histiocytic lymphoma cell line) and HUT-78 T cell lymphoma cells by flow cytometry.

Anti-IL-27 antibodies were tested for their ability to inhibit IL-27-mediated phosphorylation of STAT1 in human whole blood. Briefly, EDTA anticoagulated whole human blood, stored at room temperature, was used in this assay. 45 μL blood was distributed into each well of a deep well, round bottom plate (Phenix #850356) and warmed for 30 minutes at 37° C. on a plate warmer (EchoTherm IC20) or in a 37° C. incubator. Anti-IL-27 antibodies were diluted to a 10× top concentration in endotoxin-free PBS (Teknova #P0300) in a polypropylene V-bottom plate (Corning #3363). Anti-IL-27 antibodies were serially diluted as desired in endotoxin-free PBS. PBS alone was added to wells for unstimulated and stimulated controls. 5 μL of each dilution was added to a well of 45 μL blood and mixed by shaking on plate shaker 15 seconds 1000 RPM (Eppendorf Mix Mate). The plate was incubated for 60 minutes at 37° C. on a plate warmer or in a 37° C. incubator.

A 10 μg vial of recombinant human IL-27 (R&D Systems #2526-IL) was reconstituted to 100 μg/mL by adding 100 μL PBS+0.1% BSA (made from 10% BSA Sigma #A1595). A working stock of the recombinant hIL-27 (rhIL-27) was prepared by dilution to 200 ng/mL in endotoxin-free PBS. After the 60-minute incubation, 5 μL of 200 ng/mL rhIL-27 was added to each well of stimulated blood. 5 μL PBS was added to unstimulated control wells. The plate was shaken on a plate shaker for 15 seconds at 1000 RPM. The plate was incubated for 30 minutes at 37° C.

After the 30-minute incubation, cells were fixed. Lyse/Fix reagent (BD #558049) was diluted 1:5 in sterile water (Hyclone #SH3052902) and warmed to 37° C. in a water bath. 500 μL Lyse/Fix reagent was added to each well of the deep well plate and the plate was mixed on a plate shaker for 15 seconds at 1000 RPM. The plate was incubated for 15 min at 37° C.

After the 15-minute incubation, the plate was centrifuged for 5 minutes at 1500 RPM at room temperature (Eppendorf centrifuge 5810R) and supernatant was discarded by flicking. 1 mL of endotoxin-free PBS was added per well and the plate was shaken on plate shaker for 15 seconds at 1000 RPM. The plate was centrifuged for 5 minutes at 1500 RPM at room temperature (Eppendorf centrifuge 5810R) and supernatant was discarded by flicking. Cell pellets remained in the plate.

Cell pellets were resuspended in 50 μL 1:200 CD14-Pacific Blue (Biolegend #325616) in FACS Buffer (PBS, Gibco #14190-144/2% FBS, Sigma #F8317/1 mM EDTA, Fisher #BP2482) and transferred to U-bottom 96 well plate (Costar #3799). The plate was sealed with plate sealer (VWR #89134-432) and incubated for 30 minutes at room temperature in the dark.

After the 30 minute incubation, 150 μL FACS buffer was added to each well and the plate was centrifuged at 1500 RPM for 5 minutes at room temperature. The cell pellets were then resuspended in 100 μL Perm III (stored at −20° C.) (BD #558050) with pipetting and the plate was sealed with plate sealer and lid. The plate was incubated overnight at −20° C. or 15 minutes at 4° C. After the incubation, 150 μL PBS was added and the plate was centrifuged at 1500 RPM for 5 minutes at room temperature. The supernatant was discarded from the plate by flicking and the plate was resuspended in 50 μL staining cocktail prepared as described in the Table 6 below:

TABLE 6

| BD Catalog # | Antibody | Color | Dilution |
|---|---|---|---|
| 561807 | CD3 | FITC | 1:10 |
| 562069 | pSTAT1 Y701 | PE | 1:100 |
| 562071 | pSTAT3 Y705 | APC | 1:20 |

The plate was incubated for 1 hour at room temperature in the dark. After the 1-hour incubation, 100 μL of FACS buffer was added and the plate was centrifuged at 1500 RPM for 5 minutes at room temperature. The supernatant was discarded from the plate by flicking and the plate was resuspended in 100 μL FACS buffer for analysis by flow cytometry.

Figure 3A:
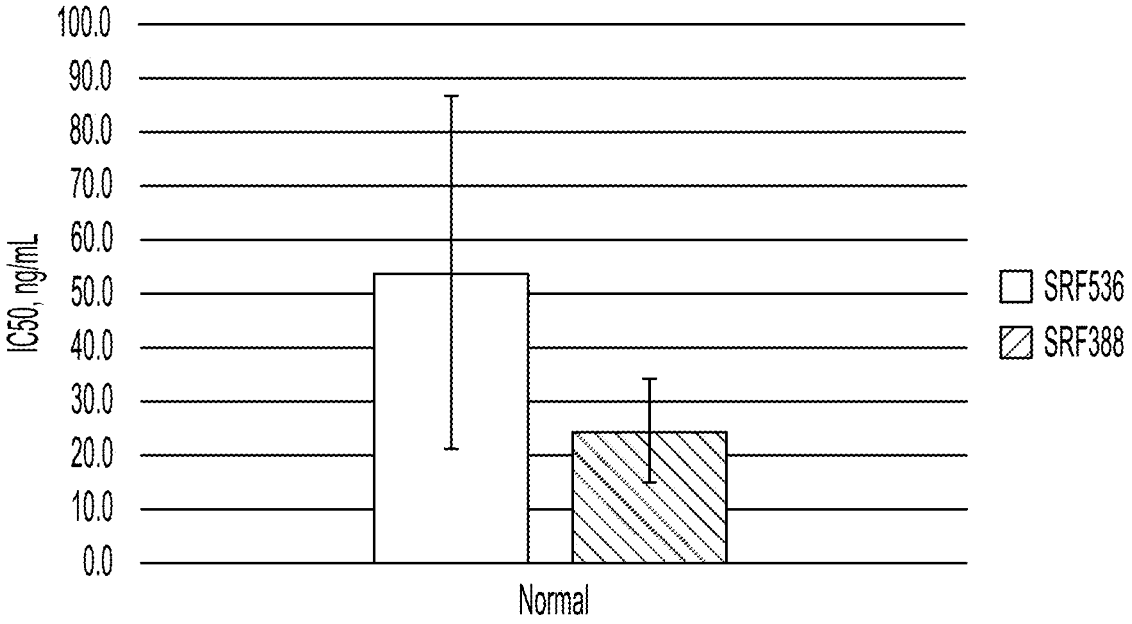
FIGS. 3A-3E are a bar chart, two graphs, a bar chart, and a graph, respectively.

As shown in FIG. 3A, anti-IL-27 antibodies inhibit the phosphorylation of STAT1 in human whole blood. The anti-IL-27 antibody Ab14 inhibited the phosphorylation of STAT1 at an $IC_{50}$ of 24.7 ng/mL—in human whole blood.

The anti-IL-27 antibodies described in Example 2 were further tested for their ability to inhibit IL-27-mediated phosphorylation of STAT1 in pooled human PBMCs by flow cytometry. Briefly, frozen cryovials of human PBMC's (peripheral blood mononuclear cells), obtained from buffy coats, were removed from liquid nitrogen storage and quickly thawed in a 37° C. water bath. The contents of each cryovial was removed with a P1000 pipet and transferred to a 15 mL conical falcon tube. 2-3 mLs of complete RPMI-1640 (Gibco, 61870-036) was slowly added to the thawed cells and cells were gently swirled or flicked to suspend. Conical tubes were topped-off up to 10 mLs with complete RPMI-1640 and tubes were inverted to mix. Conical tubes were centrifuged tube at 1400 RPM at room temperature for 8 minutes.

PBMC cells were resuspended at a density of 4 million cells per mL in warm, serum-free RPMI-1640 and plated at a density of 200,000 cells per well (50μ) in a round bottom 96-well plate (Costar, 3799). Anti-IL-27 antibodies were diluted in serum-free RPMI-1640 in the first row of a 96-well polypropylene plate to a top concentration of 40 μg/ml (will be 10 μg/ml final). Serial dilutions as desired (1:2, 1:3, etc. . . . ) were made in the remainder of the first 10 rows of the plate. Fifty microliters (μL) of the antibody stock (4×) was added to the first 10 rows the plate of PBMC cells in the round bottom plate. In rows 11 and 12, 50 μL of serum-free RPMI-1640 cell media was added. The plate was then incubated at 37° C. for 2 hours.

After the 2-hour incubation, 100μ of 50 ng/ml recombinant human IL-27 (R&D Systems, 2526-IL) diluted in serum-free RPMI-1640 cell media was added to each well (except, the control wells which included serum-free media alone or antibody alone) for a final concentration of 25 ng/ml. 100 μL serum-free RPMI-1640 cell media was added to control wells or wells with antibody alone. The plate was incubated for 20 minutes at 37° C.

After the 20-minute incubation, 50 μL of 4% PFA (Pierce, 28906) in DI water was added directly to each well and the plate was incubated at 37° C. for 5 minutes to fix the cells. The plate was centrifuged at 2000 RPM for 5 minutes. Media was discarded by flicking and plate was washed with 150 μL DPBS. The washing steps were repeated 2 more times. 50μ ice cold 90% methanol (MeOH) (Sigma, 439193) diluted in $H_2O$ was added quickly to each well using a 12-channel pipette. When adding the MeOH special care was taken to mix each well. The plate was incubated at 20° C. for at least 15 minutes. 100 μL of DPBS was added to each well on top of the 90% methanol and the plate was centrifuged at 2000 RPM for 5 minutes. Plate contents were discarded by flicking and the plate was washed 3 times as described previously. After the last wash, cell pellets remained in the wells of the plate.

The pelleted PBMC's were stained with pSTAT1 PE (BD Phosflow, 526069) 1:100 in FACS buffer (2% FBS, 2 mM EDTA in DPBS) for 45 minutes at room temperature in the dark. Special care was taken to mix each well with a 12-channel pipette when adding the stain. After the 45-minute incubation, 100 μL FACS buffer was added into each well and the plate was centrifuged at 2000 RPM for 5 minutes. Supernatant was discarded by flicking and the plate was washed 2 times as described previously. Cells were resuspended in 100 μL FACS buffer and analyzed by flow cytometry.

Figure 3B:
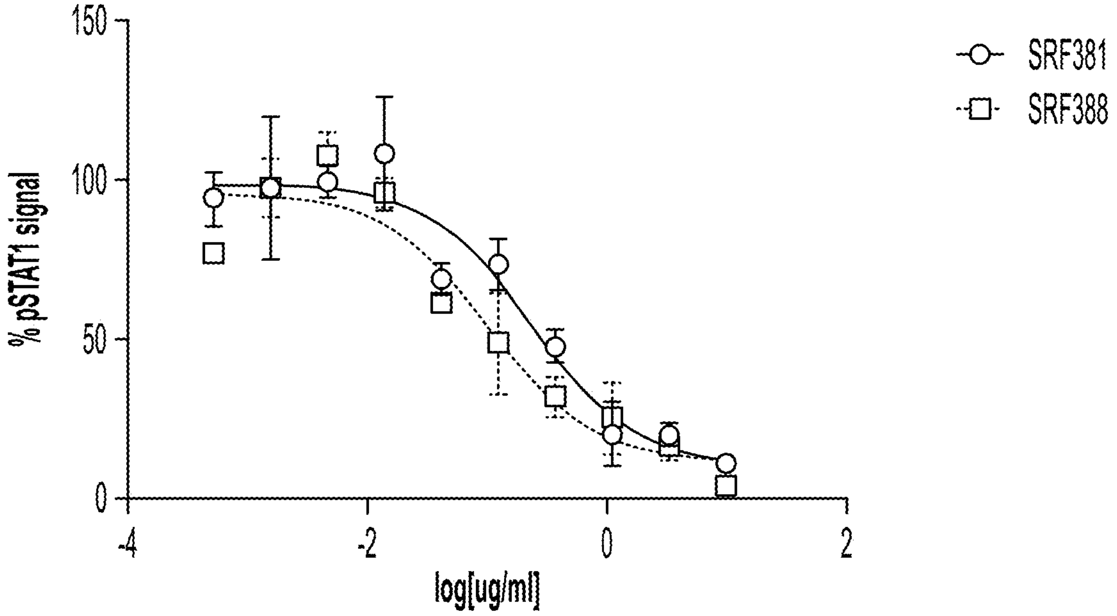

As shown in FIG. 3B, anti-IL-27 antibodies inhibited phosphorylation of STAT1 in human pooled PBMCs. The anti-IL-27 antibody SRF381 inhibited phosphorylation of STAT1 at an average $IC_{50}$ of 140.5 ng/ml (n=2) in pooled human PBMCs. The anti-IL-27 antibody SRF388 inhibited phosphorylation of STAT1 at an average $IC_{50}$ of 58.3 ng/ml (n=3) in pooled human PBMCs.

Figure 3C:
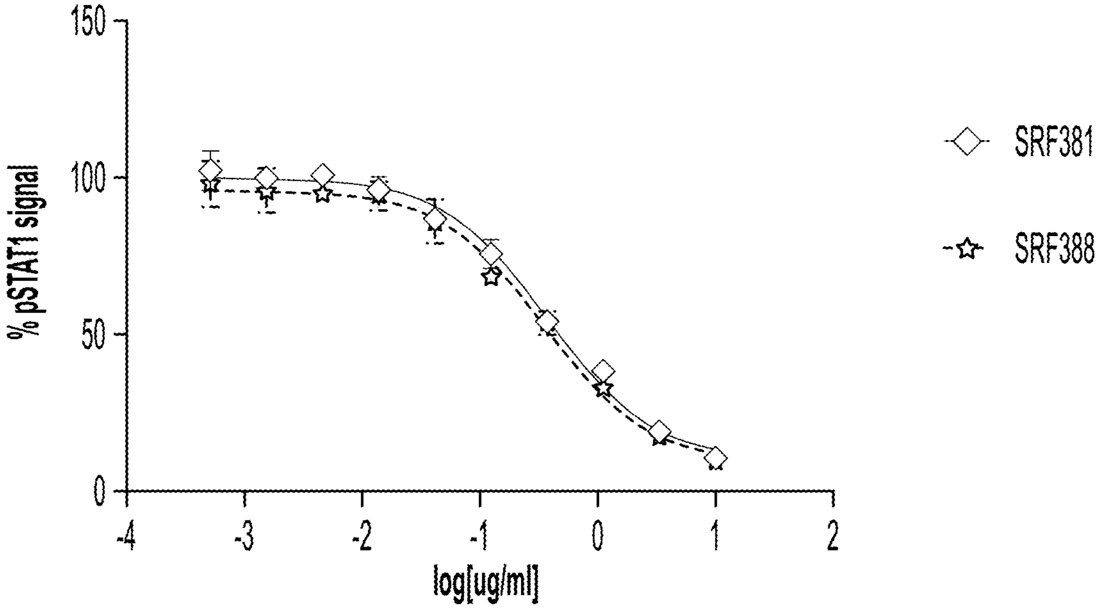

Anti-IL-27 antibodies were further tested for their ability to inhibit IL-27-mediated phosphorylation of STAT1 in U937 cells, a cell line known to express Fc receptors, by flow cytometry essentially as described for FIG. 3B. As shown in FIG. 3C, anti-IL-27 antibodies inhibit the phosphorylation of STAT1 in U-937 cells, as indicated. Antibody SRF381 inhibited the phosphorylation of STAT1 at an average $IC_{50}$ of 81 ng/ml (n=2) in U937 cells. Antibody SRF388 inhibited the phosphorylation of STAT1 at an average $IC_{50}$ of 96 ng/ml (n=2) in U937 cells.

Figure 3D:
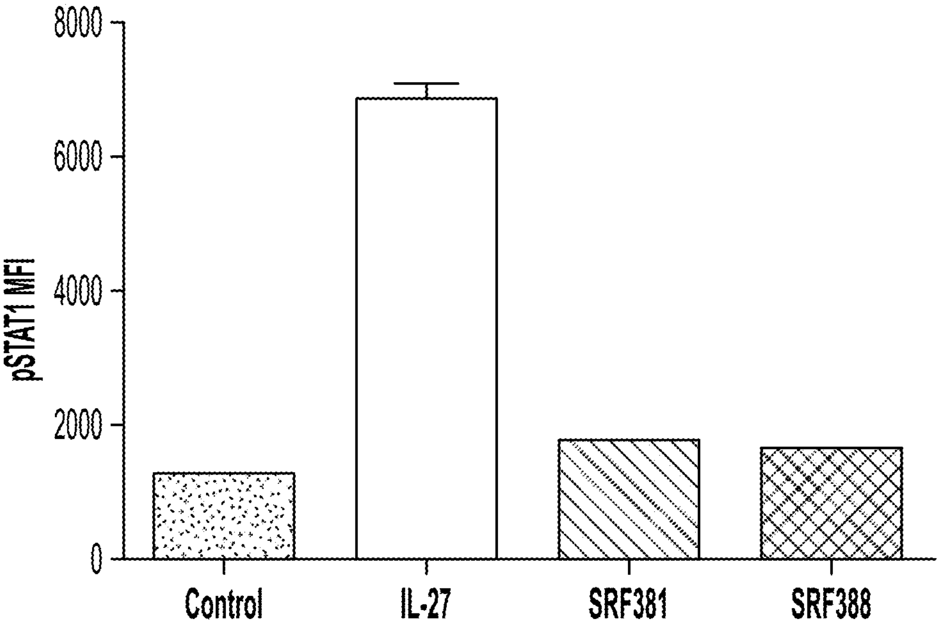

Anti-IL-27 antibodies were tested for their ability to inhibit IL-27-mediated phosphorylation of STAT1 in the cutaneous T-cell lymphoma line HUT-78, which does not express cell surface Fc receptors, by flow cytometry essentially as described for FIG. 3B. As shown in FIG. 3D, anti-IL-27 antibodies inhibited the phosphorylation of STAT1 in HUT-78 cells. Antibody SRF381 inhibited the phosphorylation of STAT1 at an IC50 of 80 ng/ml (n=1) in HUT-78 cells. Antibody SRF388 inhibited the phosphorylation of STAT1 at an $IC_{50}$ of 95 ng/ml (n=1) in HUT-78 cells.

The present disclosure also assessed IL-27 inhibition by SRF388 across species in a whole blood assay. To characterize SRF388 activity across species, recombinant IL-27 from human, cynomolgus monkey, rat, and mouse was tested to stimulate pSTAT1 signaling in T lymphocytes from whole blood samples obtained from these species (data not shown).

Briefly, whole blood was warmed to 37° C. followed by a 60-minute pre-incubation with SRF388, and 20 ng/mL of human IL-27 was added. Samples were incubated for another 30 minutes. White blood cells were fixed, and red blood cells were lysed. After washing, fixed cells were permeabilized and stained with anti-CD3 and anti-phospho-STAT1 (Y701). After a 1-hour incubation, samples were washed and resuspended for flow cytometry. Percent inhibition was calculated using stimulated and unstimulated control wells, and IC50 values were calculated using GraphPad Prism.

Figure 3E:
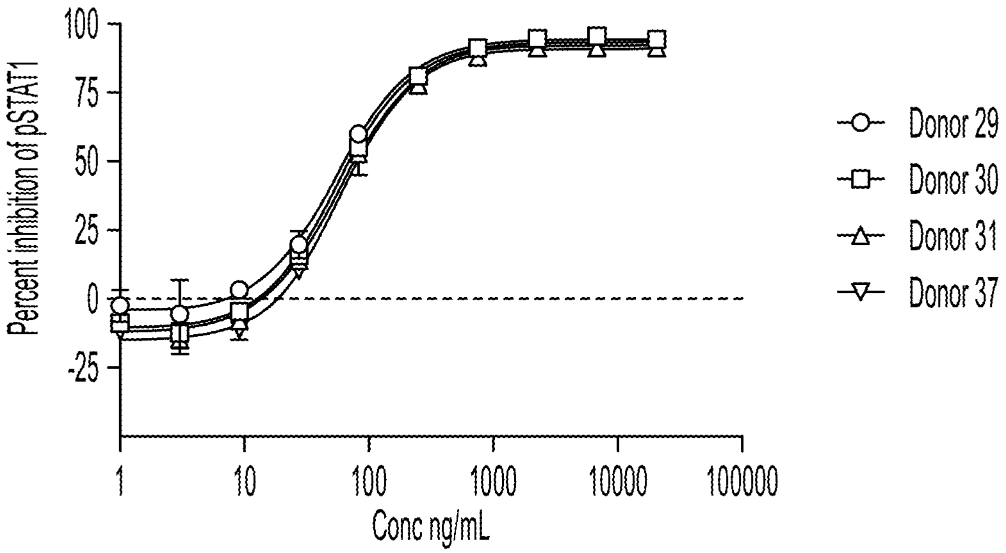

Representative data for SRF388 signaling inhibition in human T cells are shown in FIG. 3E. Consistent with observations made on the affinity of SRF388 to different species, the potency of IL-27 signaling inhibition by SRF388 was strongest in human, followed by cynomolgus monkey, rat, and mouse (see e.g., Table 7).

TABLE 7

SRF388 $IC_{50}$ Values in Peripheral Blood T Cells from Different Species

| Species | Average $IC_{50}$, ng/mL | Standard Deviation | Number |
|---|---|---|---|
| Human | 78.4 | 35 | 7 |
| Cynomolgus monkey | 118.1 | 36.4 | 4 |
| Rat | 273.2 | 133.5 | 8 |
| Mouse | 1721 | N/A | 1 (pool of 10) |

Abbreviations:

$IC_{50}$ = half maximal inhibitory concentration,

N/A = not applicable

Example 5: Reduction of IL-27-Mediated Inhibition of CD161 by Anti-IL-27 Antibodies The C-type lectin CD161 is a marker of T cells whose expression is suppressed by IL-27. Anti-IL-27 antibodies described in Example 2 were tested for their ability to reverse the IL-27-mediated inhibition of CD161 in pooled human PBMC cells by flow cytometry. Briefly, frozen cryovials of pooled human PBMC's (peripheral blood mononuclear cells), obtained from buffy coats, were removed from liquid nitrogen storage and quickly thawed in a 37° C. water bath. Contents of each cryovial was removed with a P1000 pipet and transferred to a 15 mL conical falcon tube. 2-3 mLs of complete RPMI-1640 (Gibco, 61870-036) was slowly added to the thawed cells and cells were gently swirled or flicked to suspend. Conical tubes were topped-off up to 10 mLs with complete RPMI-1640 and tubes were inverted to mix. Conical tubes were centrifuged tube at 1400 RPM, room temperature for 8 minutes.

Use of outer walls was avoided to minimize the effects of evaporation during the 5-day assay. Outer wells should be filled with 200 μL per well of DPBS (Gibco, 14190-144). PBMC cells were resuspended at a density of 2 million cells per mL in warm, complete RPMI-1640. Purified human anti-CD3 antibody (Biolegend, UCTH1, #300402) was added at a concentration of 0.5 μg/mL (this is 2× the final concentration). Plate 100 μL per well of this cell mixture (200,000 cells per well) in a round bottom 96 well plate (Costar, 3799).

Anti-IL-27 antibodies were diluted in complete RPMI-1640 in the first row of a 96 well polypropylene plate to a top concentration of 40 μg/ml (will be 10 ug/ml final). Serial dilutions as desired (1:2, 1:3, etc. . . . ) were made in the remainder of the first 10 rows of the plate. 50 μL of the antibody stock (4×) was added to the first 10 rows the plate of PBMC cells in the round bottom plate. In rows 11 and 12, 50 μL of complete RPMI-1640 was added.

After the addition of the anti-IL-27 antibodies, 50 μl of 100 ng/ml recombinant human IL-27 (R&D Systems, #2526-IL) diluted in complete RPMI-1640 was added to each well (except control wells which included serum free media or antibody alone) for a final concentration of 25 ng/ml. Fifty μL of complete RPMI-1640 was added to control wells. The plate was incubated for 5 days at 37.0 in a tissue culture incubator with minimal interference.

After the 5-day incubation the plate was removed from the incubator and agitated on a plate shaker for 30 seconds at 600 RPM. The plate was centrifuged at 1800 RPM for 5 minutes. Media was removed and set aside for additional assays and the plate was washed with 150 μL DPBS (Gibco, #14190-144). The washing steps were repeated 2 more times. The cell pellets were stained with 50 μL per well of staining cocktail as described in the Table 8 below:

TABLE 8

| Biolegend Catalog # | Antibody Target | Color | Dilution |
|---|---|---|---|
| 300532 | CD4 | BV421 | 1:100 |
| 304204 | CD45RO | FITC | 1:100 |
| 339910 | CD161 | AF647 | 1:100 |
| 353410 | CCR6 | PE | 1:100 |

The plate agitated on a plate shaker for 30 seconds at 600 RPM and the plate was incubated for 30 minutes at room temperature in the dark.

After the 30-minute incubation the plate was centrifuged and supernatant was discarded by flicking. The plate was washed 2 times as described previously. After the last wash, cell pellets were fixed by adding 50 μL 4% PFA (Pierce, 28906) in DI water at room temperature for 10 mins. 100 μL of FASC buffer was added to each well, and the plate was centrifuged at 1800 RPM for 5 minutes. Cells were resuspended in 100 μL FACS buffer and read by flow cytometry.

Figure 4:
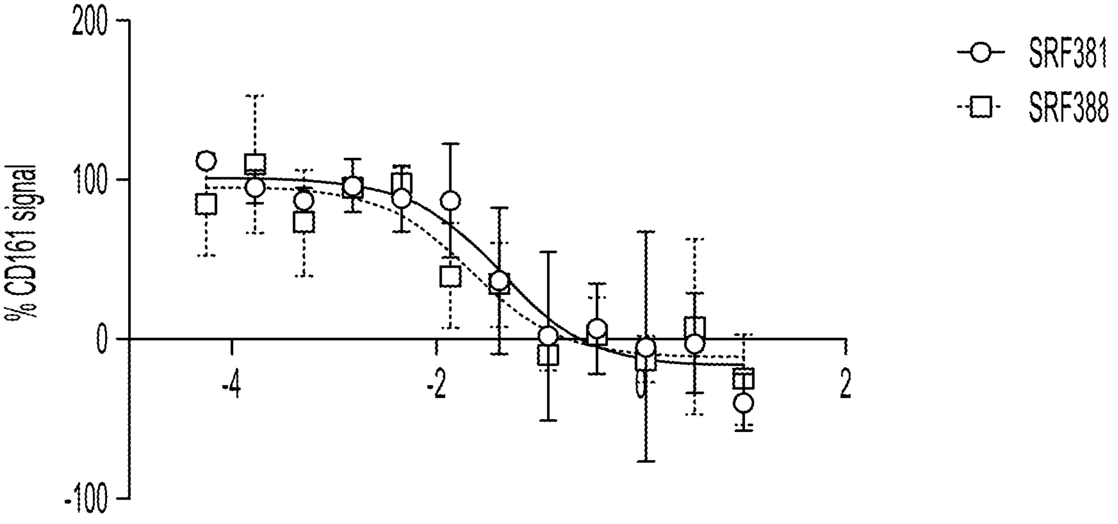
FIG. 4 is a graph depicting the reversal of IL-27-mediated inhibition of CD161 expression in T cells by a range of concentrations of anti-IL-27 antibodies, as indicated. CD161 expression was determined using flow cytometry.

As shown in FIG. 4, anti-IL-27 antibodies, as indicated, reduce the IL-27 mediated inhibition of CD161.

Figure 5A:
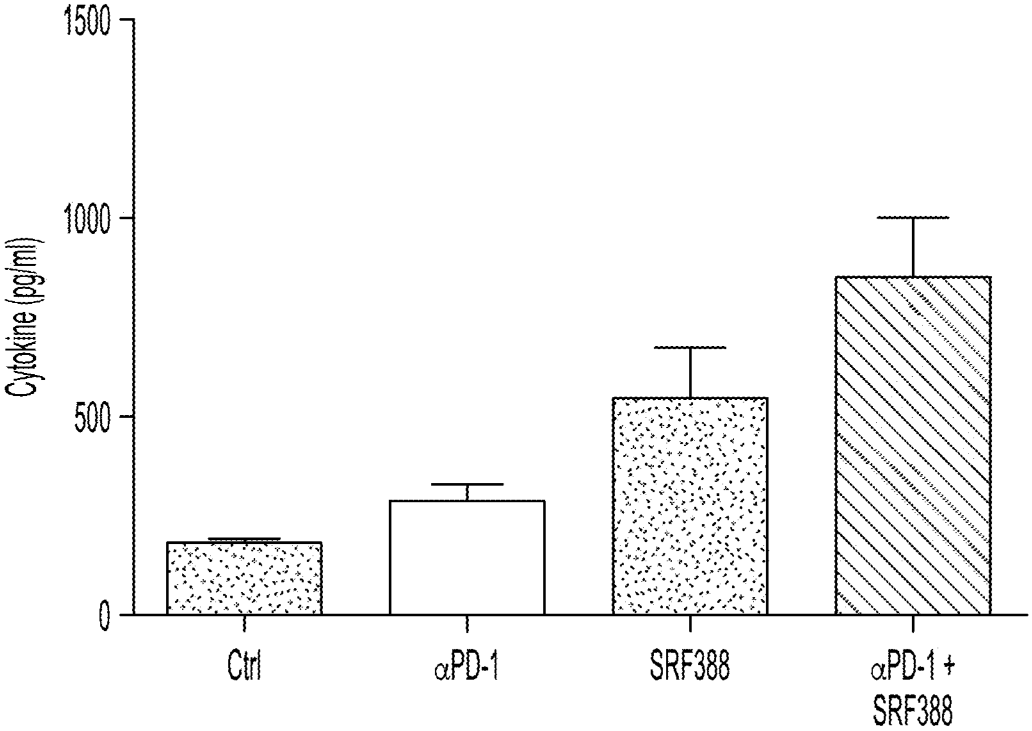
FIG. 5A is a graph depicting the extent of anti-IL-27 antibodies to enhance the PD-1-mediated secretion of TNFα in human PBMCs as measured by ELISA.
Figure 5B:
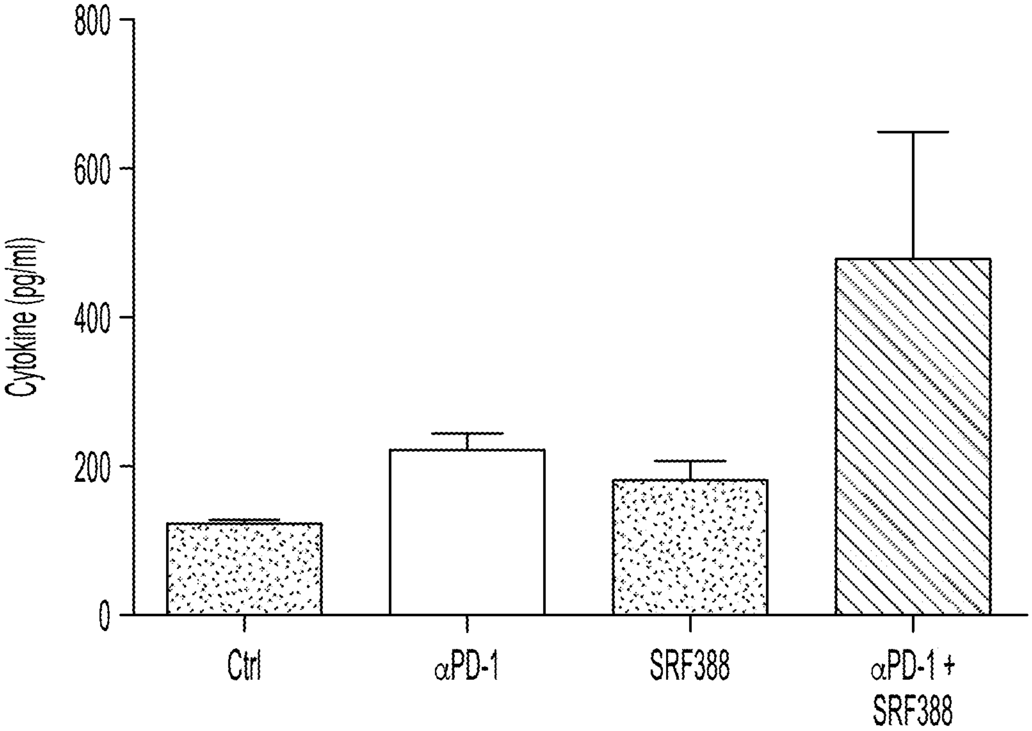
FIG. 5B is a graph depicting the extent of anti-IL-27 antibodies to enhance the PD-1-mediated secretion of IL-6 in human PBMCs as measured by ELISA.

Example 6: Enhancement of PD-1-Mediated Secretion of TNFα, IL-6 and Other Cytokines by Anti-IL-27 Antibodies, Including Additional In Vitro Characterization of Anti-IL-27 Antibodies Anti-IL-27 antibodies were tested for their ability to enhance PD-1-mediated secretion of TNFα and IL-6 in human PBMC cells from cancer patients. Human PBMC cells from cancer patients were cultured essentially as described in Example 5 with the addition of wells also receiving anti-PD-1 antibody, as indicated, at 1 μg/mL. Supernatants from the assay were analyzed for TNFα and IL-6 using Human CBA Th1/Th2/Th17 Kit (BD, 560484). As shown in FIGS. 5A and 5B, anti-IL-27 antibodies enhance the PD-1-mediated secretion of TNFα and IL-6 in pooled human PBMC cells.

The techniques herein also show cytokine-inducing activity of SRF388 monotherapy and in combination with anti-PD-1 in human PBMCs. IL-27 is known to negatively regulate the expression of several inflammatory cytokines. To determine the effects of IL-27 blockade on cytokine production, human PBMCs from healthy donors, patients with RCC, and patients with ovarian cancer were activated with anti-CD3 in the presence or absence of SRF388 for several days and tested for levels of secreted cytokines including IL-17, IFNγ, TNFα, and IL-6. Briefly, PBMCs isolated from fresh whole blood from 4 healthy donors, 5 patients with RCC, and 2 patients with ovarian cancer were activated by 0.25 μg/mL anti-CD3 antibody in the absence or presence of SRF388 (1 μg/mL), anti PD1 (pembrolizumab, 1 μg/mL) or both antibodies. After 5 days, supernatants were collected and tested for levels of TNFα (A) or IFNγ (B) by MSD or CBA. Data shown represent the fold-change in cytokine production compared to anti-CD3 stimulation alone. Statistics were calculated by paired t-test (*$p<0.005$).

Figure 5C:
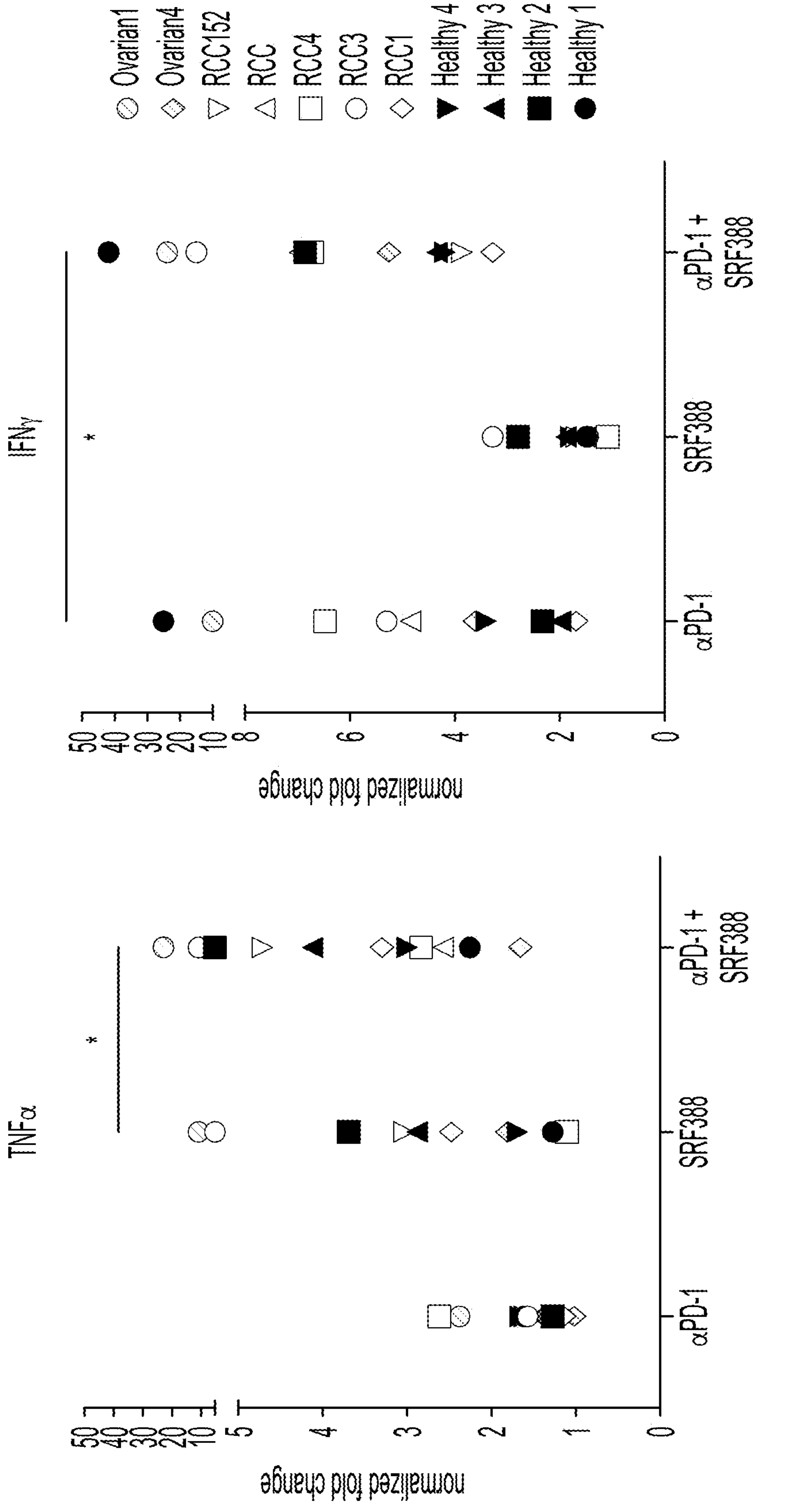
FIG. 5C is a dotplot showing that SRF388 in combination with PD-1 blockade leads to increased cytokine production in PBMCs from healthy donors and patients with RCC (Abbreviations: CBA=Cytometric Bead Array, IFNγ=interferon gamma, MSD=Meso Scale Discovery, PBMCs=peripheral blood mononuclear cells, PD-1=programmed death receptor-1, RCC=renal cell carcinoma, TNFα=tumor necrosis factor alpha).
Figure 5D:
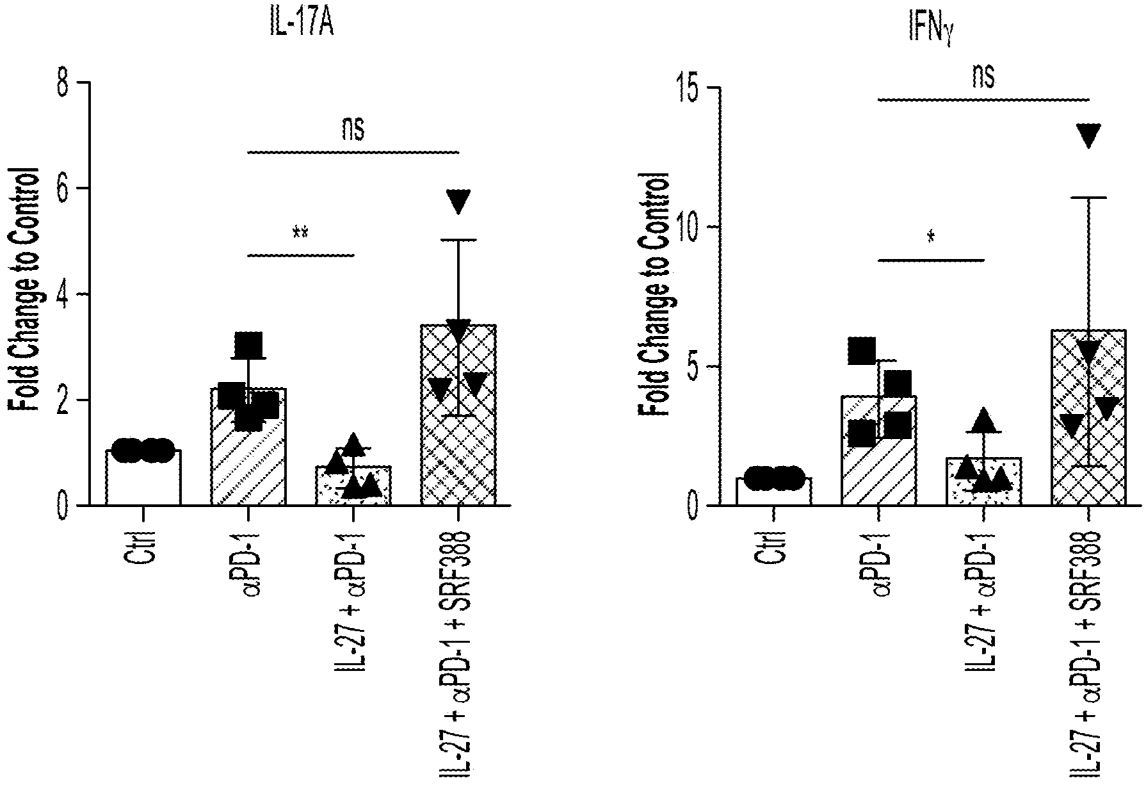
FIG. 5D shows that IL-27 inhibits cytokine production following PD-1 blockade and is restored in combination with SRF388 (Abbreviations: Ctrl=control, ns=not significant, PBMCs=peripheral blood mononuclear cells, rhIL-27=recombinant human IL-27).

Anti-PD-1 antibody was used as a control in these assays and the combination of PD-1 and IL-27 blockade was also explored as shown in FIG. 5C. SRF388 treatment led to increased TNF a production in 6 of 11 PBMC samples tested (determined by >2 fold increase) including 2 of 4 healthy donors, 3 of 5 patients with RCC, and 1 of 2 patients with ovarian cancer. When tested in a subset of donors this activity was SRF388 dose dependent (data not shown). Anti-PD-1 (pembrolizumab) treatment showed an increase in TNFα in 2 of the 11 donors tested (1 of 5 RCC and 1 of 2 ovarian cancer) while the combination of SRF388 and anti-PD-1 led to an increase in 10 of 11 donors. The increased TNFα seen in the combination treatment conditions appeared to be additive in 8 of 10 responders. An additive effect for IFNγ production was observed in these cultures after SRF388 and anti-PD-1 treatment (10 of 11 donors); however, responses to anti-PD-1 treatment alone were more frequently seen (10 of 11 donors) compared to SRF388 (2 of 11 donors). Together, these data suggest that SRF388 increases TNFα levels in activated PBMC cultures from healthy donors and patients with cancer and the combination of SRF388 and anti-PD-1 treatment leads to higher levels of TNFα and IFNγ compared to either treatment alone.

To further explore the role of IL-27 and PD-1 blockade, the same activated PBMC culture system was used to determine whether IL-27 could directly counteract the effect of increased cytokine production caused by PD-1 blockade. Briefly, freshly isolated PBMCs from human whole blood were activated by 0.25 μg/mL anti-CD3 antibody. Cells were treated either control IgG1 (1 μg/mL), αPD-1 antibody (pembrolizumab, 1 μg/mL) alone, rhIL-27 (25 ng/mL) plus αPD-1 or rhIL-27 plus αPD-1 with SRF388 (1 μg/mL) at 37° C. for 5 days. Supernatants were collected for CBA detection. The example cytokines (IL-17A and IFNγ) from 4 healthy donors were shown as fold change to control. Mean and standard deviation were depicted. Statistics were calculated by paired t-test (*$p<0.05$, $p<0.01$). Similar results were also seen in PBMCs from patients with RCC.PD-1 blockade increased both IL-17 and IFNγ in these cultures and IL-27 could completely inhibit this activity, a response that was reversed in the presence of SRF388 as shown in FIG. 5**D. These data show that IL-27 can attenuate the effects of anti PD-1 treatment on cytokine production.

Therefore, IL-27 was shown to inhibit anti-PD-1 mediated pro-inflammatory cytokine production in activated human PBMCs, a property that was blocked by SRF388. Moreover, SRF388 in combination with PD-1 blockade led to increased cytokine production in activated PBMCs from healthy donors and patients with RCC. Thus, by blocking IL-27, SRF388 enhances immune cell activation by altering immunoregulatory receptor expression and increasing inflammatory cytokine production.

Figure 5E:
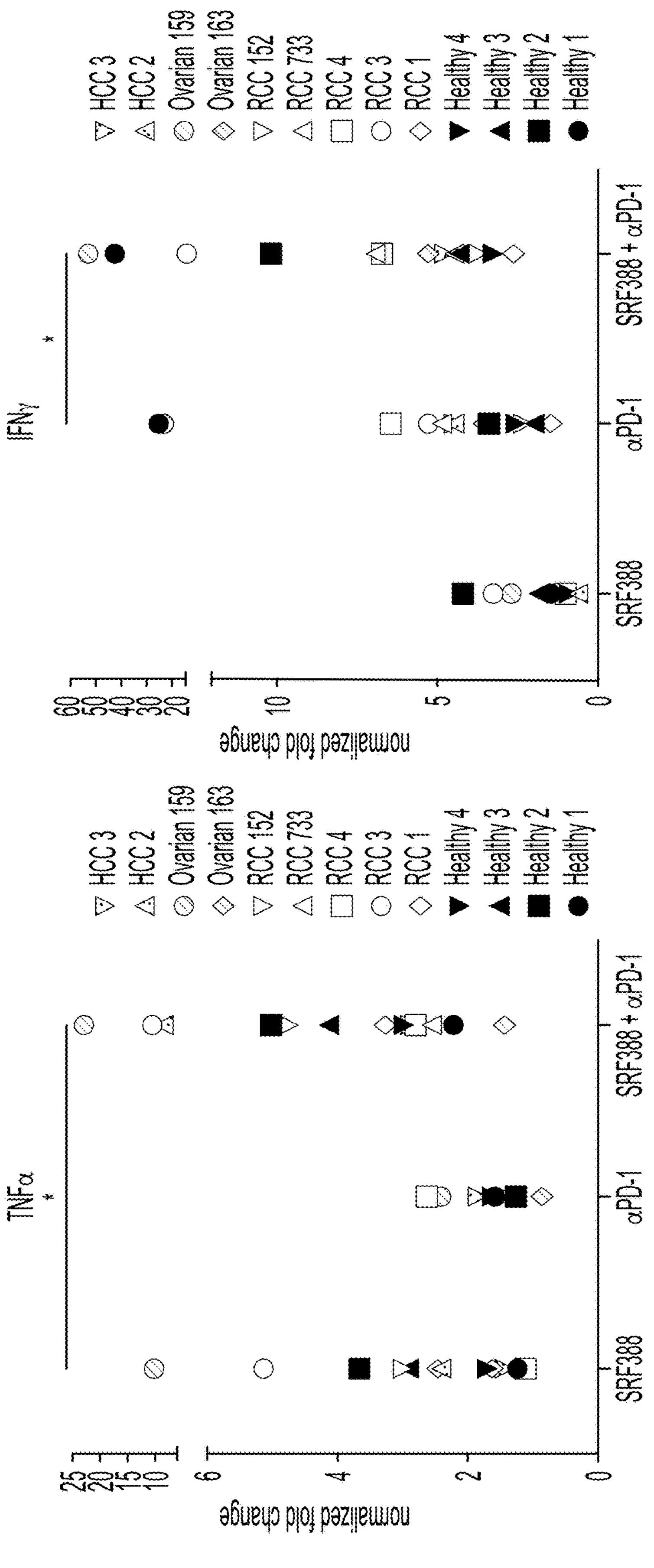
FIG. 5E summarizes observed cytokine induction (specifically, TNFα, IFNγ, IL-6 and IL-17A) in PBMC culture for various indicated types of cells, when such cells were contacted with SRF388 antibody, αPD-1 antibody, or a combination of SRF388 and αPD-1 antibodies.
Figure 5E:
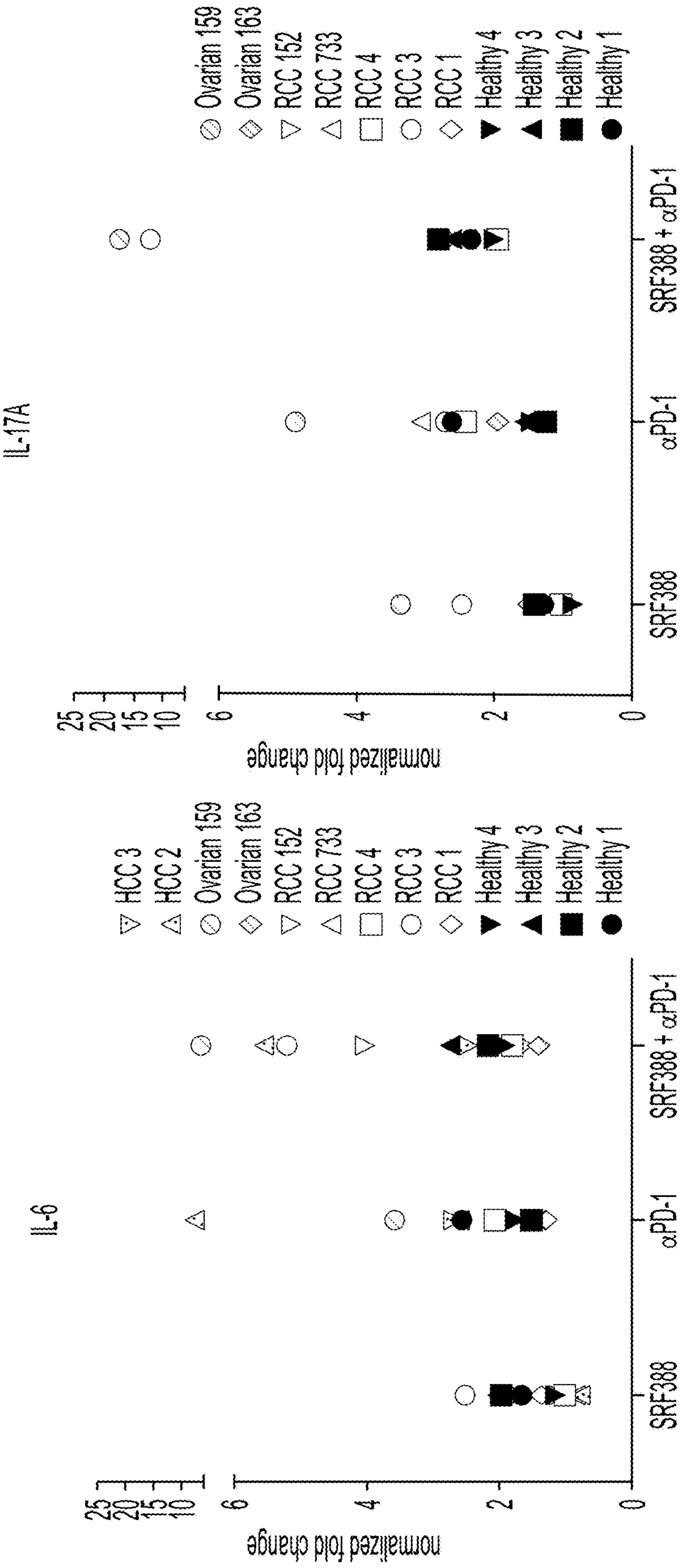
Figure 5F:
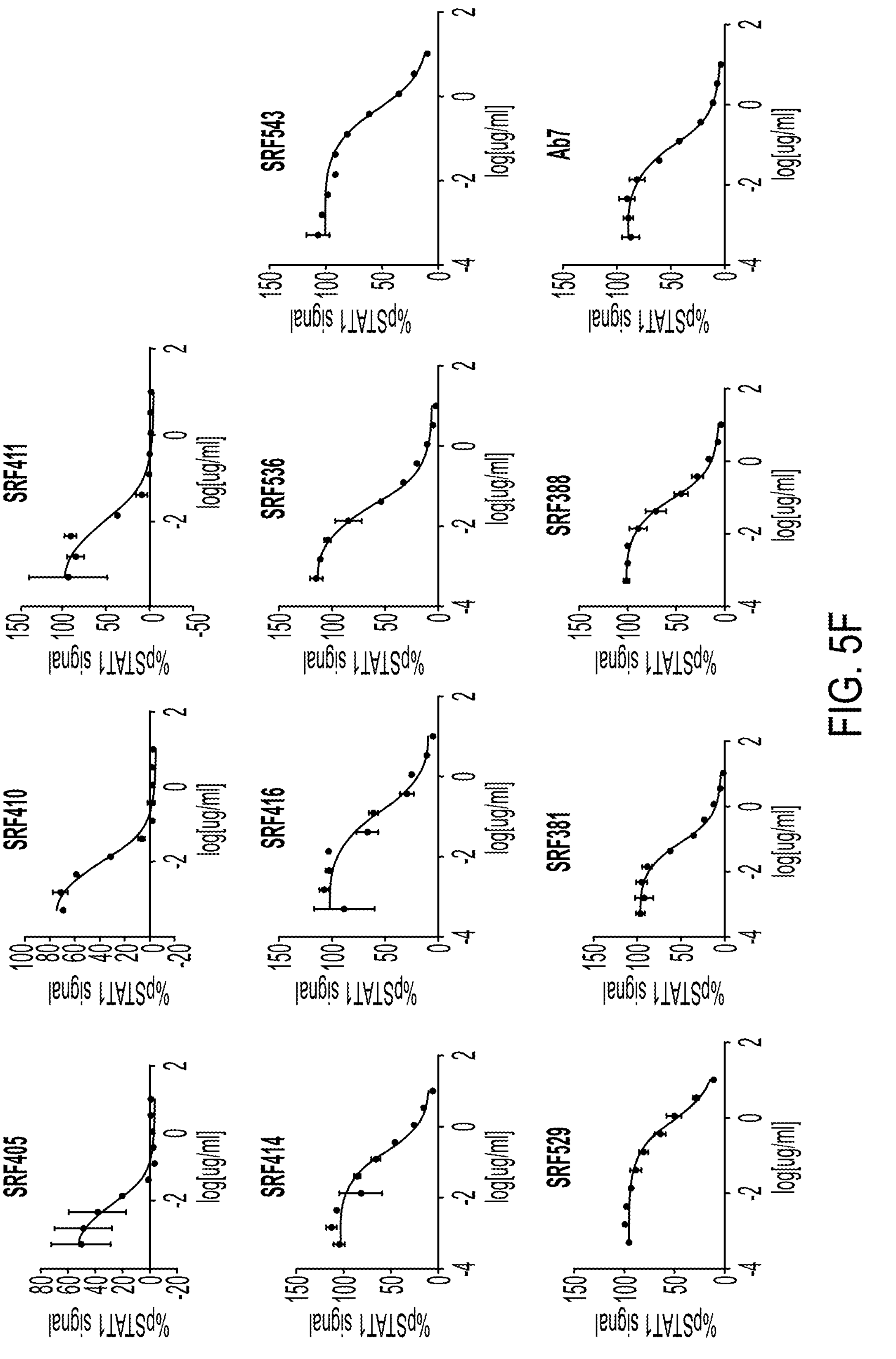
FIG. 5F shows the impact upon pSTAT1 signal in U937 (lymphoma) cells of varying concentrations of the individual antibodies indicated (SRF405, SRF410, SRF411, SRF414, SRF416, SRF536, SRF543, SRF529, SRF381, SRF388 and Ab7).
Figure 5G:
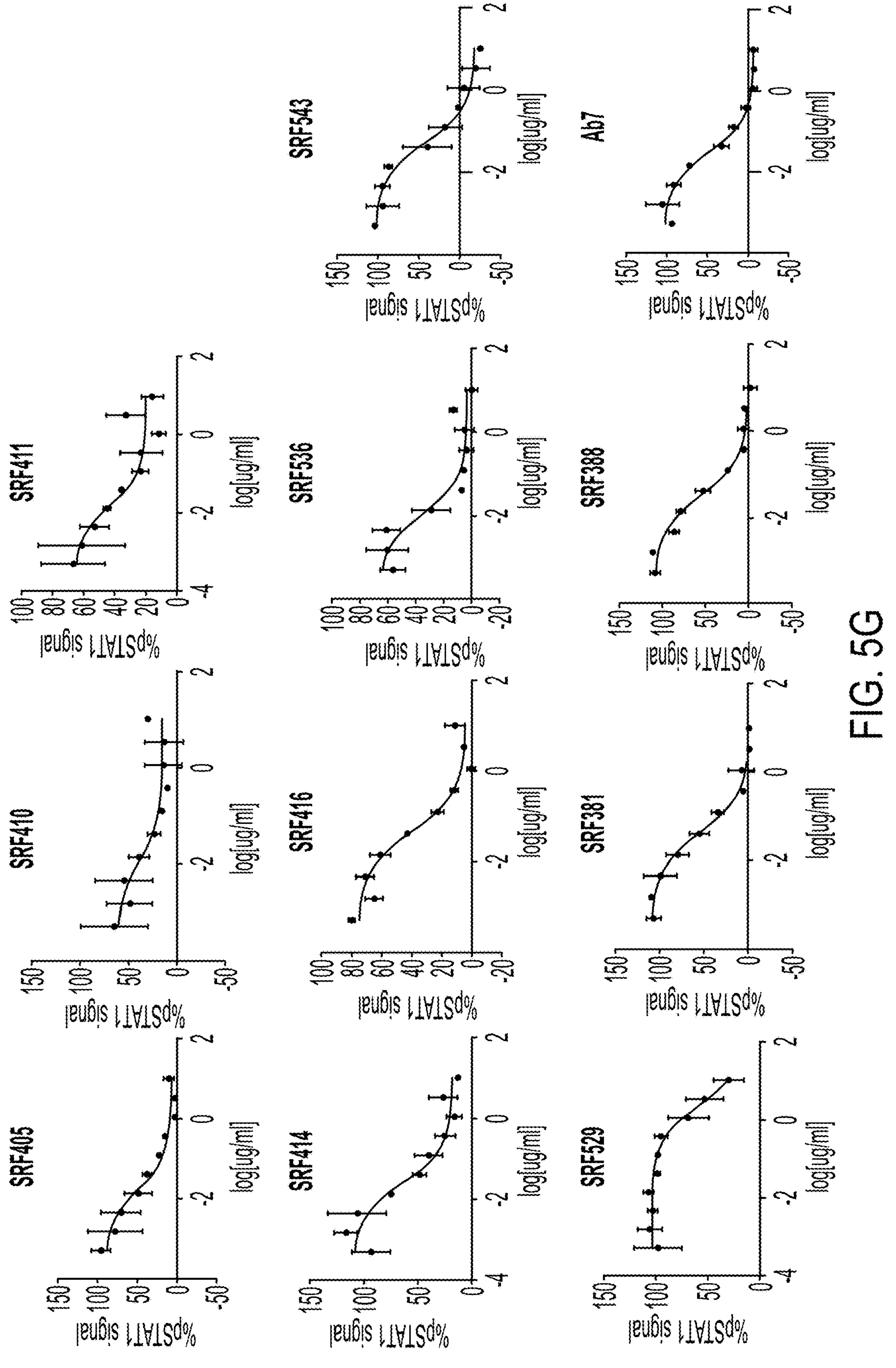
FIG. 5G shows the impact upon pSTAT1 signal in PBMCs (peripheral blood mononuclear cells) of varying concentrations of these individual antibodies.
Figure 5H:
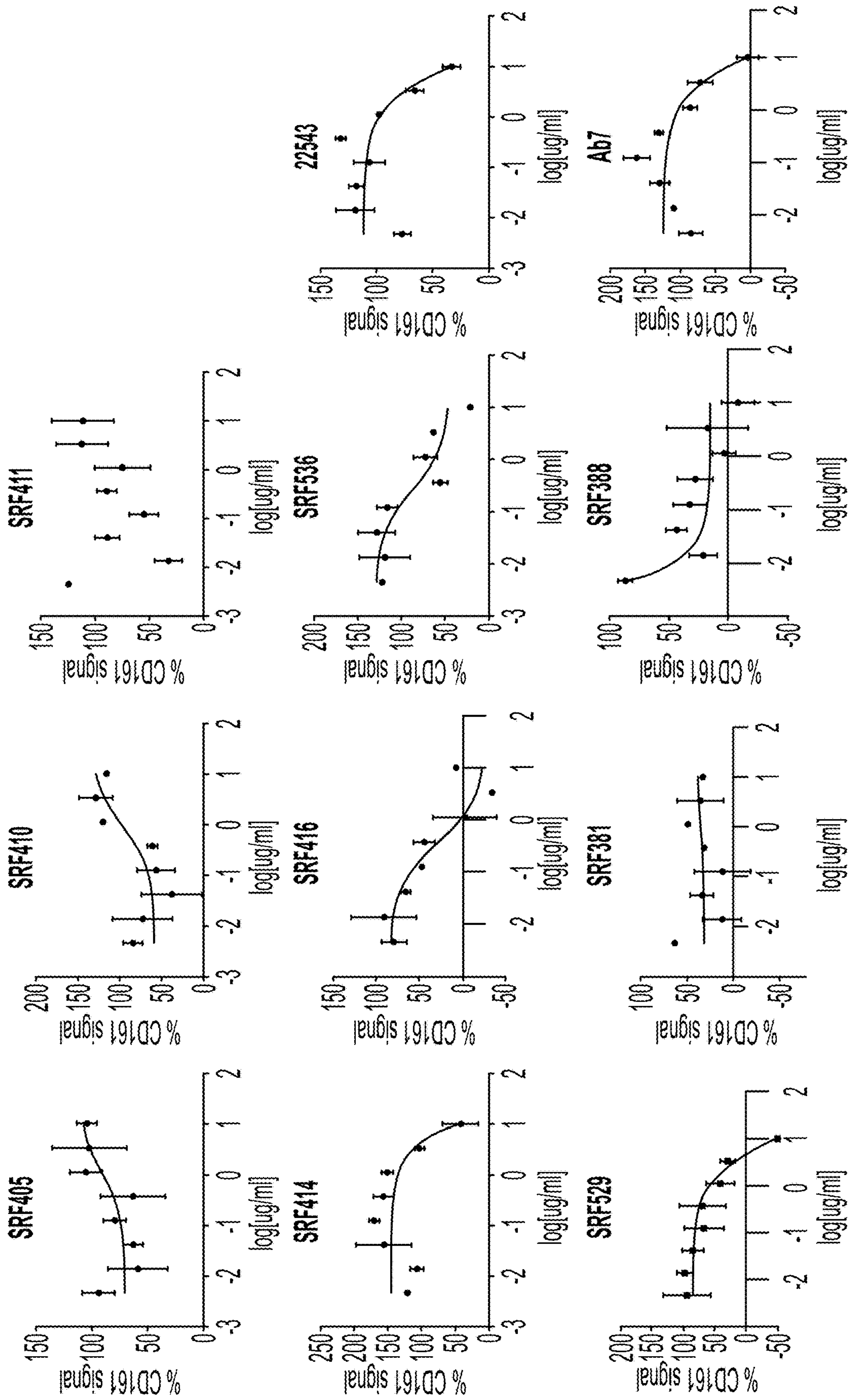
FIG. 5H shows the impact upon CD161 signal in PBMCs (peripheral blood mononuclear cells) of varying concentrations of these individual antibodies.
Figure 5I:
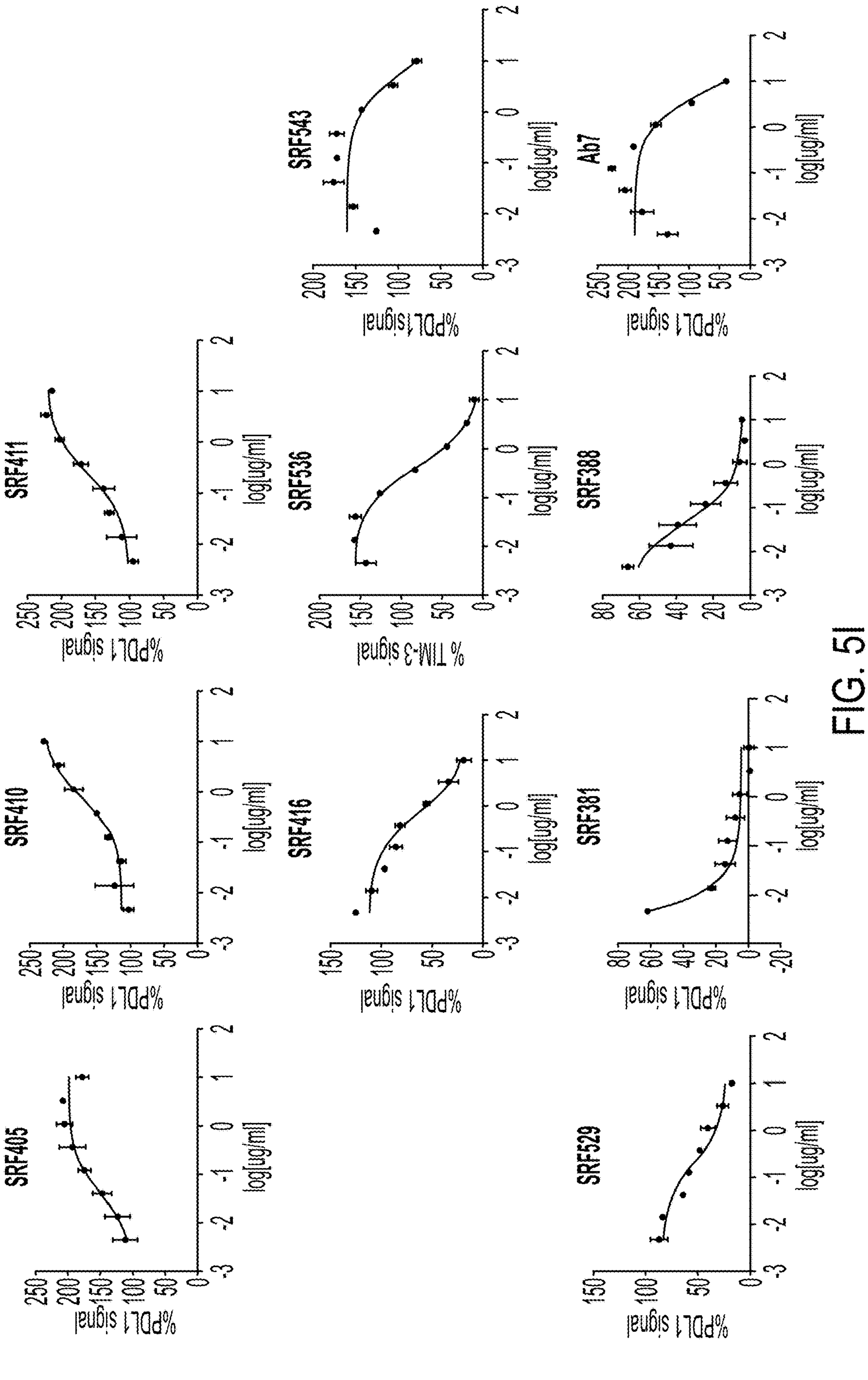
FIG. 5I shows the impact upon PD-L1 signal in CD4 T lymphocytes (CD4 cells) of varying concentrations of these individual antibodies (excluding SRF414).
Figure 5J:
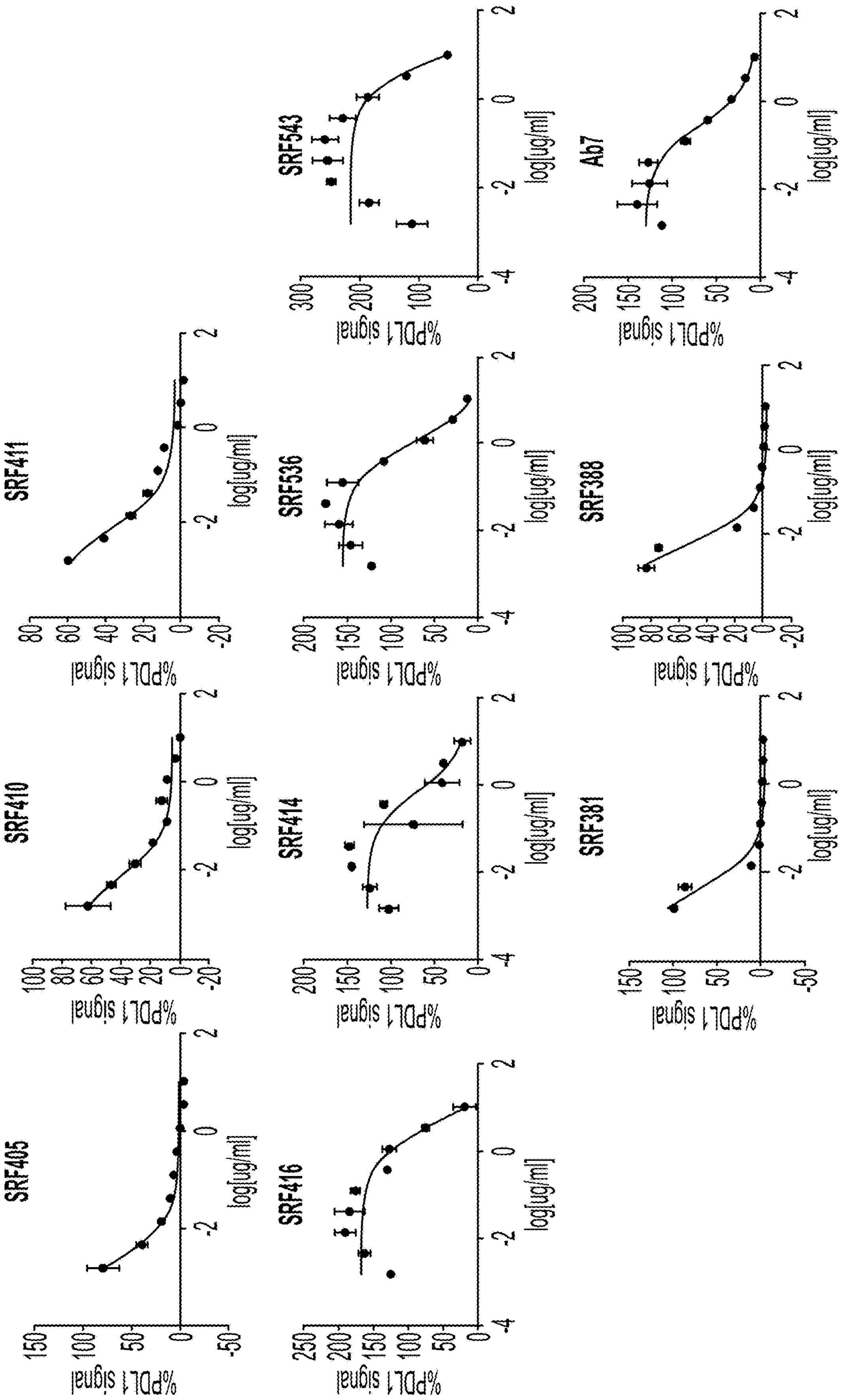
FIG. 5J shows the impact upon PD-L1 signal in monocytes of varying concentrations of these individual antibodies (excluding SRF529).
Figure 5K:
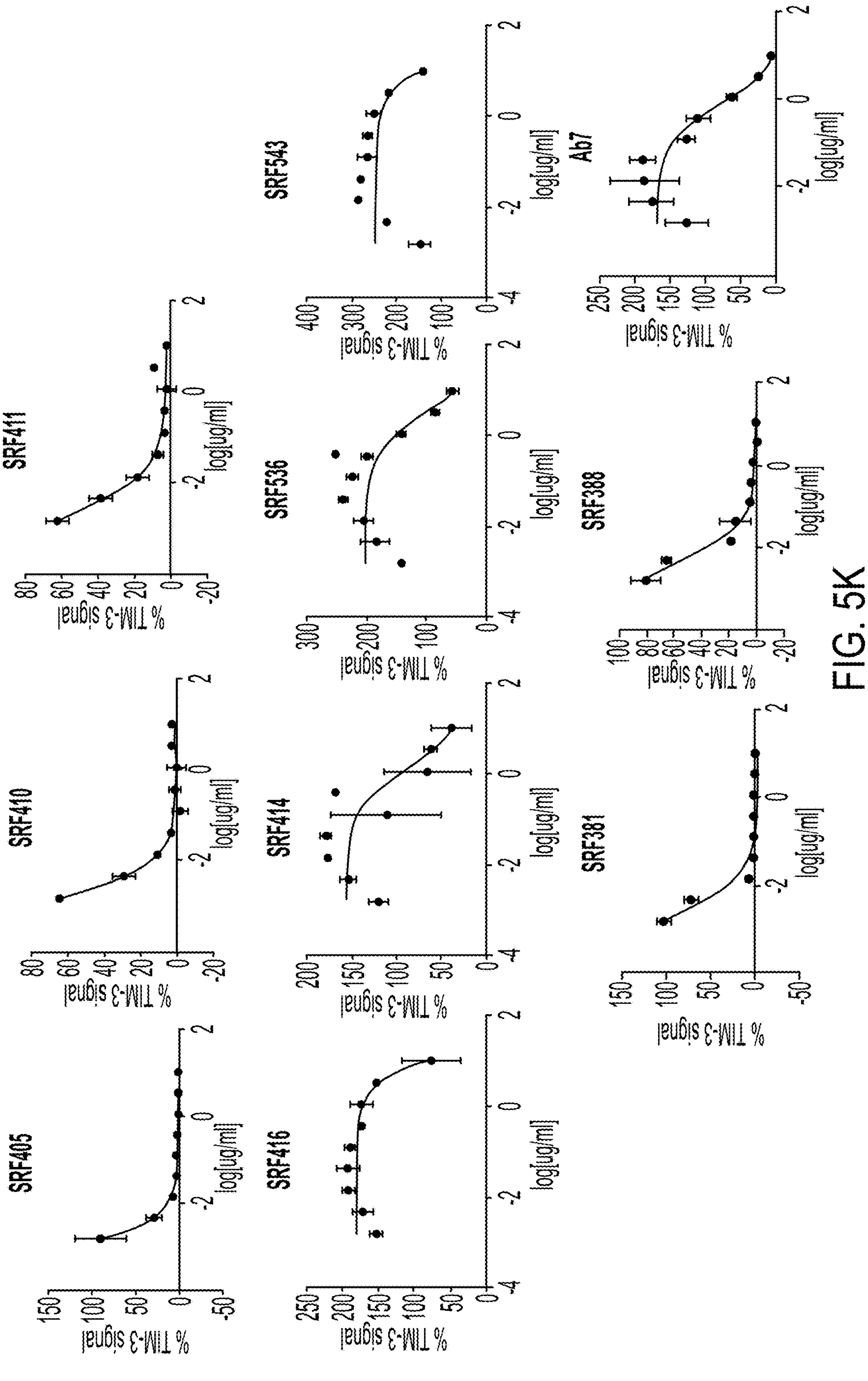
FIG. 5K shows the impact upon TIM-3 signal in monocytes of varying concentrations of these individual antibodies (excluding SRF529).

In additional characterization of individual anti-IL-27 antibodies in the presence of anti-IL-27 antibody (here, SRF388), αPD-1 antibody, or combined anti-IL-27 and αPD-1 antibodies, further characterization of cytokine induction/secretion was performed (FIG. 5E, specifically for TNFα, IFNγ, IL-6 and IL-17A). In vitro dose-response curves were also obtained across a number of IL-27-mediated signaling effects for SRF405, SRF410, SRF411, SRF414, SRF416, SRF536, SRF543, SRF529, SRF381, SRF388 and Ab7 antibodies (FIGS. 5F-5K, where: FIG. 5F shows inhibition of pSTAT1 signal in U937 (lymphoma) cells across increasing concentrations of anti-IL-27 antibodies; FIG. 5G shows inhibition of pSTAT1 signal in PBMCs (peripheral blood mononuclear cells) across increasing concentrations of anti-IL-27 antibodies; FIG. 5H shows varying effects upon CD161 signal in PBMCs (peripheral blood mononuclear cells) across increasing concentrations of anti-IL-27 antibodies; FIG. 5I shows varying effects upon PD-L1 signal in CD4 T lymphocytes (CD4 cells) across increasing concentrations of anti-IL-27 antibodies; FIG. 5J shows varying effects upon PD-L1 signal in monocytes across increasing concentrations of anti-IL-27 antibodies; and FIG. 5K shows inhibitory effects of varying degree upon TIM-3 signal in monocytes across increasing concentrations of anti-IL-27 antibodies).

Example 7: Inhibition of IL-27-Mediated Expression of PD-L1 and TIM3 by Anti-IL-27 Antibodies Anti-IL-27 antibodies described in Examples 1 and 2 were tested for their ability to inhibit IL-27-mediated expression PD-L1 and TIM-3 in pooled human monocytes by flow cytometry.

Fresh Monocytes were isolated from human buffy coats using RosetteSep™ Human Monocyte Enrichment Cocktail (Stemcell #15068).

Use of outer walls was avoided to minimize the effects of evaporation during the 5 day assay. Outer wells should be filled with 200 μL per well of DPBS (Gibco, 14190-144). Monocytes were resuspended at a density of 2 million cells per mL in warm, complete RPMI-1640. 100 μL per well of this cell mixture was plated (200,000 cells per well) in a round bottom 96-well plate (Costar, 3799).

Anti-IL-27 antibodies were diluted in complete RPMI-1640 in the first row of a 96-well polypropylene plate to a top concentration of 40 μg/ml (10 m/ml final concentration). Serial dilutions as desired (1:2, 1:3, etc. . . . ) were made in the remainder of the first 10 rows of the plate. 50 μL of the antibody stock (4×) was added to the first 10 rows the plate of PBMC cells in the round bottom plate. In rows 11 and 12, 1250 μL of complete RPMI-1640 was added.

After the addition of the anti-IL-27 antibodies, 50 μL of 80 ng/ml recombinant human IL-27 (R&D Systems, 2526-IL) diluted in complete RPMI-1640 was added to each well (except, control wells which included serum-free media or antibody alone) for a final concentration of 20 ng/ml. 100 μL serum-free RPMI-1640 was added to control wells. The plate was incubated for 3 days at 37° C. with minimal interference.

After the 3-day incubation the plate was removed from the incubator and agitated on a plate shaker for 30 seconds at 600 RPM. The plate was centrifuged at 1800 RPM for 5 minutes. Media was discarded by flicking and plate was washed with 150 μL DPBS (Gibco, 14190-144). The washing steps were repeated twice. The cell pellets were stained with 50 μL per well of staining cocktail as described in the Table 9 below:

TABLE 9

| Biolegend Catalog # | Antibody Target | Color | Dilution |
|---|---|---|---|
| 345006 | TIM3 | PE | 1:100 |
| 301310 | CD11b | APC | 1:100 |
| 329714 | PD-L1 | BV421 | 1:100 |

The plate was agitated on a plate shaker for 30 seconds at 600 RPM and the plate was incubated for 30 minutes 4° C. in the dark.

After the 30-minute incubation, the plate was centrifuged and supernatant was discarded by flicking. The plate was washed 2 times as described previously. After the last wash cell pellets were fixed by adding 50 μL 4% PFA (Pierce, 28906) in deionized (DI) water at room temperature for 10 mins. 100 μL of FACS buffer was added to each well, and the plate was centrifuged at 1800 RPM for 5 minutes. Cells were resuspended in 100 μL FACS buffer and analyzed by flow cytometry.

Figure 6A:
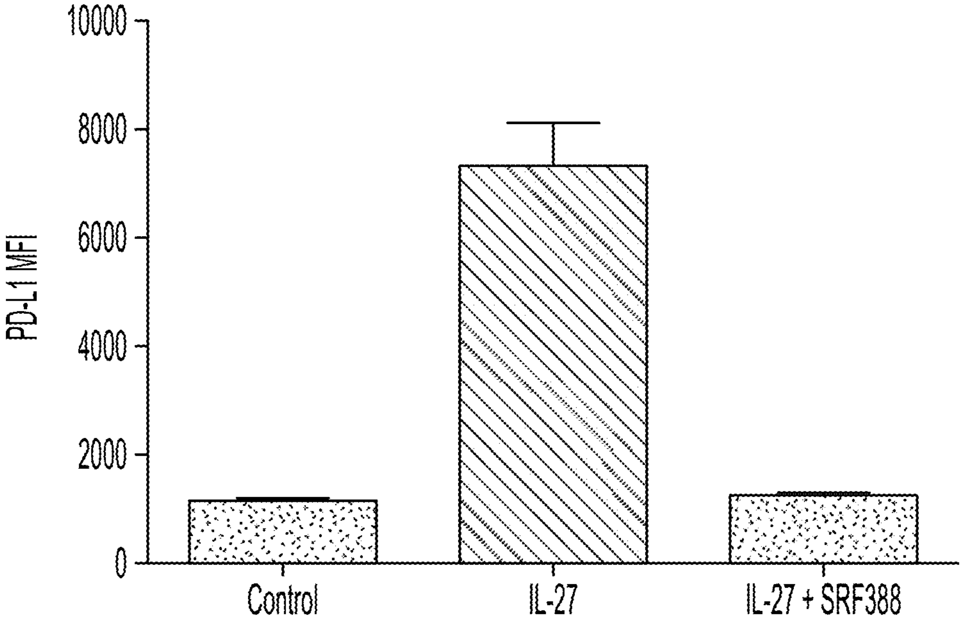
FIG. 6A is a graph depicting the inhibition of IL-27-mediated expression of PD-L1 by treatment of human monocytes with anti-IL-27 antibody as determined by flow cytometry.
Figure 6B:
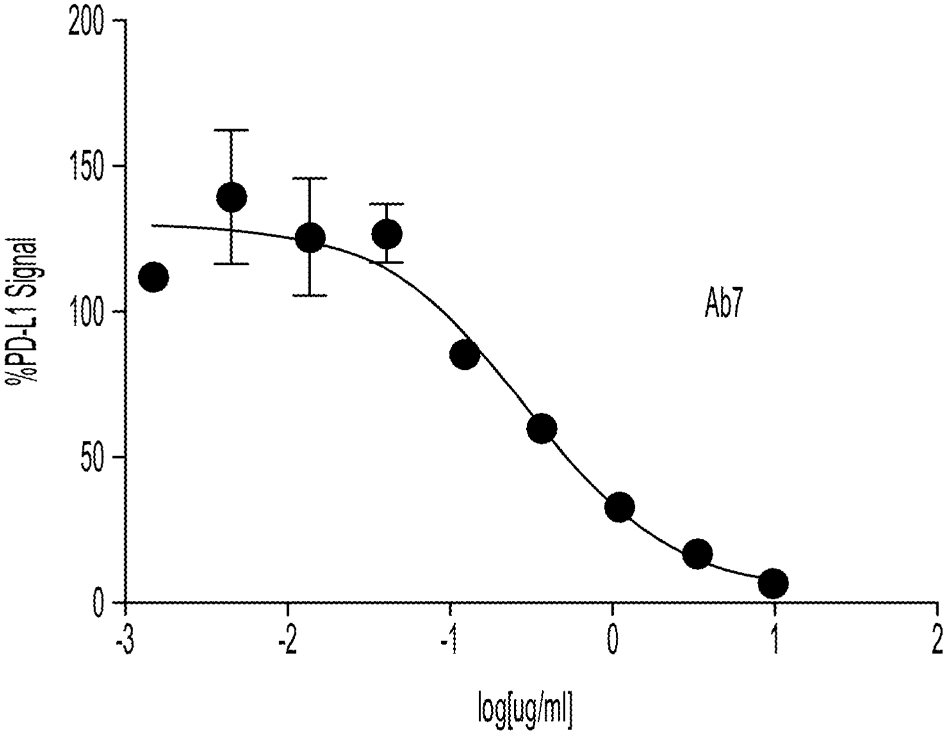
FIG. 6B is a graph depicting the dose-dependent inhibition of IL-27-mediated expression of PD-L1 by treatment of human monocytes with a range of concentrations of an anti-IL-27 antibody that specifically binds to the EBI3 monomer, as determined by flow cytometry.
Figure 6C:
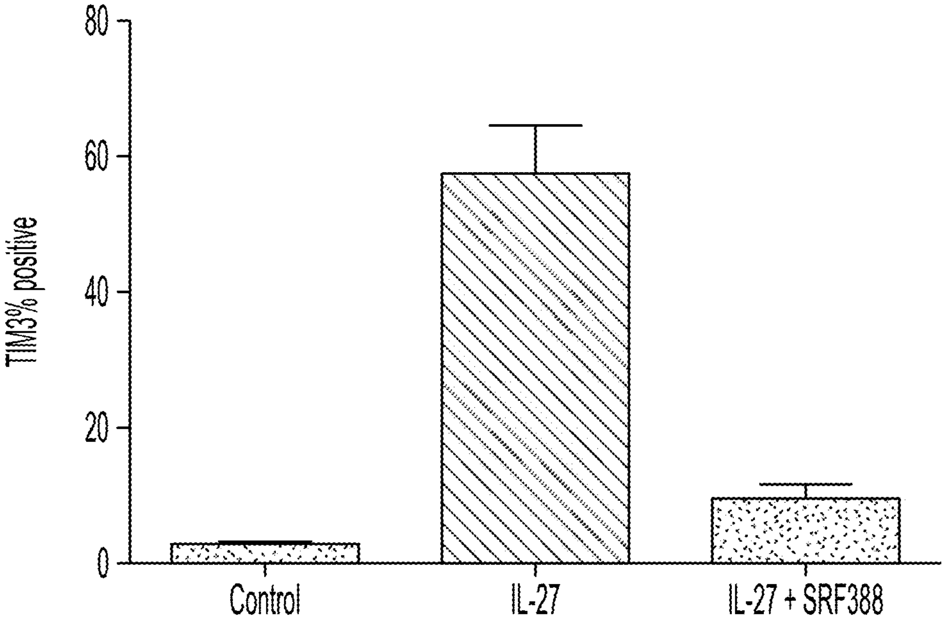
FIG. 6C is a graph depicting the inhibition of IL-27-mediated expression of TIM3 by treatment of human monocytes with anti-IL-27 antibody, as determined by flow cytometry.

As shown in FIGS. 6A, 6B and 6C, anti-IL-27 antibodies potently inhibit the IL-27 mediated expression of PD-L1 and TIM3 in pooled human monocytes.

Anti-IL-27 antibodies were further tested for their ability to inhibit IL-27-mediated expression of PD-L1 in resting T cells (inactivated) essentially as described for FIGS. 6A, 6B and 6C. Resting T-cells were isolated from human buffy coats using RosetteSep™ Human T cell Enrichment Cocktail (Stemcell #15061).

At the conclusion of the assay, the cell pellets were stained with 50 μL per well of staining cocktail as described in the Table 10 below:

TABLE 10

| Biolegend Catalog # | Antibody Target | Color | Dilution |
|---|---|---|---|
| 345006 | TIM3 | PE | 1:100 |
| 555349 | CD4 | APC | 1:100 |
| 329714 | PD-L1 | BV421 | 1:100 |
| 555366 | CD8 | FITC | 1:100 |

The plate was agitated on a plate shaker for 30 seconds at 600 RPM and the plate was incubated for 30 minutes at 4° C. in the dark.

Figure 6D:
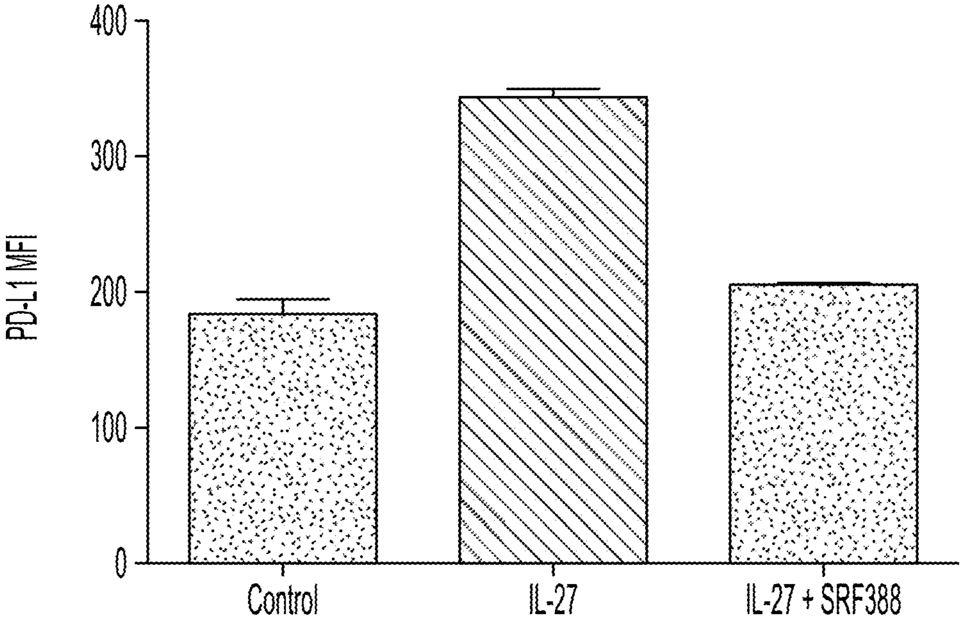
FIG. 6D is a graph depicting the inhibition of IL-27-mediated expression of PD-L1 by treatment of resting human T cells with anti-IL-27 antibody, as determined by flow cytometry.

After the 30-minute incubation, the plate was centrifuged and supernatant was discarded by flicking. The plate was washed 2 times as described previously. After the last wash cell pellets were fixed by adding 50 μL 4% PFA (Pierce, 28906) in DI water at room temperature for 10 mins. 100 μL of FACS buffer was added to each well, and the plate was centrifuged at 1800 RPM for 5 minutes. Cells were resuspended in 100 μL FACS buffer and read by flow cytometry. As shown in FIG. 6D, anti-IL-27 antibodies potently inhibit the IL-27-mediated expression of PD-L1 in pooled human resting T cells.

Example 8: In Vivo Efficacy of an Anti-IL-27 Antibody in a Disseminated B16F10 Model of Melanoma A model of melanoma lung metastasis was used to assess the antitumor activity of IL-27 blockade using the clinical candidate SRF388. The growth of disseminated B16F10 lung metastases is known to be significantly reduced in EBI3 and Il27ra (Wsx-1)-deficient mice (Sauer et al., *J. Immunology* 181: 6148-6157). Since lung nodule size and growth kinetics are dependent on the number of B16F10 cells transferred and can proceed variably and rapidly, the combination of anti-PD-1 and anti-CTLA-4 was studied as a benchmark for therapeutic activity. SRF388 pre-treatment resulted in a significant reduction in overall tumor burden. To evaluate the anti-tumor efficacy of an anti-IL-27 antibody in vivo, the effect of Ab14 on tumor growth in a B16F10 melanoma tumor model was evaluated.

Briefly, six to eight-week-old female C57BL/6 mice (n=10/group) were inoculated intravenously (i.v.) with either $2.5\times10^5$ B16F10 cells or $1\times10^5$ B16-Luc cells via the tail vein in 2004, phosphate-buffered saline (PBS). Animals were injected intraperitoneally (i.p.) with SRF388 (1 mg dose) (Wuxi; lot 2108SD170316K01X01I01) or polyclonal human IgG isotype control (1 mg dose) (Bioxcell; BE0092; lot 658417D1). Antibodies were dosed once weekly beginning 7 days before tumor injection for a total of four doses (days −7, 0, 7, and 14). For visual enumeration of lung metastases, B16F10 tumor bearing mice were euthanized by $CO_2$ asphyxiation 18 days-post tumor cell injection and lungs were perfused with PBS via cardiac puncture, removed, and fixed in 10% neutral buffered formalin for 24 hours. Fixed lungs were then transferred to 70% ethanol and surface lung metastases were counted visually. For immunohistochemical analysis, formalin fixed lungs (n=5/group) were paraffin embedded, sectioned and stained with hematoxylin and eosin for quantification of total tumor area as a percentage of total tissue area in each section. For in vivo tumor imaging of lung metastases, B16-Luc tumor-bearing animals were injected i.v. via the tail vein with 3 mg of VivoGlo D-luciferin in 200 μl PBS (Promega) twice weekly. Five minutes after luciferin injection animals were anesthetized and bioluminescent imaging was performed using an IVIS Lumina LT Series III imager. Images were analyzed using Living Image (version 4.5.5) software and represented as total flux measurements in photons/second.

Figure 7A:
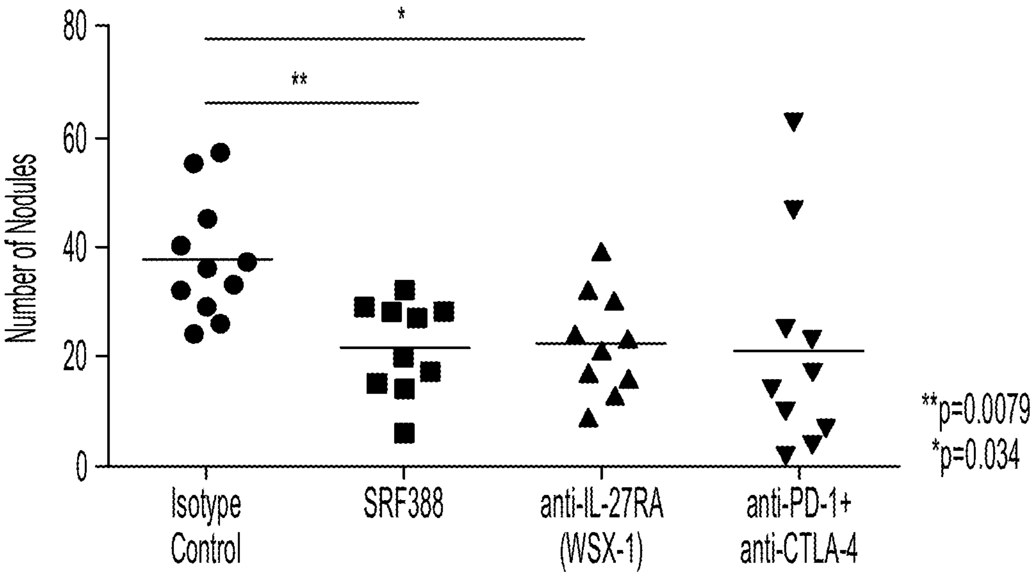
FIG. 7A is a dotplot depicting the number of surface lung B16F10 metastatic nodules (pulmonary nodules) from B16F10 tumor-bearing mice treated with anti-IL27 antibody (SRF388), isotype control antibody, αWSX-1 antibody or combined αPD-1 and αCTLA-4 antibodies, as indicated, as determined by visual counting of nodules from lungs isolated from mice.
Figure 7B:
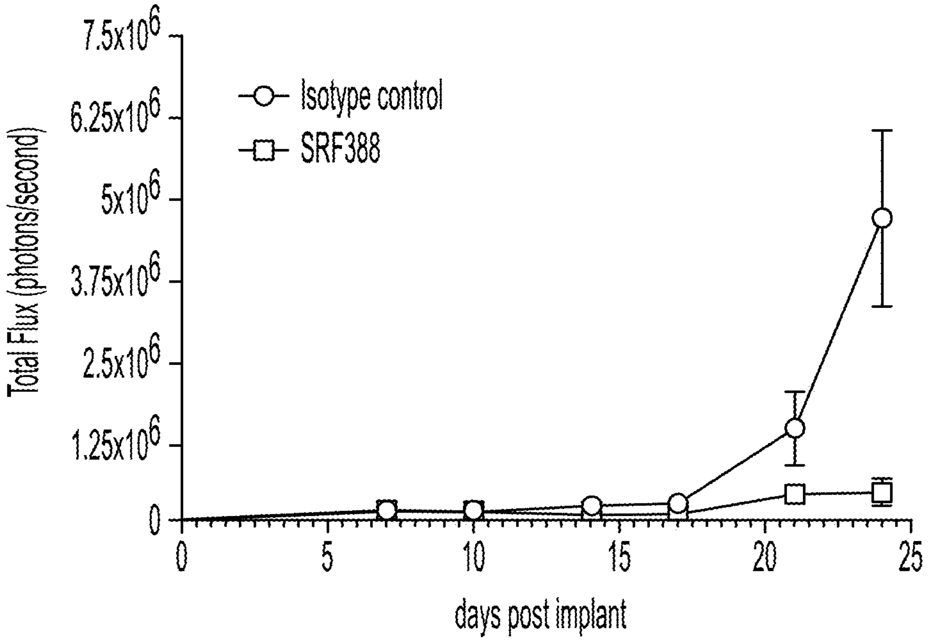
FIG. 7B provides a graph depicting the growth kinetics of bioluminescent B16-Luc tumors in mice treated with anti-IL-27 antibody (SRF388) or isotype control antibody, as determined by bioluminescent imaging analysis.
Figure 7C:
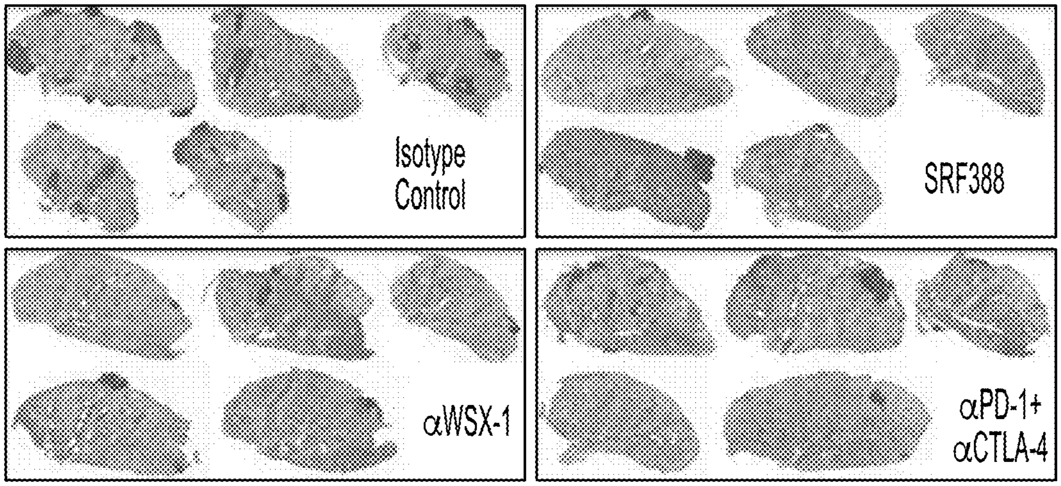
FIG. 7C shows a series of images of fixed, sectioned lung tissue stained with hematoxylin and eosin isolated from B16F10 tumor-bearing mice treated with anti-IL27 antibody (SRF388), isotype control antibody, αWSX-1 antibody or combined αPD-1 and αCTLA-4 antibodies, as indicated.
Figure 7D:
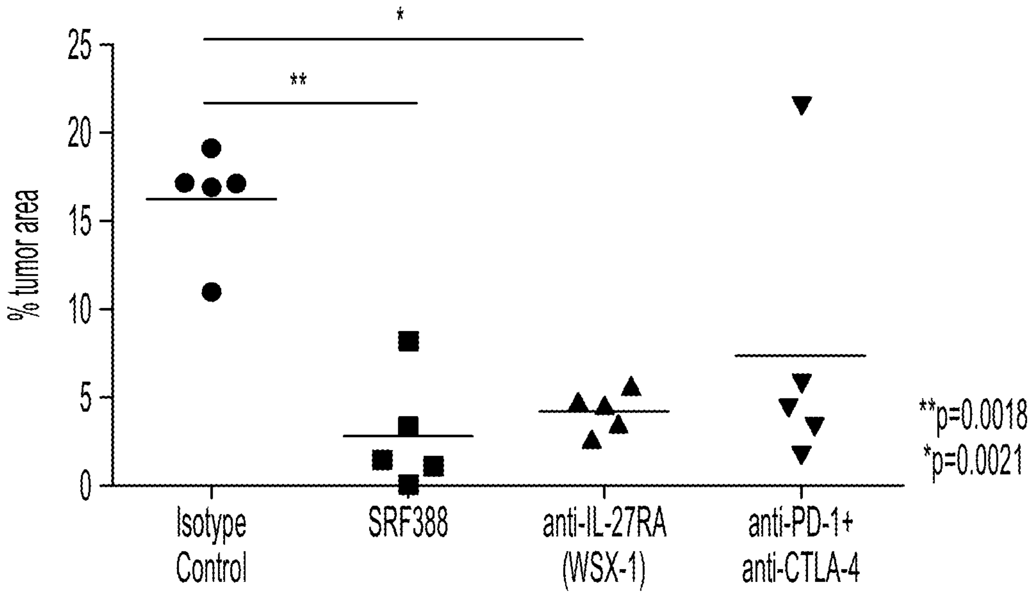
FIG. 7D is a dotplot depicting the total tumor area as a percentage of total tissue area of fixed, sectioned lung tissue B16F10 tumor tissue stained with hematoxylin and eosin isolated from B16F10 tumor-bearing mice treated with anti-IL27 antibody (SRF388), isotype control antibody, αWSX-1 antibody or combined αPD-1 and αCTLA-4 antibodies, as indicated, as determined by image analysis software. A similar reduction in surface lung metastasis number and total tumor area was observed with IL-27RA (WSX-1)

As shown in FIGS. 7A-7D, treatment of B16F10 tumor-bearing mice with the anti-IL-27 antibody SRF388 resulted in a significant reduction in overall tumor burden as measured by both total counts of surface lung metastases (# pulmonary nodules, FIG. 7A), and by a reduction of tumor area in lung tissue sections by immunohistochemistry (IHC) analysis (FIG. 7C and FIG. 7D). Blockade of p28 with SRF388 resulted in a 42% reduction in the number of pulmonary B16 nodules compared to isotype control treatment. SRF388 treatment significantly inhibited (p=0.0079) the growth of B16F10 lung metastases compared to isotype control (21.6±8.4 versus 37.6±10.9 lung nodules, respectively). SRF388 treatment resulted in an 83% reduction in overall lung tumor metastasis area as measured by IHC (16.43±1.39% in the isotype control group versus 2.83±1.45% in the SRF388 treatment group). Similarly, bioluminescent imaging revealed that SRF388 treatment significantly (p=0.0062) delayed the growth of B16-Luc lung metastases (FIG. 7B). A similar reduction in surface lung metastasis number and total tumor area was observed with IL-27RA (WSX-1) mediated antibody blockade and with anti-PD-1+anti-CTLA-4 combination therapy, as shown in FIG. 7D. These data are from 2 independent experiments in which anti-PD-1 and anti-CTLA-4 benchmark combination demonstrated antitumor activity. B16F10 cells ($2.5\times10^5$) were injected intravenously in C57BL/6 mice (n=10/group). Mice were treated IP with 1 mg of either SRF388, anti-IL-27RA (WSX-1), or human IgG isotype control antibody (Days −7, 0, 7, 14). Some animals were treated IP with anti-PD-1 and anti-CTLA-4 (Days 0, 4, 7, and 11). Lungs were collected from animals (n=5/group) bearing B16F10 lung metastases treated as described above were sectioned and stained with H&E. B16F10 tumor tissue was delineated from normal lung tissue in H&E stained lung sections from treated animals (FIG. 7A). Tumor area was calculated as a percentage of total lung area (FIG. 7D). Statistics were calculated by t-test. Collectively, these data indicate that SRF388 can phenocopy Il27ra (WSX-1) and EBI3 deficiency in a tumor model and shows similar activity to combined blockade of PD-1 and CTLA-4.

These data demonstrate that treatment with an anti-IL-27 antibody (SRF388) results in anti-tumor effects, reducing both tumor growth and metastasis to a greater extent that treatment with an isotype control antibody that does not bind IL-27.

Example 9: Gene Expression Profiling of Murine Splenocytes from Mice Hydrodynamically Transfected with Human IL-27 Minicircles To examine the effect of IL-27 on T cell phenotype in vivo, DNA minicircles encoding IL-27 were used to overexpress IL-27 in mice and T cell responses were assessed by RNA-Seq and flow cytometry. Human IL-27 is known to be species cross-reactive and can induce pSTAT1 signaling and PD L1 in murine splenocytes in vitro. This species cross-reactivity was used to study the effects of human IL-27 overexpression in mice and its inhibition by SRF388. To do this, DNA plasmid minicircles encoding human IL-27 (p28 tethered to EBI3 by a glycine serine linker) were administered to mice by hydrodynamic transfection, as described below, which resulted in high systemic levels of IL-27.

Hydrodynamic Transfection of Human IL-27 Minicircles

Six-week-old female BALB/c mice were injected with 20 μg of either empty vector or linked human IL-27 minicircle DNA (System Biosciences, Palo Alto, Calif.) in 2 mL 0.9% normal saline via the tail vein over the course of 5 seconds. Injected animals were transferred to an empty cage with a heating pad to recover for 5 minutes. Whole blood was collected into K2-EDTA tubes for plasma separation 24 hours after minicircle injection and plasma IL-27 levels were confirmed by ELISA. PBMCs and total splenocytes were collected 5 days after transfection and cells were stained and analyzed by flow cytometry. Expression of the indicated markers were analyzed on CD4+ T cells and CD8+ T cells. Analysis was performed using FlowJo software.

Gene Expression Profiling

Mouse splenocytes were prepared by mechanical dissociation of whole spleens, followed by ACK lysis of red blood cells. Total RNA was extracted from splenocytes with the RNeasy® Mini Kit (Qiagen, Cat. No: 74104) and adjusted to 20 ng/ul in nuclease free water (Qiagen, Cat. No: 19101). Gene expression profiling on was performed on Affymetrix GeneChip™ Mouse Gene 2.0 ST Arrays (Applied Biosystems, Cat. No: 902118). Processing of RNA samples, hybridization and array scanning were carried out using standard Affymetrix GeneChip™ protocols at the Boston University Microarray and Sequencing Resource (BUMSR). All CEL files were normalized by Robust Multi-array Average (RMA) (Irizarry et al., 2003) and gene expression data were preprocessed by removing unexpressed probes and discarding transcripts with high inter-replicate coefficient of variance. Subsequent analyses (mean expression, fold change, t test) were performed in R.

Flow Cytometric Analysis

Whole blood and spleens were collected from mice five days after minicircle injection. Splenocytes were collected from IL 27-expressing mice 5 days after transfection and analyzed by Affymetrix GeneChip Mouse Gene 2.0 ST Array. Single cell splenocyte suspensions were prepared by mechanical dissociation through a 40 μm nylon cell strainer followed by red blood cell lysis in ACK buffer. Whole blood cells were stained directly followed by red blood cell lysis and fixation in BD Phosflow Lyse/Fix Buffer according to the manufacturer's instructions (BD Biosciences, San Jose, Calif.). FcγRIII/II was blocked by preincubating cells with rat anti-mouse CD16/CD32 mAb (1 μg per million cells; Biolegend, San Diego, Calif.) in PBS with 2% FBS and 2 mM EDTA. Cells were stained with APC-, PE-, Brilliant Violet 510-, and Brilliant Violet 711-conjugated mAbs against murine CD4 (clone GK1.5), CD8 (53-6.7), PD-L1 (10F.9G2), TIM3 (RMT3-23), LAG3 (C9B7W), and TIGIT (1G9) (Biolegend). Cell-associated fluorescence was measured using an LSRFortessa X-20 flow cytometer (BD Biosciences), and analysis was performed using FlowJo software (Tree Star, Ashland, Oreg.).

Statistical Analysis

Statistical significance was determined using GraphPad Prism software, using a paired, unpaired, or ratio Student's t test, as indicated. When the ratio t test was used, 0.1 was added to zero values to make them non-zero. P values less than 0.05 were considered significant.

IL-27 Promotes Expression of Inhibitory Receptors by T Cells In Vivo

Over 400 genes were changed by ≥1.0 fold in response to administration of IL-27, as shown in FIG. 8A. A subset of these genes is shown in Table 11. Among these genes were those that encode immune inhibitory receptors that play key roles in the immune response. As shown in FIG. 8B, Ly6a (encodes Sca-1), Lag3, Tigit and Il10 were upregulated on splenocytes in response to IL-27. There was also a trend toward IL-27-mediated upregulation of Ctla4 and Cd274 (encodes PD-L1) that was less than 1-fold induction (data not shown). To validate the expression data, flow cytometry was utilized to assess the protein expression of PD-L1, LAG-3, TIGIT and TIM-3 on T cells from these mice. Administration of IL-27 minicircles led to upregulation of PD-L1, LAG-3 and TIGIT in splenic (Spleen) and peripheral blood (PBMC) $CD4^+$ T cells. In $CD8^+$ T cells, IL-27 minicircles upregulated PD-L1, LAG-3, TIGIT, and TIM-3. As shown in FIG. 8C, administration of IL-27 minicircles led to upregulation of PD-L1, Lag-3, and Tigit in splenic and peripheral blood $CD4^+$ T cells. In $CD8^+$ T cells, IL-27 minicircles upregulated PD-L1, Lag-3, Tigit, and Tim-3. These data suggest that IL-27 can play a key role in driving immunoregulatory receptor expression in vivo.

To investigate the ability of SRF388 to block minicircle-derived human IL-27 in vivo, both target engagement by enzyme-linked immunosorbent assay (ELISA) and immunoregulatory receptor expression in splenocytes were studied. Five days after IL-27 transfection and treatment with SRF388 (50 mg/kg), plasma was collected from mice to analyze IL-27 heterodimer and EBI3 levels by Meso Scale Discovery (MSD). The IL-27 heterodimer assay utilizes a p28 capture antibody that cross blocks SRF388 and a human specific EBI3 detection antibody; therefore, if SRF388 is bound to IL-27 then its detection will be masked. The EBI3 assay utilizes both capture and detection antibodies specific for 2 distinct epitopes of human EBI3 and since the minicircle derived IL-27 is a tethered heterodimer this assay allows for detection of total IL 27 irrespective of SRF388 binding.

Briefly, Six-week-old female Balb/c mice were injected with empty vector (control) or human IL-27. Mice were treated with 1 mg of either SRF388 or anti-DNP IgG1 isotype control antibody 7 days before and on the day of minicircle transfection (Day −7 and 0). Whole blood was collected, and plasma was analyzed for IL-27 (FIG. 8D) by Meso Scale Discovery. FIG. 8D shows that SRF388 treatment completely inhibits IL-27 detection in plasma by MSD. Similar data were seen when a dose of 25 mg/kg of SRF388 was tested. These data suggest that SRF388 at a dose of 25 mg/kg or higher can completely saturate minicircle derived IL-27 in vivo. This complete target engagement was also confirmed in a pSTAT1 functional assay.

To assess the ability of SRF388 to block the activity of IL-27 in vivo, the expression of PD L1, Tim-3, Lag-3, and Tigit were analyzed in murine PBMCs and splenocytes by flow cytometry. SRF388 significantly blocked IL 27-induced PD-L1 and Lag 3 expression in CD4+ PBMCs and PD-L1, Tim-3, Lag-3, and Tigit expression in CD8+ PBMCs. SRF388 treatment also blocked IL 27 induced PD-L1, Lag-3, and Tigit expression in CD4+ splenocytes and PD-L1 and Lag 3 expression in CD8+ splenocytes. These data suggest that SRF388 can both engage and block the activity of human IL-27 in vivo.

These results demonstrate that ectopic expression of IL-27 in vivo leads to upregulation of multiple inhibitory receptors by T cells, and several other molecules with immunomodulatory activity in splenocytes. These data suggest that IL-27 antagonism (e.g., by treatment with an anti-IL-27 antibody) would decrease the expression of inhibitor receptors on T cells, thereby increasing immune responses.

TABLE 11

Genes Upregulated in Response to Administration of IL-27

| Gene Symbol | Fold Change | p value |
|---|---|---|
| GM4841 | 3.824228667 | 0.012331653 |
| LY6A | 3.568709 | 0.000991642 |
| IIGP1 | 3.294783 | 0.000455248 |
| TUBB1 | 3.145617 | 0.002782618 |
| MPO | 3.112051333 | 0.026667968 |
| CTSG | 2.954178333 | 0.018177934 |
| PPBP | 2.878417333 | 0.006623845 |
| ELANE | 2.845762333 | 0.024770656 |
| MT2 | 2.757525667 | 0.004548988 |
| MUC13 | 2.696042667 | 0.018195326 |
| F830016B08RIK | 2.603319667 | 0.011330985 |
| GM4951 | 2.583066667 | 0.01529863 |
| APOL11B | 2.565688667 | 0.006885943 |
| GZMB | 2.515642667 | 0.004012308 |
| PRTN3 | 2.450033 | 0.028785527 |
| CLCA3A1 | 2.345778333 | 0.018175529 |
| GM11505 | 2.331628667 | 0.023451392 |

TABLE 11-continued

Genes Upregulated in Response to Administration of IL-27

| Gene Symbol | Fold Change | p value |
|---|---|---|
| IL10 | 2.324278 | 0.008857442 |
| GBP11 | 2.307386 | 0.005204674 |
| PF4 | 2.270045 | 0.016210658 |
| IRG1 | 2.269440667 | 0.003861367 |
| CES2G | 2.252403333 | 0.033921335 |
| OASL2 | 2.243393 | 0.00470682 |
| LAG3 | 2.203067 | 0.002539095 |
| HIST1H2AG | 2.197938 | 0.03499933 |
| OAS1G | 2.184084667 | 0.007645573 |
| MFSD2B | 2.179382333 | 0.030664254 |
| RHAG | 2.146212667 | 0.072130267 |
| TIGIT | 2.145155 | 0.005421349 |
| SLC6A4 | 2.121439 | 0.009945773 |
| SHCBP1 | 2.092208667 | 0.038685767 |
| BC023105 | 2.079652 | 0.002582842 |
| PKLR | 2.045597333 | 0.053459171 |
| TFR2 | 2.037887333 | 0.033394313 |
| F13A1 | 2.010803333 | 0.010612157 |
| HIST1H2AB | 2.002687333 | 0.025241 |
| SERPINA3F | 1.991916 | 0.002220854 |
| ERMAP | 1.940590333 | 0.042680673 |
| MCPT8 | 1.930212667 | 0.018921256 |
| SLC26A1 | 1.926420667 | 0.025126602 |
| PRKAR2B | 1.924056667 | 0.016881189 |
| BIRC5 | 1.914826333 | 0.032959509 |
| FADS2 | 1.91223 | 0.013830993 |
| TOP2A | 1.88339 | 0.034852729 |
| NCAPG | 1.881082333 | 0.036612626 |
| A730089K16RIK | 1.870258667 | 0.061491704 |
| MNS1 | 1.860366 | 0.014834618 |
| GP9 | 1.859234333 | 0.002956835 |
| GFI1B | 1.852962 | 0.0291761 |
| NUF2 | 1.850953 | 0.032872517 |
| CHIL3 | 1.848470667 | 0.001494932 |
| KIF11 | 1.83252 | 0.040535377 |
| ALOX12 | 1.823174 | 0.006931665 |
| ADGRG7 | 1.822065 | 0.017542834 |
| KLF1 | 1.820262333 | 0.060689421 |
| E2F8 | 1.817455333 | 0.069143254 |
| ATP1B2 | 1.811274333 | 0.024016123 |
| KIF2C | 1.811223333 | 0.061246458 |
| FADS3 | 1.803859667 | 0.050197663 |
| MS4A6D | 1.801871667 | 0.01036878 |
| SLC25A21 | 1.801518667 | 0.048282826 |
| HIST1H1B | 1.800434 | 0.037242995 |
| CKAP2L | 1.783850333 | 0.061646634 |
| SAMD14 | 1.782388333 | 0.02384128 |
| CAR1 | 1.770098667 | 0.025511071 |
| DEPDC1A | 1.765839667 | 0.03875749 |
| CENPE | 1.765095667 | 0.039288425 |
| ASPM | 1.753558 | 0.054145246 |
| CCNB2 | 1.751291667 | 0.036336189 |
| RYK | 1.749673 | 0.035413093 |
| MMP14 | 1.747348667 | 0.010510984 |
| BUB1 | 1.738322667 | 0.02139336 |
| MYO1D | 1.734508 | 0.006655486 |
| PARVB | 1.733820333 | 0.010799396 |
| GM5593 | 1.728317 | 0.008578526 |
| CCNA2 | 1.724975667 | 0.026630845 |
| PRR11 | 1.724352667 | 0.04875805 |
| AQP1 | 1.719081667 | 0.064562051 |
| CASP3 | 1.709594333 | 0.009087444 |
| KIF15 | 1.708689667 | 0.026782535 |
| ASNS | 1.708074333 | 0.037928738 |
| CPOX | 1.706113 | 0.030298001 |
| MT1 | 1.699002667 | 0.010159345 |
| CDC6 | 1.694586667 | 0.049970924 |
| GBP2B | 1.694018 | 0.000929009 |
| GBP2 | 1.689558667 | 0.004961011 |
| HMMR | 1.687253333 | 0.063769534 |
| KIF20A | 1.686718333 | 0.020639142 |
| GSTM5 | 1.681807333 | 0.04316743 |
| REEP6 | 1.677204667 | 0.056071877 |
| GM12250 | 1.675485 | 0.003251181 |
| GBP10 | 1.673458 | 0.009333312 |
| ATP7B | 1.671614 | 0.029798535 |
| GM22973 | 1.663495667 | 0.004472758 |
| CASC5 | 1.659578 | 0.044333895 |
| ADD2 | 1.659553667 | 0.053938067 |
| CAMP | 1.659111667 | 0.066745225 |
| CLEC5A | 1.654882667 | 0.00665055 |

TABLE 12

SEQUENCE LISTING

| SEQ ID NO | Description | Sequence |
|---|---|---|
| | | SRF529-A |
| 51 | HCDR1 (IMGT) | GFTFSSYS |
| 52 | HCDR2 (IMGT) | ISSSSSYI |
| 53 | HCDR3 (IMGT) | ARDGGRTSYTATAHNWFDP |
| 54 | HCDR1 (NT) | FTFSSYSMN |
| 55 | HCDR2 (NT) | SISSSSSYIYYADSVKG |
| 56 | HCDR3 (NT) | ARDGGRTSYTATAHNWFDP |
| 57 | VH | EVQLVESGGGLVKPGGSLRLSCAASGFTFSSYSMNWVRQAPGKG LEWVSSISSSSSYIYYADSVKGRFTISRDNAKNSLYLQMNSLRA EDTAVYYCARDGGRTSYTATAHNWFDPWGQGTLVTVSS |
| 58 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGCTATAGCATGAACTGGGTCCGCCAGGCTCCAGGGAAGGGG CTGGAGTGGGTCTCATCCATTAGTAGTAGTAGTAGTTACATATA |

TABLE 12-continued

SEQUENCE LISTING

| SEQ ID NO | Description | Sequence |
|---|---|---|
| | | CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 59 | LCDR1 (IMGT) | QSVLFSSNNKNY |
| 60 | LCDR2 (IMGT) | WAS |
| 61 | LCDR3 (IMGT) | QQHASAPPT |
| 62 | LCDR1 (NT) | KSSQSVLFSSNNKNYLA |
| 63 | LCDR2 (NT) | WASTRES |
| 64 | LCDR3 (NT) | QQHASAPPT |
| 65 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 66 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 67 | Heavy Chain | EVQLVESGGGLVKPGGSLRLSCAASGFTFSSYSMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 68 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGCTATAGCATGAACTGGGTCCGCCAGGCTCCAGGGAAGGGG CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT |

TABLE 12-continued

SEQUENCE LISTING

| SEQ ID NO | Description | Sequence |
|---|---|---|
| | | GGCAGCAGGGCAACGTGTTTAGCTGCAGCGTGATGCATGAAGCG CTGCATAACCATTATACCCAGAAAAGCCTGAGCCTGAGCCCGGG CAAA |
| 69 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 70 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC |
| | | SRF529-B |
| 71 | Heavy Chain | EVQLVESGGGLVKPGGSLRLSCAASGFTFSSYSMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 72 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGCTATAGCATGAACTGGGTCCGCCAGGCTCCAGGGAAGGGG CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA |

TABLE 12-continued

SEQUENCE LISTING

| SEQ ID NO | Description | Sequence |
|---|---|---|
| | | TCAAGTGTCCCTGACTTGTCTGGTCAAGGGCTTCTACCCCTCCG<br>ATATCGCCGTGGAGTGGGAGTCCAACGGCCAGCCCGAGAACAAC<br>TACAAGACCACCCCTCCCGTGCTGGACTCCGACGGCTCCTTCTT<br>CCTGTACTCTCGGCTGACCGTGGACAAGTCCCGGTGGCAGGAAG<br>GCAACGTCTTCTCCTGCTCCGTGATGCACGAGGCCCTGCACAAC<br>CACTACACCCAGAAGTCCCTGTCCCTGTCTCTGGGC |

SRF381-A

| SEQ ID NO | Description | Sequence |
|---|---|---|
| 73 | HCDR1 (IMGT) | GFTFRSYG |
| 74 | HCDR2 (IMGT) | ISSSSSYI |
| 75 | HCDR3 (IMGT) | ARDGGRTSYTATAHNWFDP |
| 76 | HCDR1 (NT) | FTFRSYGMN |
| 77 | HCDR2 (NT) | SISSSSSYIYYADSVKG |
| 78 | HCDR3 (NT) | ARDGGRTSYTATAHNWFDP |
| 79 | VH | EVQLVESGGGLVKPGGSLRLSCAASGFTFRSYGMNWVRQAPGKG<br>LEWVSSISSSSSYIYYADSVKGRFTISRDNAKNSLYLQMNSLRA<br>EDTAVYYCARDGGRTSYTATAHNWFDPWGQGTLVTVSS |
| 80 | DNA VH | GAGGTGCAGCTGGTGGAGTCTGGGGGAGGCCTGGTCAAGCCTGG<br>GGGGTCCCTGAGACTCTCCTGTGCAGCCTCTGGATTCACCTTCC<br>GGAGCTATGGGATGAACTGGGTCCGCCAGGCTCCAGGGAAGGGG<br>CTGGAGTGGGTCTCATCCATTAGTAGTAGTAGTAGTTACATATA<br>CTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCA |
| 81 | LCDR1 (IMGT) | QSVLFSSNNKNY |
| 82 | LCDR2 (IMGT) | WAS |
| 83 | LCDR3 (IMGT) | QQHASAPPT |
| 84 | LCDR1 (NT) | KSSQSVLFSSNNKNYLA |
| 85 | LCDR2 (NT) | WASTRES |
| 86 | LCDR3 (NT) | QQHASAPPT |
| 87 | VL | DIVMTQSPDSLAVSLGERATINCKSSQSVLFSSNNKNYLAWYQQ<br>KPGQPPKLLIYWASTRESGVPDRFSGSGSGTDFTLTISSLQAED<br>VAVYYCQQHASAPPTFGGGTKVEIK |
| 88 | DNA VL | GACATCGTGATGACCCAGTCTCCAGACTCCCTGGCTGTGTCTCT<br>GGGCGAGAGGGCCACCATCAACTGCAAGTCCAGCCAGAGTGTTT<br>TATTCAGCTCCAACAATAAGAACTACTTAGCTTGGTACCAGCAG<br>AAACCAGGACAGCCTCCTAAGCTGCTCATTTACTGGGCATCTAC<br>CCGGGAATCCGGGGTCCCTGACCGATTCAGTGGCAGCGGGTCTG<br>GGACAGATTTCACTCTCACCATCAGCAGCCTGCAGGCTGAAGAT<br>GTGGCAGTTTATTACTGTCAGCAGCACGCCAGTGCCCCTCCTAC<br>TTTTGGCGGAGGGACCAAGGTTGAGATCAAA |
| 89 | Heavy Chain | EVQLVESGGGLVKPGGSLRLSCAASGFTFRSYGMNWVRQAPGKG<br>LEWVSSISSSSSYIYYADSVKGRFTISRDNAKNSLYLQMNSLRA<br>EDTAVYYCARDGGRTSYTATAHNWFDPWGQGTLVTVSSASTKGP<br>SVFPLAPSSKSTSGGTAALGCLVKDYFPEPVTVSWNSGALTSGV<br>HTFPAVLQSSGLYSLSSVVTVPSSSLGTQTYICNVNHKPSNTKV<br>DKKVEPKSCDKTHTCPPCPAPELLGGPSVFLFPPKPKDTLMISR<br>TPEVTCVVVDVSHEDPEVKFNWYVDGVEVHNAKTKPREEQYNST<br>YRVVSVLTVLHQDWLNGKEYKCKVSNKALPAPIEKTISKAKGQP<br>REPQVYTLPPSRDELTKNQVSLTCLVKGFYPSDIAVEWESNGQP |

TABLE 12-continued

SEQUENCE LISTING

| SEQ ID NO | Description | Sequence |
|---|---|---|
| | | ENNYKTTPPVLDSDGSFFLYSKLTVDKSRWQQGNVFSCSVMHEA<br>LHNHYTQKSLSLSPGK |
| 90 | DNA Heavy Chain | GAGGTGCAGCTGGTGGAGTCTGGGGGAGGCCTGGTCAAGCCTGG<br>GGGGTCCCTGAGACTCTCCTGTGCAGCCTCTGGATTCACCTTCC<br>GGAGCTATGGGATGAACTGGGTCCGCCAGGCTCCAGGGAAGGGG<br>CTGGAGTGGGTCTCATCCATTAGTAGTAGTAGTAGTTACATATA<br>CTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCAGCGAGCACCAAAGGCCCG<br>AGCGTGTTTCCGCTGGCGCCGAGCAGCAAAAGCACCAGCGGCGG<br>CACCGCGGCGCTGGGCTGCCTGGTGAAAGATTATTTTCCGGAAC<br>CGGTGACCGTGAGCTGGAACAGCGGCGCGCTGACCAGCGGCGTG<br>CATACCTTTCCGGCGGTGCTGCAGAGCAGCGGCCTGTATAGCCT<br>GAGCAGCGTGGTGACCGTGCCGAGCAGCAGCCTGGGCACCCAGA<br>CCTATATTTGCAACGTGAACCATAAACCGAGCAACACCAAAGTG<br>GATAAAAAAGTGGAACCGAAAAGCTGCGATAAAACCCATACCTG<br>CCCGCCGTGCCCGGCGCCGGAACTGCTGGGCGGCCCGAGCGTGT<br>TTCTGTTTCCGCCGAAACCGAAAGATACCCTGATGATTAGCCGC<br>ACCCCGGAAGTGACCTGCGTGGTGGTGGATGTGAGCCATGAAGA<br>TCCGGAAGTGAAATTTAACTGGTATGTGGATGGCGTGGAAGTGC<br>ATAACGCGAAAACCAAACCGCGCGAAGAACAGTATAACAGCACC<br>TATCGCGTGGTGAGCGTGCTGACCGTGCTGCATCAGGATTGGCT<br>GAACGGCAAAGAATATAAATGCAAAGTGAGCAACAAAGCGCTGC<br>CGGCGCCGATTGAAAAAACCATTAGCAAAGCGAAAGGCCAGCCG<br>CGCGAACCGCAGGTGTATACCCTGCCGCCGAGCCGCGATGAACT<br>GACCAAAAACCAGGTGAGCCTGACCTGCCTGGTGAAAGGCTTTT<br>ATCCGAGCGATATTGCGGTGGAATGGGAAAGCAACGGCCAGCCG<br>GAAAACAACTATAAAACCACCCCGCCGGTGCTGGATAGCGATGG<br>CAGCTTTTTTCTGTATAGCAAACTGACCGTGGATAAAAGCCGCT<br>GGCAGCAGGGCAACGTGTTTAGCTGCAGCGTGATGCATGAAGCG<br>CTGCATAACCATTATACCCAGAAAAGCCTGAGCCTGAGCCCGGG<br>CAAA |
| 91 | Light Chain | DIVMTQSPDSLAVSLGERATINCKSSQSVLFSSNNKNYLAWYQQ<br>KPGQPPKLLIYWASTRESGVPDRFSGSGSGTDFTLTISSLQAED<br>VAVYYCQQHASAPPTFGGGTKVEIKRTVAAPSVFIFPPSDEQLK<br>SGTASVVCLLNNFYPREAKVQWKVDNALQSGNSQESVTEQDSKD<br>STYSLSSTLTLSKADYEKHKVYACEVTHQGLSSPVTKSFNRGEC |
| 92 | DNA Light Chain | GACATCGTGATGACCCAGTCTCCAGACTCCCTGGCTGTGTCTCT<br>GGGCGAGAGGGCCACCATCAACTGCAAGTCCAGCCAGAGTGTTT<br>TATTCAGCTCCAACAATAAGAACTACTTAGCTTGGTACCAGCAG<br>AAACCAGGACAGCCTCCTAAGCTGCTCATTTACTGGGCATCTAC<br>CCGGGAATCCGGGGTCCCTGACCGATTCAGTGGCAGCGGGTCTG<br>GGACAGATTTCACTCTCACCATCAGCAGCCTGCAGGCTGAAGAT<br>GTGGCAGTTTATTACTGTCAGCAGCACGCCAGTGCCCCTCCTAC<br>TTTTGGCGGAGGGACCAAGGTTGAGATCAAACGTACGGTGGCCG<br>CTCCCTCCGTGTTCATCTTCCCACCCTCCGACGAGCAGCTGAAG<br>TCCGGCACCGCCTCCGTCGTGTGCCTGCTGAACAACTTCTACCC<br>TCGCGAGGCCAAAGTGCAGTGGAAAGTGGACAACGCCCTGCAGT<br>CCGGCAACTCCCAGGAATCCGTCACCGAGCAGGACTCCAAGGAC<br>AGCACCTACTCCCTGTCCTCCACCCTGACCCTGTCCAAGGCCGA<br>CTACGAGAAGCACAAAGTGTACGCCTGCGAAGTGACCCACCAGG<br>GCCTGTCCAGCCCCGTGACCAAGTCCTTCAACCGGGGCGAGTGC |
| | | SRF381-B |
| 93 | Heavy Chain | EVQLVESGGGLVKPGGSLRLSCAASGFTFRSYGMNWVRQAPGKG<br>LEWVSSISSSSSYIYYADSVKGRFTISRDNAKNSLYLQMNSLRA<br>EDTAVYYCARDGGRTSYTATAHNWFDPWGQGTLVTVSSASTKGP<br>SVFPLAPCSRSTSESTAALGCLVKDYFPEPVTVSWNSGALTSGV<br>HTFPAVLQSSGLYSLSSVVTVPSSSLGTKTYTCNVDHKPSNTKV<br>DKRVESKYGPPCPSCPAPEFLGGPSVFLFPPKPKDTLMISRTPE<br>VTCVVVDVSQEDPEVQFNWYVDGVEVHNAKTKPREEQFNSTYRV<br>VSVLTVLHQDWLNGKEYKCKVSNKGLPSSIEKTISKAKGQPREP<br>QVYTLPPSQEEMTKNQVSLTCLVKGFYPSDIAVEWESNGQPENN<br>YKTTPPVLDSDGSFFLYSRLTVDKSRWQEGNVFSCSVMHEALHN<br>HYTQKSLSLSLG |
| 94 | DNA Heavy Chain | GAGGTGCAGCTGGTGGAGTCTGGGGGAGGCCTGGTCAAGCCTGG<br>GGGGTCCCTGAGACTCTCCTGTGCAGCCTCTGGATTCACCTTCC<br>GGAGCTATGGGATGAACTGGGTCCGCCAGGCTCCAGGGAAGGGG |

TABLE 12-continued

| SEQ ID NO | Description | Sequence |
|---|---|---|
| | | SEQUENCE LISTING |
| | | CTGGAGTGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA TCAAGTGTCCCTGACTTGTCTGGTCAAGGGCTTCTACCCCTCCG ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC |
| | | SRF382-A |
| 95 | HCDR1 (IMGT) | GFTFSRTG |
| 96 | HCDR2 (IMGT) | ISSSSSYI |
| 97 | HCDR3 (IMGT) | ARDGGRTSYTATAHNWFDP |
| 98 | HCDR1 (NT) | FTFSRTGMN |
| 99 | HCDR2 (NT) | SISSSSSYIYYADSVKG |
| 100 | HCDR3 (NT) | ARDGGRTSYTATAHNWFDP |
| 101 | VH | EVQLVESGGGLVKPGGSLRLSCAASGFTFSRTGMNWVRQAPGKG LEWVSSISSSSSYIYYADSVKGRFTISRDNAKNSLYLQMNSLRA EDTAVYYCARDGGRTSYTATAHNWFDPWGQGTLVTVSS |
| 102 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGGACTGGGATGAACTGGGTCCGCCAGGCTCCAGGGAAGGGG CTGGAATGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 103 | LCDR1 (IMGT) | QSVLFSSNNKNY |
| 104 | LCDR2 (IMGT) | WAS |
| 105 | LCDR3 (IMGT) | QQHASAPPT |
| 106 | LCDR1 (NT) | KSSQSVLFSSNNKNYLA |
| 107 | LCDR2 (NT) | WASTRES |
| 108 | LCDR3 (NT) | QQHASAPPT |

TABLE 12-continued

SEQUENCE LISTING

| SEQ ID NO | Description | Sequence |
|---|---|---|
| 109 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 110 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 111 | Heavy Chain | EVQLVESGGGLVKPGGSLRLSCAASGFTFSRTGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 112 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGGACTGGGATGAACTGGGTCCGCCAGGCTCCAGGGAAGGGG CTGGAATGGGTCTCATCCATTAGTAGTAGTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 113 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 114 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT |

TABLE 12-continued

SEQUENCE LISTING

| SEQ ID NO | Description | Sequence |
|---|---|---|
| | | CCGGCAACTCCCAGGAATCCGTCACCGAGCAGGACTCCAAGGAC<br>AGCACCTACTCCCTGTCCTCCACCCTGACCCTGTCCAAGGCCGA<br>CTACGAGAAGCACAAAGTGTACGCCTGCGAAGTGACCCACCAGG<br>GCCTGTCCAGCCCCGTGACCAAGTCCTTCAACCGGGGCGAGTGC |
| | | SRF382-B |
| 115 | Heavy Chain | EVQLVESGGGLVKPGGSLRLSCAASGFTFSRTGMNWVRQAPGKG<br>LEWVSSISSSSSYIYYADSVKGRFTISRDNAKNSLYLQMNSLRA<br>EDTAVYYCARDGGRTSYTATAHNWFDPWGQGTLVTVSSASTKGP<br>SVFPLAPCSRSTSESTAALGCLVKDYFPEPVTVSWNSGALTSGV<br>HTFPAVLQSSGLYSLSSVVTVPSSSLGTKTYTCNVDHKPSNTKV<br>DKRVESKYGPPCPSCPAPEFLGGPSVFLFPPKPKDTLMISRTPE<br>VTCVVVDVSQEDPEVQFNWYVDGVEVHNAKTKPREEQFNSTYRV<br>VSVLTVLHQDWLNGKEYKCKVSNKGLPSSIEKTISKAKGQPREP<br>QVYTLPPSQEEMTKNQVSLTCLVKGFYPSDIAVEWESNGQPENN<br>YKTTPPVLDSDGSFFLYSRLTVDKSRWQEGNVFSCSVMHEALHN<br>HYTQKSLSLSLG |
| 116 | DNA Heavy Chain | GAGGTGCAGCTGGTGGAGTCTGGGGGAGGCCTGGTCAAGCCTGG<br>GGGGTCCCTGAGACTCTCCTGTGCAGCCTCTGGATTCACCTTCA<br>GTAGGACTGGGATGAACTGGGTCCGCCAGGCTCCAGGGAAGGGG<br>CTGGAATGGGTCTCATCCATTAGTAGTAGTAGTAGTTACATATA<br>CTACGCAGACTCAGTGAAGGGCCGATTCACCATCTCCAGAGACA<br>ACGCCAAGAACTCACTGTATCTGCAAATGAACAGCCTGAGAGCC<br>GAGGACACGGCGGTGTACTACTGCGCCAGAGATGGTGGAAGAAC<br>GTCCTACACCGCCACAGCCCACAATTGGTTCGACCCCTGGGGAC<br>AGGGTACATTGGTCACCGTCTCCTCAGCTTCCACCAAGGGCCCC<br>TCCGTGTTCCCTCTGGCCCCTTGCTCCCGGTCCACCTCCGAGTC<br>TACCGCCGCTCTGGGCTGCCTCGTGAAGGACTACTTCCCCGAGC<br>CCGTGACCGTGTCCTGGAACTCTGGCGCCCTGACCTCCGGCGTG<br>CACACCTTCCCTGCCGTGCTGCAGTCCTCCGGCCTGTACTCCCT<br>GTCCAGCGTCGTGACCGTGCCCTCCTCCAGCCTGGGCACCAAGA<br>CCTACACCTGTAACGTGGACCACAAGCCCTCCAACACCAAAGTG<br>GACAAGCGGGTGGAATCTAAGTACGGCCCTCCCTGCCCTTCCTG<br>CCCTGCCCCTGAGTTCCTGGGCGGACCTTCCGTGTTCCTGTTCC<br>CTCCAAAGCCCAAGGACACCCTGATGATCTCCCGGACCCCTGAA<br>GTGACCTGCGTGGTGGTGGACGTGTCCCAGGAAGATCCCGAAGT<br>CCAGTTCAATTGGTACGTGGACGGCGTGGAAGTGCACAACGCCA<br>AGACCAAGCCCAGAGAGGAACAGTTCAACTCCACCTACCGGGTG<br>GTGTCCGTGCTGACCGTGCTGCACCAGGACTGGCTGAACGGCAA<br>AGAGTACAAGTGCAAAGTGTCCAACAAGGGCCTGCCCTCCAGCA<br>TCGAAAAGACCATCTCCAAGGCCAAGGGCCAGCCCCGCGAGCCC<br>CAAGTGTACACCCTGCCTCCCAGCCAGGAAGAGATGACCAAGAA<br>TCAAGTGTCCCTGACTTGTCTGGTCAAGGGCTTCTACCCCTCCG<br>ATATCGCCGTGGAGTGGGAGTCCAACGGCCAGCCCGAGAACAAC<br>TACAAGACCACCCCTCCCGTGCTGGACTCCGACGGCTCCTTCTT<br>CCTGTACTCTCGGCTGACCGTGGACAAGTCCCGGTGGCAGGAAG<br>GCAACGTCTTCTCCTGCTCCGTGATGCACGAGGCCCTGCACAAC<br>CACTACACCCAGAAGTCCCTGTCCCTGTCTCTGGGC |
| | | SRF384-A |
| 117 | HCDR1 (IMGT) | GFTFSRYG |
| 118 | HCDR2 (IMGT) | ISSSSAYI |
| 119 | HCDR3 (IMGT) | ARDGGRTSYTATAHNWFDP |
| 120 | HCDR1 (NT) | FTFSRYGMN |
| 121 | HCDR2 (NT) | SISSSSAYILYADSVKG |
| 122 | HCDR3 (NT) | ARDGGRTSYTATAHNWFDP |
| 123 | VH | EVQLVESGGGLVKPGGSLRLSCAASGFTFSRYGMNWVRQAPGKG<br>LEWVSSISSSSAYILYADSVKGRFTISRDNAKNSLYLQMNSLRA<br>EDTAVYYCARDGGRTSYTATAHNWFDPWGQGTLVTVSS |
| 124 | DNA VH | GAGGTGCAGCTGGTGGAGTCTGGGGGAGGCCTGGTCAAGCCTGG<br>GGGGTCCCTGAGACTCTCCTGTGCAGCCTCTGGATTCACCTTCA<br>GTAGGTATGGGATGAACTGGGTCCGCCAGGCTCCAGGGAAGGGG |

TABLE 12-continued

| SEQ ID NO | Description | Sequence |
|---|---|---|
| | | SEQUENCE LISTING |
| | | CTGGAGTGGGTCTCATCCATTAGTAGTAGTAGTGCTTACATACT GTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 125 | LCDR1 (IMGT) | QSVLFSSNNKNY |
| 126 | LCDR2 (IMGT) | WAS |
| 127 | LCDR3 (IMGT) | QQHASAPPT |
| 128 | LCDR1 (NT) | KSSQSVLFSSNNKNYLA |
| 129 | LCDR2 (NT) | WASTRES |
| 130 | LCDR3 (NT) | QQHASAPPT |
| 131 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 132 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 133 | Heavy Chain | EVQLVESGGGLVKPGGSLRLSCAASGFTFSRYGMNWVRQAPGKG LEWVSSISSSSAYILYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 134 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGGTATGGGATGAACTGGGTCCGCCAGGCTCCAGGGAAGGGG CTGGAGTGGGTCTCATCCATTAGTAGTAGTAGTGCTTACATACT GTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG |

TABLE 12-continued

SEQUENCE LISTING

| SEQ ID NO | Description | Sequence |
|---|---|---|
| | | CAGCTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 135 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 136 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC |
| | | SRF384-B |
| 137 | Heavy Chain | EVQLVESGGGLVKPGGSLRLSCAASGFTFSRYGMNWVRQAPGKG LEWVSSISSSSAYILYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 138 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCA GTAGGTATGGGATGAACTGGGTCCGCCAGGCTCCAGGGAAGGGG CTGGAGTGGGTCTCATCCATTAGTAGTAGTAGTGCTTACATACT GTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA TCAAGTGTCCCTGACTTGTCTGGTCAAGGGCTTCTACCCCTCCG ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC |

TABLE 12-continued

SEQUENCE LISTING

| SEQ ID NO | Description | Sequence |
|---|---|---|
| | | SRF386-A |
| 139 | HCDR1 (IMGT) | GFTFASYG |
| 140 | HCDR2 (IMGT) | ISSSSSYI |
| 141 | HCDR3 (IMGT) | ARDGGRTSYTATAHNWFDP |
| 142 | HCDR1 (NT) | FTFASYGMN |
| 143 | HCDR2 (NT) | SISSSSSYIYYADSVKG |
| 144 | HCDR3 (NT) | ARDGGRTSYTATAHNWFDP |
| 145 | VH | EVQLVESGGGLVKPGGSLRLSCAASGFTFASYGMNWVRQAPGKG LEWVSSISSSSSYIYYADSVKGRFTISRDNAKNSLYLQMNSLRA EDTAVYYCARDGGRTSYTATAHNWFDPWGQGTLVTVSS |
| 146 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCG CTAGCTATGGGATGAACTGGGTCCGCCAGGCTCCAGGGAAGGGG CTGGAGTGGGTCTCATCCATTAGTAGTTCTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 147 | LCDR1 (IMGT) | QSVLFSSNNKNY |
| 148 | LCDR2 (IMGT) | WAS |
| 149 | LCDR3 (IMGT) | QQHASAPPT |
| 150 | LCDR1 (NT) | KSSQSVLFSSNNKNYLA |
| 151 | LCDR2 (NT) | WASTRES |
| 152 | LCDR3 (NT) | QQHASAPPT |
| 153 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 154 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 155 | Heavy Chain | EVQLVESGGGLVKPGGSLRLSCAASGFTFASYGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 156 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCG CTAGCTATGGGATGAACTGGGTCCGCCAGGCTCCAGGGAAGGGG CTGGAGTGGGTCTCATCCATTAGTAGTTCTAGTAGTTACATATA |

TABLE 12-continued

SEQUENCE LISTING

| SEQ ID NO | Description | Sequence |
|---|---|---|
| | | CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 157 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 158 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC |
| | | SRF386-B |
| 159 | Heavy Chain | EVQLVESGGGLVKPGGSLRLSCAASGFTFASYGMNWVRQAPGKG LEWVSSISSSSSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 160 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCG CTAGCTATGGGATGAACTGGGTCCGCCAGGCTCCAGGGAAGGGG CTGGAGTGGGTCTCATCCATTAGTAGTTCTAGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC |

TABLE 12-continued

| SEQ ID NO | Description | Sequence |
|---|---|---|
| | | SEQUENCE LISTING |
| | | TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA TCAAGTGTCCCTGACTTGTCTGGTCAAGGGCTTCTACCCCTCCG ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC |
| | | SRF388-A |
| 161 | HCDR1 (IMGT) | GFTFRSYG |
| 162 | HCDR2 (IMGT) | ISSSGSYI |
| 163 | HCDR3 (IMGT) | ARDGGRTSYTATAHNWFDP |
| 164 | HCDR1 (NT) | FTFRSYGMN |
| 165 | HCDR2 (NT) | GISSSGSYIYYADSVKG |
| 166 | HCDR3 (NT) | ARDGGRTSYTATAHNWFDP |
| 167 | VH | EVQLVESGGGLVKPGGSLRLSCAASGFTFRSYGMNWVRQAPGKG LEWVSGISSSGSYIYYADSVKGRFTISRDNAKNSLYLQMNSLRA EDTAVYYCARDGGRTSYTATAHNWFDPWGQGTLVTVSS |
| 168 | DNA VH | GAGGTGCAGCTGGTGGAGTCTGGGGGAGGCCTGGTCAAGCCTGG GGGGTCCCTGAGACTCTCCTGTGCAGCCTCTGGATTCACCTTCC GTAGCTATGGGATGAACTGGGTCCGCCAGGCTCCAGGGAAGGGG CTGGAGTGGGTCTCAGGTATTAGTAGTAGTGGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCA |
| 169 | LCDR1 (IMGT) | QSVLFSSNNKNY |
| 170 | LCDR2 (IMGT) | WAS |
| 171 | LCDR3 (IMGT) | QQHASAPPT |
| 172 | LCDR1 (NT) | KSSQSVLFSSNNKNYLA |
| 173 | LCDR2 (NT) | WASTRES |
| 174 | LCDR3 (NT) | QQHASAPPT |
| 175 | VL | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIK |
| 176 | DNA VL | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG |

TABLE 12-continued

| SEQ ID NO | Description | Sequence |
|---|---|---|
| | | AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAA |
| 177 | Heavy Chain | EVQLVESGGGLVKPGGSLRLSCAASGFTFRSYGMNWVRQAPGKG LEWVSGISSSGSYIYYADSVKGRFTISRDNAKNSLYLQMNSLRA EDTAVYYCARDGGRTSYTATAHNWFDPWGQGTLVTVSSASTKGP SVFPLAPSSKSTSGGTAALGCLVKDYFPEPVTVSWNSGALTSGV HTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 178 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCC GTAGCTATGGGATGAACTGGGTCCGCCAGGCTCCAGGGAAGGGG CTGGAGTGGGTCTCAGGTATTAGTAGTAGTGGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCGAGCACCAAAGGCCCG AGCGTGTTTCCGCTGGCGCCGAGCAGCAAAAGCACCAGCGGCGG CACCGCGGCGCTGGGCTGCCTGGTGAAAGATTATTTTCCGGAAC CGGTGACCGTGAGCTGGAACAGCGGCGCGCTGACCAGCGGCGTG CATACCTTTCCGGCGGTGCTGCAGAGCAGCGGCCTGTATAGCCT GAGCAGCGTGGTGACCGTGCCGAGCAGCAGCCTGGGCACCCAGA CCTATATTTGCAACGTGAACCATAAACCGAGCAACACCAAAGTG GATAAAAAAGTGGAACCGAAAAGCTGCGATAAAACCCATACCTG CCCGCCGTGCCCGGCGCCGGAACTGCTGGGCGGCCCGAGCGTGT TTCTGTTTCCGCCGAAACCGAAAGATACCCTGATGATTAGCCGC ACCCCGGAAGTGACCTGCGTGGTGGTGGATGTGAGCCATGAAGA TCCGGAAGTGAAATTTAACTGGTATGTGGATGGCGTGGAAGTGC ATAACGCGAAAACCAAACCGCGCGAAGAACAGTATAACAGCACC TATCGCGTGGTGAGCGTGCTGACCGTGCTGCATCAGGATTGGCT GAACGGCAAAGAATATAAATGCAAAGTGAGCAACAAAGCGCTGC CGGCGCCGATTGAAAAAACCATTAGCAAAGCGAAAGGCCAGCCG CGCGAACCGCAGGTGTATACCCTGCCGCCGAGCCGCGATGAACT GACCAAAAACCAGGTGAGCCTGACCTGCCTGGTGAAAGGCTTTT ATCCGAGCGATATTGCGGTGGAATGGGAAAGCAACGGCCAGCCG GAAAACAACTATAAAACCACCCCGCCGGTGCTGGATAGCGATGG CAGCTTTTTTCTGTATAGCAAACTGACCGTGGATAAAAGCCGCT GGCAGCAGGGCAACGTGTTTAGCTGCAGCGTGATGCATGAAGCG CTGCATAACCATTATACCCAGAAAAGCCTGAGCCTGAGCCCGGG CAAA |
| 179 | Light Chain | DIVMTQSPDSLAVSLGERATINCKSSQSVLFSSNNKNYLAWYQQ KPGQPPKLLIYWASTRESGVPDRFSGSGSGTDFTLTISSLQAED VAVYYCQQHASAPPTFGGGTKVEIKRTVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC |
| 180 | DNA Light Chain | GACATCGTGATGACCCAGTCTCCAGACTCCCTGGCTGTGTCTCT GGGCGAGAGGGCCACCATCAACTGCAAGTCCAGCCAGAGTGTTT TATTCAGCTCCAACAATAAGAACTACTTAGCTTGGTACCAGCAG AAACCAGGACAGCCTCCTAAGCTGCTCATTTACTGGGCATCTAC CCGGGAATCCGGGGTCCCTGACCGATTCAGTGGCAGCGGGTCTG GGACAGATTTCACTCTCACCATCAGCAGCCTGCAGGCTGAAGAT GTGGCAGTTTATTACTGTCAGCAGCACGCCAGTGCCCCTCCTAC TTTTGGCGGAGGGACCAAGGTTGAGATCAAACGTACGGTGGCCG CTCCCTCCGTGTTCATCTTCCCACCCTCCGACGAGCAGCTGAAG TCCGGCACCGCCTCCGTCGTGTGCCTGCTGAACAACTTCTACCC TCGCGAGGCCAAAGTGCAGTGGAAAGTGGACAACGCCCTGCAGT CCGGCAACTCCCAGGAATCCGTCACCGAGCAGGACTCCAAGGAC AGCACCTACTCCCTGTCCTCCACCCTGACCCTGTCCAAGGCCGA CTACGAGAAGCACAAAGTGTACGCCTGCGAAGTGACCCACCAGG GCCTGTCCAGCCCCGTGACCAAGTCCTTCAACCGGGGCGAGTGC |

TABLE 12-continued

| SEQ ID NO | Description | Sequence |
|---|---|---|
| | | SRF388-B |
| 181 | Heavy Chain | EVQLVESGGGLVKPGGSLRLSCAASGFTFRSYGMNWVRQAPGKG LEWVSGISSSGSYIYYADSVKGRFTISRDNAKNSLYLQMNSLRA EDTAVYYCARDGGRTSYTATAHNWFDPWGQGTLVTVSSASTKGP SVFPLAPCSRSTSESTAALGCLVKDYFPEPVTVSWNSGALTSGV HTFPAVLQSSGLYSLSSVVTVPSSSLGTKTYTCNVDHKPSNTKV DKRVESKYGPPCPSCPAPEFLGGPSVFLFPPKPKDTLMISRTPE VTCVVVDVSQEDPEVQFNWYVDGVEVHNAKTKPREEQFNSTYRV VSVLTVLHQDWLNGKEYKCKVSNKGLPSSIEKTISKAKGQPREP QVYTLPPSQEEMTKNQVSLTCLVKGFYPSDIAVEWESNGQPENN YKTTPPVLDSDGSFFLYSRLTVDKSRWQEGNVFSCSVMHEALHN HYTQKSLSLSLG |
| 182 | DNA Heavy Chain | GAGGTGCAGCTGGTGGAGTCTGGGGGAGGCCTGGTCAAGCCTGG GGGGTCCCTGAGACTCTCCTGTGCAGCCTCTGGATTCACCTTCC GTAGCTATGGGATGAACTGGGTCCGCCAGGCTCCAGGGAAGGGG CTGGAGTGGGTCTCAGGTATTAGTAGTAGTGGTAGTTACATATA CTACGCAGACTCAGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGGTGGAAGAAC GTCCTACACCGCCACAGCCCACAATTGGTTCGACCCCTGGGGAC AGGGTACATTGGTCACCGTCTCCTCAGCTTCCACCAAGGGCCCC TCCGTGTTCCCTCTGGCCCCTTGCTCCCGGTCCACCTCCGAGTC TACCGCCGCTCTGGGCTGCCTCGTGAAGGACTACTTCCCCGAGC CCGTGACCGTGTCCTGGAACTCTGGCGCCCTGACCTCCGGCGTG CACACCTTCCCTGCCGTGCTGCAGTCCTCCGGCCTGTACTCCCT GTCCAGCGTCGTGACCGTGCCCTCCTCCAGCCTGGGCACCAAGA CCTACACCTGTAACGTGGACCACAAGCCCTCCAACACCAAAGTG GACAAGCGGGTGGAATCTAAGTACGGCCCTCCCTGCCCTTCCTG CCCTGCCCCTGAGTTCCTGGGCGGACCTTCCGTGTTCCTGTTCC CTCCAAAGCCCAAGGACACCCTGATGATCTCCCGGACCCCTGAA GTGACCTGCGTGGTGGTGGACGTGTCCCAGGAAGATCCCGAAGT CCAGTTCAATTGGTACGTGGACGGCGTGGAAGTGCACAACGCCA AGACCAAGCCCAGAGAGGAACAGTTCAACTCCACCTACCGGGTG GTGTCCGTGCTGACCGTGCTGCACCAGGACTGGCTGAACGGCAA AGAGTACAAGTGCAAAGTGTCCAACAAGGGCCTGCCCTCCAGCA TCGAAAAGACCATCTCCAAGGCCAAGGGCCAGCCCCGCGAGCCC CAAGTGTACACCCTGCCTCCCAGCCAGGAAGAGATGACCAAGAA TCAAGTGTCCCTGACTTGTCTGGTCAAGGGCTTCTACCCCTCCG ATATCGCCGTGGAGTGGGAGTCCAACGGCCAGCCCGAGAACAAC TACAAGACCACCCCTCCCGTGCTGGACTCCGACGGCTCCTTCTT CCTGTACTCTCGGCTGACCGTGGACAAGTCCCGGTGGCAGGAAG GCAACGTCTTCTCCTGCTCCGTGATGCACGAGGCCCTGCACAAC CACTACACCCAGAAGTCCCTGTCCCTGTCTCTGGGC |
| | | SRF410-A |
| 185 | HCDR1 (IMGT) | GGTFSAYA |
| 186 | HCDR2 (IMGT) | IIPIFGTA |
| 187 | HCDR3 (IMGT) | ARSYYSSRWHYYYYMDV |
| 188 | HCDR1 (NT) | GTFSAYAIS |
| 189 | HCDR2 (NT) | GIIPIFGTANYAQKFQG |
| 190 | HCDR3 (NT) | ARSYYSSRWHYYYYMDV |
| 191 | VH | QVQLVQSGAEVKKPGSSVKVSCKASGGTFSAYAISWVRQAPGQG LEWMGGIIPIFGTANYAQKFQGRVTITADESTSTAYMELSSLRS EDTAVYYCARSYYSSRWHYYYYMDVWGKGTTVTVSS |
| 192 | DNA VH | CAGGTGCAGCTGGTGCAGTCTGGGGCTGAGGTGAAGAAGCCTGG GTCCTCGGTGAAGGTCTCCTGCAAGGCTTCTGGAGGCACCTTCA GCGCTTATGCGATCAGCTGGGTGCGACAGGCCCCTGGACAAGGG CTTGAGTGGATGGGAGGGATCATCCCTATCTTTGGTACAGCAAA CTACGCACAGAAGTTCCAGGGCAGAGTCACGATTACCGCGGACG |

TABLE 12-continued

SEQUENCE LISTING

| SEQ ID NO | Description | Sequence |
|---|---|---|
| | | AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCA |
| 193 | LCDR1 (IMGT) | QGISSW |
| 194 | LCDR2 (IMGT) | AAS |
| 195 | LCDR3 (IMGT) | QQADDLPLT |
| 196 | LCDR1 (NT) | RASQGISSWLA |
| 197 | LCDR2 (NT) | AASNLQS |
| 198 | LCDR3 (NT) | QQADDLPLT |
| 199 | VL | DIQMTQSPSSVSASVGDRVTITCRASQGISSWLAWYQQKPGKAP KLLIYAASNLQSGVPSRFSGSGSGTDFTLTISSLQPEDFATYYC QQADDLPLTFGGGTKVEIK |
| 200 | DNA VL | GACATCCAGATGACACAGTCTCCATCTTCCGTGTCTGCATCTGT AGGAGACAGAGTCACCATCACTTGTCGGGCGAGTCAGGGTATTA GCAGCTGGTTAGCCTGGTATCAGCAGAAACCAGGGAAAGCCCCT AAGCTCCTGATCTATGCTGCATCCAATTTGCAAAGTGGGGTCCC ATCAAGGTTCAGCGGCAGTGGATCTGGGACAGATTTCACTCTCA CCATCAGCAGCCTGCAGCCTGAAGATTTTGCAACTTATTACTGT CAGCAGGCAGACGACCTCCCTCTCACTTTTGGCGGAGGGACCAA GGTTGAGATCAAA |
| 201 | Heavy Chain | QVQLVQSGAEVKKPGSSVKVSCKASGGTFSAYAISWVRQAPGQG LEWMGGIIPIFGTANYAQKFQGRVTITADESTSTAYMELSSLRS EDTAVYYCARSYYSSRWHYYYYMDVWGKGTTVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| 202 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCA GCGCTTATGCGATCAGCTGGGTGCGACAGGCCCCTGGACAAGGG CTTGAGTGGATGGGAGGGATCATCCCTATCTTTGGTACAGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCAGCGAGCACCAAAGGCCCGAGCGTG TTTCCGCTGGCGCCGAGCAGCAAAAGCACCAGCGGCGGCACCGC GGCGCTGGGCTGCCTGGTGAAAGATTATTTTCCGGAACCGGTGA CCGTGAGCTGGAACAGCGGCGCGCTGACCAGCGGCGTGCATACC TTTCCGGCGGTGCTGCAGAGCAGCGGCCTGTATAGCCTGAGCAG CGTGGTGACCGTGCCGAGCAGCAGCCTGGGCACCCAGACCTATA TTTGCAACGTGAACCATAAACCGAGCAACACCAAAGTGGATAAA AAAGTGGAACCGAAAAGCTGCGATAAAACCCATACCTGCCCGCC GTGCCCGGCGCCGGAACTGCTGGGCGGCCCGAGCGTGTTTCTGT TTCCGCCGAAACCGAAAGATACCCTGATGATTAGCCGCACCCCG GAAGTGACCTGCGTGGTGGTGGATGTGAGCCATGAAGATCCGGA AGTGAAATTTAACTGGTATGTGGATGGCGTGGAAGTGCATAACG CGAAAACCAAACCGCGCGAAGAACAGTATAACAGCACCTATCGC GTGGTGAGCGTGCTGACCGTGCTGCATCAGGATTGGCTGAACGG CAAAGAATATAAATGCAAAGTGAGCAACAAAGCGCTGCCGGCGC CGATTGAAAAAACCATTAGCAAAGCGAAAGGCCAGCCGCGCGAA CCGCAGGTGTATACCCTGCCGCCGAGCCGCGATGAACTGACCAA AAACCAGGTGAGCCTGACCTGCCTGGTGAAAGGCTTTTATCCGA |

TABLE 12-continued

SEQUENCE LISTING

| SEQ ID NO | Description | Sequence |
|---|---|---|
| | | GCGATATTGCGGTGGAATGGGAAAGCAACGGCCAGCCGGAAAAC AACTATAAAACCACCCCGCCGGTGCTGGATAGCGATGGCAGCTT TTTTCTGTATAGCAAACTGACCGTGGATAAAAGCCGCTGGCAGC AGGGCAACGTGTTTAGCTGCAGCGTGATGCATGAAGCGCTGCAT AACCATTATACCCAGAAAAGCCTGAGCCTGAGCCCGGGCAAA |
| 203 | Light Chain | DIQMTQSPSSVSASVGDRVTITCRASQGISSWLAWYQQKPGKAP KLLIYAASNLQSGVPSRFSGSGSGTDFTLTISSLQPEDFATYYC QQADDLPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 204 | DNA Light Chain | GACATCCAGATGACACAGTCTCCATCTTCCGTGTCTGCATCTGT AGGAGACAGAGTCACCATCACTTGTCGGGCGAGTCAGGGTATTA GCAGCTGGTTAGCCTGGTATCAGCAGAAACCAGGGAAAGCCCCT AAGCTCCTGATCTATGCTGCATCCAATTTGCAAAGTGGGGTCCC ATCAAGGTTCAGCGGCAGTGGATCTGGGACAGATTTCACTCTCA CCATCAGCAGCCTGCAGCCTGAAGATTTTGCAACTTATTACTGT CAGCAGGCAGACGACCTCCCTCTCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF410-B |
| 205 | Heavy Chain | QVQLVQSGAEVKKPGSSVKVSCKASGGTFSAYAISWVRQAPGQG LEWMGGIIPIFGTANYAQKFQGRVTITADESTSTAYMELSSLRS EDTAVYYCARSYYSSRWHYYYYMDVWGKGTTVTVSSASTKGPSV FPLAPCSRSTSESTAALGCLVKDYFPEPVTVSWNSGALTSGVHT FPAVLQSSGLYSLSSVVTVPSSSLGTKTYTCNVDHKPSNTKVDK RVESKYGPPCPSCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQV YTLPPSQEEMTKNQVSLTCLVKGFYPSDIAVEWESNGQPENNYK TTPPVLDSDGSFFLYSRLTVDKSRWQEGNVFSCSVMHEALHNHY TQKSLSLSLG |
| 206 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCA GCGCTTATGCGATCAGCTGGGTGCGACAGGCCCCTGGACAAGGG CTTGAGTGGATGGGAGGGATCATCCCTATCTTTGGTACAGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCAGCTTCCACCAAGGGCCCCTCCGTG TTCCCTCTGGCCCCTTGCTCCCGGTCCACCTCCGAGTCTACCGC CGCTCTGGGCTGCCTCGTGAAGGACTACTTCCCCGAGCCCGTGA CCGTGTCCTGGAACTCTGGCGCCCTGACCTCCGGCGTGCACACC TTCCCTGCCGTGCTGCAGTCCTCCGGCCTGTACTCCCTGTCCAG CGTCGTGACCGTGCCCTCCTCCAGCCTGGGCACCAAGACCTACA CCTGTAACGTGGACCACAAGCCCTCCAACACCAAAGTGGACAAG CGGGTGGAATCTAAGTACGGCCCTCCCTGCCCTTCCTGCCCTGC CCCTGAGTTCCTGGGCGGACCTTCCGTGTTCCTGTTCCCTCCAA AGCCCAAGGACACCCTGATGATCTCCCGGACCCCTGAAGTGACC TGCGTGGTGGTGGACGTGTCCCAGGAAGATCCCGAAGTCCAGTT CAATTGGTACGTGGACGGCGTGGAAGTGCACAACGCCAAGACCA AGCCCAGAGAGGAACAGTTCAACTCCACCTACCGGGTGGTGTCC GTGCTGACCGTGCTGCACCAGGACTGGCTGAACGGCAAAGAGTA CAAGTGCAAAGTGTCCAACAAGGGCCTGCCCTCCAGCATCGAAA AGACCATCTCCAAGGCCAAGGGCCAGCCCCGCGAGCCCCAAGTG TACACCCTGCCTCCCAGCCAGGAAGAGATGACCAAGAATCAAGT GTCCCTGACTTGTCTGGTCAAGGGCTTCTACCCCTCCGATATCG CCGTGGAGTGGGAGTCCAACGGCCAGCCCGAGAACAACTACAAG ACCACCCCTCCCGTGCTGGACTCCGACGGCTCCTTCTTCCTGTA CTCTCGGCTGACCGTGGACAAGTCCCGGTGGCAGGAAGGCAACG TCTTCTCCTGCTCCGTGATGCACGAGGCCCTGCACAACCACTAC ACCCAGAAGTCCCTGTCCCTGTCTCTGGGC |

TABLE 12-continued

SEQUENCE LISTING

| SEQ ID NO | Description | Sequence |
|---|---|---|
| | | SRF411-A |
| 207 | HCDR1 (IMGT) | GGTFESYT |
| 208 | HCDR2 (IMGT) | IAPIFGTA |
| 209 | HCDR3 (IMGT) | ARSYYSSRWHYYYYMDV |
| 210 | HCDR1 (NT) | GTFESYTIS |
| 211 | HCDR2 (NT) | GIAPIFGTAHYAQKFQG |
| 212 | HCDR3 (NT) | ARSYYSSRWHYYYYMDV |
| 213 | VH | QVQLVQSGAEVKKPGSSVKVSCKASGGTFESYTISWVRQAPGQG LEWMGGIAPIFGTAHYAQKFQGRVTITADESTSTAYMELSSLRS EDTAVYYCARSYYSSRWHYYYYMDVWGKGTTVTVSS |
| 214 | DNA VH | CAGGTGCAGCTGGTGCAGTCTGGGGCTGAGGTGAAGAAGCCTGG GTCCTCGGTGAAGGTCTCCTGCAAGGCTTCTGGAGGCACCTTCG AGAGCTATACGATCAGCTGGGTGCGACAGGCCCCTGGACAAGGG CTTGAGTGGATGGGAGGGATCGCGCCTATCTTTGGTACAGCACA TTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCA |
| 215 | LCDR1 (IMGT) | QGISSW |
| 216 | LCDR2 (IMGT) | AAS |
| 217 | LCDR3 (IMGT) | QQADDLPLT |
| 218 | LCDR1 (NT) | RASQGISSWLA |
| 219 | LCDR2 (NT) | AASNLQS |
| 220 | LCDR3 (NT) | QQADDLPLT |
| 221 | VL | DIQMTQSPSSVSASVGDRVTITCRASQGISSWLAWYQQKPGKAP KLLIYAASNLQSGVPSRFSGSGSGTDFTLTISSLQPEDFATYYC QQADDLPLTFGGGTKVEIK |
| 222 | DNA VL | GACATCCAGATGACCCAGTCTCCATCTTCCGTGTCTGCATCTGT AGGAGACAGAGTCACCATCACTTGTCGGGCGAGTCAGGGTATTA GCAGCTGGTTAGCCTGGTATCAGCAGAAACCAGGGAAAGCCCCT AAGCTCCTGATCTATGCTGCATCCAATTTGCAAAGTGGGGTCCC ATCAAGGTTCAGCGGCAGTGGATCTGGGACAGATTTCACTCTCA CCATCAGCAGCCTGCAGCCTGAAGATTTTGCAACTTACTATTGT CAGCAGGCAGACGACCTCCCTCTCACTTTTGGCGGAGGGACCAA GGTTGAGATCAAA |
| 223 | Heavy Chain | QVQLVQSGAEVKKPGSSVKVSCKASGGTFESYTISWVRQAPGQG LEWMGGIAPIFGTAHYAQKFQGRVTITADESTSTAYMELSSLRS EDTAVYYCARSYYSSRWHYYYYMDVWGKGTTVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| 224 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCG AGAGCTATACGATCAGCTGGGTGCGACAGGCCCCTGGACAAGGG CTTGAGTGGATGGGAGGGATCGCGCCTATCTTTGGTACAGCACA |

TABLE 12-continued

| SEQUENCE LISTING | | |
|---|---|---|
| SEQ ID NO | Description | Sequence |
| | | TTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCAGCGAGCACCAAAGGCCCGAGCGTG TTTCCGCTGGCGCCGAGCAGCAAAAGCACCAGCGGCGGCACCGC GGCGCTGGGCTGCCTGGTGAAAGATTATTTTCCGGAACCGGTGA CCGTGAGCTGGAACAGCGGCGCGCTGACCAGCGGCGTGCATACC TTTCCGGCGGTGCTGCAGAGCAGCGGCCTGTATAGCCTGAGCAG CGTGGTGACCGTGCCGAGCAGCAGCCTGGGCACCCAGACCTATA TTTGCAACGTGAACCATAAACCGAGCAACACCAAAGTGGATAAA AAAGTGGAACCGAAAAGCTGCGATAAAACCCATACCTGCCCGCC GTGCCCGGCGCCGGAACTGCTGGGCGGCCCGAGCGTGTTTCTGT TTCCGCCGAAACCGAAAGATACCCTGATGATTAGCCGCACCCCG GAAGTGACCTGCGTGGTGGTGGATGTGAGCCATGAAGATCCGGA AGTGAAATTTAACTGGTATGTGGATGGCGTGGAAGTGCATAACG CGAAAACCAAACCGCGCGAAGAACAGTATAACAGCACCTATCGC GTGGTGAGCGTGCTGACCGTGCTGCATCAGGATTGGCTGAACGG CAAAGAATATAAATGCAAAGTGAGCAACAAAGCGCTGCCGGCGC CGATTGAAAAAACCATTAGCAAAGCGAAAGGCCAGCCGCGCGAA CCGCAGGTGTATACCCTGCCGCCGAGCCGCGATGAACTGACCAA AAACCAGGTGAGCCTGACCTGCCTGGTGAAAGGCTTTTATCCGA GCGATATTGCGGTGGAATGGGAAAGCAACGGCCAGCCGGAAAAC AACTATAAAACCACCCCGCCGGTGCTGGATAGCGATGGCAGCTT TTTTCTGTATAGCAAACTGACCGTGGATAAAAGCCGCTGGCAGC AGGGCAACGTGTTTAGCTGCAGCGTGATGCATGAAGCGCTGCAT AACCATTATACCCAGAAAAGCCTGAGCCTGAGCCCGGGCAAA |
| 225 | Light Chain | DIQMTQSPSSVSASVGDRVTITCRASQGISSWLAWYQQKPGKAP KLLIYAASNLQSGVPSRFSGSGSGTDFTLTISSLQPEDFATYYC QQADDLPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 226 | DNA Light Chain | GACATCCAGATGACCCAGTCTCCATCTTCCGTGTCTGCATCTGT AGGAGACAGAGTCACCATCACTTGTCGGGCGAGTCAGGGTATTA GCAGCTGGTTAGCCTGGTATCAGCAGAAACCAGGGAAAGCCCCT AAGCTCCTGATCTATGCTGCATCCAATTTGCAAAGTGGGGTCCC ATCAAGGTTCAGCGGCAGTGGATCTGGGACAGATTTCACTCTCA CCATCAGCAGCCTGCAGCCTGAAGATTTTGCAACTTACTATTGT CAGCAGGCAGACGACCTCCCTCTCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF411-B |
| 227 | Heavy Chain | QVQLVQSGAEVKKPGSSVKVSCKASGGTFESYTISWVRQAPGQG LEWMGGIAPIFGTAHYAQKFQGRVTITADESTSTAYMELSSLRS EDTAVYYCARSYYSSRWHYYYYMDVWGKGTTVTVSSASTKGPSV FPLAPCSRSTSESTAALGCLVKDYFPEPVTVSWNSGALTSGVHT FPAVLQSSGLYSLSSVVTVPSSSLGTKTYTCNVDHKPSNTKVDK RVESKYGPPCPSCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQV YTLPPSQEEMTKNQVSLTCLVKGFYPSDIAVEWESNGQPENNYK TTPPVLDSDGSFFLYSRLTVDKSRWQEGNVFSCSVMHEALHNHY TQKSLSLSLG |
| 228 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCG AGAGCTATACGATCAGCTGGGTGCGACAGGCCCCTGGACAAGGG CTTGAGTGGATGGGAGGGATCGCGCCTATCTTTGGTACAGCACA TTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCAGCTTCCACCAAGGGCCCCTCCGTG TTCCCTCTGGCCCCTTGCTCCCGGTCCACCTCCGAGTCTACCGC CGCTCTGGGCTGCCTCGTGAAGGACTACTTCCCCGAGCCCGTGA |

TABLE 12-continued

SEQUENCE LISTING

| SEQ ID NO | Description | Sequence |
|---|---|---|
| | | CCGTGTCCTGGAACTCTGGCGCCCTGACCTCCGGCGTGCACACC TTCCCTGCCGTGCTGCAGTCCTCCGGCCTGTACTCCCTGTCCAG CGTCGTGACCGTGCCCTCCTCCAGCCTGGGCACCAAGACCTACA CCTGTAACGTGGACCACAAGCCCTCCAACACCAAAGTGGACAAG CGGGTGGAATCTAAGTACGGCCCTCCCTGCCCTTCCTGCCCTGC CCCTGAGTTCCTGGGCGGACCTTCCGTGTTCCTGTTCCCTCCAA AGCCCAAGGACACCCTGATGATCTCCCGGACCCCTGAAGTGACC TGCGTGGTGGTGGACGTGTCCCAGGAAGATCCCGAAGTCCAGTT CAATTGGTACGTGGACGGCGTGGAAGTGCACAACGCCAAGACCA AGCCCAGAGAGGAACAGTTCAACTCCACCTACCGGGTGGTGTCC GTGCTGACCGTGCTGCACCAGGACTGGCTGAACGGCAAAGAGTA CAAGTGCAAAGTGTCCAACAAGGGCCTGCCCTCCAGCATCGAAA AGACCATCTCCAAGGCCAAGGGCCAGCCCCGCGAGCCCCAAGTG TACACCCTGCCTCCCAGCCAGGAAGAGATGACCAAGAATCAAGT GTCCCTGACTTGTCTGGTCAAGGGCTTCTACCCCTCCGATATCG CCGTGGAGTGGGAGTCCAACGGCCAGCCCGAGAACAACTACAAG ACCACCCCTCCCGTGCTGGACTCCGACGGCTCCTTCTTCCTGTA CTCTCGGCTGACCGTGGACAAGTCCCGGTGGCAGGAAGGCAACG TCTTCTCCTGCTCCGTGATGCACGAGGCCCTGCACAACCACTAC ACCCAGAAGTCCCTGTCCCTGTCTCTGGGC |
| | | SRF543-A |
| 229 | HCDR1 (IMGT) | GGSFSDYE |
| 230 | HCDR2 (IMGT) | IDWSGIT |
| 231 | HCDR3 (IMGT) | ARLPMYYYDSSVSTGSVDV |
| 232 | HCDR1 (NT) | GSFSDYEWS |
| 233 | HCDR2 (NT) | EIDWSGITNYNPSLKS |
| 234 | HCDR3 (NT) | ARLPMYYYDSSVSTGSVDV |
| 235 | VH | QVQLQQWGAGLLKPSETLSLTCAVYGGSFSDYEWSWIRQPPGKG LEWIGEIDWSGITNYNPSLKSRVTISVDTSKNQFSLKLSSVTAA DTAVYYCARLPMYYYDSSVSTGSVDVWGQGTMVTVSS |
| 236 | DNA VH | CAAGTACAATTACAACAGTGGGGAGCTGGTTTATTAAAGCCTTC AGAAACTTTAAGTTTGACCTGTGCTGTTTACGGTGGATCATTTT CTGATTATGAGTGGAGTTGGATTCGTCAACCACCAGGCAAAGGA TTGGAGTGGATCGGTGAGATAGACTGGTCAGGCATTACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGACTTCCTATGTACTACTA CGACAGCAGCGTCTCAACCGGAAGCGTAGACGTATGGGGTCAGG GTACAATGGTCACCGTCTCCTCA |
| 237 | LCDR1 (IMGT) | QSVSSY |
| 238 | LCDR2 (IMGT) | DSS |
| 239 | LCDR3 (IMGT) | QQDSDHPIT |
| 240 | LCDR1 (NT) | RASQSVSSYLA |
| 241 | LCDR2 (NT) | DSSNRAT |
| 242 | LCDR3 (NT) | QQDSDHPIT |
| 243 | VL | EIVLTQSPATLSLSPGERATLSCRASQSVSSYLAWYQQKPGQAP RLLIYDSSNRATGIPARFSGSGSGTDFTLTISSLEPEDFAVYYC QQDSDHPITFGGGTKVEIK |
| 244 | DNA VL | GAAATTGTGTTGACACAGTCTCCAGCCACCCTGTCTTTGTCTCC AGGGGAAAGAGCCACCCTCTCCTGCAGGGCCAGTCAGAGTGTTA GCAGCTACTTAGCCTGGTACCAACAGAAACCTGGCCAGGCTCCC AGGCTCCTCATCTATGATTCATCCAACAGGGCCACTGGCATCCC |

TABLE 12-continued

| SEQUENCE LISTING | | |
|---|---|---|
| SEQ ID NO | Description | Sequence |
| | | AGCCAGGTTCAGTGGCAGTGGGTCTGGGACAGACTTCACTCTCA CCATCAGCAGCCTAGAGCCTGAAGATTTTGCAGTTTATTACTGT CAGCAGGACAGTGACCACCCTATCACTTTTGGCGGAGGGACCAA GGTTGAGATCAAA |
| 245 | Heavy Chain | QVQLQQWGAGLLKPSETLSLTCAVYGGSFSDYEWSWIRQPPGKG LEWIGEIDWSGITNYNPSLKSRVTISVDTSKNQFSLKLSSVTAA DTAVYYCARLPMYYYDSSVSTGSVDVWGQGTMVTVSSASTKGPS VFPLAPSSKSTSGGTAALGCLVKDYFPEPVTVSWNSGALTSGVH TFPAVLQSSGLYSLSSVVTVPSSSLGTQTYICNVNHKPSNTKVD KKVEPKSCDKTHTCPPCPAPELLGGPSVFLFPPKPKDTLMISRT PEVTCVVVDVSHEDPEVKFNWYVDGVEVHNAKTKPREEQYNSTY RVVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 246 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTGATTATGAGTGGAGTTGGATTCGTCAACCACCAGGCAAAGGA TTGGAGTGGATCGGTGAGATAGACTGGTCAGGCATTACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGACTTCCTATGTACTACTA CGACAGCAGCGTCTCAACCGGAAGCGTAGACGTATGGGGTCAGG GTACAATGGTCACCGTCTCCTCAGCGAGCACCAAAGGCCCGAGC GTGTTTCCGCTGGCGCCGAGCAGCAAAAGCACCAGCGGCGGCAC CGCGGCGCTGGGCTGCCTGGTGAAAGATTATTTTCCGGAACCGG TGACCGTGAGCTGGAACAGCGGCGCGCTGACCAGCGGCGTGCAT ACCTTTCCGGCGGTGCTGCAGAGCAGCGGCCTGTATAGCCTGAG CAGCGTGGTGACCGTGCCGAGCAGCAGCCTGGGCACCCAGACCT ATATTTGCAACGTGAACCATAAACCGAGCAACACCAAAGTGGAT AAAAAAGTGGAACCGAAAAGCTGCGATAAAACCCATACCTGCCC GCCGTGCCCGGCGCCGGAACTGCTGGGCGGCCCGAGCGTGTTTC TGTTTCCGCCGAAACCGAAAGATACCCTGATGATTAGCCGCACC CCGGAAGTGACCTGCGTGGTGGTGGATGTGAGCCATGAAGATCC GGAAGTGAAATTTAACTGGTATGTGGATGGCGTGGAAGTGCATA ACGCGAAAACCAAACCGCGCGAAGAACAGTATAACAGCACCTAT CGCGTGGTGAGCGTGCTGACCGTGCTGCATCAGGATTGGCTGAA CGGCAAAGAATATAAATGCAAAGTGAGCAACAAAGCGCTGCCGG CGCCGATTGAAAAAACCATTAGCAAAGCGAAAGGCCAGCCGCGC GAACCGCAGGTGTATACCCTGCCGCCGAGCCGCGATGAACTGAC CAAAAACCAGGTGAGCCTGACCTGCCTGGTGAAAGGCTTTTATC CGAGCGATATTGCGGTGGAATGGGAAAGCAACGGCCAGCCGGAA AACAACTATAAAACCACCCCGCCGGTGCTGGATAGCGATGGCAG CTTTTTTCTGTATAGCAAACTGACCGTGGATAAAAGCCGCTGGC AGCAGGGCAACGTGTTTAGCTGCAGCGTGATGCATGAAGCGCTG CATAACCATTATACCCAGAAAAGCCTGAGCCTGAGCCCGGGCAA A |
| 247 | Light Chain | EIVLTQSPATLSLSPGERATLSCRASQSVSSYLAWYQQKPGQAP RLLIYDSSNRATGIPARFSGSGSGTDFTLTISSLEPEDFAVYYC QQDSDHPITFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 248 | DNA Light Chain | GAAATTGTGTTGACACAGTCTCCAGCCACCCTGTCTTTGTCTCC AGGGGAAAGAGCCACCCTCTCCTGCAGGGCCAGTCAGAGTGTTA GCAGCTACTTAGCCTGGTACCAACAGAAACCTGGCCAGGCTCCC AGGCTCCTCATCTATGATTCATCCAACAGGGCCACTGGCATCCC AGCCAGGTTCAGTGGCAGTGGGTCTGGGACAGACTTCACTCTCA CCATCAGCAGCCTAGAGCCTGAAGATTTTGCAGTTTATTACTGT CAGCAGGACAGTGACCACCCTATCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |

TABLE 12-continued

SEQUENCE LISTING

| SEQ ID NO | Description | Sequence |
|---|---|---|
| | | SRF543-B |
| 249 | Heavy Chain | QVQLQQWGAGLLKPSETLSLTCAVYGGSFSDYEWSWIRQPPGKG LEWIGEIDWSGITNYNPSLKSRVTISVDTSKNQFSLKLSSVTAA DTAVYYCARLPMYYYDSSVSTGSVDVWGQGTMVTVSSASTKGPS VFPLAPCSRSTSESTAALGCLVKDYFPEPVTVSWNSGALTSGVH TFPAVLQSSGLYSLSSVVTVPSSSLGTKTYTCNVDHKPSNTKVD KRVESKYGPPCPSCPAPEFLGGPSVFLFPPKPKDTLMISRTPEV TCVVVDVSQEDPEVQFNWYVDGVEVHNAKTKPREEQFNSTYRVV SVLTVLHQDWLNGKEYKCKVSNKGLPSSIEKTISKAKGQPREPQ VYTLPPSQEEMTKNQVSLTCLVKGFYPSDIAVEWESNGQPENNY KTTPPVLDSDGSFFLYSRLTVDKSRWQEGNVFSCSVMHEALHNH YTQKSLSLSLG |
| 250 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTGATTATGAGTGGAGTTGGATTCGTCAACCACCAGGCAAAGGA TTGGAGTGGATCGGTGAGATAGACTGGTCAGGCATTACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGACTTCCTATGTACTACTA CGACAGCAGCGTCTCAACCGGAAGCGTAGACGTATGGGGTCAGG GTACAATGGTCACCGTCTCCTCAGCTTCCACCAAGGGCCCCTCC GTGTTCCCTCTGGCCCCTTGCTCCCGGTCCACCTCCGAGTCTAC CGCCGCTCTGGGCTGCCTCGTGAAGGACTACTTCCCCGAGCCCG TGACCGTGTCCTGGAACTCTGGCGCCCTGACCTCCGGCGTGCAC ACCTTCCCTGCCGTGCTGCAGTCCTCCGGCCTGTACTCCCTGTC CAGCGTCGTGACCGTGCCCTCCTCCAGCCTGGGCACCAAGACCT ACACCTGTAACGTGGACCACAAGCCCTCCAACACCAAAGTGGAC AAGCGGGTGGAATCTAAGTACGGCCCTCCCTGCCCTTCCTGCCC TGCCCCTGAGTTCCTGGGCGGACCTTCCGTGTTCCTGTTCCCTC CAAAGCCCAAGGACACCCTGATGATCTCCCGGACCCCTGAAGTG ACCTGCGTGGTGGTGGACGTGTCCCAGGAAGATCCCGAAGTCCA GTTCAATTGGTACGTGGACGGCGTGGAAGTGCACAACGCCAAGA CCAAGCCCAGAGAGGAACAGTTCAACTCCACCTACCGGGTGGTG TCCGTGCTGACCGTGCTGCACCAGGACTGGCTGAACGGCAAAGA GTACAAGTGCAAAGTGTCCAACAAGGGCCTGCCCTCCAGCATCG AAAAGACCATCTCCAAGGCCAAGGGCCAGCCCCGCGAGCCCCAA GTGTACACCCTGCCTCCCAGCCAGGAAGAGATGACCAAGAATCA AGTGTCCCTGACTTGTCTGGTCAAGGGCTTCTACCCCTCCGATA TCGCCGTGGAGTGGGAGTCCAACGGCCAGCCCGAGAACAACTAC AAGACCACCCCTCCCGTGCTGGACTCCGACGGCTCCTTCTTCCT GTACTCTCGGCTGACCGTGGACAAGTCCCGGTGGCAGGAAGGCA ACGTCTTCTCCTGCTCCGTGATGCACGAGGCCCTGCACAACCAC TACACCCAGAAGTCCCTGTCCCTGTCTCTGGGC |
| | | SRF414-A |
| 251 | HCDR1 (IMGT) | GGSFSRYY |
| 252 | HCDR2 (IMGT) | IDYSGST |
| 253 | HCDR3 (IMGT) | ARDGVYYDSSDLGFDI |
| 254 | HCDR1 (NT) | GSFSRYYWS |
| 255 | HCDR2 (NT) | SIDYSGSTEYNPSLKS |
| 256 | HCDR3 (NT) | ARDGVYYDSSDLGFDI |
| 257 | VH | QVQLQQWGAGLLKPSETLSLTCAVYGGSFSRYYWSWIRQPPGKG LEWIGSIDYSGSTEYNPSLKSRVTISVDTSKNQFSLKLSSVTAA DTAVYYCARDGVYYDSSDLGFDIWGQGTMVTVSS |
| 258 | DNA VH | CAAGTACAATTACAACAGTGGGGAGCTGGTTTATTAAAGCCTTC AGAAACTTTAAGTTTGACCTGTGCTGTTTACGGTGGATCATTTT CTCGTTATTACTGGAGTTGGATTCGTCAACCACCAGGCAAAGGA TTGGAGTGGATCGGTAGTATAGACTATTCAGGCTCCACTGAGTA |

TABLE 12-continued

| SEQ ID NO | Description | Sequence |
|---|---|---|
| | | CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGAGATGGTGTGTACTACGA CAGCAGCGACTTGGGATTCGACATATGGGGTCAGGGTACAATGG TCACCGTCTCCTCA |
| 259 | LCDR1 (IMGT) | QDISNY |
| 260 | LCDR2 (IMGT) | DAS |
| 261 | LCDR3 (IMGT) | QQYDDLPIT |
| 262 | LCDR1 (NT) | QASQDISNYLN |
| 263 | LCDR2 (NT) | DASNLET |
| 264 | LCDR3 (NT) | QQYDDLPIT |
| 265 | VL | DIQMTQSPSSLSASVGDRVTITCQASQDISNYLNWYQQKPGKAP KLLIYDASNLETGVPSRFSGSGSGTDFTFTISSLQPEDIATYYC QQYDDLPITFGGGTKVEIK |
| 266 | DNA VL | GACATCCAGATGACCCAGTCTCCATCCTCCCTGTCTGCATCTGT AGGAGACAGAGTCACCATCACTTGCCAGGCGAGTCAGGACATTA GCAACTATTTAAATTGGTATCAGCAGAAACCAGGGAAAGCCCCT AAGCTCCTGATCTACGATGCATCCAATTTGGAAACAGGGGTCCC ATCAAGGTTCAGTGGAAGTGGATCTGGGACAGATTTTACTTTCA CCATCAGCAGCCTGCAGCCTGAAGATATTGCAACATATTACTGT CAGCAGTACGACGACCTCCCTATCACTTTTGGCGGAGGGACCAA GGTTGAGATCAAA |
| 267 | Heavy Chain | QVQLQQWGAGLLKPSETLSLTCAVYGGSFSRYYWSWIRQPPGKG LEWIGSIDYSGSTEYNPSLKSRVTISVDTSKNQFSLKLSSVTAA DTAVYYCARDGVYYDSSDLGFDIWGQGTMVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGK |
| 268 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTCGTTATTACTGGAGTTGGATTCGTCAACCACCAGGCAAAGGA TTGGAGTGGATCGGTAGTATAGACTATTCAGGCTCCACTGAGTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGAGATGGTGTGTACTACGA CAGCAGCGACTTGGGATTCGACATATGGGGTCAGGGTACAATGG TCACCGTCTCCTCAGCGAGCACCAAAGGCCCGAGCGTGTTTCCG CTGGCGCCGAGCAGCAAAAGCACCAGCGGCGGCACCGCGGCGCT GGGCTGCCTGGTGAAAGATTATTTTCCGGAACCGGTGACCGTGA GCTGGAACAGCGGCGCGCTGACCAGCGGCGTGCATACCTTTCCG GCGGTGCTGCAGAGCAGCGGCCTGTATAGCCTGAGCAGCGTGGT GACCGTGCCGAGCAGCAGCCTGGGCACCCAGACCTATATTTGCA ACGTGAACCATAAACCGAGCAACACCAAAGTGGATAAAAAAGTG GAACCGAAAAGCTGCGATAAAACCCATACCTGCCCGCCGTGCCC GGCGCCGGAACTGCTGGGCGGCCCGAGCGTGTTTCTGTTTCCGC CGAAACCGAAAGATACCCTGATGATTAGCCGCACCCCGGAAGTG ACCTGCGTGGTGGTGGATGTGAGCCATGAAGATCCGGAAGTGAA ATTTAACTGGTATGTGGATGGCGTGGAAGTGCATAACGCGAAAA CCAAACCGCGCGAAGAACAGTATAACAGCACCTATCGCGTGGTG AGCGTGCTGACCGTGCTGCATCAGGATTGGCTGAACGGCAAAGA ATATAAATGCAAAGTGAGCAACAAAGCGCTGCCGGCGCCGATTG AAAAAACCATTAGCAAAGCGAAAGGCCAGCCGCGCGAACCGCAG GTGTATACCCTGCCGCCGAGCCGCGATGAACTGACCAAAAACCA GGTGAGCCTGACCTGCCTGGTGAAAGGCTTTTATCCGAGCGATA TTGCGGTGGAATGGGAAAGCAACGGCCAGCCGGAAAACAACTAT AAAACCACCCCGCCGGTGCTGGATAGCGATGGCAGCTTTTTTCT GTATAGCAAACTGACCGTGGATAAAAGCCGCTGGCAGCAGGGCA |

TABLE 12-continued

| SEQ ID NO | Description | Sequence |
|---|---|---|
| SEQUENCE LISTING | | |
| | | ACGTGTTTAGCTGCAGCGTGATGCATGAAGCGCTGCATAACCAT TATACCCAGAAAAGCCTGAGCCTGAGCCCGGGCAAA |
| 269 | Light Chain | DIQMTQSPSSLSASVGDRVTITCQASQDISNYLNWYQQKPGKAP KLLIYDASNLETGVPSRFSGSGSGTDFTFTISSLQPEDIATYYC QQYDDLPITFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 270 | DNA Light Chain | GACATCCAGATGACCCAGTCTCCATCCTCCCTGTCTGCATCTGT AGGAGACAGAGTCACCATCACTTGCCAGGCGAGTCAGGACATTA GCAACTATTTAAATTGGTATCAGCAGAAACCAGGGAAAGCCCCT AAGCTCCTGATCTACGATGCATCCAATTTGGAAACAGGGGTCCC ATCAAGGTTCAGTGGAAGTGGATCTGGGACAGATTTTACTTTCA CCATCAGCAGCCTGCAGCCTGAAGATATTGCAACATATTACTGT CAGCAGTACGACGACCTCCCTATCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF414-B |
| 271 | Heavy Chain | QVQLQQWGAGLLKPSETLSLTCAVYGGSFSRYYWSWIRQPPGKG LEWIGSIDYSGSTEYNPSLKSRVTISVDTSKNQFSLKLSSVTAA DTAVYYCARDGVYYDSSDLGFDIWGQGTMVTVSSASTKGPSVFP LAPCSRSTSESTAALGCLVKDYFPEPVTVSWNSGALTSGVHTFP AVLQSSGLYSLSSVVTVPSSSLGTKTYTCNVDHKPSNTKVDKRV ESKYGPPCPSCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLG |
| 272 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTCGTTATTACTGGAGTTGGATTCGTCAACCACCAGGCAAAGGA TTGGAGTGGATCGGTAGTATAGACTATTCAGGCTCCACTGAGTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGAGATGGTGTGTACTACGA CAGCAGCGACTTGGGATTCGACATATGGGGTCAGGGTACAATGG TCACCGTCTCCTCAGCTTCCACCAAGGGCCCCTCCGTGTTCCCT CTGGCCCCTTGCTCCCGGTCCACCTCCGAGTCTACCGCCGCTCT GGGCTGCCTCGTGAAGGACTACTTCCCCGAGCCCGTGACCGTGT CCTGGAACTCTGGCGCCCTGACCTCCGGCGTGCACACCTTCCCT GCCGTGCTGCAGTCCTCCGGCCTGTACTCCCTGTCCAGCGTCGT GACCGTGCCCTCCTCCAGCCTGGGCACCAAGACCTACACCTGTA ACGTGGACCACAAGCCCTCCAACACCAAAGTGGACAAGCGGGTG GAATCTAAGTACGGCCCTCCCTGCCCTTCCTGCCCTGCCCCTGA GTTCCTGGGCGGACCTTCCGTGTTCCTGTTCCCTCCAAAGCCCA AGGACACCCTGATGATCTCCCGGACCCCTGAAGTGACCTGCGTG GTGGTGGACGTGTCCCAGGAAGATCCCGAAGTCCAGTTCAATTG GTACGTGGACGGCGTGGAAGTGCACAACGCCAAGACCAAGCCCA GAGAGGAACAGTTCAACTCCACCTACCGGGTGGTGTCCGTGCTG ACCGTGCTGCACCAGGACTGGCTGAACGGCAAAGAGTACAAGTG CAAAGTGTCCAACAAGGGCCTGCCCTCCAGCATCGAAAAGACCA TCTCCAAGGCCAAGGGCCAGCCCCGCGAGCCCCAAGTGTACACC CTGCCTCCCAGCCAGGAAGAGATGACCAAGAATCAAGTGTCCCT GACTTGTCTGGTCAAGGGCTTCTACCCCTCCGATATCGCCGTGG AGTGGGAGTCCAACGGCCAGCCCGAGAACAACTACAAGACCACC CCTCCCGTGCTGGACTCCGACGGCTCCTTCTTCCTGTACTCTCG GCTGACCGTGGACAAGTCCCGGTGGCAGGAAGGCAACGTCTTCT CCTGCTCCGTGATGCACGAGGCCCTGCACAACCACTACACCCAG AAGTCCCTGTCCCTGTCTCTGGGC |
| | | SRF557-A |
| 273 | HCDR1 (IMGT) | GGTFSSYA |

TABLE 12-continued

SEQUENCE LISTING

| SEQ ID NO | Description | Sequence |
|---|---|---|
| 274 | HCDR2 (IMGT) | IIPIFGTA |
| 275 | HCDR3 (IMGT) | ARLGGRGYADEGWYFDL |
| 276 | HCDR1 (NT) | GTFSSYAIS |
| 277 | HCDR2 (NT) | GIIPIFGTANYAQKFQG |
| 278 | HCDR3 (NT) | ARLGGRGYADEGWYFDL |
| 279 | VH | QVQLVQSGAEVKKPGSSVKVSCKASGGTFSSYAISWVRQAPGQG LEWMGGIIPIFGTANYAQKFQGRVTITADESTSTAYMELSSLRS EDTAVYYCARLGGRGYADEGWYFDLWGRGTLVTVSS |
| 280 | DNA VH | CAGGTGCAGCTGGTGCAGTCTGGGGCTGAGGTGAAGAAGCCTGG GTCCTCGGTGAAGGTCTCCTGCAAGGCTTCTGGAGGCACCTTCA GCAGCTATGCTATCAGCTGGGTGCGACAGGCCCCTGGACAAGGG CTTGAGTGGATGGGAGGGATCATCCCTATCTTTGGTACAGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATTGGGCGGACGGGG ATACGCCGACGAGGGCTGGTACTTCGACCTATGGGGGAGAGGTA CCTTGGTCACCGTCTCCTCA |
| 281 | LCDR1 (IMGT) | QSVSSSY |
| 282 | LCDR2 (IMGT) | GAS |
| 283 | LCDR3 (IMGT) | QQYYGSPIT |
| 284 | LCDR1 (NT) | RASQSVSSSYLA |
| 285 | LCDR2 (NT) | GASSRAT |
| 286 | LCDR3 (NT) | QQYYGSPIT |
| 287 | VL | EIVLTQSPGTLSLSPGERATLSCRASQSVSSSYLAWYQQKPGQA PRLLIYGASSRATGIPDRFSGSGSGTDFTLTISRLEPEDFAVYY CQQYYGSPITFGGGTKVEIK |
| 288 | DNA VL | GAAATTGTGTTGACGCAGTCTCCAGGCACCCTGTCTTTGTCTCC AGGGGAAAGAGCCACCCTCTCCTGCAGGGCCAGTCAGAGTGTTA GCAGCAGCTACTTAGCCTGGTACCAGCAGAAACCTGGCCAGGCT CCCAGGCTCCTCATCTATGGTGCATCCAGCAGGGCCACTGGCAT CCCAGACAGGTTCAGTGGCAGTGGGTCTGGGACAGACTTCACTC TCACCATCAGCAGACTGGAGCCTGAAGATTTTGCAGTGTATTAC TGTCAGCAGTACTACGGCAGTCCTATCACTTTTGGCGGAGGGAC CAAGGTTGAGATCAAA |
| 289 | Heavy Chain | QVQLVQSGAEVKKPGSSVKVSCKASGGTFSSYAISWVRQAPGQG LEWMGGIIPIFGTANYAQKFQGRVTITADESTSTAYMELSSLRS EDTAVYYCARLGGRGYADEGWYFDLWGRGTLVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| 290 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCA GCAGCTATGCTATCAGCTGGGTGCGACAGGCCCCTGGACAAGGG CTTGAGTGGATGGGAGGGATCATCCCTATCTTTGGTACAGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATTGGGCGGACGGGG ATACGCCGACGAGGGCTGGTACTTCGACCTATGGGGGAGAGGTA |

TABLE 12-continued

SEQUENCE LISTING

| SEQ ID NO | Description | Sequence |
|---|---|---|
| | | CCTTGGTCACCGTCTCCTCAGCGAGCACCAAAGGCCCGAGCGTG<br>TTTCCGCTGGCGCCGAGCAGCAAAAGCACCAGCGGCGGCACCGC<br>GGCGCTGGGCTGCCTGGTGAAAGATTATTTTCCGGAACCGGTGA<br>CCGTGAGCTGGAACAGCGGCGCGCTGACCAGCGGCGTGCATACC<br>TTTCCGGCGGTGCTGCAGAGCAGCGGCCTGTATAGCCTGAGCAG<br>CGTGGTGACCGTGCCGAGCAGCAGCCTGGGCACCCAGACCTATA<br>TTTGCAACGTGAACCATAAACCGAGCAACACCAAAGTGGATAAA<br>AAAGTGGAACCGAAAAGCTGCGATAAAACCCATACCTGCCCGCC<br>GTGCCCGGCGCCGGAACTGCTGGGCGGCCCGAGCGTGTTTCTGT<br>TTCCGCCGAAACCGAAAGATACCCTGATGATTAGCCGCACCCCG<br>GAAGTGACCTGCGTGGTGGTGGATGTGAGCCATGAAGATCCGGA<br>AGTGAAATTTAACTGGTATGTGGATGGCGTGGAAGTGCATAACG<br>CGAAAACCAAACCGCGCGAAGAACAGTATAACAGCACCTATCGC<br>GTGGTGAGCGTGCTGACCGTGCTGCATCAGGATTGGCTGAACGG<br>CAAAGAATATAAATGCAAAGTGAGCAACAAAGCGCTGCCGGCGC<br>CGATTGAAAAAACCATTAGCAAAGCGAAAGGCCAGCCGCGCGAA<br>CCGCAGGTGTATACCCTGCCGCCGAGCCGCGATGAACTGACCAA<br>AAACCAGGTGAGCCTGACCTGCCTGGTGAAAGGCTTTTATCCGA<br>GCGATATTGCGGTGGAATGGGAAAGCAACGGCCAGCCGGAAAAC<br>AACTATAAAACCACCCCGCCGGTGCTGGATAGCGATGGCAGCTT<br>TTTTCTGTATAGCAAACTGACCGTGGATAAAAGCCGCTGGCAGC<br>AGGGCAACGTGTTTAGCTGCAGCGTGATGCATGAAGCGCTGCAT<br>AACCATTATACCCAGAAAAGCCTGAGCCTGAGCCCGGGCAAA |
| 291 | Light Chain | EIVLTQSPGTLSLSPGERATLSCRASQSVSSSYLAWYQQKPGQA<br>PRLLIYGASSRATGIPDRFSGSGSGTDFTLTISRLEPEDFAVYY<br>CQQYYGSPITFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC |
| 292 | DNA Light Chain | GAAATTGTGTTGACGCAGTCTCCAGGCACCCTGTCTTTGTCTCC<br>AGGGGAAAGAGCCACCCTCTCCTGCAGGGCCAGTCAGAGTGTTA<br>GCAGCAGCTACTTAGCCTGGTACCAGCAGAAACCTGGCCAGGCT<br>CCCAGGCTCCTCATCTATGGTGCATCCAGCAGGGCCACTGGCAT<br>CCCAGACAGGTTCAGTGGCAGTGGGTCTGGGACAGACTTCACTC<br>TCACCATCAGCAGACTGGAGCCTGAAGATTTTGCAGTGTATTAC<br>TGTCAGCAGTACTACGGCAGTCCTATCACTTTTGGCGGAGGGAC<br>CAAGGTTGAGATCAAACGTACGGTGGCCGCTCCCTCCGTGTTCA<br>TCTTCCCACCCTCCGACGAGCAGCTGAAGTCCGGCACCGCCTCC<br>GTCGTGTGCCTGCTGAACAACTTCTACCCTCGCGAGGCCAAAGT<br>GCAGTGGAAAGTGGACAACGCCCTGCAGTCCGGCAACTCCCAGG<br>AATCCGTCACCGAGCAGGACTCCAAGGACAGCACCTACTCCCTG<br>TCCTCCACCCTGACCCTGTCCAAGGCCGACTACGAGAAGCACAA<br>AGTGTACGCCTGCGAAGTGACCCACCAGGGCCTGTCCAGCCCCG<br>TGACCAAGTCCTTCAACCGGGGCGAGTGC |
| | | SRF557-B |
| 293 | Heavy Chain | QVQLVQSGAEVKKPGSSVKVSCKASGGTFSSYAISWVRQAPGQG<br>LEWMGGIIPIFGTANYAQKFQGRVTITADESTSTAYMELSSLRS<br>EDTAVYYCARLGGRGYADEGWYFDLWGRGTLVTVSSASTKGPSV<br>FPLAPCSRSTSESTAALGCLVKDYFPEPVTVSWNSGALTSGVHT<br>FPAVLQSSGLYSLSSVVTVPSSSLGTKTYTCNVDHKPSNTKVDK<br>RVESKYGPPCPSCPAPEFLGGPSVFLFPPKPKDTLMISRTPEVT<br>CVVVDVSQEDPEVQFNWYVDGVEVHNAKTKPREEQFNSTYRVVS<br>VLTVLHQDWLNGKEYKCKVSNKGLPSSIEKTISKAKGQPREPQV<br>YTLPPSQEEMTKNQVSLTCLVKGFYPSDIAVEWESNGQPENNYK<br>TTPPVLDSDGSFFLYSRLTVDKSRWQEGNVFSCSVMHEALHNHY<br>TQKSLSLSLG |
| 294 | DNA Heavy Chain | CAGGTGCAGCTGGTGCAGTCTGGGGCTGAGGTGAAGAAGCCTGG<br>GTCCTCGGTGAAGGTCTCCTGCAAGGCTTCTGGAGGCACCTTCA<br>GCAGCTATGCTATCAGCTGGGTGCGACAGGCCCCTGGACAAGGG<br>CTTGAGTGGATGGGAGGGATCATCCCTATCTTTGGTACAGCAAA<br>CTACGCACAGAAGTTCCAGGGCAGAGTCACGATTACCGCGGACG<br>AATCCACGAGCACAGCCTACATGGAGCTGAGCAGCCTGAGATCT<br>GAGGACACGGCGGTGTACTACTGCGCCAGATTGGGCGGACGGGG<br>ATACGCCGACGAGGGCTGGTACTTCGACCTATGGGGGAGAGGTA<br>CCTTGGTCACCGTCTCCTCAGCTTCCACCAAGGGCCCCTCCGTG<br>TTCCCTCTGGCCCCTTGCTCCCGGTCCACCTCCGAGTCTACCGC<br>CGCTCTGGGCTGCCTCGTGAAGGACTACTTCCCCGAGCCCGTGA<br>CCGTGTCCTGGAACTCTGGCGCCCTGACCTCCGGCGTGCACACC<br>TTCCCTGCCGTGCTGCAGTCCTCCGGCCTGTACTCCCTGTCCAG<br>CGTCGTGACCGTGCCCTCCTCCAGCCTGGGCACCAAGACCTACA<br>CCTGTAACGTGGACCACAAGCCCTCCAACACCAAAGTGGACAAG |

TABLE 12-continued

SEQUENCE LISTING

| SEQ ID NO | Description | Sequence |
|---|---|---|
| | | CGGGTGGAATCTAAGTACGGCCCTCCCTGCCCTTCCTGCCCTGC CCCTGAGTTCCTGGGCGGACCTTCCGTGTTCCTGTTCCCTCCAA AGCCCAAGGACACCCTGATGATCTCCCGGACCCCTGAAGTGACC TGCGTGGTGGTGGACGTGTCCCAGGAAGATCCCGAAGTCCAGTT CAATTGGTACGTGGACGGCGTGGAAGTGCACAACGCCAAGACCA AGCCCAGAGAGGAACAGTTCAACTCCACCTACCGGGTGGTGTCC GTGCTGACCGTGCTGCACCAGGACTGGCTGAACGGCAAAGAGTA CAAGTGCAAAGTGTCCAACAAGGGCCTGCCCTCCAGCATCGAAA AGACCATCTCCAAGGCCAAGGGCCAGCCCCGCGAGCCCCAAGTG TACACCCTGCCTCCCAGCCAGGAAGAGATGACCAAGAATCAAGT GTCCCTGACTTGTCTGGTCAAGGGCTTCTACCCCTCCGATATCG CCGTGGAGTGGGAGTCCAACGGCCAGCCCGAGAACAACTACAAG ACCACCCCTCCCGTGCTGGACTCCGACGGCTCCTTCTTCCTGTA CTCTCGGCTGACCGTGGACAAGTCCCGGTGGCAGGAAGGCAACG TCTTCTCCTGCTCCGTGATGCACGAGGCCCTGCACAACCACTAC ACCCAGAAGTCCCTGTCCCTGTCTCTGGGC |
| | | SRF536-A |
| 295 | HCDR1 (IMGT) | GGSFSEYY |
| 296 | HCDR2 (IMGT) | IDEVGST |
| 297 | HCDR3 (IMGT) | ARLPMYYYDSSDLPMDV |
| 298 | HCDR1 (NT) | GSFSEYYWA |
| 299 | HCDR2 (NT) | EIDEVGSTNYNPSLKS |
| 300 | HCDR3 (NT) | ARLPMYYYDSSDLPMDV |
| 301 | VH | QVQLQQWGAGLLKPSETLSLTCAVYGGSFSEYYWAWIRQPPGKG LEWIGEIDEVGSTNYNPSLKSRVTISVDTSKNQFSLKLSSVTAA DTAVYYCARLPMYYYDSSDLPMDVWGQGTTVTVSS |
| 302 | DNA VH | CAAGTACAATTACAACAGTGGGGAGCTGGTTTATTAAAGCCTTC AGAAACTTTAAGTTTGACCTGTGCTGTTTACGGTGGATCATTTT CTGAGTATTACTGGGCTTGGATTCGTCAACCACCAGGCAAAGGA TTGGAGTGGATCGGTGAGATAGACGAGGTTGGCTCCACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGACTTCCTATGTACTACTA CGACAGCAGCGACTTGCCAATGGACGTATGGGGCCAGGGAACAA CTGTCACCGTCTCCTCA |
| 303 | LCDR1 (IMGT) | QDISNY |
| 304 | LCDR2 (IMGT) | DAS |
| 305 | LCDR3 (IMGT) | QQYDTLPLT |
| 306 | LCDR1 (NT) | QASQDISNYLN |
| 307 | LCDR2 (NT) | DASNLAT |
| 308 | LCDR3 (NT) | QQYDTLPLT |
| 309 | VL | DIQMTQSPSSLSASVGDRVTITCQASQDISNYLNWYQQKPGKAP KLLIYDASNLATGVPSRFSGSGSGTDFTFTISSLQPEDIATYYC QQYDTLPLTFGGGTKVEIK |
| 310 | DNA VL | GACATCCAGATGACCCAGTCTCCATCCTCCCTGTCTGCATCTGT AGGAGACAGAGTCACCATCACTTGCCAGGCGAGTCAGGACATTA GCAACTATTTAAATTGGTATCAGCAGAAACCAGGGAAAGCCCCT AAGCTCCTGATCTACGATGCATCCAATTTGGCAACAGGGGTCCC ATCAAGGTTCAGTGGAAGTGGATCTGGGACAGATTTTACTTTCA CCATCAGCAGCCTGCAGCCTGAAGATATTGCAACATATTACTGT CAGCAGTACGATACCCTCCCTCTCACTTTTGGCGGAGGGACCAA GGTTGAGATCAAA |

TABLE 12-continued

| SEQ ID NO | Description | Sequence |
|---|---|---|
| | | SEQUENCE LISTING |
| 311 | Heavy Chain | QVQLQQWGAGLLKPSETLSLTCAVYGGSFSEYYWAWIRQPPGKG LEWIGEIDEVGSTNYNPSLKSRVTISVDTSKNQFSLKLSSVTAA DTAVYYCARLPMYYYDSSDLPMDVWGQGTTVTVSSASTKGPSVF PLAPSSKSTSGGTAALGCLVKDYFPEPVTVSWNSGALTSGVHTF PAVLQSSGLYSLSSVVTVPSSSLGTQTYICNVNHKPSNTKVDKK VEPKSCDKTHTCPPCPAPELLGGPSVFLFPPKPKDTLMISRTPE VTCVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLTCLVKGFYPSDIAVEWESNGQPENN YKTTPPVLDSDGSFFLYSKLTVDKSRWQQGNVFSCSVMHEALHN HYTQKSLSLSPGK |
| 312 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTGAGTATTACTGGGCTTGGATTCGTCAACCACCAGGCAAAGGA TTGGAGTGGATCGGTGAGATAGACGAGGTTGGCTCCACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGACTTCCTATGTACTACTA CGACAGCAGCGACTTGCCAATGGACGTATGGGGCCAGGGAACAA CTGTCACCGTCTCCTCAGCGAGCACCAAAGGCCCGAGCGTGTTT CCGCTGGCGCCGAGCAGCAAAAGCACCAGCGGCGGCACCGCGGC GCTGGGCTGCCTGGTGAAAGATTATTTTCCGGAACCGGTGACCG TGAGCTGGAACAGCGGCGCGCTGACCAGCGGCGTGCATACCTTT CCGGCGGTGCTGCAGAGCAGCGGCCTGTATAGCCTGAGCAGCGT GGTGACCGTGCCGAGCAGCAGCCTGGGCACCCAGACCTATATTT GCAACGTGAACCATAAACCGAGCAACACCAAAGTGGATAAAAAA GTGGAACCGAAAAGCTGCGATAAAACCCATACCTGCCCGCCGTG CCCGGCGCCGGAACTGCTGGGCGGCCCGAGCGTGTTTCTGTTTC CGCCGAAACCGAAAGATACCCTGATGATTAGCCGCACCCCGGAA GTGACCTGCGTGGTGGTGGATGTGAGCCATGAAGATCCGGAAGT GAAATTTAACTGGTATGTGGATGGCGTGGAAGTGCATAACGCGA AAACCAAACCGCGCGAAGAACAGTATAACAGCACCTATCGCGTG GTGAGCGTGCTGACCGTGCTGCATCAGGATTGGCTGAACGGCAA AGAATATAAATGCAAAGTGAGCAACAAAGCGCTGCCGGCGCCGA TTGAAAAAACCATTAGCAAAGCGAAAGGCCAGCCGCGCGAACCG CAGGTGTATACCCTGCCGCCGAGCCGCGATGAACTGACCAAAAA CCAGGTGAGCCTGACCTGCCTGGTGAAAGGCTTTTATCCGAGCG ATATTGCGGTGGAATGGGAAAGCAACGGCCAGCCGGAAAACAAC TATAAAACCACCCCGCCGGTGCTGGATAGCGATGGCAGCTTTTT TCTGTATAGCAAACTGACCGTGGATAAAAGCCGCTGGCAGCAGG GCAACGTGTTTAGCTGCAGCGTGATGCATGAAGCGCTGCATAAC CATTATACCCAGAAAAGCCTGAGCCTGAGCCCGGGCAAA |
| 313 | Light Chain | DIQMTQSPSSLSASVGDRVTITCQASQDISNYLNWYQQKPGKAP KLLIYDASNLATGVPSRFSGSGSGTDFTFTISSLQPEDIATYYC QQYDTLPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 314 | DNA Light Chain | GACATCCAGATGACCCAGTCTCCATCCTCCCTGTCTGCATCTGT AGGAGACAGAGTCACCATCACTTGCCAGGCGAGTCAGGACATTA GCAACTATTTAAATTGGTATCAGCAGAAACCAGGGAAAGCCCCT AAGCTCCTGATCTACGATGCATCCAATTTGGCAACAGGGGTCCC ATCAAGGTTCAGTGGAAGTGGATCTGGGACAGATTTTACTTTCA CCATCAGCAGCCTGCAGCCTGAAGATATTGCAACATATTACTGT CAGCAGTACGATACCCTCCCTCTCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF536-B |
| 315 | Heavy Chain | QVQLQQWGAGLLKPSETLSLTCAVYGGSFSEYYWAWIRQPPGKG LEWIGEIDEVGSTNYNPSLKSRVTISVDTSKNQFSLKLSSVTAA DTAVYYCARLPMYYYDSSDLPMDVWGQGTTVTVSSASTKGPSVF PLAPCSRSTSESTAALGCLVKDYFPEPVTVSWNSGALTSGVHTF PAVLQSSGLYSLSSVVTVPSSSLGTKTYTCNVDHKPSNTKVDKR VESKYGPPCPSCPAPEFLGGPSVFLFPPKPKDTLMISRTPEVTC |

TABLE 12-continued

| SEQ ID NO | Description | Sequence |
|---|---|---|
| | | SEQUENCE LISTING |
| | | VVVDVSQEDPEVQFNWYVDGVEVHNAKTKPREEQFNSTYRVVSV LTVLHQDWLNGKEYKCKVSNKGLPSSIEKTISKAKGQPREPQVY TLPPSQEEMTKNQVSLTCLVKGFYPSDIAVEWESNGQPENNYKT TPPVLDSDGSFFLYSRLTVDKSRWQEGNVFSCSVMHEALHNHYT QKSLSLSLG |
| 316 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTGAGTATTACTGGGCTTGGATTCGTCAACCACCAGGCAAAGGA TTGGAGTGGATCGGTGAGATAGACGAGGTTGGCTCCACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGACTTCCTATGTACTACTA CGACAGCAGCGACTTGCCAATGGACGTATGGGGCCAGGGAACAA CTGTCACCGTCTCCTCAGCTTCCACCAAGGGCCCCTCCGTGTTC CCTCTGGCCCCTTGCTCCCGGTCCACCTCCGAGTCTACCGCCGC TCTGGGCTGCCTCGTGAAGGACTACTTCCCCGAGCCCGTGACCG TGTCCTGGAACTCTGGCGCCCTGACCTCCGGCGTGCACACCTTC CCTGCCGTGCTGCAGTCCTCCGGCCTGTACTCCCTGTCCAGCGT CGTGACCGTGCCCTCCTCCAGCCTGGGCACCAAGACCTACACCT GTAACGTGGACCACAAGCCCTCCAACACCAAAGTGGACAAGCGG GTGGAATCTAAGTACGGCCCTCCCTGCCCTTCCTGCCCTGCCCC TGAGTTCCTGGGCGGACCTTCCGTGTTCCTGTTCCCTCCAAAGC CCAAGGACACCCTGATGATCTCCCGGACCCCTGAAGTGACCTGC GTGGTGGTGGACGTGTCCCAGGAAGATCCCGAAGTCCAGTTCAA TTGGTACGTGGACGGCGTGGAAGTGCACAACGCCAAGACCAAGC CCAGAGAGGAACAGTTCAACTCCACCTACCGGGTGGTGTCCGTG CTGACCGTGCTGCACCAGGACTGGCTGAACGGCAAAGAGTACAA GTGCAAAGTGTCCAACAAGGGCCTGCCCTCCAGCATCGAAAAGA CCATCTCCAAGGCCAAGGGCCAGCCCCGCGAGCCCCAAGTGTAC ACCCTGCCTCCCAGCCAGGAAGAGATGACCAAGAATCAAGTGTC CCTGACTTGTCTGGTCAAGGGCTTCTACCCCTCCGATATCGCCG TGGAGTGGGAGTCCAACGGCCAGCCCGAGAACAACTACAAGACC ACCCCTCCCGTGCTGGACTCCGACGGCTCCTTCTTCCTGTACTC TCGGCTGACCGTGGACAAGTCCCGGTGGCAGGAAGGCAACGTCT TCTCCTGCTCCGTGATGCACGAGGCCCTGCACAACCACTACACC CAGAAGTCCCTGTCCCTGTCTCTGGGC |
| | | SRF416-A |
| 317 | HCDR1 (IMGT) | GGSFSGYY |
| 318 | HCDR2 (IMGT) | IDVDGST |
| 319 | HCDR3 (IMGT) | ARDGYYYDTSPYDV |
| 320 | HCDR1 (NT) | GSFSGYYWS |
| 321 | HCDR2 (NT) | EIDVDGSTNYNPSLKS |
| 322 | HCDR3 (NT) | ARDGYYYDTSPYDV |
| 323 | VH | QVQLQQWGAGLLKPSETLSLTCAVYGGSFSGYYWSWIRQPPGKG LEWIGEIDVDGSTNYNPSLKSRVTISVDTSKNQFSLKLSSVTAA DTAVYYCARDGYYYDTSPYDVWGQGTMVTVSS |
| 324 | DNA VH | CAAGTACAATTACAACAGTGGGGAGCTGGTTTATTAAAGCCTTC AGAAACTTTAAGTTTGACCTGTGCTGTTTACGGTGGATCATTTT CTGGTTATTACTGGAGTTGGATTCGTCAACCACCAGGCAAAGGA TTGGAGTGGATCGGTGAGATAGACGTGGATGGCTCCACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGAGACGGATACTACTACGA CACCAGTCCATACGACGTATGGGGTCAGGGTACAATGGTCACCG TCTCCTCA |
| 325 | LCDR1 (IMGT) | QSVSSY |
| 326 | LCDR2 (IMGT) | DAS |

TABLE 12-continued

| SEQUENCE LISTING | | |
|---|---|---|
| SEQ ID NO | Description | Sequence |
| 327 | LCDR3 (IMGT) | QQRDSFPLT |
| 328 | LCDR1 (NT) | RASQSVSSYLA |
| 329 | LCDR2 (NT) | DASNRAT |
| 330 | LCDR3 (NT) | QQRDSFPLT |
| 331 | VL | EIVLTQSPATLSLSPGERATLSCRASQSVSSYLAWYQQKPGQAP RLLIYDASNRATGIPARFSGSGSGTDFTLTISSLEPEDFAVYYC QQRDSFPLTFGGGTKVEIK |
| 332 | DNA VL | GAAATTGTGTTGACACAGTCTCCAGCCACCCTGTCTTTGTCTCC AGGGGAAAGAGCCACCCTCTCCTGCAGGGCCAGTCAGAGTGTTA GCAGCTACTTAGCCTGGTACCAACAGAAACCTGGCCAGGCTCCC AGGCTCCTCATCTATGATGCATCCAACAGGGCCACTGGCATCCC AGCCAGGTTCAGTGGCAGTGGGTCTGGGACAGACTTCACTCTCA CCATCAGCAGCCTAGAGCCTGAAGATTTTGCAGTTTATTACTGT CAGCAGAGAGACTCCTTCCCTCTCACTTTTGGCGGAGGGACCAA GGTTGAGATCAAA |
| 333 | Heavy Chain | QVQLQQWGAGLLKPSETLSLTCAVYGGSFSGYYWSWIRQPPGKG LEWIGEIDVDGSTNYNPSLKSRVTISVDTSKNQFSLKLSSVTAA DTAVYYCARDGYYYDTSPYDVWGQGTMVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTCPPCPAPELLGGPSVFLFPPKPKDTLMISRTPEVTC VVVDVSHEDPEVKFNWYVDGVEVHNAKTKPREEQYNSTYRVVSV LTVLHQDWLNGKEYKCKVSNKALPAPIEKTISKAKGQPREPQVY TLPPSRDELTKNQVSLTCLVKGFYPSDIAVEWESNGQPENNYKT TPPVLDSDGSFFLYSKLTVDKSRWQQGNVFSCSVMHEALHNHYT QKSLSLSPGK |
| 334 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTGGTTATTACTGGAGTTGGATTCGTCAACCACCAGGCAAAGGA TTGGAGTGGATCGGTGAGATAGACGTGGATGGCTCCACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGAGACGGATACTACTACGA CACCAGTCCATACGACGTATGGGGTCAGGGTACAATGGTCACCG TCTCCTCAGCGAGCACCAAAGGCCCGAGCGTGTTTCCGCTGGCG CCGAGCAGCAAAAGCACCAGCGGCGGCACCGCGGCGCTGGGCTG CCTGGTGAAAGATTATTTTCCGGAACCGGTGACCGTGAGCTGGA ACAGCGGCGCGCTGACCAGCGGCGTGCATACCTTTCCGGCGGTG CTGCAGAGCAGCGGCCTGTATAGCCTGAGCAGCGTGGTGACCGT GCCGAGCAGCAGCCTGGGCACCCAGACCTATATTTGCAACGTGA ACCATAAACCGAGCAACACCAAAGTGGATAAAAAAGTGGAACCG AAAAGCTGCGATAAAACCCATACCTGCCCGCCGTGCCCGGCGCC GGAACTGCTGGGCGGCCCGAGCGTGTTTCTGTTTCCGCCGAAAC CGAAAGATACCCTGATGATTAGCCGCACCCCGGAAGTGACCTGC GTGGTGGTGGATGTGAGCCATGAAGATCCGGAAGTGAAATTTAA CTGGTATGTGGATGGCGTGGAAGTGCATAACGCGAAAACCAAAC CGCGCGAAGAACAGTATAACAGCACCTATCGCGTGGTGAGCGTG CTGACCGTGCTGCATCAGGATTGGCTGAACGGCAAAGAATATAA ATGCAAAGTGAGCAACAAAGCGCTGCCGGCGCCGATTGAAAAAA CCATTAGCAAAGCGAAAGGCCAGCCGCGCGAACCGCAGGTGTAT ACCCTGCCGCCGAGCCGCGATGAACTGACCAAAAACCAGGTGAG CCTGACCTGCCTGGTGAAAGGCTTTTATCCGAGCGATATTGCGG TGGAATGGGAAAGCAACGGCCAGCCGGAAAACAACTATAAAACC ACCCCGCCGGTGCTGGATAGCGATGGCAGCTTTTTTCTGTATAG CAAACTGACCGTGGATAAAAGCCGCTGGCAGCAGGGCAACGTGT TTAGCTGCAGCGTGATGCATGAAGCGCTGCATAACCATTATACC CAGAAAAGCCTGAGCCTGAGCCCGGGCAAA |
| 335 | Light Chain | EIVLTQSPATLSLSPGERATLSCRASQSVSSYLAWYQQKPGQAP RLLIYDASNRATGIPARFSGSGSGTDFTLTISSLEPEDFAVYYC QQRDSFPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 336 | DNA Light Chain | GAAATTGTGTTGACACAGTCTCCAGCCACCCTGTCTTTGTCTCC AGGGGAAAGAGCCACCCTCTCCTGCAGGGCCAGTCAGAGTGTTA GCAGCTACTTAGCCTGGTACCAACAGAAACCTGGCCAGGCTCCC |

TABLE 12-continued

SEQUENCE LISTING

| SEQ ID NO | Description | Sequence |
|---|---|---|
| | | AGGCTCCTCATCTATGATGCATCCAACAGGGCCACTGGCATCCC AGCCAGGTTCAGTGGCAGTGGGTCTGGGACAGACTTCACTCTCA CCATCAGCAGCCTAGAGCCTGAAGATTTTGCAGTTTATTACTGT CAGCAGAGAGACTCCTTCCCTCTCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF416-B |
| 337 | Heavy Chain | QVQLQQWGAGLLKPSETLSLTCAVYGGSFSGYYWSWIRQPPGKG LEWIGEIDVDGSTNYNPSLKSRVTISVDTSKNQFSLKLSSVTAA DTAVYYCARDGYYYDTSPYDVWGQGTMVTVSSASTKGPSVFPLA PCSRSTSESTAALGCLVKDYFPEPVTVSWNSGALTSGVHTFPAV LQSSGLYSLSSVVTVPSSSLGTKTYTCNVDHKPSNTKVDKRVES KYGPPCPSCPAPEFLGGPSVFLFPPKPKDTLMISRTPEVTCVVV DVSQEDPEVQFNWYVDGVEVHNAKTKPREEQFNSTYRVVSVLTV LHQDWLNGKEYKCKVSNKGLPSSIEKTISKAKGQPREPQVYTLP PSQEEMTKNQVSLTCLVKGFYPSDIAVEWESNGQPENNYKTTPP VLDSDGSFFLYSRLTVDKSRWQEGNVFSCSVMHEALHNHYTQKS LSLSLG |
| 338 | DNA Heavy Chain | CAAGTACAATTACAACAGTGGGGAGCTGGTTTATTAAAGCCTTC AGAAACTTTAAGTTTGACCTGTGCTGTTTACGGTGGATCATTTT CTGGTTATTACTGGAGTTGGATTCGTCAACCACCAGGCAAAGGA TTGGAGTGGATCGGTGAGATAGACGTGGATGGCTCCACTAACTA CAATCCAAGTTTAAAATCCAGGGTTACTATCTCCGTAGACACGT CCAAGAACCAGTTCTCCCTGAAGCTGAGTTCTGTGACCGCCGCA GACACGGCGGTGTACTACTGCGCCAGAGACGGATACTACTACGA CACCAGTCCATACGACGTATGGGGTCAGGGTACAATGGTCACCG TCTCCTCAGCTTCCACCAAGGGCCCCTCCGTGTTCCCTCTGGCC CCTTGCTCCCGGTCCACCTCCGAGTCTACCGCCGCTCTGGGCTG CCTCGTGAAGGACTACTTCCCCGAGCCCGTGACCGTGTCCTGGA ACTCTGGCGCCCTGACCTCCGGCGTGCACACCTTCCCTGCCGTG CTGCAGTCCTCCGGCCTGTACTCCCTGTCCAGCGTCGTGACCGT GCCCTCCTCCAGCCTGGGCACCAAGACCTACACCTGTAACGTGG ACCACAAGCCCTCCAACACCAAAGTGGACAAGCGGGTGGAATCT AAGTACGGCCCTCCCTGCCCTTCCTGCCCTGCCCCTGAGTTCCT GGGCGGACCTTCCGTGTTCCTGTTCCCTCCAAAGCCCAAGGACA CCCTGATGATCTCCCGGACCCCTGAAGTGACCTGCGTGGTGGTG GACGTGTCCCAGGAAGATCCCGAAGTCCAGTTCAATTGGTACGT GGACGGCGTGGAAGTGCACAACGCCAAGACCAAGCCCAGAGAGG AACAGTTCAACTCCACCTACCGGGTGGTGTCCGTGCTGACCGTG CTGCACCAGGACTGGCTGAACGGCAAAGAGTACAAGTGCAAAGT GTCCAACAAGGGCCTGCCCTCCAGCATCGAAAAGACCATCTCCA AGGCCAAGGGCCAGCCCCGCGAGCCCCAAGTGTACACCCTGCCT CCCAGCCAGGAAGAGATGACCAAGAATCAAGTGTCCCTGACTTG TCTGGTCAAGGGCTTCTACCCCTCCGATATCGCCGTGGAGTGGG AGTCCAACGGCCAGCCCGAGAACAACTACAAGACCACCCCTCCC GTGCTGGACTCCGACGGCTCCTTCTTCCTGTACTCTCGGCTGAC CGTGGACAAGTCCCGGTGGCAGGAAGGCAACGTCTTCTCCTGCT CCGTGATGCACGAGGCCCTGCACAACCACTACACCCAGAAGTCC CTGTCCCTGTCTCTGGGC |
| | | SRF405-A |
| 339 | HCDR1 (IMGT) | GGTFVGYA |
| 340 | HCDR2 (IMGT) | IIPIFGIA |
| 341 | HCDR3 (IMGT) | ARSYYSSRWHYYYYMDV |
| 342 | HCDR1 (NT) | GTFVGYAIS |
| 343 | HCDR2 (NT) | GIIPIFGIANYAQKFQG |
| 344 | HCDR3 (NT) | ARSYYSSRWHYYYYMDV |

TABLE 12-continued

SEQUENCE LISTING

| SEQ ID NO | Description | Sequence |
|---|---|---|
| 345 | VH | QVQLVQSGAEVKKPGSSVKVSCKASGGTFVGYAISWVRQAPGQG LEWMGGIIPIFGIANYAQKFQGRVTITADESTSTAYMELSSLRS EDTAVYYCARSYYSSRWHYYYYMDVWGKGTTVTVSS |
| 346 | DNA VH | CAGGTGCAGCTGGTGCAGTCTGGGGCTGAGGTGAAGAAGCCTGG GTCCTCGGTGAAGGTCTCCTGCAAGGCTTCTGGAGGCACCTTCG TTGGGTATGCTATCAGCTGGGTGCGACAGGCCCCTGGACAAGGG CTTGAGTGGATGGGAGGGATCATCCCTATCTTTGGTATTGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCA |
| 347 | LCDR1 (IMGT) | QGISSW |
| 348 | LCDR2 (IMGT) | AAS |
| 349 | LCDR3 (IMGT) | QQADDLPLT |
| 350 | LCDR1 (NT) | RASQGISSWLA |
| 351 | LCDR2 (NT) | AASNLQS |
| 352 | LCDR3 (NT) | QQADDLPLT |
| 353 | VL | DIQMTQSPSSVSASVGDRVTITCRASQGISSWLAWYQQKPGKAP KLLIYAASNLQSGVPSRFSGSGSGTDFTLTISSLQPEDFATYYC QQADDLPLTFGGGTKVEIK |
| 354 | DNA VL | GACATCCAGATGACCCAGTCTCCATCTTCCGTGTCTGCATCTGT AGGAGACAGAGTCACCATCACTTGTCGGGCGAGTCAGGGTATTA GCAGCTGGTTAGCCTGGTATCAGCAGAAACCAGGGAAAGCCCCT AAGCTCCTGATCTATGCTGCATCCAATTTGCAAAGTGGGGTCCC ATCAAGGTTCAGCGGCAGTGGATCTGGGACAGATTTCACTCTCA CCATCAGCAGCCTGCAGCCTGAAGATTTTGCAACTTATTACTGT CAGCAGGCAGACGACCTCCCTCTCACTTTTGGCGGAGGGACCAA GGTTGAGATCAAA |
| 355 | Heavy Chain | QVQLVQSGAEVKKPGSSVKVSCKASGGTFVGYAISWVRQAPGQG LEWMGGIIPIFGIANYAQKFQGRVTITADESTSTAYMELSSLRS EDTAVYYCARSYYSSRWHYYYYMDVWGKGTTVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| 356 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCG TTGGGTATGCTATCAGCTGGGTGCGACAGGCCCCTGGACAAGGG CTTGAGTGGATGGGAGGGATCATCCCTATCTTTGGTATTGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCAGCGAGCACCAAAGGCCCGAGCGTG TTTCCGCTGGCGCCGAGCAGCAAAAGCACCAGCGGCGGCACCGC GGCGCTGGGCTGCCTGGTGAAAGATTATTTTCCGGAACCGGTGA CCGTGAGCTGGAACAGCGGCGCGCTGACCAGCGGCGTGCATACC TTTCCGGCGGTGCTGCAGAGCAGCGGCCTGTATAGCCTGAGCAG CGTGGTGACCGTGCCGAGCAGCAGCCTGGGCACCCAGACCTATA TTTGCAACGTGAACCATAAACCGAGCAACACCAAAGTGGATAAA AAAGTGGAACCGAAAAGCTGCGATAAAACCCATACCTGCCCGCC GTGCCCGGCGCCGGAACTGCTGGGCGGCCCGAGCGTGTTTCTGT TTCCGCCGAAACCGAAAGATACCCTGATGATTAGCCGCACCCCG GAAGTGACCTGCGTGGTGGTGGATGTGAGCCATGAAGATCCGGA AGTGAAATTTAACTGGTATGTGGATGGCGTGGAAGTGCATAACG |

TABLE 12-continued

| SEQ ID NO | Description | Sequence |
|---|---|---|
| | | SEQUENCE LISTING |
| | | CGAAAACCAAACCGCGCGAAGAACAGTATAACAGCACCTATCGC GTGGTGAGCGTGCTGACCGTGCTGCATCAGGATTGGCTGAACGG CAAAGAATATAAATGCAAAGTGAGCAACAAAGCGCTGCCGGCGC CGATTGAAAAAACCATTAGCAAAGCGAAAGGCCAGCCGCGCGAA CCGCAGGTGTATACCCTGCCGCCGAGCCGCGATGAACTGACCAA AAACCAGGTGAGCCTGACCTGCCTGGTGAAAGGCTTTTATCCGA GCGATATTGCGGTGGAATGGGAAAGCAACGGCCAGCCGGAAAAC AACTATAAAACCACCCCGCCGGTGCTGGATAGCGATGGCAGCTT TTTTCTGTATAGCAAACTGACCGTGGATAAAAGCCGCTGGCAGC AGGGCAACGTGTTTAGCTGCAGCGTGATGCATGAAGCGCTGCAT AACCATTATACCCAGAAAAGCCTGAGCCTGAGCCCGGGCAAA |
| 357 | Light Chain | DIQMTQSPSSVSASVGDRVTITCRASQGISSWLAWYQQKPGKAP KLLIYAASNLQSGVPSRFSGSGSGTDFTLTISSLQPEDFATYYC QQADDLPLTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 358 | DNA Light Chain | GACATCCAGATGACCCAGTCTCCATCTTCCGTGTCTGCATCTGT AGGAGACAGAGTCACCATCACTTGTCGGGCGAGTCAGGGTATTA GCAGCTGGTTAGCCTGGTATCAGCAGAAACCAGGGAAAGCCCCT AAGCTCCTGATCTATGCTGCATCCAATTTGCAAAGTGGGGTCCC ATCAAGGTTCAGCGGCAGTGGATCTGGGACAGATTTCACTCTCA CCATCAGCAGCCTGCAGCCTGAAGATTTTGCAACTTATTACTGT CAGCAGGCAGACGACCTCCCTCTCACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF405-B |
| 359 | Heavy Chain | QVQLVQSGAEVKKPGSSVKVSCKASGGTFVGYAISWVRQAPGQG LEWMGGIIPIFGIANYAQKFQGRVTITADESTSTAYMELSSLRS EDTAVYYCARSYYSSRWHYYYYMDVWGKGTTVTVSSASTKGPSV FPLAPCSRSTSESTAALGCLVKDYFPEPVTVSWNSGALTSGVHT FPAVLQSSGLYSLSSVVTVPSSSLGTKTYTCNVDHKPSNTKVDK RVESKYGPPCPSCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQV YTLPPSQEEMTKNQVSLTCLVKGFYPSDIAVEWESNGQPENNYK TTPPVLDSDGSFFLYSRLTVDKSRWQEGNVFSCSVMHEALHNHY TQKSLSLSLG |
| 360 | DNA Heavy Chain | CAGGTGCAGCTGGTGCAGTCTGGGGCTGAGGTGAAGAAGCCTGG GTCCTCGGTGAAGGTCTCCTGCAAGGCTTCTGGAGGCACCTTCG TTGGGTATGCTATCAGCTGGGTGCGACAGGCCCCTGGACAAGGG CTTGAGTGGATGGGAGGGATCATCCCTATCTTTGGTATTGCAAA CTACGCACAGAAGTTCCAGGGCAGAGTCACGATTACCGCGGACG AATCCACGAGCACAGCCTACATGGAGCTGAGCAGCCTGAGATCT GAGGACACGGCGGTGTACTACTGCGCCAGATCTTACTACTCCAG CCGATGGCACTACTACTACTACATGGACGTGTGGGGCAAGGGTA CAACTGTCACCGTCTCCTCAGCTTCCACCAAGGGCCCCTCCGTG TTCCCTCTGGCCCCTTGCTCCCGGTCCACCTCCGAGTCTACCGC CGCTCTGGGCTGCCTCGTGAAGGACTACTTCCCCGAGCCCGTGA CCGTGTCCTGGAACTCTGGCGCCCTGACCTCCGGCGTGCACACC TTCCCTGCCGTGCTGCAGTCCTCCGGCCTGTACTCCCTGTCCAG CGTCGTGACCGTGCCCTCCTCCAGCCTGGGCACCAAGACCTACA CCTGTAACGTGGACCACAAGCCCTCCAACACCAAAGTGGACAAG CGGGTGGAATCTAAGTACGGCCCTCCCTGCCCTTCCTGCCCTGC CCCTGAGTTCCTGGGCGGACCTTCCGTGTTCCTGTTCCCTCCAA AGCCCAAGGACACCCTGATGATCTCCCGGACCCCTGAAGTGACC TGCGTGGTGGTGGACGTGTCCCAGGAAGATCCCGAAGTCCAGTT CAATTGGTACGTGGACGGCGTGGAAGTGCACAACGCCAAGACCA AGCCCAGAGAGGAACAGTTCAACTCCACCTACCGGGTGGTGTCC GTGCTGACCGTGCTGCACCAGGACTGGCTGAACGGCAAAGAGTA CAAGTGCAAAGTGTCCAACAAGGGCCTGCCCTCCAGCATCGAAA AGACCATCTCCAAGGCCAAGGGCCAGCCCCGCGAGCCCCAAGTG TACACCCTGCCTCCCAGCCAGGAAGAGATGACCAAGAATCAAGT GTCCCTGACTTGTCTGGTCAAGGGCTTCTACCCCTCCGATATCG CCGTGGAGTGGGAGTCCAACGGCCAGCCCGAGAACAACTACAAG |

TABLE 12-continued

| SEQUENCE LISTING | | |
|---|---|---|
| SEQ ID NO | Description | Sequence |
| | | ACCACCCCTCCCGTGCTGGACTCCGACGGCTCCTTCTTCCTGTA CTCTCGGCTGACCGTGGACAAGTCCCGGTGGCAGGAAGGCAACG TCTTCTCCTGCTCCGTGATGCACGAGGCCCTGCACAACCACTAC ACCCAGAAGTCCCTGTCCCTGTCTCTGGGC |
| | | SRF535-A |
| 361 | HCDR1 (IMGT) | GFTFSSYG |
| 362 | HCDR2 (IMGT) | IKQDGSEK |
| 363 | HCDR3 (IMGT) | ARDAPWDIYDYYMDV |
| 364 | HCDR1 (NT) | FTFSSYGMS |
| 365 | HCDR2 (NT) | NIKQDGSEKYYVDSVKG |
| 366 | HCDR3 (NT) | ARDAPWDIYDYYMDV |
| 367 | VH | EVQLVESGGGLVQPGGSLRLSCAASGFTFSSYGMSWVRQAPGKG LEWVANIKQDGSEKYYVDSVKGRFTISRDNAKNSLYLQMNSLRA EDTAVYYCARDAPWDIYDYYMDVWGKGTTVTVSS |
| 368 | DNA VH | GAGGTGCAGCTGGTGGAGTCTGGGGGAGGCTTGGTCCAGCCTGG GGGGTCCCTGAGACTCTCCTGTGCAGCCTCTGGATTCACCTTTA GTAGCTATGGGATGAGCTGGGTCCGCCAGGCTCCAGGGAAGGGG CTGGAGTGGGTGGCCAACATAAAGCAAGATGGAAGTGAGAAATA CTATGTGGACTCTGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGCTCCTTGGGA CATCTACGACTACTACATGGACGTATGGGGCAAGGGTACAACTG TCACCGTCTCCTCA |
| 369 | LCDR1 (IMGT) | QSISSY |
| 370 | LCDR2 (IMGT) | AAS |
| 371 | LCDR3 (IMGT) | QQSYVPPWT |
| 372 | LCDR1 (NT) | RASQSISSYLN |
| 373 | LCDR2 (NT) | AASSLQS |
| 374 | LCDR3 (NT) | QQSYVPPWT |
| 375 | VL | DIQMTQSPSSLSASVGDRVTITCRASQSISSYLNWYQQKPGKAP KLLIYAASSLQSGVPSRFSGSGSGTDFTLTISSLQPEDFATYYC QQSYVPPWTFGGGTKVEIK |
| 376 | DNA VL | GACATCCAGATGACCCAGTCTCCATCCTCCCTGTCTGCATCTGT AGGAGACAGAGTCACCATCACTTGCCGGGCAAGTCAGAGCATTA GCAGCTATTTAAATTGGTATCAGCAGAAACCAGGGAAAGCCCCT AAGCTCCTGATCTATGCTGCATCCAGTTTGCAAAGTGGGGTCCC ATCAAGGTTCAGTGGCAGTGGATCTGGGACAGATTTCACTCTCA CCATCAGCAGTCTGCAACCTGAAGATTTTGCAACTTACTACTGT CAGCAAAGCTACGTCCCCCCTTGGACTTTTGGCGGAGGGACCAA GGTTGAGATCAAA |
| 377 | Heavy Chain | EVQLVESGGGLVQPGGSLRLSCAASGFTFSSYGMSWVRQAPGKG LEWVANIKQDGSEKYYVDSVKGRFTISRDNAKNSLYLQMNSLRA EDTAVYYCARDAPWDIYDYYMDVWGKGTTVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGK |

TABLE 12-continued

| SEQUENCE LISTING | | |
|---|---|---|
| SEQ ID NO | Description | Sequence |
| 378 | DNA Heavy Chain | GAGGTGCAGCTGGTGGAGTCTGGGGGAGGCTTGGTCCAGCCTGG GGGGTCCCTGAGACTCTCCTGTGCAGCCTCTGGATTCACCTTTA GTAGCTATGGGATGAGCTGGGTCCGCCAGGCTCCAGGGAAGGGG CTGGAGTGGGTGGCCAACATAAAGCAAGATGGAAGTGAGAAATA CTATGTGGACTCTGTGAAGGGCCGATTCACCATCTCCAGAGACA ACGCCAAGAACTCACTGTATCTGCAAATGAACAGCCTGAGAGCC GAGGACACGGCGGTGTACTACTGCGCCAGAGATGCTCCTTGGGA CATCTACGACTACTACATGGACGTATGGGGCAAGGGTACAACTG TCACCGTCTCCTCAGCGAGCACCAAAGGCCCGAGCGTGTTTCCG CTGGCGCCGAGCAGCAAAAGCACCAGCGGCGGCACCGCGGCGCT GGGCTGCCTGGTGAAAGATTATTTTCCGGAACCGGTGACCGTGA GCTGGAACAGCGGCGCGCTGACCAGCGGCGTGCATACCTTTCCG GCGGTGCTGCAGAGCAGCGGCCTGTATAGCCTGAGCAGCGTGGT GACCGTGCCGAGCAGCAGCCTGGGCACCCAGACCTATATTTGCA ACGTGAACCATAAACCGAGCAACACCAAAGTGGATAAAAAAGTG GAACCGAAAAGCTGCGATAAAACCCATACCTGCCCGCCGTGCCC GGCGCCGGAACTGCTGGGCGGCCCGAGCGTGTTTCTGTTTCCGC CGAAACCGAAAGATACCCTGATGATTAGCCGCACCCCGGAAGTG ACCTGCGTGGTGGTGGATGTGAGCCATGAAGATCCGGAAGTGAA ATTTAACTGGTATGTGGATGGCGTGGAAGTGCATAACGCGAAAA CCAAACCGCGCGAAGAACAGTATAACAGCACCTATCGCGTGGTG AGCGTGCTGACCGTGCTGCATCAGGATTGGCTGAACGGCAAAGA ATATAAATGCAAAGTGAGCAACAAAGCGCTGCCGGCGCCGATTG AAAAAACCATTAGCAAAGCGAAAGGCCAGCCGCGCGAACCGCAG GTGTATACCCTGCCGCCGAGCCGCGATGAACTGACCAAAAACCA GGTGAGCCTGACCTGCCTGGTGAAAGGCTTTTATCCGAGCGATA TTGCGGTGGAATGGGAAAGCAACGGCCAGCCGGAAAACAACTAT AAAACCACCCCGCCGGTGCTGGATAGCGATGGCAGCTTTTTTCT GTATAGCAAACTGACCGTGGATAAAAGCCGCTGGCAGCAGGGCA ACGTGTTTAGCTGCAGCGTGATGCATGAAGCGCTGCATAACCAT TATACCCAGAAAAGCCTGAGCCTGAGCCCGGGCAAA |
| 379 | Light Chain | DIQMTQSPSSLSASVGDRVTITCRASQSISSYLNWYQQKPGKAP KLLIYAASSLQSGVPSRFSGSGSGTDFTLTISSLQPEDFATYYC QQSYVPPWTFGGGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 380 | DNA Light Chain | GACATCCAGATGACCCAGTCTCCATCCTCCCTGTCTGCATCTGT AGGAGACAGAGTCACCATCACTTGCCGGGCAAGTCAGAGCATTA GCAGCTATTTAAATTGGTATCAGCAGAAACCAGGGAAAGCCCCT AAGCTCCTGATCTATGCTGCATCCAGTTTGCAAAGTGGGGTCCC ATCAAGGTTCAGTGGCAGTGGATCTGGGACAGATTTCACTCTCA CCATCAGCAGTCTGCAACCTGAAGATTTTGCAACTTACTACTGT CAGCAAAGCTACGTCCCCCCTTGGACTTTTGGCGGAGGGACCAA GGTTGAGATCAAACGTACGGTGGCCGCTCCCTCCGTGTTCATCT TCCCACCCTCCGACGAGCAGCTGAAGTCCGGCACCGCCTCCGTC GTGTGCCTGCTGAACAACTTCTACCCTCGCGAGGCCAAAGTGCA GTGGAAAGTGGACAACGCCCTGCAGTCCGGCAACTCCCAGGAAT CCGTCACCGAGCAGGACTCCAAGGACAGCACCTACTCCCTGTCC TCCACCCTGACCCTGTCCAAGGCCGACTACGAGAAGCACAAAGT GTACGCCTGCGAAGTGACCCACCAGGGCCTGTCCAGCCCCGTGA CCAAGTCCTTCAACCGGGGCGAGTGC |
| | | SRF535-B |
| 381 | Heavy Chain | EVQLVESGGGLVQPGGSLRLSCAASGFTFSSYGMSWVRQAPGKG LEWVANIKQDGSEKYYVDSVKGRFTISRDNAKNSLYLQMNSLRA EDTAVYYCARDAPWDIYDYYMDVWGKGTTVTVSSASTKGPSVFP LAPCSRSTSESTAALGCLVKDYFPEPVTVSWNSGALTSGVHTFP AVLQSSGLYSLSSVVTVPSSSLGTKTYTCNVDHKPSNTKVDKRV ESKYGPPCPSCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTT PPVLDSDGSFFLYSRLTVDKSRWQEGNVFSCSVMHEALHNHYTQ KSLSLSLG |
| 382 | DNA Heavy Chain | GAGGTGCAGCTGGTGGAGTCTGGGGGAGGCTTGGTCCAGCCTGG GGGGTCCCTGAGACTCTCCTGTGCAGCCTCTGGATTCACCTTTA GTAGCTATGGGATGAGCTGGGTCCGCCAGGCTCCAGGGAAGGGG CTGGAGTGGGTGGCCAACATAAAGCAAGATGGAAGTGAGAAATA CTATGTGGACTCTGTGAAGGGCCGATTCACCATCTCCAGAGACA ACGCCAAGAACTCACTGTATCTGCAAATGAACAGCCTGAGAGCC |

TABLE 12-continued

SEQUENCE LISTING

| SEQ ID NO | Description | Sequence |
|---|---|---|
| | | GAGGACACGGCGGTGTACTACTGCGCCAGAGATGCTCCTTGGGA CATCTACGACTACTACATGGACGTATGGGGCAAGGGTACAACTG TCACCGTCTCCTCAGCTTCCACCAAGGGCCCCTCCGTGTTCCCT CTGGCCCCTTGCTCCCGGTCCACCTCCGAGTCTACCGCCGCTCT GGGCTGCCTCGTGAAGGACTACTTCCCCGAGCCCGTGACCGTGT CCTGGAACTCTGGCGCCCTGACCTCCGGCGTGCACACCTTCCCT GCCGTGCTGCAGTCCTCCGGCCTGTACTCCCTGTCCAGCGTCGT GACCGTGCCCTCCTCCAGCCTGGGCACCAAGACCTACACCTGTA ACGTGGACCACAAGCCCTCCAACACCAAAGTGGACAAGCGGGTG GAATCTAAGTACGGCCCTCCCTGCCCTTCCTGCCCTGCCCCTGA GTTCCTGGGCGGACCTTCCGTGTTCCTGTTCCCTCCAAAGCCCA AGGACACCCTGATGATCTCCCGGACCCCTGAAGTGACCTGCGTG GTGGTGGACGTGTCCCAGGAAGATCCCGAAGTCCAGTTCAATTG GTACGTGGACGGCGTGGAAGTGCACAACGCCAAGACCAAGCCCA GAGAGGAACAGTTCAACTCCACCTACCGGGTGGTGTCCGTGCTG ACCGTGCTGCACCAGGACTGGCTGAACGGCAAAGAGTACAAGTG CAAAGTGTCCAACAAGGGCCTGCCCTCCAGCATCGAAAAGACCA TCTCCAAGGCCAAGGGCCAGCCCCGCGAGCCCCAAGTGTACACC CTGCCTCCCAGCCAGGAAGAGATGACCAAGAATCAAGTGTCCCT GACTTGTCTGGTCAAGGGCTTCTACCCCTCCGATATCGCCGTGG AGTGGGAGTCCAACGGCCAGCCCGAGAACAACTACAAGACCACC CCTCCCGTGCTGGACTCCGACGGCTCCTTCTTCCTGTACTCTCG GCTGACCGTGGACAAGTCCCGGTGGCAGGAAGGCAACGTCTTCT CCTGCTCCGTGATGCACGAGGCCCTGCACAACCACTACACCCAG AAGTCCCTGTCCCTGTCTCTGGGC |
| | | SRF538-A |
| 383 | HCDR1 (IMGT) | GFTFSSYG |
| 384 | HCDR2 (IMGT) | IWYDGSNK |
| 385 | HCDR3 (IMGT) | ARGAPEYVDV |
| 386 | HCDR1 (NT) | FTFSSYGMH |
| 387 | HCDR2 (NT) | VIWYDGSNKYYADSVKG |
| 388 | HCDR3 (NT) | ARGAPEYVDV |
| 389 | VH | QVQLVESGGGVVQPGRSLRLSCAASGFTFSSYGMHWVRQAPGKG LEWVAVIWYDGSNKYYADSVKGRFTISRDNSKNTLYLQMNSLRA EDTAVYYCARGAPEYVDVWGQGTMVTVSS |
| 390 | DNA VH | CAGGTGCAGCTGGTGGAGTCTGGGGGAGGCGTGGTCCAGCCTGG GAGGTCCCTGAGACTCTCCTGTGCAGCGTCTGGATTCACCTTCA GTAGCTATGGCATGCACTGGGTCCGCCAGGCTCCAGGCAAGGGG CTGGAGTGGGTGGCAGTTATATGGTATGATGGAAGTAATAAATA CTATGCAGACTCCGTGAAGGGCCGATTCACCATCTCCAGAGACA ATTCCAAGAACACGCTGTATCTGCAAATGAACAGCCTGAGAGCC GAGGACACGGCGGTGTACTACTGCGCCAGAGGGGCCCCTGAATA TGTAGACGTATGGGGTCAGGGTACAATGGTCACCGTCTCCTCA |
| 391 | LCDR1 (IMGT) | QSVSSY |
| 392 | LCDR2 (IMGT) | DSS |
| 393 | LCDR3 (IMGT) | QQYSLYPT |
| 394 | LCDR1 (NT) | RASQSVSSYLA |
| 395 | LCDR2 (NT) | DSSNRAT |
| 396 | LCDR3 (NT) | QQYSLYPT |
| 397 | VL | EIVLTQSPATLSLSPGERATLSCRASQSVSSYLAWYQQKPGQAP RLLIYDSSNRATGIPARFSGSGSGTDFTLTISSLEPEDFAVYYC QQYSLYPTFGGGTKVEIK |

TABLE 12-continued

SEQUENCE LISTING

| SEQ ID NO | Description | Sequence |
|---|---|---|
| 398 | DNA VL | GAAATTGTGTTGACACAGTCTCCAGCCACCCTGTCTTTGTCTCC AGGGGAAAGAGCCACCCTCTCCTGCAGGGCCAGTCAGAGTGTTA GCAGCTACTTAGCCTGGTACCAACAGAAACCTGGCCAGGCTCCC AGGCTCCTCATCTATGATTCATCCAACAGGGCCACTGGCATCCC AGCCAGGTTCAGTGGCAGTGGGTCTGGGACAGACTTCACTCTCA CCATCAGCAGCCTAGAGCCTGAAGATTTTGCAGTTTATTACTGT CAGCAGTACAGTCTCTACCCTACTTTTGGCGGAGGGACCAAGGT TGAGATCAAA |
| 399 | Heavy Chain | QVQLVESGGGVVQPGRSLRLSCAASGFTFSSYGMHWVRQAPGKG LEWVAVIWYDGSNKYYADSVKGRFTISRDNSKNTLYLQMNSLRA EDTAVYYCARGAPEYVDVWGQGTMVTVSSASTKGPSVFPLAPSS KSTSGGTAALGCLVKDYFPEPVTVSWNSGALTSGVHTFPAVLQS SGLYSLSSVVTVPSSSLGTQTYICNVNHKPSNTKVDKKVEPKSC DKTHTCPPCPAPELLGGPSVFLFPPKPKDTLMISRTPEVTCVVV DVSHEDPEVKFNWYVDGVEVHNAKTKPREEQYNSTYRVVSVLTV LHQDWLNGKEYKCKVSNKALPAPIEKTISKAKGQPREPQVYTLP PSRDELTKNQVSLTCLVKGFYPSDIAVEWESNGQPENNYKTTPP VLDSDGSFFLYSKLTVDKSRWQQGNVFSCSVMHEALHNHYTQKS LSLSPGK |
| 400 | DNA Heavy Chain | CAGGTGCAGCTGGTGGAGTCTGGGGGAGGCGTGGTCCAGCCTGG GAGGTCCCTGAGACTCTCCTGTGCAGCGTCTGGATTCACCTTCA GTAGCTATGGCATGCACTGGGTCCGCCAGGCTCCAGGCAAGGGG CTGGAGTGGGTGGCAGTTATATGGTATGATGGAAGTAATAAATA CTATGCAGACTCCGTGAAGGGCCGATTCACCATCTCCAGAGACA ATTCCAAGAACACGCTGTATCTGCAAATGAACAGCCTGAGAGCC GAGGACACGGCGGTGTACTACTGCGCCAGAGGGGCCCCTGAATA TGTAGACGTATGGGGTCAGGGTACAATGGTCACCGTCTCCTCAG CGAGCACCAAAGGCCCGAGCGTGTTTCCGCTGGCGCCGAGCAGC AAAAGCACCAGCGGCGGCACCGCGGCGCTGGGCTGCCTGGTGAA AGATTATTTTCCGGAACCGGTGACCGTGAGCTGGAACAGCGGCG CGCTGACCAGCGGCGTGCATACCTTTCCGGCGGTGCTGCAGAGC AGCGGCCTGTATAGCCTGAGCAGCGTGGTGACCGTGCCGAGCAG CAGCCTGGGCACCCAGACCTATATTTGCAACGTGAACCATAAAC CGAGCAACACCAAAGTGGATAAAAAAGTGGAACCGAAAAGCTGC GATAAAACCCATACCTGCCCGCCGTGCCCGGCGCCGGAACTGCT GGGCGGCCCGAGCGTGTTTCTGTTTCCGCCGAAACCGAAAGATA CCCTGATGATTAGCCGCACCCCGGAAGTGACCTGCGTGGTGGTG GATGTGAGCCATGAAGATCCGGAAGTGAAATTTAACTGGTATGT GGATGGCGTGGAAGTGCATAACGCGAAAACCAAACCGCGCGAAG AACAGTATAACAGCACCTATCGCGTGGTGAGCGTGCTGACCGTG CTGCATCAGGATTGGCTGAACGGCAAAGAATATAAATGCAAAGT GAGCAACAAAGCGCTGCCGGCGCCGATTGAAAAAACCATTAGCA AAGCGAAAGGCCAGCCGCGCGAACCGCAGGTGTATACCCTGCCG CCGAGCCGCGATGAACTGACCAAAAACCAGGTGAGCCTGACCTG CCTGGTGAAAGGCTTTTATCCGAGCGATATTGCGGTGGAATGGG AAAGCAACGGCCAGCCGGAAAACAACTATAAAACCACCCCGCCG GTGCTGGATAGCGATGGCAGCTTTTTTCTGTATAGCAAACTGAC CGTGGATAAAAGCCGCTGGCAGCAGGGCAACGTGTTTAGCTGCA GCGTGATGCATGAAGCGCTGCATAACCATTATACCCAGAAAAGC CTGAGCCTGAGCCCGGGCAAA |
| 401 | Light Chain | EIVLTQSPATLSLSPGERATLSCRASQSVSSYLAWYQQKPGQAP RLLIYDSSNRATGIPARFSGSGSGTDFTLTISSLEPEDFAVYYC QQYSLYPTFGGGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| 402 | DNA Light Chain | GAAATTGTGTTGACACAGTCTCCAGCCACCCTGTCTTTGTCTCC AGGGGAAAGAGCCACCCTCTCCTGCAGGGCCAGTCAGAGTGTTA GCAGCTACTTAGCCTGGTACCAACAGAAACCTGGCCAGGCTCCC AGGCTCCTCATCTATGATTCATCCAACAGGGCCACTGGCATCCC AGCCAGGTTCAGTGGCAGTGGGTCTGGGACAGACTTCACTCTCA CCATCAGCAGCCTAGAGCCTGAAGATTTTGCAGTTTATTACTGT CAGCAGTACAGTCTCTACCCTACTTTTGGCGGAGGGACCAAGGT TGAGATCAAACGTACGGTGGCCGCTCCCTCCGTGTTCATCTTCC CACCCTCCGACGAGCAGCTGAAGTCCGGCACCGCCTCCGTCGTG TGCCTGCTGAACAACTTCTACCCTCGCGAGGCCAAAGTGCAGTG GAAAGTGGACAACGCCCTGCAGTCCGGCAACTCCCAGGAATCCG TCACCGAGCAGGACTCCAAGGACAGCACCTACTCCCTGTCCTCC ACCCTGACCCTGTCCAAGGCCGACTACGAGAAGCACAAAGTGTA CGCCTGCGAAGTGACCCACCAGGGCCTGTCCAGCCCCGTGACCA AGTCCTTCAACCGGGGCGAGTGC |

TABLE 12-continued

| SEQUENCE LISTING | | |
|---|---|---|
| SEQ ID NO | Description | Sequence |
| | | SRF538-B |
| 403 | Heavy Chain | QVQLVESGGGVVQPGRSLRLSCAASGFTFSSYGMHWVRQAPGKG LEWVAVIWYDGSNKYYADSVKGRFTISRDNSKNTLYLQMNSLRA EDTAVYYCARGAPEYVDVWGQGTMVTVSSASTKGPSVFPLAPCS RSTSESTAALGCLVKDYFPEPVTVSWNSGALTSGVHTFPAVLQS SGLYSLSSVVTVPSSSLGTKTYTCNVDHKPSNTKVDKRVESKYG PPCPSCPAPEFLGGPSVFLFPPKPKDTLMISRTPEVTCVVVDVS QEDPEVQFNWYVDGVEVHNAKTKPREEQFNSTYRVVSVLTVLHQ DWLNGKEYKCKVSNKGLPSSIEKTISKAKGQPREPQVYTLPPSQ EEMTKNQVSLTCLVKGFYPSDIAVEWESNGQPENNYKTTPPVLD SDGSFFLYSRLTVDKSRWQEGNVFSCSVMHEALHNHYTQKSLSL SLG |
| 404 | DNA Heavy Chain | CAGGTGCAGCTGGTGGAGTCTGGGGGAGGCGTGGTCCAGCCTGG GAGGTCCCTGAGACTCTCCTGTGCAGCGTCTGGATTCACCTTCA GTAGCTATGGCATGCACTGGGTCCGCCAGGCTCCAGGCAAGGGG CTGGAGTGGGTGGCAGTTATATGGTATGATGGAAGTAATAAATA CTATGCAGACTCCGTGAAGGGCCGATTCACCATCTCCAGAGACA ATTCCAAGAACACGCTGTATCTGCAAATGAACAGCCTGAGAGCC GAGGACACGGCGGTGTACTACTGCGCCAGAGGGGCCCCTGAATA TGTAGACGTATGGGGTCAGGGTACAATGGTCACCGTCTCCTCAG CTTCCACCAAGGGCCCCTCCGTGTTCCCTCTGGCCCCTTGCTCC CGGTCCACCTCCGAGTCTACCGCCGCTCTGGGCTGCCTCGTGAA GGACTACTTCCCCGAGCCCGTGACCGTGTCCTGGAACTCTGGCG CCCTGACCTCCGGCGTGCACACCTTCCCTGCCGTGCTGCAGTCC TCCGGCCTGTACTCCCTGTCCAGCGTCGTGACCGTGCCCTCCTC CAGCCTGGGCACCAAGACCTACACCTGTAACGTGGACCACAAGC CCTCCAACACCAAAGTGGACAAGCGGGTGGAATCTAAGTACGGC CCTCCCTGCCCTTCCTGCCCTGCCCCTGAGTTCCTGGGCGGACC TTCCGTGTTCCTGTTCCCTCCAAAGCCCAAGGACACCCTGATGA TCTCCCGGACCCCTGAAGTGACCTGCGTGGTGGTGGACGTGTCC CAGGAAGATCCCGAAGTCCAGTTCAATTGGTACGTGGACGGCGT GGAAGTGCACAACGCCAAGACCAAGCCCAGAGAGGAACAGTTCA ACTCCACCTACCGGGTGGTGTCCGTGCTGACCGTGCTGCACCAG GACTGGCTGAACGGCAAAGAGTACAAGTGCAAAGTGTCCAACAA GGGCCTGCCCTCCAGCATCGAAAAGACCATCTCCAAGGCCAAGG GCCAGCCCCGCGAGCCCCAAGTGTACACCCTGCCTCCCAGCCAG GAAGAGATGACCAAGAATCAAGTGTCCCTGACTTGTCTGGTCAA GGGCTTCTACCCCTCCGATATCGCCGTGGAGTGGGAGTCCAACG GCCAGCCCGAGAACAACTACAAGACCACCCCTCCCGTGCTGGAC TCCGACGGCTCCTTCTTCCTGTACTCTCGGCTGACCGTGGACAA GTCCCGGTGGCAGGAAGGCAACGTCTTCTCCTGCTCCGTGATGC ACGAGGCCCTGCACAACCACTACACCCAGAAGTCCCTGTCCCTG TCTCTGGGC |
| 405 | FLAG | DYKDDDDK |
| 406 | 6-HIS | HHHHHH |
| 407 | HA | YPYDVPDYA |

TABLE 13

| Fc Sequences (=CH2 + CH3) | | |
|---|---|---|
| Name | Alias | Amino Acid Sequence |
| Human IgG1 | 1.0 | EPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPP SRDELTKNQVSLTCLVKGFYPSDIAVEWESNGQPENNYKTTPPVLD SDGSFFLYSKLTVDKSRWQQGNVFSCSVMHEALHNHYTQKSLSLSP GK (SEQ ID NO: 702) |
| Human IgG4 | 4.0 | ESKYGPPCPSCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID NO: 703) |

TABLE 13-continued

| Fc Sequences (=CH2 + CH3) | | |
|---|---|---|
| Name | Alias | Amino Acid Sequence |
| Human IgG4 (S228P) | 4.1 | ESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID NO: 704) |
| Human IgG4 (S228P/ L235E) | 4.2 | ESKYGPPCPPCPAPEFEGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK (SEQ ID NO: 705) |

Example 10: SRF388 Binding Properties and IL-27 Receptor Blockade

The association and dissociation of recombinant human IL-27 at concentrations ranging from 0 to 5.0 μg/mL with an SRF388 concentration of 1 μg/mL were determined. Final binding kinetic parameters are shown in Table 14 along with binding model fit parameters (R2 and χ2) that demonstrate goodness of the model fitting to the data.

Human IL-27 displayed the strongest binding affinity for SRF388 of all species tested in this study (3.86 pM). Recombinant rat and cynomolgus monkey IL-27 also showed strong affinities for SRF388 with values of 80.9 and 37.4 pM, respectively, although somewhat weaker than the human protein. Recombinant mouse IL-27 had the weakest affinity for SRF388 by comparison with the human protein, with a value in the nM range (4.43 nM) as indicated by its slower association and faster dissociation rates.

TABLE 14

| Data Summary for IL-27 Binding to SRF388 and Species Cross-Reactivity | | | | | |
|---|---|---|---|---|---|
| Analyte | $K_D$ (M) | $k_a$ (1/Ms) | $k_d$ (1/s) | Full $\chi^2$ | Full $R^2$ |
| Human IL-27 | 3.86E−12 | 5.10E+05 | 1.97E−06 | 0.4055 | 0.9991 |
| Mouse IL-27 | 4.43E−09 | 5.50E+04 | 2.44E−04 | 0.6732 | 0.9963 |
| Rat IL-27 | 8.09E−11 | 2.34E+06 | 1.89E−04 | 0.4685 | 0.9945 |
| Cynomolgus monkey IL-27 | 3.74E−11 | 3.18E+05 | 1.19E−05 | 1.3431 | 0.9979 |

Abbreviations:
IL-27 = interleukin 27,
$k_a$ = association constant,
$k_d$ = dissociation constant,
$K_D$ = binding affinity
Note:
$R^2$ values > 0.95 and $\chi^2$ values < 3.0 are demonstrative of a good fit of the model to the data.

Example 11: CDR Sequence Alignments

A number of sub-selections of anti-IL-27 antibodies of the instant disclosure share sequence homology across their CDR regions, providing a diversity of variant CDR sequences that have been validated as retaining functionality. It is expressly contemplated herein that the following consensus CDR sequences are fully supported by—and are therefore within the scope of—the instant disclosure.

For SRF388, SRF381, SRF382, SRF384, SRF386 and SRF529 antibodies, alignments of the CDR sequences of each of these anti-IL-27 antibodies revealed extensive homology, punctuated by variable residues. In particular, heavy chain CDR1 alignments revealed the following variable residues:

```
HCDR1 (IMGT)
CLUSTAL O(1.2.4) multiple sequence alignment
     1     GFTFRSYG     8     (SEQ ID NO: 161)

     5     GFTFRSYG     8     (SEQ ID NO: 73)

     4     GFTFASYG     8     (SEQ ID NO: 139)

     2     GFTFSRTG     8     (SEQ ID NO: 95)

     3     GFTFSRYG     8     (SEQ ID NO: 117)

     6     GFTFSSYS     8     (SEQ ID NO: 51)
           ****
```

A consensus heavy chain CDR1 (IMGT) sequence for these homologous antibodies is therefore N-GFTF[S/A/R][S/R][T/Y][G/S]-C (SEQ ID NO: 412) and, accordingly, more generally contemplated herein as a consensus heavy chain CDR1 (IMGT) sequence is N-GFTFXXXX-C (SEQ ID NO: 408), where X is any amino acid residue.

Alignment of the SRF388, SRF381, SRF382, SRF384, SRF386 and SRF529 antibody heavy chain CDR2 (IMGT) sequences revealed the following:

```
HCDR2 (IMGT)
CLUSTAL O(1.2.4) multiple sequence alignment
    10     ISSSGSYI     8     (SEQ ID NO: 162)

    11     ISSSSSYI     8     (SEQ ID NO: 140)

     7     ISSSSSYI     8     (SEQ ID NO: 74)

     9     ISSSSSYI     8     (SEQ ID NO: 96)

     8     ISSSSAYI     8     (SEQ ID NO: 118)

    12     ISSSSSYI     8     (SEQ ID NO: 52)
           ****.:**
```

A consensus heavy chain CDR2 (IMGT) sequence for these homologous antibodies is therefore N-ISSS[S/G][S/A]YI-C (SEQ ID NO: 413) and, accordingly, more generally contemplated herein as a consensus heavy chain CDR2 (IMGT) sequence is N-ISSSXXYI-C (SEQ ID NO: 409), where X is any amino acid residue.

Alignments of the human CDR1 (NT) and human CDR2 (NT) sequences also revealed the following:

HCDR1 (NT)
CLUSTAL O(1.2.4) multiple sequence alignment

```
13    FTFRSYGMN           9    (SEQ ID NO: 76)

16    FTFRSYGMN           9    (SEQ ID NO: 164)

17    FTFASYGMN           9    (SEQ ID NO: 142)

14    FTFSRTGMN           9    (SEQ ID NO: 98)

15    FTFSRYGMN           9    (SEQ ID NO: 120)

18    FTFSSYSMN           9    (SEQ ID NO: 54)
      ***   ***
```

HCDR2 (NT)
CLUSTAL O(1.2.4) multiple sequence alignment

```
23    GISSSGSYIYYADSVKG   17   (SEQ ID NO: 165)

19    SISSSSSYIYYADSVKG   17   (SEQ ID NO: 77)

20    SISSSSSYIYYADSVKG   17   (SEQ ID NO: 99)

22    SISSSSSYIYYADSVKG   17   (SEQ ID NO: 143)

21    SISSSSAYILYADSVKG   17   (SEQ ID NO: 121)

24    SISSSSSYIYYADSVKG   17   (SEQ ID NO: 55)
      .****.:** *******
```

Consensus heavy chain CDR1 (NT) and CDR2 (NT) sequences for these homologous antibodies are therefore N-FTF[S/A/R][S/R][T/Y][G/S]MN-C (SEQ ID NO: 414) and N-[G/S]ISSS[S/G][S/A]YI[L/Y]YADSVKG-C (SEQ ID NO: 415), respectively. In view of these consensus sequences, more generally contemplated herein are consensus heavy chain CDR1 (NT) and CDR2 (NT) sequences N-FTFXXXXMN-C (SEQ ID NO: 410) and N-XISSSXXYIXYADSVKG-C (SEQ ID NO: 411), respectively, where X is any amino acid residue.

Heavy chain CDR3 (IMGT or NT) and light chain CDRs CDR1 (IMGT or NT), CDR2 (IMGT or NT) and CDR3 (IMGT or NT) were fully conserved between SRF388, SRF381, SRF382, SRF384, SRF386 and SRF529.

Similar CDR sequence alignments performed upon SRF535 and SRF538 monoclonal antibodies revealed the following consensus CDR sequences for these two related antibodies:

Observed Variation (IMGT):

HCDR1 (IMGT) (SEQ ID NO: 361)
N-GFTFSSYG-C

HCDR2 (IMGT) (SEQ ID NO: 445)
N-I[K/W][Q/Y]DGS[E/N]K-C

HCDR3 (IMGT) (SEQ ID NO: 446)
N-AR[D/G]AP[WDIYDYYM/EYV]DV-C

LCDR1 (IMGT) (SEQ ID NO: 447)
N-QS[I/V]SSY-C

LCDR2 (IMGT) (SEQ ID NO: 448)
N-[A/D][A/S]S-C

LCDR3 (IMGT) (SEQ ID NO: 449)
N-QQ[S/Y][Y/S][V/L][P/Y]P[W/-]T-C

Consensus (IMGT):

HCDR1 (IMGT) (SEQ ID NO: 361)
N-GFTFSSYG-C

HCDR2 (IMGT) (SEQ ID NO: 436)
N-IXXDGSXK-C

HCDR3 (IMGT) (SEQ ID NO: 437)
N-ARXAP$[X]_{n=3-8}$DV-C

LCDR1 (IMGT) (SEQ ID NO: 438)
N-QSXSSY-C

LCDR2 (IMGT) (SEQ ID NO: 439)
N-XXS-C

LCDR3 (IMGT) (SEQ ID NO: 440)
N-QQXXXXP$[X]_{n=0-1}$T-C

Observed Variation (NT):

HCDR1 (NT) (SEQ ID NO: 450)
N-FTFSSYGM[S/H]-C

HCDR2 (NT) (SEQ ID NO: 451)
N-[N/V]I[K/W][Q/Y]DGS[E/N]KYY[V/A]DSVKG-C

HCDR3 (NT) (SEQ ID NO: 446)
N-AR[D/G]AP[WDIYDYYM/EYV]DV-C

LCDR1 (NT) (SEQ ID NO: 452)
N-RASQS[I/V]SSYL[N/A]-C

LCDR2 (NT) (SEQ ID NO: 453)
N-[AA/D]SS[LQS/NRAT]-C

LCDR3 (NT) (SEQ ID NO: 449)
N-QQ[S/Y][Y/S][V/L][P/Y]P[W/-]T-C

Consensus (NT):

HCDR1 (NT) (SEQ ID NO: 441)
N-FTFSSYGMX-C

HCDR2 (NT) (SEQ ID NO: 442)
N-XIXXDGSXKYYXDSVKG-C

HCDR3 (NT) (SEQ ID NO: 437)
N-ARXAP$[X]_{n=3-8}$DV-C

LCDR1 (NT) (SEQ ID NO: 443)
N-RASQSXSSYLX-C

LCDR2 (NT) (SEQ ID NO: 444)
N-$[X]_{n=1-2}$SS$[X]_{n=3-4}$-C

LCDR3 (NT) (SEQ ID NO: 440)
N-QQXXXXP$[X]_{n=0-1}$T-C

Alignments of CDR sequences were also performed between the entirety of SRF388, SRF381, SRF382, SRF384, SRF386, SRF529, SRF535 and SRF538 antibodies, which resulted in the following observed variation and consensus sequences:

Observed Variation (IMGT):

HCDR1 (IMGT)
(SEQ ID NO: 454)
N-GFTF[S/A/R][S/R][T/Y][G/S]-C

HCDR2 (IMGT)
(SEQ ID NO: 455)
N-I[S/K/W][S/Q/Y][S/D][S/G][S/A][Y/E/N][I/K]-C

HCDR3 (IMGT)
(SEQ ID NO: 457)
N-AR[DGGRTSYTATAHNWF/DAPWDIYDYYM/GAPEYV]D[P/V]-C

LCDR1 (IMGT)
(SEQ ID NO: 459)
N-QS[VLF/I/V]SS[NNKN/-]Y-C

LCDR2 (IMGT)
(SEQ ID NO: 461)
N-[W/A/D][A/S]S-C

LCDR3 (IMGT)
(SEQ ID NO: 463)
N-QQ[H/S/Y][A/Y/S][S/V/L][A/P/Y]P[P/W/-]T-C

Consensus (IMGT):

HCDR1 (IMGT)
(SEQ ID NO: 408)
N-GFTFXXXX-C

HCDR2 (IMGT)
(SEQ ID NO: 456)
N-IXXXXXXX-C

HCDR3 (IMGT)
(SEQ ID NO: 458)
N-AR$[X]_{n=6-15}$DX-C

LCDR1 (IMGT)
(SEQ ID NO: 460)
N-QS$[X]_{n=1-3}$SS$[X]_{n=0-4}$Y-C

LCDR2 (IMGT)
(SEQ ID NO: 462)
N-XXS-C

LCDR3 (IMGT)
(SEQ ID NO: 464)
N-QQXXXXP$[X]_{n=0-1}$T-C

Observed Variation (NT):

HCDR1 (NT)
(SEQ ID NO: 465)
N-FTF[S/A/R][S/R][T/Y][G/S]M[N/S/H]-C

HCDR2 (NT)
(SEQ ID NO: 467)
N-[G/S/N/V]I[S/K/W][S/Q/Y][S/D][S/G][S/A][Y/E/N][I/K][L/Y]Y[V/A]DSVKG-C

HCDR3 (NT)
(SEQ ID NO: 469)
N-AR[D/G][GGRTSYTATAHNWF/APWDIYDYYM/APEYV]D[P/V]-C

LCDR1 (NT)
(SEQ ID NO: 471)
N-RASQS[I/V]SSYL[N/A]-C

-continued

LCDR2 (NT)
(SEQ ID NO: 473)
N-[WA/AA/D]S[TRES/SLQS/SNRAT]-C

LCDR3 (NT)
(SEQ ID NO: 475)
N-QQ[H/S/Y][A/Y/S][S/V/L][A/P/Y]P[P/W/-]T-C

Consensus (NT):

HCDR1 (NT)
(SEQ ID NO: 466)
N-FTFXXXXMX-C

HCDR2 (NT)
(SEQ ID NO: 468)
N-XIXXXXXXXXYXDSVKG-C

HCDR3 (NT)
(SEQ ID NO: 470)
N-AR$[X]_{n=6-15}$DX-C

LCDR1 (NT)
(SEQ ID NO: 472)
N-RASQSXSSYLX-C

LCDR2 (NT)
(SEQ ID NO: 474)
N-$[X]_{n=1-2}$S$[X]_{n=4-5}$-C

LCDR3 (NT)
(SEQ ID NO: 476)
N-QQXXXXP$[X]_{n=0-1}$T-C

Alignments of SRF543 and SRF414 were also performed, and yielded the following observed variation and consensus sequences:

Observed Variation (IMGT):

HCDR1 (IMGT)
(SEQ ID NO: 426)
N-GGSFS[R/D]Y[E/Y]-C

HCDR2 (IMGT)
(SEQ ID NO: 427)
N-ID[W/Y]SG[I/S]T-C

HCDR3 (IMGT)
(SEQ ID NO: 428)
N-AR[D/L][P/G][M/V]YY[-/Y]DSS[VSTGSV/DLGF]D[V/I]-C

LCDR1 (IMGT)
(SEQ ID NO: 429)
N-Q[S/D][V/I]S[S/N]Y-C

LCDR2 (IMGT)
(SEQ ID NO: 430)
N-D[S/A]S-C

LCDR3 (IMGT)
(SEQ ID NO: 431)
N-QQ[D/Y][S/D]D[H/L]PIT-C

Consensus (IMGT):

HCDR1 (IMGT)
(SEQ ID NO: 416)
N-GGSFSXYX-C

HCDR2 (IMGT)
(SEQ ID NO: 417)
N-IDXSGXT-C

-continued

HCDR3 (IMGT)

(SEQ ID NO: 418)

N-ARXXXYY[X]$_{n=0-1}$DSS[X]$_{n=4-6}$

LCDR1 (IMGT)

(SEQ ID NO: 419)

N-QXXSXY-C

LCDR2 (IMGT)

(SEQ ID NO: 420)

N-DXS-C

LCDR3 (IMGT)

(SEQ ID NO: 421)

N-QQXXDXPIT-C

Observed Variation (NT):

HCDR1 (NT)

(SEQ ID NO: 432)

N-GSFS[R/D]Y[E/Y]WS-C

HCDR2 (NT)

(SEQ ID NO: 433)

N-SID[W/Y]SG[I/S]T[N/E]YNPSLKS-C

HCDR3 (NT)

(SEQ ID NO: 428)

N-AR[D/L][P/G][M/V]YY[-/Y]DSS[VSTGSV/DLGF]D[V/I]-C

LCDR1 (NT)

(SEQ ID NO: 434)

N-[Q/R]ASQ[S/D][V/I]S[S/N]YL[N/A]-C

LCDR2 (NT)

(SEQ ID NO: 435)

N-D[S/A]SN[R/L][A/E]T-C

LCDR3 (NT)

(SEQ ID NO: 431)

N-QQ[D/Y][S/D]D[H/L]PIT-C

Consensus (NT):

HCDR1 (NT)

(SEQ ID NO: 422)

N-GSFSXYXWS-C

HCDR2 (NT)

(SEQ ID NO: 423)

N-SIDXSGXTXYNPSLKS-C

HCDR3 (NT)

(SEQ ID NO: 418)

N-ARXXXYY[X]$_{n=0-1}$DSS[X]$_{n=4-6}$DX-C

LCDR1 (NT)

(SEQ ID NO: 424)

N-XASQXXSXYLX-C

LCDR2 (NT)

(SEQ ID NO: 425)

N-DXSNXXT-C

LCDR3 (NT)

-continued (SEQ ID NO: 421)

N-QQXXDXPIT-C

Example 12: Properties of Selected Monoclonal Antibodies

Selected monoclonal antibodies of the instant disclosure were assessed for various functional properties. The outcome of certain such assessment is tabulated in FIG. 9. Remarkably, a wide array of monoclonal antibodies were identified that exhibited binding to human IL-27 (as determined by surface plasmon resonance (SPR) technology in a BIACORE 2000 instrument, as described above) ("Property (i)") with an equilibrium dissociation constant (KD) of 15 nM or less, including Ab7, SRF557, SRF536, SRF416, SRF543, SRF414, SRF529, SRF381, SRF388, SRF382, SRF384, SRF386, SRF410, SRF411, SRF405, SRF535 and SRF538.

Unexpectedly, a selection of monoclonal antibodies were identified to be WSX-1 competitive ("Property (ii)"), including Ab7, SRF536, SRF416, SRF543, SRF414, SRF529, SRF381, SRF388, SRF382, SRF384, SRF386, SRF535 and SRF538.

Surprisingly, a selection of monoclonal antibodies were identified that inhibited pSTAT1 U937 ("Property (iii)"), including Ab7, SRF536, SRF416, SRF543, SRF414, SRF529, SRF381, SRF388, SRF382, SRF384, SRF386, SRF410, SRF411, SRF405, SRF535 and SRF538.

Remarkably, a selection of monoclonal antibodies were also identified that inhibited CD161 expression ("Property (iv)"), including Ab7, SRF536, SRF416, SRF543, SRF529, SRF381, SRF388, SRF382, SRF384 and SRF386.

A selection of monoclonal antibodies that, remarkably, inhibited PD-L1 expression in $CD4^+$ T cells ("Property (v)") were also identified, including Ab7, SRF536, SRF416, SRF543, SRF414, SRF529, SRF381, SRF388, SRF382, SRF384, SRF386 and SRF535.

While only tested for a limited number of monoclonal antibodies, variability in the ability of those antibodies tested to enhance PD-1-mediated cytokine secretion ("Property (vi)") was also observed. Specifically, SRF381 and SRF388 antibodies were remarkably identified to enhance PD-1-mediated cytokine secretion, whereas SRF536 did not.

Monoclonal antibodies possessing each of properties (i)-(vi), as recited above, have therefore been identified herein. Not all antibodies examined were identified to possess each of properties (i)-(vi), and it is therefore expressly contemplated that selections of antibodies can be assembled that possess a sub-selection of these properties. For example, antibodies Ab7, SRF536, SRF416, SRF543, SRF529, SRF381, SRF388, SRF382, SRF384 and SRF386 were identified to possess each of properties (i)-(v). Meanwhile, antibodies Ab7, SRF536, SRF416, SRF543, SRF529, SRF381, SRF388, SRF382, SRF384 and SRF386 were identified to possess each of properties (iii) and (iv). As will be apparent to the skilled artisan, similar sub-selections of antibodies and associated properties are readily assembled from the information presented in FIG. 9.

What is claimed is:

1. An isolated monoclonal antibody that specifically binds human IL-27, or antigen binding portion thereof, wherein the antibody or antigen binding portion thereof comprises heavy and light chain CDRs selected from the group consisting of:

(i) heavy chain CDR1 consisting of N-GFTFXXXX-C (SEQ ID NO: 408), heavy chain CDR2 consisting of N-ISSSXXYI-C (SEQ ID NO: 409), and heavy chain CDR3 sequence set forth in SEQ ID NO: 163; and light chain CDR1, CDR2 and CDR3 sequences set forth in SEQ ID NOs: 169, 170 and 171, respectively; or (ii) heavy chain CDR1 consisting of N-FTFXXXXMN-C (SEQ ID NO: 410), heavy chain CDR2 consisting of N-XISSSXXYIXYADSVKG-C (SEQ ID NO: 411), and heavy chain CDR3 sequence set forth in SEQ ID NO: 166; and light chain CDR1, CDR2 and CDR3 sequences set forth in SEQ ID NOs: 172, 173 and 174, respectively.

2. The isolated monoclonal antibody of claim 1, wherein: the heavy chain CDR1 consists of N-GFTF[S/A/R][ S/R][T/Y][G/S]-C (SEQ ID NO: 412) and the heavy chain CDR2 consists of N-ISSS[S/G][S/A]YI-C (SEQ ID NO: 413); or the heavy chain CDR1 consists of N-FTF[S/A/R][S/R][T/Y][G/S]MN-C (SEQ ID NO: 414) and the heavy chain CDR2 consists N-[G/S]ISSS[S/G][S/A]YI[L/Y]YADSVKG-C (SEQ ID NO: 415).

3. The isolated monoclonal antibody, or antigen binding portion thereof, of claim 1, wherein:

(a) the antibody or antigen binding portion thereof antagonizes IL-27; and/or (b) the antibody or antigen binding portion thereof inhibits or reduces STAT1 and/or STAT3 phosphorylation in a cell, optionally wherein the cell is an immune cell or a cancer cell;

(c) the antibody or antigen binding portion thereof inhibits or reduces inhibition of CD161 expression in a cell;

(d) the antibody or antigen binding portion thereof inhibits or reduces PD-L1 and/or TIM-3 expression in a cell;

(e) the antibody or antigen binding portion thereof induces or enhances the PD-1-mediated secretion of one or more cytokines from a cell;

(f) the antibody is selected from the group consisting of an IgG1, an IgG2, an IgG3, an IgG4, an IgM, an IgA1 an IgA2, an IgD, and an IgE antibody;

(g) the antibody comprises an Fc domain comprising at least one mutation, optionally wherein the antibody comprises a mutant IgG1 heavy chain constant region or a mutant IgG4 heavy chain constant region; or (h) any combination of (a)-(g).

4. The isolated monoclonal antibody, or antigen binding portion thereof, of claim 1, wherein the heavy chain CDR1 comprises the amino acid sequence set forth in SEQ ID NO: 161, the heavy chain CDR2 comprises the amino acid sequence set forth in SEQ ID NO: 162, the heavy chain CDR3 comprises the amino acid sequence set forth in SEQ ID NO: 163 the light chain CDR1 comprises the amino acid sequence set forth in SEQ ID NO: 169, the light chain CDR2 comprises the amino acid sequence set forth in SEQ ID NO: 170, and the light chain CDR3 comprises the amino acid sequence set forth in SEQ ID NO: 171.

5. The isolated monoclonal antibody, or antigen binding portion thereof, of claim 1, wherein the heavy chain CDR1 comprises the amino acid sequence set forth in SEQ ID NO: 164, the heavy chain CDR2 comprises the amino acid sequence set forth in SEQ ID NO: 165, the heavy chain CDR3 comprises the amino acid sequence set forth in SEQ ID NO: 166 the light chain CDR1 comprises the amino acid sequence set forth in SEQ ID NO: 172, the light chain CDR2 comprises the amino acid sequence set forth in SEQ ID NO: 173, and the light chain CDR3 comprises the amino acid sequence set forth in SEQ ID NO: 174.

6. The isolated monoclonal antibody, or antigen binding portion thereof, of claim 3, wherein the cell is an immune cell or a cancer cell.

7. The isolated monoclonal antibody, or antigen binding portion thereof, of claim 3, wherein the one or more cytokines comprise IFNg, IL-17, TNFα, IL-6, or any combination thereof.

8. The isolated monoclonal antibody of claim 1, wherein the antibody comprises an IgG1 heavy chain constant region or an IgG4 heavy chain constant region.

9. The isolated monoclonal antibody of claim 1, wherein the mutant IgG4 heavy chain constant region comprises any one of the substitutions S228P, L235E, L235A, or a combination thereof, according to EU numbering.

10. The isolated antibody, or antigen-binding portion thereof, of claim 1, wherein the heavy chain variable region comprises an amino acid sequence at least 90% identical to the amino acid sequence set forth in SEQ ID NO: 167.

11. The isolated antibody, or antigen-binding portion thereof, of claim 1, wherein the light chain variable region comprises an amino acid sequence at least 90% identical to the amino acid sequence set forth in SEQ ID NO: 175.

12. The isolated antibody, or antigen-binding portion thereof, of claim 1, wherein the heavy chain variable region comprises the amino acid sequence set forth in SEQ ID NO: 167, and the light chain variable region comprises the amino acid sequence set forth in SEQ ID NO: 175.

13. The isolated antibody, or antigen-binding portion thereof, of claim 1, which comprises an IgG1 heavy chain constant region or an IgG4 heavy chain constant region.

14. The isolated antibody, or antigen-binding portion thereof, of claim 12, which comprises (i) a heavy chain comprising the amino acid sequence set forth in SEQ ID NO: 177, and (ii) a light chain comprising the amino acid sequence set forth in SEQ ID NO: 179.

15. An isolated monoclonal antibody that specifically binds to and antagonizes human IL-27, or antigen binding portion thereof, wherein the antibody or antigen binding portion thereof comprises heavy and light chain CDRs, wherein the heavy chain CDR1, CDR2 and CDR3 sequences are set forth in SEQ ID NOs: 161, 162 and 163, respectively, and the light chain CDR1, CDR2 and CDR3 sequences are set forth in SEQ ID NOs: 169, 170 and 171, respectively.

16. The isolated monoclonal antibody, or antigen binding portion thereof, of claim 15, wherein the antibody or antigen binding portion thereof comprises a variable heavy chain comprising an amino acid sequence at least 90% identical to the amino acid sequence set forth in SEQ ID NO: 167.

17. The isolated monoclonal antibody of claim 15, or antigen binding portion thereof, wherein the antibody or antigen binding portion thereof comprises a variable light chain comprising an amino acid sequence at least 90% identical to the amino acid sequence set forth in SEQ ID NO: 175.

18. The isolated monoclonal antibody, or antigen binding portion thereof, of claim 15, wherein the antibody or antigen binding portion thereof comprises a variable heavy chain comprising the amino acid sequence set forth in SEQ ID NO: 167, and a variable light chain comprising the amino acid sequence set forth in SEQ ID NO: 175.

19. The isolated monoclonal antibody of claim 15, wherein the antibody comprises a heavy chain comprising the amino acid sequence set forth in SEQ ID NO: 177, and a light chain comprising the amino acid sequence set forth in SEQ ID NO: 179.

* * * * *

SEQUENCE LISTING

<160> NUMBER OF SEQ ID NOS: 705

<210> SEQ ID NO 1
<211> LENGTH: 121
<212> TYPE: PRT
<213> ORGANISM: Artificial

<220> FEATURE:
<223> OTHER INFORMATION: Synthetic

<400> SEQUENCE: 1

Glu Val Lys Leu Val Glu Ser Gly Gly Gly Leu Val Gln Pro Gly Gly
1 5 10 15

Ser Leu Lys Leu Phe Cys Ala Ala Ser Gly Phe Thr Phe Thr Ser Tyr
20 25 30

Ser Met Ser Trp Val Arg Gln Thr Pro Glu Lys Arg Leu Glu Trp Val
35 40 45

Ala Tyr Ile Ser Tyr Asp Gly Gly Ser Ala Tyr Tyr Pro Asp Thr Val
50 55 60

Lys Gly Arg Phe Ser Ile Ser Arg Asp Asn Ala Lys Lys Thr Leu Tyr
65 70 75 80

Leu Gln Met Ser Ser Leu Lys Ser Glu Asp Thr Ala Met Tyr Tyr Cys
85 90 95

Ala Arg His Gly Asp Tyr Asp Asp Asp Asp Ala Met Asp Tyr Trp Gly
100 105 110

Gln Gly Thr Ser Val Thr Val Ser Ser
115 120

<210> SEQ ID NO 2
<211> LENGTH: 363
<212> TYPE: DNA
<213> ORGANISM: Artificial
<220> FEATURE:
<223> OTHER INFORMATION: Synthetic

<400> SEQUENCE: 2
gaggtgaagc tggtggagtc tgggggaggc ttggtacagc ctgggggtc cctgaaactc 60 ttctgtgcag cctctggatt cacctttacc agctattcca tgagctgggt ccgccagact 120
ccagagaaga ggctggagtg ggtcgcatac attagttatg atggtggtag cgcctactac 180
cctgacactg tgaagggccg gttctccatc tccagagaca atgccaagaa aaccctgtat 240
ctgcaaatga gcagcctgaa gtctgaggac acggccatgt attactgtgc aagacatgga 300
gactatgacg acgacgacgc gatggactac tggggccaag gaacctcagt caccgtctcc 360
tca 363

<210> SEQ ID NO 3
<211> LENGTH: 107
<212> TYPE: PRT
<213> ORGANISM: Artificial
<220> FEATURE:
<223> OTHER INFORMATION: Synthetic

<400> SEQUENCE: 3

Asp Ile Gln Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Tyr
20 25 30

Leu Ala Trp Tyr Gln Gln Lys Gln Gly Lys Ser Pro Gln Leu Leu Val
35 40 45

Tyr Asn Ala Glu Thr Leu Thr Glu Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Asn Tyr Tyr Cys Gln His His Tyr Gly Thr Pro Leu 85 90 95

Thr Phe Gly Ala Gly Thr Lys Leu Asp Leu Lys
100 105

<210> SEQ ID NO 4
<211> LENGTH: 321
<212> TYPE: DNA
<213> ORGANISM: Artificial
<220> FEATURE:
<223> OTHER INFORMATION: Synthetic

<400> SEQUENCE: 4
gacatccaga tgacccagtc tccagcctcc ctgtctgcat ctgtaggaga aactgtcacc 60
atcacttgcc gggcaagtga gaacatttac agctatttag catggtatca gcagaaacag 120
gggaaatctc ctcagctcct ggtctataat gcagaaacct tgacagaagg ggtcccatca 180
aggttcagcg gcagtggatc tgggacacaa ttctctctca agatcaacag tctgcaacct 240
gaagattttg ggaattacta ctgtcaacat cattacggta ccccgctcac attcggcgct 300
gggaccaagc tggatctgaa a 321

<210> SEQ ID NO 5
<211> LENGTH: 121
<212> TYPE: PRT
<213> ORGANISM: Artificial
<220> FEATURE:
<223> OTHER INFORMATION: Synthetic

<400> SEQUENCE: 5

Glu Val Lys Leu Val Glu Ser Gly Gly Gly Leu Val Gln Pro Gly Gly
1 5 10 15

Ser Leu Arg Leu Ser Cys Ala Ala Ser Gly Phe Thr Phe Thr Ser Tyr
20 25 30

Ser Met Ser Trp Val Arg Gln Ala Pro Gly Lys Gly Leu Glu Trp Val
35 40 45

Ala Tyr Ile Ser Tyr Asp Gly Gly Ser Ala Tyr Tyr Pro Asp Thr Val
50 55 60

Lys Gly Arg Phe Thr Ile Ser Arg Asp Asn Ser Lys Lys Thr Leu Tyr
65 70 75 80

Leu Gln Met Ser Ser Leu Lys Ser Glu Asp Thr Ala Met Tyr Tyr Cys
85 90 95

Ala Arg His Gly Asp Tyr Asp Asp Asp Asp Ala Met Asp Tyr Trp Gly
100 105 110

Gln Gly Thr Ser Val Thr Val Ser Ser
115 120

<210> SEQ ID NO 6
<211> LENGTH: 363
<212> TYPE: DNA
<213> ORGANISM: Artificial
<220> FEATURE:
<223> OTHER INFORMATION: Synthetic

<400> SEQUENCE: 6
gaggtgaagc tggtggagtc tgggggaggc ttggtacagc ctgggggtc cctgagactc 60 tcctgtgcag cctctggatt cacctttacc agctattcca tgagctgggt ccgccaggct 120
ccagggaagg ggctggagtg ggtcgcatac attagttatg atggtggtag cgcctactac 180
cctgacactg tgaagggccg gttcaccatc tccagagaca attccaagaa aaccctgtat 240

```
ctgcaaatga gcagcctgaa gtctgaggac acggccatgt attactgtgc aagacatgga    300

gactatgacg acgacgacgc gatggactac tggggccaag gaacctcagt caccgtctcc    360

tca                                                                  363


<210> SEQ ID NO 7
<211> LENGTH: 121
<212> TYPE: PRT
<213> ORGANISM: Artificial
<220> FEATURE:
<223> OTHER INFORMATION: Synthetic

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser
        115                 120


<210> SEQ ID NO 8
<211> LENGTH: 363
<212> TYPE: DNA
<213> ORGANISM: Artificial
<220> FEATURE:
<223> OTHER INFORMATION: Synthetic

<400> SEQUENCE: 8

gaggtgcagc tggtggagtc tgggggaggc ttggtacagc ctggggggtc cctgagactc     60

tcctgtgcag cctctggatt cacctttacc agctattcca tgagctgggt ccgccaggct    120

ccagggaagg ggctggagtg ggtcgcatac attagttatg atggtggtag cgcctactac    180

cctgacactg tgaagggccg gttcaccatc tccagagaca attccaagaa caccctgtat    240

ctgcaaatga gcagcctgaa gtctgaggac acggccatgt attactgtgc aagacatgga    300

gactatgacg acgacgacgc gatggactac tggggccaag gaaccctggt caccgtctcc    360

tca                                                                  363


<210> SEQ ID NO 9
<211> LENGTH: 121
<212> TYPE: PRT
<213> ORGANISM: Artificial
<220> FEATURE:
<223> OTHER INFORMATION: Synthetic

<400> SEQUENCE: 9

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30
```

```
Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser
        115                 120


<210> SEQ ID NO 10
<211> LENGTH: 363
<212> TYPE: DNA
<213> ORGANISM: Artificial
<220> FEATURE:
<223> OTHER INFORMATION: Synthetic

<400> SEQUENCE: 10

gaggtgaagc tggtggagtc tgggggaggc ttggtacagc ctggggggtc cctgagactc      60

tcctgtgcag cctctggatt cacctttacc agctattcca tgagctgggt ccgccaggct     120

ccagggaagg ggctggagtg ggtcgcatac attagttatg atggtggtag cgcctactat     180

cctgacactg tgaagggccg gttcaccatc tccagagaca attccaagaa aaccctgtat     240

ctgcaaatga acagcctgag agccgaggac acggccgtat attactgtgc aagacatgga     300

gactatgacg acgacgacgc gatggactac tggggccaag gaaccctggt caccgtctcc     360

tca                                                                   363


<210> SEQ ID NO 11
<211> LENGTH: 121
<212> TYPE: PRT
<213> ORGANISM: Artificial
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser
        115                 120


<210> SEQ ID NO 12
```

<211> LENGTH: 363
<212> TYPE: DNA
<213> ORGANISM: Artificial
<220> FEATURE:
<223> OTHER INFORMATION: Synthetic

<400> SEQUENCE: 12
gaggtgcagc tggtggagtc tgggggaggc ttggtacagc ctggggggtc cctgagactc 60
tcctgtgcag cctctggatt cacctttacc agctattcca tgagctgggt ccgccaggct 120
ccagggaagg ggctggagtg ggtcgcatac attagttatg atggtggtag cgcctactat 180
cctgacactg tgaagggccg gttcaccatc tccagagaca attccaagaa caccctgtat 240
ctgcaaatga acagcctgag agccgaggac acggccgtat attactgtgc aagacatgga 300
gactatgacg acgacgacgc gatggactac tggggccaag gaaccctggt caccgtctcc 360
tca 363

<210> SEQ ID NO 13
<211> LENGTH: 121
<212> TYPE: PRT
<213> ORGANISM: Artificial
<220> FEATURE:
<223> OTHER INFORMATION: Synthetic

<400> SEQUENCE: 13

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Ser Tyr
20 25 30

Ser Met Ser Trp Val Arg Gln Ala Pro Gly Lys Gly Leu Glu Trp Val
35 40 45

Ser Tyr Ile Ser Tyr Asp Gly Gly Ser Ala Tyr Tyr Pro Asp Thr Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Gly Asp Tyr Asp Asp Asp Asp Ala Met Asp Tyr Trp Gly
100 105 110

Gln Gly Thr Leu Val Thr Val Ser Ser
115 120

<210> SEQ ID NO 14
<211> LENGTH: 363
<212> TYPE: DNA
<213> ORGANISM: Artificial
<220> FEATURE:
<223> OTHER INFORMATION: Synthetic

<400> SEQUENCE: 14
gaggtgcagc tggtggagtc tgggggaggc ttggtacagc ctggggggtc cctgagactc 60
tcctgtgcag cctctggatt cacctttacc agctattcca tgagctgggt ccgccaggct 120
ccagggaagg ggctggagtg ggtgtcttac attagttatg atggtggtag cgcctactat 180
cctgacactg tgaagggccg gttcaccatc tccagagaca attccaagaa caccctgtat 240
ctgcaaatga acagcctgag agccgaggac acggccgtat attactgtgc aagacatgga 300
gactatgacg acgacgacgc gatggactac tggggccaag gaaccctggt caccgtctcc 360
tca 363

<210> SEQ ID NO 15
<211> LENGTH: 107
<212> TYPE: PRT
<213> ORGANISM: Artificial
<220> FEATURE:
<223> OTHER INFORMATION: Synthetic

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Gln Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asn Tyr Tyr Cys Gln His His Tyr Gly Thr Pro Leu
                85                  90                  95

Thr Phe Gly Gln Gly Thr Lys Leu Asp Ile Lys
            100                 105
```

<210> SEQ ID NO 16
<211> LENGTH: 321
<212> TYPE: DNA
<213> ORGANISM: Artificial
<220> FEATURE:
<223> OTHER INFORMATION: Synthetic

<400> SEQUENCE: 16

```
gacatccaga tgacccagtc tccatcctcc ctgtctgcat ctgtaggaga cagagtcacc     60

atcacttgcc gggcaagtga gaacatttac agctatttag catggtatca gcagaaacag    120

gggaaagccc ctaagctcct ggtctataat gcagaaacct tgacagaagg ggtcccatca    180

aggttcagcg gcagtggatc tgggacagat ttcactctca ccatcagcag tctgcaacct    240

gaagattttg caaattacta ctgtcaacat cattacggta ccccgctcac attcggccaa    300

gggaccaagc tggatatcaa a                                              321
```

<210> SEQ ID NO 17
<211> LENGTH: 107
<212> TYPE: PRT
<213> ORGANISM: Artificial
<220> FEATURE:
<223> OTHER INFORMATION: Synthetic

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Asn Tyr Tyr Cys Gln His His Tyr Gly Thr Pro Leu
                85                  90                  95

Thr Phe Gly Gln Gly Thr Lys Leu Glu Ile Lys
            100                 105


<210> SEQ ID NO 18
<211> LENGTH: 321
<212> TYPE: DNA
<213> ORGANISM: Artificial
<220> FEATURE:
<223> OTHER INFORMATION: Synthetic

<400> SEQUENCE: 18

gacatccaga tgacccagtc tccatcctcc ctgtctgcat ctgtaggaga cagagtcacc     60

atcacttgcc gggcaagtga gaacatttac agctatttag catggtatca gcagaaacca    120

gggaaagccc ctaagctcct ggtctataat gcagaaacct tgacagaagg ggtcccatca    180

aggttcagcg gcagtggatc tgggacagat ttcactctca ccatcagcag tctgcaacct    240

gaagattttg caaattacta ctgtcaacat cattacggta ccccgctcac attcggccaa    300

gggaccaagc tggaaatcaa a                                              321


<210> SEQ ID NO 19
<211> LENGTH: 107
<212> TYPE: PRT
<213> ORGANISM: Artificial
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Leu Glu Ile Lys
            100                 105


<210> SEQ ID NO 20
<211> LENGTH: 321
<212> TYPE: DNA
<213> ORGANISM: Artificial
<220> FEATURE:
<223> OTHER INFORMATION: Synthetic

<400> SEQUENCE: 20

gacatccaga tgacccagtc tccatcctcc ctgtctgcat ctgtaggaga cagagtcacc     60

atcacttgcc gggcaagtga gaacatttac agctatttag catggtatca gcagaaacca    120

gggaaagccc ctaagctcct ggtctataat gcagaaacct tgacagaagg ggtcccatca    180

aggttcagcg gcagtggatc tgggacagat ttcactctca ccatcagcag tctgcaacct    240

gaagattttg caacttacta ctgtcaacat cattacggta ccccgctcac attcggccaa    300
```

gggaccaagc tggaaatcaa a 321

<210> SEQ ID NO 21
<211> LENGTH: 107
<212> TYPE: PRT
<213> ORGANISM: Artificial
<220> FEATURE:
<223> OTHER INFORMATION: Synthetic

<400> SEQUENCE: 21

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Tyr
20 25 30

Leu Asn Trp Tyr Gln Gln Lys Pro Gly Lys Ala Pro Lys Leu Leu Val
35 40 45

Tyr Asn Ala Glu Thr Leu Thr Glu Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His His Tyr Gly Thr Pro Leu
85 90 95

Thr Phe Gly Gln Gly Thr Lys Leu Glu Ile Lys
100 105

<210> SEQ ID NO 22
<211> LENGTH: 321
<212> TYPE: DNA
<213> ORGANISM: Artificial
<220> FEATURE:
<223> OTHER INFORMATION: Synthetic

<400> SEQUENCE: 22
gacatccaga tgacccagtc tccatcctcc ctgtctgcat ctgtaggaga cagagtcacc 60
atcacttgcc gggcaagtga gaacatttac agctatttaa attggtatca gcagaaacca 120
gggaaagccc ctaagctcct ggtctataat gcagaaacct tgacagaagg ggtcccatca 180
aggttcagcg gcagtggatc tgggacagat ttcactctca ccatcagcag tctgcaacct 240
gaagattttg caacttacta ctgtcaacat cattacggta ccccgctcac attcggccaa 300
gggaccaagc tggaaatcaa a 321

<210> SEQ ID NO 23
<211> LENGTH: 5
<212> TYPE: PRT
<213> ORGANISM: Artificial
<220> FEATURE:
<223> OTHER INFORMATION: Synthetic

<400> SEQUENCE: 23

Ser Tyr Ser Met Ser
1 5

<210> SEQ ID NO 24
<211> LENGTH: 17
<212> TYPE: PRT
<213> ORGANISM: Artificial
<220> FEATURE:
<223> OTHER INFORMATION: Synthetic

<400> SEQUENCE: 24

Tyr Ile Ser Tyr Asp Gly Gly Ser Ala Tyr Tyr Pro Asp Thr Val Lys 1 5 10 15

Gly

<210> SEQ ID NO 25
<211> LENGTH: 12
<212> TYPE: PRT
<213> ORGANISM: Artificial
<220> FEATURE:
<223> OTHER INFORMATION: Synthetic

<400> SEQUENCE: 25

His Gly Asp Tyr Asp Asp Asp Asp Ala Met Asp Tyr
1 5 10

<210> SEQ ID NO 26
<211> LENGTH: 11
<212> TYPE: PRT
<213> ORGANISM: Artificial
<220> FEATURE:
<223> OTHER INFORMATION: Synthetic

<400> SEQUENCE: 26

Arg Ala Ser Glu Asn Ile Tyr Ser Tyr Leu Ala
1 5 10

<210> SEQ ID NO 27
<211> LENGTH: 7
<212> TYPE: PRT
<213> ORGANISM: Artificial
<220> FEATURE:
<223> OTHER INFORMATION: Synthetic

<400> SEQUENCE: 27

Asn Ala Glu Thr Leu Thr Glu
1 5

<210> SEQ ID NO 28
<211> LENGTH: 9
<212> TYPE: PRT
<213> ORGANISM: Artificial
<220> FEATURE:
<223> OTHER INFORMATION: Synthetic

<400> SEQUENCE: 28

Gln His His Tyr Gly Thr Pro Leu Thr
1 5

<210> SEQ ID NO 29
<211> LENGTH: 451
<212> TYPE: PRT
<213> ORGANISM: Artificial
<220> FEATURE:
<223> OTHER INFORMATION: Synthetic

<400> SEQUENCE: 29

Glu Val Lys Leu Val Glu Ser Gly Gly Gly Leu Val Gln Pro Gly Gly
1 5 10 15

Ser Leu Lys Leu Phe Cys Ala Ala Ser Gly Phe Thr Phe Thr Ser Tyr
20 25 30

Ser Met Ser Trp Val Arg Gln Thr Pro Glu Lys Arg Leu Glu Trp Val
35 40 45

Ala Tyr Ile Ser Tyr Asp Gly Gly Ser Ala Tyr Tyr Pro Asp Thr Val
50 55 60

Lys Gly Arg Phe Ser Ile Ser Arg Asp Asn Ala Lys Lys Thr Leu Tyr

-continued

```
65                  70                  75                  80

Leu Gln Met Ser Ser Leu Lys Ser Glu Asp Thr Ala Met Tyr Tyr Cys
                85                  90                  95

Ala Arg His Gly Asp Tyr Asp Asp Asp Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 30
<211> LENGTH: 1356
<212> TYPE: DNA
<213> ORGANISM: Artificial
<220> FEATURE:
<223> OTHER INFORMATION: Synthetic

<400> SEQUENCE: 30

```
gaggtgaagc tggtggagtc tgggggaggc ttggtacagc ctgggggtc cctgaaactc      60
ttctgtgcag cctctggatt cacctttacc agctattcca tgagctgggt ccgccagact    120
ccagagaaga ggctggagtg ggtcgcatac attagttatg atggtggtag cgcctactac    180
cctgacactg tgaagggccg gttctccatc tccagagaca atgccaagaa aaccctgtat    240
ctgcaaatga gcagcctgaa gtctgaggac acggccatgt attactgtgc aagacatgga    300
gactatgacg acgacgacgc gatggactac tggggccaag gaacctcagt caccgtctcc    360
tcagcctcca ccaaaggccc cagcgtcttc cccctcgcgc cgtcctccaa gtccacctcg    420
ggtggcaccg ccgccctggg ctgcctggtc aaggactact tcccggagcc tgtgaccgtg    480
tcctggaact cgggcgcgct cacgagcggc gtacacacct tcccggcggt gctccagtcc    540
tccgggctgt actcgctctc gtcggtcgtc acggtgccgt cctcctccct gggcacccag    600
acctacatct gcaacgtgaa ccacaagccg tccaacacca aggtggataa gaaggtcgag    660
cccaagtcgt gcgacaagac gcacacgtgc ccgccgtgcc cggccccgga gctgctgggc    720
ggcccctcgg tcttcctgtt ccccccgaag cccaaggata cgctgatgat ctcccgcacc    780
ccggaggtca cctgcgtggt ggtggacgtc tcccacgagg acccggaggt gaaattcaac    840
tggtacgtcg acggagtgga ggtccacaac gccaagacca agccccggga ggagcagtac    900
aactccacgt accgcgtcgt ctccgtcctg accgtcctcc accaggactg gctgaacggc    960
aaggagtaca agtgtaaggt ctccaacaag gcgctgcccg cccccatcga gaagaccatc   1020
tccaaggcaa agggtcagcc gcgggagccg caggtctata ccctcccccc gtcccgcgac   1080
gagctgacga aaaaccaggt ctccctgacc tgcctggtga agggtttcta cccctccgac   1140
atcgcggtcg agtgggagtc gaacggccag ccggagaaca actacaagac caccccccc    1200
gtgctcgaca gtgacggctc gttcttcctg tactcgaagc tgaccgtcga caagtcgcgc   1260
tggcagcagg gcaacgtctt ctcgtgctcc gttatgcacg aggccctgca caaccactac   1320
acgcagaaga gtctttcgct gtccccgggg aagtga                              1356
```

<210> SEQ ID NO 31
<211> LENGTH: 451
<212> TYPE: PRT
<213> ORGANISM: Artificial
<220> FEATURE:
<223> OTHER INFORMATION: Synthetic

<400> SEQUENCE: 31

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Lys Thr Leu Tyr
65                  70                  75                  80

Leu Gln Met Ser Ser Leu Lys Ser Glu Asp Thr Ala Met Tyr Tyr Cys
                85                  90                  95
```

-continued

```
Ala Arg His Gly Asp Tyr Asp Asp Asp Asp Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 32
<211> LENGTH: 1356
<212> TYPE: DNA
<213> ORGANISM: Artificial
<220> FEATURE:
<223> OTHER INFORMATION: Synthetic

<400> SEQUENCE: 32

-continued

```
gaggtgaagc tggtggagtc tgggggaggc ttggtacagc ctggggggtc cctgagactc      60
tcctgtgcag cctctggatt cacctttacc agctattcca tgagctgggt ccgccaggct     120
ccagggaagg ggctggagtg ggtcgcatac attagttatg atggtggtag cgcctactac     180
cctgacactg tgaagggccg gttcaccatc tccagagaca attccaagaa aaccctgtat     240
ctgcaaatga gcagcctgaa gtctgaggac acggccatgt attactgtgc aagacatgga     300
gactatgacg acgacgacgc gatggactac tggggccaag gaacctcagt caccgtctcc     360
tcagcctcca ccaaaggccc cagcgtcttc cccctcgcgc cgtcctccaa gtccacctcg     420
ggtggcaccg ccgccctggg ctgcctggtc aaggactact tcccggagcc tgtgaccgtg     480
tcctggaact cgggcgcgct cacgagcggc gtacacacct tcccggcggt gctccagtcc     540
tccgggctgt actcgctctc gtcggtcgtc acggtgccgt cctcctccct gggcacccag     600
acctacatct gcaacgtgaa ccacaagccg tccaacacca aggtggataa gaaggtcgag     660
cccaagtcgt gcgacaagac gcacacgtgc ccgccgtgcc cggccccgga gctgctgggc     720
ggcccctcgg tcttcctgtt ccccccgaag cccaaggata cgctgatgat ctcccgcacc     780
ccggaggtca cctgcgtggt ggtggacgtc tcccacgagg acccggaggt gaaattcaac     840
tggtacgtcg acggagtgga ggtccacaac gccaagacca agccccggga ggagcagtac     900
aactccacgt accgcgtcgt ctccgtcctg accgtcctcc accaggactg gctgaacggc     960
aaggagtaca agtgtaaggt ctccaacaag gcgctgcccg cccccatcga gaagaccatc    1020
tccaaggcaa agggtcagcc gcgggagccg caggtctata ccctcccccc gtcccgcgac    1080
gagctgacga aaaaccaggt ctccctgacc tgcctggtga agggtttcta cccctccgac    1140
atcgcggtcg agtgggagtc gaacggccag ccggagaaca actacaagac caccccccc    1200
gtgctcgaca gtgacggctc gttcttcctg tactcgaagc tgaccgtcga caagtcgcgc    1260
tggcagcagg gcaacgtctt ctcgtgctcc gttatgcacg aggccctgca caaccactac    1320
acgcagaaga gtctttcgct gtccccgggg aagtga                              1356
```

<210> SEQ ID NO 33
<211> LENGTH: 451
<212> TYPE: PRT
<213> ORGANISM: Artificial
<220> FEATURE:
<223> OTHER INFORMATION: Synthetic

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser Ala Ser Thr Lys Gly Pro Ser
        115                 120                 125
```

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 34
<211> LENGTH: 1356
<212> TYPE: DNA
<213> ORGANISM: Artificial
<220> FEATURE:
<223> OTHER INFORMATION: Synthetic

<400> SEQUENCE: 34

```
gaggtgcagc tggtggagtc tgggggaggc ttggtacagc ctgggggtc cctgagactc      60

tcctgtgcag cctctggatt cacctttacc agctattcca tgagctgggt ccgccaggct    120

ccagggaagg ggctggagtg ggtcgcatac attagttatg atggtggtag cgcctactac    180
```

```
cctgacactg tgaagggccg gttcaccatc tccagagaca attccaagaa caccctgtat    240

ctgcaaatga gcagcctgaa gtctgaggac acggccatgt attactgtgc aagacatgga    300

gactatgacg acgacgacgc gatggactac tggggccaag gaaccctggt caccgtctcc    360

tcagcctcca ccaaaggccc cagcgtcttc cccctcgcgc cgtcctccaa gtccacctcg    420

ggtggcaccg ccgccctggg ctgcctggtc aaggactact tcccggagcc tgtgaccgtg    480

tcctggaact cgggcgcgct cacgagcggc gtacacacct tcccggcggt gctccagtcc    540

tccgggctgt actcgctctc gtcggtcgtc acggtgccgt cctcctccct gggcacccag    600

acctacatct gcaacgtgaa ccacaagccg tccaacacca aggtggataa gaaggtcgag    660

cccaagtcgt gcgacaagac gcacacgtgc ccgccgtgcc cggccccgga gctgctgggc    720

ggcccctcgg tcttcctgtt ccccccgaag cccaaggata cgctgatgat ctcccgcacc    780

ccggaggtca cctgcgtggt ggtggacgtc tcccacgagg acccggaggt gaaattcaac    840

tggtacgtcg acggagtgga ggtccacaac gccaagacca agccccggga ggagcagtac    900

aactccacgt accgcgtcgt ctccgtcctg accgtcctcc accaggactg gctgaacggc    960

aaggagtaca agtgtaaggt ctccaacaag gcgctgcccg cccccatcga gaagaccatc   1020

tccaaggcaa agggtcagcc gcgggagccg caggtctata ccctcccccc gtcccgcgac   1080

gagctgacga aaaaccaggt ctccctgacc tgcctggtga agggtttcta cccctccgac   1140

atcgcggtcg agtgggagtc gaacggccag ccggagaaca actacaagac caccccccc    1200

gtgctcgaca gtgacggctc gttcttcctg tactcgaagc tgaccgtcga caagtcgcgc   1260

tggcagcagg gcaacgtctt ctcgtgctcc gttatgcacg aggccctgca caaccactac   1320

acgcagaaga gtctttcgct gtccccgggg aagtga                              1356
```

<210> SEQ ID NO 35
<211> LENGTH: 451
<212> TYPE: PRT
<213> ORGANISM: Artificial
<220> FEATURE:
<223> OTHER INFORMATION: Synthetic

<400> SEQUENCE: 35

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
```

-continued

```
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 36
<211> LENGTH: 1356
<212> TYPE: DNA
<213> ORGANISM: Artificial
<220> FEATURE:
<223> OTHER INFORMATION: Synthetic

<400> SEQUENCE: 36

```
gaggtgaagc tggtggagtc tgggggaggc ttggtacagc ctggggggtc cctgagactc      60

tcctgtgcag cctctggatt cacctttacc agctattcca tgagctgggt ccgccaggct     120

ccagggaagg ggctggagtg ggtcgcatac attagttatg atggtggtag cgcctactat     180

cctgacactg tgaagggccg gttcaccatc tccagagaca attccaagaa aaccctgtat     240

ctgcaaatga acagcctgag agccgaggac acggccgtat attactgtgc aagacatgga     300
```

-continued

```
gactatgacg acgacgacgc gatggactac tggggccaag gaaccctggt caccgtctcc    360

tcagcctcca ccaaaggccc cagcgtcttc cccctcgcgc cgtcctccaa gtccacctcg    420

ggtggcaccg ccgccctggg ctgcctggtc aaggactact tcccggagcc tgtgaccgtg    480

tcctggaact cgggcgcgct cacgagcggc gtacacacct tcccggcggt gctccagtcc    540

tccgggctgt actcgctctc gtcggtcgtc acggtgccgt cctcctccct gggcacccag    600

acctacatct gcaacgtgaa ccacaagccg tccaacacca aggtggataa gaaggtcgag    660

cccaagtcgt gcgacaagac gcacacgtgc ccgccgtgcc cggccccgga gctgctgggc    720

ggcccctcgg tcttcctgtt ccccccgaag cccaaggata cgctgatgat ctcccgcacc    780

ccggaggtca cctgcgtggt ggtggacgtc tcccacgagg acccggaggt gaaattcaac    840

tggtacgtcg acggagtgga ggtccacaac gccaagacca agccccggga ggagcagtac    900

aactccacgt accgcgtcgt ctccgtcctg accgtcctcc accaggactg gctgaacggc    960

aaggagtaca agtgtaaggt ctccaacaag gcgctgcccg cccccatcga gaagaccatc   1020

tccaaggcaa agggtcagcc gcgggagccg caggtctata ccctcccccc gtcccgcgac   1080

gagctgacga aaaaccaggt ctccctgacc tgcctggtga agggtttcta cccctccgac   1140

atcgcggtcg agtgggagtc gaacggccag ccggagaaca actacaagac caccccccc    1200

gtgctcgaca gtgacggctc gttcttcctg tactcgaagc tgaccgtcga caagtcgcgc   1260

tggcagcagg gcaacgtctt ctcgtgctcc gttatgcacg aggccctgca caaccactac   1320

acgcagaaga gtctttcgct gtccccgggg aagtga                             1356


<210> SEQ ID NO 37
<211> LENGTH: 451
<212> TYPE: PRT
<213> ORGANISM: Artificial
<220> FEATURE:
<223> OTHER INFORMATION: Synthetic

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 38
<211> LENGTH: 1356
<212> TYPE: DNA
<213> ORGANISM: Artificial
<220> FEATURE:
<223> OTHER INFORMATION: Synthetic

<400> SEQUENCE: 38

gaggtgcagc tggtggagtc tgggggaggc ttggtacagc ctgggggtc cctgagactc      60

tcctgtgcag cctctggatt cacctttacc agctattcca tgagctgggt ccgccaggct    120

ccagggaagg ggctggagtg ggtcgcatac attagttatg atggtggtag cgcctactat    180

cctgacactg tgaagggccg gttcaccatc tccagagaca attccaagaa caccctgtat    240

ctgcaaatga acagcctgag agccgaggac acggccgtat attactgtgc aagacatgga    300

gactatgacg acgacgacgc gatggactac tggggccaag gaaccctggt caccgtctcc    360

tcagcctcca ccaaaggccc cagcgtcttc cccctcgcgc cgtcctccaa gtccacctcg    420

ggtggcaccg ccgccctggg ctgcctggtc aaggactact tcccggagcc tgtgaccgtg    480
```

```
tcctggaact cgggcgcgct cacgagcggc gtacacacct tcccggcggt gctccagtcc    540

tccgggctgt actcgctctc gtcggtcgtc acggtgccgt cctcctccct gggcacccag    600

acctacatct gcaacgtgaa ccacaagccg tccaacacca aggtggataa gaaggtcgag    660

cccaagtcgt gcgacaagac gcacacgtgc ccgccgtgcc cggcccccgga gctgctgggc    720

ggcccctcgg tcttcctgtt ccccccgaag cccaaggata cgctgatgat ctcccgcacc    780

ccggaggtca cctgcgtggt ggtggacgtc tcccacgagg acccggaggt gaaattcaac    840

tggtacgtcg acggagtgga ggtccacaac gccaagacca agccccggga ggagcagtac    900

aactccacgt accgcgtcgt ctccgtcctg accgtcctcc accaggactg gctgaacggc    960

aaggagtaca agtgtaaggt ctccaacaag gcgctgcccg cccccatcga gaagaccatc   1020

tccaaggcaa agggtcagcc gcgggagccg caggtctata ccctcccccc gtcccgcgac   1080

gagctgacga aaaaccaggt ctccctgacc tgcctggtga agggtttcta cccctccgac   1140

atcgcggtcg agtgggagtc gaacggccag ccggagaaca actacaagac caccccccc   1200

gtgctcgaca gtgacggctc gttcttcctg tactcgaagc tgaccgtcga caagtcgcgc   1260

tggcagcagg gcaacgtctt ctcgtgctcc gttatgcacg aggccctgca caaccactac   1320

acgcagaaga gtctttcgct gtccccgggg aagtga                              1356
```

```
<210> SEQ ID NO 39
<211> LENGTH: 451
<212> TYPE: PRT
<213> ORGANISM: Artificial
<220> FEATURE:
<223> OTHER INFORMATION: Synthetic

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Met Ser Trp Val Arg Gln Ala Pro Gly Lys Gly Leu Glu Trp Val
        35                  40                  45

Ser Tyr Ile Ser Tyr Asp Gly Gly Ser Ala Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Asp Asp Asp Asp Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 40
<211> LENGTH: 1356
<212> TYPE: DNA
<213> ORGANISM: Artificial
<220> FEATURE:
<223> OTHER INFORMATION: Synthetic

<400> SEQUENCE: 40

```
gaggtgcagc tggtggagtc tgggggaggc ttggtacagc ctggggggtc cctgagactc      60

tcctgtgcag cctctggatt cacctttacc agctattcca tgagctgggt ccgccaggct     120

ccagggaagg ggctggagtg ggtgtcttac attagttatg atggtggtag cgcctactat     180

cctgacactg tgaagggccg gttcaccatc tccagagaca attccaagaa caccctgtat     240

ctgcaaatga acagcctgag agccgaggac acggccgtat attactgtgc aagacatgga     300

gactatgacg acgacgacgc gatggactac tggggccaag gaaccctggt caccgtctcc     360

tcagcctcca ccaaaggccc cagcgtcttc cccctcgcgc cgtcctccaa gtccacctcg     420

ggtggcaccg ccgccctggg ctgcctggtc aaggactact tcccggagcc tgtgaccgtg     480

tcctggaact cgggcgcgct cacgagcggc gtacacacct tcccggcggt gctccagtcc     540

tccgggctgt actcgctctc gtcggtcgtc acggtgccgt cctcctccct gggcacccag     600
```

-continued

```
acctacatct gcaacgtgaa ccacaagccg tccaacacca aggtggataa gaaggtcgag    660

cccaagtcgt gcgacaagac gcacacgtgc ccgccgtgcc cggccccgga gctgctgggc    720

ggcccctcgg tcttcctgtt ccccccgaag cccaaggata cgctgatgat ctcccgcacc    780

ccggaggtca cctgcgtggt ggtggacgtc tcccacgagg acccggaggt gaaattcaac    840

tggtacgtcg acggagtgga ggtccacaac gccaagacca agccccggga ggagcagtac    900

aactccacgt accgcgtcgt ctccgtcctg accgtcctcc accaggactg gctgaacggc    960

aaggagtaca agtgtaaggt ctccaacaag gcgctgcccg cccccatcga gaagaccatc   1020

tccaaggcaa agggtcagcc gcgggagccg caggtctata ccctcccccc gtcccgcgac   1080

gagctgacga aaaaccaggt ctccctgacc tgcctggtga agggtttcta cccctccgac   1140

atcgcggtcg agtgggagtc gaacggccag ccggagaaca actacaagac caccccccc    1200

gtgctcgaca gtgacggctc gttcttcctg tactcgaagc tgaccgtcga caagtcgcgc   1260

tggcagcagg gcaacgtctt ctcgtgctcc gttatgcacg aggccctgca caaccactac   1320

acgcagaaga gtctttcgct gtccccgggg aagtga                             1356
```

```
<210> SEQ ID NO 41
<211> LENGTH: 214
<212> TYPE: PRT
<213> ORGANISM: Artificial
<220> FEATURE:
<223> OTHER INFORMATION: Synthetic

<400> SEQUENCE: 41

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Gly Thr Pro Leu
                85                  90                  95

Thr Phe Gly Ala Gly Thr Lys Leu Asp Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 42
<211> LENGTH: 645
<212> TYPE: DNA
<213> ORGANISM: Artificial
<220> FEATURE:
<223> OTHER INFORMATION: Synthetic

<400> SEQUENCE: 42
gacatccaga tgacccagtc tccagcctcc ctgtctgcat ctgtaggaga aactgtcacc 60
atcacttgcc gggcaagtga gaacatttac agctatttag catggtatca gcagaaacag 120
gggaaatctc ctcagctcct ggtctataat gcagaaacct tgacagaagg ggtcccatca 180
aggttcagcg gcagtggatc tgggacacaa ttctctctca agatcaacag tctgcaacct 240
gaagattttg ggaattacta ctgtcaacat cattacggta ccccgctcac attcggcgct 300
gggaccaagc tggatctgaa acgaacggtg gccgcgccga gcgtcttcat cttcccgcct 360
tccgacgagc agctcaagtc cgggaccgcc tccgtagtat gcctcctcaa taacttctac 420
ccccgggagg cgaaggtcca gtggaaggtc gacaacgccc tccaatcggg caactcccag 480
gagtcggtga ccgagcagga ttccaaggac tcgacctaca gtctaagctc caccctcaca 540
ctgtcgaagg cggactacga gaagcacaag gtgtacgcct gcgaggtcac ccaccagggc 600
ctgagcagcc cggtcaccaa gtccttcaac cggggcgagt gctga 645

<210> SEQ ID NO 43
<211> LENGTH: 214
<212> TYPE: PRT
<213> ORGANISM: Artificial
<220> FEATURE:
<223> OTHER INFORMATION: Synthetic

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Gln Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asn Tyr Tyr Cys Gln His His Tyr Gly Thr Pro Leu
                85                  90                  95

Thr Phe Gly Gln Gly Thr Lys Leu Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 645
<212> TYPE: DNA
<213> ORGANISM: Artificial
<220> FEATURE:
<223> OTHER INFORMATION: Synthetic

<400> SEQUENCE: 44
gacatccaga tgacccagtc tccatcctcc ctgtctgcat ctgtaggaga cagagtcacc 60
atcacttgcc gggcaagtga gaacatttac agctatttag catggtatca gcagaaacag 120
gggaaagccc ctaagctcct ggtctataat gcagaaacct tgacagaagg ggtcccatca 180
aggttcagcg gcagtggatc tgggacagat ttcactctca ccatcagcag tctgcaacct 240
gaagattttg caaattacta ctgtcaacat cattacggta ccccgctcac attcggccaa 300
gggaccaagc tggatatcaa acgaacggtg gccgcgccga gcgtcttcat cttcccgcct 360
tccgacgagc agctcaagtc cgggaccgcc tccgtagtat gcctcctcaa taacttctac 420
ccccgggagg cgaaggtcca gtggaaggtc gacaacgccc tccaatcggg caactcccag 480
gagtcggtga ccgagcagga ttccaaggac tcgacctaca gtctaagctc caccctcaca 540
ctgtcgaagg cggactacga gaagcacaag gtgtacgcct gcgaggtcac ccaccagggc 600
ctgagcagcc cggtcaccaa gtccttcaac cggggcgagt gctga 645

<210> SEQ ID NO 45
<211> LENGTH: 214
<212> TYPE: PRT
<213> ORGANISM: Artificial
<220> FEATURE:
<223> OTHER INFORMATION: Synthetic

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asn Tyr Tyr Cys Gln His His Tyr Gly Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 46
<211> LENGTH: 645
<212> TYPE: DNA
<213> ORGANISM: Artificial
<220> FEATURE:
<223> OTHER INFORMATION: Synthetic

<400> SEQUENCE: 46

gacatccaga tgacccagtc tccatcctcc ctgtctgcat ctgtaggaga cagagtcacc      60

atcacttgcc gggcaagtga gaacatttac agctatttag catggtatca gcagaaacca     120

gggaaagccc ctaagctcct ggtctataat gcagaaacct tgacagaagg ggtcccatca     180

aggttcagcg gcagtggatc tgggacagat ttcactctca ccatcagcag tctgcaacct     240

gaagattttg caaattacta ctgtcaacat cattacggta ccccgctcac attcggccaa     300

gggaccaagc tggaaatcaa acgaacggtg gccgcgccga gcgtcttcat cttcccgcct     360

tccgacgagc agctcaagtc cgggaccgcc tccgtagtat gcctcctcaa taacttctac     420

ccccgggagg cgaaggtcca gtggaaggtc gacaacgccc tccaatcggg caactcccag     480

gagtcggtga ccgagcagga ttccaaggac tcgacctaca gtctaagctc caccctcaca     540

ctgtcgaagg cggactacga gaagcacaag gtgtacgcct gcgaggtcac ccaccagggc     600

ctgagcagcc cggtcaccaa gtccttcaac cggggcgagt gctga                     645


<210> SEQ ID NO 47
<211> LENGTH: 214
<212> TYPE: PRT
<213> ORGANISM: Artificial
<220> FEATURE:
<223> OTHER INFORMATION: Synthetic

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 48
<211> LENGTH: 645
<212> TYPE: DNA
<213> ORGANISM: Artificial
<220> FEATURE:
<223> OTHER INFORMATION: Synthetic

<400> SEQUENCE: 48

gacatccaga tgacccagtc tccatcctcc ctgtctgcat ctgtaggaga cagagtcacc      60

atcacttgcc gggcaagtga gaacatttac agctatttag catggtatca gcagaaacca     120

gggaaagccc ctaagctcct ggtctataat gcagaaacct tgacagaagg ggtcccatca     180

aggttcagcg gcagtggatc tgggacagat ttcactctca ccatcagcag tctgcaacct     240

gaagattttg caacttacta ctgtcaacat cattacggta ccccgctcac attcggccaa     300

gggaccaagc tggaaatcaa acgaacggtg gccgcgccga gcgtcttcat cttcccgcct     360

tccgacgagc agctcaagtc cgggaccgcc tccgtagtat gcctcctcaa taacttctac     420

ccccgggagg cgaaggtcca gtggaaggtc gacaacgccc tccaatcggg caactcccag     480

gagtcggtga ccgagcagga ttccaaggac tcgacctaca gtctaagctc caccctcaca     540

ctgtcgaagg cggactacga gaagcacaag gtgtacgcct gcgaggtcac ccaccagggc     600

ctgagcagcc cggtcaccaa gtccttcaac cggggcgagt gctga                      645


<210> SEQ ID NO 49
<211> LENGTH: 214
<212> TYPE: PRT
<213> ORGANISM: Artificial
<220> FEATURE:
<223> OTHER INFORMATION: Synthetic

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Asn Trp Tyr Gln Gln Lys Pro Gly Lys Ala Pro Lys Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 50
<211> LENGTH: 645
<212> TYPE: DNA
<213> ORGANISM: Artificial
<220> FEATURE:
<223> OTHER INFORMATION: Synthetic

<400> SEQUENCE: 50

gacatccaga tgacccagtc tccatcctcc ctgtctgcat ctgtaggaga cagagtcacc     60

atcacttgcc gggcaagtga gaacatttac agctatttaa attggtatca gcagaaacca    120

gggaaagccc ctaagctcct ggtctataat gcagaaacct tgacagaagg ggtcccatca    180

aggttcagcg gcagtggatc tgggacagat ttcactctca ccatcagcag tctgcaacct    240

gaagattttg caacttacta ctgtcaacat cattacggta ccccgctcac attcggccaa    300

gggaccaagc tggaaatcaa acgaacggtg gccgcgccga gcgtcttcat cttcccgcct    360

tccgacgagc agctcaagtc cgggaccgcc tccgtagtat gcctcctcaa taacttctac    420

ccccgggagg cgaaggtcca gtggaaggtc gacaacgccc tccaatcggg caactcccag    480

gagtcggtga ccgagcagga ttccaaggac tcgacctaca gtctaagctc caccctcaca    540

ctgtcgaagg cggactacga gaagcacaag gtgtacgcct gcgaggtcac ccaccagggc    600

ctgagcagcc cggtcaccaa gtccttcaac cggggcgagt gctga                    645


<210> SEQ ID NO 51
<211> LENGTH: 8
<212> TYPE: PRT
<213> ORGANISM: Artificial
<220> FEATURE:
<223> OTHER INFORMATION: Synthetic

<400> SEQUENCE: 51

Gly Phe Thr Phe Ser Ser Tyr Ser
1               5


<210> SEQ ID NO 52
<211> LENGTH: 8
<212> TYPE: PRT
<213> ORGANISM: Artificial
<220> FEATURE:
<223> OTHER INFORMATION: Synthetic

<400> SEQUENCE: 52

Ile Ser Ser Ser Ser Ser Tyr Ile
1               5


<210> SEQ ID NO 53
```

<211> LENGTH: 19
<212> TYPE: PRT
<213> ORGANISM: Artificial
<220> FEATURE:
<223> OTHER INFORMATION: Synthetic

<400> SEQUENCE: 53

Ala Arg Asp Gly Gly Arg Thr Ser Tyr Thr Ala Thr Ala His Asn Trp
1               5                   10                  15

Phe Asp Pro

<210> SEQ ID NO 54
<211> LENGTH: 9
<212> TYPE: PRT
<213> ORGANISM: Artificial
<220> FEATURE:
<223> OTHER INFORMATION: Synthetic

<400> SEQUENCE: 54

Phe Thr Phe Ser Ser Tyr Ser Met Asn
1               5

<210> SEQ ID NO 55
<211> LENGTH: 17
<212> TYPE: PRT
<213> ORGANISM: Artificial
<220> FEATURE:
<223> OTHER INFORMATION: Synthetic

<400> SEQUENCE: 55

Ser Ile Ser Ser Ser Ser Ser Tyr Ile Tyr Tyr Ala Asp Ser Val Lys
1               5                   10                  15

Gly

<210> SEQ ID NO 56
<211> LENGTH: 19
<212> TYPE: PRT
<213> ORGANISM: Artificial
<220> FEATURE:
<223> OTHER INFORMATION: Synthetic

<400> SEQUENCE: 56

Ala Arg Asp Gly Gly Arg Thr Ser Tyr Thr Ala Thr Ala His Asn Trp
1               5                   10                  15

Phe Asp Pro

<210> SEQ ID NO 57
<211> LENGTH: 126
<212> TYPE: PRT
<213> ORGANISM: Artificial
<220> FEATURE:
<223> OTHER INFORMATION: Synthetic

<400> SEQUENCE: 57

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr

```
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
        115                 120                 125
```

<210> SEQ ID NO 58
<211> LENGTH: 378
<212> TYPE: DNA
<213> ORGANISM: Artificial
<220> FEATURE:
<223> OTHER INFORMATION: Synthetic

<400> SEQUENCE: 58

```
gaggtgcagc tggtggagtc tgggggaggc ctggtcaagc ctggggggtc cctgagactc      60

tcctgtgcag cctctggatt caccttcagt agctatagca tgaactgggt ccgccaggct     120

ccagggaagg ggctggagtg ggtctcatcc attagtagta gtagtagtta catatactac     180

gcagactcag tgaagggccg attcaccatc tccagagaca acgccaagaa ctcactgtat     240

ctgcaaatga acagcctgag agccgaggac acggcggtgt actactgcgc cagagatggt     300

ggaagaacgt cctacaccgc cacagcccac aattggttcg acccctgggg acagggtaca     360

ttggtcaccg tctcctca                                                   378
```

<210> SEQ ID NO 59
<211> LENGTH: 12
<212> TYPE: PRT
<213> ORGANISM: Artificial
<220> FEATURE:
<223> OTHER INFORMATION: Synthetic

<400> SEQUENCE: 59

```
Gln Ser Val Leu Phe Ser Ser Asn Asn Lys Asn Tyr
1               5                   10
```

<210> SEQ ID NO 60
<211> LENGTH: 3
<212> TYPE: PRT
<213> ORGANISM: Artificial
<220> FEATURE:
<223> OTHER INFORMATION: Synthetic

<400> SEQUENCE: 60

```
Trp Ala Ser
1
```

<210> SEQ ID NO 61
<211> LENGTH: 9
<212> TYPE: PRT
<213> ORGANISM: Artificial
<220> FEATURE:
<223> OTHER INFORMATION: Synthetic

<400> SEQUENCE: 61

```
Gln Gln His Ala Ser Ala Pro Pro Thr
1               5
```

<210> SEQ ID NO 62
<211> LENGTH: 17
<212> TYPE: PRT
<213> ORGANISM: Artificial

<220> FEATURE:
<223> OTHER INFORMATION: Synthetic

<400> SEQUENCE: 62

Lys Ser Ser Gln Ser Val Leu Phe Ser Ser Asn Asn Lys Asn Tyr Leu
1 5 10 15

Ala

<210> SEQ ID NO 63
<211> LENGTH: 7
<212> TYPE: PRT
<213> ORGANISM: Artificial
<220> FEATURE:
<223> OTHER INFORMATION: Synthetic

<400> SEQUENCE: 63

Trp Ala Ser Thr Arg Glu Ser
1 5

<210> SEQ ID NO 64
<211> LENGTH: 9
<212> TYPE: PRT
<213> ORGANISM: Artificial
<220> FEATURE:
<223> OTHER INFORMATION: Synthetic

<400> SEQUENCE: 64

Gln Gln His Ala Ser Ala Pro Pro Thr
1 5

<210> SEQ ID NO 65
<211> LENGTH: 113
<212> TYPE: PRT
<213> ORGANISM: Artificial
<220> FEATURE:
<223> OTHER INFORMATION: Synthetic

<400> SEQUENCE: 65

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Phe Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

His Ala Ser Ala Pro Pro Thr Phe Gly Gly Gly Thr Lys Val Glu Ile
100 105 110

Lys

<210> SEQ ID NO 66
<211> LENGTH: 339
<212> TYPE: DNA
<213> ORGANISM: Artificial
<220> FEATURE:
<223> OTHER INFORMATION: Synthetic

<400> SEQUENCE: 66

-continued gacatcgtga tgacccagtc tccagactcc ctggctgtgt ctctgggcga gagggccacc 60
atcaactgca agtccagcca gagtgtttta ttcagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcagca cgccagtgcc 300
cctcctactt ttggcggagg gaccaaggtt gagatcaaa 339

<210> SEQ ID NO 67
<211> LENGTH: 456
<212> TYPE: PRT
<213> ORGANISM: Artificial
<220> FEATURE:
<223> OTHER INFORMATION: Synthetic

<400> SEQUENCE: 67

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Gly Arg Thr Ser Tyr Thr Ala Thr Ala His Asn Trp
100 105 110

Phe Asp Pro Trp Gly Gln Gly Thr Leu Val Thr Val Ser Ser Ala Ser
115 120 125

Thr Lys Gly Pro Ser Val Phe Pro Leu Ala Pro Ser Ser Lys Ser Thr
130 135 140

Ser Gly Gly Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Ser Leu Gly Thr Gln Thr Tyr Ile
195 200 205

Cys Asn Val Asn His Lys Pro Ser Asn Thr Lys Val Asp Lys Lys Val
210 215 220

Glu Pro Lys Ser Cys Asp Lys Thr His Thr Cys Pro Pro Cys Pro Ala
225 230 235 240

Pro Glu Leu Leu Gly Gly Pro Ser Val Phe Leu Phe Pro Pro Lys Pro
245 250 255

Lys Asp Thr Leu Met Ile Ser Arg Thr Pro Glu Val Thr Cys Val Val
260 265 270

Val Asp Val Ser His Glu Asp Pro Glu Val Lys Phe Asn Trp Tyr Val
275 280 285

Asp Gly Val Glu Val His Asn Ala Lys Thr Lys Pro Arg Glu Glu Gln
290 295 300

```
Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 68
<211> LENGTH: 1368
<212> TYPE: DNA
<213> ORGANISM: Artificial
<220> FEATURE:
<223> OTHER INFORMATION: Synthetic

<400> SEQUENCE: 68

gaggtgcagc tggtggagtc tggggggaggc ctggtcaagc ctgggggtc cctgagactc     60

tcctgtgcag cctctggatt caccttcagt agctatagca tgaactgggt ccgccaggct    120

ccagggaagg ggctggagtg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc gagcaccaaa ggcccgagcg tgtttccgct ggcgccgagc    420

agcaaaagca ccagcggcgg caccgcggcg ctgggctgcc tggtgaaaga ttattttccg    480

gaaccggtga ccgtgagctg gaacagcggc gcgctgacca gcggcgtgca tacctttccg    540

gcggtgctgc agagcagcgg cctgtatagc ctgagcagcg tggtgaccgt gccgagcagc    600

agcctgggca cccagaccta tatttgcaac gtgaaccata aaccgagcaa caccaaagtg    660

gataaaaaag tggaaccgaa aagctgcgat aaaacccata cctgcccgcc gtgcccggcg    720

ccggaactgc tgggcggccc gagcgtgttt ctgtttccgc cgaaaccgaa agataccctg    780

atgattagcc gcaccccgga agtgacctgc gtggtggtgg atgtgagcca tgaagatccg    840

gaagtgaaat ttaactggta tgtggatggc gtggaagtgc ataacgcgaa aaccaaaccg    900

cgcgaagaac agtataacag cacctatcgc gtggtgagcg tgctgaccgt gctgcatcag    960

gattggctga acggcaaaga atataaatgc aaagtgagca acaaagcgct gccggcgccg   1020

attgaaaaaa ccattagcaa agcgaaaggc cagccgcgcg aaccgcaggt gtataccctg   1080

ccgccgagcc gcgatgaact gaccaaaaac caggtgagcc tgacctgcct ggtgaaaggc   1140

ttttatccga gcgatattgc ggtggaatgg gaaagcaacg gccagccgga aaacaactat   1200
```

```
aaaaccaccc cgccggtgct ggatagcgat ggcagctttt ttctgtatag caaactgacc   1260

gtggataaaa gccgctggca gcagggcaac gtgtttagct gcagcgtgat gcatgaagcg   1320

ctgcataacc attataccca gaaaagcctg agcctgagcc cgggcaaa                1368


<210> SEQ ID NO 69
<211> LENGTH: 220
<212> TYPE: PRT
<213> ORGANISM: Artificial
<220> FEATURE:
<223> OTHER INFORMATION: Synthetic

<400> SEQUENCE: 69

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 70
<211> LENGTH: 660
<212> TYPE: DNA
<213> ORGANISM: Artificial
<220> FEATURE:
<223> OTHER INFORMATION: Synthetic

<400> SEQUENCE: 70

gacatcgtga tgacccagtc tccagactcc ctggctgtgt ctctgggcga gagggccacc     60

atcaactgca agtccagcca gagtgtttta ttcagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcagca cgccagtgcc    300
```

```
cctcctactt ttggcggagg gaccaaggtt gagatcaaac gtacggtggc cgctccctcc    360

gtgttcatct tcccaccctc cgacgagcag ctgaagtccg gcaccgcctc cgtcgtgtgc    420

ctgctgaaca acttctaccc tcgcgaggcc aaagtgcagt ggaaagtgga caacgccctg    480

cagtccggca actcccagga atccgtcacc gagcaggact ccaaggacag cacctactcc    540

ctgtcctcca ccctgaccct gtccaaggcc gactacgaga agcacaaagt gtacgcctgc    600

gaagtgaccc accagggcct gtccagcccc gtgaccaagt ccttcaaccg gggcgagtgc    660


<210> SEQ ID NO 71
<211> LENGTH: 452
<212> TYPE: PRT
<213> ORGANISM: Artificial
<220> FEATURE:
<223> OTHER INFORMATION: Synthetic

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300
```

-continued

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450
```

<210> SEQ ID NO 72
<211> LENGTH: 1356
<212> TYPE: DNA
<213> ORGANISM: Artificial
<220> FEATURE:
<223> OTHER INFORMATION: Synthetic

<400> SEQUENCE: 72

```
gaggtgcagc tggtggagtc tgggggaggc ctggtcaagc ctgggggtc cctgagactc      60

tcctgtgcag cctctggatt caccttcagt agctatagca tgaactgggt ccgccaggct     120

ccagggaagg ggctggagtg ggtctcatcc attagtagta gtagtagtta catatactac     180

gcagactcag tgaagggccg attcaccatc tccagagaca acgccaagaa ctcactgtat     240

ctgcaaatga acagcctgag agccgaggac acggcggtgt actactgcgc cagagatggt     300

ggaagaacgt cctacaccgc cacagcccac aattggttcg accccctgggg acagggtaca     360

ttggtcaccg tctcctcagc ttccaccaag ggcccctccg tgttccctct ggccccttgc     420

tcccggtcca cctccgagtc taccgccgct ctgggctgcc tcgtgaagga ctacttcccc     480

gagcccgtga ccgtgtcctg gaactctggc gccctgacct ccggcgtgca caccttccct     540

gccgtgctgc agtcctccgg cctgtactcc ctgtccagcg tcgtgaccgt gccctcctcc     600

agcctgggca ccaagaccta cacctgtaac gtggaccaca agccctccaa caccaaagtg     660

gacaagcggg tggaatctaa gtacggccct ccctgccctt cctgccctgc ccctgagttc     720

ctgggcggac cttccgtgtt cctgttccct ccaaagccca aggacaccct gatgatctcc     780

cggacccctg aagtgacctg cgtggtggtg gacgtgtccc aggaagatcc cgaagtccag     840

ttcaattggt acgtggacgg cgtggaagtg cacaacgcca agaccaagcc cagagaggaa     900

cagttcaact ccacctaccg ggtggtgtcc gtgctgaccg tgctgcacca ggactggctg     960

aacggcaaag agtacaagtg caaagtgtcc aacaagggcc tgccctccag catcgaaaag    1020

accatctcca aggccaaggg ccagccccgc gagccccaag tgtacaccct gcctcccagc    1080

caggaagaga tgaccaagaa tcaagtgtcc ctgacttgtc tggtcaaggg cttctacccc    1140

tccgatatcg ccgtggagtg ggagtccaac ggccagcccg agaacaacta caagaccacc    1200
```

cctcccgtgc tggactccga cggctccttc ttcctgtact ctcggctgac cgtggacaag 1260
tcccggtggc aggaaggcaa cgtcttctcc tgctccgtga tgcacgaggc cctgcacaac 1320
cactacaccc agaagtccct gtccctgtct ctgggc 1356

<210> SEQ ID NO 73
<211> LENGTH: 8
<212> TYPE: PRT
<213> ORGANISM: Artificial
<220> FEATURE:
<223> OTHER INFORMATION: Synthetic

<400> SEQUENCE: 73

Gly Phe Thr Phe Arg Ser Tyr Gly
1 5

<210> SEQ ID NO 74
<211> LENGTH: 8
<212> TYPE: PRT
<213> ORGANISM: Artificial
<220> FEATURE:
<223> OTHER INFORMATION: Synthetic

<400> SEQUENCE: 74

Ile Ser Ser Ser Ser Ser Tyr Ile
1 5

<210> SEQ ID NO 75
<211> LENGTH: 19
<212> TYPE: PRT
<213> ORGANISM: Artificial
<220> FEATURE:
<223> OTHER INFORMATION: Synthetic

<400> SEQUENCE: 75

Ala Arg Asp Gly Gly Arg Thr Ser Tyr Thr Ala Thr Ala His Asn Trp
1 5 10 15

Phe Asp Pro

<210> SEQ ID NO 76
<211> LENGTH: 9
<212> TYPE: PRT
<213> ORGANISM: Artificial
<220> FEATURE:
<223> OTHER INFORMATION: Synthetic

<400> SEQUENCE: 76

Phe Thr Phe Arg Ser Tyr Gly Met Asn
1 5

<210> SEQ ID NO 77
<211> LENGTH: 17
<212> TYPE: PRT
<213> ORGANISM: Artificial
<220> FEATURE:
<223> OTHER INFORMATION: Synthetic

<400> SEQUENCE: 77

Ser Ile Ser Ser Ser Ser Ser Tyr Ile Tyr Tyr Ala Asp Ser Val Lys
1 5 10 15

Gly

<210> SEQ ID NO 78
<211> LENGTH: 19

<212> TYPE: PRT
<213> ORGANISM: Artificial
<220> FEATURE:
<223> OTHER INFORMATION: Synthetic

<400> SEQUENCE: 78

Ala Arg Asp Gly Gly Arg Thr Ser Tyr Thr Ala Thr Ala His Asn Trp
1 5 10 15

Phe Asp Pro

<210> SEQ ID NO 79
<211> LENGTH: 126
<212> TYPE: PRT
<213> ORGANISM: Artificial
<220> FEATURE:
<223> OTHER INFORMATION: Synthetic

<400> SEQUENCE: 79

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Arg Ser Tyr
20 25 30

Gly Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Gly Arg Thr Ser Tyr Thr Ala Thr Ala His Asn Trp
100 105 110

Phe Asp Pro Trp Gly Gln Gly Thr Leu Val Thr Val Ser Ser
115 120 125

<210> SEQ ID NO 80
<211> LENGTH: 378
<212> TYPE: DNA
<213> ORGANISM: Artificial
<220> FEATURE:
<223> OTHER INFORMATION: Synthetic

<400> SEQUENCE: 80
gaggtgcagc tggtggagtc tgggggaggc ctggtcaagc ctggggggtc cctgagactc 60
tcctgtgcag cctctggatt caccttccgg agctatggga tgaactgggt ccgccaggct 120
ccagggaagg ggctggagtg ggtctcatcc attagtagta gtagtagtta catatactac 180
gcagactcag tgaagggccg attcaccatc tccagagaca acgccaagaa ctcactgtat 240
ctgcaaatga acagcctgag agccgaggac acggcggtgt actactgcgc cagagatggt 300
ggaagaacgt cctacaccgc cacagcccac aattggttcg acccctgggg acagggtaca 360
ttggtcaccg tctcctca 378

<210> SEQ ID NO 81
<211> LENGTH: 12
<212> TYPE: PRT
<213> ORGANISM: Artificial
<220> FEATURE:
<223> OTHER INFORMATION: Synthetic

<400> SEQUENCE: 81

Gln Ser Val Leu Phe Ser Ser Asn Asn Lys Asn Tyr
1 5 10

<210> SEQ ID NO 82
<211> LENGTH: 3
<212> TYPE: PRT
<213> ORGANISM: Artificial
<220> FEATURE:
<223> OTHER INFORMATION: Synthetic

<400> SEQUENCE: 82

Trp Ala Ser
1

<210> SEQ ID NO 83
<211> LENGTH: 9
<212> TYPE: PRT
<213> ORGANISM: Artificial
<220> FEATURE:
<223> OTHER INFORMATION: Synthetic

<400> SEQUENCE: 83

Gln Gln His Ala Ser Ala Pro Pro Thr
1 5

<210> SEQ ID NO 84
<211> LENGTH: 17
<212> TYPE: PRT
<213> ORGANISM: Artificial
<220> FEATURE:
<223> OTHER INFORMATION: Synthetic

<400> SEQUENCE: 84

Lys Ser Ser Gln Ser Val Leu Phe Ser Ser Asn Asn Lys Asn Tyr Leu
1 5 10 15

Ala

<210> SEQ ID NO 85
<211> LENGTH: 7
<212> TYPE: PRT
<213> ORGANISM: Artificial
<220> FEATURE:
<223> OTHER INFORMATION: Synthetic

<400> SEQUENCE: 85

Trp Ala Ser Thr Arg Glu Ser
1 5

<210> SEQ ID NO 86
<211> LENGTH: 9
<212> TYPE: PRT
<213> ORGANISM: Artificial
<220> FEATURE:
<223> OTHER INFORMATION: Synthetic

<400> SEQUENCE: 86

Gln Gln His Ala Ser Ala Pro Pro Thr
1 5

<210> SEQ ID NO 87
<211> LENGTH: 113
<212> TYPE: PRT
<213> ORGANISM: Artificial
<220> FEATURE:
<223> OTHER INFORMATION: Synthetic -continued

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys

<210> SEQ ID NO 88
<211> LENGTH: 339
<212> TYPE: DNA
<213> ORGANISM: Artificial
<220> FEATURE:
<223> OTHER INFORMATION: Synthetic

<400> SEQUENCE: 88
gacatcgtga tgacccagtc tccagactcc ctggctgtgt ctctgggcga gagggccacc 60
atcaactgca agtccagcca gagtgtttta ttcagctcca acaataagaa ctacttagct 120
tggtaccagc agaaaccagg acagcctcct aagctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcagca cgccagtgcc 300
cctcctactt ttggcggagg gaccaaggtt gagatcaaa 339

<210> SEQ ID NO 89
<211> LENGTH: 456
<212> TYPE: PRT
<213> ORGANISM: Artificial
<220> FEATURE:
<223> OTHER INFORMATION: Synthetic

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser

```
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 90
<211> LENGTH: 1368
<212> TYPE: DNA
<213> ORGANISM: Artificial
<220> FEATURE:
<223> OTHER INFORMATION: Synthetic

<400> SEQUENCE: 90

gaggtgcagc tggtggagtc tgggggaggc ctggtcaagc ctggggggtc cctgagactc      60

tcctgtgcag cctctggatt caccttccgg agctatggga tgaactgggt ccgccaggct     120
```

-continued

```
ccagggaagg ggctggagtg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc gagcaccaaa ggcccgagcg tgtttccgct ggcgccgagc    420

agcaaaagca ccagcggcgg caccgcggcg ctgggctgcc tggtgaaaga ttattttccg    480

gaaccggtga ccgtgagctg gaacagcggc gcgctgacca gcggcgtgca tacctttccg    540

gcggtgctgc agagcagcgg cctgtatagc ctgagcagcg tggtgaccgt gccgagcagc    600

agcctgggca cccagaccta tatttgcaac gtgaaccata aaccgagcaa caccaaagtg    660

gataaaaaag tggaaccgaa aagctgcgat aaaacccata cctgcccgcc gtgcccggcg    720

ccggaactgc tgggcggccc gagcgtgttt ctgtttccgc cgaaaccgaa agataccctg    780

atgattagcc gcaccccgga agtgacctgc gtggtggtgg atgtgagcca tgaagatccg    840

gaagtgaaat ttaactggta tgtggatggc gtggaagtgc ataacgcgaa aaccaaaccg    900

cgcgaagaac agtataacag cacctatcgc gtggtgagcg tgctgaccgt gctgcatcag    960

gattggctga acggcaaaga atataaatgc aaagtgagca acaaagcgct gccggcgccg   1020

attgaaaaaa ccattagcaa agcgaaaggc cagccgcgcg aaccgcaggt gtataccctg   1080

ccgccgagcc gcgatgaact gaccaaaaac caggtgagcc tgacctgcct ggtgaaaggc   1140

ttttatccga gcgatattgc ggtggaatgg gaaagcaacg gccagccgga aaacaactat   1200

aaaaccaccc cgccggtgct ggatagcgat ggcagctttt ttctgtatag caaactgacc   1260

gtggataaaa gccgctggca gcagggcaac gtgtttagct gcagcgtgat gcatgaagcg   1320

ctgcataacc attataccca gaaaagcctg agcctgagcc cgggcaaa                1368
```

<210> SEQ ID NO 91
<211> LENGTH: 220
<212> TYPE: PRT
<213> ORGANISM: Artificial
<220> FEATURE:
<223> OTHER INFORMATION: Synthetic

<400> SEQUENCE: 91

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

-continued

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 92
<211> LENGTH: 660
<212> TYPE: DNA
<213> ORGANISM: Artificial
<220> FEATURE:
<223> OTHER INFORMATION: Synthetic

<400> SEQUENCE: 92

```
gacatcgtga tgacccagtc tccagactcc ctggctgtgt ctctgggcga gagggccacc     60

atcaactgca agtccagcca gagtgtttta ttcagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcagca cgccagtgcc    300

cctcctactt ttggcggagg gaccaaggtt gagatcaaac gtacggtggc cgctccctcc    360

gtgttcatct tcccaccctc cgacgagcag ctgaagtccg gcaccgcctc cgtcgtgtgc    420

ctgctgaaca acttctaccc tcgcgaggcc aaagtgcagt ggaaagtgga caacgccctg    480

cagtccggca actcccagga atccgtcacc gagcaggact ccaaggacag cacctactcc    540

ctgtcctcca ccctgaccct gtccaaggcc gactacgaga agcacaaagt gtacgcctgc    600

gaagtgaccc accagggcct gtccagcccc gtgaccaagt ccttcaaccg gggcgagtgc    660
```

<210> SEQ ID NO 93
<211> LENGTH: 452
<212> TYPE: PRT
<213> ORGANISM: Artificial
<220> FEATURE:
<223> OTHER INFORMATION: Synthetic

<400> SEQUENCE: 93

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
```

-continued

```
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450


<210> SEQ ID NO 94
<211> LENGTH: 1356
<212> TYPE: DNA
<213> ORGANISM: Artificial
<220> FEATURE:
<223> OTHER INFORMATION: Synthetic

<400> SEQUENCE: 94

gaggtgcagc tggtggagtc tgggggaggc ctggtcaagc ctggggggtc cctgagactc      60

tcctgtgcag cctctggatt caccttccgg agctatggga tgaactgggt ccgccaggct     120
```

```
ccagggaagg ggctggagtg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc ttccaccaag ggcccctccg tgttccctct ggccccttgc    420

tcccggtcca cctccgagtc taccgccgct ctgggctgcc tcgtgaagga ctacttcccc    480

gagcccgtga ccgtgtcctg gaactctggc gccctgacct ccggcgtgca caccttccct    540

gccgtgctgc agtcctccgg cctgtactcc ctgtccagcg tcgtgaccgt gccctcctcc    600

agcctgggca ccaagaccta cacctgtaac gtggaccaca agccctccaa caccaaagtg    660

gacaagcggg tggaatctaa gtacggccct ccctgccctt cctgccctgc ccctgagttc    720

ctgggcggac cttccgtgtt cctgttccct ccaaagccca aggacaccct gatgatctcc    780

cggacccctg aagtgacctg cgtggtggtg gacgtgtccc aggaagatcc cgaagtccag    840

ttcaattggt acgtggacgg cgtggaagtg cacaacgcca agaccaagcc cagagaggaa    900

cagttcaact ccacctaccg ggtggtgtcc gtgctgaccg tgctgcacca ggactggctg    960

aacggcaaag agtacaagtg caaagtgtcc aacaagggcc tgccctccag catcgaaaag   1020

accatctcca aggccaaggg ccagccccgc gagccccaag tgtacaccct gcctcccagc   1080

caggaagaga tgaccaagaa tcaagtgtcc ctgacttgtc tggtcaaggg cttctacccc   1140

tccgatatcg ccgtggagtg ggagtccaac ggccagcccg agaacaacta caagaccacc   1200

cctcccgtgc tggactccga cggctccttc ttcctgtact ctcggctgac cgtggacaag   1260

tcccggtggc aggaaggcaa cgtcttctcc tgctccgtga tgcacgaggc cctgcacaac   1320

cactacaccc agaagtccct gtccctgtct ctgggc                              1356


<210> SEQ ID NO 95
<211> LENGTH: 8
<212> TYPE: PRT
<213> ORGANISM: Artificial
<220> FEATURE:
<223> OTHER INFORMATION: Synthetic

<400> SEQUENCE: 95

Gly Phe Thr Phe Ser Arg Thr Gly
1               5


<210> SEQ ID NO 96
<211> LENGTH: 8
<212> TYPE: PRT
<213> ORGANISM: Artificial
<220> FEATURE:
<223> OTHER INFORMATION: Synthetic

<400> SEQUENCE: 96

Ile Ser Ser Ser Ser Ser Tyr Ile
1               5


<210> SEQ ID NO 97
<211> LENGTH: 19
<212> TYPE: PRT
<213> ORGANISM: Artificial
<220> FEATURE:
<223> OTHER INFORMATION: Synthetic

<400> SEQUENCE: 97

Ala Arg Asp Gly Gly Arg Thr Ser Tyr Thr Ala Thr Ala His Asn Trp
```

1 5 10 15

Phe Asp Pro

<210> SEQ ID NO 98
<211> LENGTH: 9
<212> TYPE: PRT
<213> ORGANISM: Artificial
<220> FEATURE:
<223> OTHER INFORMATION: Synthetic

<400> SEQUENCE: 98

Phe Thr Phe Ser Arg Thr Gly Met Asn
1 5

<210> SEQ ID NO 99
<211> LENGTH: 17
<212> TYPE: PRT
<213> ORGANISM: Artificial
<220> FEATURE:
<223> OTHER INFORMATION: Synthetic

<400> SEQUENCE: 99

Ser Ile Ser Ser Ser Ser Ser Tyr Ile Tyr Tyr Ala Asp Ser Val Lys
1 5 10 15

Gly

<210> SEQ ID NO 100
<211> LENGTH: 19
<212> TYPE: PRT
<213> ORGANISM: Artificial
<220> FEATURE:
<223> OTHER INFORMATION: Synthetic

<400> SEQUENCE: 100

Ala Arg Asp Gly Gly Arg Thr Ser Tyr Thr Ala Thr Ala His Asn Trp
1 5 10 15

Phe Asp Pro

<210> SEQ ID NO 101
<211> LENGTH: 126
<212> TYPE: PRT
<213> ORGANISM: Artificial
<220> FEATURE:
<223> OTHER INFORMATION: Synthetic

<400> SEQUENCE: 101

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Arg Thr
20 25 30

Gly Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Gly Arg Thr Ser Tyr Thr Ala Thr Ala His Asn Trp
100 105 110

Phe Asp Pro Trp Gly Gln Gly Thr Leu Val Thr Val Ser Ser 115 120 125

<210> SEQ ID NO 102
<211> LENGTH: 378
<212> TYPE: DNA
<213> ORGANISM: Artificial
<220> FEATURE:
<223> OTHER INFORMATION: Synthetic

<400> SEQUENCE: 102
gaggtgcagc tggtggagtc tgggggaggc ctggtcaagc ctgggggtc cctgagactc 60 tcctgtgcag cctctggatt caccttcagt aggactggga tgaactgggt ccgccaggct 120
ccagggaagg ggctggaatg ggtctcatcc attagtagta gtagtagtta catatactac 180
gcagactcag tgaagggccg attcaccatc tccagagaca acgccaagaa ctcactgtat 240
ctgcaaatga acagcctgag agccgaggac acggcggtgt actactgcgc cagagatggt 300
ggaagaacgt cctacaccgc cacagcccac aattggttcg acccctgggg acagggtaca 360
ttggtcaccg tctcctca 378

<210> SEQ ID NO 103
<211> LENGTH: 12
<212> TYPE: PRT
<213> ORGANISM: Artificial
<220> FEATURE:
<223> OTHER INFORMATION: Synthetic

<400> SEQUENCE: 103

Gln Ser Val Leu Phe Ser Ser Asn Asn Lys Asn Tyr
1 5 10

<210> SEQ ID NO 104
<211> LENGTH: 3
<212> TYPE: PRT
<213> ORGANISM: Artificial
<220> FEATURE:
<223> OTHER INFORMATION: Synthetic

<400> SEQUENCE: 104

Trp Ala Ser
1

<210> SEQ ID NO 105
<211> LENGTH: 9
<212> TYPE: PRT
<213> ORGANISM: Artificial
<220> FEATURE:
<223> OTHER INFORMATION: Synthetic

<400> SEQUENCE: 105

Gln Gln His Ala Ser Ala Pro Pro Thr
1 5

<210> SEQ ID NO 106
<211> LENGTH: 17
<212> TYPE: PRT
<213> ORGANISM: Artificial
<220> FEATURE:
<223> OTHER INFORMATION: Synthetic

<400> SEQUENCE: 106

Lys Ser Ser Gln Ser Val Leu Phe Ser Ser Asn Asn Lys Asn Tyr Leu
1 5 10 15

Ala

<210> SEQ ID NO 107
<211> LENGTH: 7
<212> TYPE: PRT
<213> ORGANISM: Artificial
<220> FEATURE:
<223> OTHER INFORMATION: Synthetic

<400> SEQUENCE: 107

```
Trp Ala Ser Thr Arg Glu Ser
1               5
```

<210> SEQ ID NO 108
<211> LENGTH: 9
<212> TYPE: PRT
<213> ORGANISM: Artificial
<220> FEATURE:
<223> OTHER INFORMATION: Synthetic

<400> SEQUENCE: 108

```
Gln Gln His Ala Ser Ala Pro Pro Thr
1               5
```

<210> SEQ ID NO 109
<211> LENGTH: 113
<212> TYPE: PRT
<213> ORGANISM: Artificial
<220> FEATURE:
<223> OTHER INFORMATION: Synthetic

<400> SEQUENCE: 109

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys
```

<210> SEQ ID NO 110
<211> LENGTH: 339
<212> TYPE: DNA
<213> ORGANISM: Artificial
<220> FEATURE:
<223> OTHER INFORMATION: Synthetic

<400> SEQUENCE: 110

```
gacatcgtga tgacccagtc tccagactcc ctggctgtgt ctctgggcga gagggccacc     60

atcaactgca agtccagcca gagtgtttta ttcagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcagca cgccagtgcc    300
```

```
cctcctactt ttggcggagg gaccaaggtt gagatcaaa                        339


<210> SEQ ID NO 111
<211> LENGTH: 456
<212> TYPE: PRT
<213> ORGANISM: Artificial
<220> FEATURE:
<223> OTHER INFORMATION: Synthetic

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Thr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350
```

```
Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 112
<211> LENGTH: 1368
<212> TYPE: DNA
<213> ORGANISM: Artificial
<220> FEATURE:
<223> OTHER INFORMATION: Synthetic

<400> SEQUENCE: 112

```
gaggtgcagc tggtggagtc tgggggaggc ctggtcaagc ctgggggggtc cctgagactc     60

tcctgtgcag cctctggatt caccttcagt aggactggga tgaactgggt ccgccaggct    120

ccagggaagg ggctggaatg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc gagcaccaaa ggcccgagcg tgtttccgct ggcgccgagc    420

agcaaaagca ccagcggcgg caccgcggcg ctgggctgcc tggtgaaaga ttattttccg    480

gaaccggtga ccgtgagctg gaacagcggc gcgctgacca gcggcgtgca tacctttccg    540

gcggtgctgc agagcagcgg cctgtatagc ctgagcagcg tggtgaccgt gccgagcagc    600

agcctgggca cccagaccta tatttgcaac gtgaaccata aaccgagcaa caccaaagtg    660

gataaaaaag tggaaccgaa aagctgcgat aaaacccata cctgcccgcc gtgcccggcg    720

ccggaactgc tgggcggccc gagcgtgttt ctgtttccgc cgaaaccgaa agataccctg    780

atgattagcc gcaccccgga agtgacctgc gtggtggtgg atgtgagcca tgaagatccg    840

gaagtgaaat ttaactggta tgtggatggc gtggaagtgc ataacgcgaa aaccaaaccg    900

cgcgaagaac agtataacag cacctatcgc gtggtgagcg tgctgaccgt gctgcatcag    960

gattggctga acggcaaaga atataaatgc aaagtgagca acaaagcgct gccggcgccg   1020

attgaaaaaa ccattagcaa agcgaaaggc cagccgcgcg aaccgcaggt gtataccctg   1080

ccgccgagcc gcgatgaact gaccaaaaac caggtgagcc tgacctgcct ggtgaaaggc   1140

ttttatccga gcgatattgc ggtggaatgg gaaagcaacg gccagccgga aaacaactat   1200

aaaaccaccc cgccggtgct ggatagcgat ggcagctttt ttctgtatag caaactgacc   1260

gtggataaaa gccgctggca gcagggcaac gtgtttagct gcagcgtgat gcatgaagcg   1320

ctgcataacc attataccca gaaaagcctg agcctgagcc cgggcaaa                1368
```

<210> SEQ ID NO 113

<211> LENGTH: 220
<212> TYPE: PRT
<213> ORGANISM: Artificial
<220> FEATURE:
<223> OTHER INFORMATION: Synthetic

<400> SEQUENCE: 113

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 114
<211> LENGTH: 660
<212> TYPE: DNA
<213> ORGANISM: Artificial
<220> FEATURE:
<223> OTHER INFORMATION: Synthetic

<400> SEQUENCE: 114

```
gacatcgtga tgacccagtc tccagactcc ctggctgtgt ctctgggcga gagggccacc     60

atcaactgca agtccagcca gagtgtttta ttcagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcagca cgccagtgcc    300

cctcctactt ttggcggagg gaccaaggtt gagatcaaac gtacggtggc cgctccctcc    360

gtgttcatct tcccaccctc cgacgagcag ctgaagtccg gcaccgcctc cgtcgtgtgc    420

ctgctgaaca acttctaccc tcgcgaggcc aaagtgcagt ggaaagtgga caacgccctg    480

cagtccggca actcccagga atccgtcacc gagcaggact ccaaggacag cacctactcc    540

ctgtcctcca ccctgaccct gtccaaggcc gactacgaga agcacaaagt gtacgcctgc    600
```

gaagtgaccc accagggcct gtccagcccc gtgaccaagt ccttcaaccg gggcgagtgc 660

<210> SEQ ID NO 115
<211> LENGTH: 452
<212> TYPE: PRT
<213> ORGANISM: Artificial
<220> FEATURE:
<223> OTHER INFORMATION: Synthetic

<400> SEQUENCE: 115

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Arg Thr
20 25 30

Gly Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Gly Arg Thr Ser Tyr Thr Ala Thr Ala His Asn Trp
100 105 110

Phe Asp Pro Trp Gly Gln Gly Thr Leu Val Thr Val Ser Ser Ala Ser
115 120 125

Thr Lys Gly Pro Ser Val Phe Pro Leu Ala Pro Cys Ser Arg Ser Thr
130 135 140

Ser Glu Ser Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Ser Leu Gly Thr Lys Thr Tyr Thr
195 200 205

Cys Asn Val Asp His Lys Pro Ser Asn Thr Lys Val Asp Lys Arg Val
210 215 220

Glu Ser Lys Tyr Gly Pro Pro Cys Pro Ser Cys Pro Ala Pro Glu Phe
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser Gln Glu Asp Pro Glu Val Gln Phe Asn Trp Tyr Val Asp Gly Val
275 280 285

Glu Val His Asn Ala Lys Thr Lys Pro Arg Glu Glu Gln Phe Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Gly Leu Pro Ser
325 330 335

Ser Ile Glu Lys Thr Ile Ser Lys Ala Lys Gly Gln Pro Arg Glu Pro
340 345 350

-continued

```
Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450
```

<210> SEQ ID NO 116
<211> LENGTH: 1356
<212> TYPE: DNA
<213> ORGANISM: Artificial
<220> FEATURE:
<223> OTHER INFORMATION: Synthetic

<400> SEQUENCE: 116

```
gaggtgcagc tggtggagtc tgggggaggc ctggtcaagc ctgggggtc cctgagactc      60

tcctgtgcag cctctggatt caccttcagt aggactggga tgaactgggt ccgccaggct    120

ccagggaagg ggctggaatg ggtctcatcc attagtagta gtagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc ttccaccaag ggcccctccg tgttccctct ggccccttgc    420

tcccggtcca cctccgagtc taccgccgct ctgggctgcc tcgtgaagga ctacttcccc    480

gagcccgtga ccgtgtcctg gaactctggc gccctgacct ccggcgtgca caccttccct    540

gccgtgctgc agtcctccgg cctgtactcc ctgtccagcg tcgtgaccgt gccctcctcc    600

agcctgggca ccaagaccta cacctgtaac gtggaccaca agccctccaa caccaaagtg    660

gacaagcggg tggaatctaa gtacggccct ccctgccctt cctgccctgc ccctgagttc    720

ctgggcggac cttccgtgtt cctgttccct ccaaagccca aggacaccct gatgatctcc    780

cggacccctg aagtgacctg cgtggtggtg gacgtgtccc aggaagatcc cgaagtccag    840

ttcaattggt acgtggacgg cgtggaagtg cacaacgcca agaccaagcc cagagaggaa    900

cagttcaact ccacctaccg ggtggtgtcc gtgctgaccg tgctgcacca ggactggctg    960

aacggcaaag agtacaagtg caaagtgtcc aacaagggcc tgccctccag catcgaaaag   1020

accatctcca aggccaaggg ccagccccgc gagccccaag tgtacaccct gcctcccagc   1080

caggaagaga tgaccaagaa tcaagtgtcc ctgacttgtc tggtcaaggg cttctacccc   1140

tccgatatcg ccgtggagtg ggagtccaac ggccagcccg agaacaacta caagaccacc   1200

cctcccgtgc tggactccga cggctccttc ttcctgtact ctcggctgac cgtggacaag   1260

tcccggtggc aggaaggcaa cgtcttctcc tgctccgtga tgcacgaggc cctgcacaac   1320

cactacaccc agaagtccct gtccctgtct ctgggc                              1356
```

<210> SEQ ID NO 117

<211> LENGTH: 8
<212> TYPE: PRT
<213> ORGANISM: Artificial
<220> FEATURE:
<223> OTHER INFORMATION: Synthetic

<400> SEQUENCE: 117

Gly Phe Thr Phe Ser Arg Tyr Gly
1               5

<210> SEQ ID NO 118
<211> LENGTH: 8
<212> TYPE: PRT
<213> ORGANISM: Artificial
<220> FEATURE:
<223> OTHER INFORMATION: Synthetic

<400> SEQUENCE: 118

Ile Ser Ser Ser Ser Ala Tyr Ile
1               5

<210> SEQ ID NO 119
<211> LENGTH: 19
<212> TYPE: PRT
<213> ORGANISM: Artificial
<220> FEATURE:
<223> OTHER INFORMATION: Synthetic

<400> SEQUENCE: 119

Ala Arg Asp Gly Gly Arg Thr Ser Tyr Thr Ala Thr Ala His Asn Trp
1               5                   10                  15

Phe Asp Pro

<210> SEQ ID NO 120
<211> LENGTH: 9
<212> TYPE: PRT
<213> ORGANISM: Artificial
<220> FEATURE:
<223> OTHER INFORMATION: Synthetic

<400> SEQUENCE: 120

Phe Thr Phe Ser Arg Tyr Gly Met Asn
1               5

<210> SEQ ID NO 121
<211> LENGTH: 17
<212> TYPE: PRT
<213> ORGANISM: Artificial
<220> FEATURE:
<223> OTHER INFORMATION: Synthetic

<400> SEQUENCE: 121

Ser Ile Ser Ser Ser Ser Ala Tyr Ile Leu Tyr Ala Asp Ser Val Lys
1               5                   10                  15

Gly

<210> SEQ ID NO 122
<211> LENGTH: 19
<212> TYPE: PRT
<213> ORGANISM: Artificial
<220> FEATURE:
<223> OTHER INFORMATION: Synthetic

<400> SEQUENCE: 122

Ala Arg Asp Gly Gly Arg Thr Ser Tyr Thr Ala Thr Ala His Asn Trp
1               5                   10                  15

Phe Asp Pro

<210> SEQ ID NO 123
<211> LENGTH: 126
<212> TYPE: PRT
<213> ORGANISM: Artificial
<220> FEATURE:
<223> OTHER INFORMATION: Synthetic

<400> SEQUENCE: 123

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ala Tyr Ile Leu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
        115                 120                 125

<210> SEQ ID NO 124
<211> LENGTH: 378
<212> TYPE: DNA
<213> ORGANISM: Artificial
<220> FEATURE:
<223> OTHER INFORMATION: Synthetic

<400> SEQUENCE: 124
gaggtgcagc tggtggagtc tgggggaggc ctggtcaagc ctggggggtc cctgagactc 60
tcctgtgcag cctctggatt caccttcagt aggtatggga tgaactgggt ccgccaggct 120
ccagggaagg ggctggagtg ggtctcatcc attagtagta gtagtgctta catactgtac 180
gcagactcag tgaagggccg attcaccatc tccagagaca acgccaagaa ctcactgtat 240
ctgcaaatga acagcctgag agccgaggac acggcggtgt actactgcgc cagagatggt 300
ggaagaacgt cctacaccgc cacagcccac aattggttcg acccctgggg acagggtaca 360
ttggtcaccg tctcctca 378

<210> SEQ ID NO 125
<211> LENGTH: 12
<212> TYPE: PRT
<213> ORGANISM: Artificial
<220> FEATURE:
<223> OTHER INFORMATION: Synthetic

<400> SEQUENCE: 125

Gln Ser Val Leu Phe Ser Ser Asn Asn Lys Asn Tyr
1               5                   10

<210> SEQ ID NO 126
<211> LENGTH: 3
<212> TYPE: PRT
<213> ORGANISM: Artificial

<220> FEATURE:
<223> OTHER INFORMATION: Synthetic

<400> SEQUENCE: 126

Trp Ala Ser
1

<210> SEQ ID NO 127
<211> LENGTH: 9
<212> TYPE: PRT
<213> ORGANISM: Artificial
<220> FEATURE:
<223> OTHER INFORMATION: Synthetic

<400> SEQUENCE: 127

Gln Gln His Ala Ser Ala Pro Pro Thr
1               5

<210> SEQ ID NO 128
<211> LENGTH: 17
<212> TYPE: PRT
<213> ORGANISM: Artificial
<220> FEATURE:
<223> OTHER INFORMATION: Synthetic

<400> SEQUENCE: 128

Lys Ser Ser Gln Ser Val Leu Phe Ser Ser Asn Asn Lys Asn Tyr Leu
1               5                   10                  15

Ala

<210> SEQ ID NO 129
<211> LENGTH: 7
<212> TYPE: PRT
<213> ORGANISM: Artificial
<220> FEATURE:
<223> OTHER INFORMATION: Synthetic

<400> SEQUENCE: 129

Trp Ala Ser Thr Arg Glu Ser
1               5

<210> SEQ ID NO 130
<211> LENGTH: 9
<212> TYPE: PRT
<213> ORGANISM: Artificial
<220> FEATURE:
<223> OTHER INFORMATION: Synthetic

<400> SEQUENCE: 130

Gln Gln His Ala Ser Ala Pro Pro Thr
1               5

<210> SEQ ID NO 131
<211> LENGTH: 113
<212> TYPE: PRT
<213> ORGANISM: Artificial
<220> FEATURE:
<223> OTHER INFORMATION: Synthetic

<400> SEQUENCE: 131

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln

```
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys


<210> SEQ ID NO 132
<211> LENGTH: 339
<212> TYPE: DNA
<213> ORGANISM: Artificial
<220> FEATURE:
<223> OTHER INFORMATION: Synthetic

<400> SEQUENCE: 132

gacatcgtga tgacccagtc tccagactcc ctggctgtgt ctctgggcga gagggccacc      60

atcaactgca agtccagcca gagtgtttta ttcagctcca acaataagaa ctacttagct     120

tggtaccagc agaaaccagg acagcctcct aagctgctca tttactgggc atctacccgg     180

gaatccgggg tccctgaccg attcagtggc agcgggtctg ggacagattt cactctcacc     240

atcagcagcc tgcaggctga agatgtggca gtttattact gtcagcagca cgccagtgcc     300

cctcctactt ttggcggagg gaccaaggtt gagatcaaa                            339


<210> SEQ ID NO 133
<211> LENGTH: 456
<212> TYPE: PRT
<213> ORGANISM: Artificial
<220> FEATURE:
<223> OTHER INFORMATION: Synthetic

<400> SEQUENCE: 133

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ala Tyr Ile Leu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
```

```
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 134
<211> LENGTH: 1368
<212> TYPE: DNA
<213> ORGANISM: Artificial
<220> FEATURE:
<223> OTHER INFORMATION: Synthetic

<400> SEQUENCE: 134

gaggtgcagc tggtggagtc tgggggaggc ctggtcaagc ctgggggtc cctgagactc      60

tcctgtgcag cctctggatt caccttcagt aggtatggga tgaactgggt ccgccaggct    120

ccagggaagg ggctggagtg ggtctcatcc attagtagta gtagtgctta catactgtac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc gagcaccaaa ggcccgagcg tgtttccgct ggcgccgagc    420
```

```
agcaaaagca ccagcggcgg caccgcggcg ctgggctgcc tggtgaaaga ttattttccg    480

gaaccggtga ccgtgagctg gaacagcggc gcgctgacca gcggcgtgca tacctttccg    540

gcggtgctgc agagcagcgg cctgtatagc ctgagcagcg tggtgaccgt gccgagcagc    600

agcctgggca cccagaccta tatttgcaac gtgaaccata aaccgagcaa caccaaagtg    660

gataaaaaag tggaaccgaa aagctgcgat aaaacccata cctgcccgcc gtgcccggcg    720

ccggaactgc tgggcggccc gagcgtgttt ctgtttccgc cgaaaccgaa agataccctg    780

atgattagcc gcaccccgga agtgacctgc gtggtggtgg atgtgagcca tgaagatccg    840

gaagtgaaat ttaactggta tgtggatggc gtggaagtgc ataacgcgaa aaccaaaccg    900

cgcgaagaac agtataacag cacctatcgc gtggtgagcg tgctgaccgt gctgcatcag    960

gattggctga acggcaaaga atataaatgc aaagtgagca acaaagcgct gccggcgccg   1020

attgaaaaaa ccattagcaa agcgaaaggc cagccgcgcg aaccgcaggt gtataccctg   1080

ccgccgagcc gcgatgaact gaccaaaaac caggtgagcc tgacctgcct ggtgaaaggc   1140

ttttatccga gcgatattgc ggtggaatgg gaaagcaacg gccagccgga aaacaactat   1200

aaaaccaccc cgccggtgct ggatagcgat ggcagctttt ttctgtatag caaactgacc   1260

gtggataaaa gccgctggca gcagggcaac gtgtttagct gcagcgtgat gcatgaagcg   1320

ctgcataacc attataccca gaaaagcctg agcctgagcc cgggcaaa                1368
```

```
<210> SEQ ID NO 135
<211> LENGTH: 220
<212> TYPE: PRT
<213> ORGANISM: Artificial
<220> FEATURE:
<223> OTHER INFORMATION: Synthetic

<400> SEQUENCE: 135

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 136
<211> LENGTH: 660
<212> TYPE: DNA
<213> ORGANISM: Artificial
<220> FEATURE:
<223> OTHER INFORMATION: Synthetic

<400> SEQUENCE: 136

```
gacatcgtga tgacccagtc tccagactcc ctggctgtgt ctctgggcga gagggccacc     60

atcaactgca agtccagcca gagtgtttta ttcagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcagca cgccagtgcc    300

cctcctactt ttggcggagg gaccaaggtt gagatcaaac gtacggtggc cgctccctcc    360

gtgttcatct tcccaccctc cgacgagcag ctgaagtccg gcaccgcctc cgtcgtgtgc    420

ctgctgaaca acttctaccc tcgcgaggcc aaagtgcagt ggaaagtgga caacgccctg    480

cagtccggca actcccagga atccgtcacc gagcaggact ccaaggacag cacctactcc    540

ctgtcctcca ccctgaccct gtccaaggcc gactacgaga agcacaaagt gtacgcctgc    600

gaagtgaccc accagggcct gtccagcccc gtgaccaagt ccttcaaccg ggcgagtgc     660
```

<210> SEQ ID NO 137
<211> LENGTH: 452
<212> TYPE: PRT
<213> ORGANISM: Artificial
<220> FEATURE:
<223> OTHER INFORMATION: Synthetic

<400> SEQUENCE: 137

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ala Tyr Ile Leu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
```

-continued

```
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450


<210> SEQ ID NO 138
<211> LENGTH: 1356
<212> TYPE: DNA
<213> ORGANISM: Artificial
<220> FEATURE:
<223> OTHER INFORMATION: Synthetic

<400> SEQUENCE: 138

gaggtgcagc tggtggagtc tgggggaggc ctggtcaagc ctggggggtc cctgagactc      60

tcctgtgcag cctctggatt caccttcagt aggtatggga tgaactgggt ccgccaggct     120

ccagggaagg ggctggagtg ggtctcatcc attagtagta gtagtgctta catactgtac     180

gcagactcag tgaagggccg attcaccatc tccagagaca acgccaagaa ctcactgtat     240

ctgcaaatga acagcctgag agccgaggac acggcggtgt actactgcgc cagagatggt     300

ggaagaacgt cctacaccgc cacagcccac aattggttcg acccctgggg acagggtaca     360

ttggtcaccg tctcctcagc ttccaccaag ggccccctccg tgttccctct ggccccttgc     420
```

-continued

```
tcccggtcca cctccgagtc taccgccgct ctgggctgcc tcgtgaagga ctacttcccc    480

gagcccgtga ccgtgtcctg gaactctggc gccctgacct ccggcgtgca caccttccct    540

gccgtgctgc agtcctccgg cctgtactcc ctgtccagcg tcgtgaccgt gccctcctcc    600

agcctgggca ccaagaccta cacctgtaac gtggaccaca agccctccaa caccaaagtg    660

gacaagcggg tggaatctaa gtacggccct ccctgccctt cctgccctgc ccctgagttc    720

ctgggcggac cttccgtgtt cctgttccct ccaaagccca aggacaccct gatgatctcc    780

cggacccctg aagtgacctg cgtggtggtg gacgtgtccc aggaagatcc cgaagtccag    840

ttcaattggt acgtggacgg cgtggaagtg cacaacgcca agaccaagcc cagagaggaa    900

cagttcaact ccacctaccg ggtggtgtcc gtgctgaccg tgctgcacca ggactggctg    960

aacggcaaag agtacaagtg caaagtgtcc aacaagggcc tgccctccag catcgaaaag   1020

accatctcca aggccaaggg ccagccccgc gagccccaag tgtacaccct gcctcccagc   1080

caggaagaga tgaccaagaa tcaagtgtcc ctgacttgtc tggtcaaggg cttctacccc   1140

tccgatatcg ccgtggagtg ggagtccaac ggccagcccg agaacaacta caagaccacc   1200

cctcccgtgc tggactccga cggctccttc ttcctgtact ctcggctgac cgtggacaag   1260

tcccggtggc aggaaggcaa cgtcttctcc tgctccgtga tgcacgaggc cctgcacaac   1320

cactacaccc agaagtccct gtccctgtct ctgggc                              1356
```

<210> SEQ ID NO 139
<211> LENGTH: 8
<212> TYPE: PRT
<213> ORGANISM: Artificial
<220> FEATURE:
<223> OTHER INFORMATION: Synthetic

<400> SEQUENCE: 139

```
Gly Phe Thr Phe Ala Ser Tyr Gly
1               5
```

<210> SEQ ID NO 140
<211> LENGTH: 8
<212> TYPE: PRT
<213> ORGANISM: Artificial
<220> FEATURE:
<223> OTHER INFORMATION: Synthetic

<400> SEQUENCE: 140

```
Ile Ser Ser Ser Ser Ser Tyr Ile
1               5
```

<210> SEQ ID NO 141
<211> LENGTH: 19
<212> TYPE: PRT
<213> ORGANISM: Artificial
<220> FEATURE:
<223> OTHER INFORMATION: Synthetic

<400> SEQUENCE: 141

```
Ala Arg Asp Gly Gly Arg Thr Ser Tyr Thr Ala Thr Ala His Asn Trp
1               5                   10                  15

Phe Asp Pro
```

<210> SEQ ID NO 142
<211> LENGTH: 9
<212> TYPE: PRT
<213> ORGANISM: Artificial

<220> FEATURE:
<223> OTHER INFORMATION: Synthetic

<400> SEQUENCE: 142

Phe Thr Phe Ala Ser Tyr Gly Met Asn
1               5

<210> SEQ ID NO 143
<211> LENGTH: 17
<212> TYPE: PRT
<213> ORGANISM: Artificial
<220> FEATURE:
<223> OTHER INFORMATION: Synthetic

<400> SEQUENCE: 143

Ser Ile Ser Ser Ser Ser Ser Tyr Ile Tyr Tyr Ala Asp Ser Val Lys
1               5                   10                  15

Gly

<210> SEQ ID NO 144
<211> LENGTH: 19
<212> TYPE: PRT
<213> ORGANISM: Artificial
<220> FEATURE:
<223> OTHER INFORMATION: Synthetic

<400> SEQUENCE: 144

Ala Arg Asp Gly Gly Arg Thr Ser Tyr Thr Ala Thr Ala His Asn Trp
1               5                   10                  15

Phe Asp Pro

<210> SEQ ID NO 145
<211> LENGTH: 126
<212> TYPE: PRT
<213> ORGANISM: Artificial
<220> FEATURE:
<223> OTHER INFORMATION: Synthetic

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ala Ser Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser
        115                 120                 125

<210> SEQ ID NO 146
<211> LENGTH: 378
<212> TYPE: DNA
<213> ORGANISM: Artificial
<220> FEATURE:
<223> OTHER INFORMATION: Synthetic

<400> SEQUENCE: 146

```
gaggtgcagc tggtggagtc tgggggaggc ctggtcaagc ctgggggtc cctgagactc     60

tcctgtgcag cctctggatt caccttcgct agctatggga tgaactgggt ccgccaggct    120

ccagggaagg ggctggagtg ggtctcatcc attagtagtt ctagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctca                                                   378
```

<210> SEQ ID NO 147
<211> LENGTH: 12
<212> TYPE: PRT
<213> ORGANISM: Artificial
<220> FEATURE:
<223> OTHER INFORMATION: Synthetic

<400> SEQUENCE: 147

```
Gln Ser Val Leu Phe Ser Ser Asn Asn Lys Asn Tyr
1               5                   10
```

<210> SEQ ID NO 148
<211> LENGTH: 3
<212> TYPE: PRT
<213> ORGANISM: Artificial
<220> FEATURE:
<223> OTHER INFORMATION: Synthetic

<400> SEQUENCE: 148

```
Trp Ala Ser
1
```

<210> SEQ ID NO 149
<211> LENGTH: 9
<212> TYPE: PRT
<213> ORGANISM: Artificial
<220> FEATURE:
<223> OTHER INFORMATION: Synthetic

<400> SEQUENCE: 149

```
Gln Gln His Ala Ser Ala Pro Pro Thr
1               5
```

<210> SEQ ID NO 150
<211> LENGTH: 17
<212> TYPE: PRT
<213> ORGANISM: Artificial
<220> FEATURE:
<223> OTHER INFORMATION: Synthetic

<400> SEQUENCE: 150

```
Lys Ser Ser Gln Ser Val Leu Phe Ser Ser Asn Asn Lys Asn Tyr Leu
1               5                   10                  15

Ala
```

<210> SEQ ID NO 151
<211> LENGTH: 7
<212> TYPE: PRT
<213> ORGANISM: Artificial
<220> FEATURE:
<223> OTHER INFORMATION: Synthetic -continued

<400> SEQUENCE: 151

Trp Ala Ser Thr Arg Glu Ser
1               5

<210> SEQ ID NO 152
<211> LENGTH: 9
<212> TYPE: PRT
<213> ORGANISM: Artificial
<220> FEATURE:
<223> OTHER INFORMATION: Synthetic

<400> SEQUENCE: 152

Gln Gln His Ala Ser Ala Pro Pro Thr
1               5

<210> SEQ ID NO 153
<211> LENGTH: 113
<212> TYPE: PRT
<213> ORGANISM: Artificial
<220> FEATURE:
<223> OTHER INFORMATION: Synthetic

<400> SEQUENCE: 153

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys

<210> SEQ ID NO 154
<211> LENGTH: 339
<212> TYPE: DNA
<213> ORGANISM: Artificial
<220> FEATURE:
<223> OTHER INFORMATION: Synthetic

<400> SEQUENCE: 154
gacatcgtga tgacccagtc tccagactcc ctggctgtgt ctctgggcga gagggccacc     60
atcaactgca agtccagcca gagtgtttta ttcagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcagca cgccagtgcc    300
cctcctactt ttggcggagg gaccaaggtt gagatcaaa                           339

<210> SEQ ID NO 155
<211> LENGTH: 456
<212> TYPE: PRT
<213> ORGANISM: Artificial
<220> FEATURE:

<223> OTHER INFORMATION: Synthetic

<400> SEQUENCE: 155

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ala Ser Tyr
            20                  25                  30

Gly Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

-continued

```
Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 156
<211> LENGTH: 1368
<212> TYPE: DNA
<213> ORGANISM: Artificial
<220> FEATURE:
<223> OTHER INFORMATION: Synthetic

<400> SEQUENCE: 156

gaggtgcagc tggtggagtc tgggggaggc ctggtcaagc ctggggggtc cctgagactc     60

tcctgtgcag cctctggatt caccttcgct agctatggga tgaactgggt ccgccaggct    120

ccagggaagg ggctggagtg ggtctcatcc attagtagtt ctagtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc gagcaccaaa ggcccgagcg tgtttccgct ggcgccgagc    420

agcaaaagca ccagcggcgg caccgcggcg ctgggctgcc tggtgaaaga ttattttccg    480

gaaccggtga ccgtgagctg gaacagcggc gcgctgacca gcggcgtgca tacctttccg    540

gcggtgctgc agagcagcgg cctgtatagc ctgagcagcg tggtgaccgt gccgagcagc    600

agcctgggca cccagaccta tatttgcaac gtgaaccata aaccgagcaa caccaaagtg    660

gataaaaaag tggaaccgaa aagctgcgat aaaacccata cctgcccgcc gtgcccggcg    720

ccggaactgc tgggcggccc gagcgtgttt ctgtttccgc cgaaaccgaa agataccctg    780

atgattagcc gcaccccgga agtgacctgc gtggtggtgg atgtgagcca tgaagatccg    840

gaagtgaaat ttaactggta tgtggatggc gtggaagtgc ataacgcgaa aaccaaaccg    900

cgcgaagaac agtataacag cacctatcgc gtggtgagcg tgctgaccgt gctgcatcag    960

gattggctga acggcaaaga atataaatgc aaagtgagca acaaagcgct gccggcgccg   1020

attgaaaaaa ccattagcaa agcgaaaggc cagccgcgcg aaccgcaggt gtataccctg   1080

ccgccgagcc gcgatgaact gaccaaaaac caggtgagcc tgacctgcct ggtgaaaggc   1140

ttttatccga gcgatattgc ggtggaatgg gaaagcaacg gccagccgga aaacaactat   1200

aaaaccaccc cgccggtgct ggatagcgat ggcagctttt ttctgtatag caaactgacc   1260

gtggataaaa gccgctggca gcagggcaac gtgtttagct gcagcgtgat gcatgaagcg   1320

ctgcataacc attataccca gaaaagcctg agcctgagcc cgggcaaa               1368


<210> SEQ ID NO 157
<211> LENGTH: 220
<212> TYPE: PRT
<213> ORGANISM: Artificial
<220> FEATURE:
<223> OTHER INFORMATION: Synthetic

<400> SEQUENCE: 157

Asp Ile Val Met Thr Gln Ser Pro Asp Ser Leu Ala Val Ser Leu Gly
```

-continued

```
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 158
<211> LENGTH: 660
<212> TYPE: DNA
<213> ORGANISM: Artificial
<220> FEATURE:
<223> OTHER INFORMATION: Synthetic

<400> SEQUENCE: 158

```
gacatcgtga tgacccagtc tccagactcc ctggctgtgt ctctgggcga gagggccacc     60

atcaactgca agtccagcca gagtgtttta ttcagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcagca cgccagtgcc    300

cctcctactt ttggcggagg gaccaaggtt gagatcaaac gtacggtggc cgctccctcc    360

gtgttcatct tcccaccctc cgacgagcag ctgaagtccg gcaccgcctc cgtcgtgtgc    420

ctgctgaaca acttctaccc tcgcgaggcc aaagtgcagt ggaaagtgga caacgccctg    480

cagtccggca actcccagga atccgtcacc gagcaggact ccaaggacag cacctactcc    540

ctgtcctcca ccctgaccct gtccaaggcc gactacgaga agcacaaagt gtacgcctgc    600

gaagtgaccc accagggcct gtccagcccc gtgaccaagt ccttcaaccg gggcgagtgc    660
```

<210> SEQ ID NO 159
<211> LENGTH: 452
<212> TYPE: PRT
<213> ORGANISM: Artificial
<220> FEATURE:

<223> OTHER INFORMATION: Synthetic

<400> SEQUENCE: 159

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ala Ser Tyr
20 25 30

Gly Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Gly Arg Thr Ser Tyr Thr Ala Thr Ala His Asn Trp
100 105 110

Phe Asp Pro Trp Gly Gln Gly Thr Leu Val Thr Val Ser Ser Ala Ser
115 120 125

Thr Lys Gly Pro Ser Val Phe Pro Leu Ala Pro Cys Ser Arg Ser Thr
130 135 140

Ser Glu Ser Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Ser Leu Gly Thr Lys Thr Tyr Thr
195 200 205

Cys Asn Val Asp His Lys Pro Ser Asn Thr Lys Val Asp Lys Arg Val
210 215 220

Glu Ser Lys Tyr Gly Pro Pro Cys Pro Ser Cys Pro Ala Pro Glu Phe
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser Gln Glu Asp Pro Glu Val Gln Phe Asn Trp Tyr Val Asp Gly Val
275 280 285

Glu Val His Asn Ala Lys Thr Lys Pro Arg Glu Glu Gln Phe Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Gly Leu Pro Ser
325 330 335

Ser Ile Glu Lys Thr Ile Ser Lys Ala Lys Gly Gln Pro Arg Glu Pro
340 345 350

Gln Val Tyr Thr Leu Pro Pro Ser Gln Glu Glu Met Thr Lys Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

-continued

```
Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450
```

<210> SEQ ID NO 160
<211> LENGTH: 1356
<212> TYPE: DNA
<213> ORGANISM: Artificial
<220> FEATURE:
<223> OTHER INFORMATION: Synthetic

<400> SEQUENCE: 160

```
gaggtgcagc tggtggagtc tgggggaggc ctggtcaagc ctgggggtc cctgagactc      60

tcctgtgcag cctctggatt caccttcgct agctatggga tgaactgggt ccgccaggct     120

ccagggaagg ggctggagtg ggtctcatcc attagtagtt ctagtagtta catatactac     180

gcagactcag tgaagggccg attcaccatc tccagagaca acgccaagaa ctcactgtat     240

ctgcaaatga acagcctgag agccgaggac acggcggtgt actactgcgc cagagatggt     300

ggaagaacgt cctacaccgc cacagcccac aattggttcg acccctgggg acagggtaca     360

ttggtcaccg tctcctcagc ttccaccaag ggcccctccg tgttccctct ggccccttgc     420

tcccggtcca cctccgagtc taccgccgct ctgggctgcc tcgtgaagga ctacttcccc     480

gagcccgtga ccgtgtcctg gaactctggc gccctgacct ccggcgtgca caccttccct     540

gccgtgctgc agtcctccgg cctgtactcc ctgtccagcg tcgtgaccgt gccctcctcc     600

agcctgggca ccaagaccta cacctgtaac gtggaccaca agccctccaa caccaaagtg     660

gacaagcggg tggaatctaa gtacggccct ccctgccctt cctgccctgc ccctgagttc     720

ctgggcggac cttccgtgtt cctgttccct ccaaagccca aggacaccct gatgatctcc     780

cggacccctg aagtgacctg cgtggtggtg gacgtgtccc aggaagatcc cgaagtccag     840

ttcaattggt acgtggacgg cgtggaagtg cacaacgcca agaccaagcc cagagaggaa     900

cagttcaact ccacctaccg ggtggtgtcc gtgctgaccg tgctgcacca ggactggctg     960

aacggcaaag agtacaagtg caaagtgtcc aacaagggcc tgccctccag catcgaaaag    1020

accatctcca aggccaaggg ccagccccgc gagccccaag tgtacaccct gcctcccagc    1080

caggaagaga tgaccaagaa tcaagtgtcc ctgacttgtc tggtcaaggg cttctacccc    1140

tccgatatcg ccgtggagtg ggagtccaac ggccagcccg agaacaacta caagaccacc    1200

cctcccgtgc tggactccga cggctccttc ttcctgtact ctcggctgac cgtggacaag    1260

tcccggtggc aggaaggcaa cgtcttctcc tgctccgtga tgcacgaggc cctgcacaac    1320

cactacaccc agaagtccct gtccctgtct ctgggc                              1356
```

<210> SEQ ID NO 161
<211> LENGTH: 8
<212> TYPE: PRT
<213> ORGANISM: Artificial
<220> FEATURE:
<223> OTHER INFORMATION: Synthetic

<400> SEQUENCE: 161

Gly Phe Thr Phe Arg Ser Tyr Gly 1 5

<210> SEQ ID NO 162
<211> LENGTH: 8
<212> TYPE: PRT
<213> ORGANISM: Artificial
<220> FEATURE:
<223> OTHER INFORMATION: Synthetic

<400> SEQUENCE: 162

Ile Ser Ser Ser Gly Ser Tyr Ile
1 5

<210> SEQ ID NO 163
<211> LENGTH: 19
<212> TYPE: PRT
<213> ORGANISM: Artificial
<220> FEATURE:
<223> OTHER INFORMATION: Synthetic

<400> SEQUENCE: 163

Ala Arg Asp Gly Gly Arg Thr Ser Tyr Thr Ala Thr Ala His Asn Trp
1 5 10 15

Phe Asp Pro

<210> SEQ ID NO 164
<211> LENGTH: 9
<212> TYPE: PRT
<213> ORGANISM: Artificial
<220> FEATURE:
<223> OTHER INFORMATION: Synthetic

<400> SEQUENCE: 164

Phe Thr Phe Arg Ser Tyr Gly Met Asn
1 5

<210> SEQ ID NO 165
<211> LENGTH: 17
<212> TYPE: PRT
<213> ORGANISM: Artificial
<220> FEATURE:
<223> OTHER INFORMATION: Synthetic

<400> SEQUENCE: 165

Gly Ile Ser Ser Ser Gly Ser Tyr Ile Tyr Tyr Ala Asp Ser Val Lys
1 5 10 15

Gly

<210> SEQ ID NO 166
<211> LENGTH: 19
<212> TYPE: PRT
<213> ORGANISM: Artificial
<220> FEATURE:
<223> OTHER INFORMATION: Synthetic

<400> SEQUENCE: 166

Ala Arg Asp Gly Gly Arg Thr Ser Tyr Thr Ala Thr Ala His Asn Trp
1 5 10 15

Phe Asp Pro

<210> SEQ ID NO 167
<211> LENGTH: 126
<212> TYPE: PRT
<213> ORGANISM: Artificial
<220> FEATURE:

<223> OTHER INFORMATION: Synthetic

<400> SEQUENCE: 167

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Arg Ser Tyr
20 25 30

Gly Met Asn Trp Val Arg Gln Ala Pro Gly Lys Gly Leu Glu Trp Val
35 40 45

Ser Gly Ile Ser Ser Ser Gly Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly Gly Arg Thr Ser Tyr Thr Ala Thr Ala His Asn Trp
100 105 110

Phe Asp Pro Trp Gly Gln Gly Thr Leu Val Thr Val Ser Ser
115 120 125

<210> SEQ ID NO 168
<211> LENGTH: 378
<212> TYPE: DNA
<213> ORGANISM: Artificial
<220> FEATURE:
<223> OTHER INFORMATION: Synthetic

<400> SEQUENCE: 168
gaggtgcagc tggtggagtc tgggggaggc ctggtcaagc ctgggggtc cctgagactc 60 tcctgtgcag cctctggatt caccttccgt agctatggga tgaactgggt ccgccaggct 120
ccagggaagg ggctggagtg ggtctcaggt attagtagta gtggtagtta catatactac 180
gcagactcag tgaagggccg attcaccatc tccagagaca acgccaagaa ctcactgtat 240
ctgcaaatga acagcctgag agccgaggac acggcggtgt actactgcgc cagagatggt 300
ggaagaacgt cctacaccgc cacagcccac aattggttcg acccctgggg acagggtaca 360
ttggtcaccg tctcctca 378

<210> SEQ ID NO 169
<211> LENGTH: 12
<212> TYPE: PRT
<213> ORGANISM: Artificial
<220> FEATURE:
<223> OTHER INFORMATION: Synthetic

<400> SEQUENCE: 169

Gln Ser Val Leu Phe Ser Ser Asn Asn Lys Asn Tyr
1 5 10

<210> SEQ ID NO 170
<211> LENGTH: 3
<212> TYPE: PRT
<213> ORGANISM: Artificial
<220> FEATURE:
<223> OTHER INFORMATION: Synthetic

<400> SEQUENCE: 170

Trp Ala Ser
1

<210> SEQ ID NO 171
<211> LENGTH: 9
<212> TYPE: PRT
<213> ORGANISM: Artificial
<220> FEATURE:
<223> OTHER INFORMATION: Synthetic

<400> SEQUENCE: 171

Gln Gln His Ala Ser Ala Pro Pro Thr
1               5

<210> SEQ ID NO 172
<211> LENGTH: 17
<212> TYPE: PRT
<213> ORGANISM: Artificial
<220> FEATURE:
<223> OTHER INFORMATION: Synthetic

<400> SEQUENCE: 172

Lys Ser Ser Gln Ser Val Leu Phe Ser Ser Asn Asn Lys Asn Tyr Leu
1               5                   10                  15

Ala

<210> SEQ ID NO 173
<211> LENGTH: 7
<212> TYPE: PRT
<213> ORGANISM: Artificial
<220> FEATURE:
<223> OTHER INFORMATION: Synthetic

<400> SEQUENCE: 173

Trp Ala Ser Thr Arg Glu Ser
1               5

<210> SEQ ID NO 174
<211> LENGTH: 9
<212> TYPE: PRT
<213> ORGANISM: Artificial
<220> FEATURE:
<223> OTHER INFORMATION: Synthetic

<400> SEQUENCE: 174

Gln Gln His Ala Ser Ala Pro Pro Thr
1               5

<210> SEQ ID NO 175
<211> LENGTH: 113
<212> TYPE: PRT
<213> ORGANISM: Artificial
<220> FEATURE:
<223> OTHER INFORMATION: Synthetic

<400> SEQUENCE: 175

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln

```
                85                  90                  95

His Ala Ser Ala Pro Pro Thr Phe Gly Gly Gly Thr Lys Val Glu Ile
            100                 105                 110

Lys


<210> SEQ ID NO 176
<211> LENGTH: 339
<212> TYPE: DNA
<213> ORGANISM: Artificial
<220> FEATURE:
<223> OTHER INFORMATION: Synthetic

<400> SEQUENCE: 176

gacatcgtga tgacccagtc tccagactcc ctggctgtgt ctctgggcga gagggccacc      60

atcaactgca agtccagcca gagtgtttta ttcagctcca acaataagaa ctacttagct     120

tggtaccagc agaaaccagg acagcctcct aagctgctca tttactgggc atctacccgg     180

gaatccgggg tccctgaccg attcagtggc agcgggtctg ggacagattt cactctcacc     240

atcagcagcc tgcaggctga agatgtggca gtttattact gtcagcagca cgccagtgcc     300

cctcctactt ttggcggagg gaccaaggtt gagatcaaa                            339


<210> SEQ ID NO 177
<211> LENGTH: 456
<212> TYPE: PRT
<213> ORGANISM: Artificial
<220> FEATURE:
<223> OTHER INFORMATION: Synthetic

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Gly Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
```

```
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 178
<211> LENGTH: 1368
<212> TYPE: DNA
<213> ORGANISM: Artificial
<220> FEATURE:
<223> OTHER INFORMATION: Synthetic

<400> SEQUENCE: 178

gaggtgcagc tggtggagtc tgggggaggc ctggtcaagc ctggggggtc cctgagactc      60

tcctgtgcag cctctggatt caccttccgt agctatggga tgaactgggt ccgccaggct     120

ccagggaagg ggctggagtg ggtctcaggt attagtagta gtggtagtta catatactac     180

gcagactcag tgaagggccg attcaccatc tccagagaca acgccaagaa ctcactgtat     240

ctgcaaatga acagcctgag agccgaggac acggcggtgt actactgcgc cagagatggt     300

ggaagaacgt cctacaccgc cacagcccac aattggttcg acccctgggg acagggtaca     360

ttggtcaccg tctcctcagc gagcaccaaa ggcccgagcg tgtttccgct ggcgccgagc     420

agcaaaagca ccagcggcgg caccgcggcg ctgggctgcc tggtgaaaga ttattttccg     480

gaaccggtga ccgtgagctg gaacagcggc gcgctgacca gcggcgtgca tacctttccg     540

gcggtgctgc agagcagcgg cctgtatagc ctgagcagcg tggtgaccgt gccgagcagc     600

agcctgggca cccagaccta tatttgcaac gtgaaccata aaccgagcaa caccaaagtg     660
```

-continued

```
gataaaaaag tggaaccgaa aagctgcgat aaaacccata cctgcccgcc gtgcccggcg    720
ccggaactgc tgggcggccc gagcgtgttt ctgtttccgc cgaaaccgaa agataccctg    780
atgattagcc gcaccccgga agtgacctgc gtggtggtgg atgtgagcca tgaagatccg    840
gaagtgaaat ttaactggta tgtggatggc gtggaagtgc ataacgcgaa aaccaaaccg    900
cgcgaagaac agtataacag cacctatcgc gtggtgagcg tgctgaccgt gctgcatcag    960
gattggctga acggcaaaga atataaatgc aaagtgagca acaaagcgct gccggcgccg   1020
attgaaaaaa ccattagcaa agcgaaaggc cagccgcgcg aaccgcaggt gtataccctg   1080
ccgccgagcc gcgatgaact gaccaaaaac caggtgagcc tgacctgcct ggtgaaaggc   1140
ttttatccga gcgatattgc ggtggaatgg gaaagcaacg gccagccgga aaacaactat   1200
aaaaccaccc cgccggtgct ggatagcgat ggcagctttt ttctgtatag caaactgacc   1260
gtggataaaa gccgctggca gcagggcaac gtgtttagct gcagcgtgat gcatgaagcg   1320
ctgcataacc attataccca gaaaagcctg agcctgagcc cgggcaaa               1368
```

```
<210> SEQ ID NO 179
<211> LENGTH: 220
<212> TYPE: PRT
<213> ORGANISM: Artificial
<220> FEATURE:
<223> OTHER INFORMATION: Synthetic

<400> SEQUENCE: 179

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Ala Ser Ala Pro Pro Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 180
<211> LENGTH: 660
```

<212> TYPE: DNA
<213> ORGANISM: Artificial
<220> FEATURE:
<223> OTHER INFORMATION: Synthetic

<400> SEQUENCE: 180

```
gacatcgtga tgacccagtc tccagactcc ctggctgtgt ctctgggcga gagggccacc      60

atcaactgca agtccagcca gagtgtttta ttcagctcca acaataagaa ctacttagct     120

tggtaccagc agaaaccagg acagcctcct aagctgctca tttactgggc atctacccgg     180

gaatccgggg tccctgaccg attcagtggc agcgggtctg ggacagattt cactctcacc     240

atcagcagcc tgcaggctga agatgtggca gtttattact gtcagcagca cgccagtgcc     300

cctcctactt ttggcggagg gaccaaggtt gagatcaaac gtacggtggc cgctccctcc     360

gtgttcatct tcccaccctc cgacgagcag ctgaagtccg gcaccgcctc cgtcgtgtgc     420

ctgctgaaca acttctaccc tcgcgaggcc aaagtgcagt ggaaagtgga caacgccctg     480

cagtccggca actcccagga atccgtcacc gagcaggact ccaaggacag cacctactcc     540

ctgtcctcca ccctgaccct gtccaaggcc gactacgaga agcacaaagt gtacgcctgc     600

gaagtgaccc accagggcct gtccagcccc gtgaccaagt ccttcaaccg gggcgagtgc     660
```

<210> SEQ ID NO 181
<211> LENGTH: 452
<212> TYPE: PRT
<213> ORGANISM: Artificial
<220> FEATURE:
<223> OTHER INFORMATION: Synthetic

<400> SEQUENCE: 181

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Gly Met Asn Trp Val Arg Gln Ala Pro Gly Lys Gly Leu Glu Trp Val
        35                  40                  45

Ser Gly Ile Ser Ser Ser Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Arg Thr Ser Tyr Thr Ala Thr Ala His Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
```

```
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly
    450
```

<210> SEQ ID NO 182
<211> LENGTH: 1356
<212> TYPE: DNA
<213> ORGANISM: Artificial
<220> FEATURE:
<223> OTHER INFORMATION: Synthetic

<400> SEQUENCE: 182

```
gaggtgcagc tggtggagtc tgggggaggc ctggtcaagc ctggggggtc cctgagactc     60

tcctgtgcag cctctggatt caccttccgt agctatggga tgaactgggt ccgccaggct    120

ccagggaagg ggctggagtg ggtctcaggt attagtagta gtggtagtta catatactac    180

gcagactcag tgaagggccg attcaccatc tccagagaca acgccaagaa ctcactgtat    240

ctgcaaatga acagcctgag agccgaggac acggcggtgt actactgcgc cagagatggt    300

ggaagaacgt cctacaccgc cacagcccac aattggttcg acccctgggg acagggtaca    360

ttggtcaccg tctcctcagc ttccaccaag ggcccctccg tgttccctct ggccccttgc    420

tcccggtcca cctccgagtc taccgccgct ctgggctgcc tcgtgaagga ctacttcccc    480

gagcccgtga ccgtgtcctg gaactctggc gccctgacct ccggcgtgca caccttccct    540

gccgtgctgc agtcctccgg cctgtactcc ctgtccagcg tcgtgaccgt gccctcctcc    600

agcctgggca ccaagaccta cacctgtaac gtggaccaca agccctccaa caccaaagtg    660
```

-continued

```
gacaagcggg tggaatctaa gtacggccct ccctgccctt cctgccctgc ccctgagttc    720

ctgggcggac cttccgtgtt cctgttccct ccaaagccca aggacaccct gatgatctcc    780

cggacccctg aagtgacctg cgtggtggtg gacgtgtccc aggaagatcc cgaagtccag    840

ttcaattggt acgtggacgg cgtggaagtg cacaacgcca agaccaagcc cagagaggaa    900

cagttcaact ccacctaccg ggtggtgtcc gtgctgaccg tgctgcacca ggactggctg    960

aacggcaaag agtacaagtg caaagtgtcc aacaagggcc tgccctccag catcgaaaag   1020

accatctcca aggccaaggg ccagccccgc gagccccaag tgtacaccct gcctcccagc   1080

caggaagaga tgaccaagaa tcaagtgtcc ctgacttgtc tggtcaaggg cttctacccc   1140

tccgatatcg ccgtggagtg ggagtccaac ggccagcccg agaacaacta caagaccacc   1200

cctcccgtgc tggactccga cggctccttc ttcctgtact ctcggctgac cgtggacaag   1260

tcccggtggc aggaaggcaa cgtcttctcc tgctccgtga tgcacgaggc cctgcacaac   1320

cactacaccc agaagtccct gtccctgtct ctgggc                              1356


<210> SEQ ID NO 183
<211> LENGTH: 451
<212> TYPE: PRT
<213> ORGANISM: Artificial
<220> FEATURE:
<223> OTHER INFORMATION: Synthetic

<400> SEQUENCE: 183

Glu Val Lys Leu Val Glu Ser Gly Gly Gly Leu Val Gln Pro Gly Gly
1               5                   10                  15

Ser Leu Lys Leu Phe Cys Ala Ala Ser Gly Phe Thr Phe Thr Ser Tyr
            20                  25                  30

Ser Met Ser Trp Val Arg Gln Thr Pro Glu Lys Arg Leu Glu Trp Val
        35                  40                  45

Ala Tyr Ile Ser Tyr Asp Gly Gly Ser Ala Tyr Tyr Pro Asp Thr Val
    50                  55                  60

Lys Gly Arg Phe Ser Ile Ser Arg Asp Asn Ala Lys Lys Thr Leu Tyr
65                  70                  75                  80

Leu Gln Met Ser Ser Leu Lys Ser Glu Asp Thr Ala Met Tyr Tyr Cys
                85                  90                  95

Ala Arg His Gly Asp Tyr Asp Asp Asp Asp Ala Met Asp Tyr Trp Gly
            100                 105                 110

Gln Gly Thr Ser Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240
```

```
Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly Lys
    450


<210> SEQ ID NO 184
<211> LENGTH: 213
<212> TYPE: PRT
<213> ORGANISM: Artificial
<220> FEATURE:
<223> OTHER INFORMATION: Synthetic

<400> SEQUENCE: 184

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Glu Thr Leu Thr Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Gly Thr Pro Leu
                85                  90                  95

Thr Phe Gly Ala Gly Thr Lys Leu Asp Leu Lys Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140
```

Val Lys Trp Lys Ile Asp Gly Ser Glu Arg Gln Asn Gly Val Leu Asn
145 150 155 160

Ser Trp Thr Asp Gln Asp Ser Lys Asp Ser Thr Tyr Ser Met Ser Ser
165 170 175

Thr Leu Thr Leu Thr Lys Asp Glu Tyr Glu Arg His Asn Ser Tyr Thr
180 185 190

Cys Glu Ala Thr His Lys Thr Ser Thr Ser Pro Ile Val Lys Ser Phe
195 200 205

Asn Arg Asn Glu Cys
210

<210> SEQ ID NO 185
<211> LENGTH: 8
<212> TYPE: PRT
<213> ORGANISM: Artificial
<220> FEATURE:
<223> OTHER INFORMATION: Synthetic

<400> SEQUENCE: 185

Gly Gly Thr Phe Ser Ala Tyr Ala
1 5

<210> SEQ ID NO 186
<211> LENGTH: 8
<212> TYPE: PRT
<213> ORGANISM: Artificial
<220> FEATURE:
<223> OTHER INFORMATION: Synthetic

<400> SEQUENCE: 186

Ile Ile Pro Ile Phe Gly Thr Ala
1 5

<210> SEQ ID NO 187
<211> LENGTH: 17
<212> TYPE: PRT
<213> ORGANISM: Artificial
<220> FEATURE:
<223> OTHER INFORMATION: Synthetic

<400> SEQUENCE: 187

Ala Arg Ser Tyr Tyr Ser Ser Arg Trp His Tyr Tyr Tyr Tyr Met Asp
1 5 10 15

Val

<210> SEQ ID NO 188
<211> LENGTH: 9
<212> TYPE: PRT
<213> ORGANISM: Artificial
<220> FEATURE:
<223> OTHER INFORMATION: Synthetic

<400> SEQUENCE: 188

Gly Thr Phe Ser Ala Tyr Ala Ile Ser
1 5

<210> SEQ ID NO 189
<211> LENGTH: 17
<212> TYPE: PRT
<213> ORGANISM: Artificial
<220> FEATURE:
<223> OTHER INFORMATION: Synthetic

<400> SEQUENCE: 189

-continued

```
Gly Ile Ile Pro Ile Phe Gly Thr Ala Asn Tyr Ala Gln Lys Phe Gln
1               5                   10                  15

Gly


<210> SEQ ID NO 190
<211> LENGTH: 17
<212> TYPE: PRT
<213> ORGANISM: Artificial
<220> FEATURE:
<223> OTHER INFORMATION: Synthetic

<400> SEQUENCE: 190

Ala Arg Ser Tyr Tyr Ser Ser Arg Trp His Tyr Tyr Tyr Tyr Met Asp
1               5                   10                  15

Val


<210> SEQ ID NO 191
<211> LENGTH: 124
<212> TYPE: PRT
<213> ORGANISM: Artificial
<220> FEATURE:
<223> OTHER INFORMATION: Synthetic

<400> SEQUENCE: 191

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser
        115                 120


<210> SEQ ID NO 192
<211> LENGTH: 372
<212> TYPE: DNA
<213> ORGANISM: Artificial
<220> FEATURE:
<223> OTHER INFORMATION: Synthetic

<400> SEQUENCE: 192

caggtgcagc tggtgcagtc tggggctgag gtgaagaagc ctgggtcctc ggtgaaggtc      60

tcctgcaagg cttctggagg caccttcagc gcttatgcga tcagctgggt gcgacaggcc     120

cctggacaag ggcttgagtg gatgggaggg atcatcccta tctttggtac agcaaactac     180

gcacagaagt tccagggcag agtcacgatt accgcggacg aatccacgag cacagcctac     240

atggagctga gcagcctgag atctgaggac acggcggtgt actactgcgc cagatcttac     300

tactccagcc gatggcacta ctactactac atggacgtgt ggggcaaggg tacaactgtc     360

accgtctcct ca                                                         372
```

<210> SEQ ID NO 193
<211> LENGTH: 6
<212> TYPE: PRT
<213> ORGANISM: Artificial
<220> FEATURE:
<223> OTHER INFORMATION: Synthetic

<400> SEQUENCE: 193

Gln Gly Ile Ser Ser Trp
1               5

<210> SEQ ID NO 194
<211> LENGTH: 3
<212> TYPE: PRT
<213> ORGANISM: Artificial
<220> FEATURE:
<223> OTHER INFORMATION: Synthetic

<400> SEQUENCE: 194

Ala Ala Ser
1

<210> SEQ ID NO 195
<211> LENGTH: 9
<212> TYPE: PRT
<213> ORGANISM: Artificial
<220> FEATURE:
<223> OTHER INFORMATION: Synthetic

<400> SEQUENCE: 195

Gln Gln Ala Asp Asp Leu Pro Leu Thr
1               5

<210> SEQ ID NO 196
<211> LENGTH: 11
<212> TYPE: PRT
<213> ORGANISM: Artificial
<220> FEATURE:
<223> OTHER INFORMATION: Synthetic

<400> SEQUENCE: 196

Arg Ala Ser Gln Gly Ile Ser Ser Trp Leu Ala
1               5                   10

<210> SEQ ID NO 197
<211> LENGTH: 7
<212> TYPE: PRT
<213> ORGANISM: Artificial
<220> FEATURE:
<223> OTHER INFORMATION: Synthetic

<400> SEQUENCE: 197

Ala Ala Ser Asn Leu Gln Ser
1               5

<210> SEQ ID NO 198
<211> LENGTH: 9
<212> TYPE: PRT
<213> ORGANISM: Artificial
<220> FEATURE:
<223> OTHER INFORMATION: Synthetic

<400> SEQUENCE: 198

Gln Gln Ala Asp Asp Leu Pro Leu Thr
1               5

<210> SEQ ID NO 199

```
<211> LENGTH: 107
<212> TYPE: PRT
<213> ORGANISM: Artificial
<220> FEATURE:
<223> OTHER INFORMATION: Synthetic

<400> SEQUENCE: 199

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Asp Leu Pro Leu
                85                  90                  95

Thr Phe Gly Gly Gly Thr Lys Val Glu Ile Lys
            100                 105


<210> SEQ ID NO 200
<211> LENGTH: 321
<212> TYPE: DNA
<213> ORGANISM: Artificial
<220> FEATURE:
<223> OTHER INFORMATION: Synthetic

<400> SEQUENCE: 200

gacatccaga tgacacagtc tccatcttcc gtgtctgcat ctgtaggaga cagagtcacc      60

atcacttgtc gggcgagtca gggtattagc agctggttag cctggtatca gcagaaacca     120

gggaaagccc ctaagctcct gatctatgct gcatccaatt tgcaaagtgg ggtcccatca     180

aggttcagcg gcagtggatc tgggacagat ttcactctca ccatcagcag cctgcagcct     240

gaagattttg caacttatta ctgtcagcag gcagacgacc tccctctcac ttttggcgga     300

gggaccaagg ttgagatcaa a                                               321


<210> SEQ ID NO 201
<211> LENGTH: 454
<212> TYPE: PRT
<213> ORGANISM: Artificial
<220> FEATURE:
<223> OTHER INFORMATION: Synthetic

<400> SEQUENCE: 201

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 202
<211> LENGTH: 1362
<212> TYPE: DNA
<213> ORGANISM: Artificial
<220> FEATURE:
<223> OTHER INFORMATION: Synthetic

<400> SEQUENCE: 202

-continued

```
caggtgcagc tggtgcagtc tggggctgag gtgaagaagc ctgggtcctc ggtgaaggtc     60

tcctgcaagg cttctggagg caccttcagc gcttatgcga tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggcggtgt actactgcgc cagatcttac    300

tactccagcc gatggcacta ctactactac atggacgtgt ggggcaaggg tacaactgtc    360

accgtctcct cagcgagcac caaaggcccg agcgtgtttc cgctggcgcc gagcagcaaa    420

agcaccagcg gcggcaccgc ggcgctgggc tgcctggtga aagattattt tccggaaccg    480

gtgaccgtga gctggaacag cggcgcgctg accagcggcg tgcatacctt tccggcggtg    540

ctgcagagca gcggcctgta tagcctgagc agcgtggtga ccgtgccgag cagcagcctg    600

ggcacccaga cctatatttg caacgtgaac cataaaccga gcaacaccaa agtggataaa    660

aaagtggaac cgaaaagctg cgataaaacc catacctgcc cgccgtgccc ggcgccggaa    720

ctgctgggcg gcccgagcgt gtttctgttt ccgccgaaac cgaaagatac cctgatgatt    780

agccgcaccc cggaagtgac ctgcgtggtg gtggatgtga gccatgaaga tccggaagtg    840

aaatttaact ggtatgtgga tggcgtggaa gtgcataacg cgaaaaccaa accgcgcgaa    900

gaacagtata acagcaccta tcgcgtggtg agcgtgctga ccgtgctgca tcaggattgg    960

ctgaacggca aagaatataa atgcaaagtg agcaacaaag cgctgccggc gccgattgaa   1020

aaaaccatta gcaaagcgaa aggccagccg cgcgaaccgc aggtgtatac cctgccgccg   1080

agccgcgatg aactgaccaa aaaccaggtg agcctgacct gcctggtgaa aggcttttat   1140

ccgagcgata ttgcggtgga atgggaaagc aacggccagc cggaaaacaa ctataaaacc   1200

accccgccgg tgctggatag cgatggcagc tttttctgt atagcaaact gaccgtggat    1260

aaaagccgct ggcagcaggg caacgtgttt agctgcagcg tgatgcatga agcgctgcat   1320

aaccattata cccagaaaag cctgagcctg agcccgggca aa                      1362
```

<210> SEQ ID NO 203
<211> LENGTH: 214
<212> TYPE: PRT
<213> ORGANISM: Artificial
<220> FEATURE:
<223> OTHER INFORMATION: Synthetic

<400> SEQUENCE: 203

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Asp Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 204
<211> LENGTH: 642
<212> TYPE: DNA
<213> ORGANISM: Artificial
<220> FEATURE:
<223> OTHER INFORMATION: Synthetic

<400> SEQUENCE: 204

gacatccaga tgacacagtc tccatcttcc gtgtctgcat ctgtaggaga cagagtcacc      60

atcacttgtc gggcgagtca gggtattagc agctggttag cctggtatca gcagaaacca     120

gggaaagccc ctaagctcct gatctatgct gcatccaatt tgcaaagtgg ggtcccatca     180

aggttcagcg gcagtggatc tgggacagat ttcactctca ccatcagcag cctgcagcct     240

gaagattttg caacttatta ctgtcagcag gcagacgacc tccctctcac ttttggcgga     300

gggaccaagg ttgagatcaa acgtacggtg gccgctccct ccgtgttcat cttcccaccc     360

tccgacgagc agctgaagtc cggcaccgcc tccgtcgtgt gcctgctgaa caacttctac     420

cctcgcgagg ccaaagtgca gtggaaagtg gacaacgccc tgcagtccgg caactcccag     480

gaatccgtca ccgagcagga ctccaaggac agcacctact ccctgtcctc caccctgacc     540

ctgtccaagg ccgactacga gaagcacaaa gtgtacgcct gcgaagtgac ccaccagggc     600

ctgtccagcc ccgtgaccaa gtccttcaac cggggcgagt gc                        642


<210> SEQ ID NO 205
<211> LENGTH: 450
<212> TYPE: PRT
<213> ORGANISM: Artificial
<220> FEATURE:
<223> OTHER INFORMATION: Synthetic

<400> SEQUENCE: 205

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450
```

<210> SEQ ID NO 206
<211> LENGTH: 1350
<212> TYPE: DNA
<213> ORGANISM: Artificial
<220> FEATURE:
<223> OTHER INFORMATION: Synthetic

<400> SEQUENCE: 206

-continued

```
caggtgcagc tggtgcagtc tggggctgag gtgaagaagc ctgggtcctc ggtgaaggtc     60

tcctgcaagg cttctggagg caccttcagc gcttatgcga tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggcggtgt actactgcgc cagatcttac    300

tactccagcc gatggcacta ctactactac atggacgtgt ggggcaaggg tacaactgtc    360

accgtctcct cagcttccac caagggcccc tccgtgttcc ctctggcccc ttgctcccgg    420

tccacctccg agtctaccgc cgctctgggc tgcctcgtga aggactactt ccccgagccc    480

gtgaccgtgt cctggaactc tggcgccctg acctccggcg tgcacacctt ccctgccgtg    540

ctgcagtcct ccggcctgta ctccctgtcc agcgtcgtga ccgtgccctc ctccagcctg    600

ggcaccaaga cctacacctg taacgtggac cacaagccct ccaacaccaa agtggacaag    660

cgggtggaat ctaagtacgg ccctccctgc ccttcctgcc ctgcccctga gttcctgggc    720

ggaccttccg tgttcctgtt ccctccaaag cccaaggaca ccctgatgat ctcccggacc    780

cctgaagtga cctgcgtggt ggtggacgtg tcccaggaag atcccgaagt ccagttcaat    840

tggtacgtgg acggcgtgga agtgcacaac gccaagacca agcccagaga ggaacagttc    900

aactccacct accgggtggt gtccgtgctg accgtgctgc accaggactg gctgaacggc    960

aaagagtaca agtgcaaagt gtccaacaag ggcctgccct ccagcatcga aaagaccatc   1020

tccaaggcca agggccagcc ccgcgagccc caagtgtaca ccctgcctcc cagccaggaa   1080

gagatgacca agaatcaagt gtccctgact tgtctggtca agggcttcta cccctccgat   1140

atcgccgtgg agtgggagtc caacggccag cccgagaaca actacaagac cacccctccc   1200

gtgctggact ccgacggctc cttcttcctg tactctcggc tgaccgtgga caagtcccgg   1260

tggcaggaag gcaacgtctt ctcctgctcc gtgatgcacg aggccctgca caaccactac   1320

acccagaagt ccctgtccct gtctctgggc                                     1350
```

<210> SEQ ID NO 207
<211> LENGTH: 8
<212> TYPE: PRT
<213> ORGANISM: Artificial
<220> FEATURE:
<223> OTHER INFORMATION: Synthetic

<400> SEQUENCE: 207

```
Gly Gly Thr Phe Glu Ser Tyr Thr
1               5
```

<210> SEQ ID NO 208
<211> LENGTH: 8
<212> TYPE: PRT
<213> ORGANISM: Artificial
<220> FEATURE:
<223> OTHER INFORMATION: Synthetic

<400> SEQUENCE: 208

```
Ile Ala Pro Ile Phe Gly Thr Ala
1               5
```

<210> SEQ ID NO 209
<211> LENGTH: 17
<212> TYPE: PRT
<213> ORGANISM: Artificial
<220> FEATURE:
<223> OTHER INFORMATION: Synthetic

<400> SEQUENCE: 209

Ala Arg Ser Tyr Tyr Ser Ser Arg Trp His Tyr Tyr Tyr Tyr Met Asp
1 5 10 15

Val

<210> SEQ ID NO 210
<211> LENGTH: 9
<212> TYPE: PRT
<213> ORGANISM: Artificial
<220> FEATURE:
<223> OTHER INFORMATION: Synthetic

<400> SEQUENCE: 210

Gly Thr Phe Glu Ser Tyr Thr Ile Ser
1 5

<210> SEQ ID NO 211
<211> LENGTH: 17
<212> TYPE: PRT
<213> ORGANISM: Artificial
<220> FEATURE:
<223> OTHER INFORMATION: Synthetic

<400> SEQUENCE: 211

Gly Ile Ala Pro Ile Phe Gly Thr Ala His Tyr Ala Gln Lys Phe Gln
1 5 10 15

Gly

<210> SEQ ID NO 212
<211> LENGTH: 17
<212> TYPE: PRT
<213> ORGANISM: Artificial
<220> FEATURE:
<223> OTHER INFORMATION: Synthetic

<400> SEQUENCE: 212

Ala Arg Ser Tyr Tyr Ser Ser Arg Trp His Tyr Tyr Tyr Tyr Met Asp
1 5 10 15

Val

<210> SEQ ID NO 213
<211> LENGTH: 124
<212> TYPE: PRT
<213> ORGANISM: Artificial
<220> FEATURE:
<223> OTHER INFORMATION: Synthetic

<400> SEQUENCE: 213

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Glu Ser Tyr
20 25 30

Thr Ile Ser Trp Val Arg Gln Ala Pro Gly Gln Gly Leu Glu Trp Met
35 40 45

Gly Gly Ile Ala Pro Ile Phe Gly Thr Ala His Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

-continued

```
Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser
        115                 120
```

<210> SEQ ID NO 214
<211> LENGTH: 372
<212> TYPE: DNA
<213> ORGANISM: Artificial
<220> FEATURE:
<223> OTHER INFORMATION: Synthetic

<400> SEQUENCE: 214

```
caggtgcagc tggtgcagtc tggggctgag gtgaagaagc ctgggtcctc ggtgaaggtc     60

tcctgcaagg cttctggagg caccttcgag agctatacga tcagctgggt gcgacaggcc    120

cctggacaag ggcttgagtg gatgggaggg atcgcgccta tctttggtac agcacattac    180

gcacagaagt tccagggcag agtcacgatt accgcggacg aatccacgag cacagcctac    240

atggagctga gcagcctgag atctgaggac acggcggtgt actactgcgc cagatcttac    300

tactccagcc gatggcacta ctactactac atggacgtgt ggggcaaggg tacaactgtc    360

accgtctcct ca                                                        372
```

<210> SEQ ID NO 215
<211> LENGTH: 6
<212> TYPE: PRT
<213> ORGANISM: Artificial
<220> FEATURE:
<223> OTHER INFORMATION: Synthetic

<400> SEQUENCE: 215

```
Gln Gly Ile Ser Ser Trp
1               5
```

<210> SEQ ID NO 216
<211> LENGTH: 3
<212> TYPE: PRT
<213> ORGANISM: Artificial
<220> FEATURE:
<223> OTHER INFORMATION: Synthetic

<400> SEQUENCE: 216

```
Ala Ala Ser
1
```

<210> SEQ ID NO 217
<211> LENGTH: 9
<212> TYPE: PRT
<213> ORGANISM: Artificial
<220> FEATURE:
<223> OTHER INFORMATION: Synthetic

<400> SEQUENCE: 217

```
Gln Gln Ala Asp Asp Leu Pro Leu Thr
1               5
```

<210> SEQ ID NO 218
<211> LENGTH: 11
<212> TYPE: PRT
<213> ORGANISM: Artificial
<220> FEATURE:
<223> OTHER INFORMATION: Synthetic

<400> SEQUENCE: 218

-continued

```
Arg Ala Ser Gln Gly Ile Ser Ser Trp Leu Ala
1               5                   10


<210> SEQ ID NO 219
<211> LENGTH: 7
<212> TYPE: PRT
<213> ORGANISM: Artificial
<220> FEATURE:
<223> OTHER INFORMATION: Synthetic

<400> SEQUENCE: 219

Ala Ala Ser Asn Leu Gln Ser
1               5


<210> SEQ ID NO 220
<211> LENGTH: 9
<212> TYPE: PRT
<213> ORGANISM: Artificial
<220> FEATURE:
<223> OTHER INFORMATION: Synthetic

<400> SEQUENCE: 220

Gln Gln Ala Asp Asp Leu Pro Leu Thr
1               5


<210> SEQ ID NO 221
<211> LENGTH: 107
<212> TYPE: PRT
<213> ORGANISM: Artificial
<220> FEATURE:
<223> OTHER INFORMATION: Synthetic

<400> SEQUENCE: 221

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Asp Leu Pro Leu
                85                  90                  95

Thr Phe Gly Gly Gly Thr Lys Val Glu Ile Lys
            100                 105


<210> SEQ ID NO 222
<211> LENGTH: 321
<212> TYPE: DNA
<213> ORGANISM: Artificial
<220> FEATURE:
<223> OTHER INFORMATION: Synthetic

<400> SEQUENCE: 222

gacatccaga tgacccagtc tccatcttcc gtgtctgcat ctgtaggaga cagagtcacc      60

atcacttgtc gggcgagtca gggtattagc agctggttag cctggtatca gcagaaacca     120

gggaaagccc ctaagctcct gatctatgct gcatccaatt tgcaaagtgg ggtcccatca     180

aggttcagcg gcagtggatc tgggacagat ttcactctca ccatcagcag cctgcagcct     240

gaagattttg caacttacta ttgtcagcag gcagacgacc tccctctcac ttttggcgga     300
```

gggaccaagg ttgagatcaa a 321

<210> SEQ ID NO 223
<211> LENGTH: 454
<212> TYPE: PRT
<213> ORGANISM: Artificial
<220> FEATURE:
<223> OTHER INFORMATION: Synthetic

<400> SEQUENCE: 223

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Glu Ser Tyr
            20                  25                  30

Thr Ile Ser Trp Val Arg Gln Ala Pro Gly Gln Gly Leu Glu Trp Met
        35                  40                  45

Gly Gly Ile Ala Pro Ile Phe Gly Thr Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 224
<211> LENGTH: 1362
<212> TYPE: DNA
<213> ORGANISM: Artificial
<220> FEATURE:
<223> OTHER INFORMATION: Synthetic

<400> SEQUENCE: 224
caggtgcagc tggtgcagtc tggggctgag gtgaagaagc ctgggtcctc ggtgaaggtc 60
tcctgcaagg cttctggagg caccttcgag agctatacga tcagctgggt gcgacaggcc 120
cctggacaag ggcttgagtg gatgggaggg atcgcgccta tctttggtac agcacattac 180
gcacagaagt tccagggcag agtcacgatt accgcggacg aatccacgag cacagcctac 240
atggagctga gcagcctgag atctgaggac acggcggtgt actactgcgc cagatcttac 300
tactccagcc gatggcacta ctactactac atggacgtgt ggggcaaggg tacaactgtc 360
accgtctcct cagcgagcac caaaggcccg agcgtgtttc cgctggcgcc gagcagcaaa 420
agcaccagcg gcggcaccgc ggcgctgggc tgcctggtga aagattattt tccggaaccg 480
gtgaccgtga gctggaacag cggcgcgctg accagcggcg tgcatacctt tccggcggtg 540
ctgcagagca gcggcctgta tagcctgagc agcgtggtga ccgtgccgag cagcagcctg 600
ggcacccaga cctatatttg caacgtgaac cataaaccga gcaacaccaa agtggataaa 660
aaagtggaac cgaaaagctg cgataaaacc catacctgcc cgccgtgccc ggcgccggaa 720
ctgctgggcg gcccgagcgt gtttctgttt ccgccgaaac cgaaagatac cctgatgatt 780
agccgcaccc cggaagtgac ctgcgtggtg gtggatgtga gccatgaaga tccggaagtg 840
aaatttaact ggtatgtgga tggcgtggaa gtgcataacg cgaaaaccaa accgcgcgaa 900
gaacagtata acagcaccta tcgcgtggtg agcgtgctga ccgtgctgca tcaggattgg 960
ctgaacggca aagaatataa atgcaaagtg agcaacaaag cgctgccggc gccgattgaa 1020
aaaaccatta gcaaagcgaa aggccagccg cgcgaaccgc aggtgtatac cctgccgccg 1080
agccgcgatg aactgaccaa aaaccaggtg agcctgacct gcctggtgaa aggcttttat 1140
ccgagcgata ttgcggtgga atgggaaagc aacggccagc cggaaaacaa ctataaaacc 1200
accccgccgg tgctggatag cgatggcagc tttttttctgt atagcaaact gaccgtggat 1260
aaaagccgct ggcagcaggg caacgtgttt agctgcagcg tgatgcatga agcgctgcat 1320
aaccattata cccagaaaag cctgagcctg agcccgggca aa 1362

<210> SEQ ID NO 225

<211> LENGTH: 214
<212> TYPE: PRT
<213> ORGANISM: Artificial
<220> FEATURE:
<223> OTHER INFORMATION: Synthetic

<400> SEQUENCE: 225

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Asp Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 226
<211> LENGTH: 642
<212> TYPE: DNA
<213> ORGANISM: Artificial
<220> FEATURE:
<223> OTHER INFORMATION: Synthetic

<400> SEQUENCE: 226

```
gacatccaga tgacccagtc tccatcttcc gtgtctgcat ctgtaggaga cagagtcacc      60

atcacttgtc gggcgagtca gggtattagc agctggttag cctggtatca gcagaaacca     120

gggaaagccc ctaagctcct gatctatgct gcatccaatt tgcaaagtgg ggtcccatca     180

aggttcagcg gcagtggatc tgggacagat ttcactctca ccatcagcag cctgcagcct     240

gaagattttg caacttacta ttgtcagcag gcagacgacc tccctctcac ttttggcgga     300

gggaccaagg ttgagatcaa acgtacggtg gccgctccct ccgtgttcat cttcccaccc     360

tccgacgagc agctgaagtc cggcaccgcc tccgtcgtgt gcctgctgaa caacttctac     420

cctcgcgagg ccaaagtgca gtggaaagtg gacaacgccc tgcagtccgg caactcccag     480

gaatccgtca ccgagcagga ctccaaggac agcacctact ccctgtcctc caccctgacc     540

ctgtccaagg ccgactacga gaagcacaaa gtgtacgcct gcgaagtgac ccaccagggc     600
```

ctgtccagcc ccgtgaccaa gtccttcaac cggggcgagt gc 642

<210> SEQ ID NO 227
<211> LENGTH: 450
<212> TYPE: PRT
<213> ORGANISM: Artificial
<220> FEATURE:
<223> OTHER INFORMATION: Synthetic

<400> SEQUENCE: 227

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Glu Ser Tyr
20 25 30

Thr Ile Ser Trp Val Arg Gln Ala Pro Gly Gln Gly Leu Glu Trp Met
35 40 45

Gly Gly Ile Ala Pro Ile Phe Gly Thr Ala His Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Tyr Tyr Ser Ser Arg Trp His Tyr Tyr Tyr Tyr Met Asp
100 105 110

Val Trp Gly Lys Gly Thr Thr Val Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Lys Thr Tyr Thr Cys Asn
195 200 205

Val Asp His Lys Pro Ser Asn Thr Lys Val Asp Lys Arg Val Glu Ser
210 215 220

Lys Tyr Gly Pro Pro Cys Pro Ser Cys Pro Ala Pro Glu Phe Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser Gln
260 265 270

Glu Asp Pro Glu Val Gln Phe Asn Trp Tyr Val Asp Gly Val Glu Val
275 280 285

His Asn Ala Lys Thr Lys Pro Arg Glu Glu Gln Phe Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Gly Leu Pro Ser Ser Ile
325 330 335

Glu Lys Thr Ile Ser Lys Ala Lys Gly Gln Pro Arg Glu Pro Gln Val
340 345 350

```
Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450


<210> SEQ ID NO 228
<211> LENGTH: 1350
<212> TYPE: DNA
<213> ORGANISM: Artificial
<220> FEATURE:
<223> OTHER INFORMATION: Synthetic

<400> SEQUENCE: 228

caggtgcagc tggtgcagtc tggggctgag gtgaagaagc ctgggtcctc ggtgaaggtc     60

tcctgcaagg cttctggagg caccttcgag agctatacga tcagctgggt gcgacaggcc    120

cctggacaag ggcttgagtg gatgggaggg atcgcgccta tctttggtac agcacattac    180

gcacagaagt tccagggcag agtcacgatt accgcggacg aatccacgag cacagcctac    240

atggagctga gcagcctgag atctgaggac acggcggtgt actactgcgc cagatcttac    300

tactccagcc gatggcacta ctactactac atggacgtgt ggggcaaggg tacaactgtc    360

accgtctcct cagcttccac caagggcccc tccgtgttcc ctctggcccc ttgctcccgg    420

tccacctccg agtctaccgc cgctctgggc tgcctcgtga aggactactt ccccgagccc    480

gtgaccgtgt cctggaactc tggcgccctg acctccggcg tgcacacctt ccctgccgtg    540

ctgcagtcct ccggcctgta ctccctgtcc agcgtcgtga ccgtgccctc ctccagcctg    600

ggcaccaaga cctacacctg taacgtggac cacaagccct ccaacaccaa agtggacaag    660

cgggtggaat ctaagtacgg ccctccctgc ccttcctgcc ctgcccctga gttcctgggc    720

ggaccttccg tgttcctgtt ccctccaaag cccaaggaca ccctgatgat ctcccggacc    780

cctgaagtga cctgcgtggt ggtggacgtg tcccaggaag atcccgaagt ccagttcaat    840

tggtacgtgg acggcgtgga agtgcacaac gccaagacca agcccagaga ggaacagttc    900

aactccacct accgggtggt gtccgtgctg accgtgctgc accaggactg gctgaacggc    960

aaagagtaca agtgcaaagt gtccaacaag ggcctgccct ccagcatcga aaagaccatc   1020

tccaaggcca agggccagcc ccgcgagccc caagtgtaca ccctgcctcc cagccaggaa   1080

gagatgacca agaatcaagt gtccctgact tgtctggtca agggcttcta cccctccgat   1140

atcgccgtgg agtgggagtc caacggccag cccgagaaca actacaagac cacccctccc   1200

gtgctggact ccgacggctc cttcttcctg tactctcggc tgaccgtgga caagtcccgg   1260

tggcaggaag gcaacgtctt ctcctgctcc gtgatgcacg aggccctgca caaccactac   1320

acccagaagt ccctgtccct gtctctgggc                                     1350


<210> SEQ ID NO 229
```

<211> LENGTH: 8
<212> TYPE: PRT
<213> ORGANISM: Artificial
<220> FEATURE:
<223> OTHER INFORMATION: Synthetic

<400> SEQUENCE: 229

Gly Gly Ser Phe Ser Asp Tyr Glu
1               5

<210> SEQ ID NO 230
<211> LENGTH: 7
<212> TYPE: PRT
<213> ORGANISM: Artificial
<220> FEATURE:
<223> OTHER INFORMATION: Synthetic

<400> SEQUENCE: 230

Ile Asp Trp Ser Gly Ile Thr
1               5

<210> SEQ ID NO 231
<211> LENGTH: 19
<212> TYPE: PRT
<213> ORGANISM: Artificial
<220> FEATURE:
<223> OTHER INFORMATION: Synthetic

<400> SEQUENCE: 231

Ala Arg Leu Pro Met Tyr Tyr Tyr Asp Ser Ser Val Ser Thr Gly Ser
1               5                   10                  15

Val Asp Val

<210> SEQ ID NO 232
<211> LENGTH: 9
<212> TYPE: PRT
<213> ORGANISM: Artificial
<220> FEATURE:
<223> OTHER INFORMATION: Synthetic

<400> SEQUENCE: 232

Gly Ser Phe Ser Asp Tyr Glu Trp Ser
1               5

<210> SEQ ID NO 233
<211> LENGTH: 16
<212> TYPE: PRT
<213> ORGANISM: Artificial
<220> FEATURE:
<223> OTHER INFORMATION: Synthetic

<400> SEQUENCE: 233

Glu Ile Asp Trp Ser Gly Ile Thr Asn Tyr Asn Pro Ser Leu Lys Ser
1               5                   10                  15

<210> SEQ ID NO 234
<211> LENGTH: 19
<212> TYPE: PRT
<213> ORGANISM: Artificial
<220> FEATURE:
<223> OTHER INFORMATION: Synthetic

<400> SEQUENCE: 234

Ala Arg Leu Pro Met Tyr Tyr Tyr Asp Ser Ser Val Ser Thr Gly Ser
1               5                   10                  15

Val Asp Val

<210> SEQ ID NO 235
<211> LENGTH: 125
<212> TYPE: PRT
<213> ORGANISM: Artificial
<220> FEATURE:
<223> OTHER INFORMATION: Synthetic

<400> SEQUENCE: 235

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Glu Trp Ser Trp Ile Arg Gln Pro Pro Gly Lys Gly Leu Glu Trp Ile
        35                  40                  45

Gly Glu Ile Asp Trp Ser Gly Ile Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Met Tyr Tyr Tyr Asp Ser Ser Val Ser Thr Gly Ser Val
            100                 105                 110

Asp Val Trp Gly Gln Gly Thr Met Val Thr Val Ser Ser
        115                 120                 125
```

<210> SEQ ID NO 236
<211> LENGTH: 375
<212> TYPE: DNA
<213> ORGANISM: Artificial
<220> FEATURE:
<223> OTHER INFORMATION: Synthetic

<400> SEQUENCE: 236

```
caagtacaat tacaacagtg gggagctggt ttattaaagc cttcagaaac tttaagtttg     60

acctgtgctg tttacggtgg atcattttct gattatgagt ggagttggat tcgtcaacca    120

ccaggcaaag gattggagtg gatcggtgag atagactggt caggcattac taactacaat    180

ccaagtttaa aatccagggt tactatctcc gtagacacgt ccaagaacca gttctccctg    240

aagctgagtt ctgtgaccgc cgcagacacg gcggtgtact actgcgccag acttcctatg    300

tactactacg acagcagcgt ctcaaccgga agcgtagacg tatggggtca gggtacaatg    360

gtcaccgtct cctca                                                     375
```

<210> SEQ ID NO 237
<211> LENGTH: 6
<212> TYPE: PRT
<213> ORGANISM: Artificial
<220> FEATURE:
<223> OTHER INFORMATION: Synthetic

<400> SEQUENCE: 237

```
Gln Ser Val Ser Ser Tyr
1               5
```

<210> SEQ ID NO 238
<211> LENGTH: 3
<212> TYPE: PRT
<213> ORGANISM: Artificial
<220> FEATURE:
<223> OTHER INFORMATION: Synthetic

<400> SEQUENCE: 238

Asp Ser Ser
1

<210> SEQ ID NO 239
<211> LENGTH: 9
<212> TYPE: PRT
<213> ORGANISM: Artificial
<220> FEATURE:
<223> OTHER INFORMATION: Synthetic

<400> SEQUENCE: 239

Gln Gln Asp Ser Asp His Pro Ile Thr
1               5

<210> SEQ ID NO 240
<211> LENGTH: 11
<212> TYPE: PRT
<213> ORGANISM: Artificial
<220> FEATURE:
<223> OTHER INFORMATION: Synthetic

<400> SEQUENCE: 240

Arg Ala Ser Gln Ser Val Ser Ser Tyr Leu Ala
1               5                   10

<210> SEQ ID NO 241
<211> LENGTH: 7
<212> TYPE: PRT
<213> ORGANISM: Artificial
<220> FEATURE:
<223> OTHER INFORMATION: Synthetic

<400> SEQUENCE: 241

Asp Ser Ser Asn Arg Ala Thr
1               5

<210> SEQ ID NO 242
<211> LENGTH: 9
<212> TYPE: PRT
<213> ORGANISM: Artificial
<220> FEATURE:
<223> OTHER INFORMATION: Synthetic

<400> SEQUENCE: 242

Gln Gln Asp Ser Asp His Pro Ile Thr
1               5

<210> SEQ ID NO 243
<211> LENGTH: 107
<212> TYPE: PRT
<213> ORGANISM: Artificial
<220> FEATURE:
<223> OTHER INFORMATION: Synthetic

<400> SEQUENCE: 243

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asp Ser Asp His Pro Ile
                85                  90                  95

Thr Phe Gly Gly Gly Thr Lys Val Glu Ile Lys
            100                 105


<210> SEQ ID NO 244
<211> LENGTH: 321
<212> TYPE: DNA
<213> ORGANISM: Artificial
<220> FEATURE:
<223> OTHER INFORMATION: Synthetic

<400> SEQUENCE: 244

gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat tcatccaaca gggccactgg catcccagcc     180

aggttcagtg gcagtgggtc tgggacagac ttcactctca ccatcagcag cctagagcct     240

gaagattttg cagtttatta ctgtcagcag gacagtgacc accctatcac ttttggcgga     300

gggaccaagg ttgagatcaa a                                                321


<210> SEQ ID NO 245
<211> LENGTH: 455
<212> TYPE: PRT
<213> ORGANISM: Artificial
<220> FEATURE:
<223> OTHER INFORMATION: Synthetic

<400> SEQUENCE: 245

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Glu Trp Ser Trp Ile Arg Gln Pro Pro Gly Lys Gly Leu Glu Trp Ile
        35                  40                  45

Gly Glu Ile Asp Trp Ser Gly Ile Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Met Tyr Tyr Tyr Asp Ser Ser Val Ser Thr Gly Ser Val
            100                 105                 110

Asp Val Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
```

```
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 246
<211> LENGTH: 1365
<212> TYPE: DNA
<213> ORGANISM: Artificial
<220> FEATURE:
<223> OTHER INFORMATION: Synthetic

<400> SEQUENCE: 246

caagtacaat tacaacagtg gggagctggt ttattaaagc cttcagaaac tttaagtttg      60

acctgtgctg tttacggtgg atcattttct gattatgagt ggagttggat tcgtcaacca     120

ccaggcaaag gattggagtg gatcggtgag atagactggt caggcattac taactacaat     180

ccaagtttaa aatccagggt tactatctcc gtagacacgt ccaagaacca gttctccctg     240

aagctgagtt ctgtgaccgc cgcagacacg gcggtgtact actgcgccag acttcctatg     300

tactactacg acagcagcgt ctcaaccgga agcgtagacg tatggggtca gggtacaatg     360

gtcaccgtct cctcagcgag caccaaaggc ccgagcgtgt ttccgctggc gccgagcagc     420

aaaagcacca gcggcggcac cgcggcgctg ggctgcctgg tgaaagatta ttttccggaa     480

ccggtgaccg tgagctggaa cagcggcgcg ctgaccagcg gcgtgcatac ctttccggcg     540

gtgctgcaga gcagcggcct gtatagcctg agcagcgtgg tgaccgtgcc gagcagcagc     600
```

```
ctgggcaccc agacctatat ttgcaacgtg aaccataaac cgagcaacac caaagtggat    660

aaaaaagtgg aaccgaaaag ctgcgataaa acccatacct gcccgccgtg cccggcgccg    720

gaactgctgg gcggcccgag cgtgtttctg tttccgccga aaccgaaaga taccctgatg    780

attagccgca ccccggaagt gacctgcgtg gtggtggatg tgagccatga agatccggaa    840

gtgaaattta actggtatgt ggatggcgtg gaagtgcata acgcgaaaac caaaccgcgc    900

gaagaacagt ataacagcac ctatcgcgtg gtgagcgtgc tgaccgtgct gcatcaggat    960

tggctgaacg gcaaagaata taaatgcaaa gtgagcaaca aagcgctgcc ggcgccgatt   1020

gaaaaaacca ttagcaaagc gaaaggccag ccgcgcgaac cgcaggtgta taccctgccg   1080

ccgagccgcg atgaactgac caaaaaccag gtgagcctga cctgcctggt gaaaggcttt   1140

tatccgagcg atattgcggt ggaatgggaa agcaacggcc agccggaaaa caactataaa   1200

accaccccgc cggtgctgga tagcgatggc agcttttttc tgtatagcaa actgaccgtg   1260

gataaaagcc gctggcagca gggcaacgtg tttagctgca gcgtgatgca tgaagcgctg   1320

cataaccatt atacccagaa aagcctgagc ctgagcccgg gcaaa                   1365
```

<210> SEQ ID NO 247
<211> LENGTH: 214
<212> TYPE: PRT
<213> ORGANISM: Artificial
<220> FEATURE:
<223> OTHER INFORMATION: Synthetic

<400> SEQUENCE: 247

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asp Ser Asp His Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 248
<211> LENGTH: 642
<212> TYPE: DNA
<213> ORGANISM: Artificial
<220> FEATURE:
<223> OTHER INFORMATION: Synthetic

<400> SEQUENCE: 248
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat tcatccaaca gggccactgg catcccagcc 180
aggttcagtg gcagtgggtc tgggacagac ttcactctca ccatcagcag cctagagcct 240
gaagattttg cagtttatta ctgtcagcag gacagtgacc accctatcac ttttggcgga 300
gggaccaagg ttgagatcaa acgtacggtg gccgctccct ccgtgttcat cttcccaccc 360
tccgacgagc agctgaagtc cggcaccgcc tccgtcgtgt gcctgctgaa caacttctac 420
cctcgcgagg ccaaagtgca gtggaaagtg gacaacgccc tgcagtccgg caactcccag 480
gaatccgtca ccgagcagga ctccaaggac agcacctact ccctgtcctc caccctgacc 540
ctgtccaagg ccgactacga gaagcacaaa gtgtacgcct gcgaagtgac ccaccagggc 600
ctgtccagcc ccgtgaccaa gtccttcaac cggggcgagt gc 642

<210> SEQ ID NO 249
<211> LENGTH: 451
<212> TYPE: PRT
<213> ORGANISM: Artificial
<220> FEATURE:
<223> OTHER INFORMATION: Synthetic

<400> SEQUENCE: 249

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Asp Tyr
20 25 30

Glu Trp Ser Trp Ile Arg Gln Pro Pro Gly Lys Gly Leu Glu Trp Ile
35 40 45

Gly Glu Ile Asp Trp Ser Gly Ile Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Leu Pro Met Tyr Tyr Tyr Asp Ser Ser Val Ser Thr Gly Ser Val
100 105 110

Asp Val Trp Gly Gln Gly Thr Met Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys

```
        195                 200                 205

Asn Val Asp His Lys Pro Ser Asn Thr Lys Val Asp Lys Arg Val Glu
    210                 215                 220

Ser Lys Tyr Gly Pro Pro Cys Pro Ser Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450


<210> SEQ ID NO 250
<211> LENGTH: 1353
<212> TYPE: DNA
<213> ORGANISM: Artificial
<220> FEATURE:
<223> OTHER INFORMATION: Synthetic

<400> SEQUENCE: 250

caagtacaat tacaacagtg gggagctggt ttattaaagc cttcagaaac tttaagtttg      60

acctgtgctg tttacggtgg atcattttct gattatgagt ggagttggat tcgtcaacca     120

ccaggcaaag gattggagtg gatcggtgag atagactggt caggcattac taactacaat     180

ccaagtttaa aatccagggt tactatctcc gtagacacgt ccaagaacca gttctccctg     240

aagctgagtt ctgtgaccgc cgcagacacg gcggtgtact actgcgccag acttcctatg     300

tactactacg acagcagcgt ctcaaccgga agcgtagacg tatggggtca gggtacaatg     360

gtcaccgtct cctcagcttc caccaagggc ccctccgtgt tccctctggc cccttgctcc     420

cggtccacct ccgagtctac cgccgctctg ggctgcctcg tgaaggacta cttccccgag     480

cccgtgaccg tgtcctggaa ctctggcgcc ctgacctccg gcgtgcacac cttccctgcc     540

gtgctgcagt cctccggcct gtactccctg tccagcgtcg tgaccgtgcc ctcctccagc     600
```

-continued

```
ctgggcacca agacctacac ctgtaacgtg gaccacaagc cctccaacac caaagtggac    660

aagcgggtgg aatctaagta cggccctccc tgcccttcct gccctgcccc tgagttcctg    720

ggcggacctt ccgtgttcct gttccctcca aagcccaagg acaccctgat gatctcccgg    780

acccctgaag tgacctgcgt ggtggtggac gtgtcccagg aagatcccga agtccagttc    840

aattggtacg tggacggcgt ggaagtgcac aacgccaaga ccaagcccag agaggaacag    900

ttcaactcca cctaccgggt ggtgtccgtg ctgaccgtgc tgcaccagga ctggctgaac    960

ggcaaagagt acaagtgcaa agtgtccaac aagggcctgc cctccagcat cgaaaagacc   1020

atctccaagg ccaagggcca gccccgcgag ccccaagtgt acaccctgcc tcccagccag   1080

gaagagatga ccaagaatca agtgtccctg acttgtctgg tcaagggctt ctacccctcc   1140

gatatcgccg tggagtggga gtccaacggc cagcccgaga acaactacaa gaccacccct   1200

cccgtgctgg actccgacgg ctccttcttc ctgtactctc ggctgaccgt ggacaagtcc   1260

cggtggcagg aaggcaacgt cttctcctgc tccgtgatgc acgaggccct gcacaaccac   1320

tacacccaga agtccctgtc cctgtctctg ggc                                1353
```

<210> SEQ ID NO 251
<211> LENGTH: 8
<212> TYPE: PRT
<213> ORGANISM: Artificial
<220> FEATURE:
<223> OTHER INFORMATION: Synthetic

<400> SEQUENCE: 251

```
Gly Gly Ser Phe Ser Arg Tyr Tyr
1               5
```

<210> SEQ ID NO 252
<211> LENGTH: 7
<212> TYPE: PRT
<213> ORGANISM: Artificial
<220> FEATURE:
<223> OTHER INFORMATION: Synthetic

<400> SEQUENCE: 252

```
Ile Asp Tyr Ser Gly Ser Thr
1               5
```

<210> SEQ ID NO 253
<211> LENGTH: 16
<212> TYPE: PRT
<213> ORGANISM: Artificial
<220> FEATURE:
<223> OTHER INFORMATION: Synthetic

<400> SEQUENCE: 253

```
Ala Arg Asp Gly Val Tyr Tyr Asp Ser Ser Asp Leu Gly Phe Asp Ile
1               5                   10                  15
```

<210> SEQ ID NO 254
<211> LENGTH: 9
<212> TYPE: PRT
<213> ORGANISM: Artificial
<220> FEATURE:
<223> OTHER INFORMATION: Synthetic

<400> SEQUENCE: 254

```
Gly Ser Phe Ser Arg Tyr Tyr Trp Ser
1               5
```

<210> SEQ ID NO 255
<211> LENGTH: 16
<212> TYPE: PRT
<213> ORGANISM: Artificial
<220> FEATURE:
<223> OTHER INFORMATION: Synthetic

<400> SEQUENCE: 255

Ser Ile Asp Tyr Ser Gly Ser Thr Glu Tyr Asn Pro Ser Leu Lys Ser
1               5                   10                  15

<210> SEQ ID NO 256
<211> LENGTH: 16
<212> TYPE: PRT
<213> ORGANISM: Artificial
<220> FEATURE:
<223> OTHER INFORMATION: Synthetic

<400> SEQUENCE: 256

Ala Arg Asp Gly Val Tyr Tyr Asp Ser Ser Asp Leu Gly Phe Asp Ile
1               5                   10                  15

<210> SEQ ID NO 257
<211> LENGTH: 122
<212> TYPE: PRT
<213> ORGANISM: Artificial
<220> FEATURE:
<223> OTHER INFORMATION: Synthetic

<400> SEQUENCE: 257

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Arg Tyr
            20                  25                  30

Tyr Trp Ser Trp Ile Arg Gln Pro Pro Gly Lys Gly Leu Glu Trp Ile
        35                  40                  45

Gly Ser Ile Asp Tyr Ser Gly Ser Thr Glu Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Val Tyr Tyr Asp Ser Ser Asp Leu Gly Phe Asp Ile Trp
            100                 105                 110

Gly Gln Gly Thr Met Val Thr Val Ser Ser
        115                 120

<210> SEQ ID NO 258
<211> LENGTH: 366
<212> TYPE: DNA
<213> ORGANISM: Artificial
<220> FEATURE:
<223> OTHER INFORMATION: Synthetic

<400> SEQUENCE: 258
caagtacaat tacaacagtg gggagctggt ttattaaagc cttcagaaac tttaagtttg      60
acctgtgctg tttacggtgg atcattttct cgttattact ggagttggat tcgtcaacca     120
ccaggcaaag gattggagtg gatcggtagt atagactatt caggctccac tgagtacaat     180
ccaagtttaa aatccagggt tactatctcc gtagacacgt ccaagaacca gttctccctg     240
aagctgagtt ctgtgaccgc cgcagacacg gcggtgtact actgcgccag agatggtgtg     300
tactacgaca gcagcgactt gggattcgac atatggggtc agggtacaat ggtcaccgtc 360
tcctca 366

<210> SEQ ID NO 259
<211> LENGTH: 6
<212> TYPE: PRT
<213> ORGANISM: Artificial
<220> FEATURE:
<223> OTHER INFORMATION: Synthetic

<400> SEQUENCE: 259

Gln Asp Ile Ser Asn Tyr
1 5

<210> SEQ ID NO 260
<211> LENGTH: 3
<212> TYPE: PRT
<213> ORGANISM: Artificial
<220> FEATURE:
<223> OTHER INFORMATION: Synthetic

<400> SEQUENCE: 260

Asp Ala Ser
1

<210> SEQ ID NO 261
<211> LENGTH: 9
<212> TYPE: PRT
<213> ORGANISM: Artificial
<220> FEATURE:
<223> OTHER INFORMATION: Synthetic

<400> SEQUENCE: 261

Gln Gln Tyr Asp Asp Leu Pro Ile Thr
1 5

<210> SEQ ID NO 262
<211> LENGTH: 11
<212> TYPE: PRT
<213> ORGANISM: Artificial
<220> FEATURE:
<223> OTHER INFORMATION: Synthetic

<400> SEQUENCE: 262

Gln Ala Ser Gln Asp Ile Ser Asn Tyr Leu Asn
1 5 10

<210> SEQ ID NO 263
<211> LENGTH: 7
<212> TYPE: PRT
<213> ORGANISM: Artificial
<220> FEATURE:
<223> OTHER INFORMATION: Synthetic

<400> SEQUENCE: 263

Asp Ala Ser Asn Leu Glu Thr
1 5

<210> SEQ ID NO 264
<211> LENGTH: 9
<212> TYPE: PRT
<213> ORGANISM: Artificial
<220> FEATURE:
<223> OTHER INFORMATION: Synthetic

<400> SEQUENCE: 264

```
Gln Gln Tyr Asp Asp Leu Pro Ile Thr
1               5


<210> SEQ ID NO 265
<211> LENGTH: 107
<212> TYPE: PRT
<213> ORGANISM: Artificial
<220> FEATURE:
<223> OTHER INFORMATION: Synthetic

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asp Leu Pro Ile
                85                  90                  95

Thr Phe Gly Gly Gly Thr Lys Val Glu Ile Lys
            100                 105


<210> SEQ ID NO 266
<211> LENGTH: 321
<212> TYPE: DNA
<213> ORGANISM: Artificial
<220> FEATURE:
<223> OTHER INFORMATION: Synthetic

<400> SEQUENCE: 266

gacatccaga tgacccagtc tccatcctcc ctgtctgcat ctgtaggaga cagagtcacc      60

atcacttgcc aggcgagtca ggacattagc aactatttaa attggtatca gcagaaacca     120

gggaaagccc ctaagctcct gatctacgat gcatccaatt tggaaacagg ggtcccatca     180

aggttcagtg gaagtggatc tgggacagat tttactttca ccatcagcag cctgcagcct     240

gaagatattg caacatatta ctgtcagcag tacgacgacc tccctatcac ttttggcgga     300

gggaccaagg ttgagatcaa a                                               321


<210> SEQ ID NO 267
<211> LENGTH: 452
<212> TYPE: PRT
<213> ORGANISM: Artificial
<220> FEATURE:
<223> OTHER INFORMATION: Synthetic

<400> SEQUENCE: 267

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Arg Tyr
            20                  25                  30

Tyr Trp Ser Trp Ile Arg Gln Pro Pro Gly Lys Gly Leu Glu Trp Ile
        35                  40                  45

Gly Ser Ile Asp Tyr Ser Gly Ser Thr Glu Tyr Asn Pro Ser Leu Lys
    50                  55                  60
```

```
Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Val Tyr Tyr Asp Ser Ser Asp Leu Gly Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 268
<211> LENGTH: 1356
<212> TYPE: DNA

<213> ORGANISM: Artificial
<220> FEATURE:
<223> OTHER INFORMATION: Synthetic

<400> SEQUENCE: 268
caagtacaat tacaacagtg gggagctggt ttattaaagc cttcagaaac tttaagtttg 60
acctgtgctg tttacggtgg atcattttct cgttattact ggagttggat tcgtcaacca 120
ccaggcaaag gattggagtg gatcggtagt atagactatt caggctccac tgagtacaat 180
ccaagtttaa aatccagggt tactatctcc gtagacacgt ccaagaacca gttctccctg 240
aagctgagtt ctgtgaccgc cgcagacacg gcggtgtact actgcgccag agatggtgtg 300
tactacgaca gcagcgactt gggattcgac atatggggtc agggtacaat ggtcaccgtc 360
tcctcagcga gcaccaaagg cccgagcgtg tttccgctgg cgccgagcag caaaagcacc 420
agcggcggca ccgcggcgct gggctgcctg gtgaaagatt attttccgga accggtgacc 480
gtgagctgga acagcggcgc gctgaccagc ggcgtgcata cctttccggc ggtgctgcag 540
agcagcggcc tgtatagcct gagcagcgtg gtgaccgtgc cgagcagcag cctgggcacc 600
cagacctata tttgcaacgt gaaccataaa ccgagcaaca ccaaagtgga taaaaaagtg 660
gaaccgaaaa gctgcgataa aacccatacc tgcccgccgt gcccggcgcc ggaactgctg 720
ggcggcccga gcgtgtttct gtttccgccg aaaccgaaag ataccctgat gattagccgc 780
accccggaag tgacctgcgt ggtggtggat gtgagccatg aagatccgga agtgaaattt 840
aactggtatg tggatggcgt ggaagtgcat aacgcgaaaa ccaaaccgcg cgaagaacag 900
tataacagca cctatcgcgt ggtgagcgtg ctgaccgtgc tgcatcagga ttggctgaac 960
ggcaaagaat ataaatgcaa agtgagcaac aaagcgctgc cggcgccgat tgaaaaaacc 1020
attagcaaag cgaaaggcca gccgcgcgaa ccgcaggtgt ataccctgcc gccgagccgc 1080
gatgaactga ccaaaaacca ggtgagcctg acctgcctgg tgaaaggctt ttatccgagc 1140
gatattgcgg tggaatggga aagcaacggc cagccggaaa acaactataa aaccaccccg 1200
ccggtgctgg atagcgatgg cagctttttt ctgtatagca aactgaccgt ggataaaagc 1260
cgctggcagc agggcaacgt gtttagctgc agcgtgatgc atgaagcgct gcataaccat 1320
tatacccaga aaagcctgag cctgagcccg ggcaaa 1356

<210> SEQ ID NO 269
<211> LENGTH: 214
<212> TYPE: PRT
<213> ORGANISM: Artificial
<220> FEATURE:
<223> OTHER INFORMATION: Synthetic

<400> SEQUENCE: 269

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asp Leu Pro Ile
85 90 95

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 270
<211> LENGTH: 642
<212> TYPE: DNA
<213> ORGANISM: Artificial
<220> FEATURE:
<223> OTHER INFORMATION: Synthetic

<400> SEQUENCE: 270

gacatccaga tgacccagtc tccatcctcc ctgtctgcat ctgtaggaga cagagtcacc      60

atcacttgcc aggcgagtca ggacattagc aactatttaa attggtatca gcagaaacca     120

gggaaagccc ctaagctcct gatctacgat gcatccaatt tggaaacagg ggtcccatca     180

aggttcagtg gaagtggatc tgggacagat tttactttca ccatcagcag cctgcagcct     240

gaagatattg caacatatta ctgtcagcag tacgacgacc tccctatcac ttttggcgga     300

gggaccaagg ttgagatcaa acgtacggtg gccgctccct ccgtgttcat cttcccaccc     360

tccgacgagc agctgaagtc cggcaccgcc tccgtcgtgt gcctgctgaa caacttctac     420

cctcgcgagg ccaaagtgca gtggaaagtg gacaacgccc tgcagtccgg caactcccag     480

gaatccgtca ccgagcagga ctccaaggac agcacctact ccctgtcctc caccctgacc     540

ctgtccaagg ccgactacga gaagcacaaa gtgtacgcct gcgaagtgac ccaccagggc     600

ctgtccagcc ccgtgaccaa gtccttcaac cggggcgagt gc                        642


<210> SEQ ID NO 271
<211> LENGTH: 448
<212> TYPE: PRT
<213> ORGANISM: Artificial
<220> FEATURE:
<223> OTHER INFORMATION: Synthetic

<400> SEQUENCE: 271

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Arg Tyr
            20                  25                  30

Tyr Trp Ser Trp Ile Arg Gln Pro Pro Gly Lys Gly Leu Glu Trp Ile
        35                  40                  45

Gly Ser Ile Asp Tyr Ser Gly Ser Thr Glu Tyr Asn Pro Ser Leu Lys
    50                  55                  60
```

```
Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Val Tyr Tyr Asp Ser Ser Asp Leu Gly Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445
```

<210> SEQ ID NO 272
<211> LENGTH: 1344
<212> TYPE: DNA
<213> ORGANISM: Artificial
<220> FEATURE:
<223> OTHER INFORMATION: Synthetic

<400> SEQUENCE: 272
caagtacaat tacaacagtg gggagctggt ttattaaagc cttcagaaac tttaagtttg 60
acctgtgctg tttacggtgg atcattttct cgttattact ggagttggat tcgtcaacca 120
ccaggcaaag gattggagtg gatcggtagt atagactatt caggctccac tgagtacaat 180
ccaagtttaa aatccagggt tactatctcc gtagacacgt ccaagaacca gttctccctg 240
aagctgagtt ctgtgaccgc cgcagacacg gcggtgtact actgcgccag agatggtgtg 300
tactacgaca gcagcgactt gggattcgac atatggggtc agggtacaat ggtcaccgtc 360
tcctcagctt ccaccaaggg cccctccgtg ttccctctgg ccccttgctc ccggtccacc 420
tccgagtcta ccgccgctct gggctgcctc gtgaaggact acttccccga gcccgtgacc 480
gtgtcctgga actctggcgc cctgacctcc ggcgtgcaca ccttccctgc cgtgctgcag 540
tcctccggcc tgtactccct gtccagcgtc gtgaccgtgc cctcctccag cctgggcacc 600
aagacctaca cctgtaacgt ggaccacaag ccctccaaca ccaaagtgga caagcgggtg 660
gaatctaagt acggccctcc ctgcccttcc tgccctgccc ctgagttcct gggcggacct 720
tccgtgttcc tgttccctcc aaagcccaag gacaccctga tgatctcccg gacccctgaa 780
gtgacctgcg tggtggtgga cgtgtcccag gaagatcccg aagtccagtt caattggtac 840
gtggacggcg tggaagtgca caacgccaag accaagccca gagaggaaca gttcaactcc 900
acctaccggg tggtgtccgt gctgaccgtg ctgcaccagg actggctgaa cggcaaagag 960
tacaagtgca aagtgtccaa caagggcctg ccctccagca tcgaaaagac catctccaag 1020
gccaagggcc agccccgcga gccccaagtg tacaccctgc ctcccagcca ggaagagatg 1080
accaagaatc aagtgtccct gacttgtctg gtcaagggct tctacccctc cgatatcgcc 1140
gtggagtggg agtccaacgg ccagcccgag aacaactaca agaccacccc tcccgtgctg 1200
gactccgacg gctccttctt cctgtactct cggctgaccg tggacaagtc ccggtggcag 1260
gaaggcaacg tcttctcctg ctccgtgatg cacgaggccc tgcacaacca ctacacccag 1320
aagtccctgt ccctgtctct gggc 1344

<210> SEQ ID NO 273
<211> LENGTH: 8
<212> TYPE: PRT
<213> ORGANISM: Artificial
<220> FEATURE:
<223> OTHER INFORMATION: Synthetic

<400> SEQUENCE: 273

Gly Gly Thr Phe Ser Ser Tyr Ala
1 5

<210> SEQ ID NO 274
<211> LENGTH: 8
<212> TYPE: PRT
<213> ORGANISM: Artificial
<220> FEATURE:
<223> OTHER INFORMATION: Synthetic

<400> SEQUENCE: 274

Ile Ile Pro Ile Phe Gly Thr Ala
1 5

<210> SEQ ID NO 275
<211> LENGTH: 17
<212> TYPE: PRT

<213> ORGANISM: Artificial
<220> FEATURE:
<223> OTHER INFORMATION: Synthetic

<400> SEQUENCE: 275

Ala Arg Leu Gly Gly Arg Gly Tyr Ala Asp Glu Gly Trp Tyr Phe Asp
1 5 10 15

Leu

<210> SEQ ID NO 276
<211> LENGTH: 9
<212> TYPE: PRT
<213> ORGANISM: Artificial
<220> FEATURE:
<223> OTHER INFORMATION: Synthetic

<400> SEQUENCE: 276

Gly Thr Phe Ser Ser Tyr Ala Ile Ser
1 5

<210> SEQ ID NO 277
<211> LENGTH: 17
<212> TYPE: PRT
<213> ORGANISM: Artificial
<220> FEATURE:
<223> OTHER INFORMATION: Synthetic

<400> SEQUENCE: 277

Gly Ile Ile Pro Ile Phe Gly Thr Ala Asn Tyr Ala Gln Lys Phe Gln
1 5 10 15

Gly

<210> SEQ ID NO 278
<211> LENGTH: 17
<212> TYPE: PRT
<213> ORGANISM: Artificial
<220> FEATURE:
<223> OTHER INFORMATION: Synthetic

<400> SEQUENCE: 278

Ala Arg Leu Gly Gly Arg Gly Tyr Ala Asp Glu Gly Trp Tyr Phe Asp
1 5 10 15

Leu

<210> SEQ ID NO 279
<211> LENGTH: 124
<212> TYPE: PRT
<213> ORGANISM: Artificial
<220> FEATURE:
<223> OTHER INFORMATION: Synthetic

<400> SEQUENCE: 279

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

```
Met Glu Leu Ser Ser Leu Arg Ser Glu Asp Thr Ala Val Tyr Tyr Cys
                85                  90                  95

Ala Arg Leu Gly Gly Arg Gly Tyr Ala Asp Glu Gly Trp Tyr Phe Asp
            100                 105                 110

Leu Trp Gly Arg Gly Thr Leu Val Thr Val Ser Ser
        115                 120


<210> SEQ ID NO 280
<211> LENGTH: 372
<212> TYPE: DNA
<213> ORGANISM: Artificial
<220> FEATURE:
<223> OTHER INFORMATION: Synthetic

<400> SEQUENCE: 280

caggtgcagc tggtgcagtc tggggctgag gtgaagaagc ctgggtcctc ggtgaaggtc      60

tcctgcaagg cttctggagg caccttcagc agctatgcta tcagctgggt gcgacaggcc     120

cctggacaag ggcttgagtg gatgggaggg atcatcccta tctttggtac agcaaactac     180

gcacagaagt tccagggcag agtcacgatt accgcggacg aatccacgag cacagcctac     240

atggagctga gcagcctgag atctgaggac acggcggtgt actactgcgc cagattgggc     300

ggacggggat acgccgacga gggctggtac ttcgacctat gggggagagg taccttggtc     360

accgtctcct ca                                                         372


<210> SEQ ID NO 281
<211> LENGTH: 7
<212> TYPE: PRT
<213> ORGANISM: Artificial
<220> FEATURE:
<223> OTHER INFORMATION: Synthetic

<400> SEQUENCE: 281

Gln Ser Val Ser Ser Ser Tyr
1               5


<210> SEQ ID NO 282
<211> LENGTH: 3
<212> TYPE: PRT
<213> ORGANISM: Artificial
<220> FEATURE:
<223> OTHER INFORMATION: Synthetic

<400> SEQUENCE: 282

Gly Ala Ser
1


<210> SEQ ID NO 283
<211> LENGTH: 9
<212> TYPE: PRT
<213> ORGANISM: Artificial
<220> FEATURE:
<223> OTHER INFORMATION: Synthetic

<400> SEQUENCE: 283

Gln Gln Tyr Tyr Gly Ser Pro Ile Thr
1               5


<210> SEQ ID NO 284
<211> LENGTH: 12
<212> TYPE: PRT
<213> ORGANISM: Artificial
<220> FEATURE:
<223> OTHER INFORMATION: Synthetic
```

<400> SEQUENCE: 284

Arg Ala Ser Gln Ser Val Ser Ser Ser Tyr Leu Ala
1 5 10

<210> SEQ ID NO 285
<211> LENGTH: 7
<212> TYPE: PRT
<213> ORGANISM: Artificial
<220> FEATURE:
<223> OTHER INFORMATION: Synthetic

<400> SEQUENCE: 285

Gly Ala Ser Ser Arg Ala Thr
1 5

<210> SEQ ID NO 286
<211> LENGTH: 9
<212> TYPE: PRT
<213> ORGANISM: Artificial
<220> FEATURE:
<223> OTHER INFORMATION: Synthetic

<400> SEQUENCE: 286

Gln Gln Tyr Tyr Gly Ser Pro Ile Thr
1 5

<210> SEQ ID NO 287
<211> LENGTH: 108
<212> TYPE: PRT
<213> ORGANISM: Artificial
<220> FEATURE:
<223> OTHER INFORMATION: Synthetic

<400> SEQUENCE: 287

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Tyr Gly Ser Pro
85 90 95

Ile Thr Phe Gly Gly Gly Thr Lys Val Glu Ile Lys
100 105

<210> SEQ ID NO 288
<211> LENGTH: 324
<212> TYPE: DNA
<213> ORGANISM: Artificial
<220> FEATURE:
<223> OTHER INFORMATION: Synthetic

<400> SEQUENCE: 288
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180

```
gacaggttca gtggcagtgg gtctgggaca gacttcactc tcaccatcag cagactggag    240

cctgaagatt ttgcagtgta ttactgtcag cagtactacg gcagtcctat cacttttggc    300

ggagggacca aggttgagat caaa                                           324


<210> SEQ ID NO 289
<211> LENGTH: 454
<212> TYPE: PRT
<213> ORGANISM: Artificial
<220> FEATURE:
<223> OTHER INFORMATION: Synthetic

<400> SEQUENCE: 289

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Gly Arg Gly Tyr Ala Asp Glu Gly Trp Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

```
Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 290
<211> LENGTH: 1362
<212> TYPE: DNA
<213> ORGANISM: Artificial
<220> FEATURE:
<223> OTHER INFORMATION: Synthetic

<400> SEQUENCE: 290

caggtgcagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggcggtgt actactgcgc cagattgggc    300

ggacggggat acgccgacga gggctggtac ttcgacctat gggggagagg taccttggtc    360

accgtctcct cagcgagcac caaaggcccg agcgtgtttc cgctggcgcc gagcagcaaa    420

agcaccagcg gcggcaccgc ggcgctgggc tgcctggtga aagattattt tccggaaccg    480

gtgaccgtga gctggaacag cggcgcgctg accagcggcg tgcatacctt tccggcggtg    540

ctgcagagca gcggcctgta tagcctgagc agcgtggtga ccgtgccgag cagcagcctg    600

ggcacccaga cctatatttg caacgtgaac cataaaccga gcaacaccaa agtggataaa    660

aaagtggaac cgaaaagctg cgataaaacc catacctgcc cgccgtgccc ggcgccggaa    720

ctgctgggcg gcccgagcgt gtttctgttt ccgccgaaac cgaaagatac cctgatgatt    780

agccgcaccc cggaagtgac ctgcgtggtg gtggatgtga gccatgaaga tccggaagtg    840

aaatttaact ggtatgtgga tggcgtggaa gtgcataacg cgaaaaccaa accgcgcgaa    900

gaacagtata acagcaccta tcgcgtggtg agcgtgctga ccgtgctgca tcaggattgg    960

ctgaacggca aagaatataa atgcaaagtg agcaacaaag cgctgccggc gccgattgaa   1020

aaaaccatta gcaaagcgaa aggccagccg cgcgaaccgc aggtgtatac cctgccgccg   1080

agccgcgatg aactgaccaa aaaccaggtg agcctgacct gcctggtgaa aggcttttat   1140

ccgagcgata ttgcggtgga atgggaaagc aacggccagc cggaaaacaa ctataaaacc   1200

accccgccgg tgctggatag cgatggcagc tttttctgt atagcaaact gaccgtggat   1260

aaaagccgct ggcagcaggg caacgtgttt agctgcagcg tgatgcatga agcgctgcat   1320

aaccattata cccagaaaag cctgagcctg agcccgggca aa                      1362
```

<210> SEQ ID NO 291
<211> LENGTH: 215
<212> TYPE: PRT
<213> ORGANISM: Artificial
<220> FEATURE:
<223> OTHER INFORMATION: Synthetic

<400> SEQUENCE: 291

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Tyr Gly Ser Pro
85 90 95

Ile Thr Phe Gly Gly Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 292
<211> LENGTH: 645
<212> TYPE: DNA
<213> ORGANISM: Artificial
<220> FEATURE:
<223> OTHER INFORMATION: Synthetic

<400> SEQUENCE: 292
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtactacg gcagtcctat cacttttggc 300
ggagggacca aggttgagat caaacgtacg gtggccgctc cctccgtgtt catcttccca 360
ccctccgacg agcagctgaa gtccggcacc gcctccgtcg tgtgcctgct gaacaacttc 420
taccctcgcg aggccaaagt gcagtggaaa gtggacaacg ccctgcagtc cggcaactcc 480

-continued caggaatccg tcaccgagca ggactccaag gacagcacct actccctgtc ctccaccctg 540
accctgtcca aggccgacta cgagaagcac aaagtgtacg cctgcgaagt gacccaccag 600
ggcctgtcca gccccgtgac caagtccttc aaccggggcg agtgc 645

<210> SEQ ID NO 293
<211> LENGTH: 450
<212> TYPE: PRT
<213> ORGANISM: Artificial
<220> FEATURE:
<223> OTHER INFORMATION: Synthetic

<400> SEQUENCE: 293

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Gly Gly Arg Gly Tyr Ala Asp Glu Gly Trp Tyr Phe Asp
100 105 110

Leu Trp Gly Arg Gly Thr Leu Val Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Lys Thr Tyr Thr Cys Asn
195 200 205

Val Asp His Lys Pro Ser Asn Thr Lys Val Asp Lys Arg Val Glu Ser
210 215 220

Lys Tyr Gly Pro Pro Cys Pro Ser Cys Pro Ala Pro Glu Phe Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser Gln
260 265 270

Glu Asp Pro Glu Val Gln Phe Asn Trp Tyr Val Asp Gly Val Glu Val
275 280 285

His Asn Ala Lys Thr Lys Pro Arg Glu Glu Gln Phe Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Gly Leu Pro Ser Ser Ile
325 330 335

-continued

```
Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450
```

<210> SEQ ID NO 294
<211> LENGTH: 1350
<212> TYPE: DNA
<213> ORGANISM: Artificial
<220> FEATURE:
<223> OTHER INFORMATION: Synthetic

<400> SEQUENCE: 294

```
caggtgcagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggcggtgt actactgcgc cagattgggc    300

ggacggggat acgccgacga gggctggtac ttcgacctat gggggagagg taccttggtc    360

accgtctcct cagcttccac caagggcccc tccgtgttcc ctctggcccc ttgctcccgg    420

tccacctccg agtctaccgc cgctctgggc tgcctcgtga aggactactt ccccgagccc    480

gtgaccgtgt cctggaactc tggcgccctg acctccggcg tgcacacctt ccctgccgtg    540

ctgcagtcct ccggcctgta ctccctgtcc agcgtcgtga ccgtgccctc ctccagcctg    600

ggcaccaaga cctacacctg taacgtggac cacaagccct ccaacaccaa agtggacaag    660

cgggtggaat ctaagtacgg ccctccctgc ccttcctgcc ctgcccctga gttcctgggc    720

ggaccttccg tgttcctgtt ccctccaaag cccaaggaca ccctgatgat ctcccggacc    780

cctgaagtga cctgcgtggt ggtggacgtg tcccaggaag atcccgaagt ccagttcaat    840

tggtacgtgg acggcgtgga agtgcacaac gccaagacca agcccagaga ggaacagttc    900

aactccacct accgggtggt gtccgtgctg accgtgctgc accaggactg gctgaacggc    960

aaagagtaca agtgcaaagt gtccaacaag ggcctgccct ccagcatcga aaagaccatc   1020

tccaaggcca agggccagcc ccgcgagccc caagtgtaca ccctgcctcc cagccaggaa   1080

gagatgacca agaatcaagt gtccctgact tgtctggtca agggcttcta cccctccgat   1140

atcgccgtgg agtgggagtc caacggccag cccgagaaca actacaagac cacccctccc   1200

gtgctggact ccgacggctc cttcttcctg tactctcggc tgaccgtgga caagtcccgg   1260

tggcaggaag gcaacgtctt ctcctgctcc gtgatgcacg aggccctgca caaccactac   1320

acccagaagt ccctgtccct gtctctgggc                                     1350
```

<210> SEQ ID NO 295
<211> LENGTH: 8
<212> TYPE: PRT
<213> ORGANISM: Artificial
<220> FEATURE:
<223> OTHER INFORMATION: Synthetic

<400> SEQUENCE: 295

Gly Gly Ser Phe Ser Glu Tyr Tyr
1               5

<210> SEQ ID NO 296
<211> LENGTH: 7
<212> TYPE: PRT
<213> ORGANISM: Artificial
<220> FEATURE:
<223> OTHER INFORMATION: Synthetic

<400> SEQUENCE: 296

Ile Asp Glu Val Gly Ser Thr
1               5

<210> SEQ ID NO 297
<211> LENGTH: 17
<212> TYPE: PRT
<213> ORGANISM: Artificial
<220> FEATURE:
<223> OTHER INFORMATION: Synthetic

<400> SEQUENCE: 297

Ala Arg Leu Pro Met Tyr Tyr Tyr Asp Ser Ser Asp Leu Pro Met Asp
1               5                   10                  15

Val

<210> SEQ ID NO 298
<211> LENGTH: 9
<212> TYPE: PRT
<213> ORGANISM: Artificial
<220> FEATURE:
<223> OTHER INFORMATION: Synthetic

<400> SEQUENCE: 298

Gly Ser Phe Ser Glu Tyr Tyr Trp Ala
1               5

<210> SEQ ID NO 299
<211> LENGTH: 16
<212> TYPE: PRT
<213> ORGANISM: Artificial
<220> FEATURE:
<223> OTHER INFORMATION: Synthetic

<400> SEQUENCE: 299

Glu Ile Asp Glu Val Gly Ser Thr Asn Tyr Asn Pro Ser Leu Lys Ser
1               5                   10                  15

<210> SEQ ID NO 300
<211> LENGTH: 17
<212> TYPE: PRT
<213> ORGANISM: Artificial
<220> FEATURE:
<223> OTHER INFORMATION: Synthetic

<400> SEQUENCE: 300

Ala Arg Leu Pro Met Tyr Tyr Tyr Asp Ser Ser Asp Leu Pro Met Asp

-continued 1 5 10 15

Val

<210> SEQ ID NO 301
<211> LENGTH: 123
<212> TYPE: PRT
<213> ORGANISM: Artificial
<220> FEATURE:
<223> OTHER INFORMATION: Synthetic

<400> SEQUENCE: 301

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Glu Tyr
20 25 30

Tyr Trp Ala Trp Ile Arg Gln Pro Pro Gly Lys Gly Leu Glu Trp Ile
35 40 45

Gly Glu Ile Asp Glu Val Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Leu Pro Met Tyr Tyr Tyr Asp Ser Ser Asp Leu Pro Met Asp Val
100 105 110

Trp Gly Gln Gly Thr Thr Val Thr Val Ser Ser
115 120

<210> SEQ ID NO 302
<211> LENGTH: 369
<212> TYPE: DNA
<213> ORGANISM: Artificial
<220> FEATURE:
<223> OTHER INFORMATION: Synthetic

<400> SEQUENCE: 302
caagtacaat tacaacagtg gggagctggt ttattaaagc cttcagaaac tttaagtttg 60
acctgtgctg tttacggtgg atcattttct gagtattact gggcttggat tcgtcaacca 120
ccaggcaaag gattggagtg gatcggtgag atagacgagg ttggctccac taactacaat 180
ccaagtttaa aatccagggt tactatctcc gtagacacgt ccaagaacca gttctccctg 240
aagctgagtt ctgtgaccgc cgcagacacg gcggtgtact actgcgccag acttcctatg 300
tactactacg acagcagcga cttgccaatg gacgtatggg gccagggaac aactgtcacc 360
gtctcctca 369

<210> SEQ ID NO 303
<211> LENGTH: 6
<212> TYPE: PRT
<213> ORGANISM: Artificial
<220> FEATURE:
<223> OTHER INFORMATION: Synthetic

<400> SEQUENCE: 303

Gln Asp Ile Ser Asn Tyr
1 5

<210> SEQ ID NO 304
<211> LENGTH: 3
<212> TYPE: PRT

<213> ORGANISM: Artificial
<220> FEATURE:
<223> OTHER INFORMATION: Synthetic

<400> SEQUENCE: 304

Asp Ala Ser
1

<210> SEQ ID NO 305
<211> LENGTH: 9
<212> TYPE: PRT
<213> ORGANISM: Artificial
<220> FEATURE:
<223> OTHER INFORMATION: Synthetic

<400> SEQUENCE: 305

Gln Gln Tyr Asp Thr Leu Pro Leu Thr
1 5

<210> SEQ ID NO 306
<211> LENGTH: 11
<212> TYPE: PRT
<213> ORGANISM: Artificial
<220> FEATURE:
<223> OTHER INFORMATION: Synthetic

<400> SEQUENCE: 306

Gln Ala Ser Gln Asp Ile Ser Asn Tyr Leu Asn
1 5 10

<210> SEQ ID NO 307
<211> LENGTH: 7
<212> TYPE: PRT
<213> ORGANISM: Artificial
<220> FEATURE:
<223> OTHER INFORMATION: Synthetic

<400> SEQUENCE: 307

Asp Ala Ser Asn Leu Ala Thr
1 5

<210> SEQ ID NO 308
<211> LENGTH: 9
<212> TYPE: PRT
<213> ORGANISM: Artificial
<220> FEATURE:
<223> OTHER INFORMATION: Synthetic

<400> SEQUENCE: 308

Gln Gln Tyr Asp Thr Leu Pro Leu Thr
1 5

<210> SEQ ID NO 309
<211> LENGTH: 107
<212> TYPE: PRT
<213> ORGANISM: Artificial
<220> FEATURE:
<223> OTHER INFORMATION: Synthetic

<400> SEQUENCE: 309

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Thr Leu Pro Leu
                85                  90                  95

Thr Phe Gly Gly Gly Thr Lys Val Glu Ile Lys
            100                 105

<210> SEQ ID NO 310
<211> LENGTH: 321
<212> TYPE: DNA
<213> ORGANISM: Artificial
<220> FEATURE:
<223> OTHER INFORMATION: Synthetic

<400> SEQUENCE: 310
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gatctacgat gcatccaatt tggcaacagg ggtcccatca    180
aggttcagtg gaagtggatc tgggacagat tttactttca ccatcagcag cctgcagcct    240
gaagatattg caacatatta ctgtcagcag tacgataccc tccctctcac ttttggcgga    300
gggaccaagg ttgagatcaa a                                              321

<210> SEQ ID NO 311
<211> LENGTH: 453
<212> TYPE: PRT
<213> ORGANISM: Artificial
<220> FEATURE:
<223> OTHER INFORMATION: Synthetic

<400> SEQUENCE: 311

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Glu Tyr
            20                  25                  30

Tyr Trp Ala Trp Ile Arg Gln Pro Pro Gly Lys Gly Leu Glu Trp Ile
        35                  40                  45

Gly Glu Ile Asp Glu Val Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Pro Met Tyr Tyr Tyr Asp Ser Ser Asp Leu Pro Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val

-continued

```
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 312
<211> LENGTH: 1359
<212> TYPE: DNA
<213> ORGANISM: Artificial
<220> FEATURE:
<223> OTHER INFORMATION: Synthetic

<400> SEQUENCE: 312

caagtacaat tacaacagtg gggagctggt ttattaaagc cttcagaaac tttaagtttg      60

acctgtgctg tttacggtgg atcattttct gagtattact gggcttggat tcgtcaacca     120

ccaggcaaag gattggagtg gatcggtgag atagacgagg ttggctccac taactacaat     180

ccaagtttaa aatccagggt tactatctcc gtagacacgt ccaagaacca gttctccctg     240

aagctgagtt ctgtgaccgc cgcagacacg gcggtgtact actgcgccag acttcctatg     300

tactactacg acagcagcga cttgccaatg gacgtatggg gccagggaac aactgtcacc     360

gtctcctcag cgagcaccaa aggcccgagc gtgtttccgc tggcgccgag cagcaaaagc     420

accagcggcg gcaccgcggc gctgggctgc ctggtgaaag attattttcc ggaaccggtg     480
```

-continued

```
accgtgagct ggaacagcgg cgcgctgacc agcggcgtgc ataccttccc ggcggtgctg    540

cagagcagcg gcctgtatag cctgagcagc gtggtgaccg tgccgagcag cagcctgggc    600

acccagacct atatttgcaa cgtgaaccat aaaccgagca acaccaaagt ggataaaaaa    660

gtggaaccga aaagctgcga taaaacccat acctgcccgc cgtgcccggc gccggaactg    720

ctgggcggcc cgagcgtgtt tctgtttccg ccgaaaccga aagataccct gatgattagc    780

cgcaccccgg aagtgacctg cgtggtggtg gatgtgagcc atgaagatcc ggaagtgaaa    840

tttaactggt atgtggatgg cgtggaagtg cataacgcga aaaccaaacc gcgcgaagaa    900

cagtataaca gcacctatcg cgtggtgagc gtgctgaccg tgctgcatca ggattggctg    960

aacggcaaag aatataaatg caaagtgagc aacaaagcgc tgccggcgcc gattgaaaaa   1020

accattagca aagcgaaagg ccagccgcgc gaaccgcagg tgtataccct gccgccgagc   1080

cgcgatgaac tgaccaaaaa ccaggtgagc ctgacctgcc tggtgaaagg cttttatccg   1140

agcgatattg cggtggaatg ggaaagcaac ggccagccgg aaaacaacta taaaaccacc   1200

ccgccggtgc tggatagcga tggcagcttt tttctgtata gcaaactgac cgtggataaa   1260

agccgctggc agcagggcaa cgtgtttagc tgcagcgtga tgcatgaagc gctgcataac   1320

cattataccc agaaaagcct gagcctgagc ccgggcaaa                           1359
```

<210> SEQ ID NO 313
<211> LENGTH: 214
<212> TYPE: PRT
<213> ORGANISM: Artificial
<220> FEATURE:
<223> OTHER INFORMATION: Synthetic

<400> SEQUENCE: 313

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Ala Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Thr Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
210

<210> SEQ ID NO 314
<211> LENGTH: 642
<212> TYPE: DNA
<213> ORGANISM: Artificial
<220> FEATURE:
<223> OTHER INFORMATION: Synthetic

<400> SEQUENCE: 314
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaatt tggcaacagg ggtcccatca 180
aggttcagtg gaagtggatc tgggacagat tttactttca ccatcagcag cctgcagcct 240
gaagatattg caacatatta ctgtcagcag tacgataccc tccctctcac ttttggcgga 300
gggaccaagg ttgagatcaa acgtacggtg gccgctccct ccgtgttcat cttcccaccc 360
tccgacgagc agctgaagtc cggcaccgcc tccgtcgtgt gcctgctgaa caacttctac 420
cctcgcgagg ccaaagtgca gtggaaagtg gacaacgccc tgcagtccgg caactcccag 480
gaatccgtca ccgagcagga ctccaaggac agcacctact ccctgtcctc caccctgacc 540
ctgtccaagg ccgactacga gaagcacaaa gtgtacgcct gcgaagtgac ccaccagggc 600
ctgtccagcc ccgtgaccaa gtccttcaac cggggcgagt gc 642

<210> SEQ ID NO 315
<211> LENGTH: 449
<212> TYPE: PRT
<213> ORGANISM: Artificial
<220> FEATURE:
<223> OTHER INFORMATION: Synthetic

<400> SEQUENCE: 315

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Glu Tyr
20 25 30

Tyr Trp Ala Trp Ile Arg Gln Pro Pro Gly Lys Gly Leu Glu Trp Ile
35 40 45

Gly Glu Ile Asp Glu Val Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Leu Pro Met Tyr Tyr Tyr Asp Ser Ser Asp Leu Pro Met Asp Val
100 105 110

Trp Gly Gln Gly Thr Thr Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val

-continued

```
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly
```

<210> SEQ ID NO 316
<211> LENGTH: 1347
<212> TYPE: DNA
<213> ORGANISM: Artificial
<220> FEATURE:
<223> OTHER INFORMATION: Synthetic

<400> SEQUENCE: 316

```
caagtacaat tacaacagtg gggagctggt ttattaaagc cttcagaaac tttaagtttg     60

acctgtgctg tttacggtgg atcattttct gagtattact gggcttggat tcgtcaacca    120

ccaggcaaag gattggagtg gatcggtgag atagacgagg ttggctccac taactacaat    180

ccaagtttaa aatccagggt tactatctcc gtagacacgt ccaagaacca gttctccctg    240

aagctgagtt ctgtgaccgc cgcagacacg gcggtgtact actgcgccag acttcctatg    300

tactactacg acagcagcga cttgccaatg gacgtatggg gccagggaac aactgtcacc    360

gtctcctcag cttccaccaa gggcccctcc gtgttccctc tggccccttg ctcccggtcc    420

acctccgagt ctaccgccgc tctgggctgc ctcgtgaagg actacttccc cgagcccgtg    480

accgtgtcct ggaactctgg cgccctgacc tccggcgtgc acaccttccc tgccgtgctg    540
```

```
cagtcctccg gcctgtactc cctgtccagc gtcgtgaccg tgccctcctc cagcctgggc    600

accaagacct acacctgtaa cgtggaccac aagccctcca acaccaaagt ggacaagcgg    660

gtggaatcta agtacggccc tccctgccct tcctgccctg cccctgagtt cctgggcgga    720

ccttccgtgt tcctgttccc tccaaagccc aaggacaccc tgatgatctc ccggacccct    780

gaagtgacct gcgtggtggt ggacgtgtcc caggaagatc ccgaagtcca gttcaattgg    840

tacgtggacg gcgtggaagt gcacaacgcc aagaccaagc ccagagagga acagttcaac    900

tccacctacc gggtggtgtc cgtgctgacc gtgctgcacc aggactggct gaacggcaaa    960

gagtacaagt gcaaagtgtc caacaagggc ctgccctcca gcatcgaaaa gaccatctcc   1020

aaggccaagg gccagccccg cgagccccaa gtgtacaccc tgcctcccag ccaggaagag   1080

atgaccaaga atcaagtgtc cctgacttgt ctggtcaagg gcttctaccc ctccgatatc   1140

gccgtggagt gggagtccaa cggccagccc gagaacaact acaagaccac ccctcccgtg   1200

ctggactccg acggctcctt cttcctgtac tctcggctga ccgtggacaa gtcccggtgg   1260

caggaaggca acgtcttctc ctgctccgtg atgcacgagg ccctgcacaa ccactacacc   1320

cagaagtccc tgtccctgtc tctgggc                                       1347
```

<210> SEQ ID NO 317
<211> LENGTH: 8
<212> TYPE: PRT
<213> ORGANISM: Artificial
<220> FEATURE:
<223> OTHER INFORMATION: Synthetic

<400> SEQUENCE: 317

```
Gly Gly Ser Phe Ser Gly Tyr Tyr
1               5
```

<210> SEQ ID NO 318
<211> LENGTH: 7
<212> TYPE: PRT
<213> ORGANISM: Artificial
<220> FEATURE:
<223> OTHER INFORMATION: Synthetic

<400> SEQUENCE: 318

```
Ile Asp Val Asp Gly Ser Thr
1               5
```

<210> SEQ ID NO 319
<211> LENGTH: 14
<212> TYPE: PRT
<213> ORGANISM: Artificial
<220> FEATURE:
<223> OTHER INFORMATION: Synthetic

<400> SEQUENCE: 319

```
Ala Arg Asp Gly Tyr Tyr Tyr Asp Thr Ser Pro Tyr Asp Val
1               5                   10
```

<210> SEQ ID NO 320
<211> LENGTH: 9
<212> TYPE: PRT
<213> ORGANISM: Artificial
<220> FEATURE:
<223> OTHER INFORMATION: Synthetic

<400> SEQUENCE: 320

```
Gly Ser Phe Ser Gly Tyr Tyr Trp Ser
```

1 5

<210> SEQ ID NO 321
<211> LENGTH: 16
<212> TYPE: PRT
<213> ORGANISM: Artificial
<220> FEATURE:
<223> OTHER INFORMATION: Synthetic

<400> SEQUENCE: 321

Glu Ile Asp Val Asp Gly Ser Thr Asn Tyr Asn Pro Ser Leu Lys Ser
1 5 10 15

<210> SEQ ID NO 322
<211> LENGTH: 14
<212> TYPE: PRT
<213> ORGANISM: Artificial
<220> FEATURE:
<223> OTHER INFORMATION: Synthetic

<400> SEQUENCE: 322

Ala Arg Asp Gly Tyr Tyr Tyr Asp Thr Ser Pro Tyr Asp Val
1 5 10

<210> SEQ ID NO 323
<211> LENGTH: 120
<212> TYPE: PRT
<213> ORGANISM: Artificial
<220> FEATURE:
<223> OTHER INFORMATION: Synthetic

<400> SEQUENCE: 323

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp Val Asp Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Asp Gly Tyr Tyr Tyr Asp Thr Ser Pro Tyr Asp Val Trp Gly Gln
100 105 110

Gly Thr Met Val Thr Val Ser Ser
115 120

<210> SEQ ID NO 324
<211> LENGTH: 360
<212> TYPE: DNA
<213> ORGANISM: Artificial
<220> FEATURE:
<223> OTHER INFORMATION: Synthetic

<400> SEQUENCE: 324
caagtacaat tacaacagtg gggagctggt ttattaaagc cttcagaaac tttaagtttg 60
acctgtgctg tttacggtgg atcattttct ggttattact ggagttggat tcgtcaacca 120
ccaggcaaag gattggagtg gatcggtgag atagacgtgg atggctccac taactacaat 180
ccaagtttaa aatccagggt tactatctcc gtagacacgt ccaagaacca gttctccctg 240

-continued aagctgagtt ctgtgaccgc cgcagacacg gcggtgtact actgcgccag agacggatac 300
tactacgaca ccagtccata cgacgtatgg ggtcagggta caatggtcac cgtctcctca 360

<210> SEQ ID NO 325
<211> LENGTH: 6
<212> TYPE: PRT
<213> ORGANISM: Artificial
<220> FEATURE:
<223> OTHER INFORMATION: Synthetic

<400> SEQUENCE: 325

Gln Ser Val Ser Ser Tyr
1 5

<210> SEQ ID NO 326
<211> LENGTH: 3
<212> TYPE: PRT
<213> ORGANISM: Artificial
<220> FEATURE:
<223> OTHER INFORMATION: Synthetic

<400> SEQUENCE: 326

Asp Ala Ser
1

<210> SEQ ID NO 327
<211> LENGTH: 9
<212> TYPE: PRT
<213> ORGANISM: Artificial
<220> FEATURE:
<223> OTHER INFORMATION: Synthetic

<400> SEQUENCE: 327

Gln Gln Arg Asp Ser Phe Pro Leu Thr
1 5

<210> SEQ ID NO 328
<211> LENGTH: 11
<212> TYPE: PRT
<213> ORGANISM: Artificial
<220> FEATURE:
<223> OTHER INFORMATION: Synthetic

<400> SEQUENCE: 328

Arg Ala Ser Gln Ser Val Ser Ser Tyr Leu Ala
1 5 10

<210> SEQ ID NO 329
<211> LENGTH: 7
<212> TYPE: PRT
<213> ORGANISM: Artificial
<220> FEATURE:
<223> OTHER INFORMATION: Synthetic

<400> SEQUENCE: 329

Asp Ala Ser Asn Arg Ala Thr
1 5

<210> SEQ ID NO 330
<211> LENGTH: 9
<212> TYPE: PRT
<213> ORGANISM: Artificial
<220> FEATURE:
<223> OTHER INFORMATION: Synthetic

<400> SEQUENCE: 330

```
Gln Gln Arg Asp Ser Phe Pro Leu Thr
1               5


<210> SEQ ID NO 331
<211> LENGTH: 107
<212> TYPE: PRT
<213> ORGANISM: Artificial
<220> FEATURE:
<223> OTHER INFORMATION: Synthetic

<400> SEQUENCE: 331

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asp Ser Phe Pro Leu
                85                  90                  95

Thr Phe Gly Gly Gly Thr Lys Val Glu Ile Lys
            100                 105


<210> SEQ ID NO 332
<211> LENGTH: 321
<212> TYPE: DNA
<213> ORGANISM: Artificial
<220> FEATURE:
<223> OTHER INFORMATION: Synthetic

<400> SEQUENCE: 332

gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag agagactcct tccctctcac ttttggcgga    300

gggaccaagg ttgagatcaa a                                              321


<210> SEQ ID NO 333
<211> LENGTH: 450
<212> TYPE: PRT
<213> ORGANISM: Artificial
<220> FEATURE:
<223> OTHER INFORMATION: Synthetic

<400> SEQUENCE: 333

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp Val Asp Gly Ser Thr Asn Tyr Asn Pro Ser Leu Lys
    50                  55                  60
```

```
Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Tyr Tyr Tyr Asp Thr Ser Pro Tyr Asp Val Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 334
<211> LENGTH: 1350
<212> TYPE: DNA

<213> ORGANISM: Artificial
<220> FEATURE:
<223> OTHER INFORMATION: Synthetic

<400> SEQUENCE: 334
caagtacaat tacaacagtg gggagctggt ttattaaagc cttcagaaac tttaagtttg 60
acctgtgctg tttacggtgg atcattttct ggttattact ggagttggat tcgtcaacca 120
ccaggcaaag gattggagtg gatcggtgag atagacgtgg atggctccac taactacaat 180
ccaagtttaa aatccagggt tactatctcc gtagacacgt ccaagaacca gttctccctg 240
aagctgagtt ctgtgaccgc cgcagacacg gcggtgtact actgcgccag agacggatac 300
tactacgaca ccagtccata cgacgtatgg ggtcagggta caatggtcac cgtctcctca 360
gcgagcacca aaggcccgag cgtgtttccg ctggcgccga gcagcaaaag caccagcggc 420
ggcaccgcgg cgctgggctg cctggtgaaa gattattttc cggaaccggt gaccgtgagc 480
tggaacagcg gcgcgctgac cagcggcgtg catacctttc cggcggtgct gcagagcagc 540
ggcctgtata gcctgagcag cgtggtgacc gtgccgagca gcagcctggg cacccagacc 600
tatatttgca acgtgaacca taaaccgagc aacaccaaag tggataaaaa agtggaaccg 660
aaaagctgcg ataaaaccca tacctgcccg ccgtgcccgg cgccggaact gctgggcggc 720
ccgagcgtgt ttctgtttcc gccgaaaccg aaagataccc tgatgattag ccgcaccccg 780
gaagtgacct gcgtggtggt ggatgtgagc catgaagatc cggaagtgaa atttaactgg 840
tatgtggatg gcgtggaagt gcataacgcg aaaaccaaac cgcgcgaaga acagtataac 900
agcacctatc gcgtggtgag cgtgctgacc gtgctgcatc aggattggct gaacggcaaa 960
gaatataaat gcaaagtgag caacaaagcg ctgccggcgc cgattgaaaa aaccattagc 1020
aaagcgaaag gccagccgcg cgaaccgcag gtgtataccc tgccgccgag ccgcgatgaa 1080
ctgaccaaaa accaggtgag cctgacctgc ctggtgaaag gcttttatcc gagcgatatt 1140
gcggtggaat gggaaagcaa cggccagccg gaaaacaact ataaaaccac cccgccggtg 1200
ctggatagcg atggcagctt ttttctgtat agcaaactga ccgtggataa aagccgctgg 1260
cagcagggca acgtgtttag ctgcagcgtg atgcatgaag cgctgcataa ccattatacc 1320
cagaaaagcc tgagcctgag cccgggcaaa 1350

<210> SEQ ID NO 335
<211> LENGTH: 214
<212> TYPE: PRT
<213> ORGANISM: Artificial
<220> FEATURE:
<223> OTHER INFORMATION: Synthetic

<400> SEQUENCE: 335

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Asp Ser Phe Pro Leu
85 90 95

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 336
<211> LENGTH: 642
<212> TYPE: DNA
<213> ORGANISM: Artificial
<220> FEATURE:
<223> OTHER INFORMATION: Synthetic

<400> SEQUENCE: 336

```
gaaattgtgt tgacacagtc tccagccacc ctgtctttgt ctccagggga aagagccacc     60

ctctcctgca gggccagtca gagtgttagc agctacttag cctggtacca acagaaacct    120

ggccaggctc ccaggctcct catctatgat gcatccaaca gggccactgg catcccagcc    180

aggttcagtg gcagtgggtc tgggacagac ttcactctca ccatcagcag cctagagcct    240

gaagattttg cagtttatta ctgtcagcag agagactcct tccctctcac ttttggcgga    300

gggaccaagg ttgagatcaa acgtacggtg gccgctccct ccgtgttcat cttcccaccc    360

tccgacgagc agctgaagtc cggcaccgcc tccgtcgtgt gcctgctgaa caacttctac    420

cctcgcgagg ccaaagtgca gtggaaagtg gacaacgccc tgcagtccgg caactcccag    480

gaatccgtca ccgagcagga ctccaaggac agcacctact ccctgtcctc caccctgacc    540

ctgtccaagg ccgactacga gaagcacaaa gtgtacgcct gcgaagtgac ccaccagggc    600

ctgtccagcc ccgtgaccaa gtccttcaac cggggcgagt gc                       642
```

<210> SEQ ID NO 337
<211> LENGTH: 446
<212> TYPE: PRT
<213> ORGANISM: Artificial
<220> FEATURE:
<223> OTHER INFORMATION: Synthetic

<400> SEQUENCE: 337

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp Val Asp Gly Ser Thr Asn Tyr Asn Pro Ser Leu Lys
    50                  55                  60
```

```
Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Tyr Tyr Tyr Asp Thr Ser Pro Tyr Asp Val Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 338
<211> LENGTH: 1338
<212> TYPE: DNA
<213> ORGANISM: Artificial
<220> FEATURE:
<223> OTHER INFORMATION: Synthetic

<400> SEQUENCE: 338
caagtacaat tacaacagtg gggagctggt ttattaaagc cttcagaaac tttaagtttg 60
acctgtgctg tttacggtgg atcattttct ggttattact ggagttggat tcgtcaacca 120
ccaggcaaag gattggagtg gatcggtgag atagacgtgg atggctccac taactacaat 180
ccaagtttaa aatccagggt tactatctcc gtagacacgt ccaagaacca gttctccctg 240
aagctgagtt ctgtgaccgc cgcagacacg gcggtgtact actgcgccag agacggatac 300
tactacgaca ccagtccata cgacgtatgg ggtcagggta caatggtcac cgtctcctca 360
gcttccacca agggcccctc cgtgttccct ctggcccctt gctcccggtc cacctccgag 420
tctaccgccg ctctgggctg cctcgtgaag gactacttcc ccgagcccgt gaccgtgtcc 480
tggaactctg gcgccctgac ctccggcgtg cacaccttcc ctgccgtgct gcagtcctcc 540
ggcctgtact ccctgtccag cgtcgtgacc gtgccctcct ccagcctggg caccaagacc 600
tacacctgta acgtggacca caagccctcc aacaccaaag tggacaagcg ggtggaatct 660
aagtacggcc ctccctgccc ttcctgccct gccccctgagt tcctgggcgg accttccgtg 720
ttcctgttcc ctccaaagcc caaggacacc ctgatgatct cccggacccc tgaagtgacc 780
tgcgtggtgg tggacgtgtc ccaggaagat cccgaagtcc agttcaattg gtacgtggac 840
ggcgtggaag tgcacaacgc caagaccaag cccagagagg aacagttcaa ctccacctac 900
cgggtggtgt ccgtgctgac cgtgctgcac caggactggc tgaacggcaa agagtacaag 960
tgcaaagtgt ccaacaaggg cctgccctcc agcatcgaaa agaccatctc caaggccaag 1020
ggccagcccc gcgagcccca agtgtacacc ctgcctccca gccaggaaga gatgaccaag 1080
aatcaagtgt ccctgacttg tctggtcaag ggcttctacc cctccgatat cgccgtggag 1140
tgggagtcca acggccagcc cgagaacaac tacaagacca cccctcccgt gctggactcc 1200
gacggctcct tcttcctgta ctctcggctg accgtggaca agtcccggtg gcaggaaggc 1260
aacgtcttct cctgctccgt gatgcacgag gccctgcaca accactacac ccagaagtcc 1320
ctgtccctgt ctctgggc 1338

<210> SEQ ID NO 339
<211> LENGTH: 8
<212> TYPE: PRT
<213> ORGANISM: Artificial
<220> FEATURE:
<223> OTHER INFORMATION: Synthetic

<400> SEQUENCE: 339

Gly Gly Thr Phe Val Gly Tyr Ala
1               5

<210> SEQ ID NO 340
<211> LENGTH: 8
<212> TYPE: PRT
<213> ORGANISM: Artificial
<220> FEATURE:
<223> OTHER INFORMATION: Synthetic

<400> SEQUENCE: 340

Ile Ile Pro Ile Phe Gly Ile Ala
1               5

<210> SEQ ID NO 341
<211> LENGTH: 17
<212> TYPE: PRT

<213> ORGANISM: Artificial
<220> FEATURE:
<223> OTHER INFORMATION: Synthetic

<400> SEQUENCE: 341

Ala Arg Ser Tyr Tyr Ser Ser Arg Trp His Tyr Tyr Tyr Tyr Met Asp
1 5 10 15

Val

<210> SEQ ID NO 342
<211> LENGTH: 9
<212> TYPE: PRT
<213> ORGANISM: Artificial
<220> FEATURE:
<223> OTHER INFORMATION: Synthetic

<400> SEQUENCE: 342

Gly Thr Phe Val Gly Tyr Ala Ile Ser
1 5

<210> SEQ ID NO 343
<211> LENGTH: 17
<212> TYPE: PRT
<213> ORGANISM: Artificial
<220> FEATURE:
<223> OTHER INFORMATION: Synthetic

<400> SEQUENCE: 343

Gly Ile Ile Pro Ile Phe Gly Ile Ala Asn Tyr Ala Gln Lys Phe Gln
1 5 10 15

Gly

<210> SEQ ID NO 344
<211> LENGTH: 17
<212> TYPE: PRT
<213> ORGANISM: Artificial
<220> FEATURE:
<223> OTHER INFORMATION: Synthetic

<400> SEQUENCE: 344

Ala Arg Ser Tyr Tyr Ser Ser Arg Trp His Tyr Tyr Tyr Tyr Met Asp
1 5 10 15

Val

<210> SEQ ID NO 345
<211> LENGTH: 124
<212> TYPE: PRT
<213> ORGANISM: Artificial
<220> FEATURE:
<223> OTHER INFORMATION: Synthetic

<400> SEQUENCE: 345

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Val Gly Tyr
20 25 30

Ala Ile Ser Trp Val Arg Gln Ala Pro Gly Gln Gly Leu Glu Trp Met
35 40 45

Gly Gly Ile Ile Pro Ile Phe Gly Ile Ala Asn Tyr Ala Gln Lys Phe
50 55 60

Gln Gly Arg Val Thr Ile Thr Ala Asp Glu Ser Thr Ser Thr Ala Tyr
65 70 75 80

```
Met Glu Leu Ser Ser Leu Arg Ser Glu Asp Thr Ala Val Tyr Tyr Cys
                85                  90                  95

Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser
        115                 120


<210> SEQ ID NO 346
<211> LENGTH: 372
<212> TYPE: DNA
<213> ORGANISM: Artificial
<220> FEATURE:
<223> OTHER INFORMATION: Synthetic

<400> SEQUENCE: 346

caggtgcagc tggtgcagtc tggggctgag gtgaagaagc ctgggtcctc ggtgaaggtc     60

tcctgcaagg cttctggagg caccttcgtt gggtatgcta tcagctgggt gcgacaggcc    120

cctggacaag ggcttgagtg gatgggaggg atcatcccta tctttggtat tgcaaactac    180

gcacagaagt tccagggcag agtcacgatt accgcggacg aatccacgag cacagcctac    240

atggagctga gcagcctgag atctgaggac acggcggtgt actactgcgc cagatcttac    300

tactccagcc gatggcacta ctactactac atggacgtgt ggggcaaggg tacaactgtc    360

accgtctcct ca                                                        372


<210> SEQ ID NO 347
<211> LENGTH: 6
<212> TYPE: PRT
<213> ORGANISM: Artificial
<220> FEATURE:
<223> OTHER INFORMATION: Synthetic

<400> SEQUENCE: 347

Gln Gly Ile Ser Ser Trp
1               5


<210> SEQ ID NO 348
<211> LENGTH: 3
<212> TYPE: PRT
<213> ORGANISM: Artificial
<220> FEATURE:
<223> OTHER INFORMATION: Synthetic

<400> SEQUENCE: 348

Ala Ala Ser
1


<210> SEQ ID NO 349
<211> LENGTH: 9
<212> TYPE: PRT
<213> ORGANISM: Artificial
<220> FEATURE:
<223> OTHER INFORMATION: Synthetic

<400> SEQUENCE: 349

Gln Gln Ala Asp Asp Leu Pro Leu Thr
1               5


<210> SEQ ID NO 350
<211> LENGTH: 11
<212> TYPE: PRT
<213> ORGANISM: Artificial
<220> FEATURE:
<223> OTHER INFORMATION: Synthetic
```

<400> SEQUENCE: 350

Arg Ala Ser Gln Gly Ile Ser Ser Trp Leu Ala
1 5 10

<210> SEQ ID NO 351
<211> LENGTH: 7
<212> TYPE: PRT
<213> ORGANISM: Artificial
<220> FEATURE:
<223> OTHER INFORMATION: Synthetic

<400> SEQUENCE: 351

Ala Ala Ser Asn Leu Gln Ser
1 5

<210> SEQ ID NO 352
<211> LENGTH: 9
<212> TYPE: PRT
<213> ORGANISM: Artificial
<220> FEATURE:
<223> OTHER INFORMATION: Synthetic

<400> SEQUENCE: 352

Gln Gln Ala Asp Asp Leu Pro Leu Thr
1 5

<210> SEQ ID NO 353
<211> LENGTH: 107
<212> TYPE: PRT
<213> ORGANISM: Artificial
<220> FEATURE:
<223> OTHER INFORMATION: Synthetic

<400> SEQUENCE: 353

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asp Asp Leu Pro Leu
85 90 95

Thr Phe Gly Gly Gly Thr Lys Val Glu Ile Lys
100 105

<210> SEQ ID NO 354
<211> LENGTH: 321
<212> TYPE: DNA
<213> ORGANISM: Artificial
<220> FEATURE:
<223> OTHER INFORMATION: Synthetic

<400> SEQUENCE: 354
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcatccaatt tgcaaagtgg ggtcccatca 180

-continued

```
aggttcagcg gcagtggatc tgggacagat ttcactctca ccatcagcag cctgcagcct    240

gaagattttg caacttatta ctgtcagcag gcagacgacc tccctctcac ttttggcgga    300

gggaccaagg ttgagatcaa a                                              321


<210> SEQ ID NO 355
<211> LENGTH: 454
<212> TYPE: PRT
<213> ORGANISM: Artificial
<220> FEATURE:
<223> OTHER INFORMATION: Synthetic

<400> SEQUENCE: 355

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Val Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

```
Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 356
<211> LENGTH: 1362
<212> TYPE: DNA
<213> ORGANISM: Artificial
<220> FEATURE:
<223> OTHER INFORMATION: Synthetic

<400> SEQUENCE: 356

caggtgcagc tggtgcagtc tggggctgag gtgaagaagc ctgggtcctc ggtgaaggtc      60

tcctgcaagg cttctggagg caccttcgtt gggtatgcta tcagctgggt gcgacaggcc     120

cctggacaag ggcttgagtg gatgggaggg atcatcccta tctttggtat tgcaaactac     180

gcacagaagt tccagggcag agtcacgatt accgcggacg aatccacgag cacagcctac     240

atggagctga gcagcctgag atctgaggac acggcggtgt actactgcgc cagatcttac     300

tactccagcc gatggcacta ctactactac atggacgtgt ggggcaaggg tacaactgtc     360

accgtctcct cagcgagcac caaaggcccg agcgtgtttc cgctggcgcc gagcagcaaa     420

agcaccagcg gcggcaccgc ggcgctgggc tgcctggtga aagattattt tccggaaccg     480

gtgaccgtga gctggaacag cggcgcgctg accagcggcg tgcatacctt tccggcggtg     540

ctgcagagca gcggcctgta tagcctgagc agcgtggtga ccgtgccgag cagcagcctg     600

ggcacccaga cctatatttg caacgtgaac cataaaccga gcaacaccaa agtggataaa     660

aaagtggaac cgaaaagctg cgataaaacc catacctgcc cgccgtgccc ggcgccggaa     720

ctgctgggcg gcccgagcgt gtttctgttt ccgccgaaac cgaaagatac cctgatgatt     780

agccgcaccc cggaagtgac ctgcgtggtg gtggatgtga gccatgaaga tccggaagtg     840

aaatttaact ggtatgtgga tggcgtggaa gtgcataacg cgaaaaccaa accgcgcgaa     900

gaacagtata acagcaccta tcgcgtggtg agcgtgctga ccgtgctgca tcaggattgg     960

ctgaacggca aagaatataa atgcaaagtg agcaacaaag cgctgccggc gccgattgaa    1020

aaaaccatta gcaaagcgaa aggccagccg cgcgaaccgc aggtgtatac cctgccgccg    1080

agccgcgatg aactgaccaa aaaccaggtg agcctgacct gcctggtgaa aggcttttat    1140

ccgagcgata ttgcggtgga atgggaaagc aacggccagc cggaaaacaa ctataaaacc    1200

accccgccgg tgctggatag cgatggcagc tttttttctgt atagcaaact gaccgtggat    1260

aaaagccgct ggcagcaggg caacgtgttt agctgcagcg tgatgcatga agcgctgcat    1320

aaccattata cccagaaaag cctgagcctg agcccgggca aa                       1362
```

<210> SEQ ID NO 357
<211> LENGTH: 214
<212> TYPE: PRT
<213> ORGANISM: Artificial
<220> FEATURE:
<223> OTHER INFORMATION: Synthetic

<400> SEQUENCE: 357

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asp Asp Leu Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 358
<211> LENGTH: 642
<212> TYPE: DNA
<213> ORGANISM: Artificial
<220> FEATURE:
<223> OTHER INFORMATION: Synthetic

<400> SEQUENCE: 358
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcatccaatt tgcaaagtgg ggtcccatca 180
aggttcagcg gcagtggatc tgggacagat ttcactctca ccatcagcag cctgcagcct 240
gaagattttg caacttatta ctgtcagcag gcagacgacc tccctctcac ttttggcgga 300
gggaccaagg ttgagatcaa acgtacggtg gccgctccct ccgtgttcat cttcccaccc 360
tccgacgagc agctgaagtc cggcaccgcc tccgtcgtgt gcctgctgaa caacttctac 420
cctcgcgagg ccaaagtgca gtggaaagtg gacaacgccc tgcagtccgg caactcccag 480

```
gaatccgtca ccgagcagga ctccaaggac agcacctact ccctgtcctc caccctgacc    540

ctgtccaagg ccgactacga gaagcacaaa gtgtacgcct gcgaagtgac ccaccagggc    600

ctgtccagcc ccgtgaccaa gtccttcaac cggggcgagt gc                       642


<210> SEQ ID NO 359
<211> LENGTH: 450
<212> TYPE: PRT
<213> ORGANISM: Artificial
<220> FEATURE:
<223> OTHER INFORMATION: Synthetic

<400> SEQUENCE: 359

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Val Gly Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Ser Ser Arg Trp His Tyr Tyr Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450


<210> SEQ ID NO 360
<211> LENGTH: 1350
<212> TYPE: DNA
<213> ORGANISM: Artificial
<220> FEATURE:
<223> OTHER INFORMATION: Synthetic

<400> SEQUENCE: 360

caggtgcagc tggtgcagtc tggggctgag gtgaagaagc ctgggtcctc ggtgaaggtc      60

tcctgcaagg cttctggagg caccttcgtt gggtatgcta tcagctgggt gcgacaggcc     120

cctggacaag ggcttgagtg gatgggaggg atcatcccta tctttggtat tgcaaactac     180

gcacagaagt tccagggcag agtcacgatt accgcggacg aatccacgag cacagcctac     240

atggagctga gcagcctgag atctgaggac acggcggtgt actactgcgc cagatcttac     300

tactccagcc gatggcacta ctactactac atggacgtgt ggggcaaggg tacaactgtc     360

accgtctcct cagcttccac caagggcccc tccgtgttcc ctctggcccc ttgctcccgg     420

tccacctccg agtctaccgc cgctctgggc tgcctcgtga aggactactt ccccgagccc     480

gtgaccgtgt cctggaactc tggcgccctg acctccggcg tgcacacctt ccctgccgtg     540

ctgcagtcct ccggcctgta ctccctgtcc agcgtcgtga ccgtgccctc ctccagcctg     600

ggcaccaaga cctacacctg taacgtggac cacaagccct ccaacaccaa agtggacaag     660

cgggtggaat ctaagtacgg ccctccctgc ccttcctgcc ctgcccctga gttcctgggc     720

ggaccttccg tgttcctgtt ccctccaaag cccaaggaca ccctgatgat ctcccggacc     780

cctgaagtga cctgcgtggt ggtggacgtg tcccaggaag atcccgaagt ccagttcaat     840

tggtacgtgg acggcgtgga agtgcacaac gccaagacca agcccagaga ggaacagttc     900

aactccacct accgggtggt gtccgtgctg accgtgctgc accaggactg gctgaacggc     960

aaagagtaca agtgcaaagt gtccaacaag ggcctgccct ccagcatcga aaagaccatc    1020

tccaaggcca agggccagcc ccgcgagccc caagtgtaca ccctgcctcc cagccaggaa    1080

gagatgacca agaatcaagt gtccctgact tgtctggtca agggcttcta cccctccgat    1140

atcgccgtgg agtgggagtc caacggccag cccgagaaca actacaagac cacccctccc    1200

gtgctggact ccgacggctc cttcttcctg tactctcggc tgaccgtgga caagtcccgg    1260

tggcaggaag gcaacgtctt ctcctgctcc gtgatgcacg aggccctgca caaccactac    1320

acccagaagt ccctgtccct gtctctgggc                                     1350
```

<210> SEQ ID NO 361
<211> LENGTH: 8
<212> TYPE: PRT
<213> ORGANISM: Artificial
<220> FEATURE:
<223> OTHER INFORMATION: Synthetic

<400> SEQUENCE: 361

Gly Phe Thr Phe Ser Ser Tyr Gly
1               5

<210> SEQ ID NO 362
<211> LENGTH: 8
<212> TYPE: PRT
<213> ORGANISM: Artificial
<220> FEATURE:
<223> OTHER INFORMATION: Synthetic

<400> SEQUENCE: 362

Ile Lys Gln Asp Gly Ser Glu Lys
1               5

<210> SEQ ID NO 363
<211> LENGTH: 15
<212> TYPE: PRT
<213> ORGANISM: Artificial
<220> FEATURE:
<223> OTHER INFORMATION: Synthetic

<400> SEQUENCE: 363

Ala Arg Asp Ala Pro Trp Asp Ile Tyr Asp Tyr Tyr Met Asp Val
1               5                   10                  15

<210> SEQ ID NO 364
<211> LENGTH: 9
<212> TYPE: PRT
<213> ORGANISM: Artificial
<220> FEATURE:
<223> OTHER INFORMATION: Synthetic

<400> SEQUENCE: 364

Phe Thr Phe Ser Ser Tyr Gly Met Ser
1               5

<210> SEQ ID NO 365
<211> LENGTH: 17
<212> TYPE: PRT
<213> ORGANISM: Artificial
<220> FEATURE:
<223> OTHER INFORMATION: Synthetic

<400> SEQUENCE: 365

Asn Ile Lys Gln Asp Gly Ser Glu Lys Tyr Tyr Val Asp Ser Val Lys
1               5                   10                  15

Gly

<210> SEQ ID NO 366
<211> LENGTH: 15
<212> TYPE: PRT
<213> ORGANISM: Artificial
<220> FEATURE:
<223> OTHER INFORMATION: Synthetic

<400> SEQUENCE: 366

Ala Arg Asp Ala Pro Trp Asp Ile Tyr Asp Tyr Tyr Met Asp Val 1 5 10 15

<210> SEQ ID NO 367
<211> LENGTH: 122
<212> TYPE: PRT
<213> ORGANISM: Artificial
<220> FEATURE:
<223> OTHER INFORMATION: Synthetic

<400> SEQUENCE: 367

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Ala Pro Trp Asp Ile Tyr Asp Tyr Tyr Met Asp Val Trp
100 105 110

Gly Lys Gly Thr Thr Val Thr Val Ser Ser
115 120

<210> SEQ ID NO 368
<211> LENGTH: 366
<212> TYPE: DNA
<213> ORGANISM: Artificial
<220> FEATURE:
<223> OTHER INFORMATION: Synthetic

<400> SEQUENCE: 368
gaggtgcagc tggtggagtc tgggggaggc ttggtccagc ctggggggtc cctgagactc 60
tcctgtgcag cctctggatt cacctttagt agctatggga tgagctgggt ccgccaggct 120
ccagggaagg ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggcggtgt actactgcgc cagagatgct 300
ccttgggaca tctacgacta ctacatggac gtatggggca agggtacaac tgtcaccgtc 360
tcctca 366

<210> SEQ ID NO 369
<211> LENGTH: 6
<212> TYPE: PRT
<213> ORGANISM: Artificial
<220> FEATURE:
<223> OTHER INFORMATION: Synthetic

<400> SEQUENCE: 369

Gln Ser Ile Ser Ser Tyr
1 5

<210> SEQ ID NO 370
<211> LENGTH: 3
<212> TYPE: PRT
<213> ORGANISM: Artificial
<220> FEATURE:

<223> OTHER INFORMATION: Synthetic

<400> SEQUENCE: 370

Ala Ala Ser
1

<210> SEQ ID NO 371
<211> LENGTH: 9
<212> TYPE: PRT
<213> ORGANISM: Artificial
<220> FEATURE:
<223> OTHER INFORMATION: Synthetic

<400> SEQUENCE: 371

Gln Gln Ser Tyr Val Pro Pro Trp Thr
1 5

<210> SEQ ID NO 372
<211> LENGTH: 11
<212> TYPE: PRT
<213> ORGANISM: Artificial
<220> FEATURE:
<223> OTHER INFORMATION: Synthetic

<400> SEQUENCE: 372

Arg Ala Ser Gln Ser Ile Ser Ser Tyr Leu Asn
1 5 10

<210> SEQ ID NO 373
<211> LENGTH: 7
<212> TYPE: PRT
<213> ORGANISM: Artificial
<220> FEATURE:
<223> OTHER INFORMATION: Synthetic

<400> SEQUENCE: 373

Ala Ala Ser Ser Leu Gln Ser
1 5

<210> SEQ ID NO 374
<211> LENGTH: 9
<212> TYPE: PRT
<213> ORGANISM: Artificial
<220> FEATURE:
<223> OTHER INFORMATION: Synthetic

<400> SEQUENCE: 374

Gln Gln Ser Tyr Val Pro Pro Trp Thr
1 5

<210> SEQ ID NO 375
<211> LENGTH: 107
<212> TYPE: PRT
<213> ORGANISM: Artificial
<220> FEATURE:
<223> OTHER INFORMATION: Synthetic

<400> SEQUENCE: 375

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Val Pro Pro Trp
                85                  90                  95

Thr Phe Gly Gly Gly Thr Lys Val Glu Ile Lys
            100                 105


<210> SEQ ID NO 376
<211> LENGTH: 321
<212> TYPE: DNA
<213> ORGANISM: Artificial
<220> FEATURE:
<223> OTHER INFORMATION: Synthetic

<400> SEQUENCE: 376

gacatccaga tgacccagtc tccatcctcc ctgtctgcat ctgtaggaga cagagtcacc      60

atcacttgcc gggcaagtca gagcattagc agctatttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcagcaa agctacgtcc ccccttggac ttttggcgga     300

gggaccaagg ttgagatcaa a                                               321


<210> SEQ ID NO 377
<211> LENGTH: 452
<212> TYPE: PRT
<213> ORGANISM: Artificial
<220> FEATURE:
<223> OTHER INFORMATION: Synthetic

<400> SEQUENCE: 377

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Trp Asp Ile Tyr Asp Tyr Tyr Met Asp Val Trp
            100                 105                 110

Gly Lys Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

-continued

```
Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 378
<211> LENGTH: 1356
<212> TYPE: DNA
<213> ORGANISM: Artificial
<220> FEATURE:
<223> OTHER INFORMATION: Synthetic

<400> SEQUENCE: 378

```
gaggtgcagc tggtggagtc tgggggaggc ttggtccagc ctggggggtc cctgagactc      60

tcctgtgcag cctctggatt cacctttagt agctatggga tgagctgggt ccgccaggct     120

ccagggaagg ggctggagtg ggtggccaac ataaagcaag atggaagtga gaaatactat     180

gtggactctg tgaagggccg attcaccatc tccagagaca acgccaagaa ctcactgtat     240

ctgcaaatga acagcctgag agccgaggac acggcggtgt actactgcgc cagagatgct     300

ccttgggaca tctacgacta ctacatggac gtatggggca agggtacaac tgtcaccgtc     360

tcctcagcga gcaccaaagg cccgagcgtg tttccgctgg cgccgagcag caaaagcacc     420

agcggcggca ccgcggcgct gggctgcctg gtgaaagatt attttccgga accggtgacc     480

gtgagctgga acagcggcgc gctgaccagc ggcgtgcata cctttccggc ggtgctgcag     540
```

-continued

```
agcagcggcc tgtatagcct gagcagcgtg gtgaccgtgc cgagcagcag cctgggcacc    600

cagacctata tttgcaacgt gaaccataaa ccgagcaaca ccaaagtgga taaaaaagtg    660

gaaccgaaaa gctgcgataa aacccatacc tgcccgccgt gcccggcgcc ggaactgctg    720

ggcggcccga gcgtgtttct gtttccgccg aaaccgaaag ataccctgat gattagccgc    780

accccggaag tgacctgcgt ggtggtggat gtgagccatg aagatccgga agtgaaattt    840

aactggtatg tggatggcgt ggaagtgcat aacgcgaaaa ccaaaccgcg cgaagaacag    900

tataacagca cctatcgcgt ggtgagcgtg ctgaccgtgc tgcatcagga ttggctgaac    960

ggcaaagaat ataaatgcaa agtgagcaac aaagcgctgc cggcgccgat tgaaaaaacc   1020

attagcaaag cgaaaggcca gccgcgcgaa ccgcaggtgt ataccctgcc gccgagccgc   1080

gatgaactga ccaaaaacca ggtgagcctg acctgcctgg tgaaaggctt ttatccgagc   1140

gatattgcgg tggaatggga aagcaacggc cagccggaaa acaactataa aaccaccccg   1200

ccggtgctgg atagcgatgg cagctttttt ctgtatagca aactgaccgt ggataaaagc   1260

cgctggcagc agggcaacgt gtttagctgc agcgtgatgc atgaagcgct gcataaccat   1320

tatacccaga aaagcctgag cctgagcccg ggcaaa                             1356
```

```
<210> SEQ ID NO 379
<211> LENGTH: 214
<212> TYPE: PRT
<213> ORGANISM: Artificial
<220> FEATURE:
<223> OTHER INFORMATION: Synthetic

<400> SEQUENCE: 379

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Val Pro Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 380
<211> LENGTH: 642
<212> TYPE: DNA
<213> ORGANISM: Artificial
<220> FEATURE:
<223> OTHER INFORMATION: Synthetic

<400> SEQUENCE: 380
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcagcaa agctacgtcc cccttggac ttttggcgga 300 gggaccaagg ttgagatcaa acgtacggtg gccgctccct ccgtgttcat cttcccaccc 360
tccgacgagc agctgaagtc cggcaccgcc tccgtcgtgt gcctgctgaa caacttctac 420
cctcgcgagg ccaaagtgca gtggaaagtg gacaacgccc tgcagtccgg caactcccag 480
gaatccgtca ccgagcagga ctccaaggac agcacctact ccctgtcctc caccctgacc 540
ctgtccaagg ccgactacga gaagcacaaa gtgtacgcct gcgaagtgac ccaccagggc 600
ctgtccagcc ccgtgaccaa gtccttcaac cggggcgagt gc 642

<210> SEQ ID NO 381
<211> LENGTH: 448
<212> TYPE: PRT
<213> ORGANISM: Artificial
<220> FEATURE:
<223> OTHER INFORMATION: Synthetic

<400> SEQUENCE: 381

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Ala Pro Trp Asp Ile Tyr Asp Tyr Tyr Met Asp Val Trp
100 105 110

Gly Lys Gly Thr Thr Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

```
Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445
```

<210> SEQ ID NO 382
<211> LENGTH: 1344
<212> TYPE: DNA
<213> ORGANISM: Artificial
<220> FEATURE:
<223> OTHER INFORMATION: Synthetic

<400> SEQUENCE: 382

```
gaggtgcagc tggtggagtc tgggggaggc ttggtccagc ctggggggtc cctgagactc      60

tcctgtgcag cctctggatt cacctttagt agctatggga tgagctgggt ccgccaggct     120

ccagggaagg ggctggagtg ggtggccaac ataaagcaag atggaagtga gaaatactat     180

gtggactctg tgaagggccg attcaccatc tccagagaca acgccaagaa ctcactgtat     240

ctgcaaatga acagcctgag agccgaggac acggcggtgt actactgcgc cagagatgct     300

ccttgggaca tctacgacta ctacatggac gtatggggca agggtacaac tgtcaccgtc     360

tcctcagctt ccaccaaggg cccctccgtg ttccctctgg ccccttgctc ccggtccacc     420

tccgagtcta ccgccgctct gggctgcctc gtgaaggact acttccccga gcccgtgacc     480

gtgtcctgga actctggcgc cctgacctcc ggcgtgcaca ccttccctgc cgtgctgcag     540

tcctccggcc tgtactccct gtccagcgtc gtgaccgtgc cctcctccag cctgggcacc     600

aagacctaca cctgtaacgt ggaccacaag ccctccaaca ccaaagtgga caagcgggtg     660
```

```
gaatctaagt acggccctcc ctgcccttcc tgccctgccc ctgagttcct gggcggacct    720

tccgtgttcc tgttccctcc aaagcccaag gacaccctga tgatctcccg gacccctgaa    780

gtgacctgcg tggtggtgga cgtgtcccag gaagatcccg aagtccagtt caattggtac    840

gtggacggcg tggaagtgca caacgccaag accaagccca gagaggaaca gttcaactcc    900

acctaccggg tggtgtccgt gctgaccgtg ctgcaccagg actggctgaa cggcaaagag    960

tacaagtgca aagtgtccaa caagggcctg ccctccagca tcgaaaagac catctccaag   1020

gccaagggcc agccccgcga gccccaagtg tacaccctgc ctcccagcca ggaagagatg   1080

accaagaatc aagtgtccct gacttgtctg gtcaagggct tctacccctc cgatatcgcc   1140

gtggagtggg agtccaacgg ccagcccgag aacaactaca agaccacccc tcccgtgctg   1200

gactccgacg gctccttctt cctgtactct cggctgaccg tggacaagtc ccggtggcag   1260

gaaggcaacg tcttctcctg ctccgtgatg cacgaggccc tgcacaacca ctacacccag   1320

aagtccctgt ccctgtctct gggc                                          1344
```

<210> SEQ ID NO 383
<211> LENGTH: 8
<212> TYPE: PRT
<213> ORGANISM: Artificial
<220> FEATURE:
<223> OTHER INFORMATION: Synthetic

<400> SEQUENCE: 383

```
Gly Phe Thr Phe Ser Ser Tyr Gly
1               5
```

<210> SEQ ID NO 384
<211> LENGTH: 8
<212> TYPE: PRT
<213> ORGANISM: Artificial
<220> FEATURE:
<223> OTHER INFORMATION: Synthetic

<400> SEQUENCE: 384

```
Ile Trp Tyr Asp Gly Ser Asn Lys
1               5
```

<210> SEQ ID NO 385
<211> LENGTH: 10
<212> TYPE: PRT
<213> ORGANISM: Artificial
<220> FEATURE:
<223> OTHER INFORMATION: Synthetic

<400> SEQUENCE: 385

```
Ala Arg Gly Ala Pro Glu Tyr Val Asp Val
1               5                   10
```

<210> SEQ ID NO 386
<211> LENGTH: 9
<212> TYPE: PRT
<213> ORGANISM: Artificial
<220> FEATURE:
<223> OTHER INFORMATION: Synthetic

<400> SEQUENCE: 386

```
Phe Thr Phe Ser Ser Tyr Gly Met His
1               5
```

<210> SEQ ID NO 387

<211> LENGTH: 17
<212> TYPE: PRT
<213> ORGANISM: Artificial
<220> FEATURE:
<223> OTHER INFORMATION: Synthetic

<400> SEQUENCE: 387

Val Ile Trp Tyr Asp Gly Ser Asn Lys Tyr Tyr Ala Asp Ser Val Lys
1               5                   10                  15

Gly

<210> SEQ ID NO 388
<211> LENGTH: 10
<212> TYPE: PRT
<213> ORGANISM: Artificial
<220> FEATURE:
<223> OTHER INFORMATION: Synthetic

<400> SEQUENCE: 388

Ala Arg Gly Ala Pro Glu Tyr Val Asp Val
1               5                   10

<210> SEQ ID NO 389
<211> LENGTH: 117
<212> TYPE: PRT
<213> ORGANISM: Artificial
<220> FEATURE:
<223> OTHER INFORMATION: Synthetic

<400> SEQUENCE: 389

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Glu Tyr Val Asp Val Trp Gly Gln Gly Thr Met
            100                 105                 110

Val Thr Val Ser Ser
        115

<210> SEQ ID NO 390
<211> LENGTH: 351
<212> TYPE: DNA
<213> ORGANISM: Artificial
<220> FEATURE:
<223> OTHER INFORMATION: Synthetic

<400> SEQUENCE: 390
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggcggtgt actactgcgc cagaggggcc     300
cctgaatatg tagacgtatg gggtcagggt acaatggtca ccgtctcctc a 351

<210> SEQ ID NO 391
<211> LENGTH: 6
<212> TYPE: PRT
<213> ORGANISM: Artificial
<220> FEATURE:
<223> OTHER INFORMATION: Synthetic

<400> SEQUENCE: 391

Gln Ser Val Ser Ser Tyr
1 5

<210> SEQ ID NO 392
<211> LENGTH: 3
<212> TYPE: PRT
<213> ORGANISM: Artificial
<220> FEATURE:
<223> OTHER INFORMATION: Synthetic

<400> SEQUENCE: 392

Asp Ser Ser
1

<210> SEQ ID NO 393
<211> LENGTH: 8
<212> TYPE: PRT
<213> ORGANISM: Artificial
<220> FEATURE:
<223> OTHER INFORMATION: Synthetic

<400> SEQUENCE: 393

Gln Gln Tyr Ser Leu Tyr Pro Thr
1 5

<210> SEQ ID NO 394
<211> LENGTH: 11
<212> TYPE: PRT
<213> ORGANISM: Artificial
<220> FEATURE:
<223> OTHER INFORMATION: Synthetic

<400> SEQUENCE: 394

Arg Ala Ser Gln Ser Val Ser Ser Tyr Leu Ala
1 5 10

<210> SEQ ID NO 395
<211> LENGTH: 7
<212> TYPE: PRT
<213> ORGANISM: Artificial
<220> FEATURE:
<223> OTHER INFORMATION: Synthetic

<400> SEQUENCE: 395

Asp Ser Ser Asn Arg Ala Thr
1 5

<210> SEQ ID NO 396
<211> LENGTH: 8
<212> TYPE: PRT
<213> ORGANISM: Artificial
<220> FEATURE:
<223> OTHER INFORMATION: Synthetic

<400> SEQUENCE: 396

Gln Gln Tyr Ser Leu Tyr Pro Thr

```
1               5

<210> SEQ ID NO 397
<211> LENGTH: 106
<212> TYPE: PRT
<213> ORGANISM: Artificial
<220> FEATURE:
<223> OTHER INFORMATION: Synthetic

<400> SEQUENCE: 397

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Leu Tyr Pro Thr
                85                  90                  95

Phe Gly Gly Gly Thr Lys Val Glu Ile Lys
            100                 105


<210> SEQ ID NO 398
<211> LENGTH: 318
<212> TYPE: DNA
<213> ORGANISM: Artificial
<220> FEATURE:
<223> OTHER INFORMATION: Synthetic

<400> SEQUENCE: 398

gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat tcatccaaca gggccactgg catcccagcc     180

aggttcagtg gcagtgggtc tgggacagac ttcactctca ccatcagcag cctagagcct     240

gaagattttg cagtttatta ctgtcagcag tacagtctct accctacttt tggcggaggg     300

accaaggttg agatcaaa                                                   318


<210> SEQ ID NO 399
<211> LENGTH: 447
<212> TYPE: PRT
<213> ORGANISM: Artificial
<220> FEATURE:
<223> OTHER INFORMATION: Synthetic

<400> SEQUENCE: 399

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Ala Pro Glu Tyr Val Asp Val Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 400
<211> LENGTH: 1341
<212> TYPE: DNA
<213> ORGANISM: Artificial
<220> FEATURE:
<223> OTHER INFORMATION: Synthetic

<400> SEQUENCE: 400

```
caggtgcagc tggtggagtc tgggggaggc gtggtccagc ctgggaggtc cctgagactc     60

tcctgtgcag cgtctggatt caccttcagt agctatggca tgcactgggt ccgccaggct    120

ccaggcaagg ggctggagtg ggtggcagtt atatggtatg atggaagtaa taaatactat    180

gcagactccg tgaagggccg attcaccatc tccagagaca attccaagaa cacgctgtat    240

ctgcaaatga acagcctgag agccgaggac acggcggtgt actactgcgc cagaggggcc    300

cctgaatatg tagacgtatg ggtcagggt acaatggtca ccgtctcctc agcgagcacc     360

aaaggcccga gcgtgtttcc gctggcgccg agcagcaaaa gcaccagcgg cggcaccgcg    420

gcgctgggct gcctggtgaa agattatttt ccggaaccgg tgaccgtgag ctggaacagc    480

ggcgcgctga ccagcggcgt gcataccttt ccggcggtgc tgcagagcag cggcctgtat    540

agcctgagca gcgtggtgac cgtgccgagc agcagcctgg gcacccagac ctatatttgc    600

aacgtgaacc ataaaccgag caacaccaaa gtggataaaa aagtggaacc gaaaagctgc    660

gataaaaccc atacctgccc gccgtgcccg gcgccggaac tgctgggcgg cccgagcgtg    720

tttctgtttc cgccgaaacc gaaagatacc ctgatgatta gccgcacccc ggaagtgacc    780

tgcgtggtgg tggatgtgag ccatgaagat ccggaagtga aatttaactg gtatgtggat    840

ggcgtggaag tgcataacgc gaaaaccaaa ccgcgcgaag aacagtataa cagcacctat    900

cgcgtggtga gcgtgctgac cgtgctgcat caggattggc tgaacggcaa agaatataaa    960

tgcaaagtga gcaacaaagc gctgccggcg ccgattgaaa aaaccattag caaagcgaaa   1020

ggccagccgc gcgaaccgca ggtgtatacc ctgccgccga gccgcgatga actgaccaaa   1080

aaccaggtga gcctgacctg cctggtgaaa ggcttttatc cgagcgatat tgcggtggaa   1140

tgggaaagca acggccagcc ggaaaacaac tataaaacca ccccgccggt gctggatagc   1200

gatggcagct ttttctgta tagcaaactg accgtggata aaagccgctg gcagcagggc    1260

aacgtgttta gctgcagcgt gatgcatgaa gcgctgcata accattatac ccagaaaagc   1320

ctgagcctga gcccgggcaa a                                               1341
```

<210> SEQ ID NO 401
<211> LENGTH: 213
<212> TYPE: PRT
<213> ORGANISM: Artificial
<220> FEATURE:
<223> OTHER INFORMATION: Synthetic

<400> SEQUENCE: 401

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Leu Tyr Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
```

```
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 402
<211> LENGTH: 639
<212> TYPE: DNA
<213> ORGANISM: Artificial
<220> FEATURE:
<223> OTHER INFORMATION: Synthetic

<400> SEQUENCE: 402

gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat tcatccaaca gggccactgg catcccagcc     180

aggttcagtg gcagtgggtc tgggacagac ttcactctca ccatcagcag cctagagcct     240

gaagattttg cagtttatta ctgtcagcag tacagtctct accctacttt tggcggaggg     300

accaaggttg agatcaaacg tacggtggcc gctccctccg tgttcatctt cccaccctcc     360

gacgagcagc tgaagtccgg caccgcctcc gtcgtgtgcc tgctgaacaa cttctaccct     420

cgcgaggcca aagtgcagtg gaaagtggac aacgccctgc agtccggcaa ctcccaggaa     480

tccgtcaccg agcaggactc caaggacagc acctactccc tgtcctccac cctgaccctg     540

tccaaggccg actacgagaa gcacaaagtg tacgcctgcg aagtgaccca ccagggcctg     600

tccagccccg tgaccaagtc cttcaaccgg ggcgagtgc                            639


<210> SEQ ID NO 403
<211> LENGTH: 443
<212> TYPE: PRT
<213> ORGANISM: Artificial
<220> FEATURE:
<223> OTHER INFORMATION: Synthetic

<400> SEQUENCE: 403

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Ala Pro Glu Tyr Val Asp Val Trp Gly Gln Gly Thr Met
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Lys Thr Tyr Thr Cys Asn Val Asp His Lys Pro Ser Asn
195 200 205

Thr Lys Val Asp Lys Arg Val Glu Ser Lys Tyr Gly Pro Pro Cys Pro
210 215 220

Ser Cys Pro Ala Pro Glu Phe Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser Gln Glu Asp Pro Glu Val Gln Phe
260 265 270

Asn Trp Tyr Val Asp Gly Val Glu Val His Asn Ala Lys Thr Lys Pro
275 280 285

Arg Glu Glu Gln Phe Asn Ser Thr Tyr Arg Val Val Ser Val Leu Thr
290 295 300

Val Leu His Gln Asp Trp Leu Asn Gly Lys Glu Tyr Lys Cys Lys Val
305 310 315 320

Ser Asn Lys Gly Leu Pro Ser Ser Ile Glu Lys Thr Ile Ser Lys Ala
325 330 335

Lys Gly Gln Pro Arg Glu Pro Gln Val Tyr Thr Leu Pro Pro Ser Gln
340 345 350

Glu Glu Met Thr Lys Asn Gln Val Ser Leu Thr Cys Leu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Arg Leu Thr Val Asp Lys Ser Arg Trp Gln Glu
405 410 415

Gly Asn Val Phe Ser Cys Ser Val Met His Glu Ala Leu His Asn His
420 425 430

Tyr Thr Gln Lys Ser Leu Ser Leu Ser Leu Gly
435 440

<210> SEQ ID NO 404
<211> LENGTH: 1329
<212> TYPE: DNA
<213> ORGANISM: Artificial
<220> FEATURE:
<223> OTHER INFORMATION: Synthetic

<400> SEQUENCE: 404
caggtgcagc tggtggagtc tgggggaggc gtggtccagc ctgggaggtc cctgagactc 60

```
tcctgtgcag cgtctggatt caccttcagt agctatggca tgcactgggt ccgccaggct    120

ccaggcaagg ggctggagtg ggtggcagtt atatggtatg atggaagtaa taaatactat    180

gcagactccg tgaagggccg attcaccatc tccagagaca attccaagaa cacgctgtat    240

ctgcaaatga acagcctgag agccgaggac acggcggtgt actactgcgc cagaggggcc    300

cctgaatatg tagacgtatg gggtcagggt acaatggtca ccgtctcctc agcttccacc    360

aagggcccct ccgtgttccc tctggcccct tgctcccggt ccacctccga gtctaccgcc    420

gctctgggct gcctcgtgaa ggactacttc cccgagcccg tgaccgtgtc ctggaactct    480

ggcgccctga cctccggcgt gcacaccttc cctgccgtgc tgcagtcctc cggcctgtac    540

tccctgtcca gcgtcgtgac cgtgccctcc tccagcctgg gcaccaagac ctacacctgt    600

aacgtggacc acaagccctc caacaccaaa gtggacaagc gggtggaatc taagtacggc    660

cctccctgcc cttcctgccc tgcccctgag ttcctgggcg gaccttccgt gttcctgttc    720

cctccaaagc ccaaggacac cctgatgatc tcccggaccc ctgaagtgac ctgcgtggtg    780

gtggacgtgt cccaggaaga tcccgaagtc cagttcaatt ggtacgtgga cggcgtggaa    840

gtgcacaacg ccaagaccaa gcccagagag gaacagttca actccaccta ccgggtggtg    900

tccgtgctga ccgtgctgca ccaggactgg ctgaacggca aagagtacaa gtgcaaagtg    960

tccaacaagg gcctgccctc cagcatcgaa aagaccatct ccaaggccaa gggccagccc   1020

cgcgagcccc aagtgtacac cctgcctccc agccaggaag agatgaccaa gaatcaagtg   1080

tccctgactt gtctggtcaa gggcttctac ccctccgata tcgccgtgga gtgggagtcc   1140

aacggccagc ccgagaacaa ctacaagacc acccctcccg tgctggactc cgacggctcc   1200

ttcttcctgt actctcggct gaccgtggac aagtcccggt ggcaggaagg caacgtcttc   1260

tcctgctccg tgatgcacga ggccctgcac aaccactaca cccagaagtc cctgtccctg   1320

tctctgggc                                                           1329
```

<210> SEQ ID NO 405
<211> LENGTH: 8
<212> TYPE: PRT
<213> ORGANISM: Artificial
<220> FEATURE:
<223> OTHER INFORMATION: Synthetic

<400> SEQUENCE: 405

```
Asp Tyr Lys Asp Asp Asp Asp Lys
1               5
```

<210> SEQ ID NO 406
<211> LENGTH: 6
<212> TYPE: PRT
<213> ORGANISM: Artificial
<220> FEATURE:
<223> OTHER INFORMATION: Synthetic

<400> SEQUENCE: 406

```
His His His His His His
1               5
```

<210> SEQ ID NO 407
<211> LENGTH: 9
<212> TYPE: PRT
<213> ORGANISM: Artificial
<220> FEATURE:
<223> OTHER INFORMATION: Synthetic

<400> SEQUENCE: 407

Tyr Pro Tyr Asp Val Pro Asp Tyr Ala
1 5

<210> SEQ ID NO 408
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(8)
<223> OTHER INFORMATION: Xaa can be any naturally occurring amino acid

<400> SEQUENCE: 408

Gly Phe Thr Phe Xaa Xaa Xaa Xaa
1 5

<210> SEQ ID NO 409
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Xaa can be any naturally occurring amino acid

<400> SEQUENCE: 409

Ile Ser Ser Ser Xaa Xaa Tyr Ile
1 5

<210> SEQ ID NO 410
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Xaa can be any naturally occurring amino acid

<400> SEQUENCE: 410

Phe Thr Phe Xaa Xaa Xaa Xaa Met Asn
1 5

<210> SEQ ID NO 411
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 411

Xaa Ile Ser Ser Ser Xaa Xaa Tyr Ile Xaa Tyr Ala Asp Ser Val Lys
1 5 10 15

Gly

<210> SEQ ID NO 412
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(8)
<223> OTHER INFORMATION: Xaa can be any naturally occurring amino acid

<400> SEQUENCE: 412

Gly Phe Thr Phe Xaa Xaa Xaa Xaa
1               5

<210> SEQ ID NO 413
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(6)
<223> OTHER INFORMATION: Xaa can be any naturally occurring amino acid

<400> SEQUENCE: 413

Ile Ser Ser Ser Xaa Xaa Tyr Ile
1               5

<210> SEQ ID NO 414
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Xaa can be any naturally occurring amino acid

<400> SEQUENCE: 414

Phe Thr Phe Xaa Xaa Xaa Xaa Met Asn
1               5

<210> SEQ ID NO 415
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 415

Xaa Ile Ser Ser Ser Xaa Xaa Tyr Ile Xaa Tyr Ala Asp Ser Val Lys
1               5                   10                  15

Gly

<210> SEQ ID NO 416
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 416

Gly Gly Ser Phe Ser Xaa Tyr Xaa
1               5

<210> SEQ ID NO 417
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 417

Ile Asp Xaa Ser Gly Xaa Thr
1               5

<210> SEQ ID NO 418
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 418

Ala Arg Xaa Xaa Xaa Tyr Tyr Xaa Asp Ser Ser Xaa Xaa Xaa Xaa Asp
1               5                   10                  15

Xaa

<210> SEQ ID NO 419
<211> LENGTH: 6
<212> TYPE: PRT

<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 419

Gln Xaa Xaa Ser Xaa Tyr
1               5

<210> SEQ ID NO 420
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 420

Asp Xaa Ser
1

<210> SEQ ID NO 421
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 421

Gln Gln Xaa Xaa Asp Xaa Pro Ile Thr
1               5

<210> SEQ ID NO 422
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 422

Gly Ser Phe Ser Xaa Tyr Xaa Trp Ser
1               5

<210> SEQ ID NO 423
<211> LENGTH: 16

<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 423

Ser Ile Asp Xaa Ser Gly Xaa Thr Xaa Tyr Asn Pro Ser Leu Lys Ser
1               5                   10                  15

<210> SEQ ID NO 424
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 424

Xaa Ala Ser Gln Xaa Xaa Ser Xaa Tyr Leu Xaa
1               5                   10

<210> SEQ ID NO 425
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 425

Asp Xaa Ser Asn Xaa Xaa Thr
1               5

<210> SEQ ID NO 426
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 426

Gly Gly Ser Phe Ser Xaa Tyr Xaa
1               5

<210> SEQ ID NO 427
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 427

Ile Asp Xaa Ser Gly Xaa Thr
1               5

<210> SEQ ID NO 428
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 428

Ala Arg Xaa Xaa Xaa Tyr Tyr Xaa Asp Ser Ser Xaa Xaa Xaa Xaa Asp
1               5                   10                  15

Xaa

<210> SEQ ID NO 429
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 429

Gln Xaa Xaa Ser Xaa Tyr
1 5

<210> SEQ ID NO 430
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 430

Asp Xaa Ser
1

<210> SEQ ID NO 431
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 431

Gln Gln Xaa Xaa Asp Xaa Pro Ile Thr
1 5

<210> SEQ ID NO 432
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 432

Gly Ser Phe Ser Xaa Tyr Xaa Trp Ser
1 5

<210> SEQ ID NO 433
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:

<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 433

Ser Ile Asp Xaa Ser Gly Xaa Thr Xaa Tyr Asn Pro Ser Leu Lys Ser
1 5 10 15

<210> SEQ ID NO 434
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 434

Xaa Ala Ser Gln Xaa Xaa Ser Xaa Tyr Leu Xaa
1 5 10

<210> SEQ ID NO 435
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 435

Asp Xaa Ser Asn Xaa Xaa Thr
1 5

<210> SEQ ID NO 436
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 436

Ile Xaa Xaa Asp Gly Ser Xaa Lys
1 5

<210> SEQ ID NO 437
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 437

Ala Arg Xaa Ala Pro Xaa Xaa Xaa Asp Val
1 5 10

<210> SEQ ID NO 438
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 438

Gln Ser Xaa Ser Ser Tyr
1 5

<210> SEQ ID NO 439
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid

<400> SEQUENCE: 439

Xaa Xaa Ser
1

<210> SEQ ID NO 440
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 440

Gln Gln Xaa Xaa Xaa Xaa Pro Xaa Thr 1 5

<210> SEQ ID NO 441
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 441

Phe Thr Phe Ser Ser Tyr Gly Met Xaa
1 5

<210> SEQ ID NO 442
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 442

Xaa Ile Xaa Xaa Asp Gly Ser Xaa Lys Tyr Tyr Xaa Asp Ser Val Lys
1 5 10 15

Gly

<210> SEQ ID NO 443
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 443

Arg Ala Ser Gln Ser Xaa Ser Ser Tyr Leu Xaa
1 5 10

<210> SEQ ID NO 444
<211> LENGTH: 6
<212> TYPE: PRT
<213> ORGANISM: Artificial
<220> FEATURE:
<223> OTHER INFORMATION: Synthetic
<220> FEATURE:

<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 444

Xaa Ser Ser Xaa Xaa Xaa
1 5

<210> SEQ ID NO 445
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 445

Ile Xaa Xaa Asp Gly Ser Xaa Lys
1 5

<210> SEQ ID NO 446
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 446

Ala Arg Xaa Ala Pro Xaa Xaa Xaa Asp Val
1 5 10

<210> SEQ ID NO 447
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 447

Gln Ser Xaa Ser Ser Tyr
1 5

<210> SEQ ID NO 448
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid

<400> SEQUENCE: 448

Xaa Xaa Ser
1

<210> SEQ ID NO 449
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 449

Gln Gln Xaa Xaa Xaa Xaa Pro Xaa Thr
1               5

<210> SEQ ID NO 450
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 450

Phe Thr Phe Ser Ser Tyr Gly Met Xaa
1               5

<210> SEQ ID NO 451
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 451

Xaa Ile Xaa Xaa Asp Gly Ser Xaa Lys Tyr Tyr Xaa Asp Ser Val Lys
1               5                   10                  15

Gly

<210> SEQ ID NO 452
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 452

Arg Ala Ser Gln Ser Xaa Ser Ser Tyr Leu Xaa
1 5 10

<210> SEQ ID NO 453
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 453

Xaa Ser Ser Xaa Xaa Xaa
1 5

<210> SEQ ID NO 454
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(8)
<223> OTHER INFORMATION: Xaa can be any naturally occurring amino acid

<400> SEQUENCE: 454

Gly Phe Thr Phe Xaa Xaa Xaa Xaa
1 5

<210> SEQ ID NO 455
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Xaa can be any naturally occurring amino acid

<400> SEQUENCE: 455

Ile Xaa Xaa Xaa Xaa Xaa Xaa Xaa
1 5

<210> SEQ ID NO 456
<211> LENGTH: 8

```
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Xaa can be any naturally occurring amino acid

<400> SEQUENCE: 456

Ile Xaa Xaa Xaa Xaa Xaa Xaa Xaa
1               5


<210> SEQ ID NO 457
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 457

Ala Arg Xaa Xaa Xaa Xaa Xaa Xaa Asp Xaa
1               5                   10


<210> SEQ ID NO 458
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 458

Ala Arg Xaa Xaa Xaa Xaa Xaa Xaa Asp Xaa
1               5                   10


<210> SEQ ID NO 459
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid

<400> SEQUENCE: 459

Gln Ser Xaa Ser Ser Xaa Xaa Xaa Xaa Tyr
1               5                   10


<210> SEQ ID NO 460
```

<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 460

Gln Ser Xaa Ser Ser Xaa Tyr
1               5

<210> SEQ ID NO 461
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid

<400> SEQUENCE: 461

Xaa Xaa Ser
1

<210> SEQ ID NO 462
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid

<400> SEQUENCE: 462

Xaa Xaa Ser
1

<210> SEQ ID NO 463
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 463

Gln Gln Xaa Xaa Xaa Xaa Pro Xaa Thr
1               5

<210> SEQ ID NO 464
<211> LENGTH: 9
<212> TYPE: PRT
<213> ORGANISM: Artificial

<220> FEATURE:
<223> OTHER INFORMATION: Synthetic
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 464

Gln Gln Xaa Xaa Xaa Xaa Pro Xaa Thr
1               5

<210> SEQ ID NO 465
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 465

Phe Thr Phe Xaa Xaa Xaa Xaa Met Xaa
1               5

<210> SEQ ID NO 466
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 466

Phe Thr Phe Xaa Xaa Xaa Xaa Met Xaa
1               5

<210> SEQ ID NO 467
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 467

```
Xaa Ile Xaa Xaa Xaa Xaa Xaa Xaa Xaa Xaa Tyr Xaa Asp Ser Val Lys
1               5                   10                  15

Gly


<210> SEQ ID NO 468
<211> LENGTH: 17
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 468

Xaa Ile Xaa Xaa Xaa Xaa Xaa Xaa Xaa Xaa Tyr Xaa Asp Ser Val Lys
1               5                   10                  15

Gly


<210> SEQ ID NO 469
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 469

Ala Arg Xaa Xaa Xaa Xaa Xaa Xaa Xaa Asp Xaa
1               5                   10


<210> SEQ ID NO 470
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 470

Ala Arg Xaa Xaa Xaa Xaa Xaa Xaa Xaa Asp Xaa
1               5                   10


<210> SEQ ID NO 471
<211> LENGTH: 11
<212> TYPE: PRT
```

<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 471

Arg Ala Ser Gln Ser Xaa Ser Ser Tyr Leu Xaa
1 5 10

<210> SEQ ID NO 472
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 472

Arg Ala Ser Gln Ser Xaa Ser Ser Tyr Leu Xaa
1 5 10

<210> SEQ ID NO 473
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid

<400> SEQUENCE: 473

Xaa Ser Xaa Xaa Xaa Xaa
1 5

<210> SEQ ID NO 474
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid

<400> SEQUENCE: 474

Xaa Ser Xaa Xaa Xaa Xaa
1 5

<210> SEQ ID NO 475
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 475

Gln Gln Xaa Xaa Xaa Xaa Pro Xaa Thr
1               5

<210> SEQ ID NO 476
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 476

Gln Gln Xaa Xaa Xaa Xaa Pro Xaa Thr
1               5

<210> SEQ ID NO 477
<211> LENGTH: 26
<212> TYPE: PRT
<213> ORGANISM: Artificial
<220> FEATURE:
<223> OTHER INFORMATION: Synthetic

<400> SEQUENCE: 477

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 478
<211> LENGTH: 26
<212> TYPE: PRT
<213> ORGANISM: Artificial
<220> FEATURE:
<223> OTHER INFORMATION: Synthetic

<400> SEQUENCE: 478

Gln Val Gln Leu Gln Gln Trp Gly Ala Gly Leu Leu Lys Pro Ser Glu
1               5                   10                  15

Thr Leu Ser Leu Thr Cys Ala Val Tyr Gly
            20                  25

<210> SEQ ID NO 479
<211> LENGTH: 26
<212> TYPE: PRT

<213> ORGANISM: Artificial
<220> FEATURE:
<223> OTHER INFORMATION: Synthetic

<400> SEQUENCE: 479

Glu Val Gln Leu Val Glu Ser Gly Gly Gly Leu Val Lys Pro Gly Gly
1 5 10 15

Ser Leu Arg Leu Ser Cys Ala Ala Ser Gly
20 25

<210> SEQ ID NO 480
<211> LENGTH: 26
<212> TYPE: PRT
<213> ORGANISM: Artificial
<220> FEATURE:
<223> OTHER INFORMATION: Synthetic

<400> SEQUENCE: 480

Glu Val Gln Leu Val Glu Ser Gly Gly Gly Leu Val Gln Pro Gly Gly
1 5 10 15

Ser Leu Arg Leu Ser Cys Ala Ala Ser Gly
20 25

<210> SEQ ID NO 481
<211> LENGTH: 26
<212> TYPE: PRT
<213> ORGANISM: Artificial
<220> FEATURE:
<223> OTHER INFORMATION: Synthetic

<400> SEQUENCE: 481

Gln Val Gln Leu Val Glu Ser Gly Gly Gly Val Val Gln Pro Gly Arg
1 5 10 15

Ser Leu Arg Leu Ser Cys Ala Ala Ser Gly
20 25

<210> SEQ ID NO 482
<211> LENGTH: 26
<212> TYPE: PRT
<213> ORGANISM: Artificial
<220> FEATURE:
<223> OTHER INFORMATION: Synthetic

<400> SEQUENCE: 482

Gln Val Gln Leu Gln Gln Trp Gly Ala Gly Leu Leu Lys Pro Ser Glu
1 5 10 15

Thr Leu Ser Leu Thr Cys Ala Val Tyr Gly
20 25

<210> SEQ ID NO 483
<211> LENGTH: 9
<212> TYPE: PRT
<213> ORGANISM: Artificial
<220> FEATURE:
<223> OTHER INFORMATION: Synthetic

<400> SEQUENCE: 483

Gly Thr Phe Val Gly Tyr Ala Ile Ser
1 5

<210> SEQ ID NO 484
<211> LENGTH: 9
<212> TYPE: PRT
<213> ORGANISM: Artificial
<220> FEATURE:

<223> OTHER INFORMATION: Synthetic

<400> SEQUENCE: 484

Gly Thr Phe Ser Ala Tyr Ala Ile Ser
1 5

<210> SEQ ID NO 485
<211> LENGTH: 9
<212> TYPE: PRT
<213> ORGANISM: Artificial
<220> FEATURE:
<223> OTHER INFORMATION: Synthetic

<400> SEQUENCE: 485

Gly Thr Phe Glu Ser Tyr Thr Ile Ser
1 5

<210> SEQ ID NO 486
<211> LENGTH: 9
<212> TYPE: PRT
<213> ORGANISM: Artificial
<220> FEATURE:
<223> OTHER INFORMATION: Synthetic

<400> SEQUENCE: 486

Gly Thr Phe Ser Ser Tyr Ala Ile Ser
1 5

<210> SEQ ID NO 487
<211> LENGTH: 9
<212> TYPE: PRT
<213> ORGANISM: Artificial
<220> FEATURE:
<223> OTHER INFORMATION: Synthetic

<400> SEQUENCE: 487

Gly Ser Phe Ser Glu Tyr Tyr Trp Ala
1 5

<210> SEQ ID NO 488
<211> LENGTH: 9
<212> TYPE: PRT
<213> ORGANISM: Artificial
<220> FEATURE:
<223> OTHER INFORMATION: Synthetic

<400> SEQUENCE: 488

Gly Ser Phe Ser Arg Tyr Tyr Trp Ser
1 5

<210> SEQ ID NO 489
<211> LENGTH: 9
<212> TYPE: PRT
<213> ORGANISM: Artificial
<220> FEATURE:
<223> OTHER INFORMATION: Synthetic

<400> SEQUENCE: 489

Gly Ser Phe Ser Gly Tyr Tyr Trp Ser
1 5

<210> SEQ ID NO 490
<211> LENGTH: 9
<212> TYPE: PRT
<213> ORGANISM: Artificial
<220> FEATURE:
<223> OTHER INFORMATION: Synthetic

<400> SEQUENCE: 490

Phe Thr Phe Ser Ser Tyr Ser Met Asn
1               5

<210> SEQ ID NO 491
<211> LENGTH: 9
<212> TYPE: PRT
<213> ORGANISM: Artificial
<220> FEATURE:
<223> OTHER INFORMATION: Synthetic

<400> SEQUENCE: 491

Phe Thr Phe Arg Ser Tyr Gly Met Asn
1               5

<210> SEQ ID NO 492
<211> LENGTH: 9
<212> TYPE: PRT
<213> ORGANISM: Artificial
<220> FEATURE:
<223> OTHER INFORMATION: Synthetic

<400> SEQUENCE: 492

Phe Thr Phe Ser Arg Thr Gly Met Asn
1               5

<210> SEQ ID NO 493
<211> LENGTH: 9
<212> TYPE: PRT
<213> ORGANISM: Artificial
<220> FEATURE:
<223> OTHER INFORMATION: Synthetic

<400> SEQUENCE: 493

Phe Thr Phe Ser Arg Tyr Gly Met Asn
1               5

<210> SEQ ID NO 494
<211> LENGTH: 9
<212> TYPE: PRT
<213> ORGANISM: Artificial
<220> FEATURE:
<223> OTHER INFORMATION: Synthetic

<400> SEQUENCE: 494

Phe Thr Phe Ala Ser Tyr Gly Met Asn
1               5

<210> SEQ ID NO 495
<211> LENGTH: 9
<212> TYPE: PRT
<213> ORGANISM: Artificial
<220> FEATURE:
<223> OTHER INFORMATION: Synthetic

<400> SEQUENCE: 495

Phe Thr Phe Arg Ser Tyr Gly Met Asn
1               5

<210> SEQ ID NO 496
<211> LENGTH: 9
<212> TYPE: PRT
<213> ORGANISM: Artificial
<220> FEATURE:
<223> OTHER INFORMATION: Synthetic

<400> SEQUENCE: 496

Phe Thr Phe Ser Ser Tyr Gly Met Ser
1 5

<210> SEQ ID NO 497
<211> LENGTH: 9
<212> TYPE: PRT
<213> ORGANISM: Artificial
<220> FEATURE:
<223> OTHER INFORMATION: Synthetic

<400> SEQUENCE: 497

Phe Thr Phe Ser Ser Tyr Gly Met His
1 5

<210> SEQ ID NO 498
<211> LENGTH: 9
<212> TYPE: PRT
<213> ORGANISM: Artificial
<220> FEATURE:
<223> OTHER INFORMATION: Synthetic

<400> SEQUENCE: 498

Gly Ser Phe Ser Asp Tyr Glu Trp Ser
1 5

<210> SEQ ID NO 499
<211> LENGTH: 14
<212> TYPE: PRT
<213> ORGANISM: Artificial
<220> FEATURE:
<223> OTHER INFORMATION: Synthetic

<400> SEQUENCE: 499

Trp Val Arg Gln Ala Pro Gly Gln Gly Leu Glu Trp Met Gly
1 5 10

<210> SEQ ID NO 500
<211> LENGTH: 14
<212> TYPE: PRT
<213> ORGANISM: Artificial
<220> FEATURE:
<223> OTHER INFORMATION: Synthetic

<400> SEQUENCE: 500

Trp Ile Arg Gln Pro Pro Gly Lys Gly Leu Glu Trp Ile Gly
1 5 10

<210> SEQ ID NO 501
<211> LENGTH: 14
<212> TYPE: PRT
<213> ORGANISM: Artificial
<220> FEATURE:
<223> OTHER INFORMATION: Synthetic

<400> SEQUENCE: 501

Trp Val Arg Gln Ala Pro Gly Lys Gly Leu Glu Trp Val Ser
1 5 10

<210> SEQ ID NO 502
<211> LENGTH: 14
<212> TYPE: PRT
<213> ORGANISM: Artificial
<220> FEATURE:
<223> OTHER INFORMATION: Synthetic

<400> SEQUENCE: 502

Trp Val Arg Gln Ala Pro Gly Lys Gly Leu Glu Trp Val Ala
1 5 10

<210> SEQ ID NO 503
<211> LENGTH: 14
<212> TYPE: PRT
<213> ORGANISM: Artificial
<220> FEATURE:
<223> OTHER INFORMATION: Synthetic

<400> SEQUENCE: 503

Trp Ile Arg Gln Pro Pro Gly Lys Gly Leu Glu Trp Ile Gly
1 5 10

<210> SEQ ID NO 504
<211> LENGTH: 17
<212> TYPE: PRT
<213> ORGANISM: Artificial
<220> FEATURE:
<223> OTHER INFORMATION: Synthetic

<400> SEQUENCE: 504

Gly Ile Ile Pro Ile Phe Gly Ile Ala Asn Tyr Ala Gln Lys Phe Gln
1 5 10 15

Gly

<210> SEQ ID NO 505
<211> LENGTH: 17
<212> TYPE: PRT
<213> ORGANISM: Artificial
<220> FEATURE:
<223> OTHER INFORMATION: Synthetic

<400> SEQUENCE: 505

Gly Ile Ile Pro Ile Phe Gly Thr Ala Asn Tyr Ala Gln Lys Phe Gln
1 5 10 15

Gly

<210> SEQ ID NO 506
<211> LENGTH: 17
<212> TYPE: PRT
<213> ORGANISM: Artificial
<220> FEATURE:
<223> OTHER INFORMATION: Synthetic

<400> SEQUENCE: 506

Gly Ile Ala Pro Ile Phe Gly Thr Ala His Tyr Ala Gln Lys Phe Gln
1 5 10 15

Gly

<210> SEQ ID NO 507
<211> LENGTH: 17
<212> TYPE: PRT
<213> ORGANISM: Artificial
<220> FEATURE:
<223> OTHER INFORMATION: Synthetic

<400> SEQUENCE: 507

Gly Ile Ile Pro Ile Phe Gly Thr Ala Asn Tyr Ala Gln Lys Phe Gln
1 5 10 15

Gly

<210> SEQ ID NO 508

<211> LENGTH: 16
<212> TYPE: PRT
<213> ORGANISM: Artificial
<220> FEATURE:
<223> OTHER INFORMATION: Synthetic

<400> SEQUENCE: 508

Glu Ile Asp Glu Val Gly Ser Thr Asn Tyr Asn Pro Ser Leu Lys Ser
1 5 10 15

<210> SEQ ID NO 509
<211> LENGTH: 16
<212> TYPE: PRT
<213> ORGANISM: Artificial
<220> FEATURE:
<223> OTHER INFORMATION: Synthetic

<400> SEQUENCE: 509

Ser Ile Asp Tyr Ser Gly Ser Thr Glu Tyr Asn Pro Ser Leu Lys Ser
1 5 10 15

<210> SEQ ID NO 510
<211> LENGTH: 16
<212> TYPE: PRT
<213> ORGANISM: Artificial
<220> FEATURE:
<223> OTHER INFORMATION: Synthetic

<400> SEQUENCE: 510

Glu Ile Asp Val Asp Gly Ser Thr Asn Tyr Asn Pro Ser Leu Lys Ser
1 5 10 15

<210> SEQ ID NO 511
<211> LENGTH: 17
<212> TYPE: PRT
<213> ORGANISM: Artificial
<220> FEATURE:
<223> OTHER INFORMATION: Synthetic

<400> SEQUENCE: 511

Ser Ile Ser Ser Ser Ser Ser Tyr Ile Tyr Tyr Ala Asp Ser Val Lys
1 5 10 15

Gly

<210> SEQ ID NO 512
<211> LENGTH: 17
<212> TYPE: PRT
<213> ORGANISM: Artificial
<220> FEATURE:
<223> OTHER INFORMATION: Synthetic

<400> SEQUENCE: 512

Ser Ile Ser Ser Ser Ser Ala Tyr Ile Leu Tyr Ala Asp Ser Val Lys
1 5 10 15

Gly

<210> SEQ ID NO 513
<211> LENGTH: 17
<212> TYPE: PRT
<213> ORGANISM: Artificial
<220> FEATURE:
<223> OTHER INFORMATION: Synthetic

<400> SEQUENCE: 513

Gly Ile Ser Ser Ser Gly Ser Tyr Ile Tyr Tyr Ala Asp Ser Val Lys
1 5 10 15

Gly

<210> SEQ ID NO 514
<211> LENGTH: 17
<212> TYPE: PRT
<213> ORGANISM: Artificial
<220> FEATURE:
<223> OTHER INFORMATION: Synthetic

<400> SEQUENCE: 514

Asn Ile Lys Gln Asp Gly Ser Glu Lys Tyr Tyr Val Asp Ser Val Lys
1 5 10 15

Gly

<210> SEQ ID NO 515
<211> LENGTH: 17
<212> TYPE: PRT
<213> ORGANISM: Artificial
<220> FEATURE:
<223> OTHER INFORMATION: Synthetic

<400> SEQUENCE: 515

Val Ile Trp Tyr Asp Gly Ser Asn Lys Tyr Tyr Ala Asp Ser Val Lys
1 5 10 15

Gly

<210> SEQ ID NO 516
<211> LENGTH: 16
<212> TYPE: PRT
<213> ORGANISM: Artificial
<220> FEATURE:
<223> OTHER INFORMATION: Synthetic

<400> SEQUENCE: 516

Glu Ile Asp Trp Ser Gly Ile Thr Asn Tyr Asn Pro Ser Leu Lys Ser
1 5 10 15

<210> SEQ ID NO 517
<211> LENGTH: 30
<212> TYPE: PRT
<213> ORGANISM: Artificial
<220> FEATURE:
<223> OTHER INFORMATION: Synthetic

<400> SEQUENCE: 517

Arg Val Thr Ile Thr Ala Asp Glu Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 518
<211> LENGTH: 30
<212> TYPE: PRT
<213> ORGANISM: Artificial
<220> FEATURE:
<223> OTHER INFORMATION: Synthetic

<400> SEQUENCE: 518

Arg Val Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys
20 25 30

<210> SEQ ID NO 519
<211> LENGTH: 30
<212> TYPE: PRT
<213> ORGANISM: Artificial
<220> FEATURE:
<223> OTHER INFORMATION: Synthetic

<400> SEQUENCE: 519

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 520
<211> LENGTH: 30
<212> TYPE: PRT
<213> ORGANISM: Artificial
<220> FEATURE:
<223> OTHER INFORMATION: Synthetic

<400> SEQUENCE: 520

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 521
<211> LENGTH: 30
<212> TYPE: PRT
<213> ORGANISM: Artificial
<220> FEATURE:
<223> OTHER INFORMATION: Synthetic

<400> SEQUENCE: 521

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 522
<211> LENGTH: 17
<212> TYPE: PRT
<213> ORGANISM: Artificial
<220> FEATURE:
<223> OTHER INFORMATION: Synthetic

<400> SEQUENCE: 522

Ala Arg Ser Tyr Tyr Ser Ser Arg Trp His Tyr Tyr Tyr Tyr Met Asp
1               5                   10                  15

Val

<210> SEQ ID NO 523
<211> LENGTH: 17
<212> TYPE: PRT
<213> ORGANISM: Artificial
<220> FEATURE:
<223> OTHER INFORMATION: Synthetic

<400> SEQUENCE: 523

Ala Arg Leu Gly Gly Arg Gly Tyr Ala Asp Glu Gly Trp Tyr Phe Asp
1               5                   10                  15

Leu

<210> SEQ ID NO 524

<211> LENGTH: 17
<212> TYPE: PRT
<213> ORGANISM: Artificial
<220> FEATURE:
<223> OTHER INFORMATION: Synthetic

<400> SEQUENCE: 524

Ala Arg Leu Pro Met Tyr Tyr Tyr Asp Ser Ser Asp Leu Pro Met Asp
1 5 10 15

Val

<210> SEQ ID NO 525
<211> LENGTH: 16
<212> TYPE: PRT
<213> ORGANISM: Artificial
<220> FEATURE:
<223> OTHER INFORMATION: Synthetic

<400> SEQUENCE: 525

Ala Arg Asp Gly Val Tyr Tyr Asp Ser Ser Asp Leu Gly Phe Asp Ile
1 5 10 15

<210> SEQ ID NO 526
<211> LENGTH: 14
<212> TYPE: PRT
<213> ORGANISM: Artificial
<220> FEATURE:
<223> OTHER INFORMATION: Synthetic

<400> SEQUENCE: 526

Ala Arg Asp Gly Tyr Tyr Tyr Asp Thr Ser Pro Tyr Asp Val
1 5 10

<210> SEQ ID NO 527
<211> LENGTH: 19
<212> TYPE: PRT
<213> ORGANISM: Artificial
<220> FEATURE:
<223> OTHER INFORMATION: Synthetic

<400> SEQUENCE: 527

Ala Arg Asp Gly Gly Arg Thr Ser Tyr Thr Ala Thr Ala His Asn Trp
1 5 10 15

Phe Asp Pro

<210> SEQ ID NO 528
<211> LENGTH: 15
<212> TYPE: PRT
<213> ORGANISM: Artificial
<220> FEATURE:
<223> OTHER INFORMATION: Synthetic

<400> SEQUENCE: 528

Ala Arg Asp Ala Pro Trp Asp Ile Tyr Asp Tyr Tyr Met Asp Val
1 5 10 15

<210> SEQ ID NO 529
<211> LENGTH: 10
<212> TYPE: PRT
<213> ORGANISM: Artificial
<220> FEATURE:
<223> OTHER INFORMATION: Synthetic

<400> SEQUENCE: 529

Ala Arg Gly Ala Pro Glu Tyr Val Asp Val
1 5 10

<210> SEQ ID NO 530
<211> LENGTH: 19
<212> TYPE: PRT
<213> ORGANISM: Artificial
<220> FEATURE:
<223> OTHER INFORMATION: Synthetic

<400> SEQUENCE: 530

Ala Arg Leu Pro Met Tyr Tyr Tyr Asp Ser Ser Val Ser Thr Gly Ser
1 5 10 15

Val Asp Val

<210> SEQ ID NO 531
<211> LENGTH: 11
<212> TYPE: PRT
<213> ORGANISM: Artificial
<220> FEATURE:
<223> OTHER INFORMATION: Synthetic

<400> SEQUENCE: 531

Trp Gly Lys Gly Thr Thr Val Thr Val Ser Ser
1 5 10

<210> SEQ ID NO 532
<211> LENGTH: 11
<212> TYPE: PRT
<213> ORGANISM: Artificial
<220> FEATURE:
<223> OTHER INFORMATION: Synthetic

<400> SEQUENCE: 532

Trp Gly Arg Gly Thr Leu Val Thr Val Ser Ser
1 5 10

<210> SEQ ID NO 533
<211> LENGTH: 11
<212> TYPE: PRT
<213> ORGANISM: Artificial
<220> FEATURE:
<223> OTHER INFORMATION: Synthetic

<400> SEQUENCE: 533

Trp Gly Gln Gly Thr Thr Val Thr Val Ser Ser
1 5 10

<210> SEQ ID NO 534
<211> LENGTH: 11
<212> TYPE: PRT
<213> ORGANISM: Artificial
<220> FEATURE:
<223> OTHER INFORMATION: Synthetic

<400> SEQUENCE: 534

Trp Gly Gln Gly Thr Met Val Thr Val Ser Ser
1 5 10

<210> SEQ ID NO 535
<211> LENGTH: 11
<212> TYPE: PRT
<213> ORGANISM: Artificial
<220> FEATURE:
<223> OTHER INFORMATION: Synthetic

<400> SEQUENCE: 535

Trp Gly Gln Gly Thr Leu Val Thr Val Ser Ser 1 5 10

<210> SEQ ID NO 536
<211> LENGTH: 11
<212> TYPE: PRT
<213> ORGANISM: Artificial
<220> FEATURE:
<223> OTHER INFORMATION: Synthetic

<400> SEQUENCE: 536

Trp Gly Lys Gly Thr Thr Val Thr Val Ser Ser
1 5 10

<210> SEQ ID NO 537
<211> LENGTH: 11
<212> TYPE: PRT
<213> ORGANISM: Artificial
<220> FEATURE:
<223> OTHER INFORMATION: Synthetic

<400> SEQUENCE: 537

Trp Gly Gln Gly Thr Met Val Thr Val Ser Ser
1 5 10

<210> SEQ ID NO 538
<211> LENGTH: 23
<212> TYPE: PRT
<213> ORGANISM: Artificial
<220> FEATURE:
<223> OTHER INFORMATION: Synthetic

<400> SEQUENCE: 538

Asp Ile Gln Met Thr Gln Ser Pro Ser Ser Val Ser Ala Ser Val Gly
1 5 10 15

Asp Arg Val Thr Ile Thr Cys
20

<210> SEQ ID NO 539
<211> LENGTH: 23
<212> TYPE: PRT
<213> ORGANISM: Artificial
<220> FEATURE:
<223> OTHER INFORMATION: Synthetic

<400> SEQUENCE: 539

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 540
<211> LENGTH: 23
<212> TYPE: PRT
<213> ORGANISM: Artificial
<220> FEATURE:
<223> OTHER INFORMATION: Synthetic

<400> SEQUENCE: 540

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 541
<211> LENGTH: 23

-continued

<212> TYPE: PRT
<213> ORGANISM: Artificial
<220> FEATURE:
<223> OTHER INFORMATION: Synthetic

<400> SEQUENCE: 541

```
Glu Ile Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 542
<211> LENGTH: 23
<212> TYPE: PRT
<213> ORGANISM: Artificial
<220> FEATURE:
<223> OTHER INFORMATION: Synthetic

<400> SEQUENCE: 542

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 543
<211> LENGTH: 23
<212> TYPE: PRT
<213> ORGANISM: Artificial
<220> FEATURE:
<223> OTHER INFORMATION: Synthetic

<400> SEQUENCE: 543

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 544
<211> LENGTH: 23
<212> TYPE: PRT
<213> ORGANISM: Artificial
<220> FEATURE:
<223> OTHER INFORMATION: Synthetic

<400> SEQUENCE: 544

```
Glu Ile Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 545
<211> LENGTH: 11
<212> TYPE: PRT
<213> ORGANISM: Artificial
<220> FEATURE:
<223> OTHER INFORMATION: Synthetic

<400> SEQUENCE: 545

```
Arg Ala Ser Gln Gly Ile Ser Ser Trp Leu Ala
1               5                   10
```

<210> SEQ ID NO 546
<211> LENGTH: 12
<212> TYPE: PRT
<213> ORGANISM: Artificial

<220> FEATURE:
<223> OTHER INFORMATION: Synthetic

<400> SEQUENCE: 546

Arg Ala Ser Gln Ser Val Ser Ser Ser Tyr Leu Ala
1 5 10

<210> SEQ ID NO 547
<211> LENGTH: 11
<212> TYPE: PRT
<213> ORGANISM: Artificial
<220> FEATURE:
<223> OTHER INFORMATION: Synthetic

<400> SEQUENCE: 547

Gln Ala Ser Gln Asp Ile Ser Asn Tyr Leu Asn
1 5 10

<210> SEQ ID NO 548
<211> LENGTH: 11
<212> TYPE: PRT
<213> ORGANISM: Artificial
<220> FEATURE:
<223> OTHER INFORMATION: Synthetic

<400> SEQUENCE: 548

Arg Ala Ser Gln Ser Val Ser Ser Tyr Leu Ala
1 5 10

<210> SEQ ID NO 549
<211> LENGTH: 17
<212> TYPE: PRT
<213> ORGANISM: Artificial
<220> FEATURE:
<223> OTHER INFORMATION: Synthetic

<400> SEQUENCE: 549

Lys Ser Ser Gln Ser Val Leu Phe Ser Ser Asn Asn Lys Asn Tyr Leu
1 5 10 15

Ala

<210> SEQ ID NO 550
<211> LENGTH: 11
<212> TYPE: PRT
<213> ORGANISM: Artificial
<220> FEATURE:
<223> OTHER INFORMATION: Synthetic

<400> SEQUENCE: 550

Arg Ala Ser Gln Ser Ile Ser Ser Tyr Leu Asn
1 5 10

<210> SEQ ID NO 551
<211> LENGTH: 11
<212> TYPE: PRT
<213> ORGANISM: Artificial
<220> FEATURE:
<223> OTHER INFORMATION: Synthetic

<400> SEQUENCE: 551

Arg Ala Ser Gln Ser Val Ser Ser Tyr Leu Ala
1 5 10

<210> SEQ ID NO 552
<211> LENGTH: 15
<212> TYPE: PRT

<213> ORGANISM: Artificial
<220> FEATURE:
<223> OTHER INFORMATION: Synthetic

<400> SEQUENCE: 552

Trp Tyr Gln Gln Lys Pro Gly Lys Ala Pro Lys Leu Leu Ile Tyr
1 5 10 15

<210> SEQ ID NO 553
<211> LENGTH: 15
<212> TYPE: PRT
<213> ORGANISM: Artificial
<220> FEATURE:
<223> OTHER INFORMATION: Synthetic

<400> SEQUENCE: 553

Trp Tyr Gln Gln Lys Pro Gly Gln Ala Pro Arg Leu Leu Ile Tyr
1 5 10 15

<210> SEQ ID NO 554
<211> LENGTH: 15
<212> TYPE: PRT
<213> ORGANISM: Artificial
<220> FEATURE:
<223> OTHER INFORMATION: Synthetic

<400> SEQUENCE: 554

Trp Tyr Gln Gln Lys Pro Gly Lys Ala Pro Lys Leu Leu Ile Tyr
1 5 10 15

<210> SEQ ID NO 555
<211> LENGTH: 15
<212> TYPE: PRT
<213> ORGANISM: Artificial
<220> FEATURE:
<223> OTHER INFORMATION: Synthetic

<400> SEQUENCE: 555

Trp Tyr Gln Gln Lys Pro Gly Gln Ala Pro Arg Leu Leu Ile Tyr
1 5 10 15

<210> SEQ ID NO 556
<211> LENGTH: 15
<212> TYPE: PRT
<213> ORGANISM: Artificial
<220> FEATURE:
<223> OTHER INFORMATION: Synthetic

<400> SEQUENCE: 556

Trp Tyr Gln Gln Lys Pro Gly Gln Pro Pro Lys Leu Leu Ile Tyr
1 5 10 15

<210> SEQ ID NO 557
<211> LENGTH: 15
<212> TYPE: PRT
<213> ORGANISM: Artificial
<220> FEATURE:
<223> OTHER INFORMATION: Synthetic

<400> SEQUENCE: 557

Trp Tyr Gln Gln Lys Pro Gly Lys Ala Pro Lys Leu Leu Ile Tyr
1 5 10 15

<210> SEQ ID NO 558
<211> LENGTH: 15
<212> TYPE: PRT
<213> ORGANISM: Artificial

<220> FEATURE:
<223> OTHER INFORMATION: Synthetic

<400> SEQUENCE: 558

Trp Tyr Gln Gln Lys Pro Gly Gln Ala Pro Arg Leu Leu Ile Tyr
1 5 10 15

<210> SEQ ID NO 559
<211> LENGTH: 7
<212> TYPE: PRT
<213> ORGANISM: Artificial
<220> FEATURE:
<223> OTHER INFORMATION: Synthetic

<400> SEQUENCE: 559

Ala Ala Ser Asn Leu Gln Ser
1 5

<210> SEQ ID NO 560
<211> LENGTH: 7
<212> TYPE: PRT
<213> ORGANISM: Artificial
<220> FEATURE:
<223> OTHER INFORMATION: Synthetic

<400> SEQUENCE: 560

Gly Ala Ser Ser Arg Ala Thr
1 5

<210> SEQ ID NO 561
<211> LENGTH: 7
<212> TYPE: PRT
<213> ORGANISM: Artificial
<220> FEATURE:
<223> OTHER INFORMATION: Synthetic

<400> SEQUENCE: 561

Asp Ala Ser Asn Leu Ala Thr
1 5

<210> SEQ ID NO 562
<211> LENGTH: 7
<212> TYPE: PRT
<213> ORGANISM: Artificial
<220> FEATURE:
<223> OTHER INFORMATION: Synthetic

<400> SEQUENCE: 562

Asp Ala Ser Asn Leu Glu Thr
1 5

<210> SEQ ID NO 563
<211> LENGTH: 7
<212> TYPE: PRT
<213> ORGANISM: Artificial
<220> FEATURE:
<223> OTHER INFORMATION: Synthetic

<400> SEQUENCE: 563

Asp Ala Ser Asn Arg Ala Thr
1 5

<210> SEQ ID NO 564
<211> LENGTH: 7
<212> TYPE: PRT
<213> ORGANISM: Artificial
<220> FEATURE:

<223> OTHER INFORMATION: Synthetic

<400> SEQUENCE: 564

Trp Ala Ser Thr Arg Glu Ser
1 5

<210> SEQ ID NO 565
<211> LENGTH: 7
<212> TYPE: PRT
<213> ORGANISM: Artificial
<220> FEATURE:
<223> OTHER INFORMATION: Synthetic

<400> SEQUENCE: 565

Ala Ala Ser Ser Leu Gln Ser
1 5

<210> SEQ ID NO 566
<211> LENGTH: 7
<212> TYPE: PRT
<213> ORGANISM: Artificial
<220> FEATURE:
<223> OTHER INFORMATION: Synthetic

<400> SEQUENCE: 566

Asp Ser Ser Asn Arg Ala Thr
1 5

<210> SEQ ID NO 567
<211> LENGTH: 32
<212> TYPE: PRT
<213> ORGANISM: Artificial
<220> FEATURE:
<223> OTHER INFORMATION: Synthetic

<400> SEQUENCE: 567

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 568
<211> LENGTH: 32
<212> TYPE: PRT
<213> ORGANISM: Artificial
<220> FEATURE:
<223> OTHER INFORMATION: Synthetic

<400> SEQUENCE: 568

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 569
<211> LENGTH: 32
<212> TYPE: PRT
<213> ORGANISM: Artificial
<220> FEATURE:
<223> OTHER INFORMATION: Synthetic

<400> SEQUENCE: 569

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys 20 25 30

<210> SEQ ID NO 570
<211> LENGTH: 32
<212> TYPE: PRT
<213> ORGANISM: Artificial
<220> FEATURE:
<223> OTHER INFORMATION: Synthetic

<400> SEQUENCE: 570

Gly Ile Pro Ala Arg Phe Ser Gly Ser Gly Ser Gly Thr Asp Phe Thr
1 5 10 15

Leu Thr Ile Ser Ser Leu Glu Pro Glu Asp Phe Ala Val Tyr Tyr Cys
20 25 30

<210> SEQ ID NO 571
<211> LENGTH: 32
<212> TYPE: PRT
<213> ORGANISM: Artificial
<220> FEATURE:
<223> OTHER INFORMATION: Synthetic

<400> SEQUENCE: 571

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 572
<211> LENGTH: 32
<212> TYPE: PRT
<213> ORGANISM: Artificial
<220> FEATURE:
<223> OTHER INFORMATION: Synthetic

<400> SEQUENCE: 572

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 573
<211> LENGTH: 32
<212> TYPE: PRT
<213> ORGANISM: Artificial
<220> FEATURE:
<223> OTHER INFORMATION: Synthetic

<400> SEQUENCE: 573

Gly Ile Pro Ala Arg Phe Ser Gly Ser Gly Ser Gly Thr Asp Phe Thr
1 5 10 15

Leu Thr Ile Ser Ser Leu Glu Pro Glu Asp Phe Ala Val Tyr Tyr Cys
20 25 30

<210> SEQ ID NO 574
<211> LENGTH: 9
<212> TYPE: PRT
<213> ORGANISM: Artificial
<220> FEATURE:
<223> OTHER INFORMATION: Synthetic

<400> SEQUENCE: 574

Gln Gln Ala Asp Asp Leu Pro Leu Thr
1 5

<210> SEQ ID NO 575
<211> LENGTH: 9
<212> TYPE: PRT
<213> ORGANISM: Artificial
<220> FEATURE:
<223> OTHER INFORMATION: Synthetic

<400> SEQUENCE: 575

Gln Gln Tyr Tyr Gly Ser Pro Ile Thr
1 5

<210> SEQ ID NO 576
<211> LENGTH: 9
<212> TYPE: PRT
<213> ORGANISM: Artificial
<220> FEATURE:
<223> OTHER INFORMATION: Synthetic

<400> SEQUENCE: 576

Gln Gln Tyr Asp Thr Leu Pro Leu Thr
1 5

<210> SEQ ID NO 577
<211> LENGTH: 9
<212> TYPE: PRT
<213> ORGANISM: Artificial
<220> FEATURE:
<223> OTHER INFORMATION: Synthetic

<400> SEQUENCE: 577

Gln Gln Tyr Asp Asp Leu Pro Ile Thr
1 5

<210> SEQ ID NO 578
<211> LENGTH: 9
<212> TYPE: PRT
<213> ORGANISM: Artificial
<220> FEATURE:
<223> OTHER INFORMATION: Synthetic

<400> SEQUENCE: 578

Gln Gln Arg Asp Ser Phe Pro Leu Thr
1 5

<210> SEQ ID NO 579
<211> LENGTH: 9
<212> TYPE: PRT
<213> ORGANISM: Artificial
<220> FEATURE:
<223> OTHER INFORMATION: Synthetic

<400> SEQUENCE: 579

Gln Gln His Ala Ser Ala Pro Pro Thr
1 5

<210> SEQ ID NO 580
<211> LENGTH: 9
<212> TYPE: PRT
<213> ORGANISM: Artificial
<220> FEATURE:
<223> OTHER INFORMATION: Synthetic

<400> SEQUENCE: 580

Gln Gln Ser Tyr Val Pro Pro Trp Thr
1 5

<210> SEQ ID NO 581
<211> LENGTH: 8
<212> TYPE: PRT
<213> ORGANISM: Artificial
<220> FEATURE:
<223> OTHER INFORMATION: Synthetic

<400> SEQUENCE: 581

Gln Gln Tyr Ser Leu Tyr Pro Thr
1               5

<210> SEQ ID NO 582
<211> LENGTH: 9
<212> TYPE: PRT
<213> ORGANISM: Artificial
<220> FEATURE:
<223> OTHER INFORMATION: Synthetic

<400> SEQUENCE: 582

Gln Gln Asp Ser Asp His Pro Ile Thr
1               5

<210> SEQ ID NO 583
<211> LENGTH: 10
<212> TYPE: PRT
<213> ORGANISM: Artificial
<220> FEATURE:
<223> OTHER INFORMATION: Synthetic

<400> SEQUENCE: 583

Phe Gly Gly Gly Thr Lys Val Glu Ile Lys
1               5                   10

<210> SEQ ID NO 584
<211> LENGTH: 25
<212> TYPE: PRT
<213> ORGANISM: Artificial
<220> FEATURE:
<223> OTHER INFORMATION: Synthetic

<400> SEQUENCE: 584

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 585
<211> LENGTH: 25
<212> TYPE: PRT
<213> ORGANISM: Artificial
<220> FEATURE:
<223> OTHER INFORMATION: Synthetic

<400> SEQUENCE: 585

Gln Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 586
<211> LENGTH: 25
<212> TYPE: PRT
<213> ORGANISM: Artificial
<220> FEATURE:
<223> OTHER INFORMATION: Synthetic

<400> SEQUENCE: 586

Glu Val Gln Leu Val Glu Ser Gly Gly Gly Leu Val Lys Pro Gly Gly
1 5 10 15

Ser Leu Arg Leu Ser Cys Ala Ala Ser
20 25

<210> SEQ ID NO 587
<211> LENGTH: 25
<212> TYPE: PRT
<213> ORGANISM: Artificial
<220> FEATURE:
<223> OTHER INFORMATION: Synthetic

<400> SEQUENCE: 587

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 588
<211> LENGTH: 25
<212> TYPE: PRT
<213> ORGANISM: Artificial
<220> FEATURE:
<223> OTHER INFORMATION: Synthetic

<400> SEQUENCE: 588

Gln Val Gln Leu Val Glu Ser Gly Gly Gly Val Val Gln Pro Gly Arg
1 5 10 15

Ser Leu Arg Leu Ser Cys Ala Ala Ser
20 25

<210> SEQ ID NO 589
<211> LENGTH: 25
<212> TYPE: PRT
<213> ORGANISM: Artificial
<220> FEATURE:
<223> OTHER INFORMATION: Synthetic

<400> SEQUENCE: 589

Gln Val Gln Leu Gln Gln Trp Gly Ala Gly Leu Leu Lys Pro Ser Glu
1 5 10 15

Thr Leu Ser Leu Thr Cys Ala Val Tyr
20 25

<210> SEQ ID NO 590
<211> LENGTH: 8
<212> TYPE: PRT
<213> ORGANISM: Artificial
<220> FEATURE:
<223> OTHER INFORMATION: Synthetic

<400> SEQUENCE: 590

Gly Gly Thr Phe Val Gly Tyr Ala
1 5

<210> SEQ ID NO 591
<211> LENGTH: 8
<212> TYPE: PRT
<213> ORGANISM: Artificial
<220> FEATURE:
<223> OTHER INFORMATION: Synthetic

<400> SEQUENCE: 591

Gly Gly Thr Phe Ser Ala Tyr Ala 1 5

<210> SEQ ID NO 592
<211> LENGTH: 8
<212> TYPE: PRT
<213> ORGANISM: Artificial
<220> FEATURE:
<223> OTHER INFORMATION: Synthetic

<400> SEQUENCE: 592

Gly Gly Thr Phe Glu Ser Tyr Thr
1 5

<210> SEQ ID NO 593
<211> LENGTH: 8
<212> TYPE: PRT
<213> ORGANISM: Artificial
<220> FEATURE:
<223> OTHER INFORMATION: Synthetic

<400> SEQUENCE: 593

Gly Gly Thr Phe Ser Ser Tyr Ala
1 5

<210> SEQ ID NO 594
<211> LENGTH: 8
<212> TYPE: PRT
<213> ORGANISM: Artificial
<220> FEATURE:
<223> OTHER INFORMATION: Synthetic

<400> SEQUENCE: 594

Gly Gly Ser Phe Ser Glu Tyr Tyr
1 5

<210> SEQ ID NO 595
<211> LENGTH: 8
<212> TYPE: PRT
<213> ORGANISM: Artificial
<220> FEATURE:
<223> OTHER INFORMATION: Synthetic

<400> SEQUENCE: 595

Gly Gly Ser Phe Ser Arg Tyr Tyr
1 5

<210> SEQ ID NO 596
<211> LENGTH: 8
<212> TYPE: PRT
<213> ORGANISM: Artificial
<220> FEATURE:
<223> OTHER INFORMATION: Synthetic

<400> SEQUENCE: 596

Gly Gly Ser Phe Ser Gly Tyr Tyr
1 5

<210> SEQ ID NO 597
<211> LENGTH: 8
<212> TYPE: PRT
<213> ORGANISM: Artificial
<220> FEATURE:
<223> OTHER INFORMATION: Synthetic

<400> SEQUENCE: 597

Gly Phe Thr Phe Ser Ser Tyr Ser
1 5

<210> SEQ ID NO 598
<211> LENGTH: 8
<212> TYPE: PRT
<213> ORGANISM: Artificial
<220> FEATURE:
<223> OTHER INFORMATION: Synthetic

<400> SEQUENCE: 598

Gly Phe Thr Phe Arg Ser Tyr Gly
1 5

<210> SEQ ID NO 599
<211> LENGTH: 8
<212> TYPE: PRT
<213> ORGANISM: Artificial
<220> FEATURE:
<223> OTHER INFORMATION: Synthetic

<400> SEQUENCE: 599

Gly Phe Thr Phe Ser Arg Thr Gly
1 5

<210> SEQ ID NO 600
<211> LENGTH: 8
<212> TYPE: PRT
<213> ORGANISM: Artificial
<220> FEATURE:
<223> OTHER INFORMATION: Synthetic

<400> SEQUENCE: 600

Gly Phe Thr Phe Ser Arg Tyr Gly
1 5

<210> SEQ ID NO 601
<211> LENGTH: 8
<212> TYPE: PRT
<213> ORGANISM: Artificial
<220> FEATURE:
<223> OTHER INFORMATION: Synthetic

<400> SEQUENCE: 601

Gly Phe Thr Phe Ala Ser Tyr Gly
1 5

<210> SEQ ID NO 602
<211> LENGTH: 8
<212> TYPE: PRT
<213> ORGANISM: Artificial
<220> FEATURE:
<223> OTHER INFORMATION: Synthetic

<400> SEQUENCE: 602

Gly Phe Thr Phe Arg Ser Tyr Gly
1 5

<210> SEQ ID NO 603
<211> LENGTH: 8
<212> TYPE: PRT
<213> ORGANISM: Artificial
<220> FEATURE:
<223> OTHER INFORMATION: Synthetic

<400> SEQUENCE: 603

Gly Phe Thr Phe Ser Ser Tyr Gly
1 5

<210> SEQ ID NO 604
<211> LENGTH: 8
<212> TYPE: PRT
<213> ORGANISM: Artificial
<220> FEATURE:
<223> OTHER INFORMATION: Synthetic

<400> SEQUENCE: 604

Gly Gly Ser Phe Ser Asp Tyr Glu
1 5

<210> SEQ ID NO 605
<211> LENGTH: 17
<212> TYPE: PRT
<213> ORGANISM: Artificial
<220> FEATURE:
<223> OTHER INFORMATION: Synthetic

<400> SEQUENCE: 605

Ile Ser Trp Val Arg Gln Ala Pro Gly Gln Gly Leu Glu Trp Met Gly
1 5 10 15

Gly

<210> SEQ ID NO 606
<211> LENGTH: 17
<212> TYPE: PRT
<213> ORGANISM: Artificial
<220> FEATURE:
<223> OTHER INFORMATION: Synthetic

<400> SEQUENCE: 606

Trp Ala Trp Ile Arg Gln Pro Pro Gly Lys Gly Leu Glu Trp Ile Gly
1 5 10 15

Glu

<210> SEQ ID NO 607
<211> LENGTH: 17
<212> TYPE: PRT
<213> ORGANISM: Artificial
<220> FEATURE:
<223> OTHER INFORMATION: Synthetic

<400> SEQUENCE: 607

Trp Ser Trp Ile Arg Gln Pro Pro Gly Lys Gly Leu Glu Trp Ile Gly
1 5 10 15

Ser

<210> SEQ ID NO 608
<211> LENGTH: 17
<212> TYPE: PRT
<213> ORGANISM: Artificial
<220> FEATURE:
<223> OTHER INFORMATION: Synthetic

<400> SEQUENCE: 608

Trp Ser Trp Ile Arg Gln Pro Pro Gly Lys Gly Leu Glu Trp Ile Gly
1 5 10 15

Glu

<210> SEQ ID NO 609
<211> LENGTH: 17
<212> TYPE: PRT
<213> ORGANISM: Artificial
<220> FEATURE:

<223> OTHER INFORMATION: Synthetic

<400> SEQUENCE: 609

Met Asn Trp Val Arg Gln Ala Pro Gly Lys Gly Leu Glu Trp Val Ser
1 5 10 15

Ser

<210> SEQ ID NO 610
<211> LENGTH: 17
<212> TYPE: PRT
<213> ORGANISM: Artificial
<220> FEATURE:
<223> OTHER INFORMATION: Synthetic

<400> SEQUENCE: 610

Met Asn Trp Val Arg Gln Ala Pro Gly Lys Gly Leu Glu Trp Val Ser
1 5 10 15

Gly

<210> SEQ ID NO 611
<211> LENGTH: 17
<212> TYPE: PRT
<213> ORGANISM: Artificial
<220> FEATURE:
<223> OTHER INFORMATION: Synthetic

<400> SEQUENCE: 611

Met Ser Trp Val Arg Gln Ala Pro Gly Lys Gly Leu Glu Trp Val Ala
1 5 10 15

Asn

<210> SEQ ID NO 612
<211> LENGTH: 17
<212> TYPE: PRT
<213> ORGANISM: Artificial
<220> FEATURE:
<223> OTHER INFORMATION: Synthetic

<400> SEQUENCE: 612

Met His Trp Val Arg Gln Ala Pro Gly Lys Gly Leu Glu Trp Val Ala
1 5 10 15

Val

<210> SEQ ID NO 613
<211> LENGTH: 17
<212> TYPE: PRT
<213> ORGANISM: Artificial
<220> FEATURE:
<223> OTHER INFORMATION: Synthetic

<400> SEQUENCE: 613

Trp Ser Trp Ile Arg Gln Pro Pro Gly Lys Gly Leu Glu Trp Ile Gly
1 5 10 15

Glu

<210> SEQ ID NO 614
<211> LENGTH: 8
<212> TYPE: PRT
<213> ORGANISM: Artificial
<220> FEATURE:
<223> OTHER INFORMATION: Synthetic

<400> SEQUENCE: 614

Ile Ile Pro Ile Phe Gly Ile Ala
1               5

<210> SEQ ID NO 615
<211> LENGTH: 8
<212> TYPE: PRT
<213> ORGANISM: Artificial
<220> FEATURE:
<223> OTHER INFORMATION: Synthetic

<400> SEQUENCE: 615

Ile Ile Pro Ile Phe Gly Thr Ala
1               5

<210> SEQ ID NO 616
<211> LENGTH: 8
<212> TYPE: PRT
<213> ORGANISM: Artificial
<220> FEATURE:
<223> OTHER INFORMATION: Synthetic

<400> SEQUENCE: 616

Ile Ala Pro Ile Phe Gly Thr Ala
1               5

<210> SEQ ID NO 617
<211> LENGTH: 7
<212> TYPE: PRT
<213> ORGANISM: Artificial
<220> FEATURE:
<223> OTHER INFORMATION: Synthetic

<400> SEQUENCE: 617

Ile Asp Glu Val Gly Ser Thr
1               5

<210> SEQ ID NO 618
<211> LENGTH: 7
<212> TYPE: PRT
<213> ORGANISM: Artificial
<220> FEATURE:
<223> OTHER INFORMATION: Synthetic

<400> SEQUENCE: 618

Ile Asp Tyr Ser Gly Ser Thr
1               5

<210> SEQ ID NO 619
<211> LENGTH: 7
<212> TYPE: PRT
<213> ORGANISM: Artificial
<220> FEATURE:
<223> OTHER INFORMATION: Synthetic

<400> SEQUENCE: 619

Ile Asp Val Asp Gly Ser Thr
1               5

<210> SEQ ID NO 620
<211> LENGTH: 8
<212> TYPE: PRT
<213> ORGANISM: Artificial
<220> FEATURE:
<223> OTHER INFORMATION: Synthetic

<400> SEQUENCE: 620

Ile Ser Ser Ser Ser Ser Tyr Ile 1 5

<210> SEQ ID NO 621
<211> LENGTH: 8
<212> TYPE: PRT
<213> ORGANISM: Artificial
<220> FEATURE:
<223> OTHER INFORMATION: Synthetic

<400> SEQUENCE: 621

Ile Ser Ser Ser Ser Ala Tyr Ile
1 5

<210> SEQ ID NO 622
<211> LENGTH: 8
<212> TYPE: PRT
<213> ORGANISM: Artificial
<220> FEATURE:
<223> OTHER INFORMATION: Synthetic

<400> SEQUENCE: 622

Ile Ser Ser Ser Gly Ser Tyr Ile
1 5

<210> SEQ ID NO 623
<211> LENGTH: 8
<212> TYPE: PRT
<213> ORGANISM: Artificial
<220> FEATURE:
<223> OTHER INFORMATION: Synthetic

<400> SEQUENCE: 623

Ile Lys Gln Asp Gly Ser Glu Lys
1 5

<210> SEQ ID NO 624
<211> LENGTH: 8
<212> TYPE: PRT
<213> ORGANISM: Artificial
<220> FEATURE:
<223> OTHER INFORMATION: Synthetic

<400> SEQUENCE: 624

Ile Trp Tyr Asp Gly Ser Asn Lys
1 5

<210> SEQ ID NO 625
<211> LENGTH: 7
<212> TYPE: PRT
<213> ORGANISM: Artificial
<220> FEATURE:
<223> OTHER INFORMATION: Synthetic

<400> SEQUENCE: 625

Ile Asp Trp Ser Gly Ile Thr
1 5

<210> SEQ ID NO 626
<211> LENGTH: 38
<212> TYPE: PRT
<213> ORGANISM: Artificial
<220> FEATURE:
<223> OTHER INFORMATION: Synthetic

<400> SEQUENCE: 626

Asn Tyr Ala Gln Lys Phe Gln Gly Arg Val Thr Ile Thr Ala Asp Glu
1 5 10 15

```
Ser Thr Ser Thr Ala Tyr Met Glu Leu Ser Ser Leu Arg Ser Glu Asp
            20                  25                  30

Thr Ala Val Tyr Tyr Cys
        35


<210> SEQ ID NO 627
<211> LENGTH: 38
<212> TYPE: PRT
<213> ORGANISM: Artificial
<220> FEATURE:
<223> OTHER INFORMATION: Synthetic

<400> SEQUENCE: 627

His Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35


<210> SEQ ID NO 628
<211> LENGTH: 38
<212> TYPE: PRT
<213> ORGANISM: Artificial
<220> FEATURE:
<223> OTHER INFORMATION: Synthetic

<400> SEQUENCE: 628

Asn Tyr Ala Gln Lys Phe Gln Gly Arg Val Thr Ile Thr Ala Asp Glu
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35


<210> SEQ ID NO 629
<211> LENGTH: 38
<212> TYPE: PRT
<213> ORGANISM: Artificial
<220> FEATURE:
<223> OTHER INFORMATION: Synthetic

<400> SEQUENCE: 629

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35


<210> SEQ ID NO 630
<211> LENGTH: 38
<212> TYPE: PRT
<213> ORGANISM: Artificial
<220> FEATURE:
<223> OTHER INFORMATION: Synthetic

<400> SEQUENCE: 630

Glu Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30
```

```
Thr Ala Val Tyr Tyr Cys
        35


<210> SEQ ID NO 631
<211> LENGTH: 38
<212> TYPE: PRT
<213> ORGANISM: Artificial
<220> FEATURE:
<223> OTHER INFORMATION: Synthetic

<400> SEQUENCE: 631

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35


<210> SEQ ID NO 632
<211> LENGTH: 38
<212> TYPE: PRT
<213> ORGANISM: Artificial
<220> FEATURE:
<223> OTHER INFORMATION: Synthetic

<400> SEQUENCE: 632

Leu Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35


<210> SEQ ID NO 633
<211> LENGTH: 38
<212> TYPE: PRT
<213> ORGANISM: Artificial
<220> FEATURE:
<223> OTHER INFORMATION: Synthetic

<400> SEQUENCE: 633

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35


<210> SEQ ID NO 634
<211> LENGTH: 38
<212> TYPE: PRT
<213> ORGANISM: Artificial
<220> FEATURE:
<223> OTHER INFORMATION: Synthetic

<400> SEQUENCE: 634

Tyr Tyr Val Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35
```

<210> SEQ ID NO 635
<211> LENGTH: 38
<212> TYPE: PRT
<213> ORGANISM: Artificial
<220> FEATURE:
<223> OTHER INFORMATION: Synthetic

<400> SEQUENCE: 635

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 636
<211> LENGTH: 38
<212> TYPE: PRT
<213> ORGANISM: Artificial
<220> FEATURE:
<223> OTHER INFORMATION: Synthetic

<400> SEQUENCE: 636

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
            20                  25                  30

Thr Ala Val Tyr Tyr Cys
        35

<210> SEQ ID NO 637
<211> LENGTH: 17
<212> TYPE: PRT
<213> ORGANISM: Artificial
<220> FEATURE:
<223> OTHER INFORMATION: Synthetic

<400> SEQUENCE: 637

Ala Arg Ser Tyr Tyr Ser Ser Arg Trp His Tyr Tyr Tyr Tyr Met Asp
1               5                   10                  15

Val

<210> SEQ ID NO 638
<211> LENGTH: 17
<212> TYPE: PRT
<213> ORGANISM: Artificial
<220> FEATURE:
<223> OTHER INFORMATION: Synthetic

<400> SEQUENCE: 638

Ala Arg Leu Gly Gly Arg Gly Tyr Ala Asp Glu Gly Trp Tyr Phe Asp
1               5                   10                  15

Leu

<210> SEQ ID NO 639
<211> LENGTH: 17
<212> TYPE: PRT
<213> ORGANISM: Artificial
<220> FEATURE:
<223> OTHER INFORMATION: Synthetic

<400> SEQUENCE: 639

-continued

Ala Arg Leu Pro Met Tyr Tyr Tyr Asp Ser Ser Asp Leu Pro Met Asp
1               5                   10                  15

Val

<210> SEQ ID NO 640
<211> LENGTH: 16
<212> TYPE: PRT
<213> ORGANISM: Artificial
<220> FEATURE:
<223> OTHER INFORMATION: Synthetic

<400> SEQUENCE: 640

Ala Arg Asp Gly Val Tyr Tyr Asp Ser Ser Asp Leu Gly Phe Asp Ile
1               5                   10                  15

<210> SEQ ID NO 641
<211> LENGTH: 14
<212> TYPE: PRT
<213> ORGANISM: Artificial
<220> FEATURE:
<223> OTHER INFORMATION: Synthetic

<400> SEQUENCE: 641

Ala Arg Asp Gly Tyr Tyr Tyr Asp Thr Ser Pro Tyr Asp Val
1               5                   10

<210> SEQ ID NO 642
<211> LENGTH: 19
<212> TYPE: PRT
<213> ORGANISM: Artificial
<220> FEATURE:
<223> OTHER INFORMATION: Synthetic

<400> SEQUENCE: 642

Ala Arg Asp Gly Gly Arg Thr Ser Tyr Thr Ala Thr Ala His Asn Trp
1               5                   10                  15

Phe Asp Pro

<210> SEQ ID NO 643
<211> LENGTH: 15
<212> TYPE: PRT
<213> ORGANISM: Artificial
<220> FEATURE:
<223> OTHER INFORMATION: Synthetic

<400> SEQUENCE: 643

Ala Arg Asp Ala Pro Trp Asp Ile Tyr Asp Tyr Tyr Met Asp Val
1               5                   10                  15

<210> SEQ ID NO 644
<211> LENGTH: 10
<212> TYPE: PRT
<213> ORGANISM: Artificial
<220> FEATURE:
<223> OTHER INFORMATION: Synthetic

<400> SEQUENCE: 644

Ala Arg Gly Ala Pro Glu Tyr Val Asp Val
1               5                   10

<210> SEQ ID NO 645
<211> LENGTH: 19
<212> TYPE: PRT
<213> ORGANISM: Artificial
<220> FEATURE:
<223> OTHER INFORMATION: Synthetic

<400> SEQUENCE: 645

Ala Arg Leu Pro Met Tyr Tyr Tyr Asp Ser Ser Val Ser Thr Gly Ser
1 5 10 15

Val Asp Val

<210> SEQ ID NO 646
<211> LENGTH: 11
<212> TYPE: PRT
<213> ORGANISM: Artificial
<220> FEATURE:
<223> OTHER INFORMATION: Synthetic

<400> SEQUENCE: 646

Trp Gly Lys Gly Thr Thr Val Thr Val Ser Ser
1 5 10

<210> SEQ ID NO 647
<211> LENGTH: 11
<212> TYPE: PRT
<213> ORGANISM: Artificial
<220> FEATURE:
<223> OTHER INFORMATION: Synthetic

<400> SEQUENCE: 647

Trp Gly Arg Gly Thr Leu Val Thr Val Ser Ser
1 5 10

<210> SEQ ID NO 648
<211> LENGTH: 11
<212> TYPE: PRT
<213> ORGANISM: Artificial
<220> FEATURE:
<223> OTHER INFORMATION: Synthetic

<400> SEQUENCE: 648

Trp Gly Gln Gly Thr Thr Val Thr Val Ser Ser
1 5 10

<210> SEQ ID NO 649
<211> LENGTH: 11
<212> TYPE: PRT
<213> ORGANISM: Artificial
<220> FEATURE:
<223> OTHER INFORMATION: Synthetic

<400> SEQUENCE: 649

Trp Gly Gln Gly Thr Met Val Thr Val Ser Ser
1 5 10

<210> SEQ ID NO 650
<211> LENGTH: 11
<212> TYPE: PRT
<213> ORGANISM: Artificial
<220> FEATURE:
<223> OTHER INFORMATION: Synthetic

<400> SEQUENCE: 650

Trp Gly Gln Gly Thr Leu Val Thr Val Ser Ser
1 5 10

<210> SEQ ID NO 651
<211> LENGTH: 11
<212> TYPE: PRT
<213> ORGANISM: Artificial
<220> FEATURE:

<223> OTHER INFORMATION: Synthetic

<400> SEQUENCE: 651

Trp Gly Lys Gly Thr Thr Val Thr Val Ser Ser
1 5 10

<210> SEQ ID NO 652
<211> LENGTH: 11
<212> TYPE: PRT
<213> ORGANISM: Artificial
<220> FEATURE:
<223> OTHER INFORMATION: Synthetic

<400> SEQUENCE: 652

Trp Gly Gln Gly Thr Met Val Thr Val Ser Ser
1 5 10

<210> SEQ ID NO 653
<211> LENGTH: 26
<212> TYPE: PRT
<213> ORGANISM: Artificial
<220> FEATURE:
<223> OTHER INFORMATION: Synthetic

<400> SEQUENCE: 653

Asp Ile Gln Met Thr Gln Ser Pro Ser Ser Val Ser Ala Ser Val Gly
1 5 10 15

Asp Arg Val Thr Ile Thr Cys Arg Ala Ser
20 25

<210> SEQ ID NO 654
<211> LENGTH: 26
<212> TYPE: PRT
<213> ORGANISM: Artificial
<220> FEATURE:
<223> OTHER INFORMATION: Synthetic

<400> SEQUENCE: 654

Glu Ile Val Leu Thr Gln Ser Pro Gly Thr Leu Ser Leu Ser Pro Gly
1 5 10 15

Glu Arg Ala Thr Leu Ser Cys Arg Ala Ser
20 25

<210> SEQ ID NO 655
<211> LENGTH: 26
<212> TYPE: PRT
<213> ORGANISM: Artificial
<220> FEATURE:
<223> OTHER INFORMATION: Synthetic

<400> SEQUENCE: 655

Asp Ile Gln Met Thr Gln Ser Pro Ser Ser Leu Ser Ala Ser Val Gly
1 5 10 15

Asp Arg Val Thr Ile Thr Cys Gln Ala Ser
20 25

<210> SEQ ID NO 656
<211> LENGTH: 25
<212> TYPE: PRT
<213> ORGANISM: Artificial
<220> FEATURE:
<223> OTHER INFORMATION: Synthetic

<400> SEQUENCE: 656

Glu Ile Val Leu Thr Gln Ser Pro Ala Thr Leu Ser Leu Ser Pro Gly

```
1               5                   10                  15

Glu Arg Ala Thr Leu Ser Cys Arg Ala
            20                  25


<210> SEQ ID NO 657
<211> LENGTH: 26
<212> TYPE: PRT
<213> ORGANISM: Artificial
<220> FEATURE:
<223> OTHER INFORMATION: Synthetic

<400> SEQUENCE: 657

Asp Ile Val Met Thr Gln Ser Pro Asp Ser Leu Ala Val Ser Leu Gly
1               5                   10                  15

Glu Arg Ala Thr Ile Asn Cys Lys Ser Ser
            20                  25


<210> SEQ ID NO 658
<211> LENGTH: 26
<212> TYPE: PRT
<213> ORGANISM: Artificial
<220> FEATURE:
<223> OTHER INFORMATION: Synthetic

<400> SEQUENCE: 658

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25


<210> SEQ ID NO 659
<211> LENGTH: 26
<212> TYPE: PRT
<213> ORGANISM: Artificial
<220> FEATURE:
<223> OTHER INFORMATION: Synthetic

<400> SEQUENCE: 659

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25


<210> SEQ ID NO 660
<211> LENGTH: 6
<212> TYPE: PRT
<213> ORGANISM: Artificial
<220> FEATURE:
<223> OTHER INFORMATION: Synthetic

<400> SEQUENCE: 660

Gln Gly Ile Ser Ser Trp
1               5


<210> SEQ ID NO 661
<211> LENGTH: 7
<212> TYPE: PRT
<213> ORGANISM: Artificial
<220> FEATURE:
<223> OTHER INFORMATION: Synthetic

<400> SEQUENCE: 661

Gln Ser Val Ser Ser Ser Tyr
1               5
```

<210> SEQ ID NO 662
<211> LENGTH: 6
<212> TYPE: PRT
<213> ORGANISM: Artificial
<220> FEATURE:
<223> OTHER INFORMATION: Synthetic

<400> SEQUENCE: 662

Gln Asp Ile Ser Asn Tyr
1 5

<210> SEQ ID NO 663
<211> LENGTH: 7
<212> TYPE: PRT
<213> ORGANISM: Artificial
<220> FEATURE:
<223> OTHER INFORMATION: Synthetic

<400> SEQUENCE: 663

Ser Gln Ser Val Ser Ser Tyr
1 5

<210> SEQ ID NO 664
<211> LENGTH: 12
<212> TYPE: PRT
<213> ORGANISM: Artificial
<220> FEATURE:
<223> OTHER INFORMATION: Synthetic

<400> SEQUENCE: 664

Gln Ser Val Leu Phe Ser Ser Asn Asn Lys Asn Tyr
1 5 10

<210> SEQ ID NO 665
<211> LENGTH: 6
<212> TYPE: PRT
<213> ORGANISM: Artificial
<220> FEATURE:
<223> OTHER INFORMATION: Synthetic

<400> SEQUENCE: 665

Gln Ser Ile Ser Ser Tyr
1 5

<210> SEQ ID NO 666
<211> LENGTH: 6
<212> TYPE: PRT
<213> ORGANISM: Artificial
<220> FEATURE:
<223> OTHER INFORMATION: Synthetic

<400> SEQUENCE: 666

Gln Ser Val Ser Ser Tyr
1 5

<210> SEQ ID NO 667
<211> LENGTH: 17
<212> TYPE: PRT
<213> ORGANISM: Artificial
<220> FEATURE:
<223> OTHER INFORMATION: Synthetic

<400> SEQUENCE: 667

Leu Ala Trp Tyr Gln Gln Lys Pro Gly Lys Ala Pro Lys Leu Leu Ile
1 5 10 15

Tyr

<210> SEQ ID NO 668
<211> LENGTH: 17
<212> TYPE: PRT
<213> ORGANISM: Artificial
<220> FEATURE:
<223> OTHER INFORMATION: Synthetic

<400> SEQUENCE: 668

Leu Ala Trp Tyr Gln Gln Lys Pro Gly Gln Ala Pro Arg Leu Leu Ile
1 5 10 15

Tyr

<210> SEQ ID NO 669
<211> LENGTH: 17
<212> TYPE: PRT
<213> ORGANISM: Artificial
<220> FEATURE:
<223> OTHER INFORMATION: Synthetic

<400> SEQUENCE: 669

Leu Asn Trp Tyr Gln Gln Lys Pro Gly Lys Ala Pro Lys Leu Leu Ile
1 5 10 15

Tyr

<210> SEQ ID NO 670
<211> LENGTH: 17
<212> TYPE: PRT
<213> ORGANISM: Artificial
<220> FEATURE:
<223> OTHER INFORMATION: Synthetic

<400> SEQUENCE: 670

Leu Ala Trp Tyr Gln Gln Lys Pro Gly Gln Ala Pro Arg Leu Leu Ile
1 5 10 15

Tyr

<210> SEQ ID NO 671
<211> LENGTH: 17
<212> TYPE: PRT
<213> ORGANISM: Artificial
<220> FEATURE:
<223> OTHER INFORMATION: Synthetic

<400> SEQUENCE: 671

Leu Ala Trp Tyr Gln Gln Lys Pro Gly Gln Pro Pro Lys Leu Leu Ile
1 5 10 15

Tyr

<210> SEQ ID NO 672
<211> LENGTH: 17
<212> TYPE: PRT
<213> ORGANISM: Artificial
<220> FEATURE:
<223> OTHER INFORMATION: Synthetic

<400> SEQUENCE: 672

Leu Asn Trp Tyr Gln Gln Lys Pro Gly Lys Ala Pro Lys Leu Leu Ile
1 5 10 15

Tyr

<210> SEQ ID NO 673
<211> LENGTH: 17

<212> TYPE: PRT
<213> ORGANISM: Artificial
<220> FEATURE:
<223> OTHER INFORMATION: Synthetic

<400> SEQUENCE: 673

Leu Ala Trp Tyr Gln Gln Lys Pro Gly Gln Ala Pro Arg Leu Leu Ile
1               5                   10                  15

Tyr

<210> SEQ ID NO 674
<211> LENGTH: 3
<212> TYPE: PRT
<213> ORGANISM: Artificial
<220> FEATURE:
<223> OTHER INFORMATION: Synthetic

<400> SEQUENCE: 674

Ala Ala Ser
1

<210> SEQ ID NO 675
<211> LENGTH: 3
<212> TYPE: PRT
<213> ORGANISM: Artificial
<220> FEATURE:
<223> OTHER INFORMATION: Synthetic

<400> SEQUENCE: 675

Gly Ala Ser
1

<210> SEQ ID NO 676
<211> LENGTH: 3
<212> TYPE: PRT
<213> ORGANISM: Artificial
<220> FEATURE:
<223> OTHER INFORMATION: Synthetic

<400> SEQUENCE: 676

Asp Ala Ser
1

<210> SEQ ID NO 677
<211> LENGTH: 3
<212> TYPE: PRT
<213> ORGANISM: Artificial
<220> FEATURE:
<223> OTHER INFORMATION: Synthetic

<400> SEQUENCE: 677

Trp Ala Ser
1

<210> SEQ ID NO 678
<211> LENGTH: 3
<212> TYPE: PRT
<213> ORGANISM: Artificial
<220> FEATURE:
<223> OTHER INFORMATION: Synthetic

<400> SEQUENCE: 678

Ala Ala Ser
1

<210> SEQ ID NO 679

<211> LENGTH: 3
<212> TYPE: PRT
<213> ORGANISM: Artificial
<220> FEATURE:
<223> OTHER INFORMATION: Synthetic

<400> SEQUENCE: 679

Asp Ser Ser
1

<210> SEQ ID NO 680
<211> LENGTH: 36
<212> TYPE: PRT
<213> ORGANISM: Artificial
<220> FEATURE:
<223> OTHER INFORMATION: Synthetic

<400> SEQUENCE: 680

Asn Leu Gln Ser Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 681
<211> LENGTH: 36
<212> TYPE: PRT
<213> ORGANISM: Artificial
<220> FEATURE:
<223> OTHER INFORMATION: Synthetic

<400> SEQUENCE: 681

Ser Arg Ala Thr Gly Ile Pro Asp Arg Phe Ser Gly Ser Gly Ser Gly
1 5 10 15

Thr Asp Phe Thr Leu Thr Ile Ser Arg Leu Glu Pro Glu Asp Phe Ala
20 25 30

Val Tyr Tyr Cys
35

<210> SEQ ID NO 682
<211> LENGTH: 36
<212> TYPE: PRT
<213> ORGANISM: Artificial
<220> FEATURE:
<223> OTHER INFORMATION: Synthetic

<400> SEQUENCE: 682

Asn Leu Ala Thr Gly Val Pro Ser Arg Phe Ser Gly Ser Gly Ser Gly
1 5 10 15

Thr Asp Phe Thr Phe Thr Ile Ser Ser Leu Gln Pro Glu Asp Ile Ala
20 25 30

Thr Tyr Tyr Cys
35

<210> SEQ ID NO 683
<211> LENGTH: 36
<212> TYPE: PRT
<213> ORGANISM: Artificial
<220> FEATURE:
<223> OTHER INFORMATION: Synthetic

<400> SEQUENCE: 683

Asn Leu Glu Thr Gly Val Pro Ser Arg Phe Ser Gly Ser Gly Ser Gly

-continued

```
1               5                   10                  15

Thr Asp Phe Thr Phe Thr Ile Ser Ser Leu Gln Pro Glu Asp Ile Ala
            20                  25                  30

Thr Tyr Tyr Cys
        35


<210> SEQ ID NO 684
<211> LENGTH: 36
<212> TYPE: PRT
<213> ORGANISM: Artificial
<220> FEATURE:
<223> OTHER INFORMATION: Synthetic

<400> SEQUENCE: 684

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35


<210> SEQ ID NO 685
<211> LENGTH: 36
<212> TYPE: PRT
<213> ORGANISM: Artificial
<220> FEATURE:
<223> OTHER INFORMATION: Synthetic

<400> SEQUENCE: 685

Thr Arg Glu Ser Gly Val Pro Asp Arg Phe Ser Gly Ser Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
        35


<210> SEQ ID NO 686
<211> LENGTH: 36
<212> TYPE: PRT
<213> ORGANISM: Artificial
<220> FEATURE:
<223> OTHER INFORMATION: Synthetic

<400> SEQUENCE: 686

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35


<210> SEQ ID NO 687
<211> LENGTH: 36
<212> TYPE: PRT
<213> ORGANISM: Artificial
<220> FEATURE:
<223> OTHER INFORMATION: Synthetic

<400> SEQUENCE: 687

Asn Arg Ala Thr Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
```

-continued

```
            20                  25                  30

Val Tyr Tyr Cys
        35


<210> SEQ ID NO 688
<211> LENGTH: 9
<212> TYPE: PRT
<213> ORGANISM: Artificial
<220> FEATURE:
<223> OTHER INFORMATION: Synthetic

<400> SEQUENCE: 688

Gln Gln Ala Asp Asp Leu Pro Leu Thr
1               5


<210> SEQ ID NO 689
<211> LENGTH: 9
<212> TYPE: PRT
<213> ORGANISM: Artificial
<220> FEATURE:
<223> OTHER INFORMATION: Synthetic

<400> SEQUENCE: 689

Gln Gln Tyr Tyr Gly Ser Pro Ile Thr
1               5


<210> SEQ ID NO 690
<211> LENGTH: 9
<212> TYPE: PRT
<213> ORGANISM: Artificial
<220> FEATURE:
<223> OTHER INFORMATION: Synthetic

<400> SEQUENCE: 690

Gln Gln Tyr Asp Thr Leu Pro Leu Thr
1               5


<210> SEQ ID NO 691
<211> LENGTH: 9
<212> TYPE: PRT
<213> ORGANISM: Artificial
<220> FEATURE:
<223> OTHER INFORMATION: Synthetic

<400> SEQUENCE: 691

Gln Gln Tyr Asp Asp Leu Pro Ile Thr
1               5


<210> SEQ ID NO 692
<211> LENGTH: 9
<212> TYPE: PRT
<213> ORGANISM: Artificial
<220> FEATURE:
<223> OTHER INFORMATION: Synthetic

<400> SEQUENCE: 692

Gln Gln Arg Asp Ser Phe Pro Leu Thr
1               5


<210> SEQ ID NO 693
<211> LENGTH: 9
<212> TYPE: PRT
<213> ORGANISM: Artificial
<220> FEATURE:
<223> OTHER INFORMATION: Synthetic

<400> SEQUENCE: 693
```

Gln Gln His Ala Ser Ala Pro Pro Thr
1 5

<210> SEQ ID NO 694
<211> LENGTH: 9
<212> TYPE: PRT
<213> ORGANISM: Artificial
<220> FEATURE:
<223> OTHER INFORMATION: Synthetic

<400> SEQUENCE: 694

Gln Gln Ser Tyr Val Pro Pro Trp Thr
1 5

<210> SEQ ID NO 695
<211> LENGTH: 8
<212> TYPE: PRT
<213> ORGANISM: Artificial
<220> FEATURE:
<223> OTHER INFORMATION: Synthetic

<400> SEQUENCE: 695

Gln Gln Tyr Ser Leu Tyr Pro Thr
1 5

<210> SEQ ID NO 696
<211> LENGTH: 9
<212> TYPE: PRT
<213> ORGANISM: Artificial
<220> FEATURE:
<223> OTHER INFORMATION: Synthetic

<400> SEQUENCE: 696

Gln Gln Asp Ser Asp His Pro Ile Thr
1 5

<210> SEQ ID NO 697
<211> LENGTH: 10
<212> TYPE: PRT
<213> ORGANISM: Artificial
<220> FEATURE:
<223> OTHER INFORMATION: Synthetic

<400> SEQUENCE: 697

Phe Gly Gly Gly Thr Lys Val Glu Ile Lys
1 5 10

<210> SEQ ID NO 698
<211> LENGTH: 229
<212> TYPE: PRT
<213> ORGANISM: Artificial
<220> FEATURE:
<223> OTHER INFORMATION: Synthetic

<400> SEQUENCE: 698

Met Thr Pro Gln Leu Leu Leu Ala Leu Val Leu Trp Ala Ser Cys Pro
1 5 10 15

Pro Cys Ser Gly Arg Lys Gly Pro Pro Ala Ala Leu Thr Leu Pro Arg
20 25 30

Val Gln Cys Arg Ala Ser Arg Tyr Pro Ile Ala Val Asp Cys Ser Trp
35 40 45

Thr Leu Pro Pro Ala Pro Asn Ser Thr Ser Pro Val Ser Phe Ile Ala
50 55 60

Thr Tyr Arg Leu Gly Met Ala Ala Arg Gly His Ser Trp Pro Cys Leu

```
65                  70                  75                  80

Gln Gln Thr Pro Thr Ser Thr Ser Cys Thr Ile Thr Asp Val Gln Leu
                85                  90                  95

Phe Ser Met Ala Pro Tyr Val Leu Asn Val Thr Ala Val His Pro Trp
            100                 105                 110

Gly Ser Ser Ser Ser Phe Val Pro Phe Ile Thr Glu His Ile Ile Lys
        115                 120                 125

Pro Asp Pro Pro Glu Gly Val Arg Leu Ser Pro Leu Ala Glu Arg Gln
    130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225
```

<210> SEQ ID NO 699
<211> LENGTH: 243
<212> TYPE: PRT
<213> ORGANISM: Artificial
<220> FEATURE:
<223> OTHER INFORMATION: Synthetic

<400> SEQUENCE: 699

```
Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
```

```
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro


<210> SEQ ID NO 700
<211> LENGTH: 636
<212> TYPE: PRT
<213> ORGANISM: Artificial
<220> FEATURE:
<223> OTHER INFORMATION: Synthetic

<400> SEQUENCE: 700

Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
            20                  25                  30

Gln Gly Ser Ala Gly Pro Leu Gln Cys Tyr Gly Val Gly Pro Leu Gly
        35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
            100                 105                 110

Pro Leu Trp Pro Pro Val Phe Val Asn Leu Glu Thr Gln Met Lys Pro
        115                 120                 125

Asn Ala Pro Arg Leu Gly Pro Asp Val Asp Phe Ser Glu Asp Asp Pro
    130                 135                 140

Leu Glu Ala Thr Val His Trp Ala Pro Pro Thr Trp Pro Ser His Lys
145                 150                 155                 160

Val Leu Ile Cys Gln Phe His Tyr Arg Arg Cys Gln Glu Ala Ala Trp
                165                 170                 175

Thr Leu Leu Glu Pro Glu Leu Lys Thr Ile Pro Leu Thr Pro Val Glu
            180                 185                 190

Ile Gln Asp Leu Glu Leu Ala Thr Gly Tyr Lys Val Tyr Gly Arg Cys
        195                 200                 205

Arg Met Glu Lys Glu Glu Asp Leu Trp Gly Glu Trp Ser Pro Ile Leu
    210                 215                 220

Ser Phe Gln Thr Pro Pro Ser Ala Pro Lys Asp Val Trp Val Ser Gly
225                 230                 235                 240

Asn Leu Cys Gly Thr Pro Gly Gly Glu Glu Pro Leu Leu Leu Trp Lys
                245                 250                 255

Ala Pro Gly Pro Cys Val Gln Val Ser Tyr Lys Val Trp Phe Trp Val
            260                 265                 270

Gly Gly Arg Glu Leu Ser Pro Glu Gly Ile Thr Cys Cys Cys Ser Leu
        275                 280                 285

Ile Pro Ser Gly Ala Glu Trp Ala Arg Val Ser Ala Val Asn Ala Thr
    290                 295                 300

Ser Trp Glu Pro Leu Thr Asn Leu Ser Leu Val Cys Leu Asp Ser Ala
305                 310                 315                 320
```

Ser Ala Pro Arg Ser Val Ala Val Ser Ser Ile Ala Gly Ser Thr Glu
325 330 335

Leu Leu Val Thr Trp Gln Pro Gly Pro Gly Glu Pro Leu Glu His Val
340 345 350

Val Asp Trp Ala Arg Asp Gly Asp Pro Leu Glu Lys Leu Asn Trp Val
355 360 365

Arg Leu Pro Pro Gly Asn Leu Ser Ala Leu Leu Pro Gly Asn Phe Thr
370 375 380

Val Gly Val Pro Tyr Arg Ile Thr Val Thr Ala Val Ser Ala Ser Gly
385 390 395 400

Leu Ala Ser Ala Ser Ser Val Trp Gly Phe Arg Glu Glu Leu Ala Pro
405 410 415

Leu Val Gly Pro Thr Leu Trp Arg Leu Gln Asp Ala Pro Pro Gly Thr
420 425 430

Pro Ala Ile Ala Trp Gly Glu Val Pro Arg His Gln Leu Arg Gly His
435 440 445

Leu Thr His Tyr Thr Leu Cys Ala Gln Ser Gly Thr Ser Pro Ser Val
450 455 460

Cys Met Asn Val Ser Gly Asn Thr Gln Ser Val Thr Leu Pro Asp Leu
465 470 475 480

Pro Trp Gly Pro Cys Glu Leu Trp Val Thr Ala Ser Thr Ile Ala Gly
485 490 495

Gln Gly Pro Pro Gly Pro Ile Leu Arg Leu His Leu Pro Asp Asn Thr
500 505 510

Leu Arg Trp Lys Val Leu Pro Gly Ile Leu Phe Leu Trp Gly Leu Phe
515 520 525

Leu Leu Gly Cys Gly Leu Ser Leu Ala Thr Ser Gly Arg Cys Tyr His
530 535 540

Leu Arg His Lys Val Leu Pro Arg Trp Val Trp Glu Lys Val Pro Asp
545 550 555 560

Pro Ala Asn Ser Ser Ser Gly Gln Pro His Met Glu Gln Val Pro Glu
565 570 575

Ala Gln Pro Leu Gly Asp Leu Pro Ile Leu Glu Val Glu Glu Met Glu
580 585 590

Pro Pro Pro Val Met Glu Ser Ser Gln Pro Ala Gln Ala Thr Ala Pro
595 600 605

Leu Asp Ser Gly Tyr Glu Lys His Phe Leu Pro Thr Pro Glu Glu Leu
610 615 620

Gly Leu Leu Gly Pro Pro Arg Pro Gln Val Leu Ala
625 630 635

<210> SEQ ID NO 701
<211> LENGTH: 918
<212> TYPE: PRT
<213> ORGANISM: Artificial
<220> FEATURE:
<223> OTHER INFORMATION: Synthetic

<400> SEQUENCE: 701

Met Leu Thr Leu Gln Thr Trp Leu Val Gln Ala Leu Phe Ile Phe Leu
1 5 10 15

Thr Thr Glu Ser Thr Gly Glu Leu Leu Asp Pro Cys Gly Tyr Ile Ser
20 25 30

Pro Glu Ser Pro Val Val Gln Leu His Ser Asn Phe Thr Ala Val Cys
35 40 45

-continued

```
Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460
```

-continued

```
Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
```

885 890 895

Thr Asp Glu Gly Met Pro Lys Ser Tyr Leu Pro Gln Thr Val Arg Gln
900 905 910

Gly Gly Tyr Met Pro Gln
915

<210> SEQ ID NO 702
<211> LENGTH: 232
<212> TYPE: PRT
<213> ORGANISM: Artificial
<220> FEATURE:
<223> OTHER INFORMATION: Synthetic

<400> SEQUENCE: 702

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 703
<211> LENGTH: 229
<212> TYPE: PRT
<213> ORGANISM: Artificial
<220> FEATURE:
<223> OTHER INFORMATION: Synthetic

<400> SEQUENCE: 703

Glu Ser Lys Tyr Gly Pro Pro Cys Pro Ser Cys Pro Ala Pro Glu Phe
1 5 10 15

Leu Gly Gly Pro Ser Val Phe Leu Phe Pro Pro Lys Pro Lys Asp Thr
20 25 30

```
Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 704
<211> LENGTH: 229
<212> TYPE: PRT
<213> ORGANISM: Artificial
<220> FEATURE:
<223> OTHER INFORMATION: Synthetic

<400> SEQUENCE: 704

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160
```

```
Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 705
<211> LENGTH: 229
<212> TYPE: PRT
<213> ORGANISM: Artificial
<220> FEATURE:
<223> OTHER INFORMATION: Synthetic

<400> SEQUENCE: 705

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```